(12) United States Patent
Medoff

(10) Patent No.: US 10,597,595 B2
(45) Date of Patent: Mar. 24, 2020

(54) PROCESSING BIOMASS

(71) Applicant: Xyleco, Inc., Wakefield, MA (US)

(72) Inventor: Marshall Medoff, Wakefield, MA (US)

(73) Assignee: XYLECO, INC., Wakefield, MA (US)

( * ) Notice: Subject to any disclaimer, the term of this patent is extended or adjusted under 35 U.S.C. 154(b) by 0 days.

(21) Appl. No.: 16/198,537

(22) Filed: Nov. 21, 2018

(65) Prior Publication Data

US 2019/0233751 A1 Aug. 1, 2019

Related U.S. Application Data

(63) Continuation of application No. PCT/US2018/057878, filed on Oct. 26, 2018.
(Continued)

(51) Int. Cl.

| | |
|---|---|
| *C10L 1/06* | (2006.01) |
| *C10G 3/00* | (2006.01) |
| *C12P 7/64* | (2006.01) |
| *C12P 7/16* | (2006.01) |
| *C12P 19/02* | (2006.01) |

(Continued)

(52) U.S. Cl.
CPC .................. *C10L 1/06* (2013.01); *C10G 3/42* (2013.01); *C10G 3/45* (2013.01); *C10G 3/47* (2013.01); *C10G 3/48* (2013.01); *C10G 3/49* (2013.01); *C10L 1/023* (2013.01); *C12P 7/10* (2013.01); *C12P 7/16* (2013.01); *C12P 7/649* (2013.01); *C12P 19/02* (2013.01); *C12P 19/12* (2013.01); *C10G 2300/1011* (2013.01); *C10G 2300/1014* (2013.01); *C10G 2300/201* (2013.01); *C10G 2300/202* (2013.01); *C10G 2300/301* (2013.01); *C10G 2300/305* (2013.01);
(Continued)

(58) Field of Classification Search
CPC combination set(s) only.
See application file for complete search history.

(56) References Cited

U.S. PATENT DOCUMENTS

| | | | |
|---|---|---|---|
| 3,844,890 | A | 10/1974 | Horikoshi et al. |
| 4,435,307 | A | 3/1984 | Barbesgaard et al. |

(Continued)

FOREIGN PATENT DOCUMENTS

| | | |
|---|---|---|
| EP | 458162 A1 | 11/1991 |
| WO | 2006/110891 A2 | 10/2006 |

(Continued)

OTHER PUBLICATIONS

Ghose, "Measurement of Cellulase Activities," Pure & Applied Chemistry, vol. 59, No. 2, pp. 257-268 (1987).
(Continued)

*Primary Examiner* — Ellen M Mcavoy
*Assistant Examiner* — Chantel L Graham
(74) *Attorney, Agent, or Firm* — Lando & Anastasi, LLP

(57) ABSTRACT

Techniques for processing biomass are disclosed herein. A method of preparing cellulosic ethanol having 100% biogenic carbon content as determined by ASTM 6866-18, includes treating ground corn cobs with electron beam radiation and saccharifying the irradiated ground corn cob to produce sugars. The method also includes fermenting the sugars with a microorganism. In addition, an unblended cellulosic-biomass derived gasoline with a research octane number of greater than about 87, as determined by ASTM D2699 is disclosed.

55 Claims, 243 Drawing Sheets

Related U.S. Application Data

(60) Provisional application No. 62/670,411, filed on May 11, 2018, provisional application No. 62/660,611, filed on Apr. 20, 2018, provisional application No. 62/656,318, filed on Apr. 11, 2018, provisional application No. 62/646,204, filed on Mar. 21, 2018, provisional application No. 62/641,216, filed on Mar. 9, 2018, provisional application No. 62/578,132, filed on Oct. 27, 2017.

(51) Int. Cl.
*C10L 1/02* (2006.01)
*C12P 7/10* (2006.01)
*C12P 19/12* (2006.01)

(52) U.S. Cl.
CPC ............ *C10G 2300/308* (2013.01); *C10L 2200/0469* (2013.01); *C10L 2270/023* (2013.01)

(56) References Cited

U.S. PATENT DOCUMENTS

| | | | |
|---|---|---|---|
| 5,563,069 A | 10/1996 | Yang | |
| 5,952,105 A | 9/1999 | Medoff et al. | |
| 5,973,035 A | 10/1999 | Medoff et al. | |
| 6,023,013 A | 2/2000 | English et al. | |
| 6,107,549 A | 8/2000 | Feng et al. | |
| 6,175,061 B1 | 1/2001 | Bright et al. | |
| 6,207,729 B1 | 3/2001 | Medoff et al. | |
| 6,258,876 B1 | 7/2001 | Medoff et al. | |
| 6,448,307 B1 | 9/2002 | Medoff et al. | |
| 6,538,178 B1 | 3/2003 | Kishore | |
| 6,822,142 B2 | 11/2004 | Karunanandaa et al. | |
| 6,841,717 B2 | 1/2005 | Boronat et al. | |
| 7,049,485 B2 | 5/2006 | Sticklen et al. | |
| 7,122,719 B2 | 10/2006 | Hakimi et al. | |
| 7,335,812 B2 | 2/2008 | Fernandes et al. | |
| 7,402,731 B2 | 7/2008 | Penner et al. | |
| 7,405,344 B2 | 7/2008 | Voelker et al. | |
| 7,498,429 B2 | 3/2009 | Kakefuda et al. | |
| 7,566,817 B2 | 7/2009 | Beazley et al. | |
| 7,615,621 B2 | 11/2009 | Dizigan et al. | |
| 7,659,448 B2 | 2/2010 | Ahrens et al. | |
| 7,674,952 B2 | 3/2010 | Hinchey | |
| 7,708,214 B2 | 5/2010 | Medoff | |
| 7,714,187 B2 | 5/2010 | Shi et al. | |
| 7,799,906 B1 | 9/2010 | Rottmann et al. | |
| 7,932,065 B2 | 4/2011 | Medoff | |
| 8,377,668 B2 | 2/2013 | Medoff et al. | |
| 8,728,782 B2 | 5/2014 | Kang et al. | |
| 9,342,294 B2 | 5/2016 | Naccache | |
| 9,388,432 B2 | 7/2016 | Medoff et al. | |
| 2009/0326286 A1 | 12/2009 | Yie et al. | |
| 2011/0287498 A1 | 11/2011 | Medoff et al. | |
| 2012/0259146 A1* | 10/2012 | Gruber | C07C 1/24 585/14 |
| 2013/0185992 A1 | 7/2013 | Cortright et al. | |
| 2014/0011258 A1 | 1/2014 | Medoff et al. | |
| 2014/0081063 A1* | 3/2014 | Viswanadham | C10G 3/49 585/408 |
| 2014/0173975 A1 | 6/2014 | Chheda et al. | |
| 2014/0303266 A1 | 10/2014 | Hyman | |
| 2016/0009628 A1 | 1/2016 | Colby et al. | |
| 2017/0369804 A1* | 12/2017 | Lilga | C10G 29/205 |
| 2018/0201843 A1* | 7/2018 | O'Neill | B01J 27/14 |
| 2019/0151834 A1* | 5/2019 | Carrette | C10G 47/10 |

FOREIGN PATENT DOCUMENTS

| | | | |
|---|---|---|---|
| WO | 2007/071818 A1 | 6/2007 | |
| WO | 2008/011598 A2 | 1/2008 | |
| WO | 2017/111691 A1 | 6/2017 | |
| WO | 2019/084518 A1 | 5/2019 | |

OTHER PUBLICATIONS

Chu, "Overview of Light-Ion Beam Therapy," Columbus-Ohio, ICRU-IAEA Meeting, Mar. 18-20, 2006 (20 pages).
Iwata et al., "Alternating-Phase-Focused IH-DTL for Heavy-Ion Medical Accelerators,"Proceedings of EPAC 2006, Edinburgh, Scotland, pp. 2328-2330 (2006) (3 pages).
Krane, "Introductory Nuclear Physics, " John Wiley & Sons, Inc., 858 pages (1988).
Corn Refiners Association, "Corn Starch" 11th Edition, 2006, pp. 1-41.
http://bcn.boulder.co.us/basin/waterworks/gasolinecomp.pdf, accessed Mar. 13, 2019 (2 pages).
Leitner et al., "Status of the Superconducting ECR Ion Source Venus," Proceedings of EPAC 2000, Vienna, Austria, pp. 1610-1612 (2000) (3 pages).
Warnick et al., "*Clostridium phytofermentans* sp. nov., a cellulolytic mesophile from forest soil," International Journal of Systematic and Evolutionary Microbiology, vol. 52, pp. 1155-1160, 2002.
Philippidis, "Cellulose Bioconversion Technology," Handbook on Bioethanol: Production and Utilization, Chapter 12, Wyman, ed., Taylor & Francis, Washington, DC, 35 pages (1996).
http://www.gabi-software.com/america/index/, accessed Mar. 13, 2019 (1 page).
International Search Report and Written Opinion for PCT/US2018/057878 dated Mar. 25, 2019.

* cited by examiner

| # | Peak Name | RT | Area | % Area | Height | Amount | Units |
|---|---|---|---|---|---|---|---|
| 1 | | 1.529 | 5 | 0.00 | 0 | | |
| 2 | | 1.885 | 1 | 0.00 | 0 | | |
| 3 | | 2.336 | 0 | 0.00 | 0 | | |
| 4 | Acetone | 2.644 | | | | | |
| 5 | | 4.087 | 29 | 0.04 | 6 | | |
| 6 | Methanol | 4.310 | 73 | 0.11 | 16 | 1663.367 | ppm |
| 7 | IPA | 4.626 | | | | | |
| 8 | | 4.972 | 6 | 0.01 | 1 | | |
| 9 | Ethanol | 5.273 | 66323 | 98.82 | 5847 | 438692.596 | ppm |
| 10 | Acetonitrile | 6.603 | | | | | |
| 11 | | 7.024 | 3 | 0.00 | 1 | | |
| 12 | | 7.124 | 0 | 0.00 | 0 | | |
| 13 | n-Propanol | 7.318 | 124 | 0.18 | 42 | 412.954 | ppm |
| 14 | 2-methyl propanol | 8.072 | 83 | 0.12 | 38 | 121.718 | ppm |
| 15 | n-butanol | 8.673 | 5 | 0.01 | 3 | 12.663 | ppm |
| 16 | 2-methyl butanol | 9.227 | 353 | 0.53 | 209 | 415.845 | ppm |
| 17 | | 9.355 | 1 | 0.00 | 0 | | |
| 18 | | 9.418 | 1 | 0.00 | 1 | | |
| 19 | | 9.458 | 1 | 0.00 | 0 | | |
| 20 | | 9.588 | 0 | 0.00 | 0 | | |
| 21 | | 9.707 | 0 | 0.00 | 0 | | |
| 22 | | 9.787 | 0 | 0.00 | 0 | | |
| 23 | | 9.879 | 24 | 0.04 | 32 | | |
| 24 | | 9.961 | 0 | 0.00 | 0 | | |
| 25 | | 9.997 | 0 | 0.00 | 0 | | |
| 26 | | 10.031 | 1 | 0.00 | 0 | | |
| 27 | | 10.050 | 1 | 0.00 | 1 | | |
| 28 | | 10.084 | 4 | 0.01 | 2 | | |
| 29 | | 10.168 | 1 | 0.00 | 1 | | |
| 30 | | 10.216 | 2 | 0.00 | 2 | | |
| 31 | | 10.283 | 1 | 0.00 | 0 | | |
| 32 | | 10.330 | 1 | 0.00 | 0 | | |
| 33 | | 10.372 | 0 | 0.00 | 0 | | |
| 34 | | 10.408 | 0 | 0.00 | 0 | | |
| 35 | | 10.433 | 0 | 0.00 | 0 | | |
| 36 | | 10.479 | 1 | 0.00 | 1 | | |
| 37 | | 10.534 | 2 | 0.00 | 2 | | |
| 38 | | 10.577 | 2 | 0.00 | 1 | | |
| 39 | | 10.650 | 2 | 0.00 | 1 | | |
| 40 | | 10.823 | 1 | 0.00 | 1 | | |
| 41 | | 10.886 | 0 | 0.00 | 0 | | |
| 42 | | 10.928 | 1 | 0.00 | 1 | | |
| 43 | | 10.989 | 1 | 0.00 | 1 | | |
| 44 | | 11.024 | 1 | 0.00 | 1 | | |
| 45 | | 11.081 | 1 | 0.00 | 0 | | |
| 46 | | 11.133 | 0 | 0.00 | 0 | | |
| 47 | | 11.284 | 0 | 0.00 | 0 | | |
| 48 | | 11.303 | 1 | 0.00 | 1 | | |
| 49 | | 11.387 | 0 | 0.00 | 0 | | |
| 50 | | 11.514 | 0 | 0.00 | 0 | | |
| 51 | | 11.577 | 1 | 0.00 | 0 | | |
| 52 | | 11.803 | 1 | 0.00 | 0 | | |

FIG. 12A CONT

| | Peak Name | RT | Area | % Area | Height | Amount | Units |
|---|---|---|---|---|---|---|---|
| 1 | | 1.629 | 0 | 0.00 | 0 | | |
| 2 | | 1.865 | 1 | 0.00 | 0 | | |
| 3 | | 2.596 | 0 | 0.00 | 0 | | |
| 4 | Acetone | 2.844 | | | | | |
| 5 | | 4.037 | 29 | 0.04 | 6 | | |
| 6 | Methanol | 4.310 | 73 | 0.11 | 16 | 1083.297 | ppm |
| 7 | IPA | 4.825 | | | | | |
| 8 | | 4.872 | 8 | 0.01 | 1 | | |
| 9 | Ethanol | 5.272 | 66323 | 98.92 | 9847 | 438892.680 | ppm |
| 10 | Acetonitrile | 6.803 | | | | | |
| 11 | | 7.024 | 3 | 0.00 | 1 | | |
| 12 | | 7.124 | 0 | 0.00 | 0 | | |
| 13 | n-Propanol | 7.318 | 328 | 0.38 | 42 | 412.954 | ppm |
| 14 | 2-methyl propanol | 8.073 | 81 | 0.12 | 39 | 121.718 | ppm |
| 15 | n-butanol | 8.671 | 5 | 0.01 | 3 | 12.853 | ppm |
| 16 | 2-methyl butanol | 9.227 | 353 | 0.53 | 208 | 415.645 | ppm |
| 17 | | 9.355 | 1 | 0.00 | 0 | | |
| 18 | | 9.418 | 1 | 0.00 | 1 | | |
| 19 | | 9.558 | 1 | 0.00 | 0 | | |
| 20 | | 9.588 | 0 | 0.00 | 0 | | |
| 21 | | 9.707 | 0 | 0.00 | 0 | | |
| 22 | | 9.787 | 0 | 0.00 | 0 | | |
| 23 | | 9.878 | 24 | 0.04 | 22 | | |
| 24 | | 9.961 | 0 | 0.00 | 0 | | |
| 25 | | 9.987 | 0 | 0.00 | 0 | | |
| 26 | | 10.031 | 1 | 0.00 | 0 | | |
| 27 | | 10.060 | 1 | 0.00 | 1 | | |
| 28 | | 10.084 | 4 | 0.01 | 2 | | |
| 29 | | 10.166 | 1 | 0.00 | 1 | | |
| 30 | | 10.218 | 2 | 0.00 | 2 | | |
| 31 | | 10.263 | 1 | 0.00 | 0 | | |
| 32 | | 10.336 | 1 | 0.00 | 0 | | |
| 33 | | 10.372 | 0 | 0.00 | 0 | | |
| 34 | | 10.408 | 0 | 0.00 | 0 | | |
| 35 | | 10.433 | 0 | 0.00 | 0 | | |
| 36 | | 10.478 | 1 | 0.00 | 1 | | |
| 37 | | 10.534 | 2 | 0.00 | 2 | | |
| 38 | | 10.577 | 2 | 0.00 | 1 | | |
| 39 | | 10.658 | 2 | 0.00 | 1 | | |
| 40 | | 10.803 | 1 | 0.00 | 0 | | |
| 41 | | 10.898 | 0 | 0.00 | 0 | | |
| 42 | | 10.926 | 1 | 0.00 | 1 | | |
| 43 | | 10.989 | 1 | 0.00 | 1 | | |
| 44 | | 11.034 | 1 | 0.00 | 1 | | |
| 45 | | 11.081 | 1 | 0.00 | 0 | | |
| 46 | | 11.133 | 0 | 0.00 | 0 | | |
| 47 | | 11.244 | 0 | 0.00 | 0 | | |
| 48 | | 11.303 | 1 | 0.00 | 1 | | |
| 49 | | 11.397 | 0 | 0.00 | 0 | | |
| 50 | | 11.514 | 0 | 0.00 | 0 | | |
| 51 | | 11.577 | 1 | 0.00 | 0 | | |
| 52 | | 11.803 | 1 | 0.00 | 0 | | |

FIG. 12B CONT

| | Peak Name | RT | Area | % Area | Height | Amount | Units |
|---|---|---|---|---|---|---|---|
| 1 | | 1.864 | 1 | 0.00 | 0 | | |
| 2 | Acetone | 2.844 | | | | | |
| 3 | | 2.973 | 0 | 0.00 | 0 | | |
| 4 | Methanol | 4.326 | 0 | 0.00 | 0 | 8.278 | ppm |
| 5 | IPA | 4.925 | | | | | |
| 6 | Ethanol | 5.268 | 64191 | 99.99 | 9701 | 416842.846 | ppm |
| 7 | Acetonitrile | 6.803 | | | | | |
| 8 | | 7.127 | 1 | 0.00 | 0 | | |
| 9 | n-Propanol | 7.320 | 0 | 0.00 | 0 | 3.422 | ppm |
| 10 | 2-methyl propanol | 8.070 | | | | | |
| 11 | n-butanol | 8.670 | | | | | |
| 12 | 2-methyl butanol | 9.221 | | | | | |
| 13 | | 9.417 | 1 | 0.00 | 0 | | |
| 14 | | 10.650 | 0 | 0.00 | 0 | | |
| 15 | | 11.582 | 0 | 0.00 | 0 | | |
| 16 | | 11.755 | 0 | 0.00 | 0 | | |

FIG. 13A CONT

| | Peak Name | RT | Area | % Area | Height | Amount | Units |
|---|---|---|---|---|---|---|---|
| 1 | | 1.864 | 1 | 0.00 | 0 | | |
| 2 | Acetone | 2.844 | | | | | |
| 3 | | 2.973 | 0 | 0.00 | 0 | | |
| 4 | Methanol | 4.326 | 0 | 0.00 | 0 | 8.276 | ppm |
| 5 | IPA | 4.925 | | | | | |
| 6 | Ethanol | 5.268 | 64191 | 99.99 | 9701 | 416842.846 | ppm |
| 7 | Acetonitrile | 6.803 | | | | | |
| 8 | | 7.127 | 1 | 0.00 | 0 | | |
| 9 | n-Propanol | 7.328 | 0 | 0.00 | 0 | 3.422 | ppm |
| 10 | 2-methyl propanol | 8.078 | | | | | |
| 11 | n-butanol | 8.678 | | | | | |
| 12 | 2-methyl butanol | 9.221 | | | | | |
| 13 | | 9.417 | 1 | 0.00 | 0 | | |
| 14 | | 10.650 | 0 | 0.00 | 0 | | |
| 15 | | 11.583 | 0 | 0.00 | 0 | | |
| 16 | | 11.755 | 0 | 0.00 | 0 | | |

FIG. 13B CONT

|    | Peak Name | RT | Area | % Area | Height | Amount | Units |
|----|-----------|-----|------|--------|--------|--------|-------|
| 1  |           | 1.233 | 2 | 0.00 | 1 |  |  |
| 2  |           | 1.581 | 1 | 0.00 | 0 |  |  |
| 3  |           | 1.866 | 3 | 0.01 | 1 |  |  |
| 4  |           | 2.764 | 0 | 0.00 | 0 |  |  |
| 5  | Acetone   | 2.844 |   |      |   |  |  |
| 6  |           | 2.974 | 0 | 0.00 | 0 |  |  |
| 7  |           | 3.990 | 3 | 0.01 | 1 |  |  |
| 8  | Methanol  | 4.310 |   |      |   |  |  |
| 9  | IPA       | 4.925 |   |      |   |  |  |
| 10 | Ethanol   | 5.242 | 48184 | 99.97 | 8161 | 312896.910 | ppm |
| 11 | Acetonitrile | 6.803 |   |   |   |  |  |
| 12 |           | 7.127 | 1 | 0.00 | 1 |  |  |
| 13 |           | 7.264 | 0 | 0.00 | 0 |  |  |
| 14 | n-Propanol | 7.319 |   |   |   |  |  |
| 15 | 2-methyl propanol | 8.070 |   |   |   |  |  |
| 16 | n-butanol | 8.670 |   |   |   |  |  |
| 17 | 2-methyl butanol | 9.221 |   |   |   |  |  |
| 18 |           | 9.413 | 1 | 0.00 | 1 |  |  |
| 19 |           | 10.650 | 1 | 0.00 | 1 |  |  |
| 20 |           | 11.263 | 0 | 0.00 | 0 |  |  |
| 21 |           | 11.583 | 0 | 0.00 | 0 |  |  |
| 22 |           | 11.756 | 0 | 0.00 | 0 |  |  |
| 23 |           | 12.106 | 0 | 0.00 | 0 |  |  |
| 24 |           | 12.385 | 0 | 0.00 | 0 |  |  |
| 25 |           | 12.675 | 0 | 0.00 | 0 |  |  |

FIG. 14A CONT.

| | Peak Name | RT | Area | % Area | Height | Amount | Units |
|---|---|---|---|---|---|---|---|
| 1 | | 1.233 | 2 | 0.00 | 1 | | |
| 2 | | 1.581 | 1 | 0.00 | 0 | | |
| 3 | | 1.866 | 3 | 0.01 | 1 | | |
| 4 | | 2.764 | 0 | 0.00 | 0 | | |
| 5 | Acetone | 2.844 | | | | | |
| 6 | | 2.974 | 0 | 0.00 | 0 | | |
| 7 | | 3.890 | 3 | 0.01 | 1 | | |
| 8 | Methanol | 4.310 | | | | | |
| 9 | IPA | 4.925 | | | | | |
| 10 | Ethanol | 5.242 | 48184 | 99.97 | 8161 | 312896.910 | ppm |
| 11 | Acetonitrile | 6.803 | | | | | |
| 12 | | 7.127 | 1 | 0.00 | 1 | | |
| 13 | | 7.264 | 0 | 0.00 | 0 | | |
| 14 | n-Propanol | 7.319 | | | | | |
| 15 | 2-methyl propanol | 8.070 | | | | | |
| 16 | n-butanol | 8.670 | | | | | |
| 17 | 2-methyl butanol | 9.231 | | | | | |
| 18 | | 9.413 | 1 | 0.00 | 1 | | |
| 19 | | 10.650 | 1 | 0.00 | 1 | | |
| 20 | | 11.263 | 0 | 0.00 | 0 | | |
| 21 | | 11.583 | 0 | 0.00 | 0 | | |
| 22 | | 11.756 | 0 | 0.00 | 0 | | |
| 23 | | 12.106 | 0 | 0.00 | 0 | | |
| 24 | | 12.385 | 0 | 0.00 | 0 | | |
| 25 | | 12.675 | 0 | 0.00 | 0 | | |

FIG. 14B CONT

| | Peak Name | RT | Area | % Area | Height | Amount | Units |
|---|---|---|---|---|---|---|---|
| 1 | | 1.218 | 3 | 0.00 | 1 | | |
| 2 | | 1.579 | 0 | 0.00 | 0 | | |
| 3 | | 1.866 | 0 | 0.00 | 0 | | |
| 4 | Acetone | 2.844 | | | | | |
| 5 | | 2.973 | 1 | 0.00 | 0 | | |
| 6 | | 4.036 | 1 | 0.00 | 0 | | |
| 7 | Methanol | 4.310 | | | | | |
| 8 | IPA | 4.925 | | | | | |
| 9 | Ethanol | 5.278 | 78487 | 99.98 | 10213 | 457729.737 | ppm |
| 10 | Acetonitrile | 6.803 | | | | | |
| 11 | | 7.138 | 2 | 0.00 | 1 | | |
| 12 | n-Propanol | 7.319 | | | | | |
| 13 | | 7.749 | 0 | 0.00 | 0 | | |
| 14 | 2-methyl propanol | 8.078 | | | | | |
| 15 | n-butanol | 8.670 | | | | | |
| 16 | 2-methyl butanol | 9.221 | | | | | |
| 17 | | 9.417 | 1 | 0.00 | 1 | | |
| 18 | | 9.453 | 1 | 0.00 | 0 | | |
| 19 | | 10.851 | 1 | 0.00 | 1 | | |
| 20 | | 11.187 | 0 | 0.00 | 0 | | |
| 21 | | 11.263 | 0 | 0.00 | 0 | | |
| 22 | | 11.583 | 0 | 0.00 | 0 | | |
| 23 | | 11.619 | 0 | 0.00 | 0 | | |
| 24 | | 11.756 | 0 | 0.00 | 0 | | |

FIG. 15A CONT

| | Peak Name | RT | Area | % Area | Height | Amount | Units |
|---|---|---|---|---|---|---|---|
| 1 | | 1.218 | 3 | 0.00 | 1 | | |
| 2 | | 1.579 | 0 | 0.00 | 0 | | |
| 3 | | 1.865 | 0 | 0.00 | 0 | | |
| 4 | Acetone | 2.644 | | | | | |
| 5 | | 2.973 | 1 | 0.00 | 0 | | |
| 6 | | 4.036 | 1 | 0.00 | 0 | | |
| 7 | Methanol | 4.319 | | | | | |
| 8 | IPA | 4.925 | | | | | |
| 9 | Ethanol | 5.276 | 70487 | 99.96 | 10213 | 457729.737 | ppm |
| 10 | Acetonitrile | 6.803 | | | | | |
| 11 | | 7.128 | 2 | 0.00 | 1 | | |
| 12 | n-Propanol | 7.319 | | | | | |
| 13 | | 7.749 | 0 | 0.00 | 0 | | |
| 14 | 2-methyl propanol | 8.070 | | | | | |
| 15 | n-butanol | 8.870 | | | | | |
| 16 | 2-methyl butanol | 9.221 | | | | | |
| 17 | | 9.417 | 1 | 0.00 | 1 | | |
| 18 | | 9.453 | 1 | 0.00 | 0 | | |
| 19 | | 10.651 | 1 | 0.00 | 1 | | |
| 20 | | 11.187 | 0 | 0.00 | 0 | | |
| 21 | | 11.263 | 0 | 0.00 | 0 | | |
| 22 | | 11.563 | 0 | 0.00 | 0 | | |
| 23 | | 11.619 | 0 | 0.00 | 0 | | |
| 24 | | 11.756 | 0 | 0.00 | 0 | | |

FIG. 15B CONT

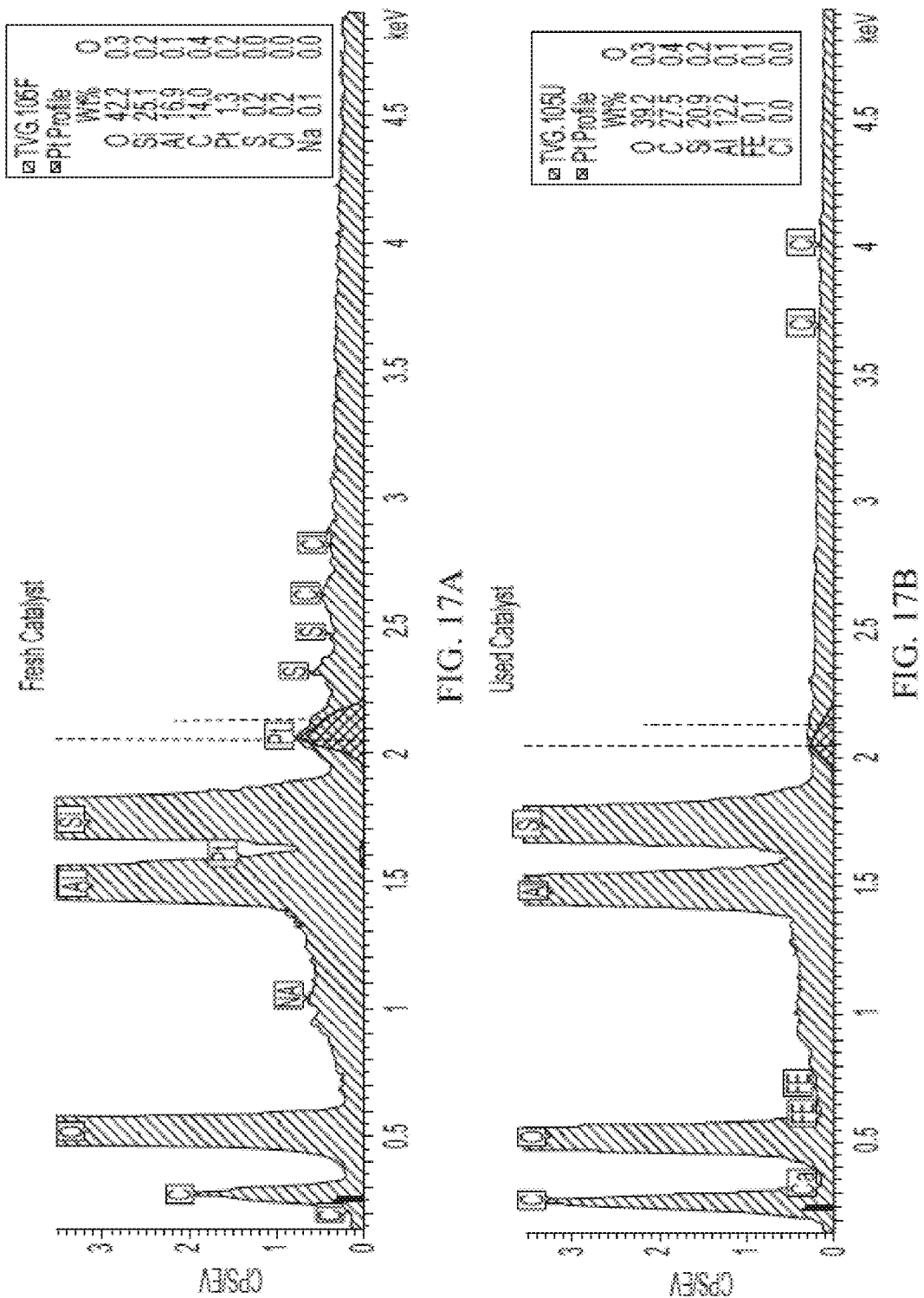
Catalyst: HZSM-5

| Reaction conditions | | | Average #C | Product distribution (%) | | | |
|---|---|---|---|---|---|---|---|
| T (°C) | P (psig) | LFR (mL/min) | | Aromatics | Alkenes | Alkanes | Oxygenates |
| 350 | 500 | 0.125 | 8.76 | 94.02 | 0.44 | 3.38 | 0.03 |

| CAS # | Compound Name | Br# | Q | Area% |
|---|---|---|---|---|
| | Major Aromatics Hydrocarbons | | | |
| 108-88-3 | Toluene | | 91 | 17.16 |
| 108-38-3 | Benzene, 1,3-dimethyl- | | 97 | 12.57 |
| 611-14-3 | Benzene, 1-ethyl-2-methyl- | | 94 | 8.93 |
| 526-73-8 | Benzene, 1,2,3-trimethyl- | | 95 | 7.48 |
| 95-47-6 | o-Xylene | | 95 | 5.13 |
| 100-41-4 | Ethylbenzene | | 91 | 5.06 |
| 106-42-3 | p-Xylene | | 97 | 4.63 |
| 874-41-9 | Benzene, 1-ethyl-2,4-dimethyl- | | 95 | 3.44 |
| 622-96-8 | Benzene, 1-ethyl-4-methyl- | | 91 | 3.40 |
| 71-43-2 | Benzene | | 91 | 2.47 |
| 91-57-6 | Naphthalene, 2-methyl- | | 94 | 1.87 |
| 95-93-2 | Benzene, 1,2,4,5-tetramethyl- | | 93 | 1.55 |
| 829-26-5 | Naphthalene, 2,3,6-trimethyl- | | 97 | 1.47 |
| 581-42-0 | Naphthalene, 2,6-dimethyl- | | 97 | 1.26 |
| 141-93-5 | Benzene, 1,3-diethyl- | | 97 | 1.11 |
| 769-57-3 | Benzene, (1,2-dimethyl-1-propenyl)- | | 94 | 1.11 |
| 874-35-1 | 1H-Indene, 2,3-dihydro-5-methyl- | | 90 | 1.05 |
| 1074-55-1 | Benzene, 1-methyl-4-propyl- | | 90 | 0.96 |
| 13632-94-5 | Benzene, 1,4-diethyl-2-methyl- | | 97 | 0.85 |
| 2050-24-0 | Benzene, 1,3-diethyl-5-methyl- | | 95 | 0.76 |
| 1758-88-9 | Benzene, 2-ethyl-1,4-dimethyl- | | 94 | 0.73 |
| 1074-43-7 | Benzene, 1-methyl-3-propyl- | | 91 | 0.70 |
| 571-58-4 | Naphthalene, 1,4-dimethyl- | | 97 | 0.70 |
| 582-16-1 | Naphthalene, 2,7-dimethyl- | | 96 | 0.69 |
| 2245-38-7 | Naphthalene, 1,6,7-trimethyl- | | 98 | 0.49 |
| 933-98-2 | Benzene, 1-ethyl-2,3-dimethyl- | | 93 | 0.48 |
| 103-65-1 | Benzene, propyl- | | 90 | 0.46 |
| 496-11-7 | Indane | | 87 | 0.42 |
| 939-27-5 | Naphthalene, 2-ethyl- | | 97 | 0.40 |
| 767-58-8 | Indan, 1-methyl- | | 87 | 0.37 |
| 108-67-8 | Mesitylene | | 93 | 0.33 |
| 2809-64-5 | 1,2,3,4-Tetrahydro-5-methyl-naphthalene | | 94 | 0.28 |
| 6682-71-9 | 1H-Indene, 2,3-dihydro-4,7-dimethyl- | | 91 | 0.28 |
| 2131-42-2 | Naphthalene, 1,4,6-trimethyl- | | 97 | 0.24 |
| 2717-39-7 | 1,4,5,8-Tetramethylnaphthalene | | 96 | 0.23 |
| 98-82-8 | Benzene, (1-methylethyl)- | | 91 | 0.22 |
| 1129-29-9 | 1-(1-methylethenyl)-3-propan-2-ylbenzene | | 81 | 0.21 |
| 20836-11-7 | 2,2-Dimethylindene, 2,3-dihydro- | | 70 | 0.18 |
| 1595-16-0 | Benzene, 1-methyl-4-(1-methylpropyl)- | | 90 | 0.17 |
| 2049-95-8 | Benzene, (1,1-dimethylpropyl)- | | 90 | 0.17 |
| 483-78-3 | 1,6-dimethyl-4-propan-2-yl-naphthalene | | 95 | 0.17 |
| 54340-86-2 | 4-[(E)-but-2-enyl]-1,2-dimethyl-benzene | | 90 | 0.17 |
| 529-05-5 | Chamazulene | | 94 | 0.16 |
| 135-01-3 | Benzene, 1,2-diethyl- | | 95 | 0.16 |
| 535-77-3 | Benzene, 1-methyl-3-(1-methylethyl)- | | 91 | 0.15 |
| 13065-07-1 | 2,7-dimethyltetralin | | 87 | 0.14 |
| 1746-23-2 | 1-(1,1-Dimethylethyl)-4-ethenylbenzene | | 81 | 0.14 |
| 1560-06-1 | Benzene, 2-butenyl- | | 80 | 0.14 |
| 490-65-3 | Naphthalene, 1-methyl-7-(1-methylethyl)- | | 93 | 0.13 |
| 2027-17-0 | Naphthalene, 2-(1-methylethyl)- | | 95 | 0.13 |
| 3031-15-0 | Naphthalene, 1,2,3,4-tetramethyl- | | 91 | 0.12 |

FIG. 18A-2 CONT

| CAS # | Compound Name | Br# | Q | Area% |
|---|---|---|---|---|
| 1127-76-0 | 1-ethylnaphthalene | | 95 | 0.12 |
| 1000383-71-7 | 4-ethyl-1,6-dimethyl-naphthalene | | 93 | 0.11 |
| 17057-82-8 | 1H-Indene, 2,3-dihydro-1,2-dimethyl- | | 76 | 0.11 |
| 575-43-9 | Naphthalene, 1,6-dimethyl- | | 97 | 0.11 |
| | Trace Aromatic Hydrocarbons | | | |
| 54774-89-9 | 2-methyl-1-propyl-naphthalene | | 90 | 0.091 |
| 1000383-71-3 | 2-Isopropyl-7-methylnaphthalene | | 90 | 0.090 |
| 2613-76-5 | 1H-Indene, 2,3-dihydro-1,1,3-trimethyl- | | 90 | 0.090 |
| 7364-19-4 | Benzene, 1-(1,1-dimethylethyl)-4-ethyl- | | 72 | 0.090 |
| 1000383-71-8 | 1,6-Dimethyl-3-ethylnaphthalene | | 91 | 0.085 |
| 40650-41-7 | 1H-Indene, 2,3-dihydro-1,1,5-trimethyl- | | 91 | 0.080 |
| 53172-84-2 | Benzene, (1-methyl-1-butenyl)- | | 94 | 0.077 |
| 2177-48-2 | 1H-Indene, 1,3-dimethyl- | | 87 | 0.076 |
| 42775-75-7 | Naphthalene, 5-ethyl-1,2,3,4-tetrahydro- | | 91 | 0.064 |
| 1060370-34-1 | 3,4-Dimethylcumene | | 90 | 0.064 |
| 2131-41-1 | Naphthalene, 1,4,5-trimethyl- | | 80 | 0.056 |
| 4175-53-5 | 1H-Indene, 2,3-dihydro-1,3-dimethyl- | | 91 | 0.056 |
| 4175-54-6 | 1,4-dimethyltetralin | | 81 | 0.053 |
| 104-51-8 | Benzene, n-butyl- | | 86 | 0.052 |
| 2765-18-6 | 1-propylnaphthalene | | 90 | 0.051 |
| 54340-87-3 | 1H-Indene, 2,3-dihydro-1,4,7-trimethyl- | | 90 | 0.048 |
| 6682-06-0 | 1H-Indene, 2,3-dihydro-4,5,7-trimethyl- | | 81 | 0.047 |
| 135-98-8 | Benzene, (1-methylpropyl)- | | 86 | 0.045 |
| 1559-81-5 | 1-methyl-1,2,3,4-tetrahydronaphthalene | | 91 | 0.042 |
| 489-84-9 | Azulene, 1,4-dimethyl-7-(1-methylethyl)- | | 91 | 0.038 |
| 538-93-2 | Benzene, (2-methylpropyl)- | | 83 | 0.037 |
| 527-53-7 | Benzene, 1,2,3,5-tetramethyl- | | 90 | 0.036 |
| 4218-48-8 | Benzene, 1-ethyl-4-(1-methylethyl)- | | 86 | 0.033 |
| 54340-85-1 | Benzene, 1-(2-butenyl)-2,3-dimethyl- | | 81 | 0.033 |
| 54758-36-0 | (1-Methylbuta-1,3-dienyl)benzene | | 91 | 0.032 |
| 14679-13-1 | 1,3,5-trimethyl-2-prop-1-en-2-yl-benzene | | 76 | 0.030 |
| 769-25-5 | Benzene, 2-ethenyl-1,3,5-trimethyl- | | 60 | 0.029 |
| 4481-30-5 | Benzene, (1,2-dimethylpropyl)- | | 74 | 0.028 |
| 4773-82-4 | 1H-Indene, 2,3-dimethyl- | | 76 | 0.028 |
| 489-77-0 | 6-Isopropyl-1,4-dimethylnaphthalene | | 89 | 0.025 |
| 527-84-4 | o-Cymene | | 90 | 0.025 |
| 1000383-71-2 | 2-Isopropyl-3-methylnaphthalene | | 91 | 0.023 |
| 6158-45-8 | Naphthalene, 1-(1-methylethyl)- | | 90 | 0.019 |
| 17851-27-3 | Benzene, 1-ethyl-2,4,5-trimethyl- | | 72 | 0.018 |
| 475-03-6 | Naphthalene, tetrahydro-1,1,6-trimethyl- | | 90 | 0.016 |
| 766-82-5 | 3-Methylphenylacetylene | | 64 | 0.014 |
| 33930-85-7 | (4,5,5-trimethylcyclopenta-1,3-dien-1-yl)benzene | | 62 | 0.013 |
| 25419-33-4 | 1,8-dimethyltetralin | | 90 | 0.007 |
| 886-65-7 | 1,4-Diphenyl-1,3-butadiene | | 72 | 0.006 |
| 16606-46-5 | Naphthalene, 1,2-dihydro-1-phenyl- | | 64 | 0.003 |
| | Trace Oxygenated Aromatics | | | |
| 35339-98-1 | Methyl 2-(ethoxymethyl)-5-methyl-3-furoate | | 74 | 0.009 |
| 832-62-2 | 4,6,8-Trimethyl-1-azulenecarbaldehyde | | 68 | 0.009 |
| | Trace n-Alkenes | | | |
| 7688-21-3 | 2-Hexene, (Z)- | | 90 | 0.007 |
| 592-47-2 | 3-Hexene | | 83 | 0.004 |
| 592-43-8 | 2-Hexene | | 83 | 0.004 |

FIG. 18A-2 CONT

| CAS # | Compound Name | Br# | Q | Area% |
|---|---|---|---|---|
| 109-68-2 | 2-Pentene | | 90 | 0.003 |
| | Trace Branched Alkenes | | | |
| 756-02-5 | 1,4-Pentadiene, 2,3,3-trimethyl- | 3 | 83 | 0.016 |
| 563-79-1 | 2-Butene, 2,3-dimethyl- | 2 | 91 | 0.020 |
| 3683-22-5 | 2-Hexene, 4-methyl-, (E)- | 1 | 83 | 0.007 |
| 3683-19-0 | (Z)-4-Methyl-2-hexene | 1 | 83 | 0.002 |
| 922-61-2 | 2-Pentene, 3-methyl- | 1 | 91 | 0.027 |
| 763-29-1 | 1-Pentene, 2-methyl- | 1 | 90 | 0.006 |
| | Major Cyclic Alkenes | | | |
| 3479-89-8 | 1,3,5-Cycloheptatriene, 3,7,7-trimethyl- | | 91 | 0.33 |
| | Trace Cyclic Alkenes | | | |
| 693-89-0 | Cyclopentene, 1-methyl- | | 87 | 0.019 |
| | Major n-Alkanes | | | |
| 110-54-3 | n-Hexane | | 91 | 0.14 |
| | Trace n-Alkanes | | | |
| 109-66-0 | Pentane | | 91 | 0.060 |
| 142-82-5 | Heptane | | 94 | 0.053 |
| 106-97-8 | Butane | | 90 | 0.014 |
| | Major Branched Alkanes | | | |
| 589-34-4 | Hexane, 3-methyl- | 1 | 81 | 0.42 |
| 591-76-4 | Hexane, 2-methyl- | 1 | 74 | 0.30 |
| 96-14-0 | Pentane, 3-methyl- | 1 | 90 | 0.44 |
| 107-83-5 | Pentane, 2-methyl- | 1 | 83 | 0.53 |
| 78-78-4 | Butane, 2-methyl- | 1 | 87 | 0.10 |
| | Trace Branched Alkanes | | | |
| 20278-89-1 | Heptane, 3,4,5-trimethyl- | 3 | 64 | 0.099 |
| 565-59-3 | Pentane, 2,3-dimethyl- | 2 | 83 | 0.041 |
| 108-08-7 | Pentane, 2,4-dimethyl- | 2 | 78 | 0.017 |
| 79-29-8 | Butane, 2,3-dimethyl- | 2 | 90 | 0.044 |
| 2216-34-4 | Octane, 4-methyl- | 1 | 83 | 0.016 |
| 589-53-7 | Heptane, 4-methyl- | 1 | 91 | 0.043 |
| 592-27-8 | Heptane, 2-methyl- | 1 | 91 | 0.062 |
| 617-78-7 | Pentane, 3-ethyl- | 1 | 83 | 0.023 |
| | Major Cyclic Alkanes | | | |
| 96-37-7 | Cyclopentane, methyl- | | 91 | 0.25 |
| 822-50-4 | Cyclopentane, 1,2-dimethyl-, trans- | | 94 | 0.11 |
| | Trace Cyclic Alkanes | | | |
| 3875-51-2 | Cyclopentane, (1-methylethyl)- | | 83 | 0.006 |
| 2207-03-6 | Cyclohexane, 1,3-dimethyl-, trans- | | 91 | 0.045 |
| 930-89-2 | Cyclopentane, 1-ethyl-2-methyl-, cis- | | 90 | 0.035 |
| 2207-04-7 | Cyclohexane, 1,4-dimethyl-, trans- | | 83 | 0.009 |
| 591-21-9 | Cyclohexane, 1,3-dimethyl- | | 72 | 0.044 |
| 2815-58-9 | Cyclopentane, 1,2,4-trimethyl- | | 91 | 0.064 |
| 1640-89-7 | Cyclopentane, ethyl- | | 95 | 0.072 |
| 108-87-2 | Cyclohexane, methyl- | | 91 | 0.067 |
| 1192-18-3 | Cyclopentane, 1,2-dimethyl-, cis- | | 91 | 0.032 |
| 2453-00-1 | Cyclopentane, 1,3-dimethyl- | | 91 | 0.093 |
| 2532-58-3 | Cyclopentane, 1,3-dimethyl-, cis- | | 64 | 0.068 |
| 287-92-3 | Cyclopentane | | 90 | 0.029 |
| 2402-06-4 | Cyclopropane, 1,2-dimethyl-, trans- | | 90 | 0.006 |
| | Trace Oxygenates | | | |
| 1000309-31-4 | Oxalic acid, cyclohexyl dodecyl ester | | 64 | 0.017 |

FIG. 18A-2 CONT

| CAS # | Compound Name | Br# | Q | Area% |
|---|---|---|---|---|
| 64-17-5 | Ethanol | | 90 | 0.013 |

FIG. 18A-2 CONT

Catalyst: 0.5%Ru/HZSM-5

| Reaction conditions | | | Average #C | Product distribution (%) | | | |
|---|---|---|---|---|---|---|---|
| T (°C) | P (psig) | LFR (mL/min) | | Aromatics | Alkenes | Alkanes | Oxygenates |
| 350 | 500 | 0.125 | 8.57 | 91.13 | 0.47 | 5.87 | 0.03 |

Hydrocarbon Report

Request: RVP-GHW-L4407    Xyleco Inc    Sample: RVP-ETG-55-2-R6-350C

| Summary | Total | Known | Major | Trace | Ave Carbon # |
|---|---|---|---|---|---|
| Peaks: | 295 | 207 | 72 | 135 | 8.58 |
| Area: | 6668294288 | 97.6% | 93.3% | 4.3% | |

| Compound Type | Total Known # Peaks | Total Known % Area | Major Components # Peaks | Major Components % Area | Average Carbon # |
|---|---|---|---|---|---|
| Aromatics (Total): | 138 | 91.24 | 53 | 88.24 | 8.69 |
| Oxygenated: | 4 | 0.23 | 1 | 0.10 | 10.23 |
| Alkenes (Total): | 27 | 0.47 | 0 | 0.00 | 6.93 |
| Straight: | 3 | 0.05 | 0 | 0.00 | 5.30 |
| Branched: | 12 | 0.19 | 0 | 0.00 | 7.03 |
| Cyclic: | 12 | 0.22 | 0 | 0.00 | 7.25 |
| Alkanes (Total): | 40 | 5.87 | 19 | 5.06 | 6.93 |
| Straight: | 4 | 0.44 | 2 | 0.38 | 6.14 |
| Branched: | 13 | 3.01 | 6 | 2.71 | 6.84 |
| Cyclic: | 23 | 2.42 | 11 | 1.98 | 7.19 |
| Oxygenated (Other): | 1 | 0.03 | 0 | 0.00 | 9.00 |

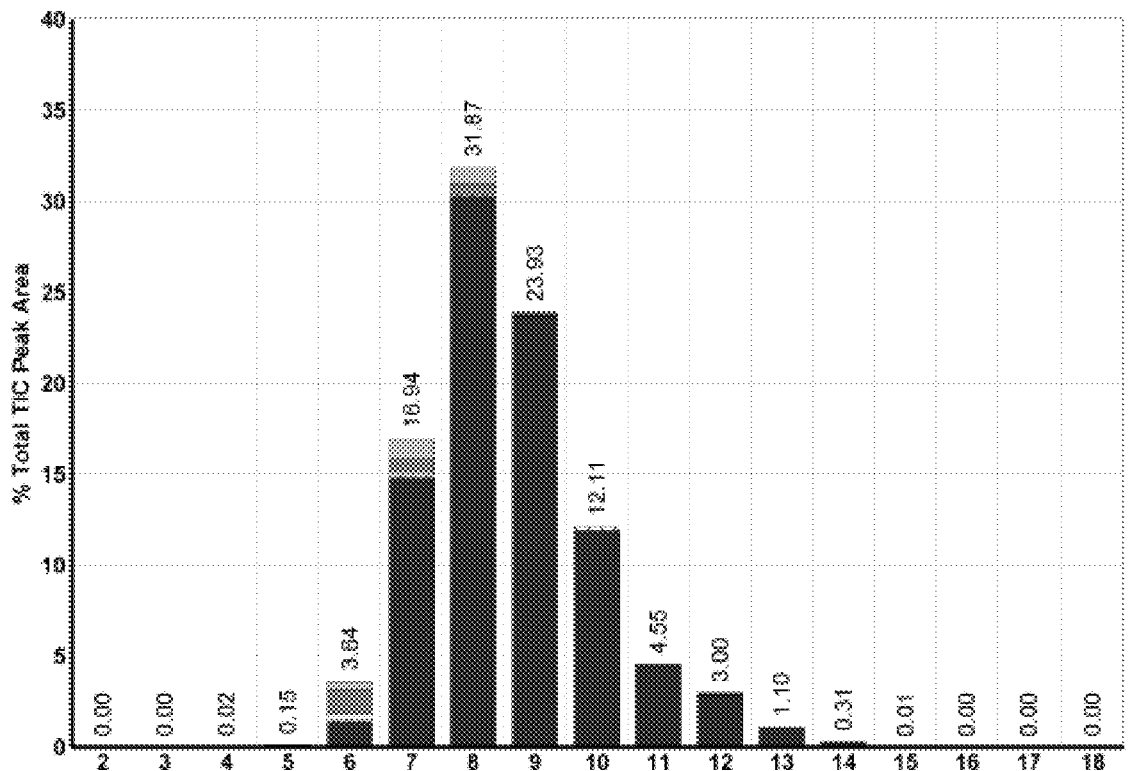

FIG. 18B-2

| CAS # | Compound Name | Bn# | Q | Area% |
|---|---|---|---|---|
| | Major Aromatics Hydrocarbons ||||
| 108-38-3 | Benzene, 1,3-dimethyl- | | 95 | 24.58 |
| 108-88-3 | Toluene | | 91 | 14.80 |
| 620-14-4 | Benzene, 1-ethyl-3-methyl- | | 95 | 9.73 |
| 526-73-8 | Benzene, 1,2,3-trimethyl- | | 97 | 7.28 |
| 95-47-6 | o-Xylene | | 95 | 5.67 |
| 108-67-8 | Mesitylene | | 97 | 4.91 |
| 874-41-9 | Benzene, 1-ethyl-2,4-dimethyl- | | 97 | 4.06 |
| 141-93-5 | Benzene, 1,3-diethyl- | | 96 | 1.69 |
| 71-43-2 | Benzene | | 91 | 1.40 |
| 1074-55-1 | Benzene, 1-methyl-4-propyl- | | 91 | 1.35 |
| 91-57-6 | Naphthalene, 2-methyl- | | 94 | 1.18 |
| 582-16-1 | Naphthalene, 2,7-dimethyl- | | 97 | 1.11 |
| 874-35-1 | 1H-Indene, 2,3-dihydro-5-methyl- | | 93 | 1.03 |
| 1074-43-7 | Benzene, 1-methyl-3-propyl- | | 94 | 1.02 |
| 611-14-3 | Benzene, 1-ethyl-2-methyl- | | 93 | 0.85 |
| 829-26-5 | Naphthalene, 2,3,6-trimethyl- | | 97 | 0.83 |
| 527-53-7 | Benzene, 1,2,3,5-tetramethyl- | | 97 | 0.59 |
| 1595-16-0 | Benzene, 1-methyl-4-(1-methylpropyl)- | | 94 | 0.57 |
| 103-65-1 | Benzene, propyl- | | 87 | 0.49 |
| 13632-94-5 | Benzene, 1,4-diethyl-2-methyl- | | 96 | 0.45 |
| 535-77-3 | Benzene, 1-methyl-3-(1-methylethyl)- | | 95 | 0.41 |
| 6682-71-9 | 1H-Indene, 2,3-dihydro-4,7-dimethyl- | | 93 | 0.38 |
| 1127-76-0 | 1-ethylnaphthalene | | 97 | 0.33 |
| 17059-48-2 | 1H-Indene, 2,3-dihydro-1,6-dimethyl- | | 93 | 0.33 |
| 1758-88-9 | Benzene, 2-ethyl-1,4-dimethyl- | | 96 | 0.33 |
| 934-80-5 | Benzene, 4-ethyl-1,2-dimethyl- | | 91 | 0.29 |
| 54340-86-2 | 4-[(E)-but-2-enyl]-1,2-dimethyl-benzene | | 96 | 0.28 |
| 527-84-4 | o-Cymene | | 97 | 0.26 |
| 496-11-7 | Indane | | 87 | 0.24 |
| 98-82-8 | Benzene, (1-methylethyl)- | | 91 | 0.22 |
| 1758-85-6 | Benzene, 2,4-diethyl-1-methyl- | | 95 | 0.22 |
| 934-74-7 | Benzene, 1-ethyl-3,5-dimethyl- | | 95 | 0.21 |
| 1680-51-9 | 6-Methyl-(1,2,3,4-tetrahydronaphthalene) | | 93 | 0.20 |
| 91-20-3 | Naphthalene | | 91 | 0.19 |
| 56253-64-6 | Benzene, (2-methyl-1-butenyl)- | | 86 | 0.17 |
| 769-25-5 | Benzene, 2-ethenyl-1,3,5-trimethyl- | | 87 | 0.15 |
| 2177-48-2 | 1H-Indene, 1,3-dimethyl- | | 95 | 0.15 |
| 1595-05-7 | Benzene, 1-methyl-4-butyl | | 93 | 0.14 |
| 700-12-9 | Benzene, pentamethyl- | | 92 | 0.14 |
| 54410-75-2 | Benzene, 1,2-diethyl-3,4-dimethyl- | | 93 | 0.13 |
| 571-61-9 | Naphthalene, 1,5-dimethyl- | | 97 | 0.12 |
| 7524-63-2 | 2,6-dimethyltetralin | | 95 | 0.12 |
| 2050-24-0 | Benzene, 1,3-diethyl-5-methyl- | | 95 | 0.12 |
| 575-37-1 | Naphthalene, 1,7-dimethyl- | | 97 | 0.11 |
| 1800210-01-1 | (1-Methylpenta-2,4-dienyl)benzene | | 93 | 0.10 |
| | Trace Aromatic Hydrocarbons ||||
| 119-64-2 | Naphthalene, 1,2,3,4-tetrahydro- | | 76 | 0.098 |
| 54774-89-9 | 2-methyl-1-propyl-naphthalene | | 95 | 0.085 |
| 54758-36-0 | (1-Methylbuta-1,3-dienyl)benzene | | 91 | 0.081 |
| 2717-44-4 | Naphthalene, 1,2-dihydro-3-methyl- | | 78 | 0.078 |
| 22531-20-0 | Naphthalene, 6-ethyl-1,2,3,4-tetrahydro- | | 90 | 0.075 |

FIG. 18B-2 CONT

| CAS # | Compound Name | Br# | Q | Area% |
|---|---|---|---|---|
| 1746-23-2 | 1-(1,1-Dimethylethyl)-4-ethenylbenzene | | 88 | 0.074 |
| 40630-41-7 | 1H-Indene, 2,3-dihydro-1,1,3-trimethyl- | | 94 | 0.072 |
| 55669-88-0 | 1,4-dimethyl-2-(2-methylpropyl)benzene | | 90 | 0.066 |
| 4218-48-8 | Benzene, 1-ethyl-4-(1-methylethyl)- | | 91 | 0.061 |
| 2027-17-0 | Naphthalene, 2-(1-methylethyl)- | | 90 | 0.061 |
| 1074-17-5 | Benzene, 1-methyl-2-propyl- | | 90 | 0.060 |
| 3877-19-8 | 2-Methyl-(1,2,3,4-tetrahydronaphtalene) | | 93 | 0.059 |
| 4773-83-3 | 1,2,3-Trimethylindene | | 94 | 0.059 |
| 135-01-3 | Benzene, 1,2-diethyl- | | 93 | 0.049 |
| 2131-41-1 | Naphtalene, 1,4,5-trimethyl- | | 97 | 0.048 |
| 1000383-71-2 | 2-Isopropyl-3-methylnaphthalene | | 91 | 0.048 |
| 14879-13-1 | 1,3,5-trimethyl-2-prop-1-en-2-yl-benzene | | 90 | 0.048 |
| 767-59-9 | 1H-Indene, 1-methyl- | | 93 | 0.047 |
| 4175-54-6 | 1,4-dimethyltetralin | | 91 | 0.045 |
| 529-05-5 | Chamazulene | | 95 | 0.045 |
| 575-41-7 | Naphthalene, 1,3-dimethyl- | | 96 | 0.043 |
| 538-93-2 | Benzene, (2-methylpropyl)- | | 90 | 0.043 |
| 2765-18-6 | 1-propylnaphthalene | | 97 | 0.042 |
| 490-65-3 | Naphthalene, 1-methyl-7-(1-methylethyl)- | | 87 | 0.042 |
| 2613-76-5 | 1H-Indene, 2,3-dihydro-1,1,3-trimethyl- | | 95 | 0.042 |
| 2717-39-7 | 1,4,5,8-Tetramethylnaphthalene | | 94 | 0.042 |
| 4810-04-2 | Benzene, 1,3,5-trimethyl-2-propyl- | | 83 | 0.031 |
| 1000383-71-8 | 1,6-Dimethyl-3-ethylnaphthalene | | 90 | 0.029 |
| 42775-77-9 | 6-propyl-1,2,3,4-tetrahydronaphthalene | | 64 | 0.029 |
| 2245-38-7 | Naphthalene, 1,6,7-trimethyl- | | 96 | 0.028 |
| 4132-72-3 | Benzene, 1,4-dimethyl-2-(1-methylethyl)- | | 91 | 0.028 |
| 673-32-5 | Benzene, 1-propynyl- | | 93 | 0.024 |
| 30316-23-5 | 2,5,8-trimethyl-1,2-dihydronaphthalene | | 64 | 0.020 |
| 637-50-3 | Benzene, 1-propenyl- | | 76 | 0.018 |
| 6571-72-8 | 1a,2,7,7a-tetrahydro-1H-cyclopropa[b]naphthalene | | 87 | 0.017 |
| 14411-36-4 | Benzene, 1-(1,1-dimethylethyl)-3-ethyl- | | 64 | 0.017 |
| 941-81-1 | 4,6,8-Trimethylazulene | | 93 | 0.017 |
| 21893-51-6 | 1,5,8-trimethyltetralin | | 80 | 0.015 |
| 2039-89-6 | Benzene, 2-ethenyl-1,4-dimethyl- | | 94 | 0.015 |
| 2131-42-2 | Naphthalene, 1,4,6-trimethyl- | | 96 | 0.013 |
| 10836-11-7 | 2,3-Dimethylindene, 2,3-dihydro- | | 91 | 0.013 |
| 99-62-7 | Benzene, 1,3-bis(1-methylethyl)- | | 64 | 0.012 |
| 877-44-1 | Benzene, 1,2,4-triethyl- | | 90 | 0.011 |
| 6189-22-4 | Anthracene, 1,2,3,4,5,6-hexahydro- | | 92 | 0.010 |
| 581-40-8 | Naphthalene, 2,3-dimethyl- | | 93 | 0.010 |
| 56147-63-8 | 2-Ethyl-2,3-dihydro-1H-indene | | 87 | 0.010 |
| 148145-44-2 | 1,2,3,3a,8,9,9a,9b-Octahydrocyclopenta[def]phenanthrene | | 64 | 0.007 |
| 1000383-71-3 | 2-Isopropyl-7-methylnaphthalene | | 81 | 0.007 |
| Major Oxygenated Aromatics | | | | |
| 33223-84-6 | 2-Methylindan-2-ol | | 78 | 0.10 |
| Trace Oxygenated Aromatics | | | | |
| 20294-32-0 | 6-Methyl-4-indanol | | 83 | 0.093 |
| 34862-94-7 | 1-Penten-3-ol, 1-phenyl- | | 74 | 0.021 |
| 35322-84-0 | 3,4,7-trimethyl-2,3-dihydroinden-1-one | | 86 | 0.015 |
| Trace n-Alkenes | | | | |
| 109-67-1 | 1-Pentene | | 72 | 0.038 |
| 7688-21-3 | 2-Hexene, (Z)- | | 74 | 0.018 |

FIG. 18B-2 CONT

| CAS # | Compound Name | Br# | Q | Area% |
|---|---|---|---|---|
| | Trace Branched Alkenes | | | |
| 756-02-5 | 1,4-Pentadiene, 2,3,3-trimethyl- | 3 | 64 | 0.003 |
| 1000195-03-3 | 6,6-Dimethylhepta-2,4-diene | 2 | 86 | 0.032 |
| 10574-37-5 | 2-Pentene, 2,3-dimethyl- | 2 | 90 | 0.006 |
| 563-79-1 | 2-Butene, 2,3-dimethyl- | 2 | 72 | 0.021 |
| 3683-19-0 | (Z)-4-Methyl-2-hexene | 1 | 80 | 0.008 |
| 2738-19-4 | 2-Hexene, 2-methyl- | 1 | 72 | 0.015 |
| 816-79-5 | 2-Pentene, 3-ethyl- | 1 | 83 | 0.004 |
| 3404-55-5 | 4-Methyl-2-hexene, c&t | 1 | 78 | 0.004 |
| 922-61-2 | 2-Pentene, 3-methyl- | 1 | 95 | 0.038 |
| 691-38-3 | 2-Pentene, 4-methyl-, (Z)- | 1 | 90 | 0.023 |
| 763-29-1 | 1-Pentene, 2-methyl- | 1 | 88 | 0.010 |
| | Trace Cyclic Alkenes | | | |
| 65378-76-9 | 1,2,4,4-Tetramethylcyclopentene | | 83 | 0.009 |
| 473-91-6 | Cyclopentene, 1,2,3-trimethyl- | | 87 | 0.049 |
| 1453-24-3 | Cyclohexene, 1-ethyl- | | 78 | 0.006 |
| 503-45-7 | Cyclohexene, 3,3,5-trimethyl- | | 64 | 0.003 |
| 591-49-1 | Cyclohexene, 1-methyl- | | 87 | 0.018 |
| 694-35-9 | Cyclopentene, 3-ethyl- | | 72 | 0.008 |
| 34462-28-7 | Cyclopropane, trimethylmethylene- | | 90 | 0.051 |
| 2808-76-6 | 1,3-Dimethyl-1-cyclohexene | | 90 | 0.015 |
| 7459-71-4 | 3,5-Dimethylcyclopentene | | 80 | 0.025 |
| 110-83-8 | Cyclohexene | | 80 | 0.004 |
| 693-89-0 | Cyclopentene, 1-methyl- | | 87 | 0.034 |
| | Major n-Alkanes | | | |
| 110-54-3 | n-Hexane | | 91 | 0.25 |
| 142-82-5 | Heptane | | 95 | 0.13 |
| | Trace n-Alkanes | | | |
| 109-66-0 | Pentane | | 80 | 0.053 |
| 106-97-8 | Butane | | 80 | 0.007 |
| | Major Branched Alkanes | | | |
| 589-81-1 | Heptane, 3-methyl- | 1 | 83 | 0.28 |
| 592-27-8 | Heptane, 2-methyl- | 1 | 95 | 0.19 |
| 589-53-7 | Heptane, 4-methyl- | 1 | 91 | 0.18 |
| 589-34-4 | Hexane, 3-methyl- | 1 | 94 | 0.78 |
| 96-14-0 | Pentane, 3-methyl- | 1 | 91 | 0.54 |
| 107-83-5 | Pentane, 2-methyl- | 1 | 64 | 0.78 |
| | Trace Branched Alkanes | | | |
| 13150-81-7 | 2,6-Dimethyldecane | 2 | 64 | 0.055 |
| 565-59-3 | Pentane, 2,3-dimethyl- | 2 | 81 | 0.050 |
| 79-29-8 | Butane, 2,3-dimethyl- | 2 | 80 | 0.042 |
| 2216-34-4 | Octane, 4-methyl- | 1 | 91 | 0.063 |
| 78-78-4 | Butane, 2-methyl- | 1 | 94 | 0.058 |
| 75-28-5 | Isobutane | 1 | 72 | 0.009 |
| | Major Cyclic Alkanes | | | |
| 96-37-7 | Cyclopentane, methyl- | | 91 | 0.45 |
| 1638-26-2 | Cyclopentane, 1,1-dimethyl- | | 64 | 0.21 |
| 1192-18-3 | Cyclopentane, 1,2-dimethyl-, cis- | | 64 | 0.21 |
| 1640-89-7 | Cyclopentane, ethyl- | | 95 | 0.19 |
| 2452-99-5 | Cyclopentane, 1,2-dimethyl- | | 95 | 0.18 |
| 108-87-2 | Cyclohexane, methyl- | | 94 | 0.15 |
| 3726-47-4 | Cyclopentane, 1-ethyl-3-methyl- | | 78 | 0.13 |

FIG. 18B-2 CONT

| CAS # | Compound Name | Br# | Q | Area% |
|---|---|---|---|---|
| 2613-66-3 | Cyclopentane, 1-ethyl-3-methyl-, cis- | | 83 | 0.12 |
| 2207-03-6 | Cyclohexane, 1,3-dimethyl-, trans- | | 94 | 0.11 |
| 4850-28-6 | 1,2,4-Trimethylcyclopentane, cis, trans | | 91 | 0.11 |
| 4516-69-2 | Cyclopentane, 1,1,3-trimethyl- | | 83 | 0.11 |
| | Trace Cyclic Alkanes | | | |
| 6236-88-0 | Cyclohexane, 1-ethyl-4-methyl-, trans- | | 83 | 0.019 |
| 3728-55-0 | 1-Ethyl-3-methylcyclohexane (c,t) | | 72 | 0.010 |
| 1755-05-1 | Pentalene, octahydro-, cis- | | 87 | 0.020 |
| 930-89-2 | Cyclopentane, 1-ethyl-2-methyl-, cis- | | 78 | 0.037 |
| 18747-30-5 | Cyclopentane, 1-ethyl-1-methyl- | | 83 | 0.072 |
| 3726-46-3 | Cyclopentane, 1-ethyl-2-methyl- | | 94 | 0.068 |
| 638-04-0 | Cyclohexane, 1,3-dimethyl-, cis- | | 91 | 0.033 |
| 2613-69-6 | (1R,2s,3S)-1,2,3-Trimethylcyclopentane | | 68 | 0.015 |
| 2815-58-9 | Cyclopentane, 1,2,4-trimethyl- | | 86 | 0.056 |
| 2532-58-3 | Cyclopentane, 1,3-dimethyl-, cis- | | 91 | 0.082 |
| 17065-19-8 | Bicyclo[2.1.0]pentane, 1,4-dimethyl- | | 64 | 0.023 |
| 110-82-7 | Cyclohexane | | 91 | 0.019 |
| | Trace Oxygenates | | | |
| 2050-01-3 | 2-methylpropionic acid isoamyl ester | | 64 | 0.033 |

FIG. 18B-2 CONT

Catalyst: 0.5%Ru/HZSM-5

| Reaction conditions | | | Average #C | Product distribution (%) | | | |
|---|---|---|---|---|---|---|---|
| T (°C) | P (psig) | LFR (mL/min) | | Aromatics | Alkenes | Alkanes | Oxygenates |
| 350 | 500 | 0.1875 | 7.78 | 69.08 | 4.73 | 22.94 | 0.97 |

| CAS # | Compound Name | Rev | Q | Area% |
|---|---|---|---|---|
| | Major Aromatics Hydrocarbons | | | |
| 611-14-3 | Benzene, 1-ethyl-2-methyl- | | 95 | 14.76 |
| 108-88-3 | Toluene | | 91 | 10.27 |
| 95-47-6 | o-Xylene | | 95 | 9.81 |
| 95-63-6 | Benzene, 1,2,4-trimethyl- | | 95 | 5.33 |
| 106-42-3 | p-Xylene | | 95 | 5.10 |
| 108-38-3 | Benzene, 1,3-dimethyl- | | 95 | 4.13 |
| 100-41-4 | Ethylbenzene | | 91 | 4.04 |
| 874-41-9 | Benzene, 1-ethyl-2,4-dimethyl- | | 95 | 2.74 |
| 135-01-3 | Benzene, 1,2-diethyl- | | 96 | 1.94 |
| 934-74-7 | Benzene, 1-ethyl-3,5-dimethyl- | | 91 | 1.60 |
| 71-43-2 | Benzene | | 91 | 1.06 |
| 135-98-8 | Benzene, (1-methylpropyl)- | | 91 | 1.02 |
| 768-00-3 | Benzene, (1-methyl-1-propenyl)-, (E)- | | 90 | 0.89 |
| 527-84-4 | o-Cymene | | 91 | 0.63 |
| 582-16-1 | Naphthalene, 2,7-dimethyl- | | 97 | 0.61 |
| 91-57-6 | Naphthalene, 2-methyl- | | 94 | 0.54 |
| 108-67-8 | Mesitylene | | 91 | 0.47 |
| 103-65-1 | Benzene, propyl- | | 90 | 0.45 |
| 829-26-5 | Naphthalene, 2,3,6-trimethyl- | | 95 | 0.35 |
| 6682-71-9 | 1H-Indene, 2,3-dihydro-4,7-dimethyl- | | 94 | 0.34 |
| 13632-94-5 | Benzene, 1,4-diethyl-2-methyl- | | 94 | 0.28 |
| 2049-95-8 | Benzene, (1,1-dimethylpropyl)- | | 78 | 0.24 |
| 1595-16-0 | Benzene, 1-methyl-4-(1-methylpropyl)- | | 90 | 0.24 |
| 99-87-6 | p-Cymene | | 91 | 0.22 |
| 527-53-7 | Benzene, 1,2,3,5-tetramethyl- | | 90 | 0.22 |
| 97664-19-2 | 1-methyl-2-(1-methylallyl)benzene | | 90 | 0.18 |
| 98-82-8 | Benzene, (1-methylethyl)- | | 91 | 0.17 |
| 54758-36-0 | (1-Methylbuta-1,3-dienyl)benzene | | 90 | 0.17 |
| 1127-76-0 | 1-ethylnaphthalene | | 95 | 0.14 |
| 611-15-4 | Benzene, 1-ethenyl-2-methyl- | | 83 | 0.13 |
| 933-98-2 | Benzene, 1-ethyl-2,3-dimethyl- | | 91 | 0.13 |
| 1595-05-7 | Benzene, 1-methyl-4-butyl- | | 72 | 0.12 |
| 1680-51-9 | 6-Methyl-(1,2,3,4-tetrahydronaphthalene) | | 93 | 0.11 |
| | Trace Aromatic Hydrocarbons | | | |
| 767-60-2 | 1H-Indene, 3-methyl- | | 90 | 0.090 |
| 91-20-3 | Naphthalene | | 91 | 0.079 |
| 1758-88-6 | Benzene, 2,4-diethyl-1-methyl- | | 90 | 0.072 |
| 13065-07-1 | 2,7-dimethyltetralin | | 91 | 0.059 |
| 1074-55-1 | Benzene, 1-methyl-4-propyl- | | 72 | 0.050 |
| 70388-46-4 | (1-Methylenebut-2-enyl)benzene | | 90 | 0.045 |
| 581-42-0 | Naphthalene, 2,6-dimethyl- | | 94 | 0.036 |
| 54774-89-9 | 2-methyl-1-propyl-naphthalene | | 90 | 0.034 |
| 2870-04-4 | Benzene, 2-ethyl-1,3-dimethyl- | | 90 | 0.034 |
| 575-37-1 | Naphthalene, 1,7-dimethyl- | | 94 | 0.033 |
| 941-81-1 | 4,6,8-Trimethylazulene | | 94 | 0.031 |
| | Major n-Alkenes | | | |
| 627-20-3 | 2-Pentene, (Z)- | | 91 | 0.21 |
| 109-68-2 | 2-Pentene | | 91 | 0.11 |
| 4050-45-7 | 2-Hexene, (E)- | | 91 | 0.10 |
| | Trace n-Alkenes | | | |
| 109-67-1 | 1-Pentene | | 93 | 0.062 |

FIG. 18C-2 CONT

| CAS # | Compound Name | Br# | Q | Area% |
|---|---|---|---|---|
| 37050-04-7 | 3,4-Decadiene | | 64 | 0.049 |
| 7642-09-3 | 3-Hexene, (Z)- | | 91 | 0.043 |
| 5194-51-4 | 2,4-Hexadiene, (E,E)- | | 86 | 0.029 |
| 14686-13-6 | 2-Heptene, (E)- | | 91 | 0.014 |
| Major Branched Alkenes | | | | |
| 563-79-1 | 2-Butene, 2,3-dimethyl- | 2 | 91 | 0.13 |
| 922-61-2 | 2-Pentene, 3-methyl- | 1 | 94 | 0.25 |
| 674-76-0 | 2-Pentene, 4-methyl-, (E)- | 1 | 91 | 0.16 |
| 763-29-1 | 1-Pentene, 2-methyl- | 1 | 94 | 0.14 |
| 513-35-9 | 2-Butene, 2-methyl- | 1 | 90 | 0.81 |
| 563-46-2 | 2-Methyl-1-butene | 1 | 91 | 0.28 |
| 115-11-7 | 1-Propene, 2-methyl- | 1 | 91 | 0.79 |
| Trace Branched Alkenes | | | | |
| 768-02-5 | 1,4-Pentadiene, 2,3,3-trimethyl- | 3 | 83 | 0.015 |
| 1515-79-3 | 5,5-Dimethyl-1,3-hexadiene | 2 | 87 | 0.032 |
| 7145-20-2 | 2-Hexene, 2,3-dimethyl- | 2 | 64 | 0.016 |
| 10574-37-5 | 2-Pentene, 2,3-dimethyl- | 2 | 91 | 0.034 |
| 4181-65-3 | 2,4-Dimethyl 1,4-pentadiene | 2 | 64 | 0.011 |
| 28292-98-4 | 2-Pentene, 4,4-dimethyl- | 2 | 90 | 0.025 |
| 2213-32-3 | 1-Pentene, 2,4-dimethyl- | 2 | 72 | 0.013 |
| 816-79-5 | 2-Pentene, 3-ethyl- | 1 | 90 | 0.017 |
| 3899-36-3 | 3-Hexene, 3-methyl-, (E)- | 1 | 91 | 0.029 |
| 2738-19-4 | 2-Hexene, 2-methyl- | 1 | 90 | 0.071 |
| 4914-89-0 | 3-Hexene, 3-methyl-, (Z)- | 1 | 91 | 0.018 |
| 13151-17-2 | (Z)-Hex-2-ene, 5-methyl- | 1 | 76 | 0.012 |
| 3683-19-0 | (Z)-4-Methyl-2-hexene | 1 | 91 | 0.028 |
| 15840-60-5 | 3-Hexene, 2-methyl-, (Z)- | 1 | 91 | 0.012 |
| 625-27-4 | 2-Pentene, 2-methyl- | 1 | 91 | 0.039 |
| 760-20-3 | 1-Pentene, 3-methyl- | 1 | 94 | 0.029 |
| 691-38-3 | 2-Pentene, 4-methyl-, (Z)- | 1 | 90 | 0.004 |
| 563-45-1 | 1-Butene, 3-methyl- | 1 | 91 | 0.036 |
| Major Cyclic Alkenes | | | | |
| 473-91-6 | Cyclopentene, 1,2,3-trimethyl- | | 91 | 0.44 |
| 1528-22-9 | Cyclobutane, (1-methylethylidene)- | | 90 | 0.19 |
| 693-89-0 | Cyclopentene, 1-methyl- | | 90 | 0.15 |
| Trace Cyclic Alkenes | | | | |
| 6053-74-3 | 2a,4a,6a,6b-Tetrahydrocyclopenta[cd]pentalene | | 72 | 0.030 |
| 56324-66-4 | Cyclopentane, 2-ethylidene-1,1-dimethyl- | | 72 | 0.028 |
| 2808-79-9 | Cyclohexene, 1,4-dimethyl- | | 87 | 0.036 |
| 823-17-6 | Cyclohexene, 3,3-dimethyl- | | 78 | 0.042 |
| 19780-56-4 | Methyl ethyl cyclopentene | | 83 | 0.079 |
| 2146-38-5 | 1-Ethylcyclopentene | | 78 | 0.028 |
| 2808-76-6 | 1,3-Dimethyl-1-cyclohexene | | 90 | 0.034 |
| 1888-90-0 | 3-Methylenecyclohexene | | 83 | 0.003 |
| 85170-90-6 | Bicyclo[2.2.1]heptane, 2-(1-buten-3-yl)- | | 64 | 0.021 |
| 110-83-8 | Cyclohexene | | 74 | 0.015 |
| 1120-62-3 | Cyclopentene, 3-methyl- | | 86 | 0.014 |
| 142-29-0 | Cyclopentene | | 91 | 0.023 |
| Major n-Alkanes | | | | |
| 106-97-8 | Butane | | 87 | 1.89 |
| 109-66-0 | Pentane | | 91 | 1.63 |
| 110-54-3 | n-Hexane | | 91 | 0.74 |

FIG. 18C-2 CONT

| CAS # | Compound Name | Br# | Q | Area% |
|---|---|---|---|---|
| 74-98-6 | Propane | | 72 | 0.32 |
| 142-82-5 | Heptane | | 95 | 0.27 |
| Major Branched Alkanes | | | | |
| 79-29-8 | Butane, 2,3-dimethyl- | 2 | 91 | 0.16 |
| 589-81-1 | Heptane, 3-methyl- | 1 | 83 | 0.30 |
| 589-53-7 | Heptane, 4-methyl- | 1 | 93 | 0.16 |
| 592-27-8 | Heptane, 2-methyl- | 1 | 95 | 0.22 |
| 589-34-4 | Hexane, 3-methyl- | 1 | 87 | 0.93 |
| 96-14-0 | Pentane, 3-methyl- | 1 | 91 | 1.56 |
| 107-83-5 | Pentane, 2-methyl- | 1 | 74 | 2.84 |
| 78-78-4 | Butane, 2-methyl- | 1 | 91 | 4.98 |
| 75-28-5 | Isobutane | 1 | 72 | 2.83 |
| Trace Branched Alkanes | | | | |
| 921-47-1 | Hexane, 2,3,4-trimethyl- | 3 | 90 | 0.078 |
| 565-59-3 | Pentane, 2,3-dimethyl- | 2 | 86 | 0.058 |
| 589-43-5 | Hexane, 2,4-dimethyl- | 2 | 74 | 0.003 |
| 75-83-2 | Butane, 2,2-dimethyl- | 2 | 90 | 0.018 |
| Major Cyclic Alkanes | | | | |
| 96-37-7 | Cyclopentane, methyl- | | 91 | 1.09 |
| 2453-00-1 | Cyclopentane, 1,3-dimethyl- | | 90 | 0.66 |
| 1640-89-7 | Cyclopentane, ethyl- | | 95 | 0.28 |
| 108-87-2 | Cyclohexane, methyl- | | 94 | 0.21 |
| 17065-18-8 | Bicyclo[2.1.0]pentane, 1,4-dimethyl- | | 83 | 0.21 |
| 2452-99-5 | Cyclopentane, 1,2-dimethyl- | | 91 | 0.21 |
| 598-61-8 | Cyclobutane, methyl- | | 86 | 0.20 |
| 2613-66-3 | Cyclopentane, 1-ethyl-3-methyl-, cis- | | 83 | 0.18 |
| 2815-58-9 | Cyclopentane, 1,2,4-trimethyl- | | 90 | 0.17 |
| 2613-65-2 | Cyclopentane, 1-ethyl-3-methyl-, trans- | | 83 | 0.16 |
| 2207-03-6 | Cyclohexane, 1,3-dimethyl-, trans- | | 90 | 0.15 |
| 4516-69-2 | Cyclopentane, 1,1,3-trimethyl- | | 83 | 0.12 |
| 2532-58-3 | Cyclopentane, 1,3-dimethyl-, cis- | | 93 | 0.11 |
| Trace Cyclic Alkanes | | | | |
| 16747-50-5 | Cyclopentane, 1-ethyl-1-methyl- | | 64 | 0.079 |
| 930-89-2 | Cyclopentane, 1-ethyl-2-methyl-, cis- | | 91 | 0.083 |
| 589-90-2 | Cyclohexane, 1,4-dimethyl- | | 91 | 0.032 |
| Major Oxygenates | | | | |
| 74421-17-3 | Hexane, 1-(hexyloxy)-2-methyl- | | 72 | 0.80 |
| Trace Oxygenates | | | | |
| 40648-24-6 | 1-tert-butoxy-3-methyl-cyclohexene | | 64 | 0.062 |
| 630-19-3 | Propanal, 2,2-dimethyl- | | 78 | 0.008 |
| 107-87-9 | 2-Pentanone | | 83 | 0.010 |
| 78-93-3 | 2-Butanone | | 64 | 0.042 |
| 60-29-7 | Ethyl ether | | 91 | 0.015 |
| 67-64-1 | Acetone | | 90 | 0.035 |

FIG. 18C-2 CONT

Catalyst: 0.5%Pt-0.5%Sn/Al₂O₃

| Reaction conditions | | | Average #C | Product distribution (%) | | | |
|---|---|---|---|---|---|---|---|
| T (°C) | P (psig) | LFR (mL/min) | | Aromatics | Alkenes | Alkanes | Oxygenates |
| 350 | 500 | 0.125 | 9.2 | 44.16 | 0.51 | 32.32 | 0.3 |

| CAS # | Compound Name | Br# | Q | Area% |
|---|---|---|---|---|
| | Major Aromatics Hydrocarbons | | | |
| 106-42-3 | p-Xylene | | 95 | 5.09 |
| 100-41-4 | Ethylbenzene | | 91 | 3.97 |
| 108-38-3 | Benzene, 1,3-dimethyl- | | 95 | 3.66 |
| 1074-55-1 | Benzene, 1-methyl-4-propyl- | | 91 | 2.59 |
| 874-41-9 | Benzene, 1-ethyl-2,4-dimethyl- | | 95 | 2.58 |
| 611-14-3 | Benzene, 1-ethyl-2-methyl- | | 95 | 2.58 |
| 95-63-6 | Benzene, 1,2,4-trimethyl- | | 91 | 2.45 |
| 108-88-3 | Toluene | | 91 | 2.13 |
| 141-93-5 | Benzene, 1,3-diethyl- | | 97 | 1.45 |
| 104-51-8 | Benzene, n-butyl- | | 91 | 1.35 |
| 1595-05-7 | Benzene, 1-methyl-4-butyl | | 87 | 1.24 |
| 1074-17-5 | Benzene, 1-methyl-2-propyl- | | 93 | 1.10 |
| 1758-88-9 | Benzene, 2-ethyl-1,4-dimethyl- | | 95 | 1.10 |
| 103-65-1 | Benzene, propyl- | | 87 | 1.06 |
| 55669-88-0 | 1,4-dimethyl-2-(2-methylpropyl)benzene | | 76 | 0.86 |
| 5161-04-6 | Benzene, 1-methyl-4-(2-methylpropyl)- | | 64 | 0.78 |
| 1587-04-8 | Benzene, 1-methyl-2-(2-propenyl)- | | 78 | 0.69 |
| 1758-85-6 | Benzene, 2,4-diethyl-1-methyl- | | 97 | 0.59 |
| 768-49-0 | Benzene, (2-methyl-1-propenyl)- | | 86 | 0.58 |
| 874-35-1 | 1H-Indene, 2,3-dihydro-5-methyl- | | 64 | 0.57 |
| 54340-86-2 | 4-[(E)-but-2-enyl]-1,2-dimethyl-benzene | | 94 | 0.49 |
| 90-12-0 | Naphthalene, 1-methyl- | | 91 | 0.41 |
| 108-67-8 | Mesitylene | | 95 | 0.35 |
| 97664-19-2 | 1-methyl-2-(1-methylallyl)benzene | | 91 | 0.32 |
| 582-16-1 | Naphthalene, 2,7-dimethyl- | | 95 | 0.30 |
| 1595-16-0 | Benzene, 1-methyl-4-(1-methylpropyl)- | | 87 | 0.28 |
| 13556-58-6 | Naphthalene, 1-ethyl-1,2,3,4-tetrahydro- | | 91 | 0.27 |
| 4175-54-6 | 1,4-dimethyltetralin | | 64 | 0.26 |
| 496-11-7 | Indane | | 81 | 0.24 |
| 91-20-3 | Naphthalene | | 90 | 0.24 |
| 22531-20-0 | Naphthalene, 6-ethyl-1,2,3,4-tetrahydro- | | 93 | 0.23 |
| 54340-85-1 | Benzene, 1-(2-butenyl)-2,3-dimethyl- | | 94 | 0.20 |
| 571-58-4 | Naphthalene, 1,4-dimethyl- | | 97 | 0.18 |
| 71-43-2 | Benzene | | 91 | 0.17 |
| 483-78-3 | 1,6-dimethyl-4-propan-2-yl-naphthalene | | 96 | 0.17 |
| 135-01-3 | Benzene, 1,2-diethyl- | | 91 | 0.16 |
| 829-26-5 | Naphthalene, 2,3,6-trimethyl- | | 95 | 0.15 |
| 529-05-5 | Chamazulene | | 83 | 0.15 |
| 135-98-8 | Benzene, (1-methylpropyl)- | | 74 | 0.14 |
| 2027-17-0 | Naphthalene, 2-(1-methylethyl)- | | 87 | 0.13 |
| 622-96-8 | Benzene, 1-ethyl-4-methyl- | | 91 | 0.12 |
| 1127-76-0 | 1-ethylnaphthalene | | 96 | 0.12 |
| 4810-04-2 | Benzene, 1,3,5-trimethyl-2-propyl- | | 87 | 0.12 |
| 17059-48-2 | 1H-Indene, 2,3-dihydro-1,6-dimethyl- | | 91 | 0.11 |
| 33830-85-7 | (4,5,5-trimethylcyclopenta-1,3-dien-1-yl)benzene | | 90 | 0.11 |
| 53172-84-2 | Benzene, (1-methyl-1-butenyl)- | | 91 | 0.10 |
| 573-98-8 | Naphthalene, 1,2-dimethyl- | | 70 | 0.10 |
| | Trace Aromatic Hydrocarbons | | | |
| 42775-75-7 | Naphthalene, 5-ethyl-1,2,3,4-tetrahydro- | | 64 | 0.093 |
| 475-03-6 | Naphthalene, tetrahydro-1,1,6-trimethyl- | | 90 | 0.093 |
| 2245-38-7 | Naphthalene, 1,6,7-trimethyl- | | 98 | 0.092 |

FIG. 19A-2 CONT

| CAS # | Compound Name | Br# | Q | Area% |
|---|---|---|---|---|
| 10222-95-4 | 1,2,4-trimethyl-5-propan-2-yl-benzene | | 72 | 0.091 |
| 68253-04-6 | Benzene, (2-methyl-1-butenyl)- | | 64 | 0.083 |
| 1000383-71-7 | 4-ethyl-1,6-dimethyl-naphthalene | | 87 | 0.077 |
| 1000383-71-4 | 3-Isopropyl-1-methylnaphthalene | | 87 | 0.077 |
| 527-53-7 | Benzene, 1,2,3,5-tetramethyl- | | 64 | 0.074 |
| 769-25-5 | Benzene, 2-ethenyl-1,3,5-trimethyl- | | 83 | 0.074 |
| 483-77-2 | Cadina-1,3,5-triene | | 91 | 0.069 |
| 30316-36-0 | 1,6,8-trimethyltetralin | | 90 | 0.066 |
| 1000187-78-5 | 3-(2-Methyl-propenyl)-1H-indene | | 90 | 0.063 |
| 3031-15-0 | Naphthalene, 1,2,3,4-tetramethyl- | | 91 | 0.052 |
| 21693-54-9 | 5,7-dimethyltetralin | | 64 | 0.050 |
| 40650-41-7 | 1H-Indene, 2,3-dihydro-1,1,5-trimethyl- | | 86 | 0.050 |
| 489-84-9 | Azulene, 1,4-dimethyl-7-(1-methylethyl)- | | 93 | 0.050 |
| 490-65-3 | Naphthalene, 1-methyl-7-(1-methylethyl)- | | 86 | 0.046 |
| 19063-11-7 | 5,6,7,8-tetramethyltetralin | | 86 | 0.044 |
| 622-78-4 | Benzene, 1-butynyl- | | 87 | 0.043 |
| 1078-04-2 | 3,3,4,7-tetramethyl-1,2-dihydroindene | | 64 | 0.035 |
| 21693-55-0 | 1,5,7-trimethyltetralin | | 86 | 0.034 |
| 612-75-9 | 3,3'-Dimethylbiphenyl | | 91 | 0.032 |
| 941-81-1 | 4,6,8-Trimethylazulene | | 78 | 0.032 |
| 4773-83-5 | 1,2,3-Trimethylindene | | 80 | 0.029 |
| 19781-34-1 | 3-Ethyl-3-phenyl-1-pentene | | 64 | 0.026 |
| 526-73-8 | Benzene, 1,2,3-trimethyl- | | 64 | 0.026 |
| 2717-39-7 | 1,4,5,8-Tetramethylnaphthalene | | 78 | 0.025 |
| 1000383-71-8 | 1,6-Dimethyl-3-ethylnaphthalene | | 91 | 0.025 |
| 18204-67-4 | 3,3,5,6,7-pentamethyl-1,2-dihydroindene | | 70 | 0.025 |
| 1000374-05-7 | 1,4-di-iso-propylnaphthalene | | 64 | 0.011 |
| Major Oxygenated Aromatics |||||
| 105-67-9 | Phenol, 2,4-dimethyl- | | 89 | 0.24 |
| 108-68-9 | Phenol, 3,5-dimethyl- | | 90 | 0.10 |
| Trace Oxygenated Aromatics |||||
| 526-75-0 | Phenol, 2,3-dimethyl- | | 94 | 0.076 |
| 1887-64-5 | Phenol, 2-ethyl-6-methyl- | | 87 | 0.053 |
| 6148-37-4 | Furan, 4-methyl-2-propyl- | | 72 | 0.033 |
| Trace n-Alkenes |||||
| 7433-56-9 | 5-Decene, (E)- | | 62 | 0.038 |
| 19689-19-1 | 5-Decene | | 78 | 0.027 |
| 592-78-9 | 3-Heptene | | 83 | 0.013 |
| 10405-85-3 | trans-4-Nonene | | 78 | 0.013 |
| 14850-23-8 | 4-Octene, (E)- | | 83 | 0.012 |
| 872-05-9 | 1-Decene | | 64 | 0.011 |
| 14850-22-7 | 3-Octene, (Z)- | | 90 | 0.008 |
| Major Branched Alkenes |||||
| 7145-23-5 | 3-Hexene, 2,3-dimethyl- | 2 | 64 | 0.25 |
| Trace Branched Alkenes |||||
| 764-13-6 | 2,4-Hexadiene, 2,5-dimethyl- | 2 | 87 | 0.034 |
| 598-37-2 | 1-Butene, 3,3-dimethyl- | 2 | 80 | 0.002 |
| 922-61-2 | 2-Pentene, 3-methyl- | 1 | 91 | 0.003 |
| 616-12-6 | 2-Pentene, 3-methyl-, (E)- | 1 | 72 | 0.003 |
| Trace Cyclic Alkenes |||||
| 19780-56-4 | Methyl ethyl cyclopentene | | 87 | 0.038 |
| 2808-71-1 | Cyclohexene, 3-ethyl- | | 64 | 0.062 |

FIG. 19A-2 CONT

| CAS # | Compound Name | Br# | Q | Area% |
|---|---|---|---|---|
| | Major n-Alkanes | | | |
| 111-84-2 | Nonane | | 95 | 4.31 |
| 142-82-5 | Heptane | | 95 | 2.34 |
| 124-18-5 | Decane | | 95 | 2.00 |
| 1120-21-4 | Undecane | | 91 | 1.27 |
| 110-54-3 | n-Hexane | | 91 | 1.23 |
| 112-40-3 | Dodecane | | 78 | 0.31 |
| 109-66-0 | Pentane | | 90 | 0.30 |
| 629-50-5 | Tridecane | | 89 | 0.22 |
| | Trace n-Alkanes | | | |
| 106-97-8 | Butane | | 80 | 0.056 |
| | Major Branched Alkanes | | | |
| 20278-89-1 | Heptane, 3,4,5-trimethyl- | 3 | 72 | 2.22 |
| 15869-94-0 | Octane, 3,6-dimethyl- | 2 | 78 | 1.12 |
| 17302-28-2 | Nonane, 2,6-dimethyl- | 2 | 72 | 0.24 |
| 2213-23-2 | Heptane, 2,4-dimethyl- | 2 | 64 | 0.26 |
| 589-43-5 | Hexane, 2,4-dimethyl- | 2 | 94 | 5.88 |
| 1002-43-3 | Undecane, 3-methyl- | 1 | 70 | 0.34 |
| 13151-35-4 | Decane, 5-methyl- | 1 | 72 | 0.11 |
| 871-83-0 | Nonane, 2-methyl- | 1 | 90 | 0.25 |
| 17301-94-9 | Nonane, 4-methyl- | 1 | 74 | 0.36 |
| 15869-85-9 | Nonane, 5-methyl- | 1 | 87 | 0.51 |
| 13287-21-3 | Tridecane, 6-methyl- | 1 | 90 | 0.61 |
| 2216-33-3 | Octane, 3-methyl- | 1 | 87 | 0.57 |
| 3221-61-2 | Octane, 2-methyl- | 1 | 94 | 0.15 |
| 2216-32-2 | Heptane, 4-ethyl- | 1 | 72 | 0.16 |
| 619-99-8 | Hexane, 3-ethyl- | 1 | 94 | 0.51 |
| 589-53-7 | Heptane, 4-methyl- | 1 | 91 | 0.26 |
| 592-27-8 | Heptane, 2-methyl- | 1 | 94 | 0.24 |
| 589-34-4 | Hexane, 3-methyl- | 1 | 83 | 0.18 |
| 96-14-0 | Pentane, 3-methyl- | 1 | 91 | 0.29 |
| | Trace Branched Alkanes | | | |
| 15869-93-9 | Octane, 3,5-dimethyl- | 2 | 83 | 0.040 |
| 922-28-1 | Heptane, 3,4-dimethyl- | 2 | 78 | 0.031 |
| 2216-30-0 | Heptane, 2,5-dimethyl- | 2 | 74 | 0.039 |
| 583-48-2 | Hexane, 3,4-dimethyl- | 2 | 83 | 0.081 |
| 15869-96-2 | Octane, 4,5-dimethyl- | 2 | 64 | 0.081 |
| 565-59-3 | Pentane, 2,3-dimethyl- | 2 | 74 | 0.022 |
| 2847-72-5 | Decane, 4-methyl- | 1 | 93 | 0.090 |
| 591-76-4 | Hexane, 2-methyl- | 1 | 91 | 0.052 |
| 107-83-5 | Pentane, 2-methyl- | 1 | 72 | 0.048 |
| 78-78-4 | Butane, 2-methyl- | 1 | 83 | 0.018 |
| | Major Cyclic Alkanes | | | |
| 3726-47-4 | Cyclopentane, 1-ethyl-3-methyl- | | 76 | 2.14 |
| 2040-96-2 | Cyclopentane, propyl- | | 81 | 0.73 |
| 13152-02-8 | Cyclooctane, ethyl- | | 64 | 0.57 |
| 930-89-2 | Cyclopentane, 1-ethyl-2-methyl-, cis- | | 95 | 0.56 |
| 3741-00-2 | Cyclopentane, pentyl- | | 93 | 0.22 |
| 61141-80-8 | Cyclohexane, 1,2-diethyl-3-methyl- | | 64 | 0.20 |
| 61142-68-5 | Cyclopentane, 1-hexyl-3-methyl- | | 94 | 0.16 |
| 96-37-7 | Cyclopentane, methyl- | | 91 | 0.13 |

FIG. 19A-2 CONT

| CAS # | Compound Name | Br# | Q | Area% |
|---|---|---|---|---|
| Trace Cyclic Alkanes | | | | |
| 72993-32-9 | Cyclopentane, 1-butyl-2-ethyl- | | 62 | 0.046 |
| 7058-05-1 | Cyclohexane, 1-ethyl-2,3-dimethyl- | | 60 | 0.052 |
| 7045-67-2 | Cyclohexane, 2-ethyl-1,3-dimethyl- | | 72 | 0.019 |
| 2040-95-1 | Cyclopentane, butyl- | | 96 | 0.095 |
| 53366-38-4 | Cyclopentane, (2-methylbutyl)- | | 76 | 0.048 |
| 4926-90-3 | Cyclohexane, 1-ethyl-1-methyl- | | 78 | 0.012 |
| 4923-78-8 | Cyclohexane, 1-ethyl-2-methyl-, trans- | | 91 | 0.040 |
| 694-72-4 | Pentalene, octahydro- | | 60 | 0.062 |
| 583-57-3 | Cyclohexane, 1,2-dimethyl- (cis/trans) | | 91 | 0.015 |
| 6876-23-9 | Cyclohexane, 1,2-dimethyl-, trans- | | 91 | 0.047 |
| 624-29-3 | Cyclohexane, 1,4-dimethyl-, cis- | | 91 | 0.034 |
| 2815-69-6 | (1R,2s,3S)-1,2,3-Trimethylcyclopentane | | 91 | 0.038 |
| 2815-57-8 | Cyclopentane, 1,2,3-trimethyl- | | 78 | 0.040 |
| 2815-58-9 | Cyclopentane, 1,2,4-trimethyl- | | 91 | 0.017 |
| 1640-89-7 | Cyclopentane, ethyl- | | 95 | 0.097 |
| 108-87-2 | Cyclohexane, methyl- | | 94 | 0.040 |
| 1192-18-3 | Cyclopentane, 1,2-dimethyl-, cis- | | 78 | 0.015 |
| 2452-99-5 | Cyclopentane, 1,2-dimethyl- | | 94 | 0.023 |
| 1759-58-6 | Cyclopentane, 1,3-dimethyl-, trans- | | 72 | 0.017 |
| 2453-00-1 | Cyclopentane, 1,3-dimethyl- | | 83 | 0.020 |
| 110-82-7 | Cyclohexane | | 90 | 0.006 |
| Major Oxygenates | | | | |
| 7212-53-5 | 5-Methyl-1-heptanol | | 72 | 0.20 |
| Trace Oxygenates | | | | |
| 28450-02-4 | 3,4-Dihydro-6-methyl-2-acetyl-2H-pyran | | 64 | 0.035 |
| 1000309-31-2 | Oxalic acid, cyclohexyl decyl ester | | 64 | 0.043 |
| 2308-18-1 | Acetoacetic acid isoamyl ester | | 78 | 0.018 |
| 584-02-1 | 3-Pentanol | | 78 | 0.006 |

FIG. 19A-2 CONT

Catalyst: 0.5%Pt-0.5%Sn/Al$_2$O$_3$

| Reaction conditions | | | Average #C | Product distribution (%) | | | |
|---|---|---|---|---|---|---|---|
| T (°C) | P (psig) | LFR (mL/min) | | Aromatics | Alkenes | Alkanes | Oxygenates |
| 350 | 500 | 0.1875 | 7.11 | 25.59 | 10.97 | 53.03 | 0.86 |

| CAS # | Compound Name | Br# | Q | Area% |
|---|---|---|---|---|
| | Major Aromatics Hydrocarbons | | | |
| 108-38-3 | Benzene, 1,3-dimethyl- | | 95 | 5.03 |
| 95-47-6 | o-Xylene | | 95 | 3.03 |
| 108-88-3 | Toluene | | 91 | 2.65 |
| 71-43-2 | Benzene | | 91 | 2.18 |
| 1074-55-1 | Benzene, 1-methyl-4-propyl- | | 93 | 1.96 |
| 874-41-9 | Benzene, 1-ethyl-2,4-dimethyl- | | 95 | 1.18 |
| 611-14-3 | Benzene, 1-ethyl-2-methyl- | | 94 | 1.03 |
| 1758-88-9 | Benzene, 2-ethyl-1,4-dimethyl- | | 95 | 0.95 |
| 620-14-4 | Benzene, 1-ethyl-3-methyl- | | 91 | 0.95 |
| 104-51-8 | Benzene, n-butyl- | | 91 | 0.71 |
| 141-93-5 | Benzene, 1,3-diethyl- | | 97 | 0.60 |
| 103-65-1 | Benzene, propyl- | | 90 | 0.54 |
| 768-00-3 | Benzene, (1-methyl-1-propenyl)-, (E)- | | 76 | 0.33 |
| 22531-20-0 | Naphthalene, 6-ethyl-1,2,3,4-tetrahydro- | | 87 | 0.23 |
| 13632-94-5 | Benzene, 1,4-diethyl-2-methyl- | | 94 | 0.22 |
| 55669-88-0 | 1,4-dimethyl-2-(2-methylpropyl)benzene | | 87 | 0.21 |
| 6682-06-0 | 1H-Indene, 2,3-dihydro-4,5,7-trimethyl- | | 91 | 0.20 |
| 106-42-3 | p-Xylene | | 91 | 0.20 |
| 4810-04-2 | Benzene, 1,3,5-trimethyl-2-propyl- | | 80 | 0.16 |
| 575-41-7 | Naphthalene, 1,3-dimethyl- | | 70 | 0.15 |
| 4175-54-6 | 1,4-dimethyltetralin | | 62 | 0.14 |
| 90-12-0 | Naphthalene, 1-methyl- | | 86 | 0.14 |
| 582-16-1 | Naphthalene, 2,7-dimethyl- | | 93 | 0.13 |
| 526-73-8 | Benzene, 1,2,3-trimethyl- | | 87 | 0.12 |
| 10222-95-4 | 1,2,4-trimethyl-5-propan-2-yl-benzene | | 64 | 0.11 |
| 91-20-3 | Naphthalene | | 90 | 0.10 |
| | Trace Aromatic Hydrocarbons | | | |
| 4489-84-3 | Benzene, (3-methyl-2-butenyl)- | | 87 | 0.100 |
| 1074-43-7 | Benzene, 1-methyl-3-propyl- | | 86 | 0.096 |
| 2131-42-2 | Naphthalene, 1,4,6-trimethyl- | | 87 | 0.070 |
| 1127-76-0 | 1-ethylnaphthalene | | 93 | 0.063 |
| 57693-77-3 | Ethyltetramethylcyclopentadiene | | 72 | 0.042 |
| | Major Oxygenated Aromatics | | | |
| 108-68-9 | Phenol, 3,5-dimethyl- | | 94 | 0.26 |
| 88-69-7 | 2-propan-2-ylphenol | | 81 | 0.17 |
| 6148-37-4 | Furan, 4-methyl-2-propyl- | | 72 | 0.14 |
| 1000364-49-1 | 4-Methylbenzyl alcohol, methyl ether | | 74 | 0.11 |
| 620-17-7 | Phenol, 3-ethyl- | | 83 | 0.11 |
| | Trace Oxygenated Aromatics | | | |
| 618-45-1 | Phenol, 3-(1-methylethyl)- | | 91 | 0.087 |
| 1197-34-8 | Phenol, 3,5-diethyl- | | 81 | 0.083 |
| 90-00-6 | Phenol, 2-ethyl- | | 91 | 0.079 |
| 876-20-0 | 2,5-Diethylphenol | | 83 | 0.051 |
| 3855-26-3 | Phenol, 3-ethyl-4-methyl- | | 91 | 0.042 |
| 2944-49-2 | 2,3-Dimethylanisole | | 90 | 0.041 |
| | Major n-Alkenes | | | |
| 4050-45-7 | 2-Hexene, (E)- | | 91 | 0.70 |
| 592-47-2 | 3-Hexene | | 95 | 0.49 |
| 592-77-8 | 2-Heptene | | 96 | 0.39 |
| 646-04-8 | 2-Pentene, (E)- | | 91 | 0.37 |
| 7642-09-3 | 3-Hexene, (Z)- | | 91 | 0.36 |

FIG. 19B-2 CONT

| CAS # | Compound Name | Br# | Q | Area% |
|---|---|---|---|---|
| 14686-14-7 | 3-Heptene, (E)- | | 95 | 0.35 |
| 7642-10-6 | (Z)-3-Heptene | | 96 | 0.27 |
| 627-20-3 | 2-Pentene, (Z)- | | 91 | 0.20 |
| 14850-23-8 | 4-Octene, (E)- | | 87 | 0.17 |
| 592-41-6 | 1-Hexene | | 91 | 0.13 |
| 2198-23-4 | 4-Nonene | | 91 | 0.11 |
| Trace n-Alkenes | | | | |
| 106-98-9 | 1-Butene | | 90 | 0.083 |
| 109-67-1 | 1-Pentene | | 87 | 0.080 |
| 20063-92-7 | 3-Nonene, (E)- | | 94 | 0.066 |
| 14919-01-8 | 3-Octene, (E)- | | 97 | 0.058 |
| 7642-04-8 | 2-Octene, (Z)- | | 95 | 0.057 |
| 6434-77-1 | cis-2-Nonene | | 95 | 0.052 |
| 592-76-7 | 1-Heptene | | 94 | 0.037 |
| 2004-70-8 | 1,3-Pentadiene, (E)- | | 80 | 0.002 |
| Major Branched Alkenes | | | | |
| 21293-02-7 | 3,5-Octadiene, 4,5-diethyl-, (E,Z)- | 2 | 76 | 0.12 |
| 6874-39-1 | (2E,4E)-3,7-Dimethyl-2,4-octadiene | 2 | 62 | 0.20 |
| 1000374-08-4 | (2Z,4E)-3,7-Dimethyl-2,4-octadiene | 2 | 72 | 0.15 |
| 1000195-03-3 | 6,6-Dimethylhepta-2,4-diene | 2 | 64 | 0.13 |
| 19780-67-7 | 2-Pentene, 3-ethyl-2-methyl- | 2 | 86 | 0.14 |
| 3404-75-9 | 2-Heptene, 3-methyl- | 1 | 91 | 0.23 |
| 2080-89-9 | 1,4-Hexadiene, 3-ethyl- | 1 | 72 | 0.52 |
| 10374-36-4 | 2-Hexene, 3-methyl-, (Z)- | 1 | 87 | 0.16 |
| 3404-65-7 | 3-Methyl-3-hexene | 1 | 91 | 0.39 |
| 922-61-2 | 2-Pentene, 3-methyl- | 1 | 94 | 2.00 |
| 674-76-0 | 2-Pentene, 4-methyl-, (E)- | 1 | 91 | 0.17 |
| 513-35-9 | 2-Butene, 2-methyl- | 1 | 90 | 9.45 |
| 563-46-2 | 2-Methyl-1-butene | 1 | 91 | 0.13 |
| 115-11-7 | 1-Propene, 2-methyl- | 1 | 93 | 9.26 |
| Trace Branched Alkenes | | | | |
| 13427-43-5 | 1-Hexene, 3,3,5-trimethyl- | 3 | 72 | 0.028 |
| 4834-87-1 | 2,4-Heptadiene, 2,6-dimethyl- | 2 | 72 | 0.040 |
| 14255-23-3 | 2-Hexene, 2,4-dimethyl- | 2 | 80 | 0.034 |
| 6196-80-7 | 1-Pentene, 3-ethyl-3-methyl- | 2 | 72 | 0.018 |
| 563-79-1 | 2-Butene, 2,3-dimethyl- | 2 | 91 | 0.040 |
| 74764-46-8 | 3-Heptene, 3-ethyl- | 1 | 72 | 0.048 |
| 4485-16-9 | 3-Heptene, 4-methyl- | 1 | 91 | 0.049 |
| 1632-16-2 | 3-Ethyl-2-hexene(c,t) | 1 | 91 | 0.053 |
| 3404-55-5 | 4-Methyl-2-hexene c&t | 1 | 91 | 0.064 |
| 15840-60-5 | 3-Hexene, 2-methyl-, (Z)- | 1 | 91 | 0.017 |
| 625-27-4 | 2-Pentene, 2-methyl- | 1 | 80 | 0.012 |
| 760-20-3 | 1-Pentene, 3-methyl- | 1 | 91 | 0.087 |
| 563-45-1 | 1-Butene, 3-methyl- | 1 | 83 | 0.010 |
| Major Cyclic Alkenes | | | | |
| 2808-71-1 | Cyclohexene, 3-ethyl- | | 78 | 0.60 |
| 53366-54-4 | Cyclopentane, (2-methylbutylidene)- | | 78 | 0.40 |
| 1120-62-3 | Cyclopentene, 3-methyl- | | 91 | 0.32 |
| 19780-56-4 | Methyl ethyl cyclopentene | | 91 | 0.31 |
| 61142-33-4 | 1,4-dimethyl-3-propan-2-yl-cyclopentene | | 80 | 0.10 |
| Trace Cyclic Alkenes | | | | |
| 3633-80-9 | Bicyclo[2.2.1]heptane, 2-(2-propenyl)- | | 64 | 0.055 |

FIG. 19B-2 CONT

| CAS # | Compound Name | Br# | Q | Area% |
|---|---|---|---|---|
| 34564-56-3 | 3-Methylenecycloheptene | | 72 | 0.013 |
| 2808-80-2 | Cyclohexane, 1-methyl-4-methylene- | | 72 | 0.020 |
| 97797-57-4 | 1-Ethyl-5-methylcyclopentene | | 87 | 0.071 |
| 2146-38-5 | 1-Ethylcyclopentene | | 74 | 0.038 |
| 3664-56-0 | 1,3,3-Trimethylcyclopropene | | 91 | 0.024 |
| Major n-Alkanes | | | | |
| 110-54-3 | n-Hexane | | 91 | 13.33 |
| 106-97-8 | Butane | | 87 | 8.13 |
| 109-66-0 | Pentane | | 91 | 5.71 |
| 111-65-9 | Octane | | 64 | 4.46 |
| 142-82-5 | Heptane | | 95 | 4.17 |
| 111-84-2 | Nonane | | 95 | 1.43 |
| 124-18-5 | Decane | | 93 | 0.87 |
| 1120-21-4 | Undecane | | 94 | 0.43 |
| 112-40-3 | Dodecane | | 86 | 0.18 |
| 74-98-6 | Propane | | 90 | 0.14 |
| 629-50-5 | Tridecane | | 91 | 0.12 |
| Major Branched Alkanes | | | | |
| 49822-18-6 | Decane, 3,3,4-trimethyl- | 3 | 78 | 0.17 |
| 5911-04-6 | Nonane, 3-methyl- | 1 | 81 | 0.33 |
| 15869-85-9 | Nonane, 5-methyl- | 1 | 72 | 0.18 |
| 2216-33-3 | Octane, 3-methyl- | 1 | 64 | 0.21 |
| 15869-80-4 | Heptane, 3-ethyl- | 1 | 83 | 0.12 |
| 619-99-8 | Hexane, 3-ethyl- | 1 | 87 | 0.34 |
| 589-81-1 | Heptane, 3-methyl- | 1 | 83 | 1.39 |
| 592-27-8 | Heptane, 2-methyl- | 1 | 87 | 0.16 |
| 588-34-4 | Hexane, 3-methyl- | 1 | 87 | 0.53 |
| 591-76-4 | Hexane, 2-methyl- | 1 | 91 | 0.22 |
| 96-14-0 | Pentane, 3-methyl- | 1 | 91 | 2.72 |
| 78-78-4 | Butane, 2-methyl- | 1 | 91 | 0.80 |
| Trace Branched Alkanes | | | | |
| 589-43-5 | Hexane, 2,4-dimethyl- | 2 | 64 | 0.018 |
| 565-59-3 | Pentane, 2,3-dimethyl- | 2 | 64 | 0.087 |
| 79-29-8 | Butane, 2,3-dimethyl- | 2 | 78 | 0.006 |
| 5881-17-4 | Octane, 3-ethyl- | 1 | 72 | 0.056 |
| 2216-34-4 | Octane, 4-methyl- | 1 | 91 | 0.081 |
| 75-28-5 | Isobutane | 1 | 72 | 0.055 |
| Major Cyclic Alkanes | | | | |
| 3726-47-4 | Cyclopentane, 1-ethyl-3-methyl- | | 83 | 1.38 |
| 96-37-7 | Cyclopentane, methyl- | | 94 | 1.34 |
| 2613-66-3 | Cyclopentane, 1-ethyl-3-methyl-, cis- | | 72 | 0.93 |
| 2040-96-2 | Cyclopentane, propyl- | | 81 | 0.65 |
| 61142-68-3 | Cyclopentane, 1-hexyl-3-methyl- | | 72 | 0.31 |
| 930-89-2 | Cyclopentane, 1-ethyl-2-methyl-, cis- | | 97 | 0.23 |
| 1640-89-7 | Cyclopentane, ethyl- | | 97 | 0.20 |
| 110-82-7 | Cyclohexane | | 93 | 0.19 |
| 2532-58-3 | Cyclopentane, 1,3-dimethyl-, cis- | | 91 | 0.15 |
| 108-87-2 | Cyclohexane, methyl- | | 94 | 0.13 |
| 3741-00-2 | Cyclopentane, pentyl- | | 64 | 0.13 |
| 932-40-1 | trans-1,2-Diethyl cyclopentane | | 64 | 0.10 |
| Trace Cyclic Alkanes | | | | |
| 62199-50-2 | Cyclopentane, 1-butyl-2-propyl- | | 62 | 0.082 |

FIG. 19B-2 CONT

| CAS # | Compound Name | Br # | Q | Area % |
|---|---|---|---|---|
| 41977-37-1 | Cyclopropane, 1-methyl-2-pentyl- | | 70 | 0.041 |
| 6236-88-0 | Cyclohexane, 1-ethyl-4-methyl-, trans- | | 80 | 0.029 |
| 4126-78-7 | Cycloheptane, methyl- | | 64 | 0.039 |
| 18747-30-5 | Cyclopentane, 1-ethyl-1-methyl- | | 74 | 0.036 |
| 19341-98-1 | Cyclobutane, 1,2-diethyl-, trans- | | 80 | 0.007 |
| 624-29-3 | Cyclohexane, 1,4-dimethyl-, cis- | | 90 | 0.043 |
| 1192-18-3 | Cyclopentane, 1,2-dimethyl-, cis- | | 78 | 0.025 |
| 2453-00-1 | Cyclopentane, 1,3-dimethyl- | | 90 | 0.053 |
| 1003-19-8 | Cyclopropane, 1,1-diethyl- | | 81 | 0.010 |
| 598-61-8 | Cyclobutane, methyl- | | 90 | 0.071 |
| 185-94-4 | Bicyclo[2.1.0]pentane | | 83 | 0.004 |
| Major Oxygenates | | | | |
| 107-87-9 | 2-Pentanone | | 87 | 0.37 |
| Trace Oxygenates | | | | |
| 5910-87-2 | 2,4-Nonadienal, (E,E)- | | 80 | 0.079 |
| 15726-15-5 | 4-Heptanone, 3-methyl- | | 90 | 0.051 |
| 630-19-3 | Propanal, 2,2-dimethyl- | | 83 | 0.010 |
| 78-93-3 | 2-Butanone | | 78 | 0.063 |
| 78-84-2 | Propanal, 2-methyl- | | 78 | 0.025 |
| 60-29-7 | Ethyl ether | | 90 | 0.073 |
| 67-64-1 | Acetone | | 86 | 0.064 |

FIG. 19B-2 CONT

Catalyst: 0.5%Pt-0.5%Bi/Al$_2$O$_3$

| Reaction conditions | | | Average #C | Product distribution (%) | | | |
|---|---|---|---|---|---|---|---|
| T (°C) | P (psig) | LFR (mL/min) | | Aromatics | Alkenes | Alkanes | Oxygenates |
| 325 | 500 | 0.125 | 7.14 | 17.08 | 11.09 | 53.62 | 6.66 |

Hydrocarbon Report

Request: MK-GHY-R1042  Xyleco Inc  Sample: MK-ETG-56-1-R3-325

| Summary | Total | Known | Major | Trace | Ave Carbon # |
|---|---|---|---|---|---|
| Peaks: | 359 | 206 | 102 | 104 | 7.14 |
| Area: | 2924822494 | 88.5% | 83.5% | 5.0% | |

| Compound Type | Total Known # Peaks | Total Known % Area | Major Components # Peaks | Major Components % Area | Average Carbon # |
|---|---|---|---|---|---|
| Aromatics (Total): | 46 | 17.11 | 26 | 16.02 | 9.00 |
| Oxygenated: | 7 | 0.63 | 2 | 0.32 | 12.68 |
| Alkenes (Total): | 67 | 11.09 | 24 | 9.13 | 6.14 |
| Straight: | 25 | 5.71 | 13 | 5.20 | 5.78 |
| Branched: | 29 | 4.16 | 7 | 3.15 | 6.08 |
| Cyclic: | 13 | 1.22 | 4 | 0.77 | 8.03 |
| Alkanes (Total): | 70 | 53.62 | 41 | 52.16 | 6.75 |
| Straight: | 13 | 33.19 | 11 | 33.06 | 6.13 |
| Branched: | 26 | 13.22 | 16 | 12.80 | 7.69 |
| Cyclic: | 31 | 7.20 | 14 | 6.29 | 7.90 |
| Oxygenated (Other): | 22 | 6.66 | 11 | 6.21 | 7.13 |

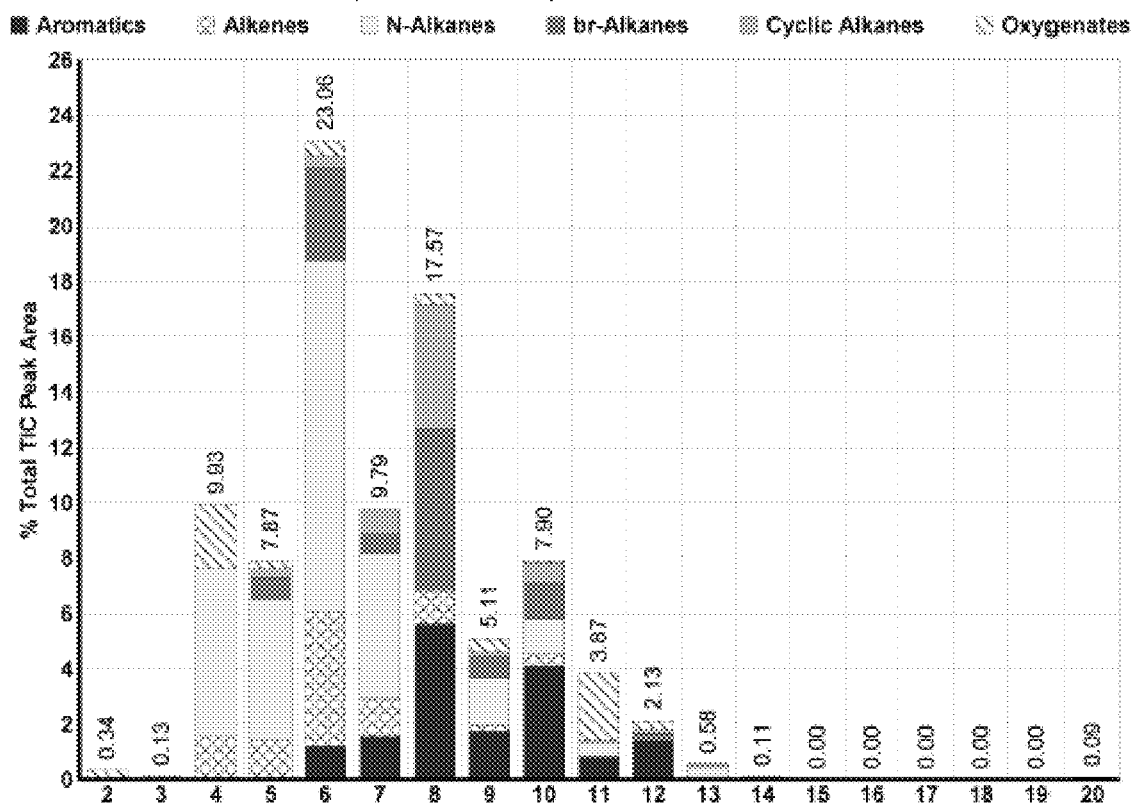

FIG. 20A

| CAS # | Compound Name | Br# | Q | Area% |
|---|---|---|---|---|
| Major Aromatics Hydrocarbons | | | | |
| 106-42-3 | p-Xylene | | 94 | 2.36 |
| 95-47-6 | o-Xylene | | 95 | 1.87 |
| 108-88-3 | Toluene | | 90 | 1.57 |
| 100-41-4 | Ethylbenzene | | 91 | 1.48 |
| 71-43-2 | Benzene | | 91 | 1.20 |
| 874-41-9 | Benzene, 1-ethyl-2,4-dimethyl- | | 94 | 1.13 |
| 1074-17-5 | Benzene, 1-methyl-2-propyl- | | 91 | 0.94 |
| 55669-88-0 | 1,4-dimethyl-2-(2-methylpropyl)benzene | | 83 | 0.86 |
| 611-14-3 | Benzene, 1-ethyl-2-methyl- | | 91 | 0.63 |
| 1758-88-9 | Benzene, 2-ethyl-1,4-dimethyl- | | 94 | 0.60 |
| 108-67-8 | Mesitylene | | 91 | 0.54 |
| 141-93-5 | Benzene, 1,3-diethyl- | | 95 | 0.49 |
| 1074-55-1 | Benzene, 1-methyl-4-propyl- | | 91 | 0.48 |
| 4481-30-5 | Benzene, (1,2-dimethylpropyl)- | | 72 | 0.37 |
| 2870-04-4 | Benzene, 2-ethyl-1,3-dimethyl- | | 91 | 0.34 |
| 103-65-1 | Benzene, propyl- | | 87 | 0.33 |
| 620-14-4 | Benzene, 1-ethyl-3-methyl- | | 90 | 0.28 |
| 1595-16-0 | Benzene, 1-methyl-4-(1-methylpropyl)- | | 80 | 0.21 |
| 2050-24-0 | Benzene, 1,3-diethyl-5-methyl- | | 94 | 0.18 |
| 4810-04-3 | Benzene, 1,3,5-trimethyl-2-propyl- | | 87 | 0.13 |
| 768-00-3 | Benzene, (1-methyl-1-propenyl)-, (E)- | | 64 | 0.12 |
| 10219-84-2 | Benzene, (1,3-dimethylbutyl)- | | 64 | 0.12 |
| 22531-20-0 | Naphthalene, 6-ethyl-1,2,3,4-tetrahydro- | | 91 | 0.11 |
| Trace Aromatic Hydrocarbons | | | | |
| 54340-85-1 | Benzene, 1-(2-butenyl)-2,3-dimethyl- | | 94 | 0.080 |
| 582-16-1 | Naphthalene, 2,7-dimethyl- | | 70 | 0.057 |
| 90-12-0 | Naphthalene, 1-methyl- | | 72 | 0.043 |
| 10222-95-4 | 1,2,4-trimethyl-5-propan-2-yl-benzene | | 72 | 0.040 |
| 1127-76-0 | 1-ethylnaphthalene | | 80 | 0.023 |
| 4489-84-3 | Benzene, (3-methyl-2-butenyl)- | | 74 | 0.022 |
| Major Oxygenated Aromatics | | | | |
| 88-60-4 | 1-tert-butyl-2-methoxy-4-methyl-benzene | | 64 | 0.18 |
| 34386-42-0 | 1-(4-tert-butylphenyl)ethanol | | 64 | 0.14 |
| Trace Oxygenated Aromatics | | | | |
| 68563-30-2 | Bacchotricuneatin c | | 72 | 0.088 |
| 6379-73-3 | 2-methoxy-1-methyl-4-propan-2-yl-benzene | | 72 | 0.063 |
| 876-20-0 | 2,5-Diethylphenol | | 80 | 0.060 |
| 1000386-47-2 | 3-Methoxy-4-methylphenylacetone | | 72 | 0.058 |
| 98-73-7 | Benzoic acid, p-tert-butyl- | | 64 | 0.035 |
| Major n-Alkenes | | | | |
| 4050-45-7 | 2-Hexene, (E)- | | 91 | 1.00 |
| 106-98-9 | 1-Butene | | 90 | 0.56 |
| 592-41-6 | 1-Hexene | | 91 | 0.53 |
| 627-20-3 | 2-Pentene, (Z)- | | 91 | 0.53 |
| 590-18-1 | 2-Butene, (Z)- | | 90 | 0.52 |
| 13269-52-8 | 3-Hexene, (E)- | | 91 | 0.51 |
| 7642-10-6 | (Z)-3-Heptene | | 95 | 0.43 |
| 592-47-2 | 3-Hexene | | 95 | 0.41 |
| 109-67-1 | 1-Pentene | | 91 | 0.22 |

FIG. 20A CONT

| CAS # | Compound Name | Br# | Q | Area% |
|---|---|---|---|---|
| 14686-13-6 | 2-Heptene, (E)- | | 94 | 0.21 |
| 592-77-8 | 2-Heptene | | 91 | 0.18 |
| 14850-23-8 | 4-Octene, (E)- | | 91 | 0.12 |
| | Trace n-Alkenes | | | |
| 6108-61-8 | (Z),(Z)-2,4-Hexadiene | | 90 | 0.083 |
| 111-67-1 | 2-Octene | | 97 | 0.082 |
| 592-76-7 | 1-Heptene | | 95 | 0.081 |
| 10405-85-3 | trans-4-Nonene | | 72 | 0.068 |
| 14850-22-7 | 3-Octene, (Z)- | | 91 | 0.048 |
| 592-48-3 | C2H5CH=CHCH=CH2 | | 91 | 0.047 |
| 20063-92-7 | 3-Nonene, (E)- | | 91 | 0.043 |
| 106-99-0 | 1,3-Butadiene | | 91 | 0.018 |
| 591-93-5 | 1,4-Pentadiene | | 93 | 0.015 |
| 115-07-1 | Propene | | 90 | 0.012 |
| 504-60-9 | 1,3-Pentadiene | | 90 | 0.010 |
| | Major Branched Alkenes | | | |
| 3404-75-9 | 2-Heptene, 3-methyl- | 1 | 90 | 0.19 |
| 7300-03-0 | 3-Heptene, 3-methyl- | 1 | 91 | 0.12 |
| 3404-55-5 | 4-Methyl-2-hexene c&t | 1 | 91 | 0.10 |
| 922-61-2 | 2-Pentene, 3-methyl- | 1 | 96 | 1.73 |
| 513-35-9 | 2-Butene, 2-methyl- | 1 | 81 | 0.59 |
| 563-46-2 | 2-Methyl-1-butene | 1 | 91 | 0.13 |
| 115-11-7 | 1-Propene, 2-methyl- | 1 | 87 | 0.46 |
| | Trace Branched Alkenes | | | |
| 6874-39-1 | (2E,4E)-3,7-Dimethyl-2,4-octadiene | 2 | 68 | 0.069 |
| 1000195-03-3 | 6,6-Dimethylhepta-2,4-diene | 2 | 64 | 0.077 |
| 14255-23-3 | 2-Hexene, 2,4-dimethyl- | 2 | 87 | 0.025 |
| 10574-37-5 | 2-Pentene, 2,3-dimethyl- | 2 | 76 | 0.053 |
| 563-78-0 | 1-Butene, 2,3-dimethyl- | 2 | 87 | 0.017 |
| 74764-46-8 | 3-Heptene, 3-ethyl- | 1 | 72 | 0.030 |
| 17803-57-3 | 4-Methyl-1,3-heptadiene | 1 | 64 | 0.035 |
| 4485-16-9 | 3-Heptene, 4-methyl- | 1 | 64 | 0.022 |
| 1632-16-2 | 3-Ethyl-2-hexene(c,t) | 1 | 91 | 0.088 |
| 10574-36-4 | 2-Hexene, 3-methyl-, (Z)- | 1 | 94 | 0.086 |
| 816-79-5 | 2-Pentene, 3-ethyl- | 1 | 91 | 0.089 |
| 3404-65-7 | 3-Methyl-3-hexene | 1 | 91 | 0.069 |
| 926-56-7 | 4-Methyl-1,3-pentadiene | 1 | 76 | 0.031 |
| 625-27-4 | 2-Pentene, 2-methyl- | 1 | 91 | 0.063 |
| 926-54-5 | 1,3-Pentadiene, 2-methyl-, (E)- | 1 | 86 | 0.041 |
| 763-29-1 | 1-Pentene, 2-methyl- | 1 | 87 | 0.028 |
| 760-20-3 | 1-Pentene, 3-methyl- | 1 | 94 | 0.092 |
| | Major Cyclic Alkenes | | | |
| 1453-24-3 | Cyclohexene, 1-ethyl- | | 70 | 0.41 |
| 53366-54-4 | Cyclopentane, (2-methylbutylidene)- | | 78 | 0.38 |
| 693-89-0 | Cyclopentene, 1-methyl- | | 90 | 0.17 |
| | Trace Cyclic Alkenes | | | |
| 13828-31-4 | Cyclohexene, 1-methyl-3-(1-methylethyl)- | | 64 | 0.058 |
| 1000113-30-9 | trans-1-Butenylcyclopentane | | 83 | 0.021 |
| 19780-56-4 | Methyl ethyl cyclopentene | | 95 | 0.098 |
| 591-49-1 | Cyclohexene, 1-methyl- | | 74 | 0.048 |
| 110-83-8 | Cyclohexene | | 90 | 0.087 |
| 592-57-4 | 1,3-Cyclohexadiene | | 72 | 0.006 |

FIG. 20A CONT

| CAS # | Compound Name | Br# | Q | Area% |
|---|---|---|---|---|
| 1120-62-3 | Cyclopentene, 3-methyl- | | 87 | 0.043 |
| Major n-Alkanes ||||||
| 110-54-3 | n-Hexane | | 91 | 12.66 |
| 106-97-8 | Butane | | 90 | 6.07 |
| 142-82-5 | Heptane | | 95 | 5.28 |
| 109-66-0 | Pentane | | 91 | 5.08 |
| 111-84-2 | Nonane | | 91 | 1.68 |
| 124-18-5 | Decane | | 95 | 1.29 |
| 1120-21-4 | Undecane | | 91 | 0.54 |
| 629-50-5 | Tridecane | | 94 | 0.47 |
| Trace n-Alkanes ||||||
| 74-98-6 | Propane | | 90 | 0.067 |
| 112-40-3 | Dodecane | | 64 | 0.064 |
| Major Branched Alkanes ||||||
| 589-43-5 | Hexane, 2,4-dimethyl- | 2 | 83 | 5.28 |
| 565-59-3 | Pentane, 2,3-dimethyl- | 2 | 87 | 0.17 |
| 1002-43-3 | Undecane, 3-methyl- | 1 | 78 | 0.21 |
| 5911-04-6 | Nonane, 3-methyl- | 1 | 91 | 0.78 |
| 15869-85-9 | Nonane, 5-methyl- | 1 | 87 | 0.31 |
| 15869-86-0 | Octane, 4-ethyl- | 1 | 83 | 0.17 |
| 2216-33-3 | Octane, 3-methyl- | 1 | 81 | 0.30 |
| 15869-80-4 | Heptane, 3-ethyl- | 1 | 74 | 0.18 |
| 3221-61-2 | Octane, 2-methyl- | 1 | 62 | 0.14 |
| 2216-34-4 | Octane, 4-methyl- | 1 | 91 | 0.12 |
| 619-99-8 | Hexane, 3-ethyl- | 1 | 91 | 0.44 |
| 592-27-8 | Heptane, 2-methyl- | 1 | 87 | 0.11 |
| 617-78-7 | Pentane, 3-ethyl- | 1 | 91 | 0.22 |
| 591-76-4 | Hexane, 2-methyl- | 1 | 74 | 0.28 |
| 96-14-0 | Pentane, 3-methyl- | 1 | 91 | 3.34 |
| 78-78-4 | Butane, 2-methyl- | 1 | 83 | 0.80 |
| Trace Branched Alkanes ||||||
| 17312-77-5 | Undecane, 2,3-dimethyl- | 2 | 64 | 0.024 |
| 922-28-1 | Heptane, 3,4-dimethyl- | 2 | 72 | 0.024 |
| 2216-30-0 | Heptane, 2,5-dimethyl- | 2 | 83 | 0.028 |
| 583-48-2 | Hexane, 3,4-dimethyl- | 2 | 83 | 0.026 |
| 79-29-8 | Butane, 2,3-dimethyl- | 2 | 90 | 0.005 |
| 6418-41-3 | Tridecane, 3-methyl- | 1 | 72 | 0.054 |
| 17312-83-9 | Nonane, 5-butyl- | 1 | 72 | 0.087 |
| 2847-72-5 | Decane, 4-methyl- | 1 | 83 | 0.044 |
| 871-83-0 | Nonane, 2-methyl- | 1 | 64 | 0.066 |
| 13287-21-3 | Tridecane, 6-methyl- | 1 | 64 | 0.058 |
| Major Cyclic Alkanes ||||||
| 2613-65-2 | Cyclopentane, 1-ethyl-3-methyl-, trans- | | 83 | 1.57 |
| 3726-47-4 | Cyclopentane, 1-ethyl-3-methyl- | | 78 | 1.22 |
| 1678-91-7 | Cyclohexane, ethyl- | | 72 | 0.74 |
| 110-82-7 | Cyclohexane | | 91 | 0.45 |
| 17065-18-8 | Bicyclo[2.1.0]pentane, 1,4-dimethyl- | | 64 | 0.43 |
| 930-89-2 | Cyclopentane, 1-ethyl-2-methyl-, cis- | | 94 | 0.37 |
| 108-87-2 | Cyclohexane, methyl- | | 95 | 0.37 |
| 7045-67-2 | Cyclohexane, 2-ethyl-1,3-dimethyl- | | 74 | 0.32 |
| 2402-06-4 | Cyclopropane, 1,2-dimethyl-, trans- | | 91 | 0.32 |
| 624-29-3 | Cyclohexane, 1,4-dimethyl-, cis- | | 74 | 0.17 |

FIG. 20A CONT

| CAS # | Compound Name | Br# | Q | Area% |
|---|---|---|---|---|
| 1678-93-9 | Cyclohexane, butyl- | | 94 | 0.17 |
| 2207-03-6 | Cyclohexane, 1,3-dimethyl-, trans- | | 90 | 0.12 |
| 294-62-2 | Cyclododecane | | 64 | 0.12 |
| Trace Cyclic Alkanes | | | | |
| 3741-00-2 | Cyclopentane, pentyl- | | 90 | 0.080 |
| 2778-68-9 | (1S,3S,6R)-3,7,7-trimethylnorcarane | | 87 | 0.091 |
| 590-66-9 | 1,1-dimethylcyclohexane | | 62 | 0.087 |
| 53366-38-4 | Cyclopentane, (2-methylbutyl)- | | 64 | 0.081 |
| 1678-92-8 | Cyclohexane, propyl- | | 87 | 0.067 |
| 638-04-0 | Cyclohexane, 1,3-dimethyl-, cis- | | 64 | 0.095 |
| 3728-56-1 | 1-Ethyl-4-methylcyclohexane | | 90 | 0.074 |
| 2207-01-4 | Cyclohexane, 1,2-dimethyl-, cis- | | 90 | 0.073 |
| 16747-50-5 | Cyclopentane, 1-ethyl-1-methyl- | | 83 | 0.011 |
| 15890-40-1 | 1,2,3-Trimethylcyclopentane, cis, trans | | 80 | 0.018 |
| 1640-89-7 | Cyclopentane, ethyl- | | 94 | 0.073 |
| 1192-18-3 | Cyclopentane, 1,2-dimethyl-, cis- | | 64 | 0.020 |
| 2453-00-1 | Cyclopentane, 1,3-dimethyl- | | 87 | 0.038 |
| 74752-93-5 | Cyclopropane, 1,1,2,3-tetramethyl- | | 64 | 0.014 |
| 287-92-3 | Cyclopentane | | 86 | 0.020 |
| Major Oxygenates | | | | |
| 83783-88-4 | 2-methylpentyl 2-methylbutanoate | | 64 | 2.39 |
| 60-29-7 | Ethyl ether | | 91 | 1.35 |
| 123-72-8 | Butanal | | 91 | 0.66 |
| 26788-91-0 | Bicyclo[3.2.2]nona-6,8-dien-3-one | | 64 | 0.46 |
| 628-81-9 | Butane, 1-ethoxy- | | 74 | 0.38 |
| 107-87-9 | 2-Pentanone | | 83 | 0.24 |
| 4423-94-3 | Cyclohexanone, 2-ethyl- | | 76 | 0.19 |
| 53229-40-6 | 2,2,3-Triethyloxirane | | 87 | 0.18 |
| 64-17-5 | Ethanol | | 83 | 0.18 |
| 71-36-3 | 1-Butanol | | 74 | 0.15 |
| 75-07-0 | Acetaldehyde | | 90 | 0.12 |
| Trace Oxygenates | | | | |
| 4485-09-0 | 4-Nonanone | | 64 | 0.050 |
| 589-63-9 | 4-Octanone | | 81 | 0.026 |
| 591-78-6 | 2-Hexanone | | 80 | 0.023 |
| 97-96-1 | Butanal, 2-ethyl- | | 64 | 0.069 |
| 565-61-7 | 2-Pentanone, 3-methyl- | | 64 | 0.053 |
| 4170-30-3 | 2-Butenal | | 90 | 0.004 |
| 78-85-3 | Methacrolein | | 86 | 0.057 |
| 64-19-7 | Acetic acid | | 90 | 0.034 |
| 78-93-3 | 2-Butanone | | 78 | 0.079 |
| 67-64-1 | Acetone | | 64 | 0.047 |

FIG. 20A CONT

Catalyst: 0.5%Pt-0.75%Ba/Al$_2$O$_3$

| Reaction conditions | | | Average #C | Product distribution (%) | | | |
|---|---|---|---|---|---|---|---|
| T (°C) | P (psig) | LFR (mL/min) | | Aromatics | Alkenes | Alkanes | Oxygenates |
| 350 | 500 | 0.125 | 8.22 | 12.01 | 4.97 | 61.88 | 15.70 |

Hydrocarbon Report

Request: TG-GGG-Q0950     Xyleco Inc     Sample: TG-ETG-46-2-R7-350C

| Summary | Total | Known | Major | Trace | Ave Carbon # |
|---|---|---|---|---|---|
| Peaks: | 236 | 154 | 81 | 73 | 8.22 |
| Area: | 1350113607 | 94.6% | 91.4% | 3.2% | |

| Compound Type | Total Known # Peaks | Total Known % Area | Major Components # Peaks | Major Components % Area | Average Carbon # |
|---|---|---|---|---|---|
| Aromatics (Total): | 35 | 12.01 | 20 | 11.45 | 8.60 |
| Oxygenated: | 12 | 0.40 | 0 | 0.00 | 10.25 |
| Alkenes (Total): | 44 | 4.97 | 14 | 3.88 | 6.69 |
| Straight: | 23 | 3.55 | 12 | 3.18 | 6.60 |
| Branched: | 14 | 1.05 | 2 | 0.69 | 6.53 |
| Cyclic: | 7 | 0.97 | 0 | 0.00 | 7.90 |
| Alkanes (Total): | 62 | 61.88 | 41 | 60.63 | 7.28 |
| Straight: | 12 | 43.14 | 10 | 43.00 | 7.08 |
| Branched: | 27 | 12.76 | 19 | 12.31 | 7.70 |
| Cyclic: | 23 | 5.98 | 12 | 5.32 | 7.85 |
| Oxygenated (Other): | 13 | 15.70 | 6 | 15.40 | 12.07 |

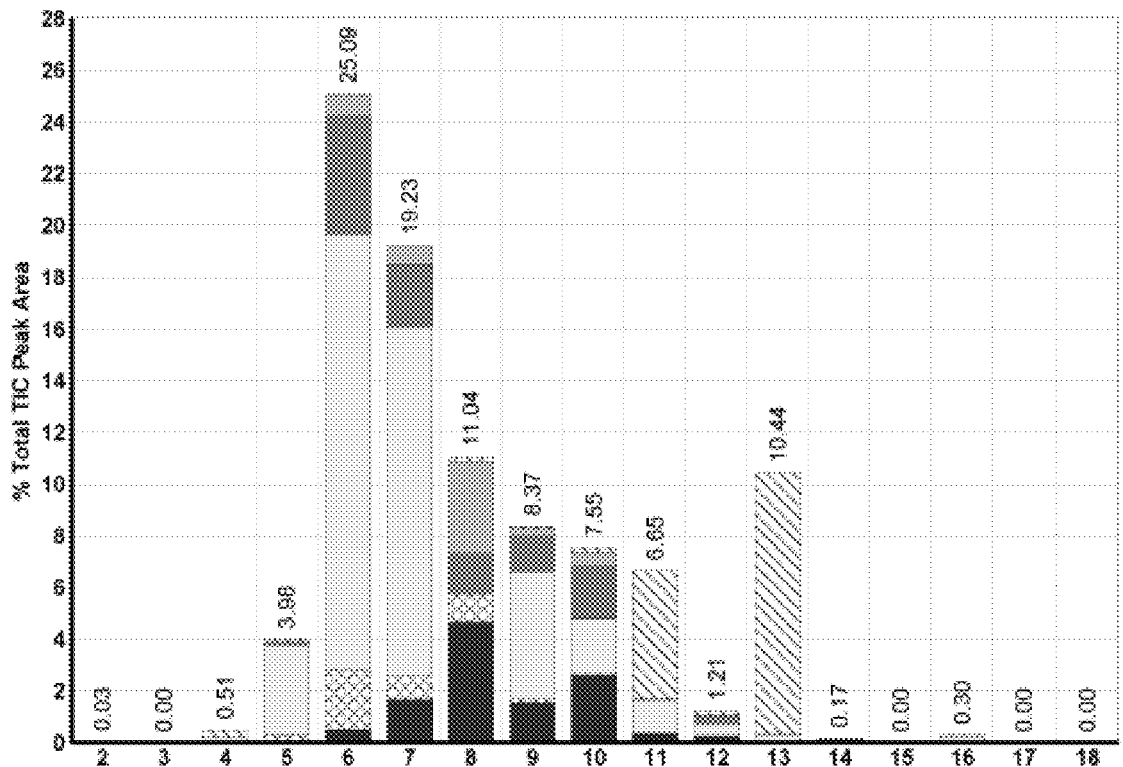

FIG. 21A-2

| CAS # | Compound Name | Br# | Q | Area% |
|---|---|---|---|---|
| | Major Aromatics Hydrocarbons | | | |
| 106-42-3 | p-Xylene | | 97 | 3.31 |
| 108-88-3 | Toluene | | 91 | 1.64 |
| 100-41-4 | Ethylbenzene | | 91 | 1.30 |
| 1074-55-1 | Benzene, 1-methyl-4-propyl- | | 91 | 0.76 |
| 620-14-4 | Benzene, 1-ethyl-3-methyl- | | 91 | 0.67 |
| 934-74-7 | Benzene, 1-ethyl-3,5-dimethyl- | | 91 | 0.59 |
| 71-43-2 | Benzene | | 91 | 0.50 |
| 108-67-8 | Mesitylene | | 91 | 0.49 |
| 141-93-5 | Benzene, 1,3-diethyl- | | 97 | 0.43 |
| 1758-88-9 | Benzene, 2-ethyl-1,4-dimethyl- | | 91 | 0.31 |
| 104-51-8 | Benzene, n-butyl- | | 91 | 0.31 |
| 35669-88-0 | 1,4-dimethyl-2-(2-methylpropyl)benzene | | 86 | 0.26 |
| 103-65-1 | Benzene, propyl- | | 90 | 0.25 |
| 1595-05-7 | Benzene, 1-methyl-4-butyl | | 86 | 0.21 |
| 2050-24-0 | Benzene, 1,3-diethyl-5-methyl- | | 81 | 0.16 |
| 874-41-9 | Benzene, 1-ethyl-2,4-dimethyl- | | 91 | 0.16 |
| 611-14-3 | Benzene, 1-ethyl-2-methyl- | | 91 | 0.15 |
| | Trace Aromatic Hydrocarbons | | | |
| 108-38-3 | Benzene, 1,3-dimethyl- | | 91 | 0.061 |
| 1074-43-7 | Benzene, 1-methyl-3-propyl- | | 90 | 0.042 |
| | Trace Oxygenated Aromatics | | | |
| 499-75-2 | Phenol, 2-methyl-5-(1-methylethyl)- | | 74 | 0.063 |
| 2934-05-6 | Phenol, 2,4-bis(1-methylethyl)- | | 64 | 0.062 |
| 88-60-4 | 1-tert-butyl-2-methoxy-4-methyl-benzene | | 72 | 0.056 |
| 526-75-0 | Phenol, 2,3-dimethyl- | | 64 | 0.035 |
| 3238-38-8 | Phenol, 2,3,4,6-tetramethyl- | | 80 | 0.034 |
| 527-35-5 | Phenol, 2,3,5,6-tetramethyl- | | 80 | 0.034 |
| 99-89-8 | p-Cumenol | | 64 | 0.030 |
| 2219-78-5 | Phenol, 3-ethyl-4,5-dimethyl- | | 64 | 0.029 |
| 698-71-5 | Phenol, 3-ethyl-5-methyl- | | 90 | 0.023 |
| 89-83-8 | Thymol | | 74 | 0.019 |
| 2219-73-0 | Phenol, 4-ethyl-3-methyl- | | 64 | 0.013 |
| | Major n-Alkenes | | | |
| 4050-45-7 | 2-Hexene, (E)- | | 91 | 1.03 |
| 14919-01-8 | 3-Octene, (E)- | | 94 | 0.40 |
| 14686-14-7 | 3-Heptene, (E)- | | 95 | 0.39 |
| 592-47-2 | 3-Hexene | | 95 | 0.39 |
| 627-20-3 | 2-Pentene, (Z)- | | 91 | 0.29 |
| 13389-42-9 | 2-Octene, (E)- | | 94 | 0.24 |
| 592-77-8 | 2-Heptene | | 95 | 0.23 |
| 592-41-6 | 1-Hexene | | 91 | 0.14 |
| 6443-92-1 | (Z)-2-Heptene | | 97 | 0.13 |
| | Trace n-Alkenes | | | |
| 14850-23-8 | 4-Octene, (E)- | | 90 | 0.088 |
| 592-76-7 | 1-Heptene | | 95 | 0.052 |
| 10405-84-2 | cis-4-Nonene | | 91 | 0.047 |
| 109-67-1 | 1-Pentene | | 83 | 0.044 |
| 2198-23-4 | 4-Nonene | | 91 | 0.036 |
| 590-18-1 | 2-Butene, (Z)- | | 86 | 0.034 |
| 6434-77-1 | cis-2-Nonene | | 83 | 0.014 |
| 115-07-1 | Propene | | 83 | 0.002 |

FIG. 21A-2 CONT

| CAS # | Compound Name | Br# | Q | Area% |
|---|---|---|---|---|
| | Major Branched Alkenes | | | |
| 922-61-2 | 2-Pentene, 3-methyl- | 1 | 94 | 0.44 |
| 922-62-3 | 2-Pentene, 3-methyl-, (Z)- | 1 | 94 | 0.25 |
| | Trace Branched Alkenes | | | |
| 59643-73-1 | 2,3-Dimethyl-3-heptene, (Z)- | 2 | 64 | 0.035 |
| 563-78-0 | 1-Butene, 2,3-dimethyl- | 2 | 90 | 0.016 |
| 3404-75-9 | 2-Heptene, 3-methyl- | 1 | 91 | 0.098 |
| 7300-03-0 | 3-Heptene, 3-methyl- | 1 | 90 | 0.054 |
| 1632-16-2 | 3-Ethyl-2-hexene(c,t) | 1 | 86 | 0.027 |
| 10574-36-4 | 2-Hexene, 3-methyl-, (Z)- | 1 | 83 | 0.019 |
| 816-79-5 | 2-Pentene, 3-ethyl- | 1 | 91 | 0.065 |
| 3404-65-7 | 3-Methyl-3-hexene | 1 | 90 | 0.018 |
| 3899-36-3 | 3-Hexene, 3-methyl-, (E)- | 1 | 74 | 0.007 |
| 3404-55-5 | 4-Methyl-2-hexene,c&t | 1 | 86 | 0.011 |
| 513-35-9 | 2-Butene, 2-methyl- | 1 | 83 | 0.006 |
| 115-11-7 | 1-Propene, 2-methyl- | 1 | 83 | 0.006 |
| | Trace Cyclic Alkenes | | | |
| 19487-09-3 | 2,2,6,6-tetramethylbicyclo[3.1.0]hex-3-ene | | 64 | 0.047 |
| 53366-54-4 | Cyclopentane, (2-methylbutylidene)- | | 83 | 0.043 |
| 19780-56-4 | Methyl ethyl cyclopentene | | 90 | 0.029 |
| 2808-79-9 | Cyclohexene, 1,4-dimethyl- | | 83 | 0.056 |
| 2808-71-1 | Cyclohexene, 3-ethyl- | | 78 | 0.080 |
| 110-83-8 | Cyclohexene | | 90 | 0.057 |
| 693-89-0 | Cyclopentene, 1-methyl- | | 90 | 0.034 |
| | Major n-Alkanes | | | |
| 110-54-3 | n-Hexane | | 91 | 16.78 |
| 142-82-5 | Heptane | | 96 | 13.46 |
| 111-84-2 | Nonane | | 95 | 4.92 |
| 109-66-0 | Pentane | | 90 | 3.43 |
| 124-18-5 | Decane | | 95 | 2.08 |
| 1120-21-4 | Undecane | | 91 | 1.39 |
| 112-40-3 | Dodecane | | 94 | 0.46 |
| 629-50-5 | Tridecane | | 94 | 0.32 |
| 544-76-3 | Hexadecane | | 83 | 0.25 |
| 106-97-8 | Butane | | 86 | 0.15 |
| | Major Branched Alkanes | | | |
| 565-75-3 | Pentane, 2,3,4-trimethyl- | 3 | 80 | 0.37 |
| 583-48-2 | Hexane, 3,4-dimethyl- | 2 | 74 | 0.15 |
| 565-59-3 | Pentane, 2,3-dimethyl- | 2 | 90 | 0.25 |
| 1002-43-3 | Undecane, 3-methyl- | 1 | 78 | 0.28 |
| 13287-21-3 | Tridecane, 6-methyl- | 1 | 64 | 0.13 |
| 5911-04-6 | Nonane, 3-methyl- | 1 | 87 | 1.30 |
| 5881-17-4 | Octane, 3-ethyl- | 1 | 83 | 0.20 |
| 15869-85-9 | Nonane, 5-methyl- | 1 | 87 | 0.51 |
| 2216-33-3 | Octane, 3-methyl- | 1 | 78 | 0.38 |
| 15869-80-4 | Heptane, 3-ethyl- | 1 | 83 | 0.59 |
| 3221-61-2 | Octane, 2-methyl- | 1 | 83 | 0.15 |
| 2216-34-4 | Octane, 4-methyl- | 1 | 83 | 0.18 |
| 619-99-8 | Hexane, 3-ethyl- | 1 | 91 | 0.83 |
| 592-27-8 | Heptane, 2-methyl- | 1 | 95 | 0.23 |
| 617-78-7 | Pentane, 3-ethyl- | 1 | 91 | 1.75 |
| 591-76-4 | Hexane, 2-methyl- | 1 | 87 | 0.43 |

FIG. 21A-2 CONT

| CAS # | Compound Name | Br# | Q | Area% |
|---|---|---|---|---|
| 96-14-0 | Pentane, 3-methyl- | 1 | 90 | 4.35 |
| 107-83-5 | Pentane, 2-methyl- | 1 | 64 | 0.25 |
| 78-78-4 | Butane, 2-methyl- | 1 | 91 | 0.13 |
| Trace Branched Alkanes | | | | |
| 62238-14-6 | Decane, 2,3,8-trimethyl- | 3 | 78 | 0.029 |
| 4110-44-5 | Octane, 3,3-dimethyl- | 2 | 83 | 0.040 |
| 2216-30-0 | Heptane, 2,5-dimethyl- | 2 | 83 | 0.061 |
| 6418-41-3 | Tridecane, 3-methyl- | 1 | 83 | 0.041 |
| 17302-36-2 | 5-Ethyldecane | 1 | 64 | 0.074 |
| 13151-35-4 | Decane, 5-methyl- | 1 | 78 | 0.050 |
| Major Cyclic Alkanes | | | | |
| 3726-47-4 | Cyclopentane, 1-ethyl-3-methyl- | | 83 | 1.13 |
| 2613-65-2 | Cyclopentane, 1-ethyl-3-methyl-, trans- | | 83 | 0.87 |
| 1678-91-7 | Cyclohexane, ethyl- | | 87 | 0.86 |
| 108-87-2 | Cyclohexane, methyl- | | 94 | 0.58 |
| 110-82-7 | Cyclohexane | | 91 | 0.41 |
| 96-37-7 | Cyclopentane, methyl- | | 91 | 0.36 |
| 930-89-2 | Cyclopentane, 1-ethyl-2-methyl-, cis- | | 96 | 0.33 |
| 7045-67-2 | Cyclohexane, 2-ethyl-1,3-dimethyl- | | 64 | 0.24 |
| 624-29-3 | Cyclohexane, 1,4-dimethyl-, cis- | | 94 | 0.19 |
| 6876-23-9 | Cyclohexane, 1,2-dimethyl-, trans- | | 95 | 0.15 |
| 3741-00-2 | Cyclopentane, pentyl- | | 94 | 0.11 |
| 1678-93-9 | Cyclohexane, butyl- | | 90 | 0.11 |
| 19489-10-2 | cis-1-Ethyl-3-methyl-cyclohexane | | 91 | 0.10 |
| Trace Cyclic Alkanes | | | | |
| 7094-27-1 | 1,1,4-Trimethylcyclohexane | | 64 | 0.087 |
| 13152-02-8 | Cyclooctane, ethyl- | | 74 | 0.080 |
| 1678-92-8 | Cyclohexane, propyl- | | 86 | 0.065 |
| 3728-54-9 | Cyclohexane, 1-ethyl-2-methyl- | | 86 | 0.096 |
| 74752-93-5 | Cyclopropane, 1,1,2,3-tetramethyl- | | 64 | 0.041 |
| 583-57-3 | Cyclohexane, 1,2-dimethyl- (cis/trans) | | 80 | 0.053 |
| 1640-89-7 | Cyclopentane, ethyl- | | 95 | 0.097 |
| 2532-58-3 | Cyclopentane, 1,3-dimethyl-, cis- | | 91 | 0.029 |
| 33778-43-1 | Cyclopropane, 1-ethyl-1-methyl- | | 90 | 0.021 |
| Major Oxygenates | | | | |
| 1000309-32-8 | Oxalic acid, isohexyl pentyl ester | | 83 | 9.96 |
| 83783-88-4 | 2-methylpentyl 2-methylbutanoate | | 72 | 4.55 |
| 60-29-7 | Ethyl ether | | 91 | 0.14 |
| 1000196-77-9 | 2-Pentene-1,4-dione, 1-(1,2,2-trimethylcyclopentyl) | | 64 | 0.13 |
| 123-72-8 | Butanal | | 91 | 0.12 |
| 15726-15-5 | 4-Heptanone, 3-methyl- | | 87 | 0.11 |
| Trace Oxygenates | | | | |
| 1000309-68-1 | O2-(cyclohexylmethyl) O1-propyl oxalate | | 64 | 0.022 |
| 1000309-38-9 | Oxalic acid, 2-ethylhexyl hexyl ester | | 78 | 0.052 |
| 66-25-1 | Hexanal | | 78 | 0.051 |
| 107-87-9 | 2-Pentanone | | 90 | 0.086 |
| 71-36-3 | 1-Butanol | | 78 | 0.058 |
| 64-17-5 | Ethanol | | 90 | 0.012 |
| 75-07-0 | Acetaldehyde | | 60 | 0.019 |

FIG. 21A-2 CONT

Catalyst: 0.5%Pt-1.0%Ba/Al₂O₃

| Reaction conditions | | | Average #C | Product distribution (%) | | | |
|---|---|---|---|---|---|---|---|
| T (°C) | P (psig) | LFR (mL/min) | | Aromatics | Alkenes | Alkanes | Oxygenates |
| 350 | 500 | 0.125 | 7.72 | 7.87 | 4.05 | 76.53 | 9.19 |

| CAS # | Compound Name | Br # | Q | Area% |
|---|---|---|---|---|
| | Major Aromatics Hydrocarbons | | | |
| 106-42-3 | p-Xylene | | 97 | 2.24 |
| 108-88-3 | Toluene | | 91 | 1.34 |
| 100-41-4 | Ethylbenzene | | 91 | 0.93 |
| 1074-55-1 | Benzene, 1-methyl-4-propyl- | | 91 | 0.48 |
| 622-96-8 | Benzene, 1-ethyl-4-methyl- | | 91 | 0.47 |
| 71-43-2 | Benzene | | 91 | 0.47 |
| 527-84-4 | o-Cymene | | 91 | 0.38 |
| 95-63-6 | Benzene, 1,2,4-trimethyl- | | 91 | 0.29 |
| 105-05-5 | Benzene, 1,4-diethyl- | | 94 | 0.27 |
| 104-51-8 | Benzene, n-butyl- | | 91 | 0.19 |
| 103-65-1 | Benzene, propyl- | | 90 | 0.17 |
| 933-98-2 | Benzene, 1-ethyl-2,3-dimethyl- | | 91 | 0.16 |
| 1595-05-7 | Benzene, 1-methyl-4-butyl | | 86 | 0.14 |
| | Trace Aromatic Hydrocarbons | | | |
| 1758-88-9 | Benzene, 2-ethyl-1,4-dimethyl- | | 91 | 0.093 |
| 620-14-4 | Benzene, 1-ethyl-3-methyl- | | 91 | 0.087 |
| 1077-16-3 | Benzene, hexyl- | | 64 | 0.047 |
| 108-67-8 | Mesitylene | | 90 | 0.035 |
| | Trace Oxygenated Aromatics | | | |
| 499-75-2 | Phenol, 2-methyl-5-(1-methylethyl)- | | 78 | 0.037 |
| 698-71-5 | Phenol, 3-ethyl-5-methyl- | | 86 | 0.026 |
| 98-89-8 | p-Cumenol | | 83 | 0.013 |
| 93-53-8 | Benzeneacetaldehyde, alpha-methyl- | | 64 | 0.011 |
| | Major n-Alkenes | | | |
| 7688-21-3 | 2-Hexene, (Z)- | | 91 | 0.38 |
| 592-47-2 | 3-Hexene | | 94 | 0.17 |
| 14686-14-7 | 3-Heptene, (E)- | | 95 | 0.17 |
| 109-68-2 | 2-Pentene | | 91 | 0.15 |
| 592-77-8 | 2-Heptene | | 95 | 0.14 |
| 6443-92-1 | (Z)-2-Heptene | | 91 | 0.10 |
| | Trace n-Alkenes | | | |
| 646-04-8 | 2-Pentene, (E)- | | 91 | 0.078 |
| 7642-10-6 | (Z)-3-Heptene | | 91 | 0.074 |
| 592-41-6 | 1-Hexene | | 90 | 0.041 |
| 624-64-6 | 2-Butene, (E)- | | 64 | 0.009 |
| 590-18-1 | 2-Butene, (Z)- | | 78 | 0.008 |
| | Major Branched Alkenes | | | |
| 3404-75-9 | 2-Heptene, 3-methyl- | 1 | 91 | 0.13 |
| 16789-51-8 | 3-Ethyl-3-hexene | 1 | 72 | 0.31 |
| 816-79-5 | 2-Pentene, 3-ethyl- | 1 | 91 | 0.30 |
| 922-61-2 | 2-Pentene, 3-methyl- | 1 | 95 | 1.45 |
| | Trace Branched Alkenes | | | |
| 1515-79-3 | 5,5-Dimethyl-1,3-hexadiene | 2 | 72 | 0.070 |
| 3404-80-6 | Hexane, 2-methyl-4-methylene- | 2 | 91 | 0.031 |
| 563-79-1 | 2-Butene, 2,3-dimethyl- | 2 | 91 | 0.089 |
| 13172-91-3 | 3-Heptene, 5-methyl- | 1 | 90 | 0.075 |
| 4914-89-0 | 3-Hexene, 3-methyl-, (Z)- | 1 | 91 | 0.045 |
| 3404-65-7 | 3-Methyl-3-hexene | 1 | 87 | 0.082 |
| 10574-36-4 | 2-Hexene, 3-methyl-, (Z)- | 1 | 91 | 0.079 |
| 3683-19-0 | (Z)-4-Methyl-2-hexene | 1 | 90 | 0.028 |
| 4038-04-4 | 1-Pentene, 3-ethyl- | 1 | 83 | 0.008 |

FIG. 21B-2 CONT

| CAS # | Compound Name | Br# | Q | Area% |
|---|---|---|---|---|
| 763-29-1 | 1-Pentene, 2-methyl- | 1 | 90 | 0.021 |
| 760-20-3 | 1-Pentene, 3-methyl- | 1 | 91 | 0.042 |
| Trace Cyclic Alkenes | | | | |
| 19487-09-3 | 2,2,6,6-tetramethylbicyclo[3.1.0]hex-3-ene | | 90 | 0.026 |
| 33366-54-4 | Cyclopentane, (2-methylbutylidene)- | | 78 | 0.061 |
| 19780-56-4 | Methyl ethyl cyclopentene | | 83 | 0.030 |
| Major n-Alkanes | | | | |
| 110-54-3 | n-Hexane | | 91 | 30.80 |
| 142-82-5 | Heptane | | 96 | 16.41 |
| 109-66-0 | Pentane | | 91 | 7.76 |
| 111-84-2 | Nonane | | 95 | 5.12 |
| 124-18-5 | Decane | | 95 | 1.69 |
| 1120-21-4 | Undecane | | 95 | 1.72 |
| 106-97-8 | Butane | | 87 | 0.73 |
| 112-40-3 | Dodecane | | 91 | 0.31 |
| 629-50-5 | Tridecane | | 94 | 0.29 |
| 544-76-3 | Hexadecane | | 83 | 0.10 |
| Major Branched Alkanes | | | | |
| 20278-89-1 | Heptane, 3,4,5-trimethyl- | 3 | 64 | 4.25 |
| 15869-94-0 | Octane, 3,6-dimethyl- | 2 | 72 | 1.03 |
| 15869-89-3 | Octane, 2,5-dimethyl- | 2 | 72 | 0.12 |
| 583-48-2 | Hexane, 3,4-dimethyl- | 2 | 78 | 0.10 |
| 565-59-3 | Pentane, 2,3-dimethyl- | 2 | 94 | 0.18 |
| 1560-97-0 | Dodecane, 2-methyl- | 1 | 72 | 0.20 |
| 17312-63-9 | Nonane, 5-butyl- | 1 | 72 | 0.15 |
| 13287-21-3 | Tridecane, 6-methyl- | 1 | 72 | 0.11 |
| 5881-17-4 | Octane, 3-ethyl- | 1 | 83 | 0.13 |
| 15869-85-9 | Nonane, 5-methyl- | 1 | 83 | 0.38 |
| 2216-33-3 | Octane, 3-methyl- | 1 | 78 | 0.54 |
| 15869-80-4 | Heptane, 3-ethyl- | 1 | 83 | 0.56 |
| 2216-34-4 | Octane, 4-methyl- | 1 | 83 | 0.14 |
| 619-99-8 | Hexane, 3-ethyl- | 1 | 91 | 0.70 |
| 589-53-7 | Heptane, 4-methyl- | 1 | 83 | 0.22 |
| 592-27-8 | Heptane, 2-methyl- | 1 | 94 | 0.25 |
| 617-78-7 | Pentane, 3-ethyl- | 1 | 90 | 1.82 |
| 591-76-4 | Hexane, 2-methyl- | 1 | 81 | 0.39 |
| 96-14-0 | Pentane, 3-methyl- | 1 | 90 | 5.29 |
| 107-83-5 | Pentane, 2-methyl- | 1 | 64 | 0.43 |
| 78-78-4 | Butane, 2-methyl- | 1 | 91 | 0.28 |
| Trace Branched Alkanes | | | | |
| 13150-81-7 | 2,6-Dimethyldecane | 2 | 83 | 0.096 |
| 17453-04-0 | Undecane, 5-ethyl- | 1 | 83 | 0.047 |
| 2980-69-0 | Undecane, 4-methyl- | 1 | 83 | 0.034 |
| Major Cyclic Alkanes | | | | |
| 2613-65-2 | Cyclopentane, 1-ethyl-3-methyl-, trans- | | 90 | 1.33 |
| 1678-91-7 | Cyclohexane, ethyl- | | 91 | 0.75 |
| 108-87-2 | Cyclohexane, methyl- | | 94 | 0.60 |
| 110-82-7 | Cyclohexane | | 91 | 0.47 |
| 96-37-7 | Cyclopentane, methyl- | | 94 | 0.33 |
| 930-89-2 | Cyclopentane, 1-ethyl-2-methyl-, cis- | | 95 | 0.19 |
| 61142-68-5 | Cyclopentane, 1-hexyl-3-methyl- | | 80 | 0.16 |
| 4823-78-8 | Cyclohexane, 1-ethyl-2-methyl-, trans- | | 91 | 0.14 |

FIG. 21B-2 CONT

| CAS # | Compound Name | Br# | Q | Area% |
|---|---|---|---|---|
| 624-29-3 | Cyclohexane, 1,4-dimethyl-, cis- | | 90 | 0.14 |
| 638-04-0 | Cyclohexane, 1,3-dimethyl-, cis- | | 91 | 0.13 |
| Trace Cyclic Alkanes | | | | |
| 1678-93-9 | Cyclohexane, butyl- | | 91 | 0.087 |
| 7058-05-1 | Cyclohexane, 1-ethyl-2,3-dimethyl- | | 64 | 0.042 |
| 824-43-1 | Cyclohexane, 1,2-diethyl-, cis- | | 78 | 0.068 |
| 489-20-3 | 1,2-dimethyl-3-propan-2-yl-cyclopentane | | 64 | 0.062 |
| 1678-92-8 | Cyclohexane, propyl- | | 86 | 0.061 |
| 1000113-87-1 | trans-1,3-Diethylcyclopentane | | 72 | 0.062 |
| 583-57-3 | Cyclohexane, 1,2-dimethyl- (cis/trans) | | 90 | 0.036 |
| 1640-89-7 | Cyclopentane, ethyl- | | 94 | 0.089 |
| 2452-99-5 | Cyclopentane, 1,2-dimethyl- | | 80 | 0.032 |
| 930-18-7 | Cyclopropane, 1,2-dimethyl-, cis- | | 90 | 0.019 |
| 1191-96-4 | Cyclopropane, ethyl- | | 83 | 0.022 |
| Major Oxygenates | | | | |
| 1000309-32-8 | Oxalic acid, isohexyl pentyl ester | | 83 | 8.85 |
| 23758-27-2 | 2-Cyclohexen-1-ol, 1-methyl- | | 72 | 0.38 |
| Trace Oxygenates | | | | |
| 589-92-4 | Cyclohexanone, 4-methyl- | | 78 | 0.050 |
| 107-87-9 | 2-Pentanone | | 83 | 0.010 |

FIG. 21B-2 CONT

Catalyst: 0.5%Pt/10%H$_3$PO$_4$-Al$_2$O$_3$

| Reaction conditions | | | Average #C | Product distribution (%) | | | |
|---|---|---|---|---|---|---|---|
| T (°C) | P (psig) | LFR (mL/min) | | Aromatics | Alkenes | Alkanes | Oxygenates |
| 350 | 300 | 0.125 | 8.4 | 31.09 | 3.84 | 48.64 | 0.41 |

| CAS # | Compound Name | Br# | Q | Area% |
|---|---|---|---|---|
| | Major Aromatics Hydrocarbons | | | |
| 108-38-3 | Benzene, 1,3-dimethyl- | | 95 | 2.89 |
| 95-47-6 | o-Xylene | | 95 | 1.78 |
| 2870-04-4 | Benzene, 2-ethyl-1,3-dimethyl- | | 95 | 1.45 |
| 100-41-4 | Ethylbenzene | | 91 | 1.26 |
| 4810-04-2 | Benzene, 1,3,5-trimethyl-2-propyl- | | 83 | 1.25 |
| 102-25-0 | Benzene, 1,3,5-triethyl- | | 97 | 1.04 |
| 1758-88-9 | Benzene, 2-ethyl-1,4-dimethyl- | | 95 | 1.01 |
| 108-88-3 | Toluene | | 91 | 1.00 |
| 1074-17-5 | Benzene, 1-methyl-2-propyl- | | 94 | 0.99 |
| 87-85-4 | Benzene, hexamethyl- | | 93 | 0.97 |
| 1074-55-1 | Benzene, 1-methyl-4-propyl- | | 76 | 0.87 |
| 95-63-6 | Benzene, 1,2,4-trimethyl- | | 95 | 0.82 |
| 611-14-3 | Benzene, 1-ethyl-2-methyl- | | 95 | 0.82 |
| 99-87-6 | p-Cymene | | 91 | 0.81 |
| 2050-24-0 | Benzene, 1,3-diethyl-5-methyl- | | 94 | 0.76 |
| 4706-89-2 | Benzene, 2,4-dimethyl-1-(1-methylethyl)- | | 91 | 0.74 |
| 141-93-5 | Benzene, 1,3-diethyl- | | 97 | 0.71 |
| 71-43-2 | Benzene | | 91 | 0.70 |
| 527-53-7 | Benzene, 1,2,3,5-tetramethyl- | | 94 | 0.66 |
| 582-16-1 | Naphthalene, 2,7-dimethyl- | | 95 | 0.62 |
| 54410-75-2 | Benzene, 1,2-diethyl-3,4-dimethyl- | | 94 | 0.61 |
| 933-98-2 | Benzene, 1-ethyl-2,3-dimethyl- | | 91 | 0.54 |
| 3031-15-0 | Naphthalene, 1,2,3,4-tetramethyl- | | 93 | 0.53 |
| 54340-85-1 | Benzene, 1-(2-butenyl)-2,3-dimethyl- | | 93 | 0.47 |
| 53669-88-0 | 1,4-dimethyl-2-(2-methylpropyl)benzene | | 80 | 0.46 |
| 1000383-71-7 | 4-ethyl-1,6-dimethyl-naphthalene | | 91 | 0.45 |
| 4920-99-4 | Benzene, 1-ethyl-3-(1-methylethyl)- | | 60 | 0.39 |
| 2245-38-7 | Naphthalene, 1,6,7-trimethyl- | | 97 | 0.38 |
| 6639-01-9 | 1-tert-butyl-3-ethyl-5-methyl-benzene | | 92 | 0.36 |
| 483-78-3 | 1,6-dimethyl-4-propan-2-yl-naphthalene | | 93 | 0.35 |
| 104-51-8 | Benzene, n-butyl- | | 83 | 0.30 |
| 14679-13-1 | 1,3,5-trimethyl-2-prop-1-en-2-yl-benzene | | 86 | 0.23 |
| 17851-27-3 | Benzene, 1-ethyl-2,4,5-trimethyl- | | 94 | 0.22 |
| 1000383-71-8 | 1,6-Dimethyl-3-ethylnaphthalene | | 93 | 0.20 |
| 54789-15-0 | Benzene, 1-(1-ethylpropyl)-2-propyl- | | 74 | 0.19 |
| 22531-20-0 | Naphthalene, 6-ethyl-1,2,3,4-tetrahydro- | | 81 | 0.19 |
| 19063-11-7 | 5,6,7,8-tetramethyltetralin | | 83 | 0.18 |
| 103-65-1 | Benzene, propyl- | | 87 | 0.17 |
| 1587-04-8 | Benzene, 1-methyl-2-(2-propenyl)- | | 87 | 0.16 |
| 95-93-2 | Benzene, 1,2,4,5-tetramethyl- | | 91 | 0.15 |
| 489-84-9 | Azulene, 1,4-dimethyl-7-(1-methylethyl)- | | 89 | 0.15 |
| 1585-05-7 | Benzene, 1-methyl-4-butyl- | | 64 | 0.15 |
| 17059-48-2 | 1H-Indene, 2,3-dihydro-1,6-dimethyl- | | 94 | 0.14 |
| 2049-95-8 | Benzene, (1,1-dimethylpropyl)- | | 78 | 0.14 |
| 108-67-8 | Mesitylene | | 94 | 0.12 |
| 488-23-3 | Benzene, 1,2,3,4-tetramethyl- | | 94 | 0.11 |
| 1595-16-0 | Benzene, 1-methyl-4-(1-methylpropyl)- | | 80 | 0.11 |
| 490-65-3 | Naphthalene, 1-methyl-7-(1-methylethyl)- | | 91 | 0.10 |
| | Trace Aromatic Hydrocarbons | | | |
| 700-12-9 | Benzene, pentamethyl- | | 91 | 0.098 |
| 4706-90-5 | Benzene, 1,3-dimethyl-5-(1-methylethyl)- | | 91 | 0.090 |

FIG. 22A-2 CONT

| CAS # | Compound Name | Br# | Q | Area% |
|---|---|---|---|---|
| 10223-95-4 | 1,2,4-trimethyl-5-propan-2-yl-benzene | | 64 | 0.087 |
| 1483-60-9 | Benzene, 1,3-dimethyl-4-(1-methylpropyl)- | | 64 | 0.079 |
| 874-41-9 | Benzene, 1-ethyl-2,4-dimethyl- | | 91 | 0.077 |
| 829-26-5 | Naphthalene, 2,3,6-trimethyl- | | 91 | 0.075 |
| 1000113-61-3 | 1,4,5,6-tetramethyltetralin | | 60 | 0.072 |
| 1000159-51-3 | 9-ethyl-1,2,3,4,5,6-hexahydroanthracene | | 76 | 0.070 |
| 1000383-71-2 | 2-Isopropyl-3-methylnaphthalene | | 70 | 0.062 |
| 1000383-71-3 | 2-Isopropyl-7-methylnaphthalene | | 86 | 0.060 |
| 24157-81-1 | 2,6-Diisopropylnaphthalene | | 64 | 0.057 |
| 475-03-6 | Naphthalene, tetrahydro-1,1,6-trimethyl- | | 64 | 0.057 |
| 1000374-06-1 | 1,7-di-iso-propylnaphthalene | | 76 | 0.050 |
| 939-27-5 | Naphthalene, 2-ethyl- | | 87 | 0.049 |
| 13556-58-6 | Naphthalene, 1-ethyl-1,2,3,4-tetrahydro- | | 93 | 0.046 |
| 1000374-05-2 | 1,3-di-iso-propylnaphthalene | | 81 | 0.041 |
| 934-80-5 | Benzene, 4-ethyl-1,2-dimethyl- | | 64 | 0.041 |
| 54340-86-2 | 1-[(E)-but-2-enyl]-1,2-dimethyl-benzene | | 64 | 0.036 |
| 264-09-5 | Benzocycloheptatriene | | 72 | 0.035 |
| 21693-55-0 | 1,5,7-trimethyltetralin | | 90 | 0.033 |
| 4773-83-3 | 1,2,3-Trimethylindene | | 76 | 0.032 |
| 4489-84-3 | Benzene, (3-methyl-2-butenyl)- | | 87 | 0.030 |
| Major Oxygenated Aromatics | | | | |
| 1000400-21-4 | 4-(2-Methyl-2-propanyl)phthalaldehyde | | 64 | 0.21 |
| 1000189-42-9 | 2,3,3,4,7-pentamethyl-2H-1-benzofuran | | 72 | 0.20 |
| 832-62-2 | 4,6,8-Trimethyl-1-azulenecarbaldehyde | | 89 | 0.15 |
| 1746-11-8 | Benzofuran, 2,3-dihydro-2-methyl- | | 90 | 0.11 |
| Trace Oxygenated Aromatics | | | | |
| 29002-54-8 | 4,5,6,7-Tetramethylphthalide | | 72 | 0.088 |
| 526-75-0 | Phenol, 2,3-dimethyl- | | 93 | 0.073 |
| 3855-26-3 | Phenol, 2-ethyl-4-methyl- | | 91 | 0.044 |
| 620-17-7 | Phenol, 3-ethyl- | | 60 | 0.039 |
| 6148-37-4 | Furan, 4-methyl-2-propyl- | | 72 | 0.033 |
| 89-83-8 | Thymol | | 80 | 0.018 |
| 527-60-6 | Phenol, 2,4,6-trimethyl- | | 90 | 0.018 |
| 95-87-4 | Phenol, 2,5-dimethyl- | | 87 | 0.014 |
| Major n-Alkenes | | | | |
| 4050-45-7 | 2-Hexene, (E)- | | 91 | 0.30 |
| 592-43-8 | 2-Hexene | | 91 | 0.14 |
| 592-47-2 | 3-Hexene | | 95 | 0.12 |
| 592-77-8 | 3-Heptene | | 94 | 0.11 |
| 646-04-8 | 2-Pentene, (E)- | | 91 | 0.10 |
| Trace n-Alkenes | | | | |
| 7642-10-6 | (Z)-3-Heptene | | 96 | 0.075 |
| 592-41-6 | 1-Hexene | | 94 | 0.064 |
| 106-98-9 | 1-Butene | | 90 | 0.047 |
| 7642-09-3 | 3-Hexene, (Z)- | | 91 | 0.044 |
| 109-67-1 | 1-Pentene | | 91 | 0.029 |
| 14850-23-8 | 4-Octene, (E)- | | 91 | 0.020 |
| 872-05-9 | 1-Decene | | 70 | 0.016 |
| 592-76-7 | 1-Heptene | | 94 | 0.014 |
| 115-07-1 | Propene | | 90 | 0.009 |
| 591-93-5 | 1,4-Pentadiene | | 86 | 0.004 |
| Major Branched Alkenes | | | | |

FIG. 22A-2 CONT

| CAS # | Compound Name | Br# | Q | Area% |
|---|---|---|---|---|
| 1515-79-3 | 5,5-Dimethyl-1,3-hexadiene | 2 | 91 | 0.13 |
| 3404-55-5 | 4-Methyl-2-hexene, c&t | 1 | 91 | 0.10 |
| 922-61-2 | 2-Pentene, 3-methyl- | 1 | 95 | 0.63 |
| 625-27-4 | 2-Pentene, 2-methyl- | 1 | 91 | 0.17 |
| 115-11-7 | 1-Propene, 2-methyl- | 1 | 91 | 0.11 |
| Trace Branched Alkenes ||||||
| 74630-13-0 | 3,7-Decadiene, 2,9-dimethyl- | 2 | 72 | 0.033 |
| 3404-79-3 | 2-Hexene, 3,5-dimethyl- | 2 | 83 | 0.087 |
| 7145-20-2 | 2-Hexene, 2,3-dimethyl- | 2 | 91 | 0.038 |
| 563-78-0 | 1-Butene, 2,3-dimethyl- | 2 | 91 | 0.047 |
| 2080-89-9 | 1,4-Hexadiene, 3-ethyl- | 1 | 64 | 0.018 |
| 4485-16-9 | 3-Heptene, 4-methyl- | 1 | 84 | 0.039 |
| 1832-16-2 | 3-Ethyl-2-hexene(c,t) | 1 | 72 | 0.009 |
| 7300-03-0 | 3-Heptene, 3-methyl- | 1 | 91 | 0.072 |
| 86225-17-0 | 2-Heptene, 4-methyl-, (E)- | 1 | 91 | 0.027 |
| 692-24-0 | 3-Hexene, 2-methyl-, (E)- | 1 | 91 | 0.022 |
| 4914-89-0 | 3-Hexene, 3-methyl-, (Z)- | 1 | 91 | 0.017 |
| 3404-65-7 | 3-Methyl-3-hexene | 1 | 91 | 0.086 |
| 2787-43-1 | 1,3-Pentadiene, 3-methyl-, (E)- | 1 | 80 | 0.008 |
| 763-29-1 | 1-Pentene, 2-methyl- | 1 | 91 | 0.073 |
| 4461-48-7 | 2-Pentene, 4-methyl- | 1 | 91 | 0.009 |
| 760-20-3 | 1-Pentene, 3-methyl- | 1 | 91 | 0.041 |
| 513-35-9 | 2-Butene, 2-methyl- | 1 | 91 | 0.058 |
| Major Cyclic Alkenes ||||||
| 53280-01-2 | 1,3-Cyclohexadiene, 2,6,6-trimethyl-1-(3-methyl-1,3-butadienyl)- |  | 66 | 0.34 |
| 97787-57-4 | 1-Ethyl-5-methylcyclopentene |  | 78 | 0.21 |
| 1000156-99-7 | 3,4-diethyl-7,7-dimethylcyclohepta-1,3,5-triene |  | 81 | 0.14 |
| Trace Cyclic Alkenes ||||||
| 1000156-99-5 | 2,5-diethyl-7,7-dimethylcyclohepta-1,3,5-triene |  | 64 | 0.077 |
| 53366-54-4 | Cyclopentane, (2-methylbutylidene)- |  | 78 | 0.063 |
| 1453-24-3 | Cyclohexene, 1-ethyl- |  | 68 | 0.074 |
| 823-17-6 | Cyclohexene, 3,5-dimethyl- |  | 83 | 0.020 |
| 19780-56-4 | Methyl ethyl cyclopentene |  | 80 | 0.018 |
| 110-83-8 | Cyclohexene |  | 72 | 0.005 |
| 693-89-0 | Cyclopentene, 1-methyl- |  | 90 | 0.073 |
| 16327-38-1 | Cyclobutene, 3,3-dimethyl- |  | 86 | 0.004 |
| 1120-62-3 | Cyclopentene, 3-methyl- |  | 78 | 0.012 |
| Major n-Alkanes ||||||
| 110-54-3 | n-Hexane |  | 91 | 12.15 |
| 142-82-5 | Heptane |  | 95 | 5.98 |
| 109-66-0 | Pentane |  | 91 | 3.31 |
| 111-84-2 | Nonane |  | 95 | 1.61 |
| 106-97-8 | Butane |  | 87 | 1.03 |
| 124-18-5 | Decane |  | 95 | 0.97 |
| 1120-21-4 | Undecane |  | 90 | 0.40 |
| Major Branched Alkanes ||||||
| 921-47-1 | Hexane, 2,3,4-trimethyl- | 3 | 90 | 0.22 |
| 20278-89-1 | Heptane, 3,4,5-trimethyl- | 3 | 83 | 2.78 |
| 2213-23-2 | Heptane, 2,4-dimethyl- | 2 | 72 | 4.97 |
| 583-48-2 | Hexane, 3,4-dimethyl- | 2 | 83 | 0.18 |
| 15869-96-2 | Octane, 4,5-dimethyl- | 2 | 83 | 0.13 |
| 589-43-5 | Hexane, 2,4-dimethyl- | 2 | 83 | 0.11 |

FIG. 22A-2 CONT

| CAS # | Compound Name | Br# | Q | Area% |
|---|---|---|---|---|
| 565-59-3 | Pentane, 2,3-dimethyl- | 2 | 83 | 0.12 |
| 1002-43-3 | Undecane, 3-methyl- | 1 | 64 | 0.13 |
| 5911-04-6 | Nonane, 3-methyl- | 1 | 90 | 0.55 |
| 5881-17-4 | Octane, 3-ethyl- | 1 | 78 | 0.13 |
| 17301-94-9 | Nonane, 4-methyl- | 1 | 72 | 0.27 |
| 13287-21-3 | Tridecane, 6-methyl- | 1 | 80 | 0.36 |
| 2216-33-3 | Octane, 3-methyl- | 1 | 81 | 0.33 |
| 3221-61-2 | Octane, 2-methyl- | 1 | 83 | 0.11 |
| 619-99-8 | Hexane, 3-ethyl- | 1 | 91 | 0.62 |
| 589-53-7 | Heptane, 4-methyl- | 1 | 81 | 0.61 |
| 592-27-8 | Heptane, 2-methyl- | 1 | 95 | 0.58 |
| 617-78-7 | Pentane, 3-ethyl- | 1 | 91 | 0.18 |
| 591-76-4 | Hexane, 2-methyl- | 1 | 81 | 0.39 |
| 96-14-0 | Pentane, 3-methyl- | 1 | 91 | 3.80 |
| 107-83-5 | Pentane, 2-methyl- | 1 | 83 | 1.44 |
| 78-78-4 | Butane, 2-methyl- | 1 | 91 | 0.29 |
| | Trace Branched Alkanes | | | |
| 15869-93-9 | Octane, 3,3-dimethyl- | 2 | 78 | 0.054 |
| 17312-50-4 | Decane, 2,5-dimethyl- | 2 | 83 | 0.029 |
| 609-26-7 | 3-ethyl-2-methyl-pentane | 2 | 74 | 0.037 |
| 563-16-6 | Hexane, 3,3-dimethyl- | 2 | 78 | 0.064 |
| 590-73-8 | Hexane, 2,2-dimethyl- | 2 | 83 | 0.018 |
| 590-35-2 | Pentane, 2,2-dimethyl- | 2 | 83 | 0.018 |
| 79-29-8 | Butane, 2,3-dimethyl- | 2 | 72 | 0.039 |
| 75-83-2 | Butane, 2,2-dimethyl- | 2 | 72 | 0.011 |
| 2847-72-5 | Decane, 4-methyl- | 1 | 91 | 0.063 |
| 13151-35-4 | Decane, 3-methyl- | 1 | 81 | 0.088 |
| 2216-32-2 | Heptane, 4-ethyl- | 1 | 83 | 0.096 |
| | Major Cyclic Alkanes | | | |
| 3726-47-4 | Cyclopentane, 1-ethyl-3-methyl- | | 83 | 1.38 |
| 110-82-7 | Cyclohexane | | 91 | 0.88 |
| 930-89-2 | Cyclopentane, 1-ethyl-2-methyl-, cis- | | 96 | 0.45 |
| 7058-05-1 | Cyclohexane, 1-ethyl-2,3-dimethyl- | | 62 | 0.23 |
| 7045-67-2 | Cyclohexane, 2-ethyl-1,3-dimethyl- | | 64 | 0.31 |
| 13152-02-8 | Cyclooctane, ethyl- | | 64 | 0.17 |
| 108-87-2 | Cyclohexane, methyl- | | 91 | 0.11 |
| 1640-89-7 | Cyclopentane, ethyl- | | 93 | 0.11 |
| | Trace Cyclic Alkanes | | | |
| 4126-78-7 | Cycloheptane, methyl- | | 87 | 0.090 |
| 3073-66-3 | Cyclohexane, 1,1,3-trimethyl- | | 64 | 0.026 |
| 2040-95-1 | Cyclopentane, butyl- | | 72 | 0.032 |
| 3728-52-3 | Cyclopentane, 1-methyl-2-propyl- | | 90 | 0.018 |
| 7667-55-2 | 1,cis-2,trans-3-Trimethylcyclohexane | | 90 | 0.014 |
| 932-40-1 | trans-1,2-Diethyl cyclopentane | | 83 | 0.069 |
| 3728-54-9 | Cyclohexane, 1-ethyl-2-methyl- | | 86 | 0.019 |
| 6876-23-9 | Cyclohexane, 1,2-dimethyl-, trans- | | 87 | 0.019 |
| 16747-50-5 | Cyclopentane, 1-ethyl-1-methyl- | | 83 | 0.061 |
| 589-90-2 | Cyclohexane, 1,4-dimethyl- | | 91 | 0.089 |
| 2613-69-6 | (1R,2s,3S)-1,2,3-Trimethylcyclopentane | | 86 | 0.044 |
| 2815-58-9 | Cyclopentane, 1,2,4-trimethyl- | | 91 | 0.040 |
| 2453-00-1 | Cyclopentane, 1,3-dimethyl- | | 90 | 0.031 |
| 5780-03-7 | Butane, 2-cyclopropyl- | | 64 | 0.012 |

FIG. 22A-2 CONT

| CAS # | Compound Name | Br# | Q | Area% |
|---|---|---|---|---|
| 2452-99-5 | Cyclopentane, 1,2-dimethyl- | | 94 | 0.088 |
| 2532-58-3 | Cyclopentane, 1,3-dimethyl-, cis- | | 86 | 0.037 |
| 1759-58-6 | Cyclopentane, 1,3-dimethyl-, trans- | | 83 | 0.055 |
| 1638-26-2 | Cyclopentane, 1,1-dimethyl- | | 74 | 0.025 |
| 4127-45-1 | Cyclopropane, 1,1,2-trimethyl- | | 91 | 0.041 |
| 287-92-3 | Cyclopentane | | 78 | 0.010 |
| 930-18-7 | Cyclopropane, 1,2-dimethyl-, cis- | | 90 | 0.022 |
| Major Oxygenates | | | | |
| 60-29-7 | Ethyl ether | | 91 | 0.38 |
| Trace Oxygenates | | | | |
| 584-02-1 | 3-Pentanol | | 64 | 0.012 |
| 107-87-9 | 2-Pentanone | | 86 | 0.028 |
| 78-93-3 | 2-Butanone | | 74 | 0.010 |
| 78-84-2 | Propanal, 2-methyl- | | 64 | 0.059 |
| 75-07-0 | Acetaldehyde | | 83 | 0.020 |

FIG. 22A-2 CONT

Catalyst: 0.5%Pt/10%$H_3PO_4$-$Al_2O_3$

| Reaction conditions | | | Average #C | Product distribution (%) | | | |
|---|---|---|---|---|---|---|---|
| T (°C) | P (psig) | LFR (mL/min) | | Aromatics | Alkenes | Alkanes | Oxygenates |
| 350 | 500 | 0.125 | 9.66 | 39.53 | 1.6 | 45.10 | 0.30 |

| CAS # | Compound Name | Br# | Q | Area % |
|---|---|---|---|---|
| \multicolumn{5}{c}{Major Aromatics Hydrocarbons} ||||||
| 874-41-9 | Benzene, 1-ethyl-2,4-dimethyl- | | 95 | 4.26 |
| 106-42-3 | p-Xylene | | 95 | 2.49 |
| 102-25-0 | Benzene, 1,3,5-triethyl- | | 97 | 2.35 |
| 87-85-4 | Benzene, hexamethyl- | | 94 | 2.12 |
| 1074-55-1 | Benzene, 1-methyl-4-propyl- | | 91 | 1.93 |
| 1483-60-9 | Benzene, 1,3-dimethyl-4-(1-methylpropyl)- | | 74 | 1.77 |
| 95-47-6 | o-Xylene | | 95 | 1.73 |
| 934-80-5 | Benzene, 4-ethyl-1,2-dimethyl- | | 95 | 1.51 |
| 100-41-4 | Ethylbenzene | | 91 | 1.48 |
| 141-93-5 | Benzene, 1,3-diethyl- | | 97 | 1.28 |
| 2050-24-0 | Benzene, 1,3-diethyl-5-methyl- | | 95 | 1.25 |
| 35668-88-0 | 1,4-dimethyl-2-(2-methylpropyl)benzene | | 80 | 1.22 |
| 526-73-8 | Benzene, 1,2,3-trimethyl- | | 97 | 0.91 |
| 4810-04-2 | Benzene, 1,3,5-trimethyl-2-propyl- | | 90 | 0.89 |
| 1074-43-7 | Benzene, 1-methyl-3-propyl- | | 91 | 0.82 |
| 1758-88-9 | Benzene, 2-ethyl-1,4-dimethyl- | | 95 | 0.82 |
| 6630-01-9 | 1-tert-butyl-3-ethyl-5-methyl-benzene | | 86 | 0.79 |
| 611-14-3 | Benzene, 1-ethyl-2-methyl- | | 94 | 0.72 |
| 58502-85-5 | 2-methyl-1,4-di(propan-2-yl)benzene | | 91 | 0.59 |
| 483-78-3 | 1,6-dimethyl-4-propan-2-yl-naphthalene | | 93 | 0.56 |
| 13632-94-5 | Benzene, 1,4-diethyl-2-methyl- | | 97 | 0.58 |
| 1595-16-0 | Benzene, 1-methyl-4-(1-methylpropyl)- | | 91 | 0.53 |
| 108-67-8 | Mesitylene | | 91 | 0.53 |
| 3031-15-0 | Naphthalene, 1,2,3,4-tetramethyl- | | 95 | 0.47 |
| 2717-39-7 | 1,4,5,8-Tetramethylnaphthalene | | 94 | 0.43 |
| 104-51-8 | Benzene, n-butyl- | | 91 | 0.41 |
| 4706-90-5 | Benzene, 1,3-dimethyl-5-(1-methylethyl)- | | 94 | 0.40 |
| 31365-98-7 | Benzene, 3-ethyl-1,2,4,5-tetramethyl- | | 64 | 0.40 |
| 1000383-71-7 | 4-ethyl-1,6-dimethyl-naphthalene | | 93 | 0.40 |
| 544-25-2 | 1,3,5-Cycloheptatriene | | 91 | 0.40 |
| 1000383-71-8 | 1,6-Dimethyl-3-ethylnaphthalene | | 95 | 0.32 |
| 54410-73-2 | Benzene, 1,2-diethyl-3,4-dimethyl- | | 94 | 0.32 |
| 99-87-6 | p-Cymene | | 91 | 0.26 |
| \multicolumn{5}{c}{Major Aromatics Hydrocarbons} ||||||
| 17851-27-3 | Benzene, 1-ethyl-2,4,5-trimethyl- | | 91 | 0.26 |
| 19063-11-7 | 5,6,7,8-tetramethyltetralin | | 78 | 0.25 |
| 135-01-3 | Benzene, 1,2-diethyl- | | 94 | 0.25 |
| 489-84-9 | Azulene, 1,4-dimethyl-7-(1-methylethyl)- | | 89 | 0.21 |
| 15181-13-2 | Benzene, 1-ethyl-3,5-diisopropyl- | | 74 | 0.21 |
| 14679-13-1 | 1,3,5-trimethyl-2-prop-1-en-2-yl-benzene | | 78 | 0.20 |
| 529-05-5 | Chamazulene | | 96 | 0.20 |
| 1000374-05-7 | 1,4-di-iso-propylnaphthalene | | 90 | 0.18 |
| 1000113-81-3 | 1,4,5,6-tetramethyltetralin | | 86 | 0.16 |
| 829-26-5 | Naphthalene, 2,3,6-trimethyl- | | 96 | 0.16 |
| 934-74-7 | Benzene, 1-ethyl-3,5-dimethyl- | | 91 | 0.15 |
| 1595-05-7 | Benzene, 1-methyl-4-butyl | | 72 | 0.15 |
| 103-65-1 | Benzene, propyl- | | 87 | 0.14 |
| 2245-38-7 | Naphthalene, 1,6,7-trimethyl- | | 97 | 0.14 |
| 18222-95-4 | 1,2,4-trimethyl-5-propan-2-yl-benzene | | 70 | 0.14 |
| 527-53-7 | Benzene, 1,2,3,5-tetramethyl- | | 81 | 0.14 |
| 4132-72-3 | Benzene, 1,4-dimethyl-2-(1-methylethyl)- | | 91 | 0.12 |

FIG. 22B-2 CONT

| CAS # | Compound Name | Br# | Q | Area % |
|---|---|---|---|---|
| 1000183-71-3 | 2-Isopropyl-7-methylnaphthalene | | 76 | 0.11 |
| 98-51-1 | 4-tert-Butyltoluene | | 64 | 0.11 |
| 24157-81-1 | 2,6-Diisopropylnaphthalene | | 76 | 0.11 |
| 527-84-4 | o-Cymene | | 91 | 0.11 |
| Trace Aromatic Hydrocarbons | | | | |
| 1000374-05-2 | 1,3-di-iso-propylnaphthalene | | 90 | 0.098 |
| 55172-84-2 | Benzene, (1-methyl-1-butenyl)- | | 70 | 0.095 |
| 2049-95-8 | Benzene, (1,1-dimethylpropyl)- | | 64 | 0.091 |
| 54340-85-1 | Benzene, 1-(2-butenyl)-2,3-dimethyl- | | 91 | 0.080 |
| 1000374-06-1 | 1,7-di-iso-propylnaphthalene | | 89 | 0.080 |
| 81603-43-2 | 8-isopropyl-1-methyl-tetralin | | 64 | 0.071 |
| 490-65-3 | Naphthalene, 1-methyl-7-(1-methylethyl)- | | 93 | 0.069 |
| 71-43-2 | Benzene | | 91 | 0.061 |
| 54774-89-9 | 2-methyl-1-propyl-naphthalene | | 70 | 0.060 |
| 22531-20-0 | Naphthalene, 6-ethyl-1,2,3,4-tetrahydro- | | 66 | 0.052 |
| 581-42-0 | Naphthalene, 2,6-dimethyl- | | 93 | 0.044 |
| 84879-58-3 | 1,3,5-trimethyl-2,4,6-trivinyl-benzene | | 90 | 0.042 |
| 4175-54-6 | 1,4-dimethyltetralin | | 64 | 0.039 |
| 1127-76-0 | 1-ethylnaphthalene | | 90 | 0.032 |
| 90-12-0 | Naphthalene, 1-methyl- | | 64 | 0.031 |
| 941-81-1 | 4,6,8-Trimethylazulene | | 95 | 0.030 |
| 1000187-78-5 | 3-(2-Methyl-propenyl)-1H-indene | | 86 | 0.023 |
| 1000159-51-3 | 9-ethyl-1,2,3,4,5,6-hexahydroanthracene | | 87 | 0.019 |
| 17059-48-2 | 1H-Indene, 2,3-dihydro-1,6-dimethyl- | | 86 | 0.018 |
| 622-96-8 | Benzene, 1-ethyl-4-methyl- | | 64 | 0.011 |
| Major Oxygenated Aromatics | | | | |
| 1518-83-8 | Phenol, 4-cyclopentyl- | | 64 | 0.36 |
| 832-62-2 | 4,6,8-Trimethyl-1-azulenecarbaldehyde | | 90 | 0.19 |
| Trace Oxygenated Aromatics | | | | |
| 35355-35-2 | Benzofuran, 5-methoxy-6,7-dimethyl- | | 76 | 0.090 |
| 834-97-9 | 1-Acetyl-4,6,8-trimethylazulene | | 70 | 0.056 |
| 28394-32-0 | 6-Methyl-4-indanol | | 80 | 0.052 |
| 39701-08-1 | 8,9-Dehydrothymol methyl ether | | 83 | 0.030 |
| 55059-21-7 | 1,1'-Biphenyl, 3-(1,1-dimethylethoxy)- | | 70 | 0.028 |
| Major n-Alkenes | | | | |
| 14850-22-7 | 3-Octene, (Z)- | | 76 | 0.21 |
| 19308-89-1 | trans-4-Decene | | 87 | 0.11 |
| 13389-42-9 | 2-Octene, (E)- | | 94 | 0.10 |
| Trace n-Alkenes | | | | |
| 7206-21-3 | 5-Octadecene, (E)- | | 72 | 0.059 |
| 14850-23-8 | 4-Octene, (E)- | | 91 | 0.051 |
| 592-77-8 | 2-Heptene | | 91 | 0.046 |
| 111-67-1 | 2-Octene | | 94 | 0.031 |
| 14686-14-7 | 3-Heptene, (E)- | | 95 | 0.029 |
| 10405-84-2 | cis-4-Nonene | | 90 | 0.028 |
| 20063-92-7 | 3-Nonene, (E)- | | 91 | 0.021 |
| 6434-77-1 | cis-2-Nonene | | 90 | 0.020 |
| 592-78-9 | 3-Heptene | | 86 | 0.019 |
| 7642-09-3 | 3-Hexene, (Z)- | | 90 | 0.010 |
| 7688-21-3 | 2-Hexene, (Z)- | | 90 | 0.010 |
| 2198-23-4 | 4-Nonene | | 90 | 0.008 |
| 592-41-6 | 1-Hexene | | 83 | 0.002 |

FIG. 22B-2 CONT

| CAS # | Compound Name | Br# | Q | Area % |
|---|---|---|---|---|
| | Trace Branched Alkenes | | | |
| 3404-75-9 | 2-Heptene, 3-methyl- | 1 | 87 | 0.074 |
| 4485-16-9 | 3-Heptene, 4-methyl- | 1 | 83 | 0.015 |
| 7300-03-0 | 3-Heptene, 3-methyl- | 1 | 91 | 0.039 |
| 1632-16-2 | 3-Ethyl-2-hexene(c,t) | 1 | 86 | 0.015 |
| 816-79-5 | 2-Pentene, 3-ethyl- | 1 | 90 | 0.007 |
| 922-61-2 | 2-Pentene, 3-methyl- | 1 | 94 | 0.021 |
| 922-62-3 | 2-Pentene, 3-methyl-, (Z)- | 1 | 90 | 0.008 |
| | Major Cyclic Alkenes | | | |
| 1000156-99-7 | 3,4-diethyl-7,7-dimethylcyclohepta-1,3,5-triene | | 76 | 0.19 |
| | Trace Cyclic Alkenes | | | |
| 94400-10-9 | 7-Ethylidenebicyclo[4.2.1]nona-2,4-diene | | 64 | 0.018 |
| 53366-54-4 | Cyclopentane, (2-methylbutylidene)- | | 72 | 0.044 |
| 19780-66-4 | Methyl ethyl cyclopentene | | 83 | 0.021 |
| | Major n-Alkanes | | | |
| 142-82-5 | Heptane | | 95 | 3.87 |
| 111-84-2 | Nonane | | 95 | 3.32 |
| 124-18-5 | Decane | | 95 | 2.72 |
| 110-54-3 | n-Hexane | | 91 | 1.78 |
| 1120-21-4 | Undecane | | 91 | 0.94 |
| 112-40-3 | Dodecane | | 94 | 0.52 |
| 629-50-5 | Tridecane | | 93 | 0.20 |
| | Trace n-Alkanes | | | |
| 109-66-0 | Pentane | | 91 | 0.053 |
| 629-62-9 | Pentadecane | | 64 | 0.039 |
| 106-97-8 | Butane | | 80 | 0.034 |
| 629-92-5 | Nonadecane | | 64 | 0.023 |
| | Major Branched Alkanes | | | |
| 62238-13-5 | Decane, 2,3,7-trimethyl- | 3 | 64 | 0.10 |
| 62016-34-6 | Octane, 2,3,7-trimethyl- | 3 | 64 | 0.41 |
| 20278-89-1 | Heptane, 3,4,5-trimethyl- | 3 | 87 | 0.86 |
| 7154-80-5 | Heptane, 3,3,5-trimethyl- | 3 | 83 | 0.15 |
| 16747-28-7 | Hexane, 2,3,3-trimethyl- | 3 | 72 | 0.13 |
| 15869-92-8 | Octane, 3,4-dimethyl- | 2 | 83 | 0.13 |
| 2051-30-1 | Octane, 2,6-dimethyl- | 2 | 72 | 0.21 |
| 15869-93-9 | Octane, 3,5-dimethyl- | 2 | 80 | 1.09 |
| 7146-60-3 | Octane, 2,3-dimethyl- | 2 | 72 | 0.35 |
| 583-48-2 | Hexane, 3,4-dimethyl- | 2 | 83 | 0.22 |
| 584-94-1 | Hexane, 2,3-dimethyl- | 2 | 83 | 0.16 |
| 563-16-6 | Hexane, 3,3-dimethyl- | 2 | 86 | 0.13 |
| 589-43-5 | Hexane, 2,4-dimethyl- | 2 | 83 | 9.35 |
| 1002-43-3 | Undecane, 3-methyl- | 1 | 64 | 0.36 |
| 17312-63-9 | Nonane, 5-butyl- | 1 | 72 | 0.11 |
| 5881-17-4 | Octane, 3-ethyl- | 1 | 83 | 0.13 |
| 13151-35-4 | Decane, 5-methyl- | 1 | 91 | 0.16 |
| 5911-04-6 | Nonane, 3-methyl- | 1 | 91 | 1.89 |
| 13287-21-3 | Tridecane, 6-methyl- | 1 | 64 | 0.80 |
| 2216-33-3 | Octane, 3-methyl- | 1 | 80 | 0.51 |
| 3221-61-2 | Octane, 2-methyl- | 1 | 72 | 0.17 |
| 2216-32-2 | Heptane, 4-ethyl- | 1 | 83 | 0.17 |
| 619-99-8 | Hexane, 3-ethyl- | 1 | 94 | 1.52 |
| 589-81-1 | Heptane, 3-methyl- | 1 | 83 | 5.49 |

FIG. 22B-2 CONT

| CAS # | Compound Name | Br# | Q | Area % |
|---|---|---|---|---|
| 589-53-7 | Heptane, 4-methyl- | 1 | 91 | 1.03 |
| 592-27-8 | Heptane, 2-methyl- | 1 | 95 | 0.87 |
| 589-34-4 | Hexane, 3-methyl- | 1 | 91 | 0.40 |
| 591-76-4 | Hexane, 2-methyl- | 1 | 91 | 0.15 |
| 96-14-0 | Pentane, 3-methyl- | 1 | 97 | 0.37 |
| Trace Branched Alkanes | | | | |
| 594-82-1 | Butane, 2,2,3,3-tetramethyl- | 4 | 74 | 0.018 |
| 17301-33-6 | Undecane, 4,8-dimethyl- | 2 | 64 | 0.032 |
| 52896-91-0 | Heptane, 3-ethyl-4-methyl- | 2 | 64 | 0.054 |
| 15869-95-1 | 4,4-Dimethyl octane | 2 | 83 | 0.054 |
| 17312-45-7 | Decane, 3,4-dimethyl- | 2 | 64 | 0.052 |
| 2216-30-0 | Heptane, 2,5-dimethyl- | 2 | 83 | 0.052 |
| 609-26-7 | 3-ethyl-2-methyl-pentane | 2 | 83 | 0.073 |
| 565-59-3 | Pentane, 2,3-dimethyl- | 2 | 83 | 0.050 |
| 108-08-7 | Pentane, 2,4-dimethyl- | 2 | 83 | 0.003 |
| 26741-18-4 | 9-methylheptadecane | 1 | 80 | 0.088 |
| 2847-72-5 | Decane, 4-methyl- | 1 | 64 | 0.026 |
| 617-78-7 | Pentane, 3-ethyl- | 1 | 90 | 0.100 |
| 107-83-5 | Pentane, 2-methyl- | 1 | 60 | 0.084 |
| Major Cyclic Alkanes | | | | |
| 2613-66-3 | Cyclopentane, 1-ethyl-3-methyl-, cis- | | 83 | 0.85 |
| 2613-65-2 | Cyclopentane, 1-ethyl-3-methyl-, trans- | | 78 | 0.77 |
| 930-89-2 | Cyclopentane, 1-ethyl-2-methyl-, cis- | | 95 | 0.73 |
| 13151-99-0 | Cyclooctane, 1,4-dimethyl-, cis- | | 60 | 0.22 |
| 61142-68-5 | Cyclopentane, 1-hexyl-3-methyl- | | 80 | 0.21 |
| 7045-67-2 | Cyclohexane, 2-ethyl-1,3-dimethyl- | | 72 | 0.18 |
| 4126-78-7 | Cycloheptane, methyl- | | 83 | 0.19 |
| Trace Cyclic Alkanes | | | | |
| 2040-96-2 | Cyclopentane, propyl- | | 62 | 0.077 |
| 7058-05-1 | Cyclohexane, 1-ethyl-2,3-dimethyl- | | 72 | 0.033 |
| 1678-81-5 | cis,trans,cis-1,2,3-Trimethylcyclohexane | | 70 | 0.035 |
| 19489-10-2 | cis-1-Ethyl-3-methyl-cyclohexane | | 80 | 0.012 |
| 624-29-3 | Cyclohexane, 1,4-dimethyl-, cis- | | 74 | 0.040 |
| 16747-50-5 | Cyclopentane, 1-ethyl-1-methyl- | | 83 | 0.050 |
| 589-90-2 | Cyclohexane, 1,4-dimethyl- | | 91 | 0.050 |
| 2815-58-9 | Cyclopentane, 1,2,4-trimethyl- | | 90 | 0.025 |
| 1640-89-7 | Cyclopentane, ethyl- | | 91 | 0.030 |
| 108-87-2 | Cyclohexane, methyl- | | 94 | 0.034 |
| 2532-58-3 | Cyclopentane, 1,3-dimethyl-, cis- | | 83 | 0.014 |
| 110-82-7 | Cyclohexane | | 91 | 0.024 |
| 96-37-7 | Cyclopentane, methyl- | | 91 | 0.055 |
| Trace Oxygenates | | | | |
| 110225-00-8 | 1-Dodecanol, 2-hexyl- | | 72 | 0.069 |
| 13726-15-5 | 4-Heptanone, 3-methyl- | | 91 | 0.050 |
| 112-42-5 | 1-Undecanol | | 64 | 0.020 |
| 628-81-9 | Butane, 1-ethoxy- | | 83 | 0.044 |
| 78-84-2 | Propanal, 2-methyl- | | 64 | 0.037 |
| 60-29-7 | Ethyl ether | | 90 | 0.024 |

FIG. 22B-2 CONT

Catalyst: 0.5%Pt/10%H$_3$PO$_4$-Al$_2$O$_3$

| Reaction conditions | | | Average #C | Product distribution (%) | | | |
|---|---|---|---|---|---|---|---|
| T (°C) | P (psig) | LFR (mL/min) | | Aromatics | Alkenes | Alkanes | Oxygenates |
| 350 | 700 | 0.125 | 8.80 | 30.43 | 1.78 | 47.27 | 1.04 |

| CAS # | Compound Name | Br# | Q | Area % |
|---|---|---|---|---|
| | Major Aromatics Hydrocarbons |||||
| 874-41-9 | Benzene, 1-ethyl-2,4-dimethyl- | | 95 | 3.06 |
| 54410-75-2 | Benzene, 1,2-diethyl-3,4-dimethyl- | | 93 | 1.73 |
| 95-47-6 | o-Xylene | | 94 | 1.68 |
| 106-42-3 | p-Xylene | | 94 | 1.62 |
| 100-41-4 | Ethylbenzene | | 91 | 1.07 |
| 1758-88-9 | Benzene, 2-ethyl-1,4-dimethyl- | | 95 | 1.06 |
| 611-14-3 | Benzene, 1-ethyl-2-methyl- | | 95 | 0.91 |
| 2050-24-0 | Benzene, 1,3-diethyl-5-methyl- | | 94 | 0.91 |
| 87-85-4 | Benzene, hexamethyl- | | 94 | 0.84 |
| 1074-17-5 | Benzene, 1-methyl-2-propyl- | | 74 | 0.83 |
| 108-38-3 | Benzene, 1,3-dimethyl- | | 95 | 0.82 |
| 99-87-6 | p-Cymene | | 91 | 0.82 |
| 108-88-3 | Toluene | | 90 | 0.75 |
| 483-78-3 | 1,6-dimethyl-4-propan-2-yl-naphthalene | | 93 | 0.66 |
| 108-67-8 | Mesitylene | | 95 | 0.66 |
| 141-93-5 | Benzene, 1,3-diethyl- | | 97 | 0.64 |
| 1074-43-7 | Benzene, 1-methyl-3-propyl- | | 94 | 0.56 |
| 71-43-2 | Benzene | | 91 | 0.52 |
| 5557-93-7 | 1-(1-methylethenyl)-2-propan-2-ylbenzene | | 70 | 0.50 |
| 4810-04-2 | Benzene, 1,3,5-trimethyl-2-propyl- | | 87 | 0.46 |
| 19063-11-7 | 5,6,7,8-tetramethyltetralin | | 78 | 0.44 |
| 1074-55-1 | Benzene, 1-methyl-4-propyl- | | 90 | 0.44 |
| 54789-15-0 | Benzene, 1-(1-ethylpropyl)-2-propyl- | | 76 | 0.44 |
| 1595-16-0 | Benzene, 1-methyl-4-(1-methylpropyl)- | | 83 | 0.42 |
| 1758-85-6 | Benzene, 2,4-diethyl-1-methyl- | | 95 | 0.41 |
| 4706-90-5 | Benzene, 1,3-dimethyl-5-(1-methylethyl)- | | 94 | 0.38 |
| 3031-15-0 | Naphthalene, 1,2,3,4-tetramethyl- | | 94 | 0.36 |
| 54340-86-2 | 4-[(E)-but-2-enyl]-1,2-dimethyl-benzene | | 94 | 0.31 |
| 489-84-9 | Azulene, 1,4-dimethyl-7-(1-methylethyl)- | | 91 | 0.30 |
| 61142-67-4 | 1,2,3,4-tetramethyl-5-propan-2-ylbenzene | | 64 | 0.30 |
| 1000319-40-2 | Benzene, 1-ethyl-4-(2-methylpropyl)- | | 64 | 0.28 |
| 104-51-8 | Benzene, n-butyl- | | 91 | 0.28 |
| 488-23-3 | Benzene, 1,2,3,4-tetramethyl- | | 90 | 0.28 |
| 55669-88-0 | 1,4-dimethyl-2-(2-methylpropyl)benzene | | 80 | 0.27 |
| 1000383-71-8 | 1,6-Dimethyl-3-ethylnaphthalene | | 90 | 0.21 |
| 1000370-34-1 | 3,4-Dimethylcumene | | 90 | 0.20 |
| 1000374-05-7 | 1,4-di-iso-propylnaphthalene | | 86 | 0.19 |
| 2717-39-7 | 1,4,5,8-Tetramethylnaphthalene | | 94 | 0.18 |
| 877-44-1 | Benzene, 1,2,4-triethyl- | | 94 | 0.18 |
| 475-03-6 | Naphthalene, tetrahydro-1,1,6-trimethyl- | | 78 | 0.17 |
| 1595-05-7 | Benzene, 1-methyl-4-butyl- | | 72 | 0.16 |
| 103-65-1 | Benzene, propyl- | | 90 | 0.15 |
| 2245-38-7 | Naphthalene, 1,6,7-trimethyl- | | 93 | 0.15 |
| 42775-75-7 | Naphthalene, 5-ethyl-1,2,3,4-tetrahydro- | | 91 | 0.14 |
| 535-77-3 | Benzene, 1-methyl-3-(1-methylethyl)- | | 91 | 0.14 |
| 622-96-8 | Benzene, 1-ethyl-4-methyl- | | 91 | 0.14 |
| 135-01-3 | Benzene, 1,2-diethyl- | | 94 | 0.11 |
| 54340-88-4 | 1H-Indene, 2,3-dihydro-1,5,7-trimethyl- | | 93 | 0.11 |
| 22531-20-0 | Naphthalene, 6-ethyl-1,2,3,4-tetrahydro- | | 89 | 0.10 |
| 100-18-5 | Benzene, 1,4-bis(1-methylethyl)- | | 86 | 0.10 |

FIG. 22C-2 CONT

| CAS # | Compound Name | B# | Q | Area % |
|---|---|---|---|---|
| Trace Aromatic Hydrocarbons ||||||
| 829-26-5 | Naphthalene, 2,3,6-trimethyl- | | 91 | 0.095 |
| 4175-54-6 | 1,4-dimethyltetralin | | 70 | 0.095 |
| 4706-89-2 | Benzene, 2,4-dimethyl-1-(1-methylethyl)- | | 91 | 0.095 |
| 768-57-2 | Benzene, (1,2-dimethyl-1-propenyl)- | | 76 | 0.093 |
| 490-65-3 | Naphthalene, 1-methyl-7-(1-methylethyl)- | | 78 | 0.090 |
| 37693-77-3 | Ethyltetramethylcyclopentadiene | | 80 | 0.083 |
| 1000374-06-1 | 1,7-di-iso-propylnaphthalene | | 86 | 0.081 |
| 50704-01-3 | Benzene, (1,3-dimethyl-2-butenyl)- | | 74 | 0.077 |
| 2027-17-0 | Naphthalene, 2-(1-methylethyl)- | | 74 | 0.076 |
| 582-16-1 | Naphthalene, 2,7-dimethyl- | | 66 | 0.075 |
| 581-42-0 | Naphthalene, 2,6-dimethyl- | | 95 | 0.073 |
| 1000159-51-3 | 9-ethyl-1,2,3,4,5,6-hexahydroanthracene | | 64 | 0.063 |
| 81603-43-2 | 8-isopropyl-1-methyl-tetralin | | 64 | 0.063 |
| 13556-58-6 | Naphthalene, 1-ethyl-1,2,3,4-tetrahydro- | | 90 | 0.060 |
| 54340-85-1 | Benzene, 1-(2-butenyl)-2,3-dimethyl- | | 78 | 0.058 |
| 1000113-61-3 | 1,4,5,6-tetramethyltetralin | | 83 | 0.057 |
| 489-77-0 | 6-Isopropyl-1,4-dimethylnaphthalene | | 83 | 0.046 |
| 17059-48-2 | 1H-Indene, 2,3-dihydro-1,6-dimethyl- | | 87 | 0.046 |
| 24157-81-1 | 2,6-Diisopropylnaphthalene | | 78 | 0.046 |
| 1127-76-0 | 1-ethylnaphthalene | | 81 | 0.042 |
| 1610-22-6 | Chrysene, 1,2,3,4,4a,7,8,9,10,11,12,12a-dodecahydro- | | 70 | 0.036 |
| 527-84-4 | o-Cymene | | 72 | 0.032 |
| 1000383-71-4 | 3-Isopropyl-1-methylnaphthalene | | 86 | 0.023 |
| Major Oxygenated Aromatics ||||||
| 1518-83-8 | Phenol, 4-cyclopentyl- | | 83 | 0.95 |
| 29002-54-8 | 4,5,6,7-Tetramethylphthalide | | 80 | 0.48 |
| 101327-54-2 | Naphthalene, 6-methoxy-2-(1-buten-3-yl)- | | 80 | 0.19 |
| 34862-94-7 | 1-Penten-3-ol, 1-phenyl- | | 72 | 0.17 |
| 36052-28-5 | (8-methyltetralin-1-yl)methanol | | 70 | 0.17 |
| 3698-49-5 | 2,2,4,6-tetramethyl-3H-1-benzofuran | | 60 | 0.13 |
| 10521-97-8 | 3-Penten-2-one, 5-phenyl- | | 64 | 0.12 |
| 1197-34-8 | Phenol, 3,5-diethyl- | | 70 | 0.11 |
| 54598-91-3 | 1,3-2H-Isobenzofurandione, 4,7-dimethyl- | | 64 | 0.11 |
| Trace Oxygenated Aromatics ||||||
| 698-71-5 | Phenol, 3-ethyl-5-methyl- | | 83 | 0.066 |
| 89-83-8 | Thymol | | 72 | 0.058 |
| 53059-21-7 | 1,1'-Biphenyl, 3-(1,1-dimethylethoxy)- | | 60 | 0.050 |
| 84922-06-5 | 2-[2-(2,4-dimethylphenyl)cyclopropyl]furan | | 62 | 0.045 |
| 5731-13-5 | 4'-Ethyl-4-biphenylcarboxylic acid | | 70 | 0.044 |
| 3689-13-3 | 1,1,3,3-tetramethylindan-2-one | | 82 | 0.044 |
| 834-97-9 | 1-Acetyl-4,6,8-trimethylazulene | | 74 | 0.040 |
| 84922-04-3 | Cis-1-(4-Ethylphenyl)-2-(2-furyl)cyclopropane | | 64 | 0.032 |
| 490-64-2 | Benzoic acid, 2,4,5-trimethoxy- | | 80 | 0.029 |
| 68873-21-2 | Naphtho[2,1-b:7,8-b']difuran, 1,2,9,10-tetrahydro-2,9-dimethyl- | | 70 | 0.021 |
| Major n-Alkenes ||||||
| 592-43-8 | 2-Hexene | | 91 | 0.18 |
| 19398-88-0 | cis-4-Decene | | 60 | 0.10 |
| Trace n-Alkenes ||||||
| 14686-13-6 | 2-Heptene, (E)- | | 95 | 0.048 |
| 592-47-2 | 3-Hexene | | 94 | 0.042 |
| 14686-14-7 | 3-Heptene, (E)- | | 96 | 0.030 |

FIG. 22C-2 CONT

| CAS # | Compound Name | Br# | Q | Area % |
|---|---|---|---|---|
| 13389-42-9 | 2-Octene, (E)- | | 74 | 0.030 |
| 592-41-6 | 1-Hexene | | 91 | 0.020 |
| 13269-52-8 | 3-Hexene, (E)- | | 91 | 0.014 |
| 627-20-3 | 2-Pentene, (Z)- | | 90 | 0.012 |
| 109-68-2 | 2-Pentene | | 86 | 0.007 |
| 624-64-6 | 2-Butene, (E)- | | 86 | 0.005 |
| 646-04-8 | 2-Pentene, (E)- | | 80 | 0.003 |
| Major Branched Alkenes | | | | |
| 922-61-2 | 2-Pentene, 3-methyl- | 1 | 94 | 0.19 |
| Trace Branched Alkenes | | | | |
| 3404-56-6 | 4-Methyl-2-heptene | 1 | 87 | 0.015 |
| 816-79-5 | 2-Pentene, 3-ethyl- | 1 | 87 | 0.023 |
| 10574-36-4 | 2-Hexene, 3-methyl-, (Z)- | 1 | 83 | 0.059 |
| 3404-65-7 | 3-Methyl-3-hexene | 1 | 78 | 0.007 |
| 3683-22-5 | 2-Hexene, 4-methyl-, (E)- | 1 | 90 | 0.009 |
| 1118-58-7 | 1,3-Pentadiene, 2-methyl- | 1 | 72 | 0.009 |
| 625-27-4 | 2-Pentene, 2-methyl- | 1 | 91 | 0.052 |
| 763-29-1 | 1-Pentene, 2-methyl- | 1 | 91 | 0.020 |
| 691-38-3 | 2-Pentene, 4-methyl-, (Z)- | 1 | 80 | 0.014 |
| 115-11-7 | 1-Propene, 2-methyl- | 1 | 90 | 0.013 |
| Major Cyclic Alkenes | | | | |
| 1000156-89-7 | 3,4-diethyl-7,7-dimethylcyclohepta-1,3,5-triene | | 86 | 0.46 |
| 4724-89-4 1, | 3-Cyclohexadiene, 1,3,5,5-tetramethyl- | | 64 | 0.12 |
| Trace Cyclic Alkenes | | | | |
| 53366-54-4 | Cyclopentane, (2-methylbutylidene)- | | 72 | 0.064 |
| 473-91-6 | Cyclopentene, 1,2,3-trimethyl- | | 83 | 0.050 |
| 19780-56-4 | Methyl ethyl cyclopentene | | 90 | 0.073 |
| 693-89-0 | Cyclopentene, 1-methyl- | | 87 | 0.019 |
| Major n-Alkanes | | | | |
| 110-54-3 | n-Hexane | | 91 | 10.43 |
| 111-65-9 | Octane | | 91 | 5.68 |
| 142-82-5 | Heptane | | 95 | 4.50 |
| 111-84-2 | Nonane | | 95 | 1.74 |
| 124-18-5 | Decane | | 94 | 1.22 |
| 109-66-0 | Pentane | | 90 | 1.13 |
| 1120-21-4 | Undecane | | 91 | 0.47 |
| 106-97-8 | Butane | | 80 | 0.24 |
| 629-59-4 | Tetradecane | | 90 | 0.21 |
| Major Branched Alkanes | | | | |
| 20278-89-1 | Heptane, 3,4,5-trimethyl- | 3 | 64 | 2.97 |
| 565-75-3 | Pentane, 2,3,4-trimethyl- | 3 | 64 | 0.90 |
| 55045-08-4 | Dodecane, 2-methyl-6-propyl- | 3 | 64 | 0.12 |
| 52896-90-9 | Heptane, 3-ethyl-5-methyl- | 2 | 64 | 0.16 |
| 583-48-2 | Hexane, 3,4-dimethyl- | 2 | 72 | 0.12 |
| 584-04-1 | Hexane, 2,3-dimethyl- | 2 | 91 | 0.16 |
| 565-59-3 | Pentane, 2,3-dimethyl- | 2 | 87 | 0.13 |
| 1002-43-3 | Undecane, 3-methyl- | 1 | 64 | 0.17 |
| 13151-35-4 | Decane, 5-methyl- | 1 | 72 | 0.13 |
| 5911-04-6 | Nonane, 3-methyl- | 1 | 90 | 0.67 |
| 10544-96-4 | Octadecane, 6-methyl- | 1 | 72 | 0.23 |
| 15869-85-9 | Nonane, 5-methyl- | 1 | 83 | 0.33 |
| 15869-86-0 | Octane, 4-ethyl- | 1 | 78 | 0.30 |

FIG. 22C-2 CONT

| CAS # | Compound Name | Br# | Q | Area % |
|---|---|---|---|---|
| 17301-94-9 | Nonane, 4-methyl- | 1 | 64 | 0.47 |
| 2216-33-3 | Octane, 3-methyl- | 1 | 64 | 0.35 |
| 15869-80-4 | Heptane, 3-ethyl- | 1 | 74 | 0.18 |
| 3221-61-2 | Octane, 2-methyl- | 1 | 95 | 0.14 |
| 2216-34-4 | Octane, 4-methyl- | 1 | 91 | 0.29 |
| 2216-32-2 | Heptane, 4-ethyl- | 1 | 64 | 0.12 |
| 589-53-7 | Heptane, 4-methyl- | 1 | 91 | 0.73 |
| 592-27-8 | Heptane, 2-methyl- | 1 | 95 | 0.70 |
| 617-78-7 | Pentane, 3-ethyl- | 1 | 91 | 0.16 |
| 591-76-4 | Hexane, 2-methyl- | 1 | 83 | 0.40 |
| 96-14-0 | Pentane, 3-methyl- | 1 | 91 | 3.07 |
| 107-83-5 | Pentane, 2-methyl- | 1 | 83 | 1.14 |
| Trace Branched Alkanes | | | | |
| 16747-28-7 | Hexane, 2,3,3-trimethyl- | 3 | 72 | 0.060 |
| 62238-13-5 | Decane, 2,3,7-trimethyl- | 3 | 78 | 0.086 |
| 1636-43-7 | Decane, 5,6-dimethyl- | 2 | 64 | 0.046 |
| 2216-30-0 | Heptane, 2,5-dimethyl- | 2 | 83 | 0.035 |
| 609-26-7 | 3-ethyl-2-methyl-pentane | 2 | 90 | 0.049 |
| 592-13-2 | Hexane, 2,5-dimethyl- | 2 | 87 | 0.033 |
| 590-73-8 | Hexane, 2,2-dimethyl- | 2 | 72 | 0.023 |
| 108-08-7 | Pentane, 2,4-dimethyl- | 2 | 72 | 0.035 |
| 590-35-2 | Pentane, 2,2-dimethyl- | 2 | 78 | 0.018 |
| 79-29-8 | Butane, 2,3-dimethyl- | 2 | 72 | 0.031 |
| 2980-69-0 | Undecane, 4-methyl- | 1 | 64 | 0.080 |
| 2847-72-5 | Decane, 4-methyl- | 1 | 83 | 0.088 |
| 13287-21-3 | Tridecane, 6-methyl- | 1 | 86 | 0.058 |
| 78-78-4 | Butane, 2-methyl- | 1 | 94 | 0.092 |
| Major Cyclic Alkanes | | | | |
| 3726-47-4 | Cyclopentane, 1-ethyl-3-methyl- | | 83 | 2.91 |
| 4806-61-5 | Cyclobutane, ethyl- | | 78 | 0.55 |
| 930-89-2 | Cyclopentane, 1-ethyl-2-methyl-, cis- | | 95 | 0.53 |
| 61142-68-5 | Cyclopentane, 1-hexyl-3-methyl- | | 80 | 0.34 |
| 13152-02-8 | Cyclooctane, ethyl- | | 80 | 0.28 |
| 3073-66-3 | Cyclohexane, 1,1,3-trimethyl- | | 72 | 0.27 |
| 13990-95-7 | Trans-1,4-diethylcyclohexane | | 62 | 0.16 |
| 4126-78-7 | Cycloheptane, methyl- | | 80 | 0.15 |
| 2207-04-7 | Cyclohexane, 1,4-dimethyl-, trans- | | 94 | 0.15 |
| 108-87-2 | Cyclohexane, methyl- | | 91 | 0.14 |
| 583-57-3 | Cyclohexane, 1,2-dimethyl- (cis/trans) | | 76 | 0.13 |
| 61142-69-6 | Cyclohexane, 1-ethyl-2,4-dimethyl- | | 62 | 0.12 |
| 110-82-7 | Cyclohexane | | 91 | 0.12 |
| 7094-26-0 | Cyclohexane, 1,1,2-trimethyl- | | 68 | 0.11 |
| 824-43-1 | Cyclohexane, 1,2-diethyl-, cis- | | 64 | 0.11 |
| Trace Cyclic Alkanes | | | | |
| 3741-00-2 | Cyclopentane, pentyl- | | 60 | 0.072 |
| 1678-93-9 | Cyclohexane, butyl- | | 83 | 0.075 |
| 7058-03-1 | Cyclohexane, 1-ethyl-2,3-dimethyl- | | 80 | 0.067 |
| 13837-67-7 | m-Menthane, (1S,3S)-(+)- | | 80 | 0.043 |
| 62238-32-8 | 1-ethyl-1,4-dimethyl-cyclohexane | | 64 | 0.036 |
| 3728-54-9 | Cyclohexane, 1-ethyl-2-methyl- | | 91 | 0.032 |
| 6876-23-9 | Cyclohexane, 1,2-dimethyl-, trans- | | 90 | 0.035 |
| 16747-50-5 | Cyclopentane, 1-ethyl-1-methyl- | | 83 | 0.050 |

FIG. 22C-2 CONT

| CAS # | Compound Name | Br# | Q | Area % |
|---|---|---|---|---|
| 16883-48-0 | 1-trans-2-trans-4-Trimethylcyclopentane | | 68 | 0.037 |
| 15890-40-1 | 1,2,3-Trimethylcyclopentane, cis, trans | | 78 | 0.043 |
| 2815-58-9 | Cyclopentane, 1,2,4-trimethyl- | | 91 | 0.043 |
| 4516-69-2 | Cyclopentane, 1,1,3-trimethyl- | | 83 | 0.028 |
| 822-50-4 | Cyclopentane, 1,2-dimethyl-, trans- | | 90 | 0.071 |
| 2532-58-3 | Cyclopentane, 1,3-dimethyl-, cis- | | 83 | 0.029 |
| 1192-18-3 | Cyclopentane, 1,2-dimethyl-, cis- | | 91 | 0.069 |
| 1638-26-2 | Cyclopentane, 1,1-dimethyl- | | 74 | 0.021 |
| 53778-43-1 | Cyclopropane, 1-ethyl-1-methyl- | | 83 | 0.009 |
| | Major Oxygenates | | | |
| 23758-27-2 | 2-Cyclohexen-1-ol, 1-methyl- | | 74 | 0.68 |
| 1003-38-9 | Furan, tetrahydro-2,5-dimethyl- | | 64 | 0.13 |
| | Trace Oxygenates | | | |
| 628-81-9 | Butane, 1-ethoxy- | | 83 | 0.069 |
| 143-08-8 | 1-Nonanol | | 64 | 0.006 |
| 107-87-9 | 2-Pentanone | | 90 | 0.020 |
| 78-84-2 | Propanal, 2-methyl- | | 72 | 0.020 |
| 625-33-2 | 3-Penten-2-one | | 80 | 0.003 |
| 60-29-7 | Ethyl ether | | 91 | 0.063 |
| 64-17-5 | Ethanol | | 78 | 0.006 |

FIG. 22C-2 CONT

Catalyst: $0.5\%Pt/5.0\%H_3BO_3-Al_2O_3$

| Reaction conditions | | | Average #C | Product distribution (%) | | | |
|---|---|---|---|---|---|---|---|
| T (°C) | P (psig) | LFR (mL/min) | | Aromatics | Alkenes | Alkanes | Oxygenates |
| 325 | 500 | 0.125 | 7.2 | 4.67 | 0.95 | 91.91 | 0.05 |

| CAS # | Compound Name | BR# | Q | Area% |
|---|---|---|---|---|
| Major Aromatics Hydrocarbons | | | | |
| 108-38-3 | Benzene, 1,3-dimethyl- | | 95 | 0.69 |
| 106-42-3 | p-Xylene | | 97 | 0.57 |
| 100-41-4 | Ethylbenzene | | 91 | 0.48 |
| 874-41-9 | Benzene, 1-ethyl-2,4-dimethyl- | | 95 | 0.44 |
| 108-88-3 | Toluene | | 91 | 0.36 |
| 141-93-5 | Benzene, 1,3-diethyl- | | 97 | 0.27 |
| 53669-88-0 | 1,4-dimethyl-2-(2-methylpropyl)benzene | | 90 | 0.26 |
| 1758-88-9 | Benzene, 2-ethyl-1,4-dimethyl- | | 95 | 0.21 |
| 526-73-8 | Benzene, 1,2,3-trimethyl- | | 93 | 0.19 |
| 1074-55-1 | Benzene, 1-methyl-4-propyl- | | 93 | 0.18 |
| 71-43-2 | Benzene | | 91 | 0.17 |
| 1074-17-5 | Benzene, 1-methyl-2-propyl- | | 91 | 0.15 |
| 104-51-8 | Benzene, n-butyl- | | 91 | 0.12 |
| 611-14-3 | Benzene, 1-ethyl-2-methyl- | | 94 | 0.10 |
| Trace Aromatic Hydrocarbons | | | | |
| 934-74-7 | Benzene, 1-ethyl-3,5-dimethyl- | | 91 | 0.085 |
| 620-14-4 | Benzene, 1-ethyl-3-methyl- | | 90 | 0.051 |
| 1595-05-7 | Benzene, 1-methyl-4-butyl- | | 91 | 0.047 |
| 103-65-1 | Benzene, propyl- | | 90 | 0.044 |
| 4810-04-2 | Benzene, 1,3,5-trimethyl-2-propyl- | | 64 | 0.043 |
| 1074-43-7 | Benzene, 1-methyl-3-propyl- | | 90 | 0.041 |
| 535-77-3 | Benzene, 1-methyl-3-(1-methylethyl)- | | 91 | 0.018 |
| 108-67-8 | Mesitylene | | 91 | 0.032 |
| 102-25-0 | Benzene, 1,3,5-triethyl- | | 95 | 0.029 |
| Trace Oxygenated Aromatics | | | | |
| 2078-54-8 | Propofol | | 74 | 0.072 |
| Major n-Alkenes | | | | |
| 592-43-8 | 2-Hexene | | 70 | 0.13 |
| Trace n-Alkenes | | | | |
| 7642-09-3 | 3-Hexene, (Z)- | | 76 | 0.061 |
| 7688-21-3 | 2-Hexene, (Z)- | | 81 | 0.045 |
| 627-20-3 | 2-Pentene, (Z)- | | 60 | 0.030 |
| 6443-92-1 | (Z)-2-Heptene | | 91 | 0.025 |
| 7642-10-6 | (Z)-3-Heptene | | 91 | 0.022 |
| 624-64-6 | 2-Butene, (E)- | | 78 | 0.008 |
| 590-18-1 | 2-Butene, (Z)- | | 83 | 0.007 |
| Major Branched Alkenes | | | | |
| 922-61-2 | 2-Pentene, 3-methyl- | 1 | 94 | 0.48 |
| Trace Branched Alkenes | | | | |
| 3404-79-3 | 2-Hexene, 3,5-dimethyl- | 2 | 90 | 0.035 |
| 1515-79-3 | 5,5-Dimethyl-1,3-hexadiene | 2 | 83 | 0.024 |
| 563-78-0 | 1-Butene, 2,3-dimethyl- | 2 | 74 | 0.038 |
| 10574-36-4 | 2-Hexene, 3-methyl-, (Z)- | 1 | 83 | 0.012 |
| 692-24-0 | 3-Hexene, 2-methyl-, (E)- | 1 | 83 | 0.020 |
| 816-79-5 | 2-Pentene, 3-ethyl- | 1 | 86 | 0.011 |
| Major n-Alkanes | | | | |
| 110-54-3 | n-Hexane | | 91 | 22.17 |
| 142-82-5 | Heptane | | 96 | 12.95 |
| 109-66-0 | Pentane | | 90 | 9.45 |
| 111-65-9 | Octane | | 72 | 9.06 |
| 111-84-2 | Nonane | | 93 | 3.95 |

FIG. 23A-2 CONT

| CAS # | Compound Name | BR# | Q | Area% |
|---|---|---|---|---|
| 106-97-8 | Butane | | 90 | 3.42 |
| 124-18-5 | Decane | | 95 | 1.84 |
| 1120-21-4 | Undecane | | 95 | 1.06 |
| 112-40-3 | Dodecane | | 94 | 0.38 |
| 629-50-5 | Tridecane | | 91 | 0.33 |
| | Trace n-Alkanes | | | |
| 74-98-6 | Propane | | 90 | 0.077 |
| 629-59-4 | Tetradecane | | 90 | 0.075 |
| | Major Branched Alkanes | | | |
| 921-47-1 | Hexane, 2,3,4-trimethyl- | 3 | 83 | 0.14 |
| 20278-89-1 | Heptane, 3,4,5-trimethyl- | 3 | 87 | 6.96 |
| 56392-85-0 | Dodecane, 2,5-dimethyl- | 2 | 83 | 0.15 |
| 583-48-2 | Hexane, 3,4-dimethyl- | 2 | 83 | 0.23 |
| 565-59-3 | Pentane, 2,3-dimethyl- | 2 | 93 | 0.30 |
| 1002-43-3 | Undecane, 3-methyl- | 1 | 90 | 0.32 |
| 1632-70-8 | Undecane, 5-methyl- | 1 | 80 | 0.33 |
| 5911-04-6 | Nonane, 3-methyl- | 1 | 91 | 1.50 |
| 5881-17-4 | Octane, 3-ethyl- | 1 | 78 | 0.20 |
| 17301-94-9 | Nonane, 4-methyl- | 1 | 83 | 0.13 |
| 2216-33-3 | Octane, 3-methyl- | 1 | 83 | 0.24 |
| 15869-80-4 | Heptane, 3-ethyl- | 1 | 83 | 0.54 |
| 619-99-8 | Hexane, 3-ethyl- | 1 | 94 | 0.97 |
| 589-53-7 | Heptane, 4-methyl- | 1 | 91 | 0.24 |
| 592-27-8 | Heptane, 2-methyl- | 1 | 90 | 0.23 |
| 617-78-7 | Pentane, 3-ethyl- | 1 | 83 | 0.75 |
| 589-34-4 | Hexane, 3-methyl- | 1 | 91 | 0.80 |
| 591-76-4 | Hexane, 2-methyl- | 1 | 81 | 0.34 |
| 96-14-0 | Pentane, 3-methyl- | 1 | 90 | 5.18 |
| 78-78-4 | Butane, 2-methyl- | 1 | 91 | 0.32 |
| | Trace Branched Alkanes | | | |
| 62238-11-3 | Decane, 2,3,5-trimethyl- | 3 | 72 | 0.037 |
| 62016-33-5 | Octane, 2,3,6-trimethyl- | 3 | 72 | 0.053 |
| 17312-80-0 | Undecane, 2,4-dimethyl- | 2 | 64 | 0.051 |
| 3074-71-3 | Heptane, 2,3-dimethyl- | 2 | 72 | 0.078 |
| 2216-30-0 | Heptane, 2,5-dimethyl- | 2 | 83 | 0.060 |
| 584-94-1 | Hexane, 2,3-dimethyl- | 2 | 64 | 0.013 |
| 589-43-5 | Hexane, 2,4-dimethyl- | 2 | 83 | 0.021 |
| 562-49-2 | Pentane, 3,3-dimethyl- | 2 | 72 | 0.011 |
| 6418-41-3 | Tridecane, 3-methyl- | 1 | 72 | 0.031 |
| 17453-94-0 | Undecane, 5-ethyl- | 1 | 78 | 0.046 |
| 2847-72-5 | Decane, 4-methyl- | 1 | 83 | 0.032 |
| 13151-35-4 | Decane, 5-methyl- | 1 | 83 | 0.040 |
| 3221-61-2 | Octane, 2-methyl- | 1 | 72 | 0.100 |
| 2216-32-2 | Heptane, 4-ethyl- | 1 | 83 | 0.054 |
| | Major Cyclic Alkanes | | | |
| 3726-47-4 | Cyclopentane, 1-ethyl-3-methyl- | | 83 | 0.96 |
| 1678-91-7 | Cyclohexane, ethyl- | | 90 | 0.56 |
| 110-82-7 | Cyclohexane | | 91 | 0.33 |
| 108-87-2 | Cyclohexane, methyl- | | 94 | 0.27 |
| 7045-67-2 | Cyclohexane, 2-ethyl-1,3-dimethyl- | | 72 | 0.26 |
| 96-37-7 | Cyclopentane, methyl- | | 91 | 0.19 |
| 3726-46-3 | Cyclopentane, 1-ethyl-2-methyl- | | 94 | 0.18 |

FIG. 23A-2 CONT

| CAS # | Compound Name | BRs | Q | Area% |
|---|---|---|---|---|
| 61142-68-5 | Cyclopentane, 1-hexyl-3-methyl- | | 72 | 0.14 |
| 2207-04-7 | Cyclohexane, 1,4-dimethyl-, trans- | | 91 | 0.11 |
| Trace Cyclic Alkanes | | | | |
| 294-62-2 | Cyclododecane | | 64 | 0.054 |
| 1678-93-9 | Cyclohexane, butyl- | | 90 | 0.079 |
| 13980-93-7 | Trans-1,4-diethylcyclohexane | | 87 | 0.098 |
| 4126-78-7 | Cycloheptane, methyl- | | 80 | 0.057 |
| 91242-57-8 | Cyclopentane, 1,2-dipropyl- | | 72 | 0.071 |
| 1678-92-8 | Cyclohexane, propyl- | | 90 | 0.029 |
| 3728-54-9 | Cyclohexane, 1-ethyl-2-methyl- | | 91 | 0.039 |
| 4926-78-7 | Cyclohexane, 1-ethyl-4-methyl-, cis- | | 91 | 0.049 |
| 2207-01-4 | Cyclohexane, 1,2-dimethyl-, cis- | | 90 | 0.029 |
| 6876-23-9 | Cyclohexane, 1,2-dimethyl-, trans- | | 90 | 0.091 |
| 1640-89-7 | Cyclopentane, ethyl- | | 91 | 0.028 |
| Trace Oxygenates | | | | |
| 15726-15-5 | 4-Heptanone, 3-methyl- | | 90 | 0.036 |
| 10264-55-8 | 3-Ethylcyclopentanone | | 83 | 0.011 |

FIG. 23A-2 CONT

Catalyst: 0.5%Pt/5.0%H₃BO₃-Al₂O₃

| Reaction conditions | | | Average #C | Product distribution (%) | | | |
|---|---|---|---|---|---|---|---|
| T (°C) | P (psig) | LFR (mL/min) | | Aromatics | Alkenes | Alkanes | Oxygenates |
| 350 | 300 | 0.125 | 7.7 | 19.24 | 1.32 | 73.01 | 0.31 |

| CAS # | Compound Name | BR # | Q | Area% |
|---|---|---|---|---|
| \multicolumn{5}{c}{Major Aromatics Hydrocarbons} ||||| 
| 100-41-4 | Ethylbenzene | | 91 | 2.38 |
| 108-88-3 | Toluene | | 91 | 2.36 |
| 106-42-3 | p-Xylene | | 95 | 1.83 |
| 95-47-6 | o-Xylene | | 95 | 1.58 |
| 1074-55-1 | Benzene, 1-methyl-4-propyl- | | 90 | 1.12 |
| 527-53-7 | Benzene, 1,2,3,5-tetramethyl- | | 94 | 0.99 |
| 622-96-8 | Benzene, 1-ethyl-4-methyl- | | 94 | 0.99 |
| 141-93-5 | Benzene, 1,3-diethyl- | | 96 | 0.83 |
| 71-43-2 | Benzene | | 91 | 0.77 |
| 611-14-3 | Benzene, 1-ethyl-2-methyl- | | 94 | 0.74 |
| 55669-88-0 | 1,4-dimethyl-2-(2-methylpropyl)benzene | | 91 | 0.60 |
| 104-51-8 | Benzene, n-butyl- | | 91 | 0.58 |
| 4481-30-5 | Benzene, (1,2-dimethylpropyl)- | | 88 | 0.47 |
| 1758-88-9 | Benzene, 2-ethyl-1,4-dimethyl- | | 94 | 0.39 |
| 103-65-1 | Benzene, propyl- | | 87 | 0.38 |
| 620-14-4 | Benzene, 1-ethyl-3-methyl- | | 91 | 0.32 |
| 1595-16-0 | Benzene, 1-methyl-4-(1-methylpropyl)- | | 87 | 0.25 |
| 1758-85-6 | Benzene, 2,4-diethyl-1-methyl- | | 94 | 0.25 |
| 1077-16-3 | Benzene, hexyl- | | 64 | 0.30 |
| 108-38-3 | Benzene, 1,3-dimethyl- | | 91 | 0.20 |
| 1074-17-5 | Benzene, 1-methyl-2-propyl- | | 90 | 0.14 |
| 1127-76-0 | 1-ethylnaphthalene | | 96 | 0.10 |
| 90-12-0 | Naphthalene, 1-methyl- | | 91 | 0.10 |
| \multicolumn{5}{c}{Trace Aromatic Hydrocarbons} ||||| 
| 526-73-8 | Benzene, 1,2,3-trimethyl- | | 91 | 0.100 |
| 91-20-3 | Naphthalene | | 90 | 0.091 |
| 135-01-3 | Benzene, 1,2-diethyl- | | 87 | 0.084 |
| 4810-04-2 | Benzene, 1,3,5-trimethyl-2-propyl- | | 88 | 0.081 |
| 529-05-5 | Chamazulene | | 93 | 0.080 |
| 19219-84-2 | Benzene, (1,3-dimethylbutyl)- | | 74 | 0.076 |
| 877-44-1 | Benzene, 1,2,4-triethyl- | | 94 | 0.073 |
| 17059-48-2 | 1H-Indene, 2,3-dihydro-1,6-dimethyl- | | 96 | 0.060 |
| 571-61-9 | Naphthalene, 1,5-dimethyl- | | 96 | 0.059 |
| 2027-17-0 | Naphthalene, 2-(1-methylethyl)- | | 94 | 0.053 |
| 1483-60-9 | Benzene, 1,3-dimethyl-4-(1-methylpropyl) | | 72 | 0.050 |
| 1000383-71-7 | 4-ethyl-1,6-dimethyl-naphthalene | | 95 | 0.050 |
| 4175-54-6 | 1,4-dimethyltetralin | | 74 | 0.047 |
| 135-98-8 | Benzene, (1-methylpropyl)- | | 87 | 0.047 |
| 21693-54-9 | 5,7-dimethyltetralin | | 64 | 0.046 |
| 582-16-1 | Naphthalene, 2,7-dimethyl- | | 91 | 0.044 |
| 527-84-4 | o-Cymene | | 91 | 0.043 |
| 571-58-4 | Naphthalene, 1,4-dimethyl- | | 95 | 0.040 |
| 54410-75-2 | Benzene, 1,2-diethyl-3,4-dimethyl- | | 87 | 0.040 |
| 103240-92-2 | 1-Phenyl-5-methylheptane | | 82 | 0.034 |
| 581-42-0 | Naphthalene, 2,6-dimethyl- | | 96 | 0.033 |
| 22531-20-0 | Naphthalene, 6-ethyl-1,2,3,4-tetrahydro- | | 72 | 0.028 |
| 4175-53-5 | 1H-Indene, 2,3-dihydro-1,3-dimethyl- | | 90 | 0.019 |
| 42775-75-7 | Naphthalene, 5-ethyl-1,2,3,4-tetrahydro- | | 64 | 0.019 |
| 2131-42-2 | Naphthalene, 1,4,6-trimethyl- | | 87 | 0.016 |
| 829-26-5 | Naphthalene, 2,3,6-trimethyl- | | 76 | 0.016 |

FIG. 23B-2 CONT

| CAS # | Compound Name | BR # | Q | Area% |
|---|---|---|---|---|
| \multicolumn{5}{l}{Trace Oxygenated Aromatics} | | | | |
| 105-67-9 | Phenol, 2,4-dimethyl- | | 91 | 0.080 |
| 90-00-6 | Phenol, 2-ethyl- | | 87 | 0.059 |
| 620-17-7 | Phenol, 3-ethyl- | | 91 | 0.047 |
| 487-68-3 | Benzaldehyde, 2,4,6-trimethyl- | | 82 | 0.043 |
| 698-71-5 | Phenol, 3-ethyl-5-methyl- | | 91 | 0.041 |
| 99-89-8 | p-Cumenol | | 86 | 0.037 |
| 108-68-9 | Phenol, 3,5-dimethyl- | | 87 | 0.032 |
| 576-26-1 | Phenol, 2,6-dimethyl- | | 91 | 0.017 |
| 16204-89-6 | 1-Indanone, 3,3,5,6,7-pentamethyl- | | 64 | 0.016 |
| 122-00-9 | Ethanone, 1-(4-methylphenyl)- | | 64 | 0.015 |
| | Major n-Alkenes | | | |
| 4050-45-7 | 2-Hexene, (E)- | | 91 | 0.17 |
| 7642-09-3 | 3-Hexene, (Z)- | | 94 | 0.15 |
| 14686-13-6 | 2-Heptene, (E)- | | 95 | 0.12 |
| | Trace n-Alkenes | | | |
| 7642-10-6 | (Z)-3-Heptene | | 95 | 0.082 |
| 106-98-9 | 1-Butene | | 90 | 0.058 |
| 646-04-8 | 2-Pentene, (E)- | | 91 | 0.045 |
| 7642-15-1 | 4-Octene, (Z)- | | 83 | 0.031 |
| 592-41-6 | 1-Hexene | | 94 | 0.030 |
| 109-67-1 | 1-Pentene | | 90 | 0.028 |
| 13389-42-9 | 2-Octene, (E)- | | 91 | 0.018 |
| 115-07-1 | Propene | | 86 | 0.011 |
| | Major Branched Alkenes | | | |
| 922-61-2 | 2-Pentene, 3-methyl- | 1 | 94 | 0.15 |
| | Trace Branched Alkenes | | | |
| 7145-23-5 | 3-Hexene, 2,3-dimethyl- | 2 | 60 | 0.068 |
| 3404-79-3 | 2-Hexene, 3,5-dimethyl- | 2 | 74 | 0.030 |
| 3404-80-6 | Hexane, 2-methyl-4-methylene- | 2 | 86 | 0.012 |
| 2080-89-9 | 1,4-Hexadiene, 3-ethyl- | 1 | 72 | 0.069 |
| 10574-36-4 | 2-Hexene, 3-methyl-, (Z)- | 1 | 78 | 0.012 |
| 816-79-5 | 2-Pentene, 3-ethyl- | 1 | 86 | 0.023 |
| 763-30-4 | 1,4-Pentadiene, 2-methyl- | 1 | 74 | 0.009 |
| 691-38-3 | 2-Pentene, 4-methyl-, (Z)- | 1 | 86 | 0.008 |
| 513-35-9 | 2-Butene, 2-methyl- | 1 | 91 | 0.081 |
| 563-45-1 | 1-Butene, 3-methyl- | 1 | 80 | 0.004 |
| | Trace Cyclic Alkenes | | | |
| 61142-33-4 | 1,4-dimethyl-3-propan-2-yl-cyclopentene | | 64 | 0.021 |
| 53366-54-4 | Cyclopentane, (2-methylbutylidene)- | | 78 | 0.041 |
| 97797-57-4 | 1-Ethyl-5-methylcyclopentene | | 78 | 0.028 |
| 1528-21-8 | Ethylidenecyclobutane | | 80 | 0.012 |
| 693-89-0 | Cyclopentene, 1-methyl- | | 90 | 0.023 |
| | Major n-Alkanes | | | |
| 110-54-3 | n-Hexane | | 91 | 14.72 |
| 142-82-5 | Heptane | | 95 | 12.73 |
| 109-66-0 | Pentane | | 91 | 4.62 |
| 111-84-2 | Nonane | | 95 | 4.56 |
| 124-18-5 | Decane | | 95 | 1.77 |
| 1120-21-4 | Undecane | | 91 | 1.28 |
| 629-59-4 | Tetradecane | | 93 | 0.49 |
| 106-97-8 | Butane | | 87 | 0.32 |

FIG. 23B-2 CONT

| CAS # | Compound Name | BR # | Q | Area% |
|---|---|---|---|---|
| 629-50-5 | Tridecane | | 93 | 0.32 |
| | Trace n-Alkanes | | | |
| 629-62-9 | Pentadecane | | 90 | 0.098 |
| 593-45-3 | Octadecane | | 64 | 0.017 |
| | Major Branched Alkanes | | | |
| 20278-89-1 | Heptane, 3,4,5-trimethyl- | 3 | 87 | 0.47 |
| 921-47-1 | Hexane, 2,3,4-trimethyl- | 3 | 87 | 0.19 |
| 2216-30-0 | Heptane, 2,5-dimethyl- | 2 | 90 | 0.38 |
| 13150-81-7 | 2,6-Dimethyldecane | 2 | 90 | 0.14 |
| 589-43-5 | Hexane, 2,4-dimethyl- | 2 | 83 | 8.45 |
| 583-48-2 | Hexane, 3,4-dimethyl- | 2 | 90 | 0.11 |
| 565-59-3 | Pentane, 2,3-dimethyl- | 2 | 90 | 0.24 |
| 1002-43-3 | Undecane, 3-methyl- | 1 | 78 | 0.29 |
| 17312-63-9 | Nonane, 5-butyl- | 1 | 78 | 0.15 |
| 13287-21-3 | Tridecane, 6-methyl- | 1 | 64 | 0.11 |
| 5911-04-6 | Nonane, 3-methyl- | 1 | 91 | 1.16 |
| 5881-17-4 | Octane, 3-ethyl- | 1 | 72 | 0.15 |
| 17301-94-9 | Nonane, 4-methyl- | 1 | 90 | 0.16 |
| 15869-80-4 | Heptane, 3-ethyl- | 1 | 94 | 0.53 |
| 2216-32-2 | Heptane, 4-ethyl- | 1 | 81 | 0.10 |
| 619-99-8 | Hexane, 3-ethyl- | 1 | 94 | 0.73 |
| 589-81-1 | Heptane, 3-methyl- | 1 | 83 | 4.45 |
| 588-53-7 | Heptane, 4-methyl- | 1 | 91 | 0.29 |
| 592-27-8 | Heptane, 2-methyl- | 1 | 94 | 0.25 |
| 617-78-7 | Pentane, 3-ethyl- | 1 | 91 | 1.72 |
| 591-76-4 | Hexane, 2-methyl- | 1 | 76 | 0.38 |
| 96-14-0 | Pentane, 3-methyl- | 1 | 91 | 4.34 |
| 107-83-5 | Pentane, 2-methyl- | 1 | 83 | 0.35 |
| 78-78-4 | Butane, 2-methyl- | 1 | 83 | 0.18 |
| | Trace Branched Alkanes | | | |
| 62238-15-7 | Decane, 2,3,4-trimethyl- | 3 | 64 | 0.015 |
| 20278-85-7 | Heptane, 2,3,5-trimethyl- | 3 | 78 | 0.087 |
| 3074-77-9 | Hexane, 3-ethyl-4-methyl- | 2 | 64 | 0.032 |
| 584-94-1 | Hexane, 2,3-dimethyl- | 2 | 72 | 0.017 |
| 562-49-2 | Pentane, 3,3-dimethyl- | 2 | 83 | 0.016 |
| 2847-72-5 | Decane, 4-methyl- | 1 | 83 | 0.051 |
| 13151-35-4 | Decane, 5-methyl- | 1 | 72 | 0.056 |
| | Major Cyclic Alkanes | | | |
| 3726-47-4 | Cyclopentane, 1-ethyl-3-methyl- | | 74 | 1.29 |
| 2613-65-2 | Cyclopentane, 1-ethyl-3-methyl-, trans- | | 78 | 1.12 |
| 1678-91-7 | Cyclohexane, ethyl- | | 64 | 0.72 |
| 96-37-7 | Cyclopentane, methyl- | | 91 | 0.47 |
| 930-89-2 | Cyclopentane, 1-ethyl-2-methyl-, cis- | | 95 | 0.45 |
| 110-82-7 | Cyclohexane | | 91 | 0.37 |
| 108-87-2 | Cyclohexane, methyl- | | 91 | 0.35 |
| 61142-69-6 | Cyclohexane, 1-ethyl-2,4-dimethyl- | | 64 | 0.34 |
| 3073-66-3 | Cyclohexane, 1,1,3-trimethyl- | | 64 | 0.15 |
| 13152-02-8 | Cyclooctane, ethyl- | | 72 | 0.12 |
| 2207-04-7 | Cyclohexane, 1,4-dimethyl-, trans- | | 91 | 0.12 |
| 1640-89-7 | Cyclopentane, ethyl- | | 91 | 0.12 |
| | Trace Cyclic Alkanes | | | |
| 61142-68-5 | Cyclopentane, 1-hexyl-3-methyl- | | 70 | 0.052 |

FIG. 23B-2 CONT

| CAS # | Compound Name | BR # | Q | Area% |
|---|---|---|---|---|
| 62199-50-2 | Cyclopentane, 1-butyl-2-propyl- | | 93 | 0.064 |
| 4457-00-5 | Cyclopentane, hexyl- | | 64 | 0.040 |
| 3741-00-2 | Cyclopentane, pentyl- | | 94 | 0.084 |
| 1678-93-9 | Cyclohexane, butyl- | | 90 | 0.067 |
| 6708-17-4 | 1,1'-Bicyclooctyl | | 78 | 0.027 |
| 293-96-9 | Cyclodecane | | 70 | 0.034 |
| 4126-78-7 | Cycloheptane, methyl- | | 64 | 0.085 |
| 1678-92-8 | Cyclohexane, propyl- | | 80 | 0.033 |
| 3728-56-1 | 1-Ethyl-4-methylcyclohexane | | 81 | 0.037 |
| 62238-04-4 | Cyclopropane, 1,2-dimethyl-1-pentyl- | | 82 | 0.025 |
| 932-40-1 | trans-1,2-Diethyl cyclopentane | | 80 | 0.038 |
| 1000113-87-1 | trans-1,3-Diethylcyclopentane | | 64 | 0.041 |
| 2207-01-4 | Cyclohexane, 1,2-dimethyl-, cis- | | 90 | 0.017 |
| 17065-18-8 | Bicyclo[2.1.0]pentane, 1,4-dimethyl- | | 72 | 0.082 |
| 6876-23-9 | Cyclohexane, 1,2-dimethyl-, trans- | | 93 | 0.078 |
| 2613-69-6 | (1R,2s,3S)-1,2,3-Trimethylcyclopentane | | 90 | 0.043 |
| 15890-40-1 | 1,2,3-Trimethylcyclopentane, cis, trans | | 87 | 0.071 |
| 2453-99-5 | Cyclopentane, 1,2-dimethyl- | | 91 | 0.021 |
| 822-50-4 | Cyclopentane, 1,2-dimethyl-, trans- | | 90 | 0.042 |
| 287-92-3 | Cyclopentane | | 64 | 0.007 |
| Major Oxygenates | | | | |
| 60-29-7 | Ethyl ether | | 91 | 0.18 |
| Trace Oxygenates | | | | |
| 1000309-34-0 | O2-(1,4-diethylhexyl) O1-propyl oxalate | | 64 | 0.034 |
| 16340-38-3 | Cycloheptanol, 2-methylene- | | 64 | 0.056 |
| 123-72-8 | Butanal | | 91 | 0.043 |

FIG. 23B-2 CONT

Catalyst: 0.5%Pt/5.0%H₃BO₃-Al₂O₃

| Reaction conditions | | | Average #C | Product distribution (%) | | | |
|---|---|---|---|---|---|---|---|
| T (°C) | P (psig) | LFR (mL/min) | | Aromatics | Alkenes | Alkanes | Oxygenates |
| 350 | 500 | 0.125 | 8.77 | 19.35 | 0.24 | 64.81 | 4.93 |

Hydrocarbon Report

Request: BM-GE5-L0358  Xyleco Inc  Sample: BM-ETG-38-2-R8

| Summary | Total | Known | Major | Trace | Ave Carbon # |
|---|---|---|---|---|---|
| Peaks: | 169 | 91 | 74 | 17 | 8.77 |
| Area: | 443037360 | 89.3% | 88.4% | 0.9% | |

| Compound Type | Total Known # Peaks | Total Known % Area | Major Components # Peaks | Major Components % Area | Average Carbon # |
|---|---|---|---|---|---|
| Aromatics (Total): | 29 | 19.35 | 24 | 19.13 | 9.24 |
| Oxygenated: | 3 | 0.20 | 1 | 0.12 | 8.00 |
| Alkenes (Total): | 4 | 0.24 | 1 | 0.13 | 7.84 |
| Straight: | 1 | 0.06 | 0 | 0.00 | 8.00 |
| Branched: | 1 | 0.13 | 1 | 0.13 | 7.00 |
| Cyclic: | 2 | 0.05 | 0 | 0.00 | 10.00 |
| Alkanes (Total): | 49 | 64.81 | 40 | 64.22 | 9.11 |
| Straight: | 12 | 29.95 | 11 | 29.91 | 9.02 |
| Branched: | 26 | 32.42 | 22 | 32.09 | 9.24 |
| Cyclic: | 11 | 2.44 | 7 | 2.23 | 8.34 |
| Oxygenated (Other): | 9 | 4.93 | 9 | 4.93 | 2.58 |

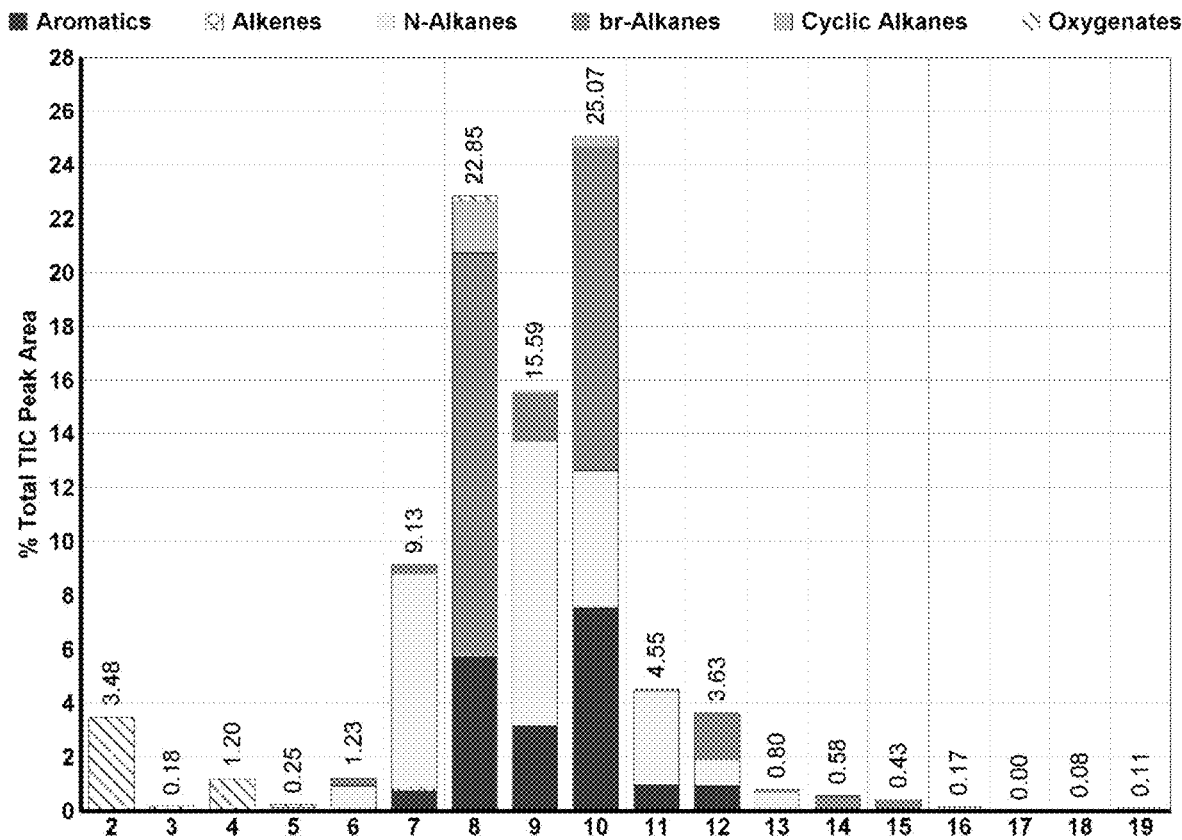

FIG. 23C-2

| CAS # | Compound Name | BR # | Q | Area% |
|---|---|---|---|---|
| \multicolumn{5}{c}{Major Aromatics Hydrocarbons} ||||| 
| 1758-88-9 | Benzene, 2-ethyl-1,4-dimethyl- | | 94 | 2.39 |
| 100-41-4 | Ethylbenzene | | 91 | 2.24 |
| 141-93-5 | Benzene, 1,3-diethyl- | | 95 | 1.99 |
| 108-38-3 | Benzene, 1,3-dimethyl- | | 95 | 1.80 |
| 106-42-3 | p-Xylene | | 93 | 1.72 |
| 611-14-3 | Benzene, 1-ethyl-2-methyl- | | 91 | 1.38 |
| 135-98-8 | Benzene, (1-methylpropyl)- | | 80 | 1.02 |
| 53669-88-0 | 1,4-dimethyl-2-(2-methylpropyl)benzene | | 87 | 0.93 |
| 95-63-6 | Benzene, 1,2,4-trimethyl- | | 90 | 0.86 |
| 104-51-8 | Benzene, n-butyl- | | 91 | 0.82 |
| 1074-55-1 | Benzene, 1-methyl-4-propyl- | | 87 | 0.75 |
| 108-88-3 | Toluene | | 91 | 0.75 |
| 526-73-8 | Benzene, 1,2,3-trimethyl- | | 91 | 0.59 |
| 1758-85-6 | Benzene, 2,4-diethyl-1-methyl- | | 94 | 0.53 |
| 4481-30-5 | Benzene, (1,2-dimethylpropyl)- | | 86 | 0.45 |
| 933-98-2 | Benzene, 1-ethyl-2,3-dimethyl- | | 91 | 0.41 |
| 103-65-1 | Benzene, propyl- | | 91 | 0.32 |
| 527-84-4 | o-Cymene | | 80 | 0.15 |
| \multicolumn{5}{c}{Trace Aromatic Hydrocarbons} |||||
| 71-43-2 | Benzene | | 83 | 0.046 |
| \multicolumn{5}{c}{Major Oxygenated Aromatics} |||||
| 105-67-9 | Phenol, 2,4-dimethyl- | | 90 | 0.12 |
| \multicolumn{5}{c}{Trace Oxygenated Aromatics} |||||
| 90-00-6 | Phenol, 2-ethyl- | | 83 | 0.055 |
| 95-65-8 | Phenol, 3,4-dimethyl- | | 90 | 0.027 |
| \multicolumn{5}{c}{Trace n-Alkenes} |||||
| 14850-22-7 | 3-Octene, (Z)- | | 78 | 0.061 |
| \multicolumn{5}{c}{Major Branched Alkenes} |||||
| 4914-91-4 | 2-Pentene, 3,4-dimethyl-, (Z)- | 2 | 72 | 0.13 |
| \multicolumn{5}{c}{Trace Cyclic Alkenes} |||||
| 586-63-0 | 3-methyl-6-propan-2-ylidene-cyclohexene | | 74 | 0.048 |
| \multicolumn{5}{c}{Major n-Alkanes} |||||
| 111-84-2 | Nonane | | 95 | 10.53 |
| 142-82-5 | Heptane | | 96 | 7.92 |
| 124-18-5 | Decane | | 95 | 5.03 |
| 1120-21-4 | Undecane | | 91 | 3.46 |
| 112-40-3 | Dodecane | | 91 | 0.95 |
| 110-54-3 | n-Hexane | | 91 | 0.89 |
| 629-50-5 | Tridecane | | 94 | 0.71 |
| 544-76-3 | Hexadecane | | 86 | 0.17 |
| 109-66-0 | Pentane | | 83 | 0.13 |
| 629-92-5 | Nonadecane | | 78 | 0.11 |
| \multicolumn{5}{c}{Trace n-Alkanes} |||||
| 106-97-8 | Butane | | 90 | 0.044 |
| \multicolumn{5}{c}{Major Branched Alkanes} |||||
| 3891-98-3 | Dodecane, 2,6,10-trimethyl- | 3 | 72 | 0.43 |
| 20278-89-1 | Heptane, 3,4,5-trimethyl- | 3 | 64 | 6.91 |
| 565-75-3 | Pentane, 2,3,4-trimethyl- | 3 | 83 | 0.24 |
| 13475-78-0 | Heptane, 5-ethyl-2-methyl- | 2 | 78 | 0.12 |
| 589-43-5 | Hexane, 2,4-dimethyl- | 2 | 83 | |
| 583-48-2 | Hexane, 3,4-dimethyl- | 2 | 74 | 0.10 |

FIG. 23C-2 CONT

| CAS # | Compound Name | BR # | Q | Area% |
|---|---|---|---|---|
| 592-13-2 | Hexane, 2,5-dimethyl- | 2 | 80 | 0.26 |
| 1560-96-9 | Tridecane, 2-methyl- | 1 | 60 | 0.16 |
| 1002-43-3 | Undecane, 3-methyl- | 1 | 83 | 0.75 |
| 1632-70-8 | Undecane, 5-methyl- | 1 | 72 | 1.80 |
| 2847-72-5 | Decane, 4-methyl- | 1 | 83 | 0.11 |
| 13287-21-3 | Tridecane, 6-methyl- | 1 | 83 | 0.32 |
| 5911-04-6 | Nonane, 3-methyl- | 1 | 90 | 3.33 |
| 17301-94-9 | Nonane, 4-methyl- | 1 | 78 | 0.35 |
| 15869-85-9 | Nonane, 5-methyl- | 1 | 81 | 1.33 |
| 2216-33-3 | Octane, 3-methyl- | 1 | 83 | 0.59 |
| 15869-80-4 | Heptane, 3-ethyl- | 1 | 83 | 1.15 |
| 2216-34-4 | Octane, 4-methyl- | 1 | 74 | 0.10 |
| 619-99-8 | Hexane, 3-ethyl- | 1 | 91 | 1.26 |
| 617-78-7 | Pentane, 3-ethyl- | 1 | 83 | 0.26 |
| 96-14-0 | Pentane, 3-methyl- | 1 | 87 | 0.26 |
| | Trace Branched Alkanes | | | |
| 17301-31-4 | Undecane, 3,9-dimethyl- | 2 | 83 | 0.082 |
| 565-59-3 | Pentane, 2,3-dimethyl- | 2 | 83 | 0.065 |
| 25117-31-1 | Tridecane, 5-methyl- | 1 | 72 | 0.099 |
| 26741-18-4 | 9-methylheptadecane | 1 | 83 | 0.084 |
| | Major Cyclic Alkanes | | | |
| 1678-91-7 | Cyclohexane, ethyl- | | 72 | 1.43 |
| 3726-46-3 | Cyclopentane, 1-ethyl-2-methyl- | | 90 | 0.26 |
| 2207-04-7 | Cyclohexane, 1,4-dimethyl-, trans- | | 83 | 0.17 |
| 1678-93-9 | Cyclohexane, butyl- | | 90 | 0.13 |
| 29053-04-1 | 1-methyl-3-(2-methylpropyl)cyclopentane | | 72 | 0.12 |
| 13152-02-8 | Cyclooctane, ethyl- | | 72 | 0.12 |
| | Trace Cyclic Alkanes | | | |
| 13990-93-7 | Trans-1,4-diethylcyclohexane | | 64 | 0.056 |
| 3728-56-1 | 1-Ethyl-4-methylcyclohexane | | 90 | 0.064 |
| 6876-23-9 | Cyclohexane, 1,2-dimethyl-, trans- | | 83 | 0.063 |
| 96-37-7 | Cyclopentane, methyl- | | 74 | 0.036 |
| | Major Oxygenates | | | |
| 64-17-5 | Ethanol | | 72 | 1.92 |
| 75-07-0 | Acetaldehyde | | 91 | 1.46 |
| 141-78-6 | Ethyl Acetate | | 90 | 0.41 |
| 78-93-3 | 2-Butanone | | 78 | 0.29 |
| 78-84-2 | Propanal, 2-methyl- | | 72 | 0.25 |
| 67-64-1 | Acetone | | 83 | 0.18 |
| 71-36-3 | 1-Butanol | | 83 | 0.17 |
| 107-87-9 | 2-Pentanone | | 90 | 0.12 |
| 64-19-7 | Acetic acid | | 90 | 0.10 |

FIG. 23C-2 CONT

Catalyst: 0.5%Pt/5.0%H₃BO₃-Al₂O₃

| Reaction conditions | | | Average #C | Product distribution (%) | | | |
|---|---|---|---|---|---|---|---|
| T (°C) | P (psig) | LFR (mL/min) | | Aromatics | Alkenes | Alkanes | Oxygenates |
| 350 | 700 | 0.125 | 8.17 | 10.42 | 1.37 | 81.65 | 0.88 |

| CAS # | Compound Name | BR # | Q | Area% |
|---|---|---|---|---|
| \multicolumn{5}{c}{Major Aromatics Hydrocarbons} ||||| 
| 106-42-3 | p-Xylene | | 97 | 2.10 |
| 100-41-4 | Ethylbenzene | | 91 | 1.08 |
| 108-88-3 | Toluene | | 91 | 0.81 |
| 874-41-9 | Benzene, 1-ethyl-2,4-dimethyl- | | 94 | 0.79 |
| 1074-55-1 | Benzene, 1-methyl-4-propyl- | | 91 | 0.77 |
| 95-63-6 | Benzene, 1,2,4-trimethyl- | | 91 | 0.60 |
| 53669-88-0 | 1,4-dimethyl-2-(2-methylpropyl)benzene | | 83 | 0.60 |
| 141-93-5 | Benzene, 1,3-diethyl- | | 96 | 0.52 |
| 488-23-3 | Benzene, 1,2,3,4-tetramethyl- | | 91 | 0.38 |
| 622-96-8 | Benzene, 1-ethyl-4-methyl- | | 91 | 0.34 |
| 71-43-2 | Benzene | | 91 | 0.32 |
| 104-51-8 | Benzene, n-butyl- | | 90 | 0.30 |
| 2050-24-0 | Benzene, 1,3-diethyl-5-methyl- | | 94 | 0.27 |
| 1595-05-7 | Benzene, 1-methyl-4-butyl | | 91 | 0.22 |
| 103-65-1 | Benzene, propyl- | | 86 | 0.18 |
| 934-74-7 | Benzene, 1-ethyl-3,5-dimethyl- | | 91 | 0.16 |
| 620-14-4 | Benzene, 1-ethyl-3-methyl- | | 91 | 0.11 |
| 1595-16-0 | Benzene, 1-methyl-4-(1-methylpropyl)- | | 83 | 0.11 |
| \multicolumn{5}{c}{Trace Aromatic Hydrocarbons} ||||| 
| 19219-84-2 | Benzene, (1,3-dimethylbutyl)- | | 72 | 0.059 |
| 99-87-6 | p-Cymene | | 68 | 0.046 |
| 135-01-3 | Benzene, 1,2-diethyl- | | 91 | 0.036 |
| 939-27-5 | Naphthalene, 2-ethyl- | | 93 | 0.033 |
| 91-57-6 | Naphthalene, 2-methyl- | | 86 | 0.033 |
| 1000383-71-3 | 2-Isopropyl-7-methylnaphthalene | | 74 | 0.033 |
| 1074-17-5 | Benzene, 1-methyl-2-propyl- | | 80 | 0.032 |
| 575-41-7 | Naphthalene, 1,3-dimethyl- | | 96 | 0.026 |
| 1127-76-0 | 1-ethylnaphthalene | | 74 | 0.025 |
| 6158-45-8 | Naphthalene, 1-(1-methylethyl)- | | 94 | 0.025 |
| 87-85-4 | Benzene, hexamethyl- | | 87 | 0.024 |
| 581-42-0 | Naphthalene, 2,6-dimethyl- | | 62 | 0.023 |
| 575-43-9 | Naphthalene, 1,6-dimethyl- | | 72 | 0.021 |
| 108-67-8 | Mesitylene | | 91 | 0.019 |
| 529-05-5 | Chamazulene | | 60 | 0.013 |
| \multicolumn{5}{c}{Major Oxygenated Aromatics} ||||| 
| 4132-48-3 | Benzene, 1-methoxy-4-(1-methylethyl)- | | 80 | 0.11 |
| \multicolumn{5}{c}{Trace Oxygenated Aromatics} ||||| 
| 52417-50-2 | 2-(2,5-dimethylphenyl)propionaldehyde | | 72 | 0.059 |
| 90-00-6 | Phenol, 2-ethyl- | | 83 | 0.055 |
| 1197-34-8 | Phenol, 3,5-diethyl- | | 64 | 0.053 |
| 1515-95-3 | Benzene, 1-ethyl-4-methoxy- | | 86 | 0.040 |
| 89-83-8 | Thymol | | 90 | 0.038 |
| 3855-26-3 | Phenol, 2-ethyl-4-methyl- | | 90 | 0.036 |
| 98-54-4 | Phenol, p-tert-butyl- | | 64 | 0.022 |
| 39877-93-5 | 1-(5,5-dimethylcyclopenten-1-yl)-2-methoxybenzene | | 72 | 0.015 |
| \multicolumn{5}{c}{Trace n-Alkenes} ||||| 
| 592-43-8 | 2-Hexene | | 91 | 0.078 |
| 14919-01-8 | 3-Octene, (E)- | | 91 | 0.069 |
| 13269-52-8 | 3-Hexene, (E)- | | 91 | 0.053 |
| 14686-14-7 | 3-Heptene, (E)- | | 94 | 0.041 |
| 592-47-2 | 3-Hexene | | 91 | 0.039 |

FIG. 23D-2 CONT

| CAS # | Compound Name | BR | Q | Area% |
|---|---|---|---|---|
| 592-77-8 | 2-Heptene | | 95 | 0.038 |
| 14850-23-8 | 4-Octene, (E)- | | 90 | 0.038 |
| 6443-92-1 | (Z)-2-Heptene | | 95 | 0.028 |
| 106-98-9 | 1-Butene | | 90 | 0.018 |
| 592-41-6 | 1-Hexene | | 91 | 0.015 |
| 627-20-3 | 2-Pentene, (Z)- | | 91 | 0.015 |
| 109-67-1 | 1-Pentene | | 83 | 0.004 |
| Major Branched Alkenes | | | | |
| 7145-23-5 | 3-Hexene, 2,3-dimethyl- | 2 | 68 | 0.21 |
| 922-62-3 | 2-Pentene, 3-methyl-, (Z)- | 1 | 91 | 0.19 |
| 922-61-2 | 2-Pentene, 3-methyl- | 1 | 94 | 0.11 |
| Trace Branched Alkenes | | | | |
| 59643-73-1 | 2,3-Dimethyl-3-heptene, (Z)- | 2 | 64 | 0.066 |
| 3404-80-6 | Hexane, 2-methyl-4-methylene- | 2 | 91 | 0.060 |
| 19780-68-8 | 3-Ethyl-4-methyl-2-pentene | 2 | 80 | 0.038 |
| 563-79-1 | 2-Butene, 2,3-dimethyl- | 2 | 86 | 0.009 |
| 13172-91-3 | 3-Heptene, 5-methyl- | 1 | 64 | 0.007 |
| 3404-65-7 | 3-Methyl-3-hexene | 1 | 90 | 0.060 |
| 4914-89-0 | 3-Hexene, 3-methyl-, (Z)- | 1 | 90 | 0.007 |
| 3683-19-0 | (Z)-4-Methyl-2-hexene | 1 | 91 | 0.006 |
| 2787-45-3 | 1,3-Pentadiene, 3-methyl-, (Z)- | 1 | 86 | 0.006 |
| 513-35-9 | 2-Butene, 2-methyl- | 1 | 91 | 0.008 |
| 115-11-7 | 1-Propene, 2-methyl- | 1 | 83 | 0.011 |
| Trace Cyclic Alkenes | | | | |
| 53366-54-4 | Cyclopentane, (2-methylbutylidene)- | | 83 | 0.054 |
| 2175-91-9 | 5-propan-2-ylidenecyclopenta-1,3-diene | | 91 | 0.050 |
| 2808-76-6 | 1,3-Dimethyl-1-cyclohexene | | 83 | 0.056 |
| 110-83-8 | Cyclohexene | | 86 | 0.005 |
| Major n-Alkanes | | | | |
| 110-54-3 | n-Hexane | | 91 | 16.66 |
| 142-82-5 | Heptane | | 95 | 11.04 |
| 111-84-2 | Nonane | | 95 | 4.87 |
| 124-18-5 | Decane | | 95 | 2.90 |
| 109-66-0 | Pentane | | 90 | 2.43 |
| 1120-21-4 | Undecane | | 91 | 1.49 |
| 629-50-5 | Tridecane | | 94 | 0.41 |
| 106-97-8 | Butane | | 87 | 0.34 |
| 628-59-4 | Tetradecane | | 76 | 0.13 |
| 629-62-9 | Pentadecane | | 94 | 0.11 |
| Trace n-Alkanes | | | | |
| 629-78-7 | Heptadecane | | 72 | 0.037 |
| 74-98-6 | Propane | | 83 | 0.014 |
| Major Branched Alkanes | | | | |
| 62238-11-3 | Decane, 2,3,5-trimethyl- | 3 | 90 | 0.18 |
| 20278-89-1 | Heptane, 3,4,5-trimethyl- | 3 | 72 | 6.73 |
| 62108-21-8 | Decane, 6-ethyl-2-methyl- | 2 | 64 | 0.11 |
| 17312-79-7 | Undecane, 4,5-dimethyl- | 2 | 72 | 2.05 |
| 583-48-2 | Hexane, 3,4-dimethyl- | 2 | 83 | 0.18 |
| 589-43-5 | Hexane, 2,4-dimethyl- | 2 | 83 | |
| 565-59-3 | Pentane, 2,3-dimethyl- | 2 | 91 | 0.23 |
| 6418-41-3 | Tridecane, 3-methyl- | 1 | 90 | 0.10 |
| 1002-43-3 | Undecane, 3-methyl- | 1 | 91 | 0.52 |

FIG. 23D-2 CONT

| CAS # | Compound Name | BR # | Q | Area% |
|---|---|---|---|---|
| 1632-70-8 | Undecane, 5-methyl- | 1 | 93 | 0.60 |
| 17302-36-2 | 5-Ethyldecane | 1 | 64 | 0.15 |
| 13287-23-5 | Heptadecane, 8-methyl- | 1 | 78 | 0.23 |
| 2847-72-5 | Decane, 4-methyl- | 1 | 83 | 0.32 |
| 17301-94-9 | Nonane, 4-methyl- | 1 | 83 | 0.17 |
| 15869-85-9 | Nonane, 5-methyl- | 1 | 90 | 0.82 |
| 13287-21-3 | Tridecane, 6-methyl- | 1 | 64 | 0.43 |
| 2216-33-3 | Octane, 3-methyl- | 1 | 83 | 0.40 |
| 17302-33-9 | Undecane, 6-methyl- | 1 | 64 | 0.64 |
| 3221-61-2 | Octane, 2-methyl- | 1 | 94 | 0.12 |
| 2216-34-4 | Octane, 4-methyl- | 1 | 72 | 0.19 |
| 619-99-8 | Hexane, 3-ethyl- | 1 | 91 | 1.03 |
| 589-53-7 | Heptane, 4-methyl- | 1 | 91 | 0.25 |
| 592-27-8 | Heptane, 2-methyl- | 1 | 95 | 0.22 |
| 617-78-7 | Pentane, 3-ethyl- | 1 | 91 | 1.54 |
| 591-76-4 | Hexane, 2-methyl- | 1 | 74 | 0.31 |
| 96-14-0 | Pentane, 3-methyl- | 1 | 91 | 5.19 |
| 107-83-5 | Pentane, 2-methyl- | 1 | 72 | 0.26 |
| Trace Branched Alkanes ||||| 
| 17301-28-9 | Undecane, 3,6-dimethyl- | 2 | 78 | 0.085 |
| 922-28-1 | Heptane, 3,4-dimethyl- | 2 | 64 | 0.036 |
| 3074-71-3 | Heptane, 2,3-dimethyl- | 2 | 90 | 0.062 |
| 17312-50-4 | Decane, 2,5-dimethyl- | 2 | 78 | 0.057 |
| 563-16-6 | Hexane, 3,3-dimethyl- | 2 | 74 | 0.012 |
| 562-49-2 | Pentane, 3,3-dimethyl- | 2 | 83 | 0.013 |
| 2980-69-0 | Undecane, 4-methyl- | 1 | 72 | 0.081 |
| 6165-40-8 | Pentadecane, 7-methyl- | 1 | 72 | 0.033 |
| 13151-35-4 | Decane, 5-methyl- | 1 | 87 | 0.064 |
| 78-78-4 | Butane, 2-methyl- | 1 | 80 | 0.084 |
| Major Cyclic Alkanes ||||| 
| 3728-47-4 | Cyclopentane, 1-ethyl-3-methyl- | | 83 | 1.77 |
| 1678-91-7 | Cyclohexane, ethyl- | | 91 | 0.93 |
| 61142-68-5 | Cyclopentane, 1-hexyl-3-methyl- | | 91 | 0.56 |
| 108-87-2 | Cyclohexane, methyl- | | 94 | 0.42 |
| 110-82-7 | Cyclohexane | | 91 | 0.39 |
| 930-89-2 | Cyclopentane, 1-ethyl-2-methyl-, cis- | | 95 | 0.26 |
| 96-37-7 | Cyclopentane, methyl- | | 91 | 0.25 |
| 2207-04-7 | Cyclohexane, 1,4-dimethyl-, trans- | | 91 | 0.22 |
| 6876-23-9 | Cyclohexane, 1,2-dimethyl-, trans- | | 95 | 0.18 |
| 1678-93-9 | Cyclohexane, butyl- | | 94 | 0.17 |
| 834-43-1 | Cyclohexane, 1,2-diethyl-, cis- | | 78 | 0.16 |
| 3728-56-1 | 1-Ethyl-4-methylcyclohexane | | 91 | 0.13 |
| 7045-67-2 | Cyclohexane, 2-ethyl-1,3-dimethyl- | | 76 | 0.12 |
| Trace Cyclic Alkanes ||||| 
| 4926-90-3 | Cyclohexane, 1-ethyl-1-methyl- | | 64 | 0.033 |
| 293-96-9 | Cyclodecane | | 90 | 0.063 |
| 6708-17-4 | 1,1'-Bicyclooctyl | | 78 | 0.023 |
| 13990-93-7 | Trans-1,4-diethylcyclohexane | | 83 | 0.097 |
| 4291-80-9 | Cyclohexane, 1-methyl-3-propyl- | | 72 | 0.042 |
| 1678-92-8 | Cyclohexane, propyl- | | 87 | 0.085 |
| 4923-77-7 | Cyclohexane, 1-ethyl-2-methyl-, cis- | | 90 | 0.024 |
| 6236-88-0 | Cyclohexane, 1-ethyl-4-methyl-, trans- | | 91 | 0.082 |

FIG. 23D-2 CONT

| CAS # | Compound Name | BR # | Q | Area% |
|---|---|---|---|---|
| 2207-01-4 | Cyclohexane, 1,2-dimethyl-, cis- | | 93 | 0.081 |
| 2613-66-3 | Cyclopentane, 1-ethyl-3-methyl-, cis- | | 81 | 0.080 |
| 15890-40-1 | 1,2,3-Trimethylcyclopentane, cis, trans | | 95 | 0.050 |
| 1640-89-7 | Cyclopentane, ethyl- | | 86 | 0.053 |
| 872-56-0 | Isopropylcyclobutane | | 91 | 0.012 |
| 1192-18-3 | Cyclopentane, 1,2-dimethyl-, cis- | | 80 | 0.025 |
| 2453-00-1 | Cyclopentane, 1,3-dimethyl- | | 78 | 0.015 |
| 1191-96-4 | Cyclopropane, ethyl- | | 90 | 0.003 |
| Major Oxygenates | | | | |
| 1000382-54-5 | Carbonic acid, tetradecyl vinyl ester | | 90 | 0.65 |
| Trace Oxygenates | | | | |
| 1000309-39-2 | Oxalic acid, 2-ethylhexyl nonyl ester | | 78 | 0.047 |
| 1000309-34-3 | 6-Ethyl-3-octanyl 4-methylpentyl oxalate | | 72 | 0.021 |
| 1000309-08-3 | Cyclohexylmethyl 4-methylpentyl oxalate | | 72 | 0.018 |
| 36653-82-4 | 1-Hexadecanol | | 72 | 0.038 |
| 1000309-38-9 | Oxalic acid, 2-ethylhexyl hexyl ester | | 72 | 0.025 |
| 7180-60-1 | 2-Cyclopenten-1-one, 3-methoxy-5-methyl- | | 64 | 0.047 |
| 765-87-7 | 1,2-Cyclohexanedione | | 87 | 0.017 |
| 60-29-7 | Ethyl ether | | 87 | 0.011 |

FIG. 23D-2 CONT

Catalyst: 0.5%Pt-0.5%Sn-0.5%Bi/Al₂O₃

| Reaction conditions | | | Average #C | Product distribution (%) | | | |
|---|---|---|---|---|---|---|---|
| T (°C) | P (psig) | LFR (mL/min) | | Aromatics | Alkenes | Alkanes | Oxygenates |
| 350 | 500 | 0.125 | 8.25 | 30.51 | 5.29 | 39.35 | 3.43 |

Hydrocarbon Report

Request: RVP-GHH-J2215    Xyleco Inc    Sample: RVP-ETG-52-2-R7-350C

| Summary | Total | Known | Major | Trace | Ave Carbon # |
|---|---|---|---|---|---|
| Peaks: | 444 | 222 | 116 | 106 | 8.26 |
| Area: | 3647589124 | 78.7% | 73.8% | 4.9% | |

| Compound Type | Total Known | | Major Components | | Average Carbon # |
|---|---|---|---|---|---|
| | # Peaks | % Area | # Peaks | % Area | |
| Aromatics (Total): | 72 | 30.56 | 42 | 28.80 | 9.12 |
| Oxygenated: | 27 | 3.10 | 13 | 2.28 | 10.79 |
| Alkenes (Total): | 58 | 5.29 | 18 | 3.71 | 7.13 |
| Straight: | 21 | 2.58 | 10 | 2.11 | 6.77 |
| Branched: | 18 | 1.31 | 4 | 0.81 | 7.24 |
| Cyclic: | 19 | 1.40 | 4 | 0.79 | 7.69 |
| Alkanes (Total): | 67 | 39.35 | 45 | 38.38 | 7.88 |
| Straight: | 10 | 21.94 | 9 | 21.93 | 7.64 |
| Branched: | 23 | 8.25 | 16 | 7.91 | 8.06 |
| Cyclic: | 34 | 9.16 | 20 | 8.54 | 8.28 |
| Oxygenated (Other): | 24 | 3.43 | 11 | 2.89 | 6.58 |

| CAS # | Compound Name | BR # | Q | Area% |
|---|---|---|---|---|
| Major Aromatics Hydrocarbons ||||||
| 95-47-6 | o-Xylene | | 95 | 3.71 |
| 108-38-3 | Benzene, 1,3-dimethyl- | | 95 | 3.01 |
| 108-88-3 | Toluene | | 91 | 2.92 |
| 100-41-4 | Ethylbenzene | | 91 | 2.80 |
| 622-96-8 | Benzene, 1-ethyl-4-methyl- | | 91 | 2.27 |
| 1074-55-1 | Benzene, 1-methyl-4-propyl- | | 91 | 2.08 |
| 874-41-9 | Benzene, 1-ethyl-2,4-dimethyl- | | 95 | 1.31 |
| 1758-88-9 | Benzene, 2-ethyl-1,4-dimethyl- | | 95 | 1.19 |
| 71-43-2 | Benzene | | 91 | 0.98 |
| 104-51-8 | Benzene, n-butyl- | | 91 | 0.89 |
| 141-93-5 | Benzene, 1,3-diethyl- | | 96 | 0.82 |
| 4481-30-5 | Benzene, (1,2-dimethylpropyl)- | | 80 | 0.74 |
| 103-65-1 | Benzene, propyl- | | 87 | 0.67 |
| 55669-88-0 | 1,4-dimethyl-2-(2-methylpropyl)benzene | | 91 | 0.65 |
| 611-14-3 | Benzene, 1-ethyl-2-methyl- | | 91 | 0.40 |
| 1758-85-6 | Benzene, 2,4-diethyl-1-methyl- | | 94 | 0.34 |
| 1077-16-3 | Benzene, hexyl- | | 72 | 0.33 |
| 1595-16-0 | Benzene, 1-methyl-4-(1-methylpropyl)- | | 64 | 0.30 |
| 1587-04-8 | Benzene, 1-methyl-3-(2-propenyl)- | | 78 | 0.24 |
| 6682-06-0 | 1H-Indene, 2,3-dihydro-4,5,7-trimethyl- | | 91 | 0.17 |
| 4920-99-4 | Benzene, 1-ethyl-3-(1-methylethyl)- | | 72 | 0.16 |
| 1074-43-7 | Benzene, 1-methyl-3-propyl- | | 80 | 0.14 |
| 275-51-4 | Azulene | | 87 | 0.14 |
| 108-67-8 | Mesitylene | | 90 | 0.14 |
| 91-57-6 | Naphthalene, 2-methyl- | | 87 | 0.13 |
| Trace Aromatic Hydrocarbons ||||||
| 2050-24-0 | Benzene, 1,3-diethyl-5-methyl- | | 72 | 0.100 |
| 6682-71-9 | 1H-Indene, 2,3-dihydro-4,7-dimethyl- | | 90 | 0.100 |
| 22531-20-0 | Naphthalene, 6-ethyl-1,2,3,4-tetrahydro- | | 87 | 0.097 |
| 1483-60-9 | Benzene, 1,3-dimethyl-4-(1-methylpropyl) | | 64 | 0.079 |
| 135-01-3 | Benzene, 1,2-diethyl- | | 86 | 0.076 |
| 581-42-0 | Naphthalene, 2,6-dimethyl- | | 93 | 0.069 |
| 581-40-8 | Naphthalene, 2,3-dimethyl- | | 90 | 0.064 |
| 6158-45-8 | Naphthalene, 1-(1-methylethyl)- | | 80 | 0.064 |
| 2613-76-5 | 1H-Indene, 2,3-dihydro-1,1,3-trimethyl- | | 81 | 0.062 |
| 939-27-5 | Naphthalene, 2-ethyl- | | 93 | 0.060 |
| 2717-39-7 | 1,4,5,8-Tetramethylnaphthalene | | 70 | 0.053 |
| 19063-11-7 | 5,6,7,8-tetramethyltetralin | | 90 | 0.035 |
| 21693-51-6 | 1,5,8-trimethyltetralin | | 74 | 0.033 |
| 98-06-6 | Benzene, tert-butyl- | | 74 | 0.020 |
| 483-78-3 | 1,6-dimethyl-4-propan-2-yl-naphthalene | | 80 | 0.018 |
| 1000353-71-2 | 2-Isopropyl-3-methylnaphthalene | | 64 | 0.015 |
| Major Oxygenated Aromatics ||||||
| 31574-44-4 | 1-methoxy-4-methyl-2-propan-2-yl-benzene | | 78 | 0.44 |
| 88-40-4 | 1-tert-butyl-2-methoxy-4-methyl-benzene | | 72 | 0.41 |
| 1687-64-5 | Phenol, 2-ethyl-6-methyl- | | 83 | 0.27 |
| 499-75-2 | Phenol, 2-methyl-5-(1-methylethyl)- | | 87 | 0.24 |
| 2409-55-4 | Phenol, 2-(1,1-dimethylethyl)-4-methyl- | | 74 | 0.23 |
| 1000113-36-0 | Phenol, 2,5-bis(1-methylethyl)-, acetate | | 64 | 0.22 |
| 3228-02-2 | 3-Methyl-4-isopropylphenol | | 74 | 0.16 |
| 89-83-8 | Thymol | | 64 | 0.16 |

FIG. 25A CONT

| CAS # | Compound Name | BR # | Q | Area% |
|---|---|---|---|---|
| 1076-56-8 | 2-methoxy-4-methyl-1-propan-2-yl-benzene | | 64 | 0.15 |
| 527-35-5 | Phenol, 2,3,5,6-tetramethyl- | | 64 | 0.13 |
| 34862-94-7 | 1-Penten-3-ol, 1-phenyl- | | 72 | 0.11 |
| | Trace Oxygenated Aromatics | | | |
| 4132-48-3 | Benzene, 1-methoxy-4-(1-methylethyl)- | | 74 | 0.087 |
| 1197-34-8 | Phenol, 3,5-diethyl- | | 68 | 0.075 |
| 1000202-02-2 | 1-(4-Methoxymethyl-2,6-dimethylphenyl)ethanone | | 64 | 0.060 |
| 90-00-6 | Phenol, 2-ethyl- | | 91 | 0.058 |
| 99-89-8 | p-Cumenol | | 86 | 0.054 |
| 6148-37-4 | Furan, 4-methyl-2-propyl- | | 72 | 0.053 |
| 26537-19-9 | Methyl 4-tert-butylbenzoate | | 72 | 0.049 |
| 585-34-2 | Phenol, m-tert-butyl- | | 72 | 0.038 |
| 13667-28-2 | 5'-Hydroxy-2',3',4'-trimethylacetophenone | | 68 | 0.033 |
| 10425-83-9 | 1-Indanone, 3,3,4,5,7-pentamethyl- | | 72 | 0.030 |
| 98-54-4 | Phenol, p-tert-butyl- | | 72 | 0.021 |
| | Major n-Alkenes | | | |
| 7642-09-3 | 3-Hexene, (Z)- | | 95 | 0.54 |
| 4050-45-7 | 2-Hexene, (E)- | | 91 | 0.51 |
| 592-77-8 | 2-Heptene | | 95 | 0.36 |
| 7642-10-6 | (Z)-3-Heptene | | 96 | 0.25 |
| 592-78-9 | 3-Heptene | | 95 | 0.14 |
| 14850-23-8 | 4-Octene, (E)- | | 94 | 0.13 |
| 592-41-6 | 1-Hexene | | 91 | 0.13 |
| 2198-23-4 | 4-Nonene | | 87 | 0.10 |
| | Trace n-Alkenes | | | |
| 13389-42-9 | 2-Octene, (E)- | | 95 | 0.094 |
| 592-76-7 | 1-Heptene | | 95 | 0.067 |
| 20063-92-7 | 3-Nonene, (E)- | | 96 | 0.066 |
| 14850-22-7 | 3-Octene, (Z)- | | 95 | 0.064 |
| 627-20-3 | 2-Pentene, (Z)- | | 90 | 0.043 |
| 10405-84-2 | cis-4-Nonene | | 90 | 0.030 |
| 592-46-1 | 2,4-Hexadiene | | 91 | 0.017 |
| 592-45-0 | 1,4-Hexadiene | | 87 | 0.006 |
| 109-67-1 | 1-Pentene | | 83 | 0.003 |
| | Major Branched Alkenes | | | |
| 75144-24-0 | 2-sec-Butyl-3-methyl-1-pentene | 2 | 62 | 0.18 |
| 3404-75-9 | 2-Heptene, 3-methyl- | 1 | 87 | 0.13 |
| 922-61-2 | 2-Pentene, 3-methyl- | 1 | 94 | 0.50 |
| | Trace Branched Alkenes | | | |
| 19780-68-8 | 3-Ethyl-4-methyl-2-pentene | 2 | 90 | 0.072 |
| 13151-10-5 | 1-Octene, 6-methyl- | 1 | 62 | 0.060 |
| 4485-16-9 | 3-Heptene, 4-methyl- | 1 | 83 | 0.009 |
| 1632-16-2 | 3-Ethyl-2-hexene(c,t) | 1 | 91 | 0.047 |
| 4049-81-4 | 1,5-Hexadiene, 3-methyl- | 1 | 64 | 0.055 |
| 10574-36-4 | 2-Hexene, 3-methyl-, (Z)- | 1 | 91 | 0.037 |
| 3404-65-7 | 3-Methyl-3-hexene | 1 | 91 | 0.060 |
| 15840-60-5 | 3-Hexene, 2-methyl-, (Z)- | 1 | 91 | 0.025 |
| 4914-89-0 | 3-Hexene, 3-methyl-, (Z)- | 1 | 78 | 0.014 |
| 926-54-5 | 1,3-Pentadiene, 2-methyl-, (E)- | 1 | 83 | 0.019 |
| 3683-22-5 | 2-Hexene, 4-methyl-, (E)- | 1 | 78 | 0.017 |
| 926-56-7 | 4-Methyl-1,3-pentadiene | 1 | 90 | 0.055 |
| 625-27-4 | 2-Pentene, 2-methyl- | 1 | 91 | 0.016 |

FIG. 25A CONT

| CAS # | Compound Name | BR # | Q | Area% |
|---|---|---|---|---|
| 760-20-3 | 1-Pentene, 3-methyl- | 1 | 91 | 0.013 |
| | Major Cyclic Alkenes | | | |
| 2808-71-1 | Cyclohexene, 3-ethyl- | | 78 | 0.30 |
| 1453-24-3 | Cyclohexene, 1-ethyl- | | 68 | 0.19 |
| 693-89-0 | Cyclopentene, 1-methyl- | | 90 | 0.17 |
| 97797-57-4 | 1-Ethyl-5-methylcyclopentene | | 90 | 0.15 |
| | Trace Cyclic Alkenes | | | |
| 61142-33-4 | 1,4-dimethyl-5-propan-2-yl-cyclopentene | | 64 | 0.087 |
| 591-48-0 | Cyclohexene, 3-methyl- | | 64 | 0.057 |
| 65378-76-9 | 1,2,4,4-Tetramethylcyclopentene | | 64 | 0.049 |
| 20348-74-7 | trans-1,3-Dimethyl-2-methylenecyclohexane | | 64 | 0.015 |
| 3742-42-5 | 4-Ethylcyclohexene | | 83 | 0.071 |
| 7086-15-9 | Cyclopentadiene, 2,3,5-trimethyl- | | 90 | 0.018 |
| 63338-00-5 | Cyclopentene, 3-ethylidene-1-methyl- | | 91 | 0.040 |
| 2808-80-2 | Cyclohexane, 1-methyl-4-methylene- | | 83 | 0.083 |
| 591-49-1 | Cyclohexene, 1-methyl- | | 72 | 0.051 |
| 2597-49-1 | Cyclobutane, ethenyl- | | 90 | 0.078 |
| 1120-62-3 | Cyclopentene, 3-methyl- | | 86 | 0.034 |
| | Major n-Alkanes | | | |
| 110-54-3 | n-Hexane | | 91 | 5.89 |
| 111-65-9 | Octane | | 72 | 5.43 |
| 142-82-5 | Heptane | | 95 | 5.21 |
| 111-84-2 | Nonane | | 95 | 2.51 |
| 124-18-5 | Decane | | 95 | 1.41 |
| 1120-21-4 | Undecane | | 95 | 0.75 |
| 629-50-5 | Tridecane | | 90 | 0.48 |
| 109-66-0 | Pentane | | 91 | 0.26 |
| | Trace n-Alkanes | | | |
| 106-97-8 | Butane | | 83 | 0.007 |
| | Major Branched Alkanes | | | |
| 565-59-3 | Pentane, 2,3-dimethyl- | 2 | 83 | 0.13 |
| 5911-04-6 | Nonane, 3-methyl- | 1 | 91 | 0.70 |
| 5881-17-4 | Octane, 3-ethyl- | 1 | 83 | 0.18 |
| 15869-85-9 | Nonane, 5-methyl- | 1 | 87 | 0.31 |
| 15869-80-4 | Heptane, 3-ethyl- | 1 | 64 | 0.34 |
| 3221-61-2 | Octane, 2-methyl- | 1 | 78 | 0.13 |
| 2216-34-4 | Octane, 4-methyl- | 1 | 80 | 0.16 |
| 2216-33-3 | Octane, 3-methyl- | 1 | 87 | 0.42 |
| 619-99-8 | Hexane, 3-ethyl- | 1 | 91 | 0.52 |
| 589-81-1 | Heptane, 3-methyl- | 1 | 83 | 2.29 |
| 592-27-8 | Heptane, 2-methyl- | 1 | 91 | 0.17 |
| 617-78-7 | Pentane, 3-ethyl- | 1 | 80 | 0.28 |
| 589-34-4 | Hexane, 3-methyl- | 1 | 91 | 0.60 |
| 591-76-4 | Hexane, 2-methyl- | 1 | 91 | 0.23 |
| 96-14-0 | Pentane, 3-methyl- | 1 | 91 | 1.29 |
| 107-83-5 | Pentane, 2-methyl- | 1 | 74 | 0.11 |
| | Trace Branched Alkanes | | | |
| 922-28-1 | Heptane, 3,4-dimethyl- | 2 | 72 | 0.026 |
| 583-48-2 | Hexane, 3,4-dimethyl- | 2 | 91 | 0.031 |
| 17453-94-0 | Undecane, 5-ethyl- | 1 | 72 | 0.091 |
| 2847-72-5 | Decane, 4-methyl- | 1 | 64 | 0.061 |
| 13287-21-3 | Tridecane, 6-methyl- | 1 | 90 | 0.091 |

FIG. 25A CONT

| CAS # | Compound Name | BR # | Q | Area% |
|---|---|---|---|---|
| 78-78-4 | Butane, 2-methyl- | 1 | 80 | 0.009 |
| Major Cyclic Alkanes ||||| 
| 3728-47-4 | Cyclopentane, 1-ethyl-3-methyl- | | 74 | 2.31 |
| 3613-65-2 | Cyclopentane, 1-ethyl-3-methyl-, trans- | | 87 | 1.99 |
| 7058-05-1 | Cyclohexane, 1-ethyl-2,3-dimethyl- | | 64 | 0.80 |
| 930-89-2 | Cyclopentane, 1-ethyl-2-methyl-, cis- | | 97 | 0.62 |
| 96-37-7 | Cyclopentane, methyl- | | 91 | 0.62 |
| 108-87-2 | Cyclohexane, methyl- | | 94 | 0.37 |
| 7045-67-2 | Cyclohexane, 2-ethyl-1,3-dimethyl- | | 64 | 0.36 |
| 110-82-7 | Cyclohexane | | 91 | 0.18 |
| 2234-75-5 | Cyclohexane, 1,2,4-trimethyl- | | 70 | 0.17 |
| 23889-46-3 | Cyclooctane, 1,2-diethyl- | | 64 | 0.15 |
| 18968-23-5 | (1S,3R,6R)-3,7,7-trimethylnorcarane | | 83 | 0.14 |
| 3741-00-2 | Cyclopentane, pentyl- | | 64 | 0.14 |
| 1678-93-9 | Cyclohexane, butyl- | | 83 | 0.13 |
| 4126-78-7 | Cycloheptane, methyl- | | 87 | 0.13 |
| 583-57-3 | Cyclohexane, 1,2-dimethyl- (cis/trans) | | 83 | 0.12 |
| 61142-68-5 | Cyclopentane, 1-hexyl-3-methyl- | | 93 | 0.11 |
| 4926-78-7 | Cyclohexane, 1-ethyl-4-methyl-, cis- | | 72 | 0.11 |
| 638-04-0 | Cyclohexane, 1,3-dimethyl-, cis- | | 91 | 0.10 |
| Trace Cyclic Alkanes ||||| 
| 2040-95-1 | Cyclopentane, butyl- | | 94 | 0.085 |
| 1678-92-8 | Cyclohexane, propyl- | | 90 | 0.079 |
| 932-40-1 | trans-1,2-Diethyl cyclopentane | | 87 | 0.028 |
| 4923-78-8 | Cyclohexane, 1-ethyl-2-methyl-, trans- | | 91 | 0.081 |
| 2207-01-4 | Cyclohexane, 1,2-dimethyl-, cis- | | 83 | 0.036 |
| 16747-50-5 | Cyclopentane, 1-ethyl-1-methyl- | | 64 | 0.037 |
| 1003-19-6 | Cyclopropane, 1,1-diethyl- | | 64 | 0.009 |
| 2815-69-6 | (1R,2s,3S)-1,2,3-Trimethylcyclopentane | | 87 | 0.038 |
| 15890-40-1 | 1,2,3-Trimethylcyclopentane, cis, trans | | 91 | 0.049 |
| 2815-58-9 | Cyclopentane, 1,2,4-trimethyl- | | 86 | 0.015 |
| 822-50-4 | Cyclopentane, 1,2-dimethyl-, trans- | | 90 | 0.066 |
| 1638-26-2 | Cyclopentane, 1,1-dimethyl- | | 70 | 0.039 |
| 1192-18-3 | Cyclopentane, 1,2-dimethyl-, cis- | | 78 | 0.055 |
| 1191-96-4 | Cyclopropane, ethyl- | | 74 | 0.003 |
| Major Oxygenates ||||| 
| 23758-27-2 | 2-Cyclohexen-1-ol, 1-methyl- | | 64 | 1.17 |
| 628-81-9 | Butane, 1-ethoxy- | | 83 | 0.31 |
| 93229-40-6 | 2,2,3-Triethyloxirane | | 86 | 0.20 |
| 60-29-7 | Ethyl ether | | 91 | 0.20 |
| 123-72-8 | Butanal | | 91 | 0.19 |
| 105-57-7 | Ethane, 1,1-diethoxy- | | 72 | 0.18 |
| 4485-09-0 | 4-Nonanone | | 90 | 0.14 |
| 107-87-9 | 2-Pentanone | | 86 | 0.13 |
| 71-36-3 | 1-Butanol | | 64 | 0.13 |
| 589-63-9 | 4-Octanone | | 93 | 0.12 |
| 13747-73-4 | Cyclohexanone, 2-(1-methylethylidene)- | | 64 | 0.12 |
| Trace Oxygenates ||||| 
| 6738-27-8 | 2,6-ditert-butyl-4-ethylidenecyclohexa-2,5-dien-1-one | | 62 | 0.025 |
| 1660-04-4 | 1-Adamantyl methyl ketone | | 64 | 0.076 |
| 1000190-18-1 | 1,2,3-Trimethyl-cyclopent-2-enecarboxaldehyde | | 64 | 0.048 |
| 110453-78-6 | S)-(+)-6-Methyl-1-octanol | | 72 | 0.024 |

FIG. 25A CONT

| CAS # | Compound Name | BR # | Q | Area% |
|---|---|---|---|---|
| 10264-55-8 | 3-Ethylcyclopentanone | | 72 | 0.011 |
| 591-78-6 | 2-Hexanone | | 83 | 0.047 |
| 1000359-07-4 | bis(oxolan-2-ylmethyl) pentanedioate | | 64 | 0.012 |
| 97-96-1 | Butanal, 2-ethyl- | | 87 | 0.060 |
| 565-61-7 | 2-Pentanone, 3-methyl- | | 91 | 0.038 |
| 4170-30-3 | 2-Butenal | | 86 | 0.040 |
| 141-78-6 | Ethyl Acetate | | 72 | 0.058 |
| 64-17-5 | Ethanol | | 72 | 0.057 |
| 75-07-0 | Acetaldehyde | | 83 | 0.018 |

FIG. 25A CONT

Catalyst: 0.5%Pt-0.5%Sn-0.5%Re/Al$_2$O$_3$

| Reaction conditions | | | Average #C | Product distribution (%) | | | |
|---|---|---|---|---|---|---|---|
| T (°C) | P (psig) | LFR (mL/min) | | Aromatics | Alkenes | Alkanes | Oxygenates |
| 350 | 500 | 0.125 | 8.19 | 31.47 | 14.34 | 31.87 | 1.53 |

Hydrocarbon Report

Request: RVP-GGF-K2719　　　Xyleco Inc　　　Sample: RVP-ETG-45-2-R2-350C

| Summary | Total | Known | Major | Trace | Ave Carbon # |
|---|---|---|---|---|---|
| Peaks: | 509 | 246 | 121 | 125 | 8.19 |
| Area: | 4202887486 | 79.4% | 74.1% | 5.3% | |

| Compound Type | Total Known # Peaks | Total Known % Area | Major Components # Peaks | Major Components % Area | Average Carbon # |
|---|---|---|---|---|---|
| Aromatics (Total): | 95 | 31.62 | 44 | 29.52 | 8.92 |
| Oxygenated: | 29 | 3.54 | 16 | 2.83 | 9.09 |
| Alkenes (Total): | 81 | 14.34 | 40 | 12.71 | 7.62 |
| Straight: | 26 | 6.18 | 17 | 5.79 | 7.06 |
| Branched: | 37 | 5.56 | 16 | 4.85 | 7.78 |
| Cyclic: | 18 | 2.60 | 7 | 2.07 | 8.59 |
| Alkanes (Total): | 57 | 31.87 | 33 | 30.70 | 7.69 |
| Straight: | 9 | 21.08 | 8 | 20.99 | 7.45 |
| Branched: | 15 | 4.37 | 10 | 4.05 | 7.96 |
| Cyclic: | 33 | 6.43 | 15 | 5.66 | 8.29 |
| Oxygenated (Other): | 13 | 1.53 | 4 | 1.15 | 8.85 |

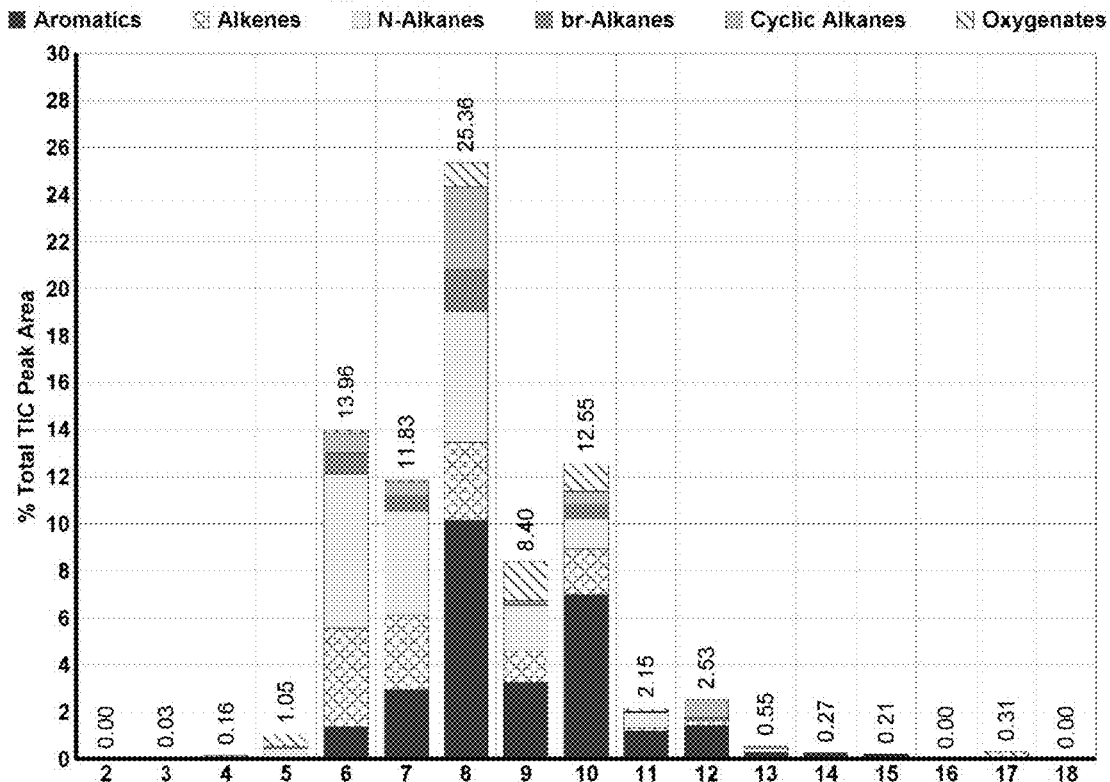

FIG 26A

| CAS # | Compound Name | BR # | Q | Area% |
|---|---|---|---|---|
| Major Aromatics Hydrocarbons | | | | |
| 108-38-3 | Benzene, 1,3-dimethyl- | | 95 | 4.10 |
| 106-42-3 | p-Xylene | | 95 | 3.05 |
| 100-41-4 | Ethylbenzene | | 91 | 3.01 |
| 108-88-3 | Toluene | | 91 | 2.95 |
| 1074-55-1 | Benzene, 1-methyl-4-propyl- | | 91 | 1.44 |
| 71-43-2 | Benzene | | 91 | 1.35 |
| 1758-88-9 | Benzene, 2-ethyl-1,4-dimethyl- | | 95 | 1.28 |
| 874-41-9 | Benzene, 1-ethyl-2,4-dimethyl- | | 94 | 1.28 |
| 108-67-8 | Mesitylene | | 91 | 1.27 |
| 104-51-8 | Benzene, n-butyl- | | 91 | 0.93 |
| 1074-43-7 | Benzene, 1-methyl-3-propyl- | | 87 | 0.81 |
| 611-14-3 | Benzene, 1-ethyl-2-methyl- | | 94 | 0.76 |
| 141-93-5 | Benzene, 1,3-diethyl- | | 97 | 0.75 |
| 55669-88-0 | 1,4-dimethyl-2-(2-methylpropyl)benzene | | 81 | 0.66 |
| 2719-52-0 | Benzene, (1-methylbutyl)- | | 74 | 0.66 |
| 103-65-1 | Benzene, propyl- | | 87 | 0.64 |
| 620-14-4 | Benzene, 1-ethyl-3-methyl- | | 90 | 0.52 |
| 1758-85-6 | Benzene, 2,4-diethyl-1-methyl- | | 93 | 0.28 |
| 7525-62-4 | Benzene, 1-ethenyl-3-ethyl- | | 60 | 0.25 |
| 22531-20-0 | Naphthalene, 6-ethyl-1,2,3,4-tetrahydro- | | 90 | 0.21 |
| 483-78-3 | 1,6-dimethyl-4-propan-2-yl-naphthalene | | 90 | 0.20 |
| 54340-86-2 | 4-[(E)-but-2-enyl]-1,2-dimethyl-benzene | | 91 | 0.13 |
| 1139-29-9 | 1-(1-methylethenyl)-3-propan-2-ylbenzene | | 64 | 0.12 |
| 1074-17-5 | Benzene, 1-methyl-2-propyl- | | 80 | 0.12 |
| 6682-71-9 | 1H-Indene, 2,3-dihydro-4,7-dimethyl- | | 70 | 0.11 |
| Trace Aromatic Hydrocarbons | | | | |
| 939-27-5 | Naphthalene, 2-ethyl- | | 90 | 0.080 |
| 526-73-8 | Benzene, 1,2,3-trimethyl- | | 83 | 0.079 |
| 582-16-1 | Naphthalene, 2,7-dimethyl- | | 82 | 0.078 |
| 135-01-3 | Benzene, 1,2-diethyl- | | 87 | 0.074 |
| 490-65-3 | Naphthalene, 1-methyl-7-(1-methylethyl)- | | 90 | 0.074 |
| 90-12-0 | Naphthalene, 1-methyl- | | 87 | 0.074 |
| 829-26-5 | Naphthalene, 2,3,6-trimethyl- | | 91 | 0.071 |
| 3031-15-0 | Naphthalene, 1,2,3,4-tetramethyl- | | 90 | 0.071 |
| 19063-11-7 | 5,6,7,8-tetramethyltetralin | | 70 | 0.066 |
| 40650-41-7 | 1H-Indene, 2,3-dihydro-1,1,5-trimethyl- | | 72 | 0.063 |
| 575-41-7 | Naphthalene, 1,3-dimethyl- | | 91 | 0.058 |
| 17059-48-2 | 1H-Indene, 2,3-dihydro-1,6-dimethyl- | | 80 | 0.056 |
| 30316-36-0 | 1,6,8-trimethyltetralin | | 93 | 0.054 |
| 2131-42-2 | Naphthalene, 1,4,6-trimethyl- | | 60 | 0.049 |
| 475-03-6 | Naphthalene, tetrahydro-1,1,6-trimethyl- | | 80 | 0.045 |
| 941-81-1 | 4,6,8-Trimethylazulene | | 94 | 0.038 |
| 527-84-4 | o-Cymene | | 72 | 0.038 |
| 529-05-5 | Chamazulene | | 70 | 0.036 |
| 4773-83-5 | 1,2,3-Trimethylindene | | 72 | 0.035 |
| 2245-38-7 | Naphthalene, 1,6,7-trimethyl- | | 89 | 0.026 |
| 1000113-61-3 | 1,4,5,6-tetramethyltetralin | | 64 | 0.022 |
| Major Oxygenated Aromatics | | | | |
| 3228-02-2 | 3-Methyl-4-isopropylphenol | | 83 | 0.49 |
| 698-71-5 | Phenol, 3-ethyl-5-methyl- | | 91 | 0.45 |
| 105-67-9 | Phenol, 2,4-dimethyl- | | 91 | 0.41 |

FIG 26A CONT

| CAS # | Compound Name | BR # | Q | Area% |
|---|---|---|---|---|
| 1687-64-5 | Phenol, 2-ethyl-6-methyl- | | 87 | 0.33 |
| 620-17-7 | Phenol, 3-ethyl- | | 80 | 0.21 |
| 6148-37-4 | Furan, 4-methyl-2-propyl- | | 78 | 0.21 |
| 499-75-2 | Phenol, 2-methyl-5-(1-methylethyl)- | | 87 | 0.19 |
| 88-69-7 | 2-propan-2-ylphenol | | 90 | 0.17 |
| 1197-34-8 | Phenol, 3,5-diethyl- | | 90 | 0.13 |
| 2416-94-6 | Phenol, 2,3,6-trimethyl- | | 90 | 0.12 |
| 108-68-9 | Phenol, 3,5-dimethyl- | | 93 | 0.11 |
| 1000364-49-1 | 4-Methylbenzyl alcohol, methyl ether | | 64 | 0.10 |
| 4132-48-3 | Benzene, 1-methoxy-4-(1-methylethyl)- | | 86 | 0.10 |
| | Trace Oxygenated Aromatics | | | |
| 90-00-6 | Phenol, 2-ethyl- | | 91 | 0.072 |
| 98-54-4 | Phenol, p-tert-butyl- | | 64 | 0.063 |
| 34862-94-7 | 1-Penten-3-ol, 1-phenyl- | | 78 | 0.063 |
| 18272-84-9 | Benzene, 1-butyl-4-methoxy- | | 64 | 0.061 |
| 1515-95-3 | Benzene, 1-ethyl-4-methoxy- | | 86 | 0.060 |
| 536-60-7 | p-Cymen-7-ol | | 68 | 0.049 |
| 3855-26-3 | Phenol, 2-ethyl-4-methyl- | | 80 | 0.048 |
| 618-45-1 | Phenol, 3-(1-methylethyl)- | | 80 | 0.039 |
| 88-18-6 | Phenol, 2-(1,1-dimethylethyl)- | | 82 | 0.032 |
| 89-72-5 | Phenol, 2-(1-methylpropyl)- | | 64 | 0.028 |
| | Major n-Alkenes | | | |
| 14686-14-7 | 3-Heptene, (E)- | | 95 | 1.17 |
| 592-43-8 | 2-Hexene | | 91 | 0.94 |
| 592-77-8 | 2-Heptene | | 95 | 0.93 |
| 7642-09-3 | 3-Hexene, (Z)- | | 95 | 0.60 |
| 4050-45-7 | 2-Hexene, (E)- | | 91 | 0.51 |
| 14850-23-8 | 4-Octene, (E)- | | 87 | 0.35 |
| 10405-85-3 | trans-4-Nonene | | 91 | 0.25 |
| 7642-04-8 | 2-Octene, (Z)- | | 97 | 0.18 |
| 20063-92-7 | 3-Nonene, (E)- | | 95 | 0.18 |
| 592-41-6 | 1-Hexene | | 94 | 0.15 |
| 6434-77-1 | cis-2-Nonene | | 91 | 0.14 |
| 14850-22-7 | 3-Octene, (Z)- | | 96 | 0.14 |
| 6434-78-2 | 2-Nonene, (E)- | | 93 | 0.14 |
| 592-76-7 | 1-Heptene | | 96 | 0.11 |
| | Trace n-Alkenes | | | |
| 20063-77-8 | 3-Nonene | | 93 | 0.086 |
| 627-20-3 | 2-Pentene, (Z)- | | 91 | 0.078 |
| 19150-21-1 | trans-3-Decene | | 70 | 0.067 |
| 15192-80-0 | (E,E)-2,4,6-Octatriene | | 91 | 0.063 |
| 764-97-6 | 5-Undecene, (E)- | | 76 | 0.051 |
| 1000192-48-8 | Octa-2,4,6-triene | | 91 | 0.024 |
| 646-04-8 | 2-Pentene, (E)- | | 86 | 0.009 |
| 106-98-9 | 1-Butene | | 86 | 0.006 |
| | Major Branched Alkenes | | | |
| 67632-84-0 | 3,5-Octadiene, 4,5-diethyl- | 2 | 80 | 0.19 |
| 6874-39-1 | (2E,4E)-3,7-Dimethyl-2,4-octadiene | 2 | 74 | 0.37 |
| 1000374-08-4 | (2Z,4E)-3,7-Dimethyl-2,4-octadiene | 2 | 64 | 0.27 |
| 1000195-03-3 | 6,6-Dimethylhepta-2,4-diene | 2 | 74 | 0.20 |
| 4634-87-1 | 2,4-Heptadiene, 2,6-dimethyl- | 3 | 80 | 0.11 |
| 758-86-1 | 2,3-Dimethyl-1,4-pentadiene | 2 | 64 | 0.14 |

FIG 26A CONT

| CAS # | Compound Name | BR # | Q | Area% |
|---|---|---|---|---|
| 15918-02-7 | 4-Nonene, 5-methyl- | 1 | 76 | 0.13 |
| 3404-75-9 | 2-Heptene, 3-methyl- | 1 | 91 | 0.34 |
| 7086-89-9 | 1,4-Hexadiene, 3-ethyl- | 1 | 74 | 0.84 |
| 13172-91-3 | 3-Heptene, 5-methyl- | 1 | 90 | 0.20 |
| 1632-16-2 | 1-Ethyl-2-hexene(c,t) | 1 | 91 | 0.10 |
| 10574-36-4 | 2-Hexene, 3-methyl-, (Z)- | 1 | 91 | 0.19 |
| 4914-89-0 | 3-Hexene, 3-methyl-, (Z)- | 1 | 90 | 0.18 |
| 3404-55-5 | 4-Methyl-2-hexene c&t | 1 | 91 | 0.12 |
| 922-62-3 | 2-Pentene, 3-methyl-, (Z)- | 1 | 91 | 0.95 |
| 922-61-2 | 2-Pentene, 3-methyl- | 1 | 84 | 0.31 |
| | Trace Branched Alkenes | | | |
| 756-02-5 | 1,4-Pentadiene, 2,3,3-trimethyl- | 3 | 78 | 0.018 |
| 74752-07-9 | 1,3-Hexadiene, 3-ethyl-2-methyl-, (Z)- | 3 | 72 | 0.033 |
| 7145-20-2 | 2-Hexene, 2,3-dimethyl- | 2 | 80 | 0.042 |
| 563-78-0 | 1-Butene, 2,3-dimethyl- | 2 | 80 | 0.006 |
| 563-79-1 | 2-Butene, 2,3-dimethyl- | 2 | 78 | 0.005 |
| 19781-31-8 | 3-Ethyl-3-octene | 1 | 64 | 0.057 |
| 74764-46-8 | 3-Heptene, 3-ethyl- | 1 | 72 | 0.063 |
| 4485-16-9 | 1-Heptene, 4-methyl- | 1 | 86 | 0.086 |
| 15870-10-7 | 1-Heptene, 3-methyl- | 1 | 78 | 0.013 |
| 4049-81-4 | 1,5-Hexadiene, 2-methyl- | 1 | 64 | 0.028 |
| 66225-17-0 | 2-Heptene, 4-methyl-, (E)- | 1 | 91 | 0.053 |
| 3404-65-7 | 3-Methyl-3-hexene | 1 | 91 | 0.067 |
| 3683-22-5 | 2-Hexene, 4-methyl-, (E)- | 1 | 91 | 0.081 |
| 3769-23-1 | 1-Hexene, 4-methyl- | 1 | 84 | 0.012 |
| 2787-43-1 | 1,3-Pentadiene, 3-methyl-, (E)- | 1 | 84 | 0.007 |
| 692-24-0 | 3-Hexene, 2-methyl-, (E)- | 1 | 91 | 0.029 |
| 4038-04-4 | 1-Pentene, 3-ethyl- | 1 | 87 | 0.019 |
| 763-29-1 | 1-Pentene, 2-methyl- | 1 | 91 | 0.045 |
| 674-76-0 | 2-Pentene, 4-methyl-, (E)- | 1 | 91 | 0.021 |
| 760-20-3 | 1-Pentene, 3-methyl- | 1 | 91 | 0.038 |
| 115-11-7 | 1-Propene, 2-methyl- | 1 | 86 | 0.005 |
| | Major Cyclic Alkenes | | | |
| 53366-54-4 | Cyclopentane, (2-methylbutylidene)- | | 78 | 0.82 |
| 1120-62-3 | Cyclopentene, 3-methyl- | | 91 | 0.44 |
| 19780-66-4 | Methyl ethyl cyclopentene | | 87 | 0.41 |
| 2633-80-9 | Bicyclo[2.2.1]heptane, 2-(2-propenyl)- | | 64 | 0.19 |
| 3874-81-1 | 1-Propylcyclopentene | | 81 | 0.18 |
| 38667-10-6 | 1,3,5,5-Tetramethylcyclopentene | | 72 | 0.10 |
| | Trace Cyclic Alkenes | | | |
| 500-00-5 | Cyclohexene, 4-methyl-1-(1-methylethyl)- | | 87 | 0.052 |
| 55170-99-6 | Bicyclo[2.2.1]heptane, 2-(1-buten-3-yl)- | | 84 | 0.099 |
| 35508-20-8 | 1-Methylcycloheptene | | 84 | 0.003 |
| 3715-27-5 | 1,3-Cyclohexadiene, 5,6-dimethyl- | | 86 | 0.029 |
| 2808-80-2 | Cyclohexane, 1-methyl-4-methylene- | | 90 | 0.075 |
| 14067-75-9 | Cyclopentene, 3-propyl- | | 78 | 0.039 |
| 97797-67-4 | 1-Ethyl-5-methylcyclopentene | | 83 | 0.097 |
| 2146-38-5 | 1-Ethylcyclopentene | | 72 | 0.063 |
| 694-35-9 | Cyclopentene, 3-ethyl- | | 84 | 0.013 |
| | Major n-Alkanes | | | |
| 110-54-3 | n-Hexane | | 91 | 6.31 |
| 111-65-9 | Octane | | 86 | 5.58 |

FIG 26A CONT

| CAS # | Compound Name | BR # | Q | Area% |
|---|---|---|---|---|
| 142-82-5 | Heptane | | 95 | 4.43 |
| 111-84-2 | Nonane | | 95 | 1.99 |
| 124-18-5 | Decane | | 95 | 1.25 |
| 1120-21-4 | Undecane | | 95 | 0.66 |
| 109-66-0 | Pentane | | 91 | 0.38 |
| 629-50-5 | Tridecane | | 81 | 0.18 |
| | Trace n-Alkanes |||| 
| 106-97-8 | Butane | | 80 | 0.088 |
| | Major Branched Alkanes ||||
| 5911-04-6 | Nonane, 3-methyl- | 1 | 74 | 0.50 |
| 5881-17-4 | Octane, 3-ethyl- | 1 | 72 | 0.10 |
| 17302-33-9 | Undecane, 6-methyl- | 1 | 78 | 0.13 |
| 619-99-8 | Hexane, 3-ethyl- | 1 | 72 | 0.38 |
| 589-81-1 | Heptane, 3-methyl- | 1 | 83 | 1.28 |
| 592-27-8 | Heptane, 2-methyl- | 1 | 83 | 0.14 |
| 617-78-7 | Pentane, 3-ethyl- | 1 | 78 | 0.16 |
| 589-34-4 | Hexane, 3-methyl- | 1 | 84 | 0.37 |
| 591-76-4 | Hexane, 2-methyl- | 1 | 91 | 0.16 |
| 96-14-0 | Pentane, 3-methyl- | 1 | 91 | 0.83 |
| | Trace Branched Alkanes ||||
| 62238-11-3 | Decane, 2,3,5-trimethyl- | 3 | 72 | 0.089 |
| 2847-72-5 | Decane, 4-methyl- | 1 | 64 | 0.042 |
| 2216-34-4 | Octane, 4-methyl- | 1 | 83 | 0.090 |
| 107-83-5 | Pentane, 2-methyl- | 1 | 84 | 0.084 |
| 78-78-4 | Butane, 2-methyl- | 1 | 91 | 0.014 |
| | Major Cyclic Alkanes ||||
| 3726-47-4 | Cyclopentane, 1-ethyl-3-methyl- | | 74 | 1.35 |
| 930-89-2 | Cyclopentane, 1-ethyl-2-methyl-, cis- | | 68 | 0.91 |
| 2613-65-2 | Cyclopentane, 1-ethyl-3-methyl-, trans- | | 78 | 0.87 |
| 96-37-7 | Cyclopentane, methyl- | | 91 | 0.61 |
| 61142-68-5 | Cyclopentane, 1-hexyl-3-methyl- | | 74 | 0.54 |
| 3728-46-3 | Cyclopentane, 1-ethyl-2-methyl- | | 95 | 0.31 |
| 108-87-2 | Cyclohexane, methyl- | | 84 | 0.21 |
| 3741-00-2 | Cyclopentane, pentyl- | | 90 | 0.18 |
| 18968-23-5 | (1S,3R,6R)-3,7,7-trimethylnorcarane | | 62 | 0.16 |
| 62199-50-2 | Cyclopentane, 1-butyl-2-propyl- | | 64 | 0.15 |
| 1640-89-7 | Cyclopentane, ethyl- | | 94 | 0.14 |
| 4127-45-1 | Cyclopropane, 1,1,2-trimethyl- | | 91 | 0.13 |
| 1678-93-9 | Cyclohexane, butyl- | | 70 | 0.13 |
| 110-82-7 | Cyclohexane | | 91 | 0.11 |
| 824-43-1 | Cyclohexane, 1,2-diethyl-, cis- | | 64 | 0.11 |
| | Trace Cyclic Alkanes ||||
| 23609-46-3 | Cyclooctane, 1,2-diethyl- | | 83 | 0.082 |
| 1678-92-8 | Cyclohexane, propyl- | | 70 | 0.045 |
| 4923-78-8 | Cyclohexane, 1-ethyl-2-methyl-, trans- | | 72 | 0.036 |
| 17065-18-8 | Bicyclo[2.1.0]pentane, 1,4-dimethyl- | | 64 | 0.100 |
| 16747-50-5 | Cyclopentane, 1-ethyl-1-methyl- | | 74 | 0.028 |
| 2207-04-7 | Cyclohexane, 1,4-dimethyl-, trans- | | 87 | 0.043 |
| 16883-48-0 | 1-trans-2-trans-4-Trimethylcyclopentane | | 72 | 0.020 |
| 2453-00-1 | Cyclopentane, 1,3-dimethyl- | | 78 | 0.033 |
| 2532-58-3 | Cyclopentane, 1,3-dimethyl-, cis- | | 80 | 0.025 |
| 1192-18-3 | Cyclopentane, 1,2-dimethyl-, cis- | | 78 | 0.036 |

FIG 26A CONT

| CAS # | Compound Name | BR # | Q | Area% |
|---|---|---|---|---|
| 74752-93-5 | Cyclopropane, 1,1,2,3-tetramethyl- | | 64 | 0.018 |
| 287-92-3 | Cyclopentane | | 72 | 0.009 |
| 2402-06-4 | Cyclopropane, 1,2-dimethyl-, trans- | | 91 | 0.043 |
| 1191-96-4 | Cyclopropane, ethyl- | | 80 | 0.008 |
| Major Oxygenates ||||| 
| 107-87-9 | 2-Pentanone | | 86 | 0.48 |
| 1000382-54-5 | Carbonic acid, tetradecyl vinyl ester | | 90 | 0.31 |
| 15780-36-6 | (1R,2R,3R,4S)-3-methylnorbornane-2-carbaldehyde | | 72 | 0.19 |
| 5910-87-2 | 2,4-Nonadienal, (E,E)- | | 72 | 0.16 |
| Trace Oxygenates ||||| 
| 1000196-81-2 | 2-Pentenoic acid, 3-methyl-5-(2,6,6-trimethyl-1-cyclohexenyl) | | 64 | 0.012 |
| 70786-44-6 | (3R,4S,8R)-3,9-epoxy-1-p-menthene | | 64 | 0.057 |
| 1000414-18-1 | Isogeranial | | 70 | 0.042 |
| 110-12-3 | 2-Hexanone, 5-methyl- | | 64 | 0.049 |
| 591-78-6 | 2-Hexanone | | 86 | 0.064 |
| 565-61-7 | 2-Pentanone, 3-methyl- | | 78 | 0.041 |
| 630-19-3 | Propanal, 2,2-dimethyl- | | 64 | 0.016 |
| 78-93-3 | 2-Butanone | | 72 | 0.061 |
| 67-64-1 | Acetone | | 78 | 0.033 |

FIG 26A CONT

| Summary | Total | Known | Major | Trace | Ave Carbon # |
|---|---|---|---|---|---|
| Peaks | 337 | 212 | 65 | 147 | 8.26 |
| Area | 802613264 | 95.8% | 92.0% | 4.8% | |

| Compound Type | Total Known | | Major Components | | Average Carbon # |
|---|---|---|---|---|---|
| | #Peaks | %Area | #Peaks | %Area | |
| Aromatics (Total) | 74 | 81.17 | 32 | 79.71 | 8.47 |
| Oxygenated | 2 | 0.05 | 0 | 0.00 | 11.00 |
| Alkenes (Total) | 80 | 5.57 | 11 | 3.52 | 8.21 |
| Straight | 10 | 0.26 | 0 | 0.00 | 5.74 |
| Branched | 29 | 1.22 | 3 | 0.42 | 6.68 |
| Cyclic | 41 | 4.08 | 8 | 3.09 | 8.84 |
| Alkanes (Total) | 44 | 9.77 | 22 | 8.81 | 6.61 |
| Straight | 4 | 1.04 | 3 | 1.02 | 5.91 |
| Branched | 14 | 5.19 | 7 | 4.81 | 6.45 |
| Cyclic | 26 | 3.54 | 12 | 2.98 | 7.05 |
| Oxygenated (Other) | 13 | 0.28 | 0 | 0.00 | 7.58 |

Composition By Carbon Number

| CAS # | Compound Name | BR# | Q | Area % |
|---|---|---|---|---|
| | Major Aromatics Hydrocarbons | | | |
| 611-14-3 | Benzene, 1-ethyl-2-methyl- | | 95 | 16.26 |
| 108-88-3 | Toluene | | 91 | 13.39 |
| 95-47-6 | o-Xylene | | 95 | 11.92 |
| 108-38-3 | Benzene, 1,3-dimethyl- | | 95 | 10.69 |
| 108-67-8 | Mesitylene | | 97 | 7.95 |
| 100-41-4 | Ethylbenzene | | 91 | 5.02 |
| 874-41-9 | Benzene, 1-ethyl-2,4-dimethyl- | | 97 | 4.23 |
| 105-05-5 | Benzene, 1,4-diethyl- | | 97 | 2.32 |
| 71-43-2 | Benzene | | 91 | 1.57 |
| 95-93-2 | Benzene, 1,2,4,5-tetramethyl- | | 97 | 1.05 |
| 1074-17-5 | Benzene, 1-methyl-2-propyl- | | 94 | 1.00 |
| 824-22-6 | 1H-Indene, 2,3-dihydro-4-methyl- | | 91 | 0.70 |
| 103-65-1 | Benzene, propyl- | | 90 | 0.52 |
| 934-80-5 | Benzene, 4-ethyl-1,2-dimethyl- | | 95 | 0.50 |
| 13632-94-5 | Benzene, 1,4-diethyl-2-methyl- | | 96 | 0.47 |
| 2050-24-0 | Benzene, 1,3-diethyl-5-methyl- | | 97 | 0.40 |
| 535-77-3 | Benzene, 1-methyl-3-(1-methylethyl)- | | 95 | 0.35 |
| 6682-71-9 | 1H-Indene, 2,3-dihydro-4,7-dimethyl- | | 97 | 0.35 |
| 527-53-7 | Benzene, 1,2,3,5-tetramethyl- | | 94 | 0.31 |
| 496-11-7 | Indane | | 87 | 0.27 |
| 1758-85-6 | Benzene, 2,4-diethyl-1-methyl- | | 95 | 0.24 |
| 527-84-4 | o-Cymene | | 95 | 0.24 |
| 1595-16-0 | Benzene, 1-methyl-4-(1-methylpropyl)- | | 94 | 0.23 |
| 98-82-8 | Benzene, (1-methylethyl)- | | 91 | 0.22 |
| | Trace Aromatic Hydrocarbons | | | |
| 135-01-3 | Benzene, 1,2-diethyl- | | 93 | 0.095 |
| 91-20-3 | Naphthalene | | 91 | 0.091 |
| 135-98-8 | Benzene, (1-methylpropyl)- | | 87 | 0.084 |
| 91-57-6 | Naphthalene, 2-methyl- | | 94 | 0.073 |
| 5161-04-6 | Benzene, 1-methyl-4-(2-methylpropyl)- | | 87 | 0.071 |
| 2719-52-0 | Benzene, (1-methylbutyl)- | | 80 | 0.059 |
| 538-93-2 | Benzene, (2-methylpropyl)- | | 74 | 0.049 |
| 1595-05-7 | Benzene, 1-methyl-4-butyl- | | 81 | 0.041 |
| 766-97-2 | Benzene, 1-ethynyl-4-methyl- | | 86 | 0.034 |
| 700-12-9 | Benzene, pentamethyl- | | 90 | 0.031 |
| 61141-97-7 | 3,5-Diphenyl-1-pentene | | 80 | 0.031 |
| 1680-51-9 | 6-Methyl-(1,2,3,4-tetrahydronaphthalene) | | 93 | 0.025 |
| 14276-95-0 | 1H-Indene, 2,3-dihydro-1,1,6-trimethyl- | | 87 | 0.025 |
| 4920-99-4 | Benzene, 1-ethyl-3-(1-methylethyl)- | | 90 | 0.024 |
| 54340-86-2 | 4-[(E)-but-2-enyl]-1,2-dimethyl-benzene | | 64 | 0.024 |
| 1587-04-8 | Benzene, 1-methyl-2-(2-propenyl)- | | 90 | 0.020 |
| 15877-15-3 | 1,1a,6,6a-tetrahydrocyclopropa[a]indene | | 93 | 0.019 |
| 3877-19-8 | 2-Methyl-(1,2,3,4-tetrahydronaphthalene) | | 88 | 0.018 |
| 1000370-34-1 | 3,4-Dimethylcumene | | 95 | 0.018 |
| 825-54-7 | Benzene, 1-cyclopenten-1-yl- | | 81 | 0.014 |
| 4218-48-8 | Benzene, 1-ethyl-4-(1-methylethyl)- | | 70 | 0.013 |
| 2039-89-6 | Benzene, 2-ethenyl-1,4-dimethyl- | | 83 | 0.012 |
| 2717-44-4 | Naphthalene, 1,2-dihydro-3-methyl- | | 72 | 0.009 |
| 3290-53-7 | Benzene, (2-methyl-2-propenyl)- | | 90 | 0.009 |
| 17059-48-2 | 1H-Indene, 2,3-dihydro-1,6-dimethyl- | | 90 | 0.009 |

FIG. 27 CONT

| CAS # | Compound Name | BR# | Q | Area % |
|---|---|---|---|---|
| 55669-88-0 | 1-Isobutyl-2,5-dimethylbenzene | | 64 | 0.008 |
| 768-49-0 | Benzene, (2-methyl-1-propenyl)- | | 74 | 0.007 |
| 3145-76-4 | 1-Methyl-2-phenylcyclopropane | | 81 | 0.004 |
| 575-41-7 | Naphthalene, 1,3-dimethyl- | | 94 | 0.004 |
| Trace Oxygenated Aromatics | | | | |
| 2040-07-5 | Ethanone, 1-(2,4,5-trimethylphenyl)- | | 93 | 0.044 |
| 52417-50-2 | 2-(2,5-dimethylphenyl)propionaldehyde | | 87 | 0.009 |
| Major n-Alkenes | | | | |
| 592-43-8 | 2-Hexene | | 91 | 0.10 |
| Trace n-Alkenes | | | | |
| 627-20-3 | 2-Pentene, (Z)- | | 91 | 0.051 |
| 7642-09-3 | 3-Hexene, (Z)- | | 95 | 0.031 |
| 646-04-8 | 2-Pentene, (E)- | | 91 | 0.026 |
| 592-77-8 | 2-Heptene | | 94 | 0.023 |
| 592-41-6 | 1-Hexene | | 91 | 0.013 |
| 13269-52-8 | 3-Hexene, (E)- | | 91 | 0.011 |
| 624-64-6 | 2-Butene, (E)- | | 64 | 0.004 |
| 590-18-1 | 2-Butene, (Z)- | | 83 | 0.003 |
| Major Branched Alkenes | | | | |
| 563-79-1 | 2-Butene, 2,3-dimethyl- | 2 | 91 | 0.23 |
| 2738-19-4 | 2-Hexene, 2-methyl- | 1 | 91 | 0.11 |
| 922-62-3 | 2-Pentene, 3-methyl-, (Z)- | 1 | 91 | 0.16 |
| Trace Branched Alkenes | | | | |
| 756-02-5 | 1,4-Pentadiene, 2,3,3-trimethyl- | 3 | 91 | 0.044 |
| 74752-97-9 | 1,3-Hexadiene, 3-ethyl-2-methyl-, (Z)- | 2 | 83 | 0.060 |
| 4634-87-1 | 2,4-Heptadiene, 2,6-dimethyl- | 2 | 90 | 0.048 |
| 764-13-6 | 2,4-Hexadiene, 2,5-dimethyl- | 2 | 64 | 0.030 |
| 3404-78-2 | 2-Hexene, 2,3-dimethyl- | 2 | 83 | 0.025 |
| 2213-37-8 | 3,4-Dimethyl-2-hexene | 2 | 64 | 0.025 |
| 4914-92-5 | 2-Pentene, 3,4-dimethyl-, (E)- | 2 | 87 | 0.030 |
| 2213-32-3 | 1-Pentene, 2,4-dimethyl- | 2 | 90 | 0.012 |
| 563-78-0 | 1-Butene, 2,3-dimethyl- | 2 | 91 | 0.060 |
| 816-79-5 | 2-Pentene, 3-ethyl- | 1 | 74 | 0.024 |
| 3404-65-7 | 3-Methyl-3-hexene | 1 | 91 | 0.044 |
| 3683-19-0 | (Z)-4-Methyl-2-hexene | 1 | 87 | 0.027 |
| 13131-17-2 | (Z)-Hex-2-ene, 5-methyl- | 1 | 81 | 0.015 |
| 3404-55-5 | 4-Methyl-2-hexene, c&t | 1 | 91 | 0.034 |
| 15840-60-5 | 3-Hexene, 2-methyl-, (Z)- | 1 | 91 | 0.018 |
| 922-61-2 | 2-Pentene, 3-methyl- | 1 | 95 | 0.091 |
| 763-29-1 | 1-Pentene, 2-methyl- | 1 | 91 | 0.060 |
| 625-27-4 | 2-Pentene, 2-methyl- | 1 | 91 | 0.010 |
| 760-20-3 | 1-Pentene, 3-methyl- | 1 | 91 | 0.010 |
| 691-37-2 | 1-Pentene, 4-methyl- | 1 | 90 | 0.006 |
| 563-46-2 | 2-Methyl-1-butene | 1 | 91 | 0.048 |
| 563-45-1 | 1-Butene, 3-methyl- | 1 | 90 | 0.003 |
| 115-11-7 | 1-Propene, 2-methyl- | 1 | 78 | 0.003 |
| Major Cyclic Alkenes | | | | |
| 18368-95-1 | 1,3,8-p-Menthatriene | | 83 | 1.78 |
| 473-91-6 | Cyclopentene, 1,2,3-trimethyl- | | 91 | 0.51 |
| 7459-71-4 | 3,5-Dimethylcyclopentene | | 91 | 0.30 |
| 78089-39-3 | 1,2,3,4-Tetramethylfulvene | | 93 | 0.30 |
| 1528-22-9 | Cyclobutane, (1-methylethylidene)- | | 90 | 0.23 |

FIG. 27 CONT

| CAS # | Compound Name | BR# | Q | Area % |
|---|---|---|---|---|
| 19780-56-4 | Methyl ethyl cyclopentene | | 91 | 0.18 |
| 693-89-0 | Cyclopentene, 1-methyl- | | 90 | 0.16 |
| 591-49-1 | Cyclohexene, 1-methyl- | | 94 | 0.13 |
| | Trace Cyclic Alkenes | | | |
| 1000189-31-0 | 2,3,4,5,6,7-Hexahydro-1H-cyclopenta[a]pentalene | | 86 | 0.053 |
| 4292-04-0 | 1-Isopropylcyclohex-1-ene | | 72 | 0.024 |
| 3983-08-2 | Cyclohexene, 3-(1-methylethyl)- | | 64 | 0.004 |
| 51999-35-0 | 1,2,3,1',2',3'-Hexamethyl-bicyclopentyl-2,2'-diene | | 64 | 0.020 |
| 2808-80-2 | Cyclohexane, 1-methyl-4-methylene- | | 90 | 0.075 |
| 36821-63-7 | trans-3,5-Dimethylcyclohexene | | 90 | 0.055 |
| 1759-64-4 | Cyclohexene, 1,6-dimethyl- | | 64 | 0.012 |
| 97797-57-4 | 1-Ethyl-5-methylcyclopentene | | 64 | 0.015 |
| 2808-76-6 | 1,3-Dimethyl-1-cyclohexene | | 90 | 0.054 |
| 2146-38-5 | 1-Ethylcyclopentene | | 90 | 0.049 |
| 55170-90-6 | Bicyclo[2.2.1]heptane, 2-(1-buten-3-yl)- | | 78 | 0.026 |
| 694-35-9 | Cyclopentene, 3-ethyl- | | 83 | 0.010 |
| 591-47-9 | Cyclohexene, 4-methyl- | | 90 | 0.037 |
| 1528-21-8 | Ethylidenecyclobutane | | 87 | 0.017 |
| 1120-62-3 | Cyclopentene, 3-methyl- | | 91 | 0.023 |
| 142-29-0 | Cyclopentene | | 91 | 0.009 |
| | Major n-Alkanes | | | |
| 110-54-3 | n-Hexane | | 91 | 0.44 |
| 109-66-0 | Pentane | | 91 | 0.31 |
| 142-82-5 | Heptane | | 93 | 0.26 |
| | Trace n-Alkanes | | | |
| 106-97-8 | Butane | | 80 | 0.021 |
| | Major Branched Alkanes | | | |
| 589-81-1 | Heptane, 3-methyl- | 1 | 81 | 0.31 |
| 589-53-7 | Heptane, 4-methyl- | 1 | 91 | 0.18 |
| 592-27-8 | Heptane, 2-methyl- | 1 | 95 | 0.23 |
| 589-34-4 | Hexane, 3-methyl- | 1 | 91 | 0.91 |
| 96-14-0 | Pentane, 3-methyl- | 1 | 91 | 0.95 |
| 107-83-5 | Pentane, 2-methyl- | 1 | 83 | 1.50 |
| 78-78-4 | Butane, 2-methyl- | 1 | 91 | 0.72 |
| | Trace Branched Alkanes | | | |
| 565-59-3 | Pentane, 2,3-dimethyl- | 2 | 87 | 0.085 |
| 590-35-2 | Pentane, 2,2-dimethyl- | 2 | 64 | 0.002 |
| 79-29-8 | Butane, 2,3-dimethyl- | 2 | 80 | 0.096 |
| 75-83-2 | Butane, 2,2-dimethyl- | 2 | 72 | 0.007 |
| 17301-94-9 | Nonane, 4-methyl- | 1 | 64 | 0.021 |
| 3221-61-2 | Octane, 2-methyl- | 1 | 64 | 0.090 |
| 2216-34-4 | Octane, 4-methyl- | 1 | 83 | 0.093 |
| | Major Cyclic Alkanes | | | |
| 96-37-7 | Cyclopentane, methyl- | | 91 | 0.74 |
| 1192-18-3 | Cyclopentane, 1,2-dimethyl-, cis- | | 64 | 0.28 |
| 2453-00-1 | Cyclopentane, 1,3-dimethyl- | | 91 | 0.27 |
| 1638-26-2 | Cyclopentane, 1,1-dimethyl- | | 83 | 0.26 |
| 872-56-0 | Isopropylcyclobutane | | 91 | 0.25 |
| 1640-89-7 | Cyclopentane, ethyl- | | 95 | 0.25 |
| 2207-03-6 | Cyclohexane, 1,3-dimethyl-, trans- | | 87 | 0.21 |
| 108-87-2 | Cyclohexane, methyl- | | 94 | 0.19 |
| 3726-47-4 | Cyclopentane, 1-ethyl-3-methyl- | | 74 | 0.17 |

FIG. 27 CONT

| CAS # | Compound Name | BR# | Q | Area % |
|---|---|---|---|---|
| 2815-58-9 | Cyclopentane, 1,2,4-trimethyl- | | 87 | 0.14 |
| 4516-69-2 | Cyclopentane, 1,1,3-trimethyl- | | 83 | 0.12 |
| 2532-58-3 | Cyclopentane, 1,3-dimethyl-, cis- | | 91 | 0.10 |
| Trace Cyclic Alkanes | | | | |
| 4126-78-7 | Cycloheptane, methyl- | | 70 | 0.020 |
| 25107-01-1 | 9-Methylbicyclo[3.3.1]nonane | | 80 | 0.029 |
| 2040-95-1 | Cyclopentane, butyl- | | 81 | 0.034 |
| 1839-88-9 | cis,cis,cis-1,2,3-Trimethylcyclohexane | | 76 | 0.010 |
| 694-72-4 | Pentalene, octahydro- | | 74 | 0.036 |
| 2207-01-4 | Cyclohexane, 1,2-dimethyl-, cis- | | 87 | 0.009 |
| 2613-68-6 | 1,2,3-Trimethylcyclopentane, cis, cis | | 72 | 0.011 |
| 16747-50-5 | Cyclopentane, 1-ethyl-1-methyl- | | 83 | 0.090 |
| 930-89-2 | Cyclopentane, 1-ethyl-2-methyl-, cis- | | 95 | 0.096 |
| 589-90-2 | Cyclohexane, 1,4-dimethyl- | | 90 | 0.046 |
| 74752-93-5 | Cyclopropane, 1,1,2,3-tetramethyl- | | 91 | 0.044 |
| 110-82-7 | Cyclohexane | | 87 | 0.040 |
| 287-92-3 | Cyclopentane | | 86 | 0.082 |
| 1191-96-4 | Cyclopropane, ethyl- | | 87 | 0.009 |
| Trace Oxygenates | | | | |
| 42452-48-2 | 2,4-Heptadienal, 2,4-dimethyl- | | 72 | 0.007 |
| 62702-89-0 | Bicyclo[3.2.1]oct-3-en-2-one, 4-methyl- | | 64 | 0.037 |
| 90823-38-2 | .alpha.-Santolinc alcohol | | 72 | 0.010 |
| 7212-53-5 | 5-Methyl-1-heptanol | | 78 | 0.029 |
| 4313-03-5 | 2,4-Heptadienal, (E,E)- | | 72 | 0.057 |
| 2050-95-3 | 1-Butanol, 3-methyl-, carbonate (2:1) | | 64 | 0.061 |
| 96-22-0 | 3-Pentanone | | 86 | 0.008 |
| 107-87-9 | 2-Pentanone | | 86 | 0.012 |
| 563-80-4 | 2-Butanone, 3-methyl- | | 80 | 0.009 |
| 78-93-3 | 2-Butanone | | 72 | 0.022 |
| 60-29-7 | Ethyl ether | | 94 | 0.031 |
| 67-64-1 | Acetone | | 80 | 0.002 |

FIG. 27 CONT

| CAS # | Compound Name | BR# | Q | Area % |
|---|---|---|---|---|
| \multicolumn{5}{c}{Major Aromatics Hydrocarbons} | | | | |
| 95-47-6 | o-Xylene | | 95 | 6.39 |
| 108-88-3 | Toluene | | 91 | 5.76 |
| 611-14-3 | Benzene, 1-ethyl-2-methyl- | | 95 | 3.70 |
| 108-38-3 | Benzene, 1,3-dimethyl- | | 95 | 3.73 |
| 100-41-4 | Ethylbenzene | | 91 | 2.79 |
| 526-73-8 | Benzene, 1,2,3-trimethyl- | | 97 | 2.17 |
| 874-41-9 | Benzene, 1-ethyl-2,4-dimethyl- | | 97 | 1.45 |
| 71-43-2 | Benzene | | 91 | 1.34 |
| 1074-55-1 | Benzene, 1-methyl-4-propyl- | | 91 | 1.33 |
| 141-93-5 | Benzene, 1,3-diethyl- | | 96 | 0.97 |
| 1758-88-9 | Benzene, 2-ethyl-1,4-dimethyl- | | 95 | 0.62 |
| 103-65-1 | Benzene, propyl- | | 90 | 0.41 |
| 104-51-8 | Benzene, n-butyl- | | 94 | 0.36 |
| 1074-43-7 | Benzene, 1-methyl-3-propyl- | | 94 | 0.31 |
| 2050-24-0 | Benzene, 1,3-diethyl-5-methyl- | | 95 | 0.30 |
| 527-84-4 | o-Cymene | | 87 | 0.29 |
| 108-67-8 | Mesitylene | | 95 | 0.22 |
| 824-22-6 | 1H-Indene, 2,3-dihydro-4-methyl- | | 83 | 0.19 |
| 496-11-7 | Indane | | 90 | 0.14 |
| 535-77-3 | Benzene, 1-methyl-3-(1-methylethyl)- | | 93 | 0.12 |
| 99-87-6 | p-Cymene | | 87 | 0.12 |
| 13632-94-5 | Benzene, 1,4-diethyl-2-methyl- | | 96 | 0.12 |
| 934-74-7 | Benzene, 1-ethyl-3,5-dimethyl- | | 95 | 0.11 |
| \multicolumn{5}{c}{Trace Aromatic Hydrocarbons} | | | | |
| 1595-05-7 | Benzene, 1-methyl-4-butyl | | 87 | 0.094 |
| 2049-95-8 | Benzene, (1,1-dimethylpropyl)- | | 76 | 0.088 |
| 98-82-8 | Benzene, (1-methylethyl)- | | 81 | 0.085 |
| 488-23-3 | Benzene, 1,2,3,4-tetramethyl- | | 94 | 0.077 |
| 135-98-8 | Benzene, (1-methylpropyl)- | | 93 | 0.074 |
| 135-01-3 | Benzene, 1,2-diethyl- | | 93 | 0.074 |
| 1595-16-0 | Benzene, 1-methyl-4-(1-methylpropyl)- | | 87 | 0.070 |
| 91-20-3 | Naphthalene | | 91 | 0.040 |
| 4489-84-3 | Benzene, (3-methyl-2-butenyl)- | | 94 | 0.037 |
| 95-93-2 | Benzene, 1,2,4,5-tetramethyl- | | 91 | 0.026 |
| 934-80-5 | Benzene, 4-ethyl-1,2-dimethyl- | | 76 | 0.025 |
| 90-12-0 | Naphthalene, 1-methyl- | | 90 | 0.015 |
| 102-25-0 | Benzene, 1,3,5-triethyl- | | 72 | 0.013 |
| 55669-88-0 | 1-Isobutyl-2,5-dimethylbenzene | | 80 | 0.010 |
| 1483-60-9 | Benzene, 1,3-dimethyl-4-(1-methylpropyl) | | 72 | 0.008 |
| \multicolumn{5}{c}{Trace Oxygenated Aromatics} | | | | |
| 6148-37-4 | Furan, 4-methyl-2-propyl- | | 64 | 0.050 |
| \multicolumn{5}{c}{Major n-Alkenes} | | | | |
| 7688-21-3 | 2-Hexene, (Z)- | | 91 | 1.27 |
| 13269-52-8 | 3-Hexene, (E)- | | 94 | 0.38 |
| 7642-10-6 | (Z)-3-Heptene | | 95 | 0.35 |
| 592-77-8 | 2-Heptene | | 95 | 0.32 |
| 592-41-6 | 1-Hexene | | 93 | 0.18 |
| 627-20-3 | 2-Pentene, (Z)- | | 87 | 0.17 |
| 14850-23-8 | 4-Octene, (E)- | | 83 | 0.14 |
| 7642-09-3 | 3-Hexene, (Z)- | | 93 | 0.13 |

FIG. 28 CONT

| CAS # | Compound Name | BR# | Q | Area % |
|---|---|---|---|---|
| | Trace n-Alkenes | | | |
| 646-04-8 | 2-Pentene, (E)- | | 87 | 0.093 |
| 7642-04-8 | 2-Octene, (Z)- | | 94 | 0.070 |
| 10405-85-3 | trans-4-Nonene | | 91 | 0.070 |
| 109-67-1 | 1-Pentene | | 74 | 0.069 |
| 7642-15-1 | 4-Octene, (Z)- | | 94 | 0.058 |
| 6434-77-1 | cis-2-Nonene | | 94 | 0.051 |
| 592-76-7 | 1-Heptene | | 84 | 0.041 |
| 7348-80-3 | 3,5-Octadiene, (Z,Z)- | | 72 | 0.030 |
| 624-64-6 | 2-Butene, (E)- | | 70 | 0.025 |
| 590-18-1 | 2-Butene, (Z)- | | 76 | 0.023 |
| 2198-23-4 | 4-Nonene | | 64 | 0.023 |
| | Major Branched Alkenes | | | |
| 19780-68-8 | 3-Ethyl-4-methyl-2-pentene | 2 | 90 | 0.10 |
| 3404-75-9 | 2-Heptene, 3-methyl- | 1 | 90 | 0.17 |
| 2980-89-9 | 1,4-Hexadiene, 3-ethyl- | 1 | 80 | 0.26 |
| 4038-04-4 | 1-Pentene, 3-ethyl- | 1 | 83 | 0.12 |
| 2738-19-4 | 2-Hexene, 2-methyl- | 1 | 90 | 0.11 |
| 616-12-6 | 2-Pentene, 3-methyl-, (E)- | 1 | 94 | 0.84 |
| 922-61-2 | 2-Pentene, 3-methyl- | 1 | 91 | 0.49 |
| 4461-48-7 | 2-Pentene, 4-methyl- | 1 | 90 | 0.15 |
| | Trace Branched Alkenes | | | |
| 1000374-08-4 | (2Z,4E)-3,7-Dimethyl-2,4-octadiene | 2 | 64 | 0.089 |
| 74753-07-9 | 1,3-Hexadiene, 3-ethyl-2-methyl-, (Z)- | 2 | 64 | 0.030 |
| 28253-64-3 | 1,3-Hexadiene, 2,5-dimethyl- | 2 | 76 | 0.024 |
| 1515-79-3 | 5,5-Dimethyl-1,3-hexadiene | 2 | 72 | 0.018 |
| 563-79-1 | 2-Butene, 2,3-dimethyl- | 2 | 62 | 0.033 |
| 1832-16-2 | 3-Ethyl-2-hexene(c,t) | 1 | 91 | 0.057 |
| 7300-03-0 | 3-Heptene, 3-methyl- | 1 | 83 | 0.027 |
| 10574-36-4 | 2-Hexene, 3-methyl-, (Z)- | 1 | 74 | 0.081 |
| 816-79-5 | 2-Pentene, 3-ethyl- | 1 | 90 | 0.069 |
| 3404-65-7 | 3-Methyl-3-hexene | 1 | 89 | 0.040 |
| 3683-22-5 | 2-Hexene, 4-methyl-, (E)- | 1 | 87 | 0.046 |
| 926-54-5 | 1,3-Pentadiene, 2-methyl-, (E)- | 1 | 70 | 0.032 |
| 15840-60-5 | 3-Hexene, 2-methyl-, (Z)- | 1 | 60 | 0.015 |
| 763-29-1 | 1-Pentene, 2-methyl- | 1 | 87 | 0.044 |
| 760-20-3 | 1-Pentene, 3-methyl- | 1 | 87 | 0.054 |
| 563-46-2 | 2-Methyl-1-butene | 1 | 74 | 0.046 |
| 115-11-7 | 1-Propene, 2-methyl- | 1 | 60 | 0.009 |
| | Major Cyclic Alkenes | | | |
| 693-89-0 | Cyclopentene, 1-methyl- | | 87 | 0.17 |
| 1453-24-3 | Cyclohexene, 1-ethyl- | | 70 | 0.12 |
| 19780-56-4 | Methyl ethyl cyclopentene | | 83 | 0.11 |
| 1528-22-9 | Cyclobutane, (1-methylethylidene)- | | 76 | 0.11 |
| | Trace Cyclic Alkenes | | | |
| 5256-65-5 | Cyclohexene, 3-methyl-6-(1-methylethyl)- | | 76 | 0.092 |
| 61143-33-4 | 1,4-dimethyl-5-propan-2-yl-cyclopentene | | 74 | 0.049 |
| 65378-76-9 | 1,2,4,4-Tetramethylcyclopentene | | 64 | 0.021 |
| 3742-42-5 | 4-Ethylcyclohexene | | 72 | 0.031 |
| 2808-80-2 | Cyclohexane, 1-methyl-4-methylene- | | 83 | 0.078 |
| 97797-57-4 | 1-Ethyl-3-methylcyclopentene | | 64 | 0.030 |
| 591-48-0 | Cyclohexene, 3-methyl- | | 80 | 0.067 |

FIG. 28 CONT

| CAS # | Compound Name | BR# | Q | Area % |
|---|---|---|---|---|
| 2146-38-5 | 1-Ethylcyclopentene | | 74 | 0.031 |
| 591-47-9 | Cyclohexene, 4-methyl- | | 72 | 0.058 |
| 2597-49-1 | Cyclobutane, ethenyl- | | 74 | 0.055 |
| 1120-62-3 | Cyclopentene, 3-methyl- | | 87 | 0.032 |
| | Major n-Alkanes | | | |
| 110-54-3 | n-Hexane | | 91 | 13.01 |
| 111-65-9 | Octane | | 91 | 6.08 |
| 142-82-5 | Heptane | | 95 | 5.38 |
| 109-66-0 | Pentane | | 91 | 2.52 |
| 111-84-2 | Nonane | | 95 | 2.04 |
| 124-18-5 | Decane | | 95 | 1.47 |
| 1120-21-4 | Undecane | | 76 | 0.48 |
| 106-97-8 | Butane | | 87 | 0.36 |
| | Trace n-Alkanes | | | |
| 112-40-3 | Dodecane | | 93 | 0.092 |
| | Major Branched Alkanes | | | |
| 20278-89-1 | Heptane, 3,4,5-trimethyl- | 3 | 87 | 0.33 |
| 565-75-3 | Pentane, 2,3,4-trimethyl- | 3 | 72 | 0.28 |
| 565-59-3 | Pentane, 2,3-dimethyl- | 2 | 83 | 0.15 |
| 5911-04-6 | Nonane, 3-methyl- | 1 | 90 | 0.81 |
| 5881-17-4 | Octane, 3-ethyl- | 1 | 83 | 0.15 |
| 13287-21-3 | Tridecane, 6-methyl- | 1 | 64 | 0.20 |
| 15869-80-4 | Heptane, 3-ethyl- | 1 | 94 | 0.22 |
| 2216-34-4 | Octane, 4-methyl- | 1 | 91 | 0.12 |
| 619-99-8 | Hexane, 3-ethyl- | 1 | 94 | 0.59 |
| 589-81-1 | Heptane, 3-methyl- | 1 | 83 | 2.76 |
| 592-27-8 | Heptane, 2-methyl- | 1 | 95 | 0.20 |
| 589-34-4 | Hexane, 3-methyl- | 1 | 91 | 0.83 |
| 591-76-4 | Hexane, 2-methyl- | 1 | 83 | 0.43 |
| 96-14-0 | Pentane, 3-methyl- | 1 | 91 | 3.63 |
| 107-83-5 | Pentane, 2-methyl- | 1 | 64 | 0.72 |
| 78-78-4 | Butane, 2-methyl- | 1 | 86 | 0.47 |
| | Trace Branched Alkanes | | | |
| 583-48-2 | Hexane, 3,4-dimethyl- | 2 | 64 | 0.062 |
| 79-29-8 | Butane, 2,3-dimethyl- | 2 | 68 | 0.033 |
| | Major Cyclic Alkanes | | | |
| 3726-47-4 | Cyclopentane, 1-ethyl-3-methyl- | | 83 | 0.67 |
| 96-37-7 | Cyclopentane, methyl- | | 91 | 0.59 |
| 110-82-7 | Cyclohexane | | 91 | 0.32 |
| 108-87-2 | Cyclohexane, methyl- | | 95 | 0.28 |
| 61142-68-5 | Cyclopentane, 1-hexyl-3-methyl- | | 80 | 0.24 |
| 930-89-2 | Cyclopentane, 1-ethyl-2-methyl-, cis- | | 96 | 0.24 |
| 7045-67-2 | Cyclohexane, 2-ethyl-1,3-dimethyl- | | 63 | 0.15 |
| 2207-04-7 | Cyclohexane, 1,4-dimethyl-, trans- | | 87 | 0.14 |
| 1640-89-7 | Cyclopentane, ethyl- | | 91 | 0.13 |
| 1678-93-9 | Cyclohexane, butyl- | | 81 | 0.13 |
| 291-64-5 | Cycloheptane | | 83 | 0.11 |
| | Trace Cyclic Alkanes | | | |
| 3741-00-2 | Cyclopentane, pentyl- | | 90 | 0.065 |
| 28388-35-8 | Pentalene, octahydro-2,5-dimethyl- | | 72 | 0.041 |
| 4126-78-7 | Cycloheptane, methyl- | | 83 | 0.084 |
| 1678-92-8 | Cyclohexane, propyl- | | 74 | 0.059 |

FIG. 28 CONT

| CAS # | Compound Name | BR# | Q | Area % |
|---|---|---|---|---|
| 706-53-0 | Bicyclo[2.2.2]octane, 2-methyl- | | 64 | 0.025 |
| 6236-88-0 | Cyclohexane, 1-ethyl-4-methyl-, trans- | | 76 | 0.074 |
| 3728-54-9 | Cyclohexane, 1-ethyl-2-methyl- | | 80 | 0.052 |
| 2613-66-3 | Cyclopentane, 1-ethyl-3-methyl-, cis- | | 80 | 0.060 |
| 16747-50-5 | Cyclopentane, 1-ethyl-1-methyl- | | 78 | 0.038 |
| 2815-58-9 | Cyclopentane, 1,2,4-trimethyl- | | 87 | 0.036 |
| 4516-69-2 | Cyclopentane, 1,1,3-trimethyl- | | 64 | 0.035 |
| 1192-18-3 | Cyclopentane, 1,2-dimethyl-, cis- | | 83 | 0.093 |
| 2532-58-3 | Cyclopentane, 1,3-dimethyl-, cis- | | 87 | 0.082 |
| 1759-58-6 | Cyclopentane, 1,3-dimethyl-, trans- | | 72 | 0.096 |
| | Major Oxygenates | | | |
| 4313-03-5 | 2,4-Heptadienal, (E,E)- | | 64 | 0.33 |
| 60-29-7 | Ethyl ether | | 96 | 0.19 |
| 107-87-9 | 2-Pentanone | | 83 | 0.15 |
| 42452-48-2 | 2,4-Heptadienal, 2,4-dimethyl- | | 80 | 0.13 |
| 628-81-9 | Butane, 1-ethoxy- | | 78 | 0.12 |
| 15726-15-5 | 4-Heptanone, 3-methyl- | | 90 | 0.10 |
| | Trace Oxygenates | | | |
| 4485-09-0 | 4-Nonanone | | 70 | 0.045 |
| 4423-94-3 | Cyclohexanone, 2-ethyl- | | 81 | 0.097 |
| 66-25-1 | Hexanal | | 72 | 0.036 |
| 565-61-7 | 2-Pentanone, 3-methyl- | | 64 | 0.039 |
| 105-57-7 | Ethane, 1,1-diethoxy- | | 72 | 0.071 |
| 141-78-6 | Ethyl Acetate | | 80 | 0.061 |
| 123-72-8 | Butanal | | 87 | 0.084 |

FIG. 28 CONT

| CAS # | Compound Name | BR# | Q | Area % |
|---|---|---|---|---|
| | Major Aromatics Hydrocarbons | | | |
| 108-88-3 | Toluene | | 91 | 15.43 |
| 108-38-3 | Benzene, 1,3-dimethyl- | | 95 | 10.44 |
| 106-42-3 | p-Xylene | | 95 | 7.20 |
| | Trace Aromatic Hydrocarbons | | | |
| 71-43-2 | Benzene | | 91 | 0.031 |
| 98-82-8 | Benzene, (1-methylethyl)- | | 80 | 0.026 |
| | Trace n-Alkenes | | | |
| 109-67-1 | 1-Pentene | | 72 | 0.009 |
| | Major n-Alkanes | | | |
| 106-97-8 | Butane | | 87 | 0.49 |
| 109-66-0 | Pentane | | 87 | 0.33 |
| 110-54-3 | n-Hexane | | 91 | 0.12 |
| | Trace n-Alkanes | | | |
| 142-82-5 | Heptane | | 91 | 0.038 |
| | Major Branched Alkanes | | | |
| 62108-31-0 | Heptane, 4-ethyl-2,2,6,6-tetramethyl- | 5 | 64 | 0.31 |
| 13475-82-6 | Heptane, 2,2,4,6,6-pentamethyl- | 5 | 72 | 0.22 |
| 127204-12-0 | Dodecane, 2,2,11,11-tetramethyl- | 4 | 72 | 0.23 |
| 1186-53-4 | Pentane, 2,2,3,4-tetramethyl- | 4 | 72 | 0.13 |
| 62237-99-4 | Decane, 2,3,7-trimethyl- | 3 | 83 | 0.32 |
| 62238-01-1 | Decane, 2,2,8-trimethyl- | 3 | 72 | 0.98 |
| 1068-87-7 | Pentane, 3-ethyl-2,4-dimethyl- | 3 | 72 | 0.47 |
| 3522-94-9 | Hexane, 2,2,5-trimethyl- | 3 | 80 | 3.41 |
| 560-21-4 | Pentane, 2,3,3-trimethyl- | 3 | 64 | 8.17 |
| 564-02-3 | Pentane, 2,2,3-trimethyl- | 3 | 83 | 0.98 |
| 540-84-1 | Pentane, 2,2,4-trimethyl- | 3 | 90 | |
| 464-06-2 | Butane, 2,2,3-trimethyl- | 3 | 83 | 0.14 |
| 52896-90-9 | Heptane, 3-ethyl-5-methyl- | 2 | 64 | 0.11 |
| 59222-86-5 | Tetradecane, 2,2-dimethyl- | 2 | 72 | 0.19 |
| 17302-01-1 | 3-Ethyl-3-methylheptane | 2 | 83 | 0.15 |
| 4110-44-5 | Octane, 3,3-dimethyl- | 2 | 83 | 0.25 |
| 2216-30-0 | Heptane, 2,5-dimethyl- | 2 | 72 | 0.22 |
| 583-48-2 | Hexane, 3,4-dimethyl- | 2 | 91 | 0.31 |
| 592-13-2 | Hexane, 2,5-dimethyl- | 2 | 94 | 2.29 |
| 565-59-3 | Pentane, 2,3-dimethyl- | 2 | 87 | 1.04 |
| 108-08-7 | Pentane, 2,4-dimethyl- | 2 | 94 | 1.73 |
| 79-29-8 | Butane, 2,3-dimethyl- | 2 | 91 | 1.82 |
| 13151-34-3 | Decane, 3-methyl- | 1 | 72 | 0.59 |
| 617-78-7 | Pentane, 3-ethyl- | 1 | 83 | 6.35 |
| 589-34-4 | Hexane, 3-methyl- | 1 | 95 | 0.19 |
| 96-14-0 | Pentane, 3-methyl- | 1 | 91 | 0.34 |
| 107-83-5 | Pentane, 2-methyl- | 1 | 74 | 0.68 |
| 78-78-4 | Butane, 2-methyl- | 1 | 91 | |
| | Trace Branched Alkanes | | | |
| 52670-34-5 | Octane, 2,3,6,7-tetramethyl- | 4 | 83 | 0.093 |
| 61868-42-6 | Heptane, 2,2,3,5-tetramethyl- | 4 | 78 | 0.011 |
| 3891-98-3 | Dodecane, 2,6,10-trimethyl- | 3 | 78 | 0.027 |
| 62338-18-3 | Decane, 3,3,8-trimethyl- | 3 | 72 | 0.057 |
| 31295-56-4 | Dodecane, 2,6,11-trimethyl- | 3 | 72 | 0.072 |
| 20278-89-1 | Heptane, 3,4,5-trimethyl- | 3 | 64 | 0.049 |

FIG. 29 CONT

| CAS # | Compound Name | BR# | Q | Area % |
|---|---|---|---|---|
| 62237-97-2 | Decane, 2,2,6-trimethyl- | 3 | 72 | 0.073 |
| 62016-28-8 | Octane, 2,2,6-trimethyl- | 3 | 78 | 0.089 |
| 31081-18-2 | Nonane, 3-methyl-5-propyl- | 2 | 72 | 0.032 |
| 2213-23-2 | Heptane, 2,4-dimethyl- | 2 | 64 | 0.014 |
| 17312-82-2 | Undecane, 4,6-dimethyl- | 2 | 72 | 0.011 |
| 62185-54-0 | Nonane, 5-(1-methylpropyl)- | 2 | 64 | 0.014 |
| 563-16-6 | Hexane, 3,3-dimethyl- | 2 | 64 | 0.036 |
| 17301-22-3 | Undecane, 2,5-dimethyl- | 2 | 72 | 0.036 |
| 17301-24-5 | Undecane, 2,7-dimethyl- | 2 | 72 | 0.036 |
| 3074-71-3 | Heptane, 2,3-dimethyl- | 2 | 64 | 0.005 |
| 7146-60-3 | Octane, 2,3-dimethyl- | 2 | 78 | 0.030 |
| 1072-05-5 | Heptane, 2,6-dimethyl- | 2 | 80 | 0.069 |
| 609-26-7 | 3-ethyl-2-methyl-pentane | 2 | 80 | 0.060 |
| 562-49-2 | Pentane, 3,3-dimethyl- | 2 | 83 | 0.012 |
| 590-35-2 | Pentane, 2,2-dimethyl- | 2 | 83 | 0.021 |
| 463-82-1 | Neopentane | 2 | 64 | 0.011 |
| 5911-04-6 | Nonane, 3-methyl- | 1 | 64 | 0.016 |
| 15869-80-4 | Heptane, 3-ethyl- | 1 | 78 | 0.006 |
| 2847-72-5 | Decane, 4-methyl- | 1 | 64 | 0.070 |
| 589-81-1 | Heptane, 3-methyl- | 1 | 91 | 0.053 |
| 589-53-7 | Heptane, 4-methyl- | 1 | 90 | 0.022 |
| 592-27-8 | Heptane, 2-methyl- | 1 | 94 | 0.065 |
| 75-28-5 | Isobutane | 1 | 72 | 0.031 |
| Major Cyclic Alkanes | | | | |
| 110-82-7 | Cyclohexane | | 91 | 0.15 |
| Trace Cyclic Alkanes | | | | |
| 108-87-2 | Cyclohexane, methyl- | | 93 | 0.053 |
| 96-37-7 | Cyclopentane, methyl- | | 87 | 0.039 |
| Major Oxygenates | | | | |
| 74421-17-3 | Hexane, 1-(hexyloxy)-2-methyl- | | 72 | 0.26 |
| Trace Oxygenates | | | | |
| 3913-02-8 | 1-Octanol, 2-butyl- | | 64 | 0.011 |
| 19780-33-7 | 2-Ethyl-1-dodecanol | | 78 | 0.009 |
| 959311-27-4 | Isobutyl nonyl carbonate | | 72 | 0.014 |
| 1000282-69-6 | Methoxyacetic acid, 2-octyl ester | | 78 | 0.028 |
| 17071-54-4 | Hexyl octyl ether | | 72 | 0.008 |

FIG. 29 CONT

| CAS # | Compound Name | BR# | Q | Area % |
|---|---|---|---|---|
| | Major Aromatics Hydrocarbons | | | |
| 108-88-3 | Toluene | | 91 | 7.93 |
| 108-38-3 | Benzene, 1,3-dimethyl- | | 95 | 7.26 |
| 874-41-9 | Benzene, 1-ethyl-2,4-dimethyl- | | 97 | 6.92 |
| 620-14-4 | Benzene, 1-ethyl-3-methyl- | | 95 | 5.59 |
| 141-93-5 | Benzene, 1,3-diethyl- | | 97 | 4.92 |
| 106-42-3 | p-Xylene | | 97 | 4.81 |
| 526-73-8 | Benzene, 1,2,3-trimethyl- | | 97 | 4.11 |
| 622-96-8 | Benzene, 1-ethyl-4-methyl- | | 91 | 3.06 |
| 13632-94-5 | Benzene, 1,4-diethyl-2-methyl- | | 96 | 1.75 |
| 1758-85-6 | Benzene, 2,4-diethyl-1-methyl- | | 97 | 0.55 |
| 824-22-6 | 1H-Indene, 2,3-dihydro-4-methyl- | | 91 | 0.53 |
| 1758-88-9 | Benzene, 2-ethyl-1,4-dimethyl- | | 97 | 0.36 |
| 611-14-3 | Benzene, 1-ethyl-2-methyl- | | 95 | 0.35 |
| 488-23-3 | Benzene, 1,2,3,4-tetramethyl- | | 97 | 0.31 |
| 1074-17-5 | Benzene, 1-methyl-2-propyl- | | 94 | 0.30 |
| 6682-71-9 | 1H-Indene, 2,3-dihydro-4,7-dimethyl- | | 94 | 0.23 |
| 1595-16-0 | Benzene, 1-methyl-4-(1-methylpropyl)- | | 91 | 0.19 |
| 2050-24-0 | Benzene, 1,3-diethyl-5-methyl- | | 97 | 0.18 |
| 789-57-3 | Benzene, (1,2-dimethyl-1-propenyl)- | | 93 | 0.17 |
| 95-93-2 | Benzene, 1,2,4,5-tetramethyl- | | 92 | 0.15 |
| 2049-95-8 | Benzene, (1,1-dimethylpropyl)- | | 87 | 0.15 |
| 56147-63-8 | 2-Ethyl-2,3-dihydro-1H-indene | | 68 | 0.15 |
| 527-84-4 | o-Cymene | | 94 | 0.14 |
| | Trace Aromatic Hydrocarbons | | | |
| 103-65-1 | Benzene, propyl- | | 81 | 0.095 |
| 71-43-2 | Benzene | | 91 | 0.080 |
| 91-57-6 | Naphthalene, 2-methyl- | | 94 | 0.079 |
| 2613-76-5 | 1H-Indene, 2,3-dihydro-1,1,3-trimethyl- | | 70 | 0.067 |
| 577-55-9 | Benzene, 1,2-bis(1-methylethyl)- | | 78 | 0.059 |
| 4132-72-3 | Benzene, 1,4-dimethyl-2-(1-methylethyl)- | | 91 | 0.051 |
| 98-82-8 | Benzene, (1-methylethyl)- | | 81 | 0.046 |
| 1680-51-9 | 6-Methyl-(1,2,3,4-tetrahydronaphthalene) | | 98 | 0.045 |
| 527-53-7 | Benzene, 1,2,3,5-tetramethyl- | | 97 | 0.044 |
| 1746-23-2 | 1-(1,1-Dimethylethyl)-4-ethenylbenzene | | 68 | 0.040 |
| 1595-05-7 | Benzene, 1-methyl-4-butyl | | 74 | 0.037 |
| 105-05-5 | Benzene, 1,4-diethyl- | | 81 | 0.036 |
| 91-20-3 | Naphthalene | | 90 | 0.034 |
| 17851-27-3 | Benzene, 1-ethyl-2,4,5-trimethyl- | | 87 | 0.031 |
| 40650-41-7 | 1H-Indene, 2,3-dihydro-1,1,5-trimethyl- | | 90 | 0.024 |
| 3877-19-8 | 3-Methyl-(1,2,3,4-tetrahydronaphthalene) | | 81 | 0.023 |
| 1195-32-0 | Benzene, 1-methyl-4-(1-methylethenyl)- | | 93 | 0.021 |
| 4218-48-8 | Benzene, 1-ethyl-4-(1-methylethyl)- | | 86 | 0.021 |
| 877-44-1 | Benzene, 1,2,4-triethyl- | | 81 | 0.021 |
| 1587-04-8 | Benzene, 1-methyl-2-(2-propenyl)- | | 81 | 0.020 |
| 13065-07-1 | 2,7-dimethyltetralin | | 91 | 0.019 |
| 934-74-7 | Benzene, 1-ethyl-3,5-dimethyl- | | 91 | 0.019 |
| 582-16-1 | Naphthalene, 2,7-dimethyl- | | 93 | 0.018 |
| 27831-13-6 | Benzene, 4-ethenyl-1,2-dimethyl- | | 84 | 0.018 |
| 55669-88-0 | 1,4-dimethyl-2-(2-methylpropyl)benzene | | 72 | 0.017 |
| 4761-36-4 | Benzene, (1-ethyl-1-propenyl)- | | 72 | 0.012 |

FIG. 30 CONT

| CAS # | Compound Name | BR* | Q | Area % |
|---|---|---|---|---|
| 4810-04-2 | Benzene, 1,3,5-trimethyl-2-propyl- | | 64 | 0.011 |
| 14679-13-1 | 1,3,5-trimethyl-2-prop-1-en-2-yl-benzene | | 60 | 0.011 |
| 4706-90-5 | Benzene, 1,3-dimethyl-5-(1-methylethyl)- | | 80 | 0.011 |
| 7364-19-4 | Benzene, 1-(1,1-dimethylethyl)-4-ethyl- | | 64 | 0.009 |
| 54340-85-1 | Benzene, 1-(2-butenyl)-2,3-dimethyl- | | 87 | 0.009 |
| 1485-80-9 | Benzene, 1,3-dimethyl-4-(1-methylpropyl)- | | 72 | 0.009 |
| 53172-84-2 | Benzene, (1-methyl-1-butenyl)- | | 72 | 0.008 |
| | Trace Aromatic Hydrocarbons | | | |
| 939-27-5 | Naphthalene, 2-ethyl- | | 90 | 0.008 |
| | Major Oxygenated Aromatics | | | |
| 6148-37-4 | Furan, 4-methyl-2-propyl- | | 80 | 0.11 |
| | Trace Oxygenated Aromatics | | | |
| 13678-51-8 | Furan, 2-(2-furanylmethyl)-5-methyl- | | 64 | 0.032 |
| | Major n-Alkenes | | | |
| 4050-45-7 | 2-Hexene, (E)- | | 91 | 0.15 |
| 627-20-3 | 2-Pentene, (Z)- | | 90 | 0.11 |
| | Trace n-Alkenes | | | |
| 592-43-8 | 2-Hexene | | 90 | 0.075 |
| 592-47-2 | 3-Hexene | | 93 | 0.064 |
| 646-04-8 | 2-Pentene, (E)- | | 90 | 0.059 |
| 592-77-8 | 2-Heptene | | 93 | 0.048 |
| 592-41-6 | 1-Hexene | | 83 | 0.029 |
| 13269-52-8 | 3-Hexene, (E)- | | 91 | 0.023 |
| 109-67-1 | 1-Pentene | | 76 | 0.022 |
| 590-18-1 | 2-Butene, (Z)- | | 64 | 0.020 |
| 624-64-6 | 2-Butene, (E)- | | 74 | 0.018 |
| | Major Branched Alkenes | | | |
| 756-02-5 | 1,4-Pentadiene, 2,3,3-trimethyl- | 3 | 90 | 0.70 |
| 74752-97-9 | 1,3-Hexadiene, 3-ethyl-2-methyl-, (Z)- | 2 | 91 | 0.35 |
| 563-79-1 | 2-Butene, 2,3-dimethyl- | 2 | 91 | 0.32 |
| 2738-19-4 | 2-Hexene, 2-methyl- | 1 | 91 | 0.23 |
| 3404-65-7 | 3-Methyl-3-hexene | 1 | 91 | 0.13 |
| 922-61-2 | 2-Pentene, 3-methyl- | 1 | 95 | 0.53 |
| 763-29-1 | 1-Pentene, 2-methyl- | 1 | 91 | 0.13 |
| 513-35-9 | 2-Butene, 2-methyl- | 1 | 90 | 0.42 |
| 563-46-2 | 2-Methyl-1-butene | 1 | 91 | 0.11 |
| | Trace Branched Alkenes | | | |
| 72014-90-5 | 1,4-Pentadiene, 2,3,4-trimethyl- | 3 | 70 | 0.080 |
| 24618-86-8 | 1,3-Heptadiene, 5,5-dimethyl- | 2 | 70 | 0.075 |
| 1515-79-3 | 5,5-Dimethyl-1,3-hexadiene | 2 | 91 | 0.076 |
| 1000195-03-3 | 6,6-Dimethylhepta-2,4-diene | 2 | 90 | 0.020 |
| 3404-79-3 | 2-Hexene, 3,5-dimethyl- | 2 | 81 | 0.043 |
| 3404-78-2 | 2-Hexene, 2,5-dimethyl- | 2 | 81 | 0.057 |
| 14255-23-3 | 2-Hexene, 2,4-dimethyl- | 2 | 87 | 0.055 |
| 1113-56-0 | 1,3-Pentadiene, 2,3-dimethyl- | 2 | 72 | 0.009 |
| 4914-92-5 | 2-Pentene, 3,4-dimethyl-, (E)- | 2 | 87 | 0.085 |
| 2213-32-3 | 1-Pentene, 2,4-dimethyl- | 2 | 87 | 0.028 |
| 563-78-0 | 1-Butene, 2,3-dimethyl- | 2 | 90 | 0.082 |
| 4485-16-9 | 3-Heptene, 4-methyl- | 1 | 87 | 0.025 |
| 816-79-5 | 2-Pentene, 3-ethyl- | 1 | 74 | 0.051 |
| 13151-17-2 | (Z)-Hex-2-ene, 5-methyl- | 1 | 70 | 0.034 |
| 3404-55-5 | 4-Methyl-2-hexene, c&t | 1 | 90 | 0.076 |

FIG. 30 CONT

| CAS # | Compound Name | BR# | Q | Area % |
|---|---|---|---|---|
| 692-24-0 | 3-Hexene, 2-methyl-, (E)- | 1 | 90 | 0.036 |
| 763-30-4 | 1,4-Pentadiene, 2-methyl- | 1 | 68 | 0.016 |
| 874-76-0 | 2-Pentene, 4-methyl-, (E)- | 1 | 90 | 0.081 |
| 760-20-3 | 1-Pentene, 3-methyl- | 1 | 91 | 0.026 |
| 691-37-2 | 1-Pentene, 4-methyl- | 1 | 81 | 0.015 |
| 563-45-1 | 1-Butene, 3-methyl- | 1 | 72 | 0.089 |
| 115-11-7 | 1-Propene, 2-methyl- | 1 | 91 | 0.019 |
| | Major Cyclic Alkenes | | | |
| 16491-15-9 | Cyclopentene, 1,5-dimethyl- | | 74 | 0.66 |
| 473-91-6 | Cyclopentene, 1,2,3-trimethyl- | | 91 | 0.53 |
| 1528-22-9 | Cyclobutane, (1-methylethylidene)- | | 90 | 0.41 |
| 7459-71-4 | 3,5-Dimethylcyclopentene | | 86 | 0.28 |
| 1120-62-3 | Cyclopentene, 3-methyl- | | 90 | 0.22 |
| 2808-80-3 | Cyclohexane, 1-methyl-4-methylene- | | 91 | 0.17 |
| 2808-71-1 | Cyclohexene, 3-ethyl- | | 87 | 0.17 |
| 591-49-1 | Cyclohexene, 1-methyl- | | 91 | 0.17 |
| 97797-57-4 | 1-Ethyl-5-methylcyclopentene | | 95 | 0.14 |
| 58021-63-7 | trans-3,5-Dimethylcyclohexene | | 80 | 0.13 |
| 2808-78-6 | 1,3-Dimethyl-1-cyclohexene | | 91 | 0.11 |
| | Trace Cyclic Alkenes | | | |
| 2272-03-9 | Cyclohexane, butylidene- | | 64 | 0.035 |
| 2539-75-5 | Cyclohexene, 1-propyl- | | 78 | 0.031 |
| 3983-03-7 | Cyclohexene, 1-(2-methylpropyl)- | | 64 | 0.049 |
| 1000113-30-9 | trans-1-Butenylcyclopentane | | 80 | 0.058 |
| 5749-72-4 | Cyclohexane, (1-methylethylidene)- | | 64 | 0.036 |
| 1453-24-3 | Cyclohexene, 1-ethyl- | | 87 | 0.070 |
| 61142-33-4 | 1,4-dimethyl-5-propan-2-yl-cyclopentene | | 64 | 0.070 |
| 65378-76-9 | 1,2,4,4-Tetramethylcyclopentene | | 90 | 0.058 |
| 765-83-3 | Cyclopentane, (1-methylethylidene)- | | 86 | 0.027 |
| 19780-56-4 | Methyl ethyl cyclopentene | | 91 | 0.043 |
| 2808-75-5 | 1-Methyl-2-methylenecyclohexane | | 72 | 0.025 |
| 2146-38-5 | 1-Ethylcyclopentene | | 91 | 0.080 |
| 55170-90-6 | Bicyclo[2.2.1]heptane, 2-(1-buten-3-yl)- | | 72 | 0.069 |
| 694-35-9 | Cyclopentene, 3-ethyl- | | 74 | 0.020 |
| 41158-41-2 | Cyclopentane, 1-methyl-2-methylene- | | 62 | 0.010 |
| 1528-21-8 | Ethylidenecyclobutane | | 87 | 0.021 |
| 3422-07-9 | Cyclopropane, 1-methyl-1-isopropenyl- | | 72 | 0.030 |
| 142-29-0 | Cyclopentene | | 68 | 0.011 |
| | Major n-Alkanes | | | |
| 110-54-3 | n-Hexane | | 91 | 0.41 |
| 109-66-0 | Pentane | | 91 | 0.29 |
| 629-78-7 | Heptadecane | | 78 | 0.24 |
| 106-97-8 | Butane | | 87 | 0.20 |
| | Major Branched Alkanes | | | |
| 122204-12-0 | Dodecane, 2,2,11,11-tetramethyl- | 4 | 83 | 0.27 |
| 62338-09-4 | Decane, 2,2,3-trimethyl- | 3 | 72 | 0.10 |
| 7154-80-5 | Heptane, 3,3,5-trimethyl- | 3 | 64 | 0.12 |
| 14720-74-2 | Heptane, 2,2,4-trimethyl- | 3 | 64 | 0.16 |
| 62237-96-1 | Decane, 2,2,5-trimethyl- | 3 | 72 | 0.15 |
| 921-47-1 | Hexane, 2,3,4-trimethyl- | 3 | 83 | 0.15 |
| 1068-87-7 | Pentane, 3-ethyl-2,4-dimethyl- | 3 | 78 | 0.20 |
| 3522-94-9 | Hexane, 2,2,5-trimethyl- | 3 | 83 | 1.42 |

FIG. 30 CONT

| CAS # | Compound Name | BR# | Q | Area % |
|---|---|---|---|---|
| 20278-89-1 | Heptane, 3,4,5-trimethyl- | 3 | 64 | 0.37 |
| 565-75-3 | Pentane, 2,3,4-trimethyl- | 3 | 83 | 2.58 |
| 564-02-3 | Pentane, 2,2,3-trimethyl- | 3 | 72 | 0.37 |
| 540-84-1 | Pentane, 2,2,4-trimethyl- | 3 | 90 | 5.64 |
| 2051-30-1 | Octane, 2,6-dimethyl- | 2 | 72 | 0.27 |
| 583-48-2 | Hexane, 3,4-dimethyl- | 2 | 72 | 0.15 |
| 584-94-1 | Hexane, 2,3-dimethyl- | 2 | 94 | 0.81 |
| 589-43-5 | Hexane, 2,4-dimethyl- | 2 | 80 | 0.90 |
| 592-13-2 | Hexane, 2,5-dimethyl- | 2 | 94 | 0.93 |
| 565-59-3 | Pentane, 2,3-dimethyl- | 2 | 74 | 0.43 |
| 108-08-7 | Pentane, 2,4-dimethyl- | 2 | 94 | 0.80 |
| 79-29-8 | Butane, 2,3-dimethyl- | 2 | 87 | 0.77 |
| 589-53-7 | Heptane, 4-methyl- | 1 | 91 | 0.23 |
| 592-27-8 | Heptane, 2-methyl- | 1 | 95 | 0.31 |
| 2216-34-4 | Octane, 4-methyl- | 1 | 83 | 3.09 |
| 589-34-4 | Hexane, 3-methyl- | 1 | 74 | 0.96 |
| 96-14-0 | Pentane, 3-methyl- | 1 | 91 | 0.81 |
| 107-83-5 | Pentane, 2-methyl- | 1 | 83 | 1.47 |
| 78-78-4 | Butane, 2-methyl- | 1 | 91 | 5.50 |
| Trace Branched Alkanes | | | | |
| 74645-98-0 | Dodecane, 2,7,10-trimethyl- | 3 | 64 | 0.049 |
| 62237-99-4 | Decane, 2,2,7-trimethyl- | 3 | 72 | 0.031 |
| 62016-30-2 | Octane, 2,3,3-trimethyl- | 3 | 78 | 0.069 |
| 62108-26-3 | Decane, 2,6,8-trimethyl- | 3 | 72 | 0.084 |
| 31081-18-2 | Nonane, 3-methyl-5-propyl- | 2 | 78 | 0.020 |
| 563-16-6 | Hexane, 3,3-dimethyl- | 2 | 72 | 0.038 |
| 17302-37-3 | Decane, 2,2-dimethyl- | 2 | 78 | 0.085 |
| 590-35-2 | Pentane, 2,2-dimethyl- | 2 | 72 | 0.061 |
| 75-28-5 | Isobutane | 1 | 72 | 0.038 |
| Major Cyclic Alkanes | | | | |
| 96-37-7 | Cyclopentane, methyl- | | 91 | 0.43 |
| 2815-58-9 | Cyclopentane, 1,2,4-trimethyl- | | 91 | 0.23 |
| 2613-66-3 | Cyclopentane, 1-ethyl-3-methyl-, cis- | | 91 | 0.21 |
| 2452-99-5 | Cyclopentane, 1,2-dimethyl- | | 85 | 0.20 |
| 108-87-2 | Cyclohexane, methyl- | | 95 | 0.19 |
| 2453-00-1 | Cyclopentane, 1,3-dimethyl- | | 83 | 0.19 |
| 1640-89-7 | Cyclopentane, ethyl- | | 87 | 0.18 |
| 2040-96-2 | Cyclopentane, propyl- | | 64 | 0.16 |
| 930-89-2 | Cyclopentane, 1-ethyl-2-methyl-, cis- | | 95 | 0.16 |
| 2613-65-2 | Cyclopentane, 1-ethyl-3-methyl-, trans- | | 83 | 0.15 |
| 110-82-7 | Cyclohexane | | 87 | 0.12 |
| 1192-18-3 | Cyclopentane, 1,2-dimethyl-, cis- | | 94 | 0.11 |
| 16747-50-5 | Cyclopentane, 1-ethyl-1-methyl- | | 86 | 0.11 |
| 74722-93-5 | Cyclopropane, 1,1,2,3-tetramethyl- | | 91 | 0.10 |
| 17065-18-8 | Bicyclo[2.1.0]pentane, 1,4-dimethyl- | | 78 | 0.10 |
| Trace Cyclic Alkanes | | | | |
| 4126-78-7 | Cycloheptane, methyl- | | 74 | 0.023 |
| 766-53-0 | Bicyclo[2.2.2]octane, 2-methyl- | | 64 | 0.013 |
| 1678-97-3 | Cyclohexane, 1,2,3-trimethyl- | | 70 | 0.018 |
| 15890-40-1 | 1,2,3-Trimethylcyclopentane, cis, trans | | 72 | 0.015 |
| 4850-28-6 | 1,2,4-Trimethylcyclopentane, cis, trans | | 70 | 0.043 |
| 287-92-3 | Cyclopentane | | 80 | 0.035 |

FIG. 30 CONT

| CAS # | Compound Name | BRs | Q | Area % |
|---|---|---|---|---|
| | Major Oxygenates | | | |
| 112-58-3 | Hexane, 1,1'-oxybis- | | 64 | 0.85 |
| 60-29-7 | Ethyl ether | | 91 | 0.41 |
| | Trace Oxygenates | | | |
| 134225-90-4 | 2-Nonen-4-yn-1-ol, (Z)- | | 64 | 0.035 |
| 55449-71-3 | OCTAHYDROPENTALENO(1,2-B)OXIRENE | | 64 | 0.010 |
| 55283-28-6 | photocitral A | | 64 | 0.006 |
| 105-57-7 | Ethane, 1,1-diethoxy- | | 83 | 0.078 |
| 107-87-9 | 2-Pentanone | | 64 | 0.013 |
| 64-17-5 | Ethanol | | 64 | 0.010 |

FIG. 30 CONT

| CAS # | Compound Name | BR# | Q | Area % |
|---|---|---|---|---|
| Major Aromatics Hydrocarbons | | | | |
| 620-14-4 | Benzene, 1-ethyl-3-methyl- | | 95 | 14.39 |
| 95-47-6 | o-Xylene | | 95 | 9.38 |
| 526-73-8 | Benzene, 1,2,3-trimethyl- | | 97 | 6.78 |
| 108-88-3 | Toluene | | 91 | 6.35 |
| 874-41-9 | Benzene, 1-ethyl-2,4-dimethyl- | | 97 | 6.05 |
| 105-05-5 | Benzene, 1,4-diethyl- | | 97 | 3.58 |
| 108-38-3 | Benzene, 1,3-dimethyl- | | 95 | 3.20 |
| 100-41-4 | Ethylbenzene | | 91 | 2.92 |
| 135-01-3 | Benzene, 1,2-diethyl- | | 98 | 2.40 |
| 13632-94-5 | Benzene, 1,4-diethyl-2-methyl- | | 97 | 1.72 |
| 527-84-4 | o-Cymene | | 94 | 1.71 |
| 611-14-3 | Benzene, 1-ethyl-2-methyl- | | 95 | 0.86 |
| 874-35-1 | 1H-Indene, 2,3-dihydro-5-methyl- | | 94 | 0.74 |
| 1074-43-7 | Benzene, 1-methyl-3-propyl- | | 91 | 0.58 |
| 1758-88-9 | Benzene, 2-ethyl-1,4-dimethyl- | | 95 | 0.53 |
| 95-93-2 | Benzene, 1,2,4,5-tetramethyl- | | 97 | 0.47 |
| 71-43-2 | Benzene | | 91 | 0.46 |
| 1595-16-0 | Benzene, 1-methyl-4-(1-methylpropyl)- | | 94 | 0.42 |
| 2050-24-0 | Benzene, 1,3-diethyl-5-methyl- | | 97 | 0.30 |
| 769-57-3 | Benzene, (1,2-dimethyl-1-propenyl)- | | 93 | 0.27 |
| 103-65-1 | Benzene, propyl- | | 87 | 0.25 |
| 535-77-3 | Benzene, 1-methyl-3-(1-methylethyl)- | | 95 | 0.19 |
| 53172-84-2 | Benzene, (1-methyl-1-butenyl)- | | 96 | 0.16 |
| 496-11-7 | Indane | | 93 | 0.12 |
| 56147-63-8 | 2-Ethyl-2,3-dihydro-1H-indene | | 72 | 0.12 |
| 1074-55-1 | Benzene, 1-methyl-4-propyl- | | 87 | 0.12 |
| 5161-04-6 | Benzene, 1-methyl-4-(2-methylpropyl)- | | 80 | 0.11 |
| 1758-85-6 | Benzene, 2,4-diethyl-1-methyl- | | 76 | 0.11 |
| Trace Aromatic Hydrocarbons | | | | |
| 98-82-8 | Benzene, (1-methylethyl)- | | 90 | 0.096 |
| 108-67-8 | Mesitylene | | 97 | 0.089 |
| 91-57-6 | Naphthalene, 2-methyl- | | 94 | 0.076 |
| 2613-76-5 | 1H-Indene, 2,3-dihydro-1,1,3-trimethyl- | | 87 | 0.058 |
| 6682-71-9 | 1H-Indene, 2,3-dihydro-4,7-dimethyl- | | 95 | 0.054 |
| 933-98-2 | Benzene, 1-ethyl-2,3-dimethyl- | | 96 | 0.053 |
| 1595-05-7 | Benzene, 1-methyl-4-butyl | | 93 | 0.051 |
| 700-12-9 | Benzene, pentamethyl- | | 93 | 0.048 |
| 91-20-3 | Naphthalene | | 93 | 0.045 |
| 1680-51-9 | 6-Methyl-(1,2,3,4-tetrahydronaphthalene) | | 95 | 0.044 |
| 17851-27-3 | Benzene, 1-ethyl-2,4,5-trimethyl- | | 87 | 0.034 |
| 54340-86-2 | 4-[(E)-but-2-enyl]-1,2-dimethyl-benzene | | 90 | 0.031 |
| 1746-23-2 | 1-(1,1-Dimethylethyl)-4-ethenylbenzene | | 63 | 0.030 |
| 488-23-3 | Benzene, 1,2,3,4-tetramethyl- | | 94 | 0.025 |
| 3877-19-8 | 2-Methyl-(1,2,3,4-tetrahydronaphthalene) | | 93 | 0.024 |
| 1005-64-7 | (E)-1-Phenyl-1-butene | | 96 | 0.021 |
| 1000370-34-1 | 3,4-Dimethylcumene | | 91 | 0.016 |
| 824-90-8 | 1-Phenyl-1-butene | | 76 | 0.015 |
| 55669-88-0 | 1,4-dimethyl-2-(2-methylpropyl)benzene | | 81 | 0.014 |
| 2234-20-0 | 2,4-Dimethylstyrene | | 94 | 0.014 |
| 15677-15-3 | 1,1a,6,6a-tetrahydrocyclopropa[a]indene | | 93 | 0.013 |
| 2717-42-7 | Naphthalene, 1,2-dihydro-6-methyl- | | 93 | 0.013 |

FIG. 31 CONT

| CAS # | Compound Name | BR# | Q | Area % |
|---|---|---|---|---|
| 13065-07-1 | 2,7-dimethyltetralin | | 72 | 0.012 |
| 826-18-6 | Benzene, 1-pentenyl- | | 64 | 0.011 |
| 7397-06-0 | 4-t-Butyl-o-xylene | | 64 | 0.011 |
| 1560-06-1 | Benzene, 2-butenyl- | | 83 | 0.010 |
| 54340-85-1 | Benzene, 1-(2-butenyl)-2,3-dimethyl- | | 64 | 0.009 |
| 97864-18-1 | 1-Methyl-4-(1-methyl-2-propenyl)benzene | | 91 | 0.009 |
| 42775-75-7 | Naphthalene, 5-ethyl-1,2,3,4-tetrahydro- | | 64 | 0.007 |
| 575-43-9 | Naphthalene, 1,6-dimethyl- | | 94 | 0.007 |
| 4810-04-2 | Benzene, 1,3,5-trimethyl-2-propyl- | | 78 | 0.006 |
| 30704-01-3 | Benzene, (1,3-dimethyl-2-butenyl)- | | 72 | 0.006 |
| 90-12-0 | Naphthalene, 1-methyl- | | 86 | 0.006 |
| 573-98-8 | Naphthalene, 1,2-dimethyl- | | 86 | 0.005 |
| Major Oxygenated Aromatics | | | | |
| 6148-37-4 | Furan, 4-methyl-2-propyl- | | 80 | 0.19 |
| Trace Oxygenated Aromatics | | | | |
| 1467-36-3 | Ethanone, 1-(2,3,4-trimethylphenyl)- | | 76 | 0.055 |
| 39701-08-1 | 8,9-Dehydrothymol methyl ether | | 70 | 0.028 |
| 100302-79-8 | Benzoic acid, 4-isopropyl-, ethyl ester | | 72 | 0.006 |
| Major n-Alkenes | | | | |
| 627-20-3 | 2-Pentene, (Z)- | | 91 | 0.20 |
| 4050-45-7 | 2-Hexene, (E)- | | 91 | 0.15 |
| 646-04-8 | 2-Pentene, (E)- | | 90 | 0.11 |
| Trace n-Alkenes | | | | |
| 7642-09-3 | 3-Hexene, (Z)- | | 93 | 0.096 |
| 13269-52-8 | 3-Hexene, (E)- | | 93 | 0.081 |
| 590-18-1 | 2-Butene, (Z)- | | 87 | 0.044 |
| 109-67-1 | 1-Pentene | | 81 | 0.043 |
| 14686-13-6 | 2-Heptene, (E)- | | 94 | 0.041 |
| 624-64-6 | 2-Butene, (E)- | | 60 | 0.040 |
| 592-41-6 | 1-Hexene | | 90 | 0.034 |
| Major Branched Alkenes | | | | |
| 756-02-5 | 1,4-Pentadiene, 2,3,3-trimethyl- | 3 | 90 | 0.31 |
| 74752-97-9 | 1,3-Hexadiene, 3-ethyl-2-methyl-, (Z)- | 2 | 87 | 0.18 |
| 1112-35-3 | 1,4-Pentadiene, 3,3-dimethyl- | 2 | 78 | 0.26 |
| 563-79-1 | 2-Butene, 2,3-dimethyl- | 2 | 90 | 0.26 |
| 2080-89-9 | 1,4-Hexadiene, 3-ethyl- | 1 | 76 | 0.12 |
| 2738-19-4 | 2-Hexene, 2-methyl- | 1 | 91 | 0.20 |
| 3404-65-7 | 3-Methyl-3-hexene | 1 | 91 | 0.13 |
| 922-61-2 | 2-Pentene, 3-methyl- | 1 | 95 | 0.36 |
| 674-76-0 | 2-Pentene, 4-methyl-, (E)- | 1 | 91 | 0.33 |
| 763-29-1 | 1-Pentene, 2-methyl- | 1 | 94 | 0.16 |
| 513-35-9 | 2-Butene, 2-methyl- | 1 | 91 | 0.74 |
| 563-46-2 | 2-Methyl-1-butene | 1 | 91 | 0.25 |
| Trace Branched Alkenes | | | | |
| 74779-85-0 | 1,3-Heptadiene, 2,3-dimethyl- | 2 | 60 | 0.087 |
| 1515-79-3 | 5,5-Dimethyl-1,3-hexadiene | 2 | 64 | 0.023 |
| 1000195-03-3 | 6,6-Dimethylhepta-2,4-diene | 2 | 90 | 0.036 |
| 15910-22-2 | 3-Hexene, 2,5-dimethyl- | 2 | 87 | 0.049 |
| 10574-37-5 | 2-Pentene, 2,3-dimethyl- | 2 | 64 | 0.031 |
| 758-86-1 | 2,3-Dimethyl-1,4-pentadiene | 2 | 68 | 0.012 |
| 4914-92-5 | 2-Pentene, 3,4-dimethyl-, (E)- | 2 | 87 | 0.060 |
| 2213-32-3 | 1-Pentene, 2,4-dimethyl- | 2 | 87 | 0.028 |

FIG. 31 CONT

| CAS # | Compound Name | BR# | Q | Area % |
|---|---|---|---|---|
| 4485-16-9 | 3-Heptene, 4-methyl- | 1 | 90 | 0.020 |
| 24587-27-7 | 1,3,5-Hexatriene, 3-methyl-, (Z)- | 1 | 72 | 0.007 |
| 3683-22-5 | 2-Hexene, 4-methyl-, (E)- | 1 | 90 | 0.072 |
| 15840-60-5 | 1-Hexene, 2-methyl-, (Z)- | 1 | 93 | 0.034 |
| 816-79-5 | 2-Pentene, 3-ethyl- | 1 | 86 | 0.055 |
| 675-27-4 | 2-Pentene, 2-methyl- | 1 | 91 | 0.099 |
| 760-20-3 | 1-Pentene, 3-methyl- | 1 | 93 | 0.034 |
| 115-11-7 | 1-Propene, 2-methyl- | 1 | 91 | 0.030 |
| *Major Cyclic Alkenes* | | | | |
| 16491-15-9 | Cyclopentene, 1,5-dimethyl- | | 76 | 0.71 |
| 473-91-6 | Cyclopentene, 1,2,3-trimethyl- | | 91 | 0.68 |
| 1528-22-9 | Cyclobutane, (1-methylethylidene)- | | 90 | 0.41 |
| 693-89-0 | Cyclopentene, 1-methyl- | | 90 | 0.25 |
| 591-49-1 | Cyclohexene, 1-methyl- | | 93 | 0.16 |
| 1674-10-8 | Cyclohexene, 1,2-dimethyl- | | 80 | 0.15 |
| 56021-63-7 | trans-3,5-Dimethylcyclohexene | | 96 | 0.13 |
| 2808-80-2 | Cyclohexane, 1-methyl-4-methylene- | | 95 | 0.13 |
| *Trace Cyclic Alkenes* | | | | |
| 3749-72-4 | Cyclohexane, (1-methylethylidene)- | | 72 | 0.033 |
| 65378-76-9 | 1,2,4,4-Tetramethylcyclopentene | | 81 | 0.081 |
| 1453-24-3 | Cyclohexene, 1-ethyl- | | 87 | 0.079 |
| 823-17-6 | Cyclohexene, 3,5-dimethyl- | | 86 | 0.097 |
| 97797-37-4 | 1-Ethyl-5-methylcyclopentene | | 78 | 0.096 |
| 55308-20-8 | 1-Methylcycloheptene | | 72 | 0.021 |
| 19780-56-4 | Methyl ethyl cyclopentene | | 93 | 0.042 |
| 2146-38-5 | 1-Ethylcyclopentene | | 94 | 0.089 |
| 35178-90-6 | Bicyclo[2.2.1]heptane, 2-(1-buten-3-yl)- | | 78 | 0.055 |
| 694-35-9 | Cyclopentene, 3-ethyl- | | 81 | 0.020 |
| 2507-49-1 | Cyclobutane, ethenyl- | | 81 | 0.028 |
| 7459-71-4 | 3,5-Dimethylcyclopentene | | 72 | 0.024 |
| 4663-22-3 | Isopropenylcyclopropane | | 87 | 0.023 |
| 1120-62-3 | Cyclopentene, 3-methyl- | | 90 | 0.045 |
| 142-29-0 | Cyclopentene | | 90 | 0.023 |
| *Major n-Alkanes* | | | | |
| 110-54-3 | n-Hexane | | 91 | 0.62 |
| 109-66-0 | Pentane | | 91 | 0.60 |
| 106-97-8 | Butane | | 87 | 0.17 |
| *Major Branched Alkanes* | | | | |
| 921-47-1 | Hexane, 2,3,4-trimethyl- | 3 | 87 | 0.14 |
| 16747-26-5 | Hexane, 2,2,4-trimethyl- | 3 | 64 | 0.40 |
| 560-21-4 | Pentane, 2,3,3-trimethyl- | 3 | 78 | 0.81 |
| 565-75-3 | Pentane, 2,3,4-trimethyl- | 3 | 83 | 0.70 |
| 540-84-1 | Pentane, 2,2,4-trimethyl- | 3 | 90 | 1.60 |
| 15869-96-2 | Octane, 4,5-dimethyl- | 2 | 72 | 0.33 |
| 589-43-5 | Hexane, 2,4-dimethyl- | 2 | 78 | 0.71 |
| 592-13-2 | Hexane, 2,5-dimethyl- | 2 | 93 | 0.26 |
| 565-59-3 | Pentane, 2,3-dimethyl- | 2 | 83 | 0.18 |
| 108-08-7 | Pentane, 2,4-dimethyl- | 2 | 91 | 0.18 |
| 79-29-8 | Butane, 2,3-dimethyl- | 2 | 91 | 0.31 |
| 2216-33-3 | Octane, 3-methyl- | 1 | 74 | 0.12 |
| 589-53-7 | Heptane, 4-methyl- | 1 | 94 | 0.23 |
| 592-27-8 | Heptane, 2-methyl- | 1 | 95 | 0.31 |

FIG. 31 CONT

| CAS # | Compound Name | BR# | Q | Area % |
|---|---|---|---|---|
| 589-34-4 | Hexane, 3-methyl- | 1 | 78 | 1.18 |
| 591-76-4 | Hexane, 2-methyl- | 1 | 74 | 0.99 |
| 96-14-0 | Pentane, 3-methyl- | 1 | 91 | 1.35 |
| 107-83-5 | Pentane, 2-methyl- | 1 | 74 | 2.17 |
| 78-78-4 | Butane, 2-methyl- | 1 | 91 | 3.03 |
| Trace Branched Alkanes ||||||
| 13475-82-6 | Heptane, 2,2,4,6,6-pentamethyl- | 5 | 78 | 0.092 |
| 127204-12-0 | Dodecane, 2,2,11,11-tetramethyl- | 4 | 72 | 0.078 |
| 62238-01-1 | Decane, 2,2,8-trimethyl- | 3 | 64 | 0.053 |
| 1069-53-0 | Hexane, 2,3,5-trimethyl- | 3 | 83 | 0.057 |
| 2051-30-1 | Octane, 2,6-dimethyl- | 2 | 64 | 0.065 |
| 56292-65-0 | Dodecane, 2,5-dimethyl- | 2 | 64 | 0.064 |
| 15869-87-1 | Octane, 2,2-dimethyl- | 2 | 64 | 0.044 |
| 583-48-2 | Hexane, 3,4-dimethyl- | 2 | 64 | 0.032 |
| 75-83-2 | Butane, 2,2-dimethyl- | 2 | 64 | 0.016 |
| 75-28-5 | Isobutane | 1 | 72 | 0.094 |
| Major Cyclic Alkanes ||||||
| 96-37-7 | Cyclopentane, methyl- | | 91 | 0.84 |
| 2453-00-1 | Cyclopentane, 1,3-dimethyl- | | 90 | 0.46 |
| 2815-57-8 | Cyclopentane, 1,2,3-trimethyl- | | 64 | 0.35 |
| 822-50-4 | Cyclopentane, 1,2-dimethyl-, trans- | | 93 | 0.31 |
| 2207-03-6 | Cyclohexane, 1,3-dimethyl-, trans- | | 81 | 0.30 |
| 1640-89-7 | Cyclopentane, ethyl- | | 91 | 0.29 |
| 3726-47-4 | Cyclopentane, 1-ethyl-3-methyl- | | 83 | 0.24 |
| 108-87-2 | Cyclohexane, methyl- | | 94 | 0.24 |
| 2613-66-3 | Cyclopentane, 1-ethyl-3-methyl-, cis- | | 87 | 0.20 |
| 2815-58-9 | Cyclopentane, 1,2,4-trimethyl- | | 91 | 0.20 |
| 930-89-2 | Cyclopentane, 1-ethyl-2-methyl-, cis- | | 87 | 0.18 |
| 2040-96-2 | Cyclopentane, propyl- | | 70 | 0.16 |
| 638-04-0 | Cyclohexane, 1,3-dimethyl-, cis- | | 76 | 0.14 |
| 4516-69-2 | Cyclopentane, 1,1,3-trimethyl- | | 83 | 0.14 |
| Trace Cyclic Alkanes ||||||
| 293-96-9 | Cyclodecane | | 64 | 0.026 |
| 2146-41-0 | Bicyclo[2.2.1]heptane, 2-ethyl- | | 87 | 0.076 |
| 61142-68-5 | Cyclopentane, 1-hexyl-3-methyl- | | 78 | 0.061 |
| 2613-65-2 | Cyclopentane, 1-ethyl-3-methyl-, trans- | | 64 | 0.029 |
| 1000142-17-5 | Bicyclo[3.1.0]hexane, 1,5-dimethyl- | | 91 | 0.091 |
| 17065-18-8 | Bicyclo[2.1.0]pentane, 1,4-dimethyl- | | 72 | 0.080 |
| 2613-89-0 | (1R,2s,3S)-1,2,3-Trimethylcyclopentane | | 72 | 0.016 |
| 589-90-2 | Cyclohexane, 1,4-dimethyl- | | 90 | 0.060 |
| 1678-91-7 | Cyclohexane, ethyl- | | 83 | 0.050 |
| 74752-93-5 | Cyclopropane, 1,1,2,3-tetramethyl- | | 91 | 0.096 |
| 110-82-7 | Cyclohexane | | 60 | 0.074 |
| 287-92-3 | Cyclopentane | | 87 | 0.095 |
| Major Oxygenates ||||||
| 60-29-7 | Ethyl ether | | 91 | 0.11 |
| Trace Oxygenates ||||||
| 80387-31-1 | Nona-3,5-dien-2-one | | 64 | 0.024 |
| 931-96-4 | 1-methyl-1-cyclohex-3-enecarboxaldehyde | | 64 | 0.018 |
| 767-05-5 | 3-Cyclopentyl-1-propanol | | 72 | 0.060 |
| 107-87-9 | 2-Pentanone | | 72 | 0.040 |
| 78-93-3 | 2-Butanone | | 64 | 0.041 |

FIG. 31 CONT

| CAS # | Compound Name | BR# | Q | Area % |
|---|---|---|---|---|
| 64-17-5 | Ethanol | | 64 | 0.015 |

FIG. 31 CONT

| CAS # | Compound Name | BR# | Q | Area % |
|---|---|---|---|---|
| | Major Aromatics Hydrocarbons | | | |
| 611-14-3 | Benzene, 1-ethyl-2-methyl- | | 95 | 13.78 |
| 108-88-3 | Toluene | | 91 | 7.86 |
| 108-38-3 | Benzene, 1,3-dimethyl- | | 95 | 7.11 |
| 526-73-8 | Benzene, 1,2,3-trimethyl- | | 97 | 6.36 |
| 135-01-3 | Benzene, 1,2-diethyl- | | 97 | 4.62 |
| 874-41-9 | Benzene, 1-ethyl-2,4-dimethyl- | | 97 | 4.54 |
| 106-42-3 | p-Xylene | | 97 | 3.97 |
| 100-41-4 | Ethylbenzene | | 91 | 3.80 |
| 95-47-6 | o-Xylene | | 95 | 3.65 |
| 71-43-2 | Benzene | | 91 | 1.23 |
| 99-87-6 | p-Cymene | | 94 | 1.02 |
| 13632-94-5 | Benzene, 1,4-diethyl-2-methyl- | | 96 | 0.78 |
| 824-22-6 | 1H-Indene, 2,3-dihydro-4-methyl- | | 91 | 0.66 |
| 1074-43-7 | Benzene, 1-methyl-3-propyl- | | 94 | 0.66 |
| 1758-88-9 | Benzene, 2-ethyl-1,4-dimethyl- | | 96 | 0.61 |
| 2050-24-0 | Benzene, 1,3-diethyl-5-methyl- | | 97 | 0.49 |
| 535-77-3 | Benzene, 1-methyl-3-(1-methylethyl)- | | 97 | 0.49 |
| 103-65-1 | Benzene, propyl- | | 90 | 0.44 |
| 1595-16-0 | Benzene, 1-methyl-4-(1-methylpropyl)- | | 91 | 0.40 |
| 933-98-2 | Benzene, 1-ethyl-2,3-dimethyl- | | 95 | 0.37 |
| 1758-85-6 | Benzene, 2,4-diethyl-1-methyl- | | 95 | 0.36 |
| 488-23-3 | Benzene, 1,2,3,4-tetramethyl- | | 93 | 0.33 |
| 1074-55-1 | Benzene, 1-methyl-4-propyl- | | 93 | 0.23 |
| 768-57-3 | Benzene, (1,2-dimethyl-1-propenyl)- | | 94 | 0.22 |
| 496-11-7 | Indane | | 93 | 0.21 |
| 104-51-8 | Benzene, n-butyl- | | 91 | 0.19 |
| 108-67-8 | Mesitylene | | 97 | 0.18 |
| 6682-71-9 | 1H-Indene, 2,3-dihydro-4,7-dimethyl- | | 96 | 0.14 |
| 98-83-9 | Benzene, (1-methylethyl)- | | 91 | 0.14 |
| 95-93-2 | Benzene, 1,2,4,5-tetramethyl- | | 97 | 0.13 |
| | Trace Aromatic Hydrocarbons | | | |
| 1595-05-7 | Benzene, 1-methyl-4-butyl | | 81 | 0.091 |
| 56253-64-6 | Benzene, (2-methyl-1-butenyl)- | | 86 | 0.082 |
| 135-98-8 | Benzene, (1-methylpropyl)- | | 81 | 0.073 |
| 527-84-4 | o-Cymene | | 93 | 0.063 |
| 91-57-6 | Naphthalene, 2-methyl- | | 94 | 0.063 |
| 102-25-0 | Benzene, 1,3,5-triethyl- | | 74 | 0.056 |
| 2471-84-3 | 1H-Indene, 1-methylene- | | 90 | 0.055 |
| 4489-84-3 | Benzene, (3-methyl-2-butenyl)- | | 94 | 0.054 |
| 4920-99-4 | Benzene, 1-ethyl-3-(1-methylethyl)- | | 91 | 0.046 |
| 4706-90-5 | Benzene, 1,3-dimethyl-5-(1-methylethyl)- | | 90 | 0.045 |
| 5557-93-7 | 1-(1-methylethenyl)-2-propan-2-ylbenzene | | 60 | 0.037 |
| 54340-87-3 | 1H-Indene, 2,3-dihydro-1,4,7-trimethyl | | 93 | 0.036 |
| 28749-81-7 | 3,5-dimethylbicyclo[4.2.0]octa-1,3,5-triene | | 90 | 0.034 |
| 2809-64-5 | 1,2,3,4-Tetrahydro-5-methyl-naphthalene | | 95 | 0.034 |
| 2049-95-8 | Benzene, (1,1-dimethylpropyl)- | | 91 | 0.033 |
| 1000370-34-1 | 3,4-Dimethylcumene | | 90 | 0.026 |
| 3877-19-8 | 2-Methyl-(1,2,3,4-tetrahydronaphthalene) | | 87 | 0.026 |
| 4810-04-2 | Benzene, 1,3,5-trimethyl-2-propyl- | | 86 | 0.022 |
| 2177-47-1 | 2-Methylindene | | 81 | 0.022 |
| 14679-13-1 | 1,3,5-trimethyl-2-prop-1-en-2-yl-benzene | | 76 | 0.020 |

FIG. 32 CONT

| CAS # | Compound Name | BR# | Q | Area % |
|---|---|---|---|---|
| 55669-88-0 | 1,4-dimethyl-2-(2-methylpropyl)benzene | | 87 | 0.018 |
| 2039-89-6 | Benzene, 2-ethenyl-1,4-dimethyl- | | 94 | 0.017 |
| 27831-13-6 | Benzene, 4-ethenyl-1,2-dimethyl- | | 70 | 0.013 |
| 7524-63-2 | 2,6-dimethyltetralin | | 72 | 0.007 |
| 90-12-0 | Naphthalene, 1-methyl- | | 86 | 0.005 |
| 582-16-1 | Naphthalene, 2,7-dimethyl- | | 86 | 0.005 |
| 575-43-9 | Naphthalene, 1,6-dimethyl- | | 87 | 0.004 |
| Major Oxygenated Aromatics | | | | |
| 33223-84-6 | 2-Methylindan-2-ol | | 74 | 0.16 |
| 6148-37-4 | Furan, 4-methyl-2-propyl- | | 86 | 0.15 |
| Trace Oxygenated Aromatics | | | | |
| 2040-07-5 | Ethanone, 1-(2,4,5-trimethylphenyl)- | | 93 | 0.049 |
| 53568-05-1 | 8-hydroxytetralin-2-one | | 64 | 0.045 |
| Major n-Alkenes | | | | |
| 4050-45-7 | 2-Hexene, (E)- | | 91 | 0.59 |
| 592-47-2 | 3-Hexene | | 95 | 0.35 |
| 7688-21-3 | 2-Hexene, (Z)- | | 91 | 0.29 |
| 592-77-8 | 2-Heptene | | 95 | 0.25 |
| 627-20-3 | 2-Pentene, (Z)- | | 90 | 0.18 |
| 14686-14-7 | 3-Heptene, (E)- | | 97 | 0.14 |
| 592-41-6 | 1-Hexene | | 94 | 0.12 |
| 14850-23-8 | 4-Octene, (E)- | | 90 | 0.12 |
| Trace n-Alkenes | | | | |
| 646-04-8 | 2-Pentene, (E)- | | 90 | 0.095 |
| 2198-23-4 | 4-Nonene | | 90 | 0.068 |
| 13389-42-9 | 2-Octene, (E)- | | 94 | 0.055 |
| 14919-01-8 | 3-Octene, (E)- | | 95 | 0.054 |
| 20237-46-1 | cis-3-Nonene | | 89 | 0.040 |
| 109-67-1 | 1-Pentene | | 91 | 0.033 |
| 590-18-1 | 2-Butene, (Z)- | | 87 | 0.033 |
| 624-64-6 | 2-Butene, (E)- | | 87 | 0.033 |
| 592-76-7 | 1-Heptene | | 90 | 0.024 |
| Major Branched Alkenes | | | | |
| 74752-97-9 | 1,3-Hexadiene, 3-ethyl-2-methyl-, (Z)- | 2 | 87 | 0.17 |
| 3404-80-6 | Hexane, 2-methyl-4-methylene- | 2 | 83 | 0.13 |
| 18669-52-8 | 1,4-Hexadiene, 2,3-dimethyl- | 2 | 91 | 0.37 |
| 563-79-1 | 2-Butene, 2,3-dimethyl- | 2 | 90 | 0.12 |
| 2738-19-4 | 2-Hexene, 2-methyl- | 1 | 90 | 0.20 |
| 816-79-5 | 2-Pentene, 3-ethyl- | 1 | 91 | 0.11 |
| 922-61-2 | 2-Pentene, 3-methyl- | 1 | 95 | 0.97 |
| 674-76-0 | 2-Pentene, 4-methyl-, (E)- | 1 | 91 | 0.20 |
| 513-35-9 | 2-Butene, 2-methyl- | 1 | 90 | 0.45 |
| 563-46-2 | 2-Methyl-1-butene | 1 | 90 | 0.12 |
| Trace Branched Alkenes | | | | |
| 756-02-5 | 1,4-Pentadiene, 2,3,3-trimethyl- | 3 | 83 | 0.040 |
| 61142-36-7 | 1,3-Hexadiene, 3-ethyl-2-methyl- | 2 | 62 | 0.036 |
| 1000195-03-3 | 6,6-Dimethylhepta-2,4-diene | 2 | 90 | 0.023 |
| 16746-86-4 | 2,3-Dimethyl-1-hexene | 2 | 64 | 0.032 |
| 625-65-0 | 2-Pentene, 2,4-dimethyl- | 2 | 90 | 0.036 |
| 4485-16-9 | 3-Heptene, 4-methyl- | 1 | 90 | 0.022 |
| 13172-91-3 | 3-Heptene, 5-methyl- | 1 | 87 | 0.071 |
| 1632-16-2 | 3-Ethyl-2-hexene(c,t) | 1 | 91 | 0.033 |

FIG. 32 CONT

| CAS # | Compound Name | BR# | Q | Area % |
|---|---|---|---|---|
| 24587-27-7 | 1,3,5-Hexatriene, 3-methyl-, (Z)- | 1 | 64 | 0.004 |
| 3404-65-7 | 3-Methyl-3-hexene | 1 | 91 | 0.076 |
| 3404-55-5 | 4-Methyl-2-hexene, c&t | 1 | 91 | 0.058 |
| 926-54-5 | 1,3-Pentadiene, 2-methyl-, (E)- | 1 | 64 | 0.023 |
| 763-29-1 | 1-Pentene, 2-methyl- | 1 | 94 | 0.085 |
| 4461-48-7 | 2-Pentene, 4-methyl- | 1 | 90 | 0.051 |
| 691-38-3 | 2-Pentene, 4-methyl-, (Z)- | 1 | 87 | 0.015 |
| 760-20-3 | 1-Pentene, 3-methyl- | 1 | 90 | 0.043 |
| 691-37-2 | 1-Pentene, 4-methyl- | 1 | 68 | 0.009 |
| 563-45-1 | 1-Butene, 3-methyl- | 1 | 72 | 0.009 |
| 115-11-7 | 1-Propene, 2-methyl- | 1 | 91 | 0.024 |
| Major Cyclic Alkenes ||||| 
| 1528-22-9 | Cyclobutane, (1-methylethylidene)- | | 90 | 0.43 |
| 473-91-6 | Cyclopentene, 1,2,3-trimethyl- | | 91 | 0.39 |
| 693-89-0 | Cyclopentene, 1-methyl- | | 90 | 0.22 |
| 19780-56-4 | Methyl ethyl cyclopentene | | 95 | 0.21 |
| 591-47-9 | Cyclohexene, 4-methyl- | | 91 | 0.15 |
| 53366-54-4 | Cyclopentane, (2-methylbutylidene)- | | 64 | 0.13 |
| 1674-10-8 | Cyclohexene, 1,2-dimethyl- | | 68 | 0.13 |
| 7459-71-4 | 3,5-Dimethylcyclopentene | | 88 | 0.12 |
| 58021-63-7 | trans-3,5-Dimethylcyclohexene | | 93 | 0.12 |
| Trace Cyclic Alkenes ||||| 
| 1000164-43-6 | 7-ethylbicyclo[4.2.1]nona-2,4,7-triene | | 78 | 0.007 |
| 61142-33-4 | 1,4-dimethyl-5-propan-2-yl-cyclopentene | | 80 | 0.045 |
| 4292-04-0 | 1-Isopropylcyclohex-1-ene | | 72 | 0.043 |
| 1453-24-3 | Cyclohexene, 1-ethyl- | | 87 | 0.083 |
| 3742-42-5 | 4-Ethylcyclohexene | | 86 | 0.023 |
| 2808-80-2 | Cyclohexane, 1-methyl-4-methylene- | | 84 | 0.098 |
| 3146-38-5 | 1-Ethylcyclopentene | | 91 | 0.056 |
| 591-49-1 | Cyclohexene, 1-methyl- | | 93 | 0.032 |
| 55170-90-6 | Bicyclo[2.2.1]heptane, 2-(1-buten-3-yl)- | | 72 | 0.026 |
| 694-35-9 | Cyclopentene, 3-ethyl- | | 72 | 0.013 |
| 2567-49-1 | Cyclobutane, ethenyl- | | 87 | 0.038 |
| 3664-56-0 | 1,3,3-Trimethylcyclopropene | | 87 | 0.020 |
| 1120-62-3 | Cyclopentene, 3-methyl- | | 90 | 0.019 |
| 142-29-0 | Cyclopentene | | 80 | 0.013 |
| Major n-Alkanes ||||| 
| 110-54-3 | n-Hexane | | 91 | 3.02 |
| 111-65-9 | Octane | | 80 | 1.25 |
| 142-82-5 | Heptane | | 91 | 0.93 |
| 109-66-0 | Pentane | | 91 | 0.82 |
| 111-84-2 | Nonane | | 94 | 0.32 |
| 124-18-5 | Decane | | 95 | 0.27 |
| 106-97-8 | Butane | | 87 | 0.21 |
| Trace n-Alkanes ||||| 
| 1120-21-4 | Undecane | | 90 | 0.094 |
| 74-98-6 | Propane | | 60 | 0.001 |
| Major Branched Alkanes ||||| 
| 921-47-1 | Hexane, 2,3,4-trimethyl- | 3 | 90 | 0.11 |
| 2216-33-3 | Octane, 3-methyl- | 1 | 64 | 0.15 |
| 589-81-1 | Heptane, 3-methyl- | 1 | 81 | 0.53 |
| 589-53-7 | Heptane, 4-methyl- | 1 | 90 | 0.27 |

FIG. 32 CONT

| CAS # | Compound Name | BR# | Q | Area % |
|---|---|---|---|---|
| 592-27-8 | Heptane, 2-methyl- | 1 | 95 | 0.23 |
| 589-34-4 | Hexane, 3-methyl- | 1 | 74 | 0.99 |
| 96-14-0 | Pentane, 3-methyl- | 1 | 91 | 1.39 |
| 78-78-4 | Butane, 2-methyl- | 1 | 91 | 1.24 |
| | Trace Branched Alkanes | | | |
| 16747-30-1 | Hexane, 2,4,4-trimethyl- | 3 | 64 | 0.007 |
| 565-59-3 | Pentane, 2,3-dimethyl- | 2 | 94 | 0.081 |
| 79-29-8 | Butane, 2,3-dimethyl- | 2 | 90 | 0.099 |
| 15869-85-9 | Nonane, 3-methyl- | 1 | 76 | 0.065 |
| 15869-80-4 | Heptane, 3-ethyl- | 1 | 64 | 0.033 |
| 75-28-5 | Isobutane | 1 | 80 | 0.061 |
| | Major Cyclic Alkanes | | | |
| 96-37-7 | Cyclopentane, methyl- | | 94 | 0.80 |
| 3726-47-4 | Cyclopentane, 1-ethyl-3-methyl- | | 74 | 0.69 |
| 2453-00-1 | Cyclopentane, 1,3-dimethyl- | | 94 | 0.37 |
| 1638-26-2 | Cyclopentane, 1,1-dimethyl- | | 64 | 0.27 |
| 2452-99-5 | Cyclopentane, 1,2-dimethyl- | | 93 | 0.26 |
| 108-87-2 | Cyclohexane, methyl- | | 95 | 0.25 |
| 1640-89-7 | Cyclopentane, ethyl- | | 94 | 0.23 |
| 6876-23-9 | Cyclohexane, 1,2-dimethyl-, trans- | | 60 | 0.19 |
| 930-89-2 | Cyclopentane, 1-ethyl-2-methyl-, cis- | | 97 | 0.14 |
| 4850-28-6 | 1,2,4-Trimethylcyclopentane, cis, trans | | 91 | 0.14 |
| 110-82-7 | Cyclohexane | | 90 | 0.12 |
| 4516-69-2 | Cyclopentane, 1,1,3-trimethyl- | | 83 | 0.11 |
| | Trace Cyclic Alkanes | | | |
| 66660-39-7 | trans, cis-2-Ethylbicyclo[4.4.0]decane | | 76 | 0.024 |
| 3741-00-2 | Cyclopentane, pentyl- | | 72 | 0.043 |
| 1678-93-9 | Cyclohexane, butyl- | | 64 | 0.072 |
| 18968-23-5 | (1S,3R,6R)-3,7,7-trimethylnorcarane | | 81 | 0.082 |
| 28588-55-8 | Pentalene, octahydro-2,5-dimethyl- | | 72 | 0.043 |
| 61142-68-5 | Cyclopentane, 1-hexyl-3-methyl- | | 64 | 0.096 |
| 7045-67-2 | Cyclohexane, 2-ethyl-1,3-dimethyl- | | 60 | 0.033 |
| 2040-95-1 | Cyclopentane, butyl- | | 64 | 0.086 |
| 7667-55-2 | 1,cis-2,trans-3-Trimethylcyclohexane | | 81 | 0.047 |
| 3728-54-9 | Cyclohexane, 1-ethyl-3-methyl- | | 72 | 0.035 |
| 694-72-4 | Pentalene, octahydro- | | 72 | 0.045 |
| 2207-01-4 | Cyclohexane, 1,2-dimethyl-, cis- | | 76 | 0.027 |
| 1000142-17-5 | Bicyclo[3.1.0]hexane, 1,5-dimethyl- | | 91 | 0.047 |
| 2613-65-2 | Cyclopentane, 1-ethyl-3-methyl-, trans- | | 87 | 0.042 |
| 16747-50-5 | Cyclopentane, 1-ethyl-1-methyl- | | 83 | 0.081 |
| 638-04-0 | Cyclohexane, 1,3-dimethyl-, cis- | | 87 | 0.081 |
| 287-92-3 | Cyclopentane | | 83 | 0.084 |
| | Major Oxygenates | | | |
| 19550-30-2 | 1-Butanol, 2,3-dimethyl- | | 64 | 1.63 |
| 112-58-3 | Hexane, 1,1'-oxybis- | | 64 | 0.76 |
| 4313-03-5 | 2,4-Heptadienal, (E,E)- | | 64 | 0.26 |
| 107-87-9 | 2-Pentanone | | 87 | 0.18 |
| 60-29-7 | Ethyl ether | | 91 | 0.12 |
| | Trace Oxygenates | | | |
| 4485-09-0 | 4-Nonanone | | 87 | 0.067 |
| 42452-48-2 | 2,4-Heptadienal, 2,4-dimethyl- | | 80 | 0.058 |
| 85136-08-9 | 2,6-Heptadienal, 2,4-dimethyl- | | 81 | 0.030 |

FIG. 32 CONT

| CAS # | Compound Name | BR# | Q | Area % |
|---|---|---|---|---|
| 15726-15-5 | 4-Heptanone, 3-methyl- | | 87 | 0.084 |
| 1000109-76-5 | (R,S)-2-Propyl-5-oxohexanal | | 72 | 0.041 |
| 55449-71-3 | OCTAHYDROPENTALENO(1,2-B)OXIRENE | | 64 | 0.021 |
| 1000302-74-9 | 2,5-Dimethylhex-5-en-3-yn-2-ol | | 72 | 0.056 |
| 19550-73-3 | trans-3,4-Dimethylcyclopentanone | | 64 | 0.026 |
| 565-61-7 | 2-Pentanone, 3-methyl- | | 80 | 0.039 |
| 105-57-7 | Ethane, 1,1-diethoxy- | | 64 | 0.018 |
| 628-81-9 | Butane, 1-ethoxy- | | 86 | 0.034 |
| 1757-42-2 | Cyclopentanone, 3-methyl- | | 83 | 0.022 |
| 64504-73-0 | 3-(2-Cyclopenten-1-yl)propanal | | 64 | 0.007 |
| 78-93-3 | 2-Butanone | | 80 | 0.064 |
| 123-72-8 | Butanal | | 94 | 0.040 |
| 64-17-5 | Ethanol | | 80 | 0.013 |

FIG. 32 CONT

| CAS # | Compound Name | BR# | Q | Area % |
|---|---|---|---|---|
| Major Aromatics Hydrocarbons | | | | |
| 108-38-3 | Benzene, 1,3-dimethyl- | | 95 | 10.82 |
| 611-14-3 | Benzene, 1-ethyl-2-methyl- | | 95 | 9.41 |
| 108-88-3 | Toluene | | 91 | 7.83 |
| 106-42-3 | p-Xylene | | 97 | 7.49 |
| 526-73-8 | Benzene, 1,2,3-trimethyl- | | 97 | 6.12 |
| 874-41-9 | Benzene, 1-ethyl-2,4-dimethyl- | | 97 | 5.10 |
| 135-01-3 | Benzene, 1,2-diethyl- | | 97 | 4.55 |
| 622-96-8 | Benzene, 1-ethyl-4-methyl- | | 91 | 4.34 |
| 71-43-2 | Benzene | | 91 | 1.18 |
| 95-93-2 | Benzene, 1,2,4,5-tetramethyl- | | 95 | 1.09 |
| 13632-94-5 | Benzene, 1,4-diethyl-2-methyl- | | 96 | 0.75 |
| 824-22-6 | 1H-Indene, 2,3-dihydro-4-methyl- | | 94 | 0.65 |
| 1074-17-5 | Benzene, 1-methyl-2-propyl- | | 94 | 0.64 |
| 1758-85-6 | Benzene, 2,4-diethyl-1-methyl- | | 97 | 0.50 |
| 103-65-1 | Benzene, propyl- | | 90 | 0.42 |
| 1595-16-0 | Benzene, 1-methyl-4-(1-methylpropyl)- | | 94 | 0.42 |
| 108-67-8 | Mesitylene | | 97 | 0.42 |
| 6682-71-9 | 1H-Indene, 2,3-dihydro-4,7-dimethyl- | | 97 | 0.38 |
| 2050-24-0 | Benzene, 1,3-diethyl-5-methyl- | | 97 | 0.33 |
| 527-53-7 | Benzene, 1,2,3,5-tetramethyl- | | 94 | 0.33 |
| 535-77-3 | Benzene, 1-methyl-3-(1-methylethyl)- | | 97 | 0.25 |
| 1074-55-1 | Benzene, 1-methyl-4-propyl- | | 90 | 0.21 |
| 496-11-7 | Indane | | 90 | 0.21 |
| 99-87-6 | p-Cymene | | 97 | 0.19 |
| 104-51-8 | Benzene, n-butyl- | | 91 | 0.18 |
| 98-82-8 | Benzene, (1-methylethyl)- | | 90 | 0.14 |
| 1595-05-7 | Benzene, 1-methyl-4-butyl | | 90 | 0.14 |
| Trace Aromatic Hydrocarbons | | | | |
| 5161-04-6 | Benzene, 1-methyl-4-(2-methylpropyl)- | | 64 | 0.091 |
| 56147-63-8 | 2-Ethyl-2,3-dihydro-1H-indene | | 83 | 0.088 |
| 135-98-8 | Benzene, (1-methylpropyl)- | | 87 | 0.077 |
| 4706-90-5 | Benzene, 1,3-dimethyl-5-(1-methylethyl)- | | 91 | 0.067 |
| 2870-04-4 | Benzene, 2-ethyl-1,3-dimethyl- | | 95 | 0.066 |
| 91-57-6 | Naphthalene, 2-methyl- | | 91 | 0.061 |
| 91-20-3 | Naphthalene | | 93 | 0.054 |
| 877-44-1 | Benzene, 1,2,4-triethyl- | | 91 | 0.051 |
| 4920-99-4 | Benzene, 1-ethyl-3-(1-methylethyl)- | | 91 | 0.046 |
| 1076-61-5 | 6,7-dimethyltetralin | | 86 | 0.037 |
| 527-84-4 | o-Cymene | | 87 | 0.035 |
| 1680-51-9 | 6-Methyl-(1,2,3,4-tetrahydronaphthalene) | | 98 | 0.033 |
| 40650-41-7 | 1H-Indene, 2,3-dihydro-1,1,3-trimethyl- | | 94 | 0.033 |
| 488-23-3 | Benzene, 1,2,3,4-tetramethyl- | | 97 | 0.032 |
| 2234-20-0 | 2,4-Dimethylstyrene | | 96 | 0.031 |
| 2039-89-6 | Benzene, 2-ethenyl-1,4-dimethyl- | | 87 | 0.029 |
| 1483-60-9 | Benzene, 1,3-dimethyl-4-(1-methylpropyl) | | 72 | 0.025 |
| 3877-19-8 | 2-Methyl-(1,2,3,4-tetrahydronaphthalene) | | 93 | 0.024 |
| 102-25-0 | Benzene, 1,3,5-triethyl- | | 90 | 0.024 |
| 2177-47-1 | 2-Methylindene | | 94 | 0.023 |
| 1129-29-9 | 1-(1-methylethenyl)-3-propan-2-ylbenzene | | 78 | 0.020 |
| 55669-88-0 | 1,4-dimethyl-2-(2-methylpropyl)benzene | | 83 | 0.016 |
| 769-57-3 | Benzene, (1,2-dimethyl-1-propenyl)- | | 91 | 0.013 |

FIG. 33 CONT

| CAS # | Compound Name | BR# | Q | Area % |
|---|---|---|---|---|
| 17057-82-8 | 1H-Indene, 2,3-dihydro-1,2-dimethyl- | | 81 | 0.011 |
| 4810-04-2 | Benzene, 1,3,5-trimethyl-2-propyl- | | 91 | 0.009 |
| 13065-07-1 | 2,7-dimethyltetralin | | 93 | 0.007 |
| 90-12-0 | Naphthalene, 1-methyl- | | 80 | 0.006 |
| 6974-97-6 | 1H-Indene, 4,7-dimethyl- | | 72 | 0.005 |
| 581-42-0 | Naphthalene, 2,6-dimethyl- | | 86 | 0.004 |
| 939-27-5 | Naphthalene, 2-ethyl- | | 80 | 0.003 |
| | Major Oxygenated Aromatics | | | |
| 6148-37-4 | Furan, 4-methyl-2-propyl- | | 86 | 0.14 |
| | Major n-Alkenes | | | |
| 4050-45-7 | 3-Hexene, (E)- | | 91 | 0.54 |
| 592-43-8 | 2-Hexene | | 91 | 0.28 |
| 7642-09-3 | 3-Hexene, (Z)- | | 85 | 0.23 |
| 627-20-3 | 2-Pentene, (Z)- | | 91 | 0.16 |
| 592-41-6 | 1-Hexene | | 91 | 0.11 |
| 14686-14-7 | 3-Heptene, (E)- | | 95 | 0.11 |
| 592-77-8 | 2-Heptene | | 95 | 0.11 |
| 14850-23-8 | 4-Octene, (E)- | | 93 | 0.10 |
| | Trace n-Alkenes | | | |
| 646-04-8 | 2-Pentene, (E)- | | 90 | 0.088 |
| 592-47-2 | 3-Hexene | | 85 | 0.083 |
| 19689-19-1 | 5-Decene | | 62 | 0.063 |
| 2198-23-4 | 4-Nonene | | 90 | 0.060 |
| 14919-01-8 | 3-Octene, (E)- | | 93 | 0.049 |
| 111-67-1 | 2-Octene | | 85 | 0.045 |
| 20063-77-8 | 3-Nonene | | 88 | 0.043 |
| 109-67-1 | 1-Pentene | | 76 | 0.032 |
| 590-18-1 | 2-Butene, (Z)- | | 81 | 0.031 |
| 624-64-6 | 2-Butene, (E)- | | 87 | 0.031 |
| 592-76-7 | 1-Heptene | | 87 | 0.022 |
| 592-46-1 | 2,4-Hexadiene | | 64 | 0.022 |
| | Major Branched Alkenes | | | |
| 3404-79-3 | 2-Hexene, 3,3-dimethyl- | 2 | 80 | 0.12 |
| 3404-83-7 | 3-Methyl-3-hexene | 1 | 86 | 0.19 |
| 922-61-2 | 2-Pentene, 3-methyl- | 1 | 95 | 0.88 |
| 513-35-9 | 2-Butene, 2-methyl- | 1 | 90 | 0.45 |
| 563-46-2 | 3-Methyl-1-butene | 1 | 90 | 0.12 |
| | Trace Branched Alkenes | | | |
| 74779-65-0 | 1,3-Heptadiene, 2,3-dimethyl- | 2 | 80 | 0.054 |
| 74752-92-9 | 1,3-Hexadiene, 3-ethyl-2-methyl-, (Z)- | 2 | 87 | 0.047 |
| 4634-87-1 | 2,4-Heptadiene, 2,6-dimethyl- | 2 | 80 | 0.054 |
| 1000195-03-3 | 6,6-Dimethylhepta-2,4-diene | 3 | 83 | 0.025 |
| 19780-68-8 | 3-Ethyl-4-methyl-2-pentene | 2 | 90 | 0.062 |
| 3404-78-2 | 2-Hexene, 2,5-dimethyl- | 2 | 72 | 0.027 |
| 10574-37-5 | 2-Pentene, 2,3-dimethyl- | 2 | 64 | 0.021 |
| 4914-92-5 | 2-Pentene, 3,4-dimethyl-, (E)- | 2 | 74 | 0.046 |
| 2213-32-3 | 1-Pentene, 2,4-dimethyl- | 2 | 70 | 0.014 |
| 563-79-1 | 2-Butene, 2,3-dimethyl- | 2 | 91 | 0.085 |
| 3404-61-3 | 1-Hexene, 3-methyl- | 1 | 60 | 0.028 |
| 4485-16-9 | 3-Heptene, 4-methyl- | 1 | 87 | 0.018 |
| 1632-16-2 | 3-Ethyl-2-hexene(c,t) | 1 | 91 | 0.027 |
| 24587-27-7 | 1,3,5-Hexatriene, 3-methyl-, (Z)- | 1 | 64 | 0.004 |

FIG. 33 CONT

| CAS # | Compound Name | BR# | Q | Area % |
|---|---|---|---|---|
| 4914-89-0 | 3-Hexene, 3-methyl-, (Z)- | 1 | 91 | 0.071 |
| 816-79-5 | 2-Pentene, 3-ethyl- | 1 | 91 | 0.098 |
| 3404-55-5 | 4-Methyl-2-hexene, c&t | 1 | 95 | 0.055 |
| 15840-60-5 | 3-Hexene, 2-methyl-, (Z)- | 1 | 80 | 0.023 |
| 763-29-1 | 1-Pentene, 2-methyl- | 1 | 91 | 0.085 |
| 625-27-4 | 2-Pentene, 2-methyl- | 1 | 80 | 0.051 |
| 691-38-3 | 2-Pentene, 4-methyl-, (Z)- | 1 | 87 | 0.014 |
| 674-76-0 | 2-Pentene, 4-methyl-, (E)- | 1 | 80 | 0.031 |
| 760-20-3 | 1-Pentene, 3-methyl- | 1 | 93 | 0.040 |
| 115-11-7 | 1-Propene, 2-methyl- | 1 | 93 | 0.023 |
| Major Cyclic Alkenes | | | | |
| 19780-56-4 | Methyl ethyl cyclopentene | | 95 | 0.53 |
| 2808-76-6 | 1,3-Dimethyl-1-cyclohexene | | 91 | 0.43 |
| 473-91-6 | Cyclopentene, 1,2,3-trimethyl- | | 91 | 0.40 |
| 76089-59-3 | 1,2,3,4-Tetramethylfulvene | | 94 | 0.35 |
| 7459-71-4 | 3,5-Dimethylcyclopentene | | 83 | 0.31 |
| 1528-22-9 | Cyclobutane, (1-methylethylidene)- | | 90 | 0.24 |
| 693-89-0 | Cyclopentene, 1-methyl- | | 87 | 0.21 |
| 1674-10-8 | Cyclohexene, 1,2-dimethyl- | | 91 | 0.12 |
| 591-49-1 | Cyclohexene, 1-methyl- | | 84 | 0.10 |
| Trace Cyclic Alkenes | | | | |
| 3256-65-3 | Cyclohexene, 3-methyl-6-(1-methylethyl)- | | 64 | 0.078 |
| 503-45-7 | Cyclohexene, 3,3,5-trimethyl- | | 74 | 0.026 |
| 4292-04-0 | 1-Isopropylcyclohex-1-ene | | 64 | 0.034 |
| 1453-24-3 | Cyclohexene, 1-ethyl- | | 81 | 0.072 |
| 3742-42-5 | 4-Ethylcyclohexene | | 87 | 0.012 |
| 1759-64-4 | 1,6-dimethylcyclohexene | | 93 | 0.056 |
| 2808-80-2 | Cyclohexane, 1-methyl-4-methylene- | | 91 | 0.093 |
| 1462-07-3 | Cyclopentene, 1-(1-methylethyl)- | | 80 | 0.009 |
| 97797-37-4 | 1-Ethyl-5-methylcyclopentene | | 84 | 0.031 |
| 2146-38-5 | 1-Ethylcyclopentene | | 90 | 0.055 |
| 591-47-9 | Cyclohexene, 4-methyl- | | 81 | 0.075 |
| 694-35-9 | Cyclopentene, 3-ethyl- | | 64 | 0.012 |
| 41158-41-2 | Cyclopentane, 1-methyl-2-methylene- | | 70 | 0.005 |
| 2397-49-1 | Cyclobutane, ethenyl- | | 87 | 0.033 |
| 16491-15-9 | Cyclopentene, 1,5-dimethyl- | | 63 | 0.019 |
| 4372-94-5 | Cyclopropane, 1,1-dimethyl-2-methylene- | | 87 | 0.019 |
| 1120-62-3 | Cyclopentene, 3-methyl- | | 87 | 0.037 |
| 142-29-0 | Cyclopentene | | 83 | 0.012 |
| Major n-Alkanes | | | | |
| 110-54-3 | n-Hexane | | 91 | 2.71 |
| 111-65-9 | Octane | | 80 | 1.13 |
| 142-82-5 | Heptane | | 95 | 0.85 |
| 109-66-0 | Pentane | | 91 | 0.77 |
| 111-84-2 | Nonane | | 95 | 0.39 |
| 124-18-5 | Decane | | 94 | 0.24 |
| 106-97-8 | Butane | | 87 | 0.19 |
| Trace n-Alkanes | | | | |
| 1120-21-4 | Undecane | | 91 | 0.085 |
| Major Branched Alkanes | | | | |
| 5911-04-6 | Nonane, 3-methyl- | 1 | 76 | 0.12 |
| 2216-33-3 | Octane, 3-methyl- | 1 | 72 | 0.15 |

FIG. 33 CONT

| CAS # | Compound Name | BR# | Q | Area % |
|---|---|---|---|---|
| 589-53-7 | Heptane, 4-methyl- | 1 | 90 | 0.36 |
| 592-27-8 | Heptane, 2-methyl- | 1 | 95 | 0.23 |
| 589-34-4 | Hexane, 3-methyl- | 1 | 74 | 0.98 |
| 96-14-0 | Pentane, 3-methyl- | 1 | 91 | 1.34 |
| 107-83-5 | Pentane, 2-methyl- | 1 | 64 | 1.62 |
| 78-78-4 | Butane, 2-methyl- | 1 | 91 | 1.34 |
| Trace Branched Alkanes ||||||
| 565-59-3 | Pentane, 2,3-dimethyl- | 2 | 83 | 0.082 |
| 79-29-8 | Butane, 2,3-dimethyl- | 2 | 90 | 0.099 |
| 617-78-7 | Pentane, 3-ethyl | 1 | 64 | 0.087 |
| 75-28-5 | Isobutane | 1 | 64 | 0.080 |
| Major Cyclic Alkanes ||||||
| 96-37-7 | Cyclopentane, methyl- | | 91 | 0.78 |
| 3726-47-4 | Cyclopentane, 1-ethyl-3-methyl- | | 83 | 0.63 |
| 2532-58-3 | Cyclopentane, 1,3-dimethyl-, cis- | | 90 | 0.37 |
| 2452-99-5 | Cyclopentane, 1,2-dimethyl- | | 95 | 0.28 |
| 2453-00-1 | Cyclopentane, 1,3-dimethyl- | | 94 | 0.24 |
| 1640-89-7 | Cyclopentane, ethyl- | | 95 | 0.23 |
| 108-87-2 | Cyclohexane, methyl- | | 94 | 0.22 |
| 4127-45-1 | Cyclopropane, 1,1,2-trimethyl- | | 91 | 0.19 |
| 2207-03-6 | Cyclohexane, 1,3-dimethyl-, trans- | | 60 | 0.18 |
| 2815-58-9 | Cyclopentane, 1,2,4-trimethyl- | | 91 | 0.14 |
| 930-89-2 | Cyclopentane, 1-ethyl-2-methyl-, cis- | | 97 | 0.14 |
| 291-64-5 | Cycloheptane | | 86 | 0.11 |
| 61142-68-5 | Cyclopentane, 1-hexyl-3-methyl- | | 64 | 0.11 |
| 110-82-7 | Cyclohexane | | 93 | 0.11 |
| Trace Cyclic Alkanes ||||||
| 2882-98-6 | Cyclopentane, nonyl- | | 64 | 0.038 |
| 1678-93-9 | Cyclohexane, butyl- | | 68 | 0.040 |
| 2040-95-1 | Cyclopentane, butyl- | | 89 | 0.059 |
| 766-53-0 | Bicyclo[2.2.2]octane, 2-methyl- | | 68 | 0.069 |
| 7667-55-2 | 1,cis-2,trans-3-Trimethylcyclohexane | | 68 | 0.037 |
| 3728-54-9 | Cyclohexane, 1-ethyl-2-methyl- | | 72 | 0.025 |
| 2307-01-4 | Cyclohexane, 1,2-dimethyl-, cis- | | 64 | 0.025 |
| 3728-46-3 | Cyclopentane, 1-ethyl-2-methyl- | | 83 | 0.039 |
| 18747-50-5 | Cyclopentane, 1-ethyl-1-methyl- | | 83 | 0.081 |
| 589-90-2 | Cyclohexane, 1,4-dimethyl- | | 81 | 0.083 |
| 2613-69-6 | (1R,2s,3S)-1,2,3-Trimethylcyclopentane | | 60 | 0.030 |
| 1678-91-7 | Cyclohexane, ethyl- | | 70 | 0.031 |
| 598-61-8 | Cyclobutane, methyl- | | 80 | 0.085 |
| Major Oxygenates ||||||
| 64-17-5 | Ethanol | | 91 | 2.68 |
| 74421-17-3 | Hexane, 1-(hexyloxy)-2-methyl- | | 72 | 0.76 |
| 107-87-9 | 2-Pentanone | | 87 | 0.15 |
| 1000190-91-3 | (1,2,3-Trimethyl-cyclopent-2-enyl)-methanol | | 64 | 0.15 |
| 60-29-7 | Ethyl ether | | 94 | 0.11 |
| 1000381-81-5 | Diglycolic acid, isohexyl 2-methylbutyl ester | | 78 | 0.10 |
| Trace Oxygenates ||||||
| 4485-09-0 | 4-Nonanone | | 74 | 0.063 |
| 589-63-9 | 4-Octanone | | 70 | 0.018 |
| 42482-48-2 | 2,4-Heptadienal, 2,4-dimethyl- | | 80 | 0.059 |
| 15726-15-5 | 4-Heptanone, 3-methyl- | | 76 | 0.069 |

FIG. 33 CONT

| CAS # | Compound Name | BR# | Q | Area % |
|---|---|---|---|---|
| 693-54-9 | 2-Decanone | | 64 | 0.028 |
| 110453-78-6 | (S)-(+)-6-Methyl-1-octanol | | 64 | 0.036 |
| 4313-03-5 | 2,4-Heptadienal, (E,E)- | | 72 | 0.037 |
| 565-61-7 | 2-Pentanone, 3-methyl- | | 86 | 0.035 |
| 628-81-9 | Butane, 1-ethoxy- | | 72 | 0.030 |
| 96-22-0 | 3-Pentanone | | 64 | 0.012 |
| 78-93-3 | 2-Butanone | | 80 | 0.059 |
| 123-72-8 | Butanal | | 87 | 0.037 |

FIG. 33 CONT

| Summary | Total | Known | Major | Trace | Ave Carbon # |
|---|---|---|---|---|---|
| Peaks: | 332 | 222 | 83 | 139 | 8.21 |
| Area: | 729947327 | 97.2% | 92.5% | 4.7% | |

| Compound Type | Total Known | | Major Components | | Average Carbon # |
|---|---|---|---|---|---|
| | # Peaks | % Area | # Peaks | % Area | |
| Aromatics (Total): | 88 | 75.96 | 37 | 74.38 | 8.73 |
| Oxygenated: | 1 | 0.05 | 0 | 0.00 | 8.00 |
| Alkenes (Total): | 82 | 4.98 | 16 | 2.91 | 6.74 |
| Straight: | 11 | 0.48 | 1 | 0.11 | 5.48 |
| Branched: | 34 | 2.39 | 8 | 1.53 | 6.39 |
| Cyclic: | 37 | 2.11 | 7 | 1.26 | 7.44 |
| Alkanes (Total): | 40 | 12.31 | 27 | 11.54 | 6.41 |
| Straight: | 4 | 1.51 | 4 | 1.51 | 5.69 |
| Branched: | 12 | 6.96 | 9 | 6.72 | 6.15 |
| Cyclic: | 24 | 3.84 | 14 | 3.31 | 7.17 |
| Oxygenated (Other): | 10 | 3.91 | 3 | 3.72 | 5.54 |

| CAS # | Compound Name | BR# | Q | Area % |
|---|---|---|---|---|
| Major Aromatics Hydrocarbons ||||||
| 95-47-6 | o-Xylene | | 95 | 12.64 |
| 611-14-3 | Benzene, 1-ethyl-2-methyl- | | 95 | 11.46 |
| 108-88-3 | Toluene | | 91 | 9.32 |
| 108-67-8 | Mesitylene | | 97 | 8.01 |
| 874-41-9 | Benzene, 1-ethyl-2,4-dimethyl- | | 97 | 5.44 |
| 95-63-6 | Benzene, 1,2,4-trimethyl- | | 91 | 5.23 |
| 100-41-4 | Ethylbenzene | | 91 | 4.15 |
| 106-42-3 | p-Xylene | | 97 | 4.13 |
| 135-01-3 | Benzene, 1,2-diethyl- | | 97 | 3.20 |
| 141-93-5 | Benzene, 1,3-diethyl- | | 97 | 2.03 |
| 99-87-6 | p-Cymene | | 97 | 1.50 |
| 71-43-2 | Benzene | | 91 | 1.07 |
| 13632-94-5 | Benzene, 1,4-diethyl-2-methyl- | | 96 | 0.91 |
| 1074-43-7 | Benzene, 1-methyl-3-propyl- | | 94 | 0.84 |
| 824-22-6 | 1H-Indene, 2,3-dihydro-4-methyl- | | 94 | 0.78 |
| 1758-88-9 | Benzene, 2-ethyl-1,4-dimethyl- | | 96 | 0.57 |
| 1758-85-6 | Benzene, 2,4-diethyl-1-methyl- | | 95 | 0.53 |
| 527-84-4 | o-Cymene | | 95 | 0.42 |
| 95-93-2 | Benzene, 1,2,4,5-tetramethyl- | | 94 | 0.38 |
| 103-65-1 | Benzene, propyl- | | 90 | 0.38 |
| 2050-24-0 | Benzene, 1,3-diethyl-5-methyl- | | 97 | 0.37 |
| 17059-48-2 | 1H-Indene, 2,3-dihydro-1,6-dimethyl- | | 93 | 0.27 |
| 33172-84-2 | Benzene, (1-methyl-1-butenyl)- | | 97 | 0.26 |
| 496-11-7 | Indane | | 87 | 0.20 |
| 535-77-3 | Benzene, 1-methyl-3-(1-methylethyl)- | | 95 | 0.19 |
| 2049-95-8 | Benzene, (1,1-dimethylpropyl)- | | 87 | 0.18 |
| 98-82-8 | Benzene, (1-methylethyl)- | | 91 | 0.16 |
| 527-53-7 | Benzene, 1,2,3,5-tetramethyl- | | 97 | 0.11 |
| 1595-05-7 | Benzene, 1-methyl-4-butyl | | 87 | 0.10 |
| Trace Aromatic Hydrocarbons ||||||
| 91-57-6 | Naphthalene, 2-methyl- | | 95 | 0.088 |
| 1595-16-0 | Benzene, 1-methyl-4-(1-methylpropyl)- | | 91 | 0.080 |
| 5161-04-6 | Benzene, 1-methyl-4-(2-methylpropyl)- | | 64 | 0.075 |
| 1074-55-1 | Benzene, 1-methyl-4-propyl- | | 93 | 0.074 |
| 91-20-3 | Naphthalene | | 94 | 0.062 |
| 99-62-7 | Benzene, 1,3-bis(1-methylethyl)- | | 81 | 0.057 |
| 104-51-8 | Benzene, n-butyl- | | 86 | 0.048 |
| 4706-89-2 | Benzene, 2,4-dimethyl-1-(1-methylethyl)- | | 91 | 0.044 |
| 6682-71-9 | 1H-Indene, 2,3-dihydro-4,7-dimethyl- | | 91 | 0.044 |
| 1139-29-9 | 1-(1-methylethyl)-3-propan-2-ylbenzene | | 60 | 0.044 |
| 1680-51-9 | 6-Methyl-(1,2,3,4-tetrahydronaphthalene) | | 96 | 0.040 |
| 100-80-1 | Benzene, 1-ethenyl-3-methyl- | | 78 | 0.037 |
| 4920-99-4 | Benzene, 1-ethenyl-3-(1-methylethyl)- | | 87 | 0.035 |
| 40650-41-7 | 1H-Indene, 2,3-dihydro-1,1,5-trimethyl- | | 95 | 0.032 |
| 488-23-3 | Benzene, 1,2,3,4-tetramethyl- | | 97 | 0.029 |
| 102-25-0 | Benzene, 1,3,5-triethyl- | | 80 | 0.028 |
| 3877-19-8 | 2-Methyl-(1,2,3,4-tetrahydronaphthalene) | | 87 | 0.025 |
| 4175-54-6 | 1,4-dimethyltetralin | | 70 | 0.024 |
| 54410-73-2 | Benzene, 1,2-diethyl-3,4-dimethyl- | | 87 | 0.024 |
| 3333-13-9 | Benzene, 1-methyl-4-(2-propenyl)- | | 83 | 0.022 |
| 2039-89-6 | Benzene, 2-ethenyl-1,4-dimethyl- | | 95 | 0.022 |

FIG. 34 CONT

| CAS # | Compound Name | BR# | Q | Area % |
|---|---|---|---|---|
| 4706-90-5 | Benzene, 1,3-dimethyl-5-(1-methylethyl)- | | 91 | 0.021 |
| 1483-60-9 | Benzene, 1,3-dimethyl-4-(1-methylpropyl) | | 72 | 0.018 |
| 95-13-6 | Indene | | 86 | 0.017 |
| 15677-15-3 | 1,1a,6,6a-tetrahydrocyclopropa[a]indene | | 93 | 0.016 |
| 7525-62-4 | Benzene, 1-ethenyl-3-ethyl- | | 78 | 0.013 |
| 6974-97-6 | 1H-Indene, 4,7-dimethyl- | | 64 | 0.011 |
| 97664-18-1 | 1-Methyl-4-(1-methyl-2-propenyl)benzene | | 91 | 0.010 |
| 7399-49-7 | o-Isopropenyltoluene | | 93 | 0.010 |
| 1587-04-8 | Benzene, 1-methyl-2-(2-propenyl)- | | 64 | 0.009 |
| 582-16-1 | Naphthalene, 2,7-dimethyl- | | 95 | 0.006 |
| 54340-85-1 | Benzene, 1-(2-butenyl)-2,3-dimethyl- | | 87 | 0.005 |
| 21693-54-9 | 5,7-dimethyltetralin | | 80 | 0.005 |
| 581-42-0 | Naphthalene, 2,6-dimethyl- | | 90 | 0.004 |
| 42775-75-7 | Naphthalene, 5-ethyl-1,2,3,4-tetrahydro- | | 72 | 0.003 |
| | Trace Oxygenated Aromatics | | | |
| 6148-37-4 | Furan, 4-methyl-2-propyl- | | 72 | 0.049 |
| | Major n-Alkenes | | | |
| 627-20-3 | 2-Pentene, (Z)- | | 90 | 0.11 |
| | Trace n-Alkenes | | | |
| 4050-45-7 | 2-Hexene, (E)- | | 91 | 0.097 |
| 592-43-8 | 2-Hexene | | 90 | 0.063 |
| 646-04-8 | 2-Pentene, (E)- | | 90 | 0.059 |
| 7642-09-3 | 3-Hexene, (Z)- | | 94 | 0.042 |
| 592-77-8 | 2-Heptene | | 93 | 0.025 |
| 109-67-1 | 1-Pentene | | 76 | 0.022 |
| 590-18-1 | 2-Butene, (Z)- | | 76 | 0.021 |
| 624-64-6 | 2-Butene, (E)- | | 60 | 0.021 |
| 592-41-6 | 1-Hexene | | 87 | 0.019 |
| | Major Branched Alkenes | | | |
| 1515-79-3 | 5,5-Dimethyl-1,3-hexadiene | 2 | 90 | 0.23 |
| 563-79-1 | 2-Butene, 2,3-dimethyl- | 2 | 91 | 0.15 |
| 2738-19-4 | 2-Hexene, 2-methyl- | 1 | 91 | 0.12 |
| 922-61-2 | 2-Pentene, 3-methyl- | 1 | 90 | 0.38 |
| 625-27-4 | 2-Pentene, 2-methyl- | 1 | 91 | 0.27 |
| 513-35-9 | 2-Butene, 2-methyl- | 1 | 90 | 0.45 |
| 563-46-2 | 2-Methyl-1-butene | 1 | 90 | 0.14 |
| | Trace Branched Alkenes | | | |
| 74421-05-9 | 2,4-Heptadiene, 2,4-dimethyl- | 2 | 64 | 0.043 |
| 74752-97-9 | 1,3-Hexadiene, 3-ethyl-2-methyl-, (Z)- | 2 | 87 | 0.093 |
| 1000195-03-3 | 6,6-Dimethylhepta-2,4-diene | 2 | 86 | 0.067 |
| 3404-78-2 | 2-Hexene, 2,5-dimethyl- | 2 | 90 | 0.028 |
| 7145-20-2 | 2-Hexene, 2,3-dimethyl- | 2 | 62 | 0.027 |
| 10374-37-5 | 2-Pentene, 2,3-dimethyl- | 2 | 60 | 0.019 |
| 4914-91-4 | 2-Pentene, 3,4-dimethyl-, (Z)- | 2 | 87 | 0.037 |
| 2213-32-3 | 1-Pentene, 2,4-dimethyl- | 2 | 81 | 0.017 |
| 4485-16-9 | 3-Heptene, 4-methyl- | 1 | 72 | 0.011 |
| 19264-50-7 | 1,3,5-Hexatriene, 2-methyl- | 1 | 72 | 0.004 |
| 816-79-5 | 2-Pentene, 3-ethyl- | 1 | 87 | 0.029 |
| 4914-89-0 | 3-Hexene, 3-methyl-, (Z)- | 1 | 91 | 0.048 |
| 3404-65-7 | 3-Methyl-3-hexene | 1 | 90 | 0.032 |
| 3683-22-5 | 2-Hexene, 4-methyl-, (E)- | 1 | 91 | 0.042 |
| 692-24-0 | 3-Hexene, 2-methyl-, (E)- | 1 | 90 | 0.020 |

FIG. 34 CONT

| CAS # | Compound Name | BR# | Q | Area % |
|---|---|---|---|---|
| 763-29-1 | 1-Pentene, 2-methyl- | 1 | 91 | 0.088 |
| 4461-48-7 | 2-Pentene, 4-methyl- | 1 | 87 | 0.018 |
| 760-20-3 | 1-Pentene, 3-methyl- | 1 | 87 | 0.018 |
| 115-11-7 | 1-Propene, 2-methyl- | 1 | 91 | 0.024 |
| Major Cyclic Alkenes | | | | |
| 473-91-6 | Cyclopentene, 1,2,3-trimethyl- | | 91 | 0.51 |
| 1528-22-9 | Cyclobutane, (1-methylethylidene)- | | 90 | 0.27 |
| 7459-71-4 | 3,5-Dimethylcyclopentene | | 80 | 0.20 |
| 19037-72-0 | Cyclopentene, 4,4-dimethyl- | | 72 | 0.17 |
| 693-89-0 | Cyclopentene, 1-methyl- | | 87 | 0.17 |
| 591-49-1 | Cyclohexene, 1-methyl- | | 97 | 0.13 |
| Trace Cyclic Alkenes | | | | |
| 1000156-99-7 | 3,4-diethyl-7,7-dimethylcyclohepta-1,3,5-triene | | 72 | 0.005 |
| 10494-87-8 | Ethylidenecycloheptane | | 60 | 0.055 |
| 61142-33-4 | 1,4-dimethyl-5-propan-2-yl-cyclopentene | | 64 | 0.010 |
| 4292-04-0 | 1-Isopropylcyclohex-1-ene | | 72 | 0.026 |
| 1453-24-3 | Cyclohexene, 1-ethyl- | | 74 | 0.040 |
| 3742-42-5 | 4-Ethylcyclohexene | | 91 | 0.009 |
| 65378-76-9 | 1,2,4,4-Tetramethylcyclopentene | | 91 | 0.030 |
| 2808-80-2 | Cyclohexane, 1-methyl-4-methylene- | | 91 | 0.073 |
| 1462-07-3 | Cyclopentene, 1-(1-methylethyl)- | | 90 | 0.011 |
| 19780-56-4 | Methyl ethyl cyclopentene | | 91 | 0.091 |
| 823-17-6 | Cyclohexene, 3,5-dimethyl- | | 91 | 0.076 |
| 2146-38-5 | 1-Ethylcyclopentene | | 90 | 0.053 |
| 591-47-9 | Cyclohexene, 4-methyl- | | 76 | 0.043 |
| 2633-80-9 | Bicyclo[2.2.1]heptane, 2-(2-propenyl)- | | 78 | 0.012 |
| 694-35-9 | Cyclopentene, 3-ethyl- | | 80 | 0.012 |
| 41158-41-2 | Cyclopentane, 1-methyl-2-methylene- | | 62 | 0.006 |
| 1528-21-8 | Ethylidenecyclobutane | | 87 | 0.020 |
| 1120-62-3 | Cyclopentene, 3-methyl- | | 87 | 0.048 |
| 142-29-0 | Cyclopentene | | 83 | 0.016 |
| Major n-Alkanes | | | | |
| 109-66-0 | Pentane | | 91 | 0.55 |
| 110-54-3 | n-Hexane | | 91 | 0.55 |
| 142-82-5 | Heptane | | 94 | 0.30 |
| 106-97-8 | Butane | | 87 | 0.11 |
| Major Branched Alkanes | | | | |
| 79-29-8 | Butane, 2,3-dimethyl- | 2 | 87 | 0.13 |
| 2216-33-3 | Octane, 3-methyl- | 1 | 74 | 0.10 |
| 619-99-8 | Hexane, 3-ethyl- | 1 | 64 | 0.10 |
| 589-53-7 | Heptane, 4-methyl- | 1 | 95 | 0.21 |
| 592-27-8 | Heptane, 2-methyl- | 1 | 94 | 0.26 |
| 589-34-4 | Hexane, 3-methyl- | 1 | 74 | 1.13 |
| 96-14-0 | Pentane, 3-methyl- | 1 | 91 | 1.24 |
| 107-83-5 | Pentane, 2-methyl- | 1 | 83 | 2.03 |
| 78-78-4 | Butane, 2-methyl- | 1 | 91 | 1.53 |
| Trace Branched Alkanes | | | | |
| 565-59-3 | Pentane, 2,3-dimethyl- | 2 | 94 | 0.086 |
| 617-78-7 | Pentane, 3-ethyl- | 1 | 64 | 0.075 |
| 75-28-5 | Isobutane | 1 | 86 | 0.078 |
| Major Cyclic Alkanes | | | | |
| 96-37-7 | Cyclopentane, methyl- | | 94 | 0.83 |

FIG. 34 CONT

| CAS # | Compound Name | BR# | Q | Area % |
|---|---|---|---|---|
| 2532-58-3 | Cyclopentane, 1,3-dimethyl-, cis- | | 93 | 0.31 |
| 1638-26-2 | Cyclopentane, 1,1-dimethyl- | | 83 | 0.30 |
| 1640-89-7 | Cyclopentane, ethyl- | | 97 | 0.27 |
| 2207-03-6 | Cyclohexane, 1,3-dimethyl-, trans- | | 87 | 0.23 |
| 108-87-2 | Cyclohexane, methyl- | | 94 | 0.22 |
| 3726-47-4 | Cyclopentane, 1-ethyl-3-methyl- | | 74 | 0.20 |
| 16883-48-0 | 1-trans-2-trans-4-Trimethylcyclopentane | | 91 | 0.18 |
| 2613-65-2 | Cyclopentane, 1-ethyl-3-methyl-, trans- | | 87 | 0.17 |
| 930-89-2 | Cyclopentane, 1-ethyl-2-methyl-, cis- | | 96 | 0.16 |
| 4516-69-2 | Cyclopentane, 1,1,3-trimethyl- | | 83 | 0.14 |
| 2453-00-1 | Cyclopentane, 1,3-dimethyl- | | 94 | 0.13 |
| 3726-46-3 | Cyclopentane, 1-ethyl-2-methyl- | | 94 | 0.11 |
| 287-92-3 | Cyclopentane | | 80 | 0.10 |
| Trace Cyclic Alkanes | | | | |
| 2040-95-1 | Cyclopentane, butyl- | | 64 | 0.035 |
| 4926-78-7 | Cyclohexane, 1-ethyl-4-methyl-, cis- | | 81 | 0.042 |
| 694-72-4 | Pentalene, octahydro- | | 72 | 0.046 |
| 1000142-17-5 | Bicyclo[3.1.0]hexane, 1,5-dimethyl- | | 91 | 0.055 |
| 2613-69-6 | (1R,2s,3S)-1,2,3-Trimethylcyclopentane | | 87 | 0.013 |
| 16747-50-5 | Cyclopentane, 1-ethyl-1-methyl- | | 83 | 0.096 |
| 624-29-3 | Cyclohexane, 1,4-dimethyl-, cis- | | 94 | 0.051 |
| 2815-58-9 | Cyclopentane, 1,2,4-trimethyl- | | 94 | 0.099 |
| 74752-93-5 | Cyclopropane, 1,1,2,3-tetramethyl- | | 91 | 0.056 |
| Major Oxygenates | | | | |
| 64-17-5 | Ethanol | | 91 | 2.46 |
| 74421-17-3 | Hexane, 1-(hexyloxy)-2-methyl- | | 72 | 0.91 |
| 83783-88-4 | 2-methylpentyl 2-methylbutanoate | | 72 | 0.34 |
| Trace Oxygenates | | | | |
| 30086-02-3 | 3,5-Octadien-2-one, (E,E)- | | 62 | 0.042 |
| 4313-03-5 | 2,4-Heptadienal, (E,E)- | | 64 | 0.047 |
| 96-22-0 | 3-Pentanone | | 72 | 0.010 |
| 107-87-9 | 2-Pentanone | | 72 | 0.014 |
| 563-80-4 | 2-Butanone, 3-methyl- | | 64 | 0.013 |
| 78-93-3 | 2-Butanone | | 72 | 0.030 |
| 60-29-7 | Ethyl ether | | 90 | 0.037 |

FIG. 34 CONT

| Method | Test | Result | Units |
|---|---|---|---|
| Submitted Sample: C1 | | | |
| ASTM D4052 | API Gravity @ 60°F | 64.7 | °API |
| ASTM D5191-13 | DVPE, EPA | 7.93 | psi |
| ASTM D4809 | Gross Heat of Combustion | 20660 | Btu/lb |
| | Gross Heat of Combustion | 126223 | BTU/gal |
| ASTM D2699 | Research O.N. | 97.8 | |
| ASTM D2700 | Motor O.N. | 90.8 | |
| ASTM D4814-X1.4 | Antiknock Index (Octane Rating) | 94.3 | |
| Submitted Sample: C2 | | | |
| ASTM D4052 | API Gravity @ 60°F | 55.6 | °API |
| ASTM D5191-13 | DVPE, EPA | 6.12 | psi |
| ASTM D4809 | Gross Heat of Combustion | 20482 | Btu/lb |
| | Gross Heat of Combustion | 128955 | BTU/gal |
| ASTM D2699 | Research O.N. | 98.6 | |
| ASTM D2700 | Motor O.N. | 87.6 | |
| ASTM D4814-X1.4 | Antiknock Index (Octane Rating) | 93.1 | |
| Submitted Sample: C3 | | | |
| ASTM D4052 | API Gravity @ 60°F | 49.4 | °API |
| ASTM D5191-13 | DVPE, EPA | 5.31 | psi |
| ASTM D4809 | Gross Heat of Combustion | 20133 | Btu/lb |
| | Gross Heat of Combustion | 131041 | BTU/gal |
| ASTM D2699 | Research O.N. | 99.3 | |
| ASTM D2700 | Motor O.N. | 87.1 | |
| ASTM D4814-X1.4 | Antiknock Index (Octane Rating) | 93.2 | |
| Submitted Sample: C4 | | | |
| ASTM D4052 | API Gravity @ 60°F | 47.6 | °API |
| ASTM D5191-13 | DVPE, EPA | 4.34 | psi |
| ASTM D4809 | Gross Heat of Combustion | 19938 | Btu/lb |
| | Gross Heat of Combustion | 131139 | BTU/gal |
| ASTM D2699 | Research O.N. | 95.4 | |
| ASTM D2700 | Motor O.N. | 84.2 | |
| ASTM D4814-X1.4 | Antiknock Index (Octane Rating) | 89.8 | |
| Submitted Sample: C5 | | | |
| ASTM D4052 | API Gravity @ 60°F | 47.4 | °API |
| ASTM D5191-13 | DVPE, EPA | 5.34 | psi |
| ASTM D4809 | Gross Heat of Combustion | 19276 | Btu/lb |
| | Gross Heat of Combustion | 126932 | BTU/gal |
| ASTM D2699 | Research O.N. | 98.2 | |
| ASTM D2700 | Motor O.N. | 85.6 | |
| ASTM D4814-X1.4 | Antiknock Index (Octane Rating) | 91.9 | |

FIG. 35

| Method | Test | Result | Units |
|---|---|---|---|
| Submitted Sample: Sample - B1 | | | |
| ASTM D5191 | Dry Vapor Pressure Equivalent, EPA | 7.74 | psi |
| ASTM D4809 | Gross Heat of Combustion | 20871 | Btu/lb |
| | Gross Heat of Combustion | 125236 | BTU/gal |
| ASTM D2699 | Research O.N. | 97.7 | |
| ASTM D2700 | Motor O.N. | 91.2 | |
| ASTM D4814-X1.4 | Antiknock Index (Octane Rating) | 94.4 | |
| Submitted Sample: Sample - B2 | | | |
| ASTM D5191 | Dry Vapor Pressure Equivalent, EPA | 7.54 | psi |
| ASTM D4809 | Gross Heat of Combustion | 20813 | Btu/lb |
| | Gross Heat of Combustion | 125981 | |
| ASTM D2699 | Research O.N. | 98.3 | |
| ASTM D2700 | Motor O.N. | 90.8 | |
| ASTM D4814-X1.4 | Antiknock Index (Octane Rating) | 94.6 | |
| Submitted Sample: Sample - B3 | | | |
| ASTM D5191 | Dry Vapor Pressure Equivalent, EPA | 7.28 | psi |
| ASTM D4809 | Gross Heat of Combustion | 20747 | Btu/lb |
| | Gross Heat of Combustion | 126557 | |
| ASTM D2699 | Research O.N. | 98.5 | |
| ASTM D2700 | Motor O.N. | 90.5 | |
| ASTM D4814-X1.4 | Antiknock Index (Octane Rating) | 94.5 | |
| Submitted Sample: Sample - B4 | | | |
| ASTM D5191 | Dry Vapor Pressure Equivalent, EPA | 6.82 | psi |
| ASTM D4809 | Gross Heat of Combustion | 20611 | Btu/lb |
| | Gross Heat of Combustion | 127582 | |
| ASTM D2699 | Research O.N. | 99.2 | |
| ASTM D2700 | Motor O.N. | 90.1 | |
| ASTM D4814-X1.4 | Antiknock Index (Octane Rating) | 94.6 | |
| Submitted Sample: Sample - B5 | | | |
| ASTM D5191 | Dry Vapor Pressure Equivalent, EPA | 8.64 | psi |
| ASTM D4809 | Gross Heat of Combustion | 20470 | Btu/lb |
| | Gross Heat of Combustion | 124355 | |
| ASTM D2699 | Research O.N. | 100.0 | |
| ASTM D2700 | Motor O.N. | 91.2 | |
| ASTM D4814-X1.4 | Antiknock Index (Octane Rating) | 95.6 | |

FIG. 36

| Method | Test | Result | Units |
|---|---|---|---|
| Submitted Sample: Sample 1 | | | |
| ASTM D2699 | Research O.N. | 97.8 | |
| ASTM D2700 | Motor O.N. | 91.0 | |
| ASTM D4814-X1.4 | Antiknock Index (Octane Rating) | 94.4 | |
| Submitted Sample: Sample 2 | | | |
| ASTM D2699 | Research O.N. | 95.8 | |
| ASTM D2700 | Motor O.N. | 90.1 | |
| ASTM D4814-X1.4 | Antiknock Index (Octane Rating) | 93.0 | |
| Submitted Sample: Sample 3 | | | |
| ASTM D2699 | Research O.N. | 94.0 | |
| ASTM D2700 | Motor O.N. | 88.8 | |
| ASTM D4814-X1.4 | Antiknock Index (Octane Rating) | 91.4 | |
| Submitted Sample: Sample 4 | | | |
| ASTM D2699 | Research O.N. | 90.2 | |
| ASTM D2700 | Motor O.N. | 85.6 | |
| ASTM D4814-X1.4 | Antiknock Index (Octane Rating) | 87.9 | |
| Submitted Sample: Sample 5 | | | |
| ASTM D2699 | Research O.N. | 98.1 | |
| ASTM D2700 | Motor O.N. | 88.8 | |
| ASTM D4814-X1.4 | Antiknock Index (Octane Rating) | 94.0 | |

FIG. 37

| RVP at 0°C (psi) | Xyleco | Corn Grain Ethanol | Xyleco % reduction to Corn Grain Ethanol | Sugarcane Ethanol | Xyleco % reduction to Sugarcane Ethanol | Unblended Gasoline E0 | Xyleco % reduction to Gasoline |
|---|---|---|---|---|---|---|---|
| E100 | 15.6 | 68.1 | 77% | 26.3 | 40% | - | 83% |
| E85 | 26.9 | 71.4 | 62% | 35.9 | 25% | - | 71% |
| E10 | 82.6 | 87.3 | 5% | 84.5 | 2% | - | 10% |
| E0 | - | - | - | - | - | 92.0 | - |

FIG. 38

| Code # | Composition (Volume %) | | | |
|---|---|---|---|---|
| | Home Depot TF-92 | BTEX (INH) | Gasoline (INH) | Ethanol (INH) |
| Sample D1 | 100 | 0 | 0 | 0 |
| Sample D2 | 0 | 90 (Fraction -2b) | 0 | 10 |
| Sample D3 | 0 | 100 (fraction-1b,2b) | 0 | 0 |
| Sample D4 | 0 | 100 (fraction-2b) | 0 | 0 |
| Sample D5 | 0 | 100 (all fractions) | 0 | 0 |
| Sample D6 | 0 | 0 | 50 (fractions-1a, 2a) | 50 |

|  | Volume (%) | | | Weight (%) | | |
| --- | --- | --- | --- | --- | --- | --- |
|  | Fraction 1 | Fraction 2 | Fraction 3 | Fraction 1 | Fraction 2 | Fraction 3 |
| HOG - Sample D3 | 13.06 | 86.93 | -- | 11.89 | 88.10 | -- |
| HOG - Sample D5 | 14.30 | 83.29 | 2.40 | 11.97 | 85.22 | 2.79 |
| LOG - Sample D6 | 12.56 | 74.89 | 4.68 | 18.61 | 75.71 | 5.67 |

FIG. 41

| CAS # | Compound Name | Br # | Q | Area % |
|---|---|---|---|---|
| | Major Aromatics Hydrocarbons | | | |
| 108-88-3 | Toluene | | 91 | 15.44 |
| 95-47-6 | o-Xylene | | 95 | 11.78 |
| 106-42-3 | p-Xylene | | 95 | 3.72 |
| 108-38-3 | Benzene, 1,3-dimethyl- | | 91 | 2.48 |
| | Trace Aromatic Hydrocarbons | | | |
| 71-43-2 | Benzene | | 91 | 0.031 |
| 526-73-8 | Benzene, 1,2,3-trimethyl- | | 80 | 0.031 |
| 620-14-4 | Benzene, 1-ethyl-3-methyl- | | 90 | 0.005 |
| | Trace n-Alkenes | | | |
| 109-67-1 | 1-Pentene | | 86 | 0.009 |
| | Major n-Alkanes | | | |
| 106-97-8 | Butane | | 87 | 0.44 |
| 109-66-0 | Pentane | | 91 | 0.32 |
| 110-54-3 | n-Hexane | | 91 | 0.12 |
| | Trace n-Alkanes | | | |
| 142-82-5 | Heptane | | 83 | 0.041 |
| 629-59-4 | Tetradecane | | 64 | 0.038 |
| 544-76-3 | Hexadecane | | 64 | 0.027 |
| | Major Branched Alkanes | | | |
| 62108-31-0 | Heptane, 4-ethyl-2,2,6,6-tetramethyl- | 5 | 72 | 0.52 |
| 62237-97-2 | Decane, 2,2,6-trimethyl- | 3 | 72 | 0.31 |
| 464-06-2 | Butane, 2,2,3-trimethyl- | 3 | 83 | 0.14 |
| 564-02-3 | Pentane, 2,2,3-trimethyl- | 3 | 83 | 0.98 |
| 565-75-3 | Pentane, 2,3,4-trimethyl- | 3 | 83 | 6.38 |
| 560-21-4 | Pentane, 2,3,3-trimethyl- | 3 | 83 | 8.25 |
| 3522-94-9 | Hexane, 2,2,5-trimethyl- | 3 | 72 | 3.45 |
| 1069-53-0 | Hexane, 2,3,5-trimethyl- | 3 | 83 | 0.54 |
| 62016-28-8 | Octane, 2,2,6-trimethyl- | 3 | 72 | 0.29 |
| 62016-37-9 | Octane, 2,4,6-trimethyl- | 3 | 64 | 0.16 |
| 14720-74-2 | Heptane, 2,2,4-trimethyl- | 3 | 78 | 0.34 |
| 4110-44-5 | Octane, 3,3-dimethyl- | 2 | 83 | 0.23 |
| 15869-87-1 | Octane, 2,2-dimethyl- | 2 | 78 | 0.50 |
| 2216-30-0 | Heptane, 2,5-dimethyl- | 2 | 83 | 0.20 |
| 17302-37-3 | Decane, 2,2-dimethyl- | 2 | 83 | 9.94 |
| 17302-01-1 | 3-Ethyl-3-methylheptan | 2 | 78 | 0.14 |
| 583-48-2 | Hexane, 3,4-dimethyl- | 2 | 87 | 0.32 |
| 2051-30-1 | Octane, 2,6-dimethyl- | 2 | 72 | 0.20 |
| 589-43-5 | Hexane, 2,4-dimethyl- | 2 | 83 | 3.05 |
| 17301-26-7 | Undecane, 2,9-dimethyl- | 2 | 64 | 0.15 |
| 592-13-2 | Hexane, 2,5-dimethyl- | 2 | 95 | 2.31 |
| 590-73-8 | Hexane, 2,2-dimethyl- | 2 | 83 | |
| 565-59-3 | Pentane, 2,3-dimethyl- | 2 | 87 | 1.04 |
| 108-08-7 | Pentane, 2,4-dimethyl- | 2 | 95 | 1.72 |
| 79-29-8 | Butane, 2,3-dimethyl- | 2 | 90 | 1.76 |
| 17301-94-9 | Nonane, 4-methyl- | 1 | 80 | 0.13 |
| 589-53-7 | Heptane, 4-methyl- | 1 | 87 | 1.72 |
| 56863-62-5 | 10-Methylnonadecane | 1 | 72 | 0.61 |
| 589-34-4 | Hexane, 3-methyl- | 1 | 81 | 0.19 |
| 17312-57-1 | Dodecane, 3-methyl- | 1 | 72 | 0.51 |
| 96-14-0 | Pentane, 3-methyl- | 1 | 91 | 0.34 |
| 78-78-4 | Butane, 2-methyl- | 1 | 91 | |

FIG. 42 CONT

| CAS # | Compound Name | Br # | Q | Area % |
|---|---|---|---|---|
| | Trace Branched Alkanes | | | |
| 127904-12-0 | Dodecane, 2,2,11,11-tetramethyl- | 4 | 78 | 0.094 |
| 62199-06-8 | Heptane, 5-ethyl-2,2,3-trimethyl- | 4 | 64 | 0.018 |
| 7154-79-2 | Pentane, 2,2,3,3-tetramethyl- | 4 | 78 | 0.018 |
| 16747-30-1 | Hexane, 2,4,4-trimethyl- | 3 | 83 | 0.079 |
| 31295-56-4 | Dodecane, 2,6,11-trimethyl- | 3 | 78 | 0.019 |
| 20278-89-1 | Heptane, 3,4,5-trimethyl- | 3 | 83 | 0.011 |
| 62338-14-1 | Decane, 3,3,6-trimethyl- | 3 | 64 | 0.011 |
| 62338-01-1 | Decane, 2,2,8-trimethyl- | 3 | 78 | 0.075 |
| 54166-32-4 | Octane, 2,6,6-trimethyl- | 3 | 72 | 0.063 |
| 3891-98-3 | Dodecane, 2,6,10-trimethyl- | 3 | 78 | 0.068 |
| 62183-55-5 | Octane, 3-ethyl-2,7-dimethyl- | 3 | 78 | 0.030 |
| 62338-09-4 | Decane, 2,2,3-trimethyl- | 3 | 72 | 0.078 |
| 16747-26-5 | Hexane, 2,2,4-trimethyl- | 3 | 64 | 0.029 |
| 17301-24-5 | Undecane, 2,7-dimethyl- | 2 | 72 | 0.038 |
| 62185-54-0 | Nonane, 5-(1-methylpropyl)- | 2 | 78 | 0.063 |
| 75-83-2 | Butane, 2,2-dimethyl- | 2 | 83 | 0.026 |
| 17301-23-4 | Undecane, 2,6-dimethyl- | 2 | 72 | 0.024 |
| 14876-29-0 | Heptane, 3-ethyl-2-methyl- | 2 | 64 | 0.007 |
| 463-82-1 | Neopentane | 2 | 74 | 0.011 |
| 590-35-2 | Pentane, 2,2-dimethyl- | 2 | 83 | 0.024 |
| 17312-73-1 | Undecane, 5,5-dimethyl- | 2 | 64 | 0.008 |
| 15869-94-0 | Octane, 3,6-dimethyl- | 2 | 83 | 0.019 |
| 17312-82-2 | Undecane, 4,6-dimethyl- | 2 | 72 | 0.027 |
| 31081-18-2 | Nonane, 3-methyl-5-propyl- | 2 | 72 | 0.017 |
| 7146-60-3 | Octane, 2,3-dimethyl- | 2 | 78 | 0.037 |
| 56292-65-0 | Dodecane, 2,5-dimethyl- | 2 | 72 | 0.008 |
| 562-49-2 | Pentane, 3,3-dimethyl- | 2 | 83 | 0.014 |
| 609-26-7 | 3-ethyl-2-methyl-pentane | 2 | 83 | 0.060 |
| 2213-23-2 | Heptane, 2,4-dimethyl- | 2 | 83 | 0.062 |
| 17312-79-3 | Nonane, 5-methyl-5-propyl- | 2 | 72 | 0.039 |
| 15869-93-9 | Octane, 3,5-dimethyl- | 2 | 78 | 0.017 |
| 589-81-1 | Heptane, 3-methyl- | 1 | 90 | 0.058 |
| 592-27-8 | Heptane, 2-methyl- | 1 | 95 | 0.070 |
| 617-78-7 | Pentane, 3-ethyl- | 1 | 83 | 0.007 |
| 2216-33-3 | Octane, 3-methyl- | 1 | 78 | 0.007 |
| 6418-41-3 | Tridecane, 3-methyl- | 1 | 72 | 0.011 |
| 13151-34-3 | Decane, 3-methyl- | 1 | 64 | 0.021 |
| 13287-21-3 | Tridecane, 6-methyl- | 1 | 78 | 0.012 |
| 75-28-5 | Isobutane | 1 | 78 | 0.029 |
| | Major Cyclic Alkanes | | | |
| 110-82-7 | Cyclohexane | | 91 | 0.15 |
| | Trace Cyclic Alkanes | | | |
| 638-04-0 | Cyclohexane, 1,3-dimethyl-, cis- | | 80 | 0.004 |
| 2207-03-6 | Cyclohexane, 1,3-dimethyl-, trans- | | 64 | 0.016 |
| 108-87-2 | Cyclohexane, methyl- | | 91 | 0.059 |
| 2532-58-3 | Cyclopentane, 1,3-dimethyl-, cis- | | 90 | 0.007 |
| 1638-26-2 | Cyclopentane, 1,1-dimethyl- | | 74 | 0.009 |
| 96-37-7 | Cyclopentane, methyl- | | 90 | 0.040 |
| | Trace Oxygenates | | | |
| 2425-77-6 | 1-Decanol, 2-hexyl- | | 64 | 0.009 |
| 19780-79-1 | 2-Hexyl-1-octanol | | 64 | 0.010 |

FIG. 42 CONT

| CAS # | Compound Name | Br # | Q | Area % |
|---|---|---|---|---|
| 3913-02-8 | 1-Octanol, 2-butyl- | | 78 | 0.076 |
| 1000382-69-6 | Methoxyacetic acid, 2-octyl ester | | 78 | 0.031 |

FIG. 42 CONT

| CAS # | Compound Name | R# | Q | Area% |
|---|---|---|---|---|
| | Major Aromatics Hydrocarbons | | | |
| 95-47-6 | o-Xylene | | 95 | 8.81 |
| 611-14-3 | Benzene, 1-ethyl-2-methyl- | | 95 | 8.43 |
| 874-41-9 | Benzene, 1-ethyl-2,4-dimethyl- | | 97 | 7.54 |
| 526-73-8 | Benzene, 1,2,3-trimethyl- | | 97 | 6.19 |
| 141-93-5 | Benzene, 1,3-diethyl- | | 97 | 5.39 |
| 108-67-8 | Mesitylene | | 97 | 5.21 |
| 108-88-3 | Toluene | | 91 | 3.39 |
| 100-41-4 | Ethylbenzene | | 91 | 1.90 |
| 13632-94-5 | Benzene, 1,4-diethyl-2-methyl- | | 96 | 1.39 |
| 1074-17-5 | Benzene, 1-methyl-2-propyl- | | 94 | 0.59 |
| 1595-16-0 | Benzene, 1-methyl-4-(1-methylpropyl)- | | 90 | 0.55 |
| 488-23-3 | Benzene, 1,2,3,4-tetramethyl- | | 97 | 0.51 |
| 527-84-4 | o-Cymene | | 95 | 0.50 |
| 1758-85-6 | Benzene, 2,4-diethyl-1-methyl- | | 96 | 0.49 |
| 71-43-2 | Benzene | | 91 | 0.30 |
| 824-22-6 | 1H-Indene, 2,3-dihydro-4-methyl- | | 90 | 0.28 |
| 103-65-1 | Benzene, propyl- | | 81 | 0.25 |
| 2049-95-8 | Benzene, (1,1-dimethylpropyl)- | | 91 | 0.20 |
| 6682-71-9 | 1H-Indene, 2,3-dihydro-4,7-dimethyl- | | 93 | 0.18 |
| 934-74-7 | Benzene, 1-ethyl-3,5-dimethyl- | | 97 | 0.17 |
| 2050-24-0 | Benzene, 1,3-diethyl-5-methyl- | | 97 | 0.17 |
| 53172-84-2 | Benzene, (1-methyl-1-butenyl)- | | 95 | 0.15 |
| 56147-63-8 | 2-Ethyl-2,3-dihydro-1H-indene | | 83 | 0.11 |
| | Trace Aromatic Hydrocarbons | | | |
| 873-49-4 | Benzene, cyclopropyl- | | 63 | 0.086 |
| 98-82-8 | Benzene, (1-methylethyl)- | | 81 | 0.076 |
| 4132-72-3 | Benzene, 1,4-dimethyl-2-(1-methylethyl)- | | 87 | 0.059 |
| 1000370-34-1 | 3,4-Dimethylcumene | | 93 | 0.058 |
| 577-55-9 | Benzene, 1,2-bis(1-methylethyl)- | | 90 | 0.057 |
| 4481-30-5 | Benzene, (1,2-dimethylpropyl)- | | 72 | 0.054 |
| 55669-88-0 | 1,4-dimethyl-2-(2-methylpropyl)benzene | | 87 | 0.051 |
| 135-01-3 | Benzene, 1,2-diethyl- | | 93 | 0.047 |
| 1129-29-9 | 1-(1-methylethenyl)-3-propan-2-ylbenzene | | 78 | 0.045 |
| 91-57-6 | Naphthalene, 2-methyl- | | 94 | 0.033 |
| 3809-64-5 | 1,2,3,4-Tetrahydro-5-methyl-naphthalene | | 91 | 0.032 |
| 1074-55-1 | Benzene, 1-methyl-4-propyl- | | 81 | 0.030 |
| 2039-89-6 | Benzene, 2-ethenyl-1,4-dimethyl- | | 96 | 0.030 |
| 1746-23-2 | 1-(1,1-Dimethylethyl)-4-ethenylbenzene | | 76 | 0.025 |
| 40650-41-7 | 1H-Indene, 2,3-dihydro-1,1,5-trimethyl- | | 90 | 0.025 |
| 91-20-3 | Naphthalene | | 81 | 0.022 |
| 3877-19-8 | 2-Methyl-(1,2,3,4-tetrahydronaphthalene) | | 76 | 0.019 |
| 54410-73-2 | Benzene, 1,2-diethyl-3,4-dimethyl- | | 78 | 0.017 |
| 1560-06-1 | Benzene, 2-butenyl- | | 92 | 0.013 |
| 7524-63-2 | 2,6-dimethyltetralin | | 78 | 0.010 |
| 87-85-4 | Benzene, hexamethyl- | | 87 | 0.010 |
| 4810-04-2 | Benzene, 1,3,5-trimethyl-2-propyl- | | 81 | 0.009 |
| 4489-84-3 | Benzene, (3-methyl-2-butenyl)- | | 94 | 0.009 |
| 54340-85-1 | Benzene, 1-(2-butenyl)-2,3-dimethyl- | | 83 | 0.008 |
| 50704-01-3 | Benzene, (1,3-dimethyl-2-butenyl)- | | 80 | 0.008 |
| 581-42-0 | Naphthalene, 2,6-dimethyl- | | 68 | 0.002 |

FIG. 43 CONT

| CAS # | Compound Name | Br# | Q | Area% |
|---|---|---|---|---|
| | Major Oxygenated Aromatics | | | |
| 6148-37-4 | Furan, 4-methyl-2-propyl- | | 86 | 0.39 |
| | Trace Oxygenated Aromatics | | | |
| 1875-89-4 | Benzeneethanol, 3-methyl- | | 80 | 0.064 |
| | Major n-Alkenes | | | |
| 627-20-3 | 2-Pentene, (Z)- | | 91 | 0.42 |
| 4050-45-7 | 2-Hexene, (E)- | | 91 | 0.33 |
| 646-04-8 | 2-Pentene, (E)- | | 90 | 0.22 |
| 592-43-8 | 2-Hexene | | 90 | 0.17 |
| 7642-09-3 | 3-Hexene, (Z)- | | 93 | 0.15 |
| 590-18-1 | 2-Butene, (Z)- | | 87 | 0.12 |
| 624-64-6 | 2-Butene, (E)- | | 81 | 0.10 |
| | Trace n-Alkenes | | | |
| 109-67-1 | 1-Pentene | | 94 | 0.090 |
| 592-77-8 | 2-Heptene | | 94 | 0.083 |
| 592-41-6 | 1-Hexene | | 90 | 0.070 |
| 13269-52-8 | 3-Hexene, (E)- | | 91 | 0.055 |
| 592-76-7 | 1-Heptene | | 94 | 0.015 |
| | Major Branched Alkenes | | | |
| 74732-97-9 | 1,3-Hexadiene, 3-ethyl-2-methyl-, (Z)- | 2 | 94 | 0.76 |
| 7145-20-2 | 2-Hexene, 2,3-dimethyl- | 2 | 64 | 0.10 |
| 10574-37-5 | 2-Pentene, 2,3-dimethyl- | 2 | 91 | 0.19 |
| 625-65-0 | 2-Pentene, 2,4-dimethyl- | 2 | 90 | 0.11 |
| 563-79-1 | 2-Butene, 2,3-dimethyl- | 2 | 91 | 0.43 |
| 17603-37-5 | 4-Methyl-1,3-heptadiene | 1 | 91 | 0.13 |
| 3899-36-3 | 3-Hexene, 3-methyl-, (E)- | 1 | 91 | 0.16 |
| 2738-19-4 | 2-Hexene, 2-methyl- | 1 | 83 | 0.39 |
| 3404-55-5 | 4-Methyl-2-hexene,c&t | 1 | 90 | 0.24 |
| 922-62-3 | 2-Pentene, 3-methyl-, (Z)- | 1 | 91 | 0.67 |
| 923-81-2 | 2-Pentene, 3-methyl- | 1 | 91 | 0.41 |
| 763-29-1 | 1-Pentene, 2-methyl- | 1 | 91 | 0.31 |
| 674-76-0 | 2-Pentene, 4-methyl-, (E)- | 1 | 90 | 0.20 |
| 625-27-4 | 2-Pentene, 2-methyl- | 1 | 91 | 0.73 |
| 513-35-9 | 2-Butene, 2-methyl- | 1 | 91 | 1.34 |
| 563-46-2 | 3-Methyl-1-butene | 1 | 91 | 0.45 |
| 115-11-7 | 1-Propene, 2-methyl- | 1 | 91 | 0.13 |
| | Trace Branched Alkenes | | | |
| 756-02-5 | 1,4-Pentadiene, 2,3,3-trimethyl- | 3 | 90 | 0.091 |
| 72014-90-5 | 1,4-Pentadiene, 2,3,4-trimethyl- | 3 | 64 | 0.018 |
| 1000374-08-4 | (2Z,4E)-3,7-Dimethyl-2,4-octadiene | 2 | 64 | 0.049 |
| 24618-86-8 | 1,3-Heptadiene, 5,5-dimethyl- | 2 | 72 | 0.010 |
| 1000195-03-3 | 6,6-Dimethylhepta-2,4-diene | 2 | 90 | 0.065 |
| 3404-80-6 | Hexane, 2-methyl-4-methylene- | 2 | 72 | 0.011 |
| 764-13-6 | 2,4-Hexadiene, 2,5-dimethyl- | 2 | 86 | 0.042 |
| 3404-78-2 | 3-Hexene, 2,5-dimethyl- | 2 | 90 | 0.095 |
| 3404-72-6 | 1-Pentene, 2,3-dimethyl- | 2 | 62 | 0.094 |
| 2213-32-3 | 1-Pentene, 2,4-dimethyl- | 2 | 80 | 0.054 |
| 1603-01-6 | 1,4-Heptadiene, 3-methyl- | 1 | 74 | 0.011 |
| 4485-16-9 | 3-Heptene, 4-methyl- | 1 | 90 | 0.047 |
| 66225-17-0 | 2-Heptene, 4-methyl-, (E)- | 1 | 76 | 0.043 |
| 24587-27-7 | 1,3,5-Hexatriene, 3-methyl-, (Z)- | 1 | 76 | 0.012 |
| 816-79-5 | 2-Pentene, 3-ethyl- | 1 | 74 | 0.094 |

FIG. 43 CONT

| CAS # | Compound Name | Br# | Q | Area% |
|---|---|---|---|---|
| 13151-17-2 | (Z)-Hex-2-ene, 5-methyl- | 1 | 70 | 0.080 |
| 692-24-0 | 3-Hexene, 2-methyl-, (E)- | 1 | 90 | 0.066 |
| 15840-60-5 | 3-Hexene, 2-methyl-, (Z)- | 1 | 76 | 0.018 |
| 763-30-4 | 1,4-Pentadiene, 2-methyl- | 1 | 83 | 0.042 |
| 760-20-3 | 1-Pentene, 3-methyl- | 1 | 93 | 0.073 |
| 691-37-2 | 1-Pentene, 4-methyl- | 1 | 83 | 0.039 |
| 563-45-1 | 1-Butene, 3-methyl- | 1 | 83 | 0.051 |
| | Major Cyclic Alkenes | | | |
| 473-91-6 | Cyclopentene, 1,2,3-trimethyl- | | 91 | 2.14 |
| 1528-22-9 | Cyclobutane, (1-methylethylidene)- | | 87 | 0.73 |
| 19037-72-0 | Cyclopentene, 4,4-dimethyl- | | 78 | 0.66 |
| 7459-71-4 | 3,5-Dimethylcyclopentene | | 87 | 0.59 |
| 16491-15-9 | Cyclopentene, 1,5-dimethyl- | | 74 | 0.49 |
| 693-89-0 | Cyclopentene, 1-methyl- | | 87 | 0.41 |
| 591-49-1 | Cyclohexene, 1-methyl- | | 95 | 0.35 |
| 97797-57-4 | 1-Ethyl-5-methylcyclopentene | | 95 | 0.30 |
| 1674-10-8 | Cyclohexene, 1,2-dimethyl- | | 95 | 0.26 |
| 823-17-6 | Cyclohexene, 3,5-dimethyl- | | 94 | 0.26 |
| 2808-80-2 | Cyclohexane, 1-methyl-4-methylene- | | 95 | 0.25 |
| 19780-56-4 | Methyl ethyl cyclopentene | | 94 | 0.25 |
| 1453-24-3 | Cyclohexene, 1-ethyl- | | 90 | 0.16 |
| 2146-38-5 | 1-Ethylcyclopentene | | 94 | 0.15 |
| 65378-76-9 | 1,2,4,4-Tetramethylcyclopentene | | 87 | 0.14 |
| 591-47-9 | Cyclohexene, 4-methyl- | | 87 | 0.10 |
| 5749-72-4 | Cyclohexane, (1-methylethylidene)- | | 87 | 0.10 |
| | Trace Cyclic Alkenes | | | |
| 13828-31-4 | Cyclohexene, 1-methyl-3-(1-methylethyl)- | | 87 | 0.046 |
| 53366-54-4 | Cyclopentane, (2-methylbutylidene)- | | 64 | 0.050 |
| 3983-03-7 | Cyclohexene, 1-(2-methylpropyl)- | | 76 | 0.079 |
| 1000113-50-9 | trans-1-Butenylcyclopentane | | 64 | 0.070 |
| 19781-46-5 | cis-1,4-Dimethyl-2-methylenecyclohexane | | 70 | 0.038 |
| 15232-95-8 | Cyclohexene, 3-(2-propenyl)- | | 64 | 0.033 |
| 2808-76-6 | 1,3-Dimethyl-1-cyclohexene | | 80 | 0.047 |
| 19781-47-6 | cis-1,3-Dimethyl-2-methylenecyclohexane | | 62 | 0.022 |
| 1000150-99-3 | (1R,2S)-1,2-dimethyl-3-methylenecyclopentane | | 62 | 0.023 |
| 694-35-9 | Cyclopentene, 3-ethyl- | | 64 | 0.035 |
| 41158-41-2 | Cyclopentane, 1-methyl-2-methylene- | | 81 | 0.020 |
| 1528-21-8 | Ethylidenecyclobutane | | 90 | 0.043 |
| 1120-62-3 | Cyclopentene, 3-methyl- | | 87 | 0.078 |
| 142-29-0 | Cyclopentene | | 87 | 0.036 |
| | Major n-Alkanes | | | |
| 110-54-3 | n-Hexane | | 90 | 1.00 |
| 109-66-0 | Pentane | | 91 | 0.90 |
| 106-97-8 | Butane | | 87 | 0.24 |
| | Major Branched Alkanes | | | |
| 79-29-8 | Butane, 2,3-dimethyl- | 2 | 86 | 0.15 |
| 2216-33-3 | Octane, 3-methyl- | 1 | 72 | 0.19 |
| 2216-34-4 | Octane, 4-methyl- | 1 | 87 | 0.22 |
| 589-81-1 | Heptane, 3-methyl- | 1 | 83 | 0.56 |
| 589-53-7 | Heptane, 4-methyl- | 1 | 91 | 0.34 |
| 592-27-8 | Heptane, 2-methyl- | 1 | 95 | 0.46 |
| 589-34-4 | Hexane, 3-methyl- | 1 | 87 | 1.49 |

FIG. 43 CONT

| CAS # | Compound Name | Br# | Q | Area% |
|---|---|---|---|---|
| 591-76-4 | Hexane, 2-methyl- | 1 | 94 | 1.34 |
| 96-14-0 | Pentane, 3-methyl- | 1 | 91 | 1.54 |
| 107-83-5 | Pentane, 2-methyl- | 1 | 74 | 2.67 |
| 78-78-4 | Butane, 2-methyl- | 1 | 91 | 2.13 |
| 75-28-5 | Isobutane | 1 | 86 | 0.16 |
| Trace Branched Alkanes ||||||
| 565-59-3 | Pentane, 2,3-dimethyl- | 2 | 78 | 0.084 |
| 17301-94-9 | Nonane, 4-methyl- | 1 | 80 | 0.054 |
| Major Cyclic Alkanes ||||||
| 96-37-7 | Cyclopentane, methyl- | | 91 | 1.01 |
| 2453-00-1 | Cyclopentane, 1,3-dimethyl- | | 83 | 0.80 |
| 2532-58-3 | Cyclopentane, 1,3-dimethyl-, cis- | | 95 | 0.43 |
| 16747-50-5 | Cyclopentane, 1-ethyl-1-methyl- | | 87 | 0.43 |
| 1640-89-7 | Cyclopentane, ethyl- | | 93 | 0.38 |
| 2613-66-3 | Cyclopentane, 1-ethyl-3-methyl-, cis- | | 83 | 0.38 |
| 108-87-2 | Cyclohexane, methyl- | | 95 | 0.31 |
| 930-89-2 | Cyclopentane, 1-ethyl-2-methyl-, cis- | | 95 | 0.29 |
| 4850-28-6 | 1,2,4-Trimethylcyclopentane, cis, trans | | 91 | 0.26 |
| 2815-58-9 | Cyclopentane, 1,2,4-trimethyl- | | 62 | 0.21 |
| 1192-18-3 | Cyclopentane, 1,2-dimethyl-, cis- | | 91 | 0.20 |
| 1000142-17-5 | Bicyclo[3.1.0]hexane, 1,3-dimethyl- | | 91 | 0.17 |
| Trace Cyclic Alkanes ||||||
| 3741-00-2 | Cyclopentane, pentyl- | | 95 | 0.032 |
| 4126-78-7 | Cycloheptane, methyl- | | 90 | 0.035 |
| 1678-97-3 | Cyclohexane, 1,2,3-trimethyl- | | 64 | 0.037 |
| 694-72-4 | Pentalene, octahydro- | | 79 | 0.088 |
| 2207-01-4 | Cyclohexane, 1,2-dimethyl-, cis- | | 60 | 0.022 |
| 2613-09-6 | (1R,2s,3S)-1,2,3-Trimethylcyclopentane | | 87 | 0.027 |
| Major Oxygenates ||||||
| 64-17-5 | Ethanol | | 91 | 2.61 |
| 60-29-7 | Ethyl ether | | 91 | 0.53 |
| 4313-03-5 | 2,4-Heptadienal, (E,E)- | | 72 | 0.26 |
| Trace Oxygenates ||||||
| 17623-46-7 | 4-ethyl-3,4-dimethyl-cyclohex-2-en-1-one | | 64 | 0.009 |
| 6752-80-3 | 5,7-Octadien-4-one, 2,6-dimethyl-, (E)- | | 83 | 0.025 |
| 40702-26-9 | 1,3,4-trimethylcyclohex-3-ene-1-carbaldehyde | | 90 | 0.010 |
| 85136-08-9 | 2,6-Heptadienal, 2,4-dimethyl- | | 64 | 0.022 |
| 42452-48-2 | 2,4-Heptadienal, 2,4-dimethyl- | | 64 | 0.032 |
| 5948-04-9 | p-Menth-8-en-2-one, trans- | | 64 | 0.009 |
| 54831-21-9 | 1,7-dimethyl-7-methylol-norbornan-2-ol | | 64 | 0.047 |
| 33383-56-1 | methyl 2,2-dimethyl-3-[(Z)-prop-1-enyl]cyclopropanecarboxylate | | 64 | 0.031 |
| 78-93-3 | 2-Butanone | | 64 | 0.060 |

FIG. 43 CONT

Composition By Carbon Number

| CAS # | Compound Name | Br# | Q | Area % |
|---|---|---|---|---|
| | Major Aromatics Hydrocarbons | | | |
| 611-14-3 | Benzene, 1-ethyl-2-methyl- | | 95 | 10.39 |
| 526-73-8 | Benzene, 1,2,3-trimethyl- | | 97 | 6.63 |
| 106-42-3 | p-Xylene | | 95 | 6.26 |
| 108-38-3 | Benzene, 1,3-dimethyl- | | 94 | 6.00 |
| 108-88-3 | Toluene | | 91 | 5.83 |
| 874-41-9 | Benzene, 1-ethyl-2,4-dimethyl- | | 97 | 5.73 |
| 622-96-8 | Benzene, 1-ethyl-4-methyl- | | 94 | 5.05 |
| 141-93-5 | Benzene, 1,3-diethyl- | | 96 | 3.24 |
| 100-41-4 | Ethylbenzene | | 91 | 2.89 |
| 135-01-3 | Benzene, 1,2-diethyl- | | 87 | 2.17 |
| 527-84-4 | o-Cymene | | 95 | 1.59 |
| 13632-94-5 | Benzene, 1,4-diethyl-2-methyl- | | 98 | 0.94 |
| 71-43-2 | Benzene | | 91 | 0.90 |
| 1074-43-7 | Benzene, 1-methyl-3-propyl- | | 91 | 0.82 |
| 824-22-6 | 1H-Indene, 2,3-dihydro-4-methyl- | | 91 | 0.59 |
| 1758-88-8 | Benzene, 2,4-diethyl-1-methyl- | | 95 | 0.41 |
| 527-53-7 | Benzene, 1,2,3,5-tetramethyl- | | 97 | 0.33 |
| 108-67-8 | Mesitylene | | 87 | 0.33 |
| 934-74-7 | Benzene, 1-ethyl-3,5-dimethyl- | | 95 | 0.32 |
| 103-65-1 | Benzene, propyl- | | 87 | 0.29 |
| 2050-24-0 | Benzene, 1,3-diethyl-5-methyl- | | 97 | 0.24 |
| 1595-16-0 | Benzene, 1-methyl-4-(1-methylpropyl)- | | 90 | 0.16 |
| 17059-48-2 | 1H-Indene, 2,3-dihydro-1,6-dimethyl- | | 93 | 0.16 |
| 99-87-6 | p-Cymene | | 97 | 0.15 |
| 2049-95-8 | Benzene, (1,1-dimethylpropyl)- | | 86 | 0.14 |
| 496-11-7 | Indane | | 90 | 0.14 |
| 98-82-8 | Benzene, (1-methylethyl)- | | 87 | 0.11 |
| | Trace Aromatic Hydrocarbons | | | |
| 769-57-3 | Benzene, (1,2-dimethyl-1-propenyl)- | | 94 | 0.085 |
| 95-93-2 | Benzene, 1,2,4,5-tetramethyl- | | 97 | 0.075 |
| 1595-05-7 | Benzene, 1-methyl-4-butyl | | 81 | 0.070 |
| 4489-84-3 | Benzene, (3-methyl-2-butenyl)- | | 64 | 0.061 |
| 5161-04-6 | Benzene, 1-methyl-4-(2-methylpropyl)- | | 80 | 0.052 |
| 1587-04-8 | Benzene, 1-methyl-2-(2-propenyl)- | | 64 | 0.043 |
| 1074-17-5 | Benzene, 1-methyl-2-propyl- | | 90 | 0.041 |
| 700-12-9 | Benzene, pentamethyl- | | 94 | 0.040 |
| 17851-27-3 | Benzene, 1-ethyl-2,4,5-trimethyl- | | 91 | 0.038 |
| 21693-54-9 | 5,7-dimethyltetralin | | 62 | 0.034 |
| 17057-82-8 | 1H-Indene, 2,3-dihydro-1,2-dimethyl- | | 93 | 0.023 |
| 488-23-3 | Benzene, 1,2,3,4-tetramethyl- | | 93 | 0.023 |
| 90-12-0 | Naphthalene, 1-methyl- | | 90 | 0.022 |
| 877-44-1 | Benzene, 1,2,4-triethyl- | | 87 | 0.021 |
| 91-20-3 | Naphthalene | | 93 | 0.021 |
| 2039-90-9 | Benzene, 2-ethenyl-1,3-dimethyl- | | 94 | 0.020 |
| 2809-64-5 | 1,2,3,4-Tetrahydro-5-methyl-naphthalene | | 93 | 0.018 |
| 54340-86-2 | 4-[(E)-but-2-enyl]-1,2-dimethyl-benzene | | 91 | 0.016 |
| 1068370-34-1 | 3,4-Dimethylcumene | | 94 | 0.016 |
| 40650-41-7 | 1H-Indene, 2,3-dihydro-1,1,5-trimethyl- | | 70 | 0.012 |
| 2039-89-6 | Benzene, 2-ethenyl-1,4-dimethyl- | | 90 | 0.009 |
| 2288-18-8 | Benzene, (1-methylene-2-propenyl)- | | 76 | 0.007 |

FIG. 44 CONT

| CAS # | Compound Name | Br# | Q | Area % |
|---|---|---|---|---|
| 769-25-5 | Benzene, 2-ethenyl-1,3,5-trimethyl- | | 91 | 0.006 |
| Major Oxygenated Aromatics | | | | |
| 6148-37-4 | Furan, 4-methyl-2-propyl- | | 86 | 0.20 |
| Trace Oxygenated Aromatics | | | | |
| 93-53-8 | Benzeneacetaldehyde, alpha.-methyl- | | 64 | 0.069 |
| 2040-07-5 | Ethanone, 1-(2,4,5-trimethylphenyl)- | | 93 | 0.033 |
| 52417-20-2 | 2-(2,3-dimethylphenyl)propenaldehyde | | 64 | 0.008 |
| Major n-Alkenes | | | | |
| 627-20-3 | 2-Pentene, (Z)- | | 91 | 1.01 |
| 7642-09-3 | 3-Hexene, (Z)- | | 93 | 0.24 |
| 4050-45-7 | 2-Hexene, (E)- | | 91 | 0.23 |
| 590-18-1 | 2-Butene, (Z)- | | 80 | 0.22 |
| 646-04-8 | 2-Pentene, (E)- | | 90 | 0.20 |
| 624-64-6 | 2-Butene, (E)- | | 81 | 0.18 |
| Trace n-Alkenes | | | | |
| 109-67-1 | 1-Pentene | | 93 | 0.092 |
| 7642-10-6 | (Z)-3-Heptene | | 90 | 0.047 |
| 592-41-6 | 1-Hexene | | 81 | 0.044 |
| 872-05-9 | 1-Decene | | 68 | 0.025 |
| 115-07-1 | Propene | | 80 | 0.003 |
| Major Branched Alkenes | | | | |
| 74753-07-0 | 1,3-Hexadiene, 3-ethyl-2-methyl-, (Z)- | 2 | 87 | 0.42 |
| 1515-79-3 | 5,5-Dimethyl-1,3-hexadiene | 2 | 90 | 0.14 |
| 563-78-0 | 1-Butene, 2,3-dimethyl- | 2 | 90 | 0.14 |
| 563-79-1 | 2-Butene, 2,3-dimethyl- | 2 | 91 | 0.55 |
| 2738-19-4 | 2-Hexene, 2-methyl- | 1 | 91 | 0.22 |
| 3404-55-5 | 4-Methyl-2-hexene, c&t | 1 | 90 | 0.14 |
| 625-27-4 | 2-Pentene, 2-methyl- | 1 | 90 | 0.19 |
| 922-61-2 | 2-Pentene, 3-methyl- | 1 | 94 | 0.43 |
| 922-62-3 | 2-Pentene, 3-methyl-, (Z)- | 1 | 91 | 0.27 |
| 763-29-1 | 1-Pentene, 2-methyl- | 1 | 91 | 0.21 |
| 563-46-2 | 2-Methyl-1-butene | 1 | 91 | 0.47 |
| 115-11-7 | 1-Propene, 2-methyl- | 1 | 91 | 0.31 |
| Trace Branched Alkenes | | | | |
| 19550-82-4 | trans-3,4-Dimethyl-2-hexene | 2 | 72 | 0.058 |
| 1112-35-2 | 1,4-Pentadiene, 3,3-dimethyl- | 2 | 64 | 0.037 |
| 625-65-0 | 2-Pentene, 2,4-dimethyl- | 2 | 83 | 0.067 |
| 2213-32-3 | 1-Pentene, 2,4-dimethyl- | 2 | 83 | 0.031 |
| 37050-05-8 | 3,4-Octadiene, 7-methyl- | 1 | 68 | 0.038 |
| 4485-16-9 | 3-Heptene, 4-methyl- | 1 | 83 | 0.025 |
| 1632-16-2 | 3-Ethyl-2-hexene(c,t) | 1 | 78 | 0.007 |
| 627-97-4 | 2-Methyl-2-heptene | 1 | 72 | 0.051 |
| 66225-17-0 | 2-Heptene, 4-methyl-, (E)- | 1 | 78 | 0.024 |
| 816-79-5 | 2-Pentene, 3-ethyl- | 1 | 80 | 0.056 |
| 4914-89-0 | 3-Hexene, 3-methyl-, (Z)- | 1 | 91 | 0.090 |
| 15840-60-5 | 3-Hexene, 2-methyl-, (Z)- | 1 | 87 | 0.038 |
| 674-76-0 | 2-Pentene, 4-methyl-, (E)- | 1 | 81 | 0.042 |
| 760-20-3 | 1-Pentene, 3-methyl- | 1 | 93 | 0.032 |
| 691-37-2 | 1-Pentene, 4-methyl- | 1 | 81 | 0.029 |
| 563-45-1 | 1-Butene, 3-methyl- | 1 | 87 | 0.055 |
| Major Cyclic Alkenes | | | | |
| 473-93-6 | Cyclopentene, 1,2,3-trimethyl- | | 91 | 1.13 |

FIG. 44 CONT

| CAS # | Compound Name | Br # | Q | Area % |
|---|---|---|---|---|
| 1528-22-9 | Cyclobutane, (1-methylethylidene)- | | 90 | 0.94 |
| 1120-62-3 | Cyclopentene, 3-methyl- | | 90 | 0.36 |
| 97797-57-4 | 1-Ethyl-5-methylcyclopentene | | 95 | 0.34 |
| 7459-71-4 | 3,5-Dimethylcyclopentene | | 78 | 0.31 |
| 16491-15-9 | Cyclopentene, 1,5-dimethyl- | | 87 | 0.31 |
| 591-49-1 | Cyclohexene, 1-methyl- | | 94 | 0.33 |
| 2808-76-6 | 1,3-Dimethyl-1-cyclohexene | | 87 | 0.23 |
| 1674-10-8 | Cyclohexene, 1,2-dimethyl- | | 95 | 0.17 |
| 2808-80-2 | Cyclohexane, 1-methyl-4-methylene- | | 93 | 0.15 |
| 65378-76-9 | 1,2,4,4-Tetramethylcyclopentene | | 81 | 0.11 |
| Trace Cyclic Alkenes ||||| 
| 2539-75-5 | Cyclohexene, 1-propyl- | | 70 | 0.015 |
| 19781-46-5 | cis-1,4-Dimethyl-2-methylenecyclohexane | | 64 | 0.021 |
| 4292-04-0 | 1-Isopropylcyclohex-1-ene | | 87 | 0.060 |
| 1453-24-3 | Cyclohexene, 1-ethyl- | | 87 | 0.078 |
| 2808-71-1 | Cyclohexene, 3-ethyl- | | 87 | 0.023 |
| 2808-75-5 | 1-Methyl-2-methylenecyclohexane | | 74 | 0.027 |
| 823-17-6 | Cyclohexene, 3,5-dimethyl- | | 64 | 0.027 |
| 2146-38-5 | 1-Ethylcyclopentene | | 91 | 0.086 |
| 591-47-9 | Cyclohexene, 4-methyl- | | 81 | 0.068 |
| 2833-80-9 | Bicyclo[2.2.1]heptane, 2-(2-propenyl)- | | 78 | 0.065 |
| 694-35-9 | Cyclopentene, 3-ethyl- | | 64 | 0.022 |
| 41158-41-2 | Cyclopentane, 1-methyl-2-methylene- | | 76 | 0.013 |
| 2597-49-1 | Cyclobutane, ethenyl- | | 81 | 0.031 |
| 19037-72-0 | Cyclopentene, 4,4-dimethyl- | | 64 | 0.012 |
| 4372-94-5 | Cyclopropane, 1,1-dimethyl-2-methylene- | | 74 | 0.032 |
| 142-29-0 | Cyclopentene | | 87 | 0.037 |
| Major n-Alkanes ||||| 
| 109-66-0 | Pentane | | 91 | 1.12 |
| 110-54-3 | n-Hexane | | 90 | 0.78 |
| 106-97-8 | Butane | | 87 | 0.69 |
| Trace n-Alkanes ||||| 
| 74-98-6 | Propane | | 72 | 0.012 |
| Major Branched Alkanes ||||| 
| 921-47-1 | Hexane, 2,3,4-trimethyl- | 3 | 91 | 0.15 |
| 79-29-8 | Butane, 2,3-dimethyl- | 2 | 86 | 0.17 |
| 589-81-1 | Heptane, 3-methyl- | 1 | 78 | 0.40 |
| 589-53-7 | Heptane, 4-methyl- | 1 | 91 | 0.24 |
| 592-27-8 | Heptane, 2-methyl- | 1 | 95 | 0.32 |
| 589-34-4 | Hexane, 3-methyl- | 1 | 83 | 1.23 |
| 591-76-4 | Hexane, 2-methyl- | 1 | 94 | 1.06 |
| 96-14-0 | Pentane, 3-methyl- | 1 | 91 | 1.58 |
| 78-78-4 | Butane, 2-methyl- | 1 | 94 | 3.73 |
| 75-28-5 | Isobutane | 1 | 87 | 0.77 |
| Trace Branched Alkanes ||||| 
| 565-59-3 | Pentane, 2,3-dimethyl- | 2 | 74 | 0.075 |
| 17301-94-9 | Nonane, 4-methyl- | 1 | 86 | 0.031 |
| 15869-85-9 | Nonane, 5-methyl- | 1 | 64 | 0.028 |
| Major Cyclic Alkanes ||||| 
| 96-37-7 | Cyclopentane, methyl- | | 91 | 0.95 |
| 2453-00-1 | Cyclopentane, 1,3-dimethyl- | | 87 | 0.80 |
| 1638-26-2 | Cyclopentane, 1,1-dimethyl- | | 90 | 0.35 |

FIG. 44 CONT

| CAS # | Compound Name | Br# | Q | Area % |
|---|---|---|---|---|
| 2207-03-6 | Cyclohexane, 1,3-dimethyl-, trans- | | 70 | 0.35 |
| 2452-99-5 | Cyclopentane, 1,2-dimethyl- | | 90 | 0.33 |
| 1640-89-7 | Cyclopentane, ethyl- | | 95 | 0.30 |
| 108-87-2 | Cyclohexane, methyl- | | 94 | 0.26 |
| 2613-65-2 | Cyclopentane, 1-ethyl-3-methyl-, trans- | | 83 | 0.25 |
| 1000142-17-5 | Bicyclo[3.1.0]hexane, 1,3-dimethyl- | | 91 | 0.25 |
| 930-89-2 | Cyclopentane, 1-ethyl-2-methyl-, cis- | | 94 | 0.19 |
| 2815-58-9 | Cyclopentane, 1,2,4-trimethyl- | | 91 | 0.18 |
| 16747-50-9 | Cyclopentane, 1-ethyl-1-methyl- | | 83 | 0.11 |
| 74752-93-5 | Cyclopropane, 1,1,2,3-tetramethyl- | | 91 | 0.10 |
| Trace Cyclic Alkanes | | | | |
| 3868-04-2 | Pentalene, octahydro-2-methyl- | | 87 | 0.014 |
| 2207-01-4 | Cyclohexane, 1,2-dimethyl-, cis- | | 72 | 0.015 |
| 17965-18-8 | Bicyclo[2.1.0]pentane, 1,4-dimethyl- | | 64 | 0.085 |
| 2613-89-6 | (1R,2s,3S)-1,2,3-Trimethylcyclopentane | | 72 | 0.018 |
| 2207-04-7 | Cyclohexane, 1,4-dimethyl-, trans- | | 90 | 0.070 |
| Trace Cyclic Alkanes | | | | |
| 60-29-7 | Ethyl ether | | 94 | 1.53 |
| Trace Oxygenates | | | | |
| 62702-89-0 | Bicyclo[3.2.1]oct-3-en-2-one, 4-methyl- | | 64 | 0.008 |
| 42452-48-2 | 2,4-Heptadienal, 2,4-dimethyl- | | 64 | 0.023 |
| 5574-35-8 | (1R,2R,4S)-norbornane-2-carbaldehyde | | 64 | 0.027 |
| 1000303-74-9 | 2,5-Dimethylhex-3-en-3-yn-2-ol | | 68 | 0.058 |
| 64-17-5 | Ethanol | | 60 | 0.066 |

FIG. 44 CONT

| CAS # | Compound Name | R# | Q | Area% |
|---|---|---|---|---|
| \multicolumn{5}{c}{Major Aromatics Hydrocarbons} ||||| 
| 611-14-3 | Benzene, 1-ethyl-2-methyl- | | 95 | 9.85 |
| 874-41-9 | Benzene, 1-ethyl-2,4-dimethyl- | | 97 | 7.60 |
| 526-73-8 | Benzene, 1,2,3-trimethyl- | | 97 | 6.85 |
| 108-38-3 | Benzene, 1,3-dimethyl- | | 95 | 5.46 |
| 95-47-6 | o-Xylene | | 95 | 5.19 |
| 622-96-8 | Benzene, 1-ethyl-4-methyl- | | 94 | 4.84 |
| 108-88-3 | Toluene | | 91 | 4.14 |
| 141-93-5 | Benzene, 1,3-diethyl- | | 96 | 3.19 |
| 100-41-4 | Ethylbenzene | | 91 | 2.36 |
| 135-01-3 | Benzene, 1,2-diethyl- | | 96 | 2.15 |
| 13632-94-5 | Benzene, 1,4-diethyl-2-methyl- | | 96 | 1.42 |
| 2050-24-0 | Benzene, 1,3-diethyl-5-methyl- | | 95 | 0.69 |
| 1074-43-7 | Benzene, 1-methyl-3-propyl- | | 94 | 0.69 |
| 1595-16-0 | Benzene, 1-methyl-4-(1-methylpropyl)- | | 87 | 0.66 |
| 527-53-7 | Benzene, 1,2,3,5-tetramethyl- | | 97 | 0.59 |
| 527-84-4 | o-Cymene | | 97 | 0.46 |
| 6682-71-9 | 1H-Indene, 2,3-dihydro-4,7-dimethyl- | | 96 | 0.40 |
| 71-43-2 | Benzene | | 91 | 0.35 |
| 108-67-8 | Mesitylene | | 95 | 0.34 |
| 824-22-6 | 1H-Indene, 2,3-dihydro-4-methyl- | | 90 | 0.32 |
| 103-65-1 | Benzene, propyl- | | 86 | 0.30 |
| 934-74-7 | Benzene, 1-ethyl-3,5-dimethyl- | | 95 | 0.24 |
| 2049-95-8 | Benzene, (1,1-dimethylpropyl)- | | 91 | 0.21 |
| 535-77-3 | Benzene, 1-methyl-3-(1-methylethyl)- | | 97 | 0.19 |
| 56147-63-8 | 2-Ethyl-2,3-dihydro-1H-indene | | 64 | 0.12 |
| \multicolumn{5}{c}{Trace Aromatic Hydrocarbons} |||||
| 637-50-3 | Benzene, 1-propenyl- | | 76 | 0.100 |
| 98-82-8 | Benzene, (1-methylethyl)- | | 98 | 0.089 |
| 700-12-9 | Benzene, pentamethyl- | | 90 | 0.077 |
| 1595-05-7 | Benzene, 1-methyl-4-butyl | | 74 | 0.063 |
| 54340-86-2 | 4-[(E)-but-2-enyl]-1,2-dimethyl-benzene | | 70 | 0.059 |
| 4706-90-5 | Benzene, 1,3-dimethyl-5-(1-methylethyl)- | | 93 | 0.053 |
| 102-25-0 | Benzene, 1,3,5-triethyl- | | 81 | 0.045 |
| 90-12-0 | Naphthalene, 1-methyl- | | 94 | 0.041 |
| 1680-51-9 | 8-Methyl-(1,2,3,4-tetrahydronaphthalene) | | 96 | 0.039 |
| 1758-85-6 | Benzene, 2,4-diethyl-1-methyl- | | 70 | 0.039 |
| 488-23-3 | Benzene, 1,2,3,4-tetramethyl- | | 97 | 0.039 |
| 1074-17-5 | Benzene, 1-methyl-2-propyl- | | 70 | 0.037 |
| 2234-20-0 | 2,4-Dimethylstyrene | | 95 | 0.033 |
| 17851-27-3 | Benzene, 1-ethyl-2,4,5-trimethyl- | | 70 | 0.033 |
| 1129-29-9 | 1-(1-methylethenyl)-3-propan-2-ylbenzene | | 70 | 0.032 |
| 40650-41-7 | 1H-Indene, 2,3-dihydro-1,1,5-trimethyl- | | 94 | 0.030 |
| 91-20-3 | Naphthalene | | 74 | 0.027 |
| 3877-19-8 | 2-Methyl-(1,2,3,4-tetrahydronaphthalene) | | 81 | 0.026 |
| 1000370-34-1 | 3,4-Dimethylcumene | | 94 | 0.025 |
| 877-44-1 | Benzene, 1,2,4-triethyl- | | 76 | 0.024 |
| 55669-88-0 | 1,4-dimethyl-2-(2-methylpropyl)benzene | | 81 | 0.023 |
| 2039-89-6 | Benzene, 2-ethenyl-1,4-dimethyl- | | 76 | 0.017 |
| 7524-63-2 | 2,6-dimethyltetralin | | 83 | 0.016 |
| 87-85-4 | Benzene, hexamethyl- | | 93 | 0.013 |
| 4175-54-6 | 1,4-dimethyltetralin | | 76 | 0.013 |

FIG. 45 CONT

| CAS # | Compound Name | Br # | Q | Area% |
|---|---|---|---|---|
| 4810-04-2 | Benzene, 1,3,5-trimethyl-2-propyl- | | 83 | 0.013 |
| 4489-84-3 | Benzene, (3-methyl-2-butenyl)- | | 94 | 0.013 |
| 96-39-9 | 1,3-Cyclopentadiene, 1-methyl- | | 64 | 0.006 |
| 582-16-1 | Naphthalene, 2,7-dimethyl- | | 93 | 0.005 |
| 581-40-8 | Naphthalene, 2,3-dimethyl- | | 91 | 0.005 |
| 28027-77-4 | 5,6-dimethyltetralin | | 80 | 0.004 |
| 22531-20-0 | Naphthalene, 6-ethyl-1,2,3,4-tetrahydro- | | 70 | 0.004 |
| | Major Oxygenated Aromatics |
| 6148-37-4 | Furan, 4-methyl-2-propyl- | | 78 | 0.15 |
| | Trace Oxygenated Aromatics |
| 33223-84-6 | 2-Methylindan-2-ol | | 72 | 0.069 |
| 2040-07-5 | Ethanone, 1-(2,4,5-trimethylphenyl)- | | 93 | 0.056 |
| 53568-05-1 | 8-hydroxytetralin-2-one | | 60 | 0.043 |
| 343852-30-6 | 6,7-Dimethyl-3H-isobenzofuran-1-one | | 62 | 0.040 |
| 52417-50-2 | 2-(2,5-dimethylphenyl)propionaldehyde | | 80 | 0.030 |
| 10487-96-4 | 1-Phenylcyclopentanol-1 | | 72 | 0.009 |
| | Major n-Alkenes |
| 627-20-3 | 2-Pentene, (Z)- | | 91 | 0.41 |
| 7688-21-3 | 2-Hexene, (Z)- | | 91 | 0.25 |
| 646-04-8 | 2-Pentene, (E)- | | 91 | 0.21 |
| 109-67-1 | 1-Pentene | | 91 | 0.21 |
| 590-18-1 | 2-Butene, (Z)- | | 81 | 0.16 |
| 624-64-6 | 2-Butene, (E)- | | 87 | 0.14 |
| 4050-45-7 | 2-Hexene, (E)- | | 91 | 0.13 |
| 7642-09-3 | 3-Hexene, (Z)- | | 95 | 0.11 |
| | Trace n-Alkenes |
| 592-77-8 | 2-Heptene | | 95 | 0.068 |
| 592-41-6 | 1-Hexene | | 91 | 0.053 |
| 13269-52-8 | 3-Hexene, (E)- | | 94 | 0.042 |
| 14919-01-8 | 3-Octene, (E)- | | 68 | 0.008 |
| 591-93-5 | 1,4-Pentadiene | | 90 | 0.002 |
| | Major Branched Alkenes |
| 756-02-5 | 1,4-Pentadiene, 2,3,3-trimethyl- | 3 | 87 | 0.12 |
| 74779-65-0 | 1,3-Heptadiene, 2,3-dimethyl- | 2 | 60 | 0.14 |
| 74752-97-9 | 1,3-Hexadiene, 3-ethyl-2-methyl-, (Z)- | 2 | 94 | 0.41 |
| 1000193-03-3 | 6,6-Dimethylhepta-2,4-diene | 2 | 91 | 0.17 |
| 1112-35-2 | 1,4-Pentadiene, 3,3-dimethyl- | 2 | 74 | 0.40 |
| 563-79-1 | 2-Butene, 2,3-dimethyl- | 2 | 91 | 0.25 |
| 563-78-0 | 1-Butene, 2,3-dimethyl- | 2 | 91 | 0.39 |
| 3738-19-4 | 2-Hexene, 2-methyl- | 1 | 91 | 0.33 |
| 3404-65-7 | 3-Methyl-3-hexene | 1 | 91 | 0.30 |
| 3683-22-5 | 3-Hexene, 4-methyl-, (E)- | 1 | 91 | 0.11 |
| 616-12-6 | 2-Pentene, 3-methyl-, (E)- | 1 | 91 | 0.56 |
| 922-61-2 | 2-Pentene, 3-methyl- | 1 | 94 | 0.34 |
| 625-27-4 | 2-Pentene, 2-methyl- | 1 | 91 | 0.57 |
| 763-29-1 | 1-Pentene, 2-methyl- | 1 | 91 | 0.26 |
| 513-35-9 | 2-Butene, 2-methyl- | 1 | 91 | 1.36 |
| 563-46-2 | 3-Methyl-1-butene | 1 | 91 | 0.49 |
| 115-11-7 | 1-Propene, 2-methyl- | 1 | 91 | 0.23 |
| | Trace Branched Alkenes |
| 3404-79-3 | 2-Hexene, 3,5-dimethyl- | 2 | 76 | 0.074 |
| 3404-78-2 | 2-Hexene, 2,5-dimethyl- | 2 | 90 | 0.080 |

FIG. 45 CONT

| CAS # | Compound Name | Br# | Q | Area% |
|---|---|---|---|---|
| 19550-83-5 | trans-4,4-Dimethyl-2-hexene | 2 | 74 | 0.085 |
| 3404-72-6 | 1-Pentene, 2,3-dimethyl- | 2 | 62 | 0.083 |
| 2213-32-3 | 1-Pentene, 2,4-dimethyl- | 2 | 87 | 0.045 |
| 7385-78-6 | 1-Pentene, 3,4-dimethyl- | 2 | 72 | 0.007 |
| 558-37-2 | 1-Butene, 3,3-dimethyl- | 2 | 91 | 0.010 |
| 1603-01-6 | 1,4-Heptadiene, 3-methyl- | 1 | 64 | 0.028 |
| 4485-16-9 | 3-Heptene, 4-methyl- | 1 | 90 | 0.035 |
| 1632-16-2 | 3-Ethyl-2-hexene(c,t) | 1 | 91 | 0.010 |
| 15918-08-8 | Heptane, 4-methylene- | 1 | 83 | 0.007 |
| 2080-89-9 | 1,4-Hexadiene, 3-ethyl- | 1 | 70 | 0.033 |
| 66225-17-0 | 2-Heptene, 4-methyl-, (E)- | 1 | 76 | 0.035 |
| 24587-27-7 | 1,3,5-Hexatriene, 3-methyl-, (Z)- | 1 | 91 | 0.010 |
| 3524-73-0 | 1-Hexene, 5-methyl- | 1 | 72 | 0.010 |
| 692-24-0 | 3-Hexene, 2-methyl-, (E)- | 1 | 91 | 0.070 |
| 926-54-5 | 1,3-Pentadiene, 2-methyl-, (E)- | 1 | 90 | 0.064 |
| 926-56-7 | 4-Methyl-1,3-pentadiene | 1 | 87 | 0.006 |
| 4461-48-7 | 2-Pentene, 4-methyl- | 1 | 91 | 0.050 |
| 760-20-3 | 1-Pentene, 3-methyl- | 1 | 91 | 0.060 |
| 691-37-2 | 1-Pentene, 4-methyl- | 1 | 91 | 0.034 |
| 563-45-1 | 1-Butene, 3-methyl- | 1 | 91 | 0.052 |
| Major Cyclic Alkenes | | | | |
| 473-91-6 | Cyclopentene, 1,2,3-trimethyl- | | 91 | 1.76 |
| 1528-22-9 | Cyclobutane, (1-methylethylidene)- | | 87 | 0.64 |
| 16491-15-9 | Cyclopentene, 1,5-dimethyl- | | 83 | 0.57 |
| 7459-71-4 | 3,5-Dimethylcyclopentene | | 91 | 0.53 |
| 693-89-0 | Cyclopentene, 1-methyl- | | 90 | 0.41 |
| 591-49-1 | Cyclohexene, 1-methyl- | | 94 | 0.31 |
| 2808-76-6 | 1,3-Dimethyl-1-cyclohexene | | 91 | 0.30 |
| 1674-10-8 | Cyclohexene, 1,2-dimethyl- | | 95 | 0.23 |
| 97797-37-4 | 1-Ethyl-2-methylcyclopentene | | 95 | 0.21 |
| 2808-80-2 | Cyclohexane, 1-methyl-4-methylene- | | 91 | 0.20 |
| 56021-63-7 | trans-3,5-Dimethylcyclohexene | | 93 | 0.18 |
| 2146-38-5 | 1-Ethylcyclopentene | | 91 | 0.13 |
| 591-47-9 | Cyclohexene, 4-methyl- | | 90 | 0.11 |
| 65378-76-9 | 1,2,4,4-Tetramethylcyclopentene | | 86 | 0.10 |
| Trace Cyclic Alkenes | | | | |
| 514-95-4 | 1,5,5-Trimethyl-6-methylene-cyclohexene | | 68 | 0.016 |
| 13828-31-4 | Cyclohexene, 1-methyl-3-(1-methylethyl)- | | 87 | 0.042 |
| 1000150-62-1 | Cyclopentane, 1-isobutylidene-3-methyl- | | 74 | 0.018 |
| 1759-64-4 | 1,6-dimethylcyclohexene | | 70 | 0.057 |
| 7712-74-5 | Cyclopentene, 1-isopropyl-4,5-dimethyl- | | 64 | 0.008 |
| 5356-65-5 | Cyclohexene, 3-methyl-6-(1-methylethyl)- | | 76 | 0.038 |
| 2539-75-5 | Cyclohexene, 1-propyl- | | 64 | 0.057 |
| 3749-73-4 | Cyclohexane, (1-methylethylidene)- | | 90 | 0.084 |
| 1453-24-3 | Cyclohexene, 1-ethyl- | | 91 | 0.092 |
| 2808-71-1 | Cyclohexene, 3-ethyl- | | 83 | 0.034 |
| 1462-07-3 | Cyclopentene, 1-(1-methylethyl)- | | 95 | 0.037 |
| 19780-56-4 | Methyl ethyl cyclopentene | | 95 | 0.057 |
| 823-17-6 | Cyclohexene, 3,5-dimethyl- | | 87 | 0.072 |
| 35170-90-6 | Bicyclo[2.2.1]heptane, 2-(1-buten-3-yl)- | | 78 | 0.086 |
| 694-35-9 | Cyclopentene, 3-ethyl- | | 72 | 0.039 |
| 110-83-8 | Cyclohexene | | 93 | 0.039 |

FIG. 45 CONT

| CAS # | Compound Name | Br# | Q | Area% |
|---|---|---|---|---|
| 1120-62-3 | Cyclopentene, 3-methyl- | | 90 | 0.070 |
| 142-29-0 | Cyclopentene | | 91 | 0.036 |
| Major n-Alkanes | | | | |
| 110-54-3 | n-Hexane | | 91 | 0.80 |
| 109-66-0 | Pentane | | 91 | 0.78 |
| 106-97-8 | Butane | | 87 | 0.30 |
| Trace n-Alkanes | | | | |
| 74-98-6 | Propane | | 72 | 0.004 |
| Major Branched Alkanes | | | | |
| 79-29-8 | Butane, 2,3-dimethyl- | 2 | 87 | 0.14 |
| 2216-33-3 | Octane, 3-methyl- | 1 | 72 | 0.16 |
| 589-81-1 | Heptane, 3-methyl- | 1 | 83 | 0.46 |
| 589-53-7 | Heptane, 4-methyl- | 1 | 93 | 0.28 |
| 592-27-8 | Heptane, 2-methyl- | 1 | 95 | 0.39 |
| 589-34-4 | Hexane, 3-methyl- | 1 | 83 | 1.28 |
| 591-76-4 | Hexane, 2-methyl- | 1 | 91 | 1.15 |
| 96-14-0 | Pentane, 3-methyl- | 1 | 91 | 1.36 |
| 78-78-4 | Butane, 2-methyl- | 1 | 91 | 2.40 |
| 75-28-5 | Isobutane | 1 | 86 | 0.33 |
| Trace Branched Alkanes | | | | |
| 565-59-3 | Pentane, 2,3-dimethyl- | 2 | 74 | 0.080 |
| 75-83-2 | Butane, 2,2-dimethyl- | 2 | 78 | 0.015 |
| 17301-94-9 | Nonane, 4-methyl- | 1 | 83 | 0.044 |
| 15869-85-9 | Nonane, 3-methyl- | 1 | 72 | 0.039 |
| Major Cyclic Alkanes | | | | |
| 96-37-7 | Cyclopentane, methyl- | | 91 | 1.04 |
| 2453-00-1 | Cyclopentane, 1,3-dimethyl- | | 91 | 1.00 |
| 2207-03-6 | Cyclohexane, 1,3-dimethyl-, trans- | | 76 | 0.64 |
| 3726-47-4 | Cyclopentane, 1-ethyl-3-methyl- | | 83 | 0.60 |
| 1638-26-2 | Cyclopentane, 1,1-dimethyl- | | 83 | 0.46 |
| 2452-99-5 | Cyclopentane, 1,2-dimethyl- | | 93 | 0.41 |
| 1640-89-7 | Cyclopentane, ethyl- | | 95 | 0.38 |
| 108-87-2 | Cyclohexane, methyl- | | 94 | 0.30 |
| 2815-58-9 | Cyclopentane, 1,2,4-trimethyl- | | 91 | 0.25 |
| 74752-93-5 | Cyclopropane, 1,1,2,3-tetramethyl- | | 91 | 0.22 |
| 930-89-2 | Cyclopentane, 1-ethyl-2-methyl-, cis- | | 94 | 0.19 |
| 4850-28-6 | 1,2,4-Trimethylcyclopentane, cis, trans | | 76 | 0.19 |
| 16747-50-5 | Cyclopentane, 1-ethyl-1-methyl- | | 83 | 0.16 |
| 2146-41-0 | Bicyclo[2.2.1]heptane, 2-ethyl- | | 60 | 0.12 |
| Trace Cyclic Alkanes | | | | |
| 3741-00-2 | Cyclopentane, pentyl- | | 91 | 0.034 |
| 4126-78-7 | Cycloheptane, methyl- | | 64 | 0.036 |
| 1678-97-3 | Cyclohexane, 1,2,3-trimethyl- | | 76 | 0.031 |
| 694-72-4 | Pentalene, octahydro- | | 81 | 0.081 |
| 2234-75-5 | Cyclohexane, 1,2,4-trimethyl- | | 86 | 0.003 |
| 2207-01-4 | Cyclohexane, 1,2-dimethyl-, cis- | | 62 | 0.023 |
| 2613-66-3 | Cyclopentane, 1-ethyl-3-methyl-, cis- | | 74 | 0.066 |
| 2815-57-8 | Cyclopentane, 1,2,3-trimethyl- | | 64 | 0.025 |
| 624-29-3 | Cyclohexane, 1,4-dimethyl-, cis- | | 81 | 0.043 |
| 1000142-17-5 | Bicyclo[3.1.0]hexane, 1,5-dimethyl- | | 78 | 0.006 |
| 4127-47-3 | Cyclopropane, 1,1,2,2-tetramethyl- | | 86 | 0.005 |
| 75-19-4 | Cyclopropane | | 83 | 0.003 |

FIG. 45 CONT

| CAS # | Compound Name | Br# | Q | Area% |
|---|---|---|---|---|
| Major Oxygenates ||||| 
| 60-29-7 | Ethyl ether | | 91 | 0.36 |
| 4313-03-5 | 2,4-Heptadienal, (E,E)- | | 78 | 0.23 |
| Trace Oxygenates ||||| 
| 53722-59-3 | (3E)-3,7-dimethylocta-3,6-dienal | | 60 | 0.015 |
| 16240-38-3 | Cycloheptanol, 2-methylene | | 90 | 0.016 |
| 42452-48-2 | 2,4-Heptadienal, 2,4-dimethyl- | | 72 | 0.034 |
| 5948-04-9 | p-Menth-8-en-2-one, trans- | | 64 | 0.059 |
| 107-87-9 | 2-Pentanone | | 86 | 0.030 |
| 563-80-4 | 2-Butanone, 3-methyl- | | 78 | 0.021 |
| 64504-73-0 | 3-(2-Cyclopenten-1-yl)propanal | | 64 | 0.013 |
| 78-93-3 | 2-Butanone | | 78 | 0.038 |
| 67-64-1 | Acetone | | 86 | 0.013 |
| 64-17-5 | Ethanol | | 90 | 0.011 |

FIG. 45 CONT

| CAS # | Compound Name | B# | Q | Area % |
|---|---|---|---|---|
| | Major Aromatics Hydrocarbons | | | |
| 611-14-3 | Benzene, 1-ethyl-2-methyl- | | 95 | 8.93 |
| 95-47-6 | o-Xylene | | 95 | 8.64 |
| 95-63-6 | Benzene, 1,2,4-trimethyl- | | 95 | 6.34 |
| 108-88-3 | Toluene | | 91 | 5.81 |
| 874-41-9 | Benzene, 1-ethyl-2,4-dimethyl- | | 97 | 5.52 |
| 622-96-8 | Benzene, 1-ethyl-4-methyl- | | 94 | 4.85 |
| 141-93-5 | Benzene, 1,3-diethyl- | | 96 | 3.16 |
| 106-42-3 | p-Xylene | | 94 | 3.11 |
| 100-41-4 | Ethylbenzene | | 91 | 2.82 |
| 135-01-3 | Benzene, 1,2-diethyl- | | 96 | 2.16 |
| 13632-94-5 | Benzene, 1,4-diethyl-2-methyl- | | 96 | 1.56 |
| 527-84-4 | o-Cymene | | 94 | 1.24 |
| 824-22-6 | 1H-Indene, 2,3-dihydro-4-methyl- | | 94 | 0.79 |
| 71-43-2 | Benzene | | 91 | 0.68 |
| 1074-43-7 | Benzene, 1-methyl-3-propyl- | | 94 | 0.60 |
| 1758-85-6 | Benzene, 2,4-diethyl-1-methyl- | | 95 | 0.57 |
| 95-93-2 | Benzene, 1,2,4,5-tetramethyl- | | 97 | 0.54 |
| 1758-88-9 | Benzene, 2-ethyl-1,4-dimethyl- | | 95 | 0.49 |
| 6682-71-9 | 1H-Indene, 2,3-dihydro-4,7-dimethyl- | | 97 | 0.43 |
| 1595-16-0 | Benzene, 1-methyl-4-(1-methylpropyl)- | | 90 | 0.42 |
| 535-77-3 | Benzene, 1-methyl-3-(1-methylethyl)- | | 95 | 0.35 |
| 934-74-7 | Benzene, 1-ethyl-3,5-dimethyl- | | 95 | 0.31 |
| 2050-24-0 | Benzene, 1,3-diethyl-5-methyl- | | 97 | 0.31 |
| 103-65-1 | Benzene, propyl- | | 87 | 0.28 |
| 934-80-5 | Benzene, 4-ethyl-1,2-dimethyl- | | 90 | 0.25 |
| 526-73-8 | Benzene, 1,2,3-trimethyl- | | 95 | 0.21 |
| 56147-63-8 | 2-Ethyl-2,3-dihydro-1H-indene | | 87 | 0.15 |
| 496-11-7 | Indane | | 81 | 0.13 |
| 108-67-8 | Mesitylene | | 95 | 0.11 |
| | Trace Aromatic Hydrocarbons | | | |
| 98-82-8 | Benzene, (1-methylethyl)- | | 87 | 0.100 |
| 102-25-0 | Benzene, 1,3,5-triethyl- | | 92 | 0.075 |
| 4706-90-5 | Benzene, 1,3-dimethyl-5-(1-methylethyl)- | | 90 | 0.072 |
| 135-98-8 | Benzene, (1-methylpropyl)- | | 70 | 0.065 |
| 54340-86-2 | 4-[(E)-but-2-enyl]-1,2-dimethyl-benzene | | 70 | 0.064 |
| 90-12-0 | Naphthalene, 1-methyl- | | 91 | 0.064 |
| 53172-84-2 | Benzene, (1-methyl-1-butenyl)- | | 87 | 0.061 |
| 5161-04-6 | Benzene, 1-methyl-4-(2-methylpropyl)- | | 83 | 0.058 |
| 1595-05-7 | Benzene, 1-methyl-4-butyl- | | 76 | 0.054 |
| 700-12-9 | Benzene, pentamethyl- | | 94 | 0.052 |
| 1680-51-9 | 6-Methyl-(1,2,3,4-tetrahydronaphthalene) | | 96 | 0.048 |
| 1560-06-1 | Benzene, 2-butenyl- | | 93 | 0.048 |
| 1074-17-5 | Benzene, 1-methyl-2-propyl- | | 90 | 0.041 |
| 4481-30-5 | Benzene, (1,2-dimethylpropyl)- | | 64 | 0.039 |
| 30704-01-3 | Benzene, (1,3-dimethyl-2-butenyl)- | | 74 | 0.034 |
| 40650-41-7 | 1H-Indene, 2,3-dihydro-1,1,5-trimethyl- | | 91 | 0.033 |
| 91-20-3 | Naphthalene | | 93 | 0.033 |
| 877-44-1 | Benzene, 1,2,4-triethyl- | | 93 | 0.029 |
| 3877-19-8 | 2-Methyl-(1,2,3,4-tetrahydronaphthalene) | | 93 | 0.027 |
| 2039-89-6 | Benzene, 2-ethenyl-1,4-dimethyl- | | 94 | 0.027 |
| 2049-95-8 | Benzene, (1,1-dimethylpropyl)- | | 83 | 0.026 |

FIG. 46 CONT

| CAS # | Compound Name | Br# | Q | Area % |
|---|---|---|---|---|
| 30316-36-0 | 1,6,8-trimethyltetralin | | 80 | 0.023 |
| 1000370-34-1 | 3,4-Dimethylcumene | | 91 | 0.020 |
| 35669-88-0 | 1,4-dimethyl-2-(2-methylpropyl)benzene | | 81 | 0.019 |
| 13065-07-1 | 2,7-dimethyltetralin | | 91 | 0.015 |
| 2717-47-7 | Naphthalene, 1,2-dihydro-6-methyl- | | 64 | 0.014 |
| 7397-06-0 | 4-t-Butyl-o-xylene | | 64 | 0.013 |
| 17059-48-2 | 1H-Indene, 2,3-dihydro-1,6-dimethyl- | | 95 | 0.012 |
| 2613-76-5 | 1H-Indene, 2,3-dihydro-1,1,3-trimethyl- | | 90 | 0.011 |
| 7525-62-4 | Benzene, 1-ethenyl-3-ethyl- | | 70 | 0.010 |
| 78920-29-3 | 7-butylbicyclo[4.2.0]octa-1,3,5-triene | | 64 | 0.010 |
| 767-59-9 | 1H-Indene, 1-methyl- | | 95 | 0.010 |
| 14678-13-1 | 1,3,5-trimethyl-2-prop-1-en-2-yl-benzene | | 87 | 0.009 |
| 91-57-6 | Naphthalene, 2-methyl- | | 80 | 0.007 |
| 3379-20-4 | Benzene, 1-ethenyl-3,5-dimethyl- | | 70 | 0.007 |
| 582-16-1 | Naphthalene, 2,7-dimethyl- | | 96 | 0.007 |
| 4175-54-6 | 1,4-dimethyltetralin | | 81 | 0.006 |
| 575-43-9 | Naphthalene, 1,6-dimethyl- | | 83 | 0.005 |
| 1127-76-0 | 1-ethylnaphthalene | | 90 | 0.004 |
| 575-41-7 | Naphthalene, 1,3-dimethyl- | | 64 | 0.003 |
| Major Oxygenated Aromatics | | | | |
| 6148-37-4 | Furan, 4-methyl-2-propyl- | | 86 | 0.11 |
| Trace Oxygenated Aromatics | | | | |
| 2040-07-5 | Ethanone, 1-(2,4,5-trimethylphenyl)- | | 94 | 0.082 |
| 1000188-08-0 | 4,5-Dimethyl-3H-isobenzofuran-1-one | | 64 | 0.015 |
| Major n-Alkenes | | | | |
| 2384-94-3 | 2,4-Heptadiene, (E,E)- | | 80 | 0.44 |
| 627-20-3 | 2-Pentene, (Z)- | | 90 | 0.39 |
| 590-18-1 | 2-Butene, (Z)- | | 87 | 0.23 |
| 109-67-1 | 1-Pentene | | 90 | 0.22 |
| 4050-45-7 | 2-Hexene, (E)- | | 90 | 0.22 |
| 109-68-2 | 2-Pentene | | 90 | 0.20 |
| 624-64-6 | 2-Butene, (E)- | | 87 | 0.19 |
| 7688-21-3 | 2-Hexene, (Z)- | | 93 | 0.10 |
| Trace n-Alkenes | | | | |
| 7642-09-3 | 3-Hexene, (Z)- | | 93 | 0.091 |
| 592-41-6 | 1-Hexene | | 87 | 0.047 |
| 592-77-8 | 2-Heptene | | 94 | 0.046 |
| 592-47-2 | 3-Hexene | | 91 | 0.033 |
| Major Branched Alkenes | | | | |
| 74752-97-9 | 1,3-Hexadiene, 3-ethyl-2-methyl-, (Z)- | 2 | 93 | 0.34 |
| 1000195-03-3 | 6,6-Dimethylhepta-2,4-diene | 2 | 87 | 0.16 |
| 10574-37-5 | 2-Pentene, 3,3-dimethyl- | 2 | 91 | 0.10 |
| 563-79-1 | 2-Butene, 2,3-dimethyl- | 2 | 91 | 0.62 |
| 2738-19-4 | 2-Hexene, 2-methyl- | 1 | 90 | 0.21 |
| 3404-55-5 | 4-Methyl-2-hexene, c&t | 1 | 90 | 0.14 |
| 922-61-2 | 2-Pentene, 3-methyl- | 1 | 94 | 0.68 |
| 763-29-1 | 1-Pentene, 2-methyl- | 1 | 91 | 0.20 |
| 625-27-4 | 2-Pentene, 2-methyl- | 1 | 90 | 0.14 |
| 513-35-9 | 2-Butene, 2-methyl- | 1 | 91 | 1.20 |
| 563-46-2 | 2-Methyl-1-butene | 1 | 91 | 0.46 |
| 115-11-7 | 1-Propene, 2-methyl- | 1 | 91 | 0.34 |
| Trace Branched Alkenes | | | | |

FIG. 46 CONT

| CAS # | Compound Name | Br# | Q | Area % |
|---|---|---|---|---|
| 51504-54-2 | 1,4-Hexadiene, 2,3,4,5-tetramethyl- | 4 | 72 | 0.005 |
| 1000154-09-2 | 1,4-Hexadiene, 3-ethyl-4,5-dimethyl- | 3 | 64 | 0.037 |
| 756-02-5 | 1,4-Pentadiene, 2,3,3-trimethyl- | 3 | 90 | 0.054 |
| 24618-86-8 | 1,3-Heptadiene, 5,5-dimethyl- | 2 | 70 | 0.070 |
| 1515-79-3 | 5,5-Dimethyl-1,3-hexadiene | 2 | 87 | 0.075 |
| 3878-98-8 | 2,4-Hexadiene, 2,3-dimethyl- | 2 | 87 | 0.052 |
| 3404-78-2 | 2-Hexene, 2,3-dimethyl- | 2 | 90 | 0.049 |
| 2213-37-8 | 3,4-Dimethyl-2-hexene | 2 | 64 | 0.053 |
| 625-65-0 | 2-Pentene, 2,4-dimethyl- | 2 | 87 | 0.065 |
| 2213-32-3 | 1-Pentene, 2,4-dimethyl- | 2 | 87 | 0.030 |
| 563-78-0 | 1-Butene, 2,3-dimethyl- | 2 | 90 | 0.100 |
| 4485-16-9 | 3-Heptene, 4-methyl- | 1 | 81 | 0.034 |
| 66225-17-0 | 2-Heptene, 4-methyl-, (E)- | 1 | 62 | 0.024 |
| 34587-27-7 | 1,3,5-Hexatriene, 3-methyl-, (Z)- | 1 | 81 | 0.088 |
| 816-79-5 | 2-Pentene, 3-ethyl- | 1 | 87 | 0.055 |
| 3404-61-7 | 3-Methyl-3-hexene | 1 | 90 | 0.087 |
| 7385-82-2 | 2-Hexene, 5-methyl-, (E)- | 1 | 60 | 0.034 |
| 692-24-0 | 3-Hexene, 2-methyl-, (E)- | 1 | 90 | 0.036 |
| 674-76-0 | 2-Pentene, 4-methyl-, (E)- | 1 | 81 | 0.042 |
| 760-20-3 | 1-Pentene, 3-methyl- | 1 | 90 | 0.052 |
| 691-37-2 | 1-Pentene, 4-methyl- | 1 | 81 | 0.039 |
| 563-45-1 | 1-Butene, 3-methyl- | 1 | 83 | 0.059 |
| Major Cyclic Alkenes | | | | |
| 473-91-6 | Cyclopentene, 1,2,3-trimethyl- | | 91 | 1.27 |
| 7459-71-4 | 3,5-Dimethylcyclopentene | | 86 | 0.65 |
| 1528-22-9 | Cyclobutane, (1-methylethylidene)- | | 90 | 0.46 |
| 97707-87-4 | 1-Ethyl-5-methylcyclopentene | | 94 | 0.33 |
| 693-89-0 | Cyclopentene, 1-methyl- | | 87 | 0.29 |
| 591-49-1 | Cyclohexene, 1-methyl- | | 94 | 0.22 |
| 1674-10-8 | Cyclohexene, 1,2-dimethyl- | | 78 | 0.17 |
| 2808-80-2 | Cyclohexane, 1-methyl-4-methylene- | | 94 | 0.14 |
| 823-17-6 | Cyclohexene, 3,5-dimethyl- | | 94 | 0.13 |
| 8007-96-1 | 1,1-Dimethyl-4-methylenecyclohexane | | 68 | 0.11 |
| 2808-76-6 | 1,3-Dimethyl-1-cyclohexene | | 95 | 0.10 |
| Trace Cyclic Alkenes | | | | |
| 1195-31-9 | 4-Isopropyl-1-methyl-1-cyclohexene, (R)- | | 72 | 0.027 |
| 2539-75-5 | Cyclohexene, 1-propyl- | | 70 | 0.024 |
| 5749-72-4 | Cyclohexane, (1-methylethylidene)- | | 87 | 0.058 |
| 1003-64-1 | Cyclohexane, ethylidene- | | 81 | 0.069 |
| 1462-07-3 | Cyclohexene, 1-(1-methylethyl)- | | 87 | 0.028 |
| 1453-24-3 | Cyclohexene, 1-ethyl- | | 72 | 0.083 |
| 2146-38-5 | 1-Ethylcyclopentene | | 94 | 0.094 |
| 591-47-9 | Cyclohexene, 4-methyl- | | 87 | 0.087 |
| 53170-90-6 | Bicyclo[2.2.1]heptane, 2-(1-buten-3-yl)- | | 64 | 0.083 |
| 694-35-9 | Cyclopentene, 3-ethyl- | | 64 | 0.021 |
| 41158-41-2 | Cyclopentane, 1-methyl-2-methylene- | | 81 | 0.013 |
| 2597-49-1 | Cyclobutane, ethenyl- | | 81 | 0.031 |
| 1759-81-5 | Cyclopentene, 4-methyl- | | 81 | 0.031 |
| 1120-62-3 | Cyclopentene, 3-methyl- | | 87 | 0.059 |
| 142-29-0 | Cyclopentene | | 87 | 0.037 |
| Major n-Alkanes | | | | |
| 109-66-0 | Pentane | | 91 | 1.10 |

FIG. 46 CONT

| CAS # | Compound Name | Br# | Q | Area % |
|---|---|---|---|---|
| 110-54-3 | n-Hexane | | 91 | 0.75 |
| 106-97-8 | Butane | | 87 | 0.74 |
| Trace n-Alkanes | | | | |
| 74-98-6 | Propane | | 86 | 0.017 |
| Major Branched Alkanes | | | | |
| 17301-23-4 | Undecane, 2,6-dimethyl- | 2 | 78 | 0.12 |
| 79-29-8 | Butane, 2,3-dimethyl- | 2 | 86 | 0.16 |
| 2216-34-4 | Octane, 4-methyl- | 1 | 94 | 0.14 |
| 589-81-1 | Heptane, 3-methyl- | 1 | 83 | 0.39 |
| 589-53-7 | Heptane, 4-methyl- | 1 | 93 | 0.23 |
| 592-27-8 | Heptane, 2-methyl- | 1 | 95 | 0.31 |
| 589-34-4 | Hexane, 3-methyl- | 1 | 83 | 1.19 |
| 591-76-4 | Hexane, 2-methyl- | 1 | 94 | 1.01 |
| 96-14-0 | Pentane, 3-methyl- | 1 | 91 | 1.51 |
| 78-78-4 | Butane, 2-methyl- | 1 | 94 | 3.72 |
| 75-28-5 | Isobutane | 1 | 87 | 0.87 |
| Trace Branched Alkanes | | | | |
| 592-13-2 | Hexane, 2,5-dimethyl- | 2 | 60 | 0.014 |
| 565-59-3 | Pentane, 2,3-dimethyl- | 2 | 81 | 0.078 |
| 17301-94-9 | Nonane, 4-methyl- | 1 | 78 | 0.029 |
| Major Cyclic Alkanes | | | | |
| 96-37-7 | Cyclopentane, methyl- | | 91 | 0.91 |
| 2453-00-1 | Cyclopentane, 1,3-dimethyl- | | 90 | 0.48 |
| 2207-03-6 | Cyclohexane, 1,3-dimethyl-, trans- | | 70 | 0.33 |
| 1192-18-3 | Cyclopentane, 1,2-dimethyl-, cis- | | 90 | 0.32 |
| 1640-89-7 | Cyclopentane, ethyl- | | 95 | 0.28 |
| 108-87-2 | Cyclohexane, methyl- | | 94 | 0.25 |
| 2613-65-2 | Cyclopentane, 1-ethyl-3-methyl-, trans- | | 74 | 0.24 |
| 1678-98-4 | Cyclohexane, (2-methylpropyl)- | | 64 | 0.19 |
| 930-89-2 | Cyclopentane, 1-ethyl-2-methyl-, cis- | | 95 | 0.18 |
| 2815-58-9 | Cyclopentane, 1,2,4-trimethyl- | | 90 | 0.18 |
| 6876-23-9 | Cyclohexane, 1,2-dimethyl-, trans- | | 62 | 0.14 |
| 16747-50-5 | Cyclopentane, 1-ethyl-1-methyl- | | 83 | 0.10 |
| Trace Cyclic Alkanes | | | | |
| 4126-78-7 | Cycloheptane, methyl- | | 62 | 0.022 |
| 20536-40-7 | Norbornane, 2,2,3-trimethyl-, endo- | | 83 | 0.021 |
| Major Oxygenates | | | | |
| 60-29-7 | Ethyl ether | | 91 | 1.50 |
| Trace Oxygenates | | | | |
| 432-24-6 | 1-Formyl-2,6,6-trimethyl-2-cyclohexene | | 86 | 0.015 |
| 85136-08-9 | 2,6-Heptadienal, 2,4-dimethyl- | | 72 | 0.022 |
| 141-14-0 | 6-Octen-1-ol, 3,7-dimethyl-, propanoate | | 72 | 0.039 |
| 55440-71-3 | OCTAHYDROPENTALENO(1,2-B)OXIRENE | | 72 | 0.028 |
| 1080163-86-4 | 1,3,5-trimethyl-6-oxabicyclo(3.2.1)octan-7-one | | 72 | 0.018 |
| 78-93-3 | 2-Butanone | | 64 | 0.051 |
| 64-17-5 | Ethanol | | 91 | 0.069 |

FIG. 46 CONT

| CAS # | Compound Name | Br# | Q | Area % |
|---|---|---|---|---|
| | Major Aromatics Hydrocarbons | | | |
| 100-41-4 | Ethylbenzene | | 90 | 0.86 |
| 106-42-3 | p-Xylene | | 97 | 0.82 |
| 108-88-3 | Toluene | | 91 | 0.70 |
| 108-38-3 | Benzene, 1,3-dimethyl- | | 94 | 0.69 |
| 71-43-2 | Benzene | | 91 | 0.58 |
| 1758-88-9 | Benzene, 2-ethyl-1,4-dimethyl- | | 95 | 0.46 |
| 611-14-3 | Benzene, 1-ethyl-2-methyl- | | 94 | 0.39 |
| 1074-55-1 | Benzene, 1-methyl-4-propyl- | | 87 | 0.33 |
| 105-05-5 | Benzene, 1,4-diethyl- | | 97 | 0.27 |
| 622-96-8 | Benzene, 1-ethyl-4-methyl- | | 91 | 0.19 |
| 104-51-8 | Benzene, n-butyl- | | 93 | 0.16 |
| 103-65-1 | Benzene, propyl- | | 83 | 0.10 |
| | Trace Aromatic Hydrocarbons | | | |
| 1074-43-7 | Benzene, 1-methyl-3-propyl- | | 86 | 0.048 |
| 95-63-6 | Benzene, 1,2,4-trimethyl- | | 91 | 0.047 |
| 933-98-2 | Benzene, 1-ethyl-2,3-dimethyl- | | 68 | 0.043 |
| 95-47-6 | o-Xylene | | 90 | 0.043 |
| 934-74-7 | Benzene, 1-ethyl-3,5-dimethyl- | | 91 | 0.040 |
| 13632-94-5 | Benzene, 1,4-diethyl-2-methyl- | | 81 | 0.031 |
| 135-01-3 | Benzene, 1,2-diethyl- | | 64 | 0.021 |
| 1595-05-7 | Benzene, 1-methyl-4-butyl | | 80 | 0.020 |
| 620-14-4 | Benzene, 1-ethyl-3-methyl- | | 86 | 0.009 |
| | Major n-Alkenes | | | |
| 4050-45-7 | 2-Hexene, (E)- | | 90 | 0.47 |
| 14919-01-8 | 3-Octene, (E)- | | 93 | 0.24 |
| 7642-09-3 | 3-Hexene, (Z)- | | 91 | 0.19 |
| 627-20-3 | 2-Pentene, (Z)- | | 90 | 0.16 |
| 592-47-2 | 3-Hexene | | 95 | 0.16 |
| 590-18-1 | 2-Butene, (Z)- | | 81 | 0.13 |
| 624-64-6 | 2-Butene, (E)- | | 64 | 0.12 |
| 592-41-6 | 1-Hexene | | 94 | 0.10 |
| 14686-14-7 | 3-Heptene, (E)- | | 94 | 0.10 |
| | Trace n-Alkenes | | | |
| 646-04-8 | 2-Pentene, (E)- | | 90 | 0.088 |
| 592-77-8 | 2-Heptene | | 93 | 0.062 |
| 13269-52-8 | 3-Hexene, (E)- | | 93 | 0.056 |
| 109-67-1 | 1-Pentene | | 90 | 0.055 |
| 7642-10-6 | (Z)-3-Heptene | | 91 | 0.048 |
| 13389-42-9 | 2-Octene, (E)- | | 90 | 0.035 |
| 111-67-1 | 2-Octene | | 81 | 0.020 |
| | Major Branched Alkenes | | | |
| 616-12-6 | 2-Pentene, 3-methyl-, (E)- | 1 | 94 | 0.27 |
| | Trace Branched Alkenes | | | |
| 3404-80-6 | Hexane, 2-methyl-4-methylene- | 2 | 80 | 0.032 |
| 674-76-0 | 2-Pentene, 4-methyl-, (E)- | 1 | 62 | 0.017 |
| 760-20-3 | 1-Pentene, 3-methyl- | 1 | 91 | 0.022 |
| 563-46-2 | 2-Methyl-1-butene | 1 | 81 | 0.016 |
| 115-11-7 | 1-Propene, 2-methyl- | 1 | 90 | 0.075 |
| | Trace Cyclic Alkenes | | | |
| 53366-54-4 | Cyclopentane, (2-methylbutylidene)- | | 72 | 0.023 |
| 97797-57-4 | 1-Ethyl-5-methylcyclopentene | | 64 | 0.040 |

FIG. 47 CONT

| CAS # | Compound Name | Br# | Q | Area % |
|---|---|---|---|---|
| 1528-21-8 | Ethylidenecyclobutane | | 76 | 0.027 |
| 693-89-0 | Cyclopentene, 1-methyl- | | 74 | 0.029 |
| Major n-Alkanes | | | | |
| 110-54-3 | n-Hexane | | 91 | 15.16 |
| 109-66-0 | Pentane | | 91 | 6.66 |
| 142-82-5 | Heptane | | 95 | 5.86 |
| 106-97-8 | Butane | | 90 | 5.48 |
| 111-84-2 | Nonane | | 95 | 2.09 |
| 124-18-5 | Decane | | 95 | 1.28 |
| 1120-21-4 | Undecane | | 91 | 0.27 |
| Trace n-Alkanes | | | | |
| 74-98-6 | Propane | | 91 | 0.022 |
| Major Branched Alkanes | | | | |
| 2213-23-2 | Heptane, 2,4-dimethyl- | 2 | 78 | 5.91 |
| 583-48-2 | Hexane, 3,4-dimethyl- | 2 | 80 | 0.12 |
| 565-59-3 | Pentane, 2,3-dimethyl- | 2 | 91 | 0.16 |
| 5911-04-6 | Nonane, 3-methyl- | 1 | 91 | 0.87 |
| 5881-17-4 | Octane, 3-ethyl- | 1 | 91 | 0.11 |
| 13860-85-9 | Nonane, 5-methyl- | 1 | 90 | 0.31 |
| 13287-21-3 | Tridecane, 6-methyl- | 1 | 64 | 0.18 |
| 2216-33-3 | Octane, 3-methyl- | 1 | 90 | 0.19 |
| 13860-80-4 | Heptane, 3-ethyl- | 1 | 87 | 0.24 |
| 619-99-8 | Hexane, 3-ethyl- | 1 | 91 | 0.54 |
| 589-53-7 | Heptane, 4-methyl- | 1 | 91 | 0.18 |
| 592-27-8 | Heptane, 2-methyl- | 1 | 90 | 0.11 |
| 589-34-4 | Hexane, 3-methyl- | 1 | 83 | 0.64 |
| 96-14-0 | Pentane, 3-methyl- | 1 | 91 | 4.91 |
| 107-83-5 | Pentane, 2-methyl- | 1 | 78 | 0.31 |
| 78-78-4 | Butane, 2-methyl- | 1 | 90 | 0.61 |
| Trace Branched Alkanes | | | | |
| 56292-65-0 | Dodecane, 2,5-dimethyl- | 2 | 72 | 0.048 |
| 17301-94-9 | Nonane, 4-methyl- | 1 | 72 | 0.083 |
| 2216-34-4 | Octane, 4-methyl- | 1 | 87 | 0.086 |
| 75-28-5 | Isobutane | 1 | 64 | 0.013 |
| Major Cyclic Alkane | | | | |
| 16747-50-5 | Cyclopentane, 1-ethyl-1-methyl- | | 64 | 0.56 |
| 1678-91-7 | Cyclohexane, ethyl- | | 90 | 0.42 |
| 96-37-7 | Cyclopentane, methyl- | | 90 | 0.30 |
| 110-82-7 | Cyclohexane | | 91 | 0.30 |
| 930-89-2 | Cyclopentane, 1-ethyl-2-methyl-, cis- | | 94 | 0.24 |
| 108-87-2 | Cyclohexane, methyl- | | 94 | 0.20 |
| 42994-19-0 | Cyclopropane, 1,2,3-trimethyl- | | 91 | 0.17 |
| Trace Cyclic Alkanes | | | | |
| 1678-98-4 | Cyclohexane, (2-methylpropyl)- | | 78 | 0.031 |
| 13990-93-7 | Trans-1,4-diethylcyclohexane | | 64 | 0.030 |
| 3741-00-2 | Cyclopentane, pentyl- | | 64 | 0.036 |
| 1678-92-8 | Cyclohexane, propyl- | | 64 | 0.020 |
| 1000113-87-1 | trans-1,3-Diethylcyclopentane | | 68 | 0.024 |
| 4926-78-7 | Cyclopentane, 1-ethyl-4-methyl-, cis- | | 80 | 0.029 |
| 295-48-7 | Cyclopentadecane | | 64 | 0.022 |
| 583-57-3 | Cyclohexane, 1,2-dimethyl- (cis/trans) | | 87 | 0.069 |
| 2207-04-7 | Cyclohexane, 1,4-dimethyl-, trans- | | 91 | 0.086 |

FIG. 47 CONT

| CAS # | Compound Name | Br# | Q | Area % |
|---|---|---|---|---|
| 15890-40-1 | 1,2,3-Trimethylcyclopentane, cis, trans | | 81 | 0.026 |
| 872-56-0 | Isopropylcyclobutane | | 64 | 0.020 |
| 1192-18-3 | Cyclopentane, 1,2-dimethyl-, cis- | | 68 | 0.025 |
| 598-61-8 | Cyclobutane, methyl- | | 82 | 0.008 |
| | Major Oxygenates | | | |
| 64-17-5 | Ethanol | | 91 | 29.66 |
| 60-29-7 | Ethyl ether | | 91 | 0.34 |
| 544-01-4 | Diisoamyl ether | | 83 | 0.32 |
| 112-58-3 | Hexane, 1,1'-oxybis- | | 72 | 0.24 |
| 123-72-8 | Butanal | | 64 | 0.13 |
| 141-78-6 | Ethyl Acetate | | 68 | 0.12 |
| 628-81-9 | Butane, 1-ethoxy- | | 64 | 0.10 |
| | Trace Oxygenates | | | |
| 286-45-3 | 8-Oxabicyclo[5.1.0]octane | | 64 | 0.021 |
| 15726-15-5 | 4-Heptanone, 3-methyl- | | 64 | 0.020 |
| 107-87-9 | 2-Pentanone | | 64 | 0.026 |
| 75-07-0 | Acetaldehyde | | 78 | 0.010 |

FIG. 47 CONT

| Description | Method | Test | Result | Units |
|---|---|---|---|---|
| Gasoline 02-Apr-2018 2018-BOST-000276-001 | Sample 01 | | | |
| | ASTM D4052 | API Gravity @ 60°F | 64.7 | °API |
| | ASTM D7039 | Sulfur | < 3.2 | mg/kg |
| | ASTM D3606 | Benzene | < 0.10 | Vol % |
| | ASTM D1298 | Odor | Noncharacteristic | |
| | ASTM E1064 | Water Content | 134 | mg/kg |
| | ASTM D5191-13 | DVPE, EPA | 7.66 | psi |
| | ASTM D4809 | Gross Heat of Combustion | 20834 | Btu/lb |
| | | BTU/gal | 125067 | Btu/gal |
| | ASTM D130 | Copper Corrosion @ 50°C (122°F)/3 hr | 1a | |
| | ASTM D4814-A1 | Corrosion, Silver Strip (3hrs @ 50°C) | 0 | |
| | ASTM D2699 | Research O.N. | 97.8 | |
| | ASTM D2700 | Motor O.N. | 90.9 | |
| | ASTM D4814-X1.4 | Antiknock Index (Octane Rating) | 94.0 | |
| Gasoline 02-Apr-2018 2018-BOST-000276-002 | Sample 02 | | | |
| | ASTM D4052 | API Gravity @ 60°F | 52.0 | °API |
| | ASTM D7039 | Sulfur | < 3.2 | mg/kg |
| | ASTM D3606 | Benzene | 0.32 | Vol % |
| | ASTM D1298 | Odor | Noncharacteristic | |
| | ASTM E1064 | Water Content | 480 | mg/kg |
| | ASTM D5191-13 | DVPE, EPA | 7.38 | psi |
| | ASTM D4809 | Gross Heat of Combustion | 19597 | Btu/lb |
| | | BTU/gal | 125813 | Btu/gal |
| | ASTM D130 | Copper Corrosion @ 50°C (122°F)/3 hr | 1b | |
| | ASTM D4814-A1 | Corrosion, Silver Strip (3hrs @ 50°C) | 0 | |
| | ASTM D2699 | Research O.N. | 97.8 | |
| | ASTM D2700 | Motor O.N. | 84.7 | |
| | ASTM D4814-X1.4 | Antiknock Index (Octane Rating) | 91.2 | |
| Gasoline 02-Apr-2018 2018-BOST-000276-003 | Sample 03 | | | |
| | ASTM D4052 | API Gravity @ 60°F | 53.6 | °API |
| | ASTM D7039 | Sulfur | < 3.2 | mg/kg |
| | ASTM D3606 | Benzene | 0.67 | Vol % |
| | ASTM D1298 | Odor | Noncharacteristic | |
| | ASTM E1064 | Water Content | 223 | mg/kg |
| | ASTM D5191-13 | DVPE, EPA | 10.49 | psi |
| | ASTM D4809 | Gross Heat of Combustion | 20084 | Btu/lb |
| | | BTU/gal | 127674 | Btu/gal |
| | ASTM D130 | Copper Corrosion @ 50°C (122°F)/3 hr | 1a | |
| | ASTM D4814-A1 | Corrosion, Silver Strip (3hrs @ 50°C) | 0 | |

FIG. 48

| Description | Method | Test | Result | Units |
|---|---|---|---|---|
| | ASTM D2699 | Research O.N. | 97.4 | |
| | ASTM D2700 | Motor O.N. | 84.2 | |
| | ASTM D4814-X1.4 | Antiknock Index (Octane Rating) | 90.8 | |
| Gasoline 02-Apr-2018 2018-BOST-000276-004 | Sample D4 | | | |
| | ASTM D4052 | API Gravity @ 60°F | 51.7 | °API |
| | ASTM D7039 | Sulfur | < 3.2 | mg/kg |
| | ASTM D3606 | Benzene | 0.40 | Vol % |
| | ASTM D1296 | Odor | Noncharacteristic | |
| | ASTM E1064 | Water Content | 114 | mg/kg |
| | ASTM D5191-13 | DVPE, EPA | 7.50 | psi |
| | ASTM D4809 | Gross Heat of Combustion | 20161 | Btu/lb |
| | | BTU/gal | 129635 | Btu/gal |
| | ASTM D130 | Copper Corrosion @ 50°C (122°F)/3 hr | 1a | |
| | ASTM D4814-A1 | Corrosion, Silver Strip (3hrs @ 50°C) | 0 | |
| | ASTM D2699 | Research O.N. | 97.6 | |
| | ASTM D2700 | Motor O.N. | 85.0 | |
| | ASTM D4814-X1.4 | Antiknock Index (Octane Rating) | 91.3 | |
| Gasoline 02-Apr-2018 2018-BOST-000276-005 | Sample D5 | | | |
| | ASTM D4052 | API Gravity @ 60°F | 53.5 | °API |
| | ASTM D7039 | Sulfur | < 3.2 | mg/kg |
| | ASTM D3606 | Benzene | 0.66 | Vol % |
| | ASTM D1296 | Odor | Noncharacteristic | |
| | ASTM E1064 | Water Content | 224 | mg/kg |
| | ASTM D5191-13 | DVPE, EPA | 10.87 | psi |
| | ASTM D4809 | Gross Heat of Combustion | 20131 | Btu/lb |
| | | BTU/gal | 128194 | Btu/gal |
| | ASTM D130 | Copper Corrosion @ 50°C (122°F)/3 hr | 1a | |
| | ASTM D4814-A1 | Corrosion, Silver Strip (3hrs @ 50°C) | 0 | |
| | ASTM D2699 | Research O.N. | 97.4 | |
| | ASTM D2700 | Motor O.N. | 85.3 | |
| | ASTM D4814-X1.4 | Antiknock Index (Octane Rating) | 91.4 | |
| Gasoline 02-Apr-2018 2018-BOST-000276-006 | Sample D6 | | | |
| | ASTM D4052 | API Gravity @ 60°F | 61.4 | °API |
| | ASTM D7039 | Sulfur | < 3.2 | mg/kg |
| | ASTM D3606 | Benzene | 0.15 | Vol % |
| | ASTM D1296 | Odor | Noncharacteristic | |
| | ASTM E1064 | Water Content | 1331 | mg/kg |
| | ASTM D5191-13 | DVPE, EPA | 12.88 | psi |
| | ASTM D4809 | Gross Heat of Combustion | 17403 | Btu/lb |
| | | BTU/gal | 106263 | Btu/gal |
| | ASTM D130 | Copper Corrosion @ 50°C (122°F)/3 hr | 1a | |
| | ASTM D4814-A1 | Corrosion, Silver Strip (3hrs @ 50°C) | 0 | |
| | ASTM D2699 | Research Octane Number | No Knock | |
| | ASTM D2700 | Motor Octane Number | No Knock | |

FIG. 48 (CONT.)

| Samples | Composition (Volume%) | | | |
|---|---|---|---|---|
| | Trufuel® | High Octane Gasoline (HOG) | Low Octane Gasoline (LOG) | Cellulosic Ethanol |
| Sample E1 | 0 | 100 (fractions 1, 2 and 3) | 0 | 0 |
| Sample E2 | 0 | 0 | 100 (fractions 1, 2 and 3) | 0 |
| Sample E3 | 0 | 0 | 0 | 100 |
| Sample E4 | 0 | 95 (fractions 1, 2 and 3) | 0 | 5 |
| Sample E5 | 0 | 0 | 95 (fractions 1, 2 and 3) | 5 |
| Sample E6 | 100 | 0 | 0 | 0 |
| Sample E7 | 50 | 50 | 0 | 0 |
| Sample E8 | 50 | 0 | 0 | 50 |

| CAS # | Compound Name | BR # | Q | Area % |
|---|---|---|---|---|
| Major Aromatics Hydrocarbons | | | | |
| 874-41-9 | 1,3-Dimethyl-4-ethylbenzene | | 94 | 2.36 |
| 700-12-9 | Pentamethylbenzene | | 94 | 2.34 |
| 55669-88-0 | 1,4-DIMETHYL-2-ISOBUTYLBENZENE | | 94 | 2.29 |
| 106-42-3 | p-xylene | | 97 | 1.67 |
| 527-84-4 | o-cymene | | 93 | 1.35 |
| 4810-04-2 | 1,3,5-trimethyl-2-propylbenz | | 74 | 1.23 |
| 95-63-6 | pseudocumene | | 94 | 1.05 |
| 90-12-0 | 1-methylnaphtalene | | 95 | 1.03 |
| 1758-88-9 | 1,4-Dimethyl-2-ethylbenzene | | 84 | 1.00 |
| 1074-43-7 | m-Propyltoluene | | 91 | 0.92 |
| 2870-04-4 | m-Xylene, 3-ethyl- | | 94 | 0.85 |
| 2050-24-0 | 1,3-diethyl-5-methylbenzene | | 95 | 0.80 |
| 1074-55-1 | p-Propyltoluene | | 92 | 0.66 |
| 622-96-8 | 4-Ethyltoluene | | 91 | 0.58 |
| 87-85-4 | mellitene | | 94 | 0.56 |
| 934-74-7 | 1,3-dimethyl-5-ethylbenzene | | 94 | 0.54 |
| 105-05-5 | 1,4-diethylbenzene | | 96 | 0.47 |
| 611-14-3 | 2-Ethyltoluene | | 94 | 0.45 |
| 91-20-3 | naphthalene | | 81 | 0.42 |
| 575-43-9 | 1,6-dimethylnaphthalene | | 96 | 0.38 |
| 108-88-3 | toluene | | 87 | 0.38 |
| 1000370-34-1 | 3,4-Dimethylcumene | | 70 | 0.32 |
| 98-51-1 | tbt | | 90 | 0.30 |
| 108-67-8 | mesitylene | | 97 | 0.30 |
| 575-37-1 | 1,7-dimethylnaphthalene | | 95 | 0.26 |
| 582-16-1 | 2,7-dimethylnaphthalene | | 97 | 0.23 |
| 100-41-4 | ethylbenzene | | 91 | 0.18 |
| 103-65-1 | propylbenzene | | 80 | 0.16 |
| 1076-61-5 | 6,7-dimethyltetralin | | 76 | 0.14 |
| 19219-84-2 | 1,3-dimethylbutylbenzene | | 87 | 0.14 |
| 573-98-8 | 1,2-dimethylnaphthalene | | 94 | 0.13 |
| 581-40-8 | Guaien | | 96 | 0.10 |
| Trace Aromatic Hydrocarbons | | | | |
| 575-41-7 | 1,3-dimethylnaphthalene | | 72 | 0.087 |
| 1595-10-4 | 1-hexyl-2-methylbenzene | | 72 | 0.084 |
| 4489-84-3 | 3-methylbut-2-enylbenzene | | 70 | 0.075 |
| 21693-51-6 | 1,5,8-trimethyltetralin | | 80 | 0.074 |
| 829-26-5 | 2,3,6-trimethylnaphthalene | | 80 | 0.063 |
| 933-98-2 | Ethyldimethylbenzene | | 90 | 0.056 |
| Major Oxygenated Aromatics | | | | |
| 1200-14-2 | 4-butylbenzaldehyde | | 80 | 0.67 |
| 4132-79-0 | p-Isopropylphenetole | | 86 | 0.41 |
| 527-35-5 | Durenol | | 70 | 0.21 |
| Branched Alkenes | | | | |
| 13151-29-6 | 4-methyl-1-decene | 1 | 72 | 0.13 |
| Trace Branched Alkenes | | | | |
| 563-46-2 | 2-Methylbutene-1 | 1 | 90 | 0.095 |
| Major Cyclic Alkenes | | | | |
| 7641-77-2 | Dewar benzene, hexamethyl- | | 91 | 1.92 |
| 1000163-57-6 | 1,2-Dimethylspiro[4.4]nona-1,3-diene | | 72 | 0.43 |
| 1000156-99-7 | 3,4-Diethyl-7,7-dimethyl-1,3,5-cycloheptatriene | | 64 | 0.10 |

FIG. 51 CONT

| CAS # | Compound Name | BR # | Q | Area % |
|---|---|---|---|---|
| Major n-Alkanes ||||| 
| 1120-21-4 | undecane | | 95 | 4.13 |
| 112-40-3 | dodecane | | 95 | 3.37 |
| 124-18-5 | decane | | 95 | 3.00 |
| 629-50-5 | tridecane | | 95 | 2.92 |
| 111-84-2 | nonane | | 95 | 1.88 |
| 629-59-4 | tetradecane | | 93 | 1.12 |
| 629-62-9 | pentadecane | | 86 | 0.82 |
| 629-78-7 | heptadecane | | 91 | 0.34 |
| 142-82-5 | heptane | | 94 | 0.28 |
| 544-76-3 | hexadecane | | 80 | 0.23 |
| 110-54-3 | hexane | | 87 | 0.20 |
| Trace n-Alkanes ||||| 
| 109-66-0 | pentane | | 86 | 0.054 |
| 629-92-5 | nonadecane | | 78 | 0.044 |
| 74-84-0 | ethane | | 83 | 0.021 |
| Major Branched Alkanes ||||| 
| 31295-56-4 | 2,6,11-Trimethyldodecane | 3 | 64 | 0.14 |
| 62238-12-4 | 2,3,6-trimethyldecane | 3 | 78 | 0.16 |
| 62185-55-1 | 4-methyl-5-propylnonane | 2 | 78 | 0.80 |
| 26293-65-0 | 2,5-dimethyldodecane | 2 | 64 | 0.49 |
| 13475-78-0 | 2-Methyl-3-ethylheptane | 2 | 78 | 0.15 |
| 589-43-5 | 2,4-dimethylhexane | 2 | 86 | 1.13 |
| 55045-10-8 | 6-propyltridecane | 1 | 80 | 0.13 |
| 6418-41-3 | 3-methyltridecane | 1 | 90 | 0.98 |
| 25117-31-1 | 5-methyltridecane | 1 | 78 | 0.99 |
| 1560-96-9 | 2-methyltridecane | 1 | 72 | 0.40 |
| 17312-58-2 | 3-ethylundecane | 1 | 90 | 0.87 |
| 17453-94-0 | 5-ethylundecane | 1 | 83 | 1.14 |
| 1002-43-3 | 3-methylundecane | 1 | 87 | 3.37 |
| 2980-69-0 | 4-methylundecane | 1 | 78 | 0.44 |
| 1632-70-8 | 5-methylundecane | 1 | 94 | 2.82 |
| 1636-44-8 | 4-ethyldecane | 1 | 78 | 0.82 |
| 17312-63-9 | 5-butylnonane | 1 | 86 | 0.69 |
| 2847-72-5 | 4-methyldecane | 1 | 83 | 0.27 |
| 13151-35-4 | 5-methyldecane | 1 | 64 | 0.27 |
| 5911-04-6 | 3-methylnonane | 1 | 94 | 2.30 |
| 5881-17-4 | 3-ethyloctane | 1 | 83 | 0.31 |
| 17301-94-9 | 4-methylnonane | 1 | 93 | 0.23 |
| 15869-85-9 | 5-methylnonane | 1 | 87 | 1.06 |
| 15869-86-0 | 4-ethyloctane | 1 | 83 | 0.71 |
| 2216-33-3 | 3-methyloctane | 1 | 83 | 0.17 |
| 15869-80-4 | 3-ethylheptane | 1 | 72 | 0.24 |
| 2216-34-4 | 4-methyloctane | 1 | 83 | 0.13 |
| 589-81-1 | 3-methylheptane | 1 | 87 | 1.05 |
| Trace Branched Alkanes ||||| 
| 3892-00-0 | 2,6,10-Trimethylpentadecane | 3 | 64 | 0.058 |
| 3891-98-3 | 2,6,10-trimethyldodecane | 3 | 78 | 0.081 |
| 21164-95-4 | 7,9-dimethylhexadecane | 2 | 64 | 0.077 |
| 3384-06-2 | 2,3-dimethylnonane | 2 | 78 | 0.054 |
| 17302-27-1 | 2,5-dimethylnonane | 2 | 64 | 0.080 |
| Major Cyclic Alkanes |||||

FIG. 51 CONT

| CAS # | Compound Name | BK # | Q | Area % |
|---|---|---|---|---|
| 62199-30-3 | 1-butyl-2-propylcyclopentane | | 64 | 0.41 |
| Trace Cyclic Alkanes | | | | |
| 3726-46-3 | 1-ethyl-2-methylcyclopentane | | 68 | 0.091 |
| Major Oxygenates | | | | |
| 64-17-5 | ethanol | | 91 | 2.34 |
| 71-36-3 | 1-butanol | | 91 | 1.47 |
| 88-09-5 | 2-ethylbutyric acid | | 78 | 1.10 |
| 107-92-6 | butyric acid | | 91 | 1.09 |
| 1000309-34-2 | Butyl 6-ethyl-3-octanyl oxalate | | 78 | 0.37 |
| 503-74-2 | 3-methylbutyric acid | | 72 | 0.30 |
| 110225-00-8 | 2-hexyldodecan-1-ol | | 86 | 0.30 |
| 1000309-34-0 | 6-Ethyl-3-octanyl propyl oxalate | | 91 | 0.13 |
| 3913-02-8 | 2-butyl-1-octanol | | 72 | 0.12 |
| Trace Oxygenates | | | | |
| 1000382-34-5 | ethenyl tetradecyl carbonate | | 64 | 0.079 |
| 7289-40-9 | 1-hexoxyheptane | | 64 | 0.039 |

FIG. 51 CONT

| Summary | Total | Known | Major | Trace | Ave Carbon # |
|---|---|---|---|---|---|
| Peaks: | 365 | 274 | 79 | 195 | 8.13 |
| Area: | 8292335382 | 98.5% | 92.0% | 6.5% | |

| Compound Type | Total Known | | Major Components | | Average Carbon # |
|---|---|---|---|---|---|
| | # Peaks | % Area | # Peaks | % Area | |
| Aromatics (Total): | 164 | 82.50 | 55 | 78.74 | 8.67 |
| Oxygenated: | 5 | 0.14 | 0 | 0.00 | 11.05 |
| Alkenes (Total): | 64 | 2.90 | 6 | 1.24 | 5.65 |
| Straight: | 12 | 0.77 | 2 | 0.39 | 4.53 |
| Branched: | 28 | 1.49 | 4 | 0.85 | 5.50 |
| Cyclic: | 24 | 0.65 | 0 | 0.00 | 7.32 |
| Alkanes (Total): | 37 | 12.48 | 15 | 11.55 | 5.19 |
| Straight: | 5 | 3.62 | 5 | 3.62 | 4.41 |
| Branched: | 15 | 7.68 | 7 | 7.36 | 5.31 |
| Cyclic: | 17 | 1.18 | 3 | 0.58 | 6.79 |
| Oxygenated (Other): | 7 | 0.47 | 3 | 0.43 | 6.55 |

| CAS # | Compound Name | Ref# | Q | Area% |
|---|---|---|---|---|
| Major Aromatics Hydrocarbons ||||||
| 108-38-3 | Benzene, 1,3-dimethyl- | | 97 | 16.50 |
| 108-88-3 | Toluene | | 91 | 15.64 |
| 611-14-3 | Benzene, 1-ethyl-2-methyl- | | 94 | 6.56 |
| 526-73-8 | Benzene, 1,2,3-trimethyl- | | 97 | 6.41 |
| 106-42-3 | p-Xylene | | 97 | 5.25 |
| 100-41-4 | Ethylbenzene | | 91 | 3.99 |
| 874-41-9 | Benzene, 1-ethyl-2,4-dimethyl- | | 97 | 3.35 |
| 108-67-8 | Mesitylene | | 91 | 3.24 |
| 71-43-2 | Benzene | | 91 | 2.72 |
| 582-16-1 | Naphthalene, 2,7-dimethyl- | | 97 | 1.48 |
| 90-12-0 | Naphthalene, 1-methyl- | | 91 | 1.26 |
| 95-63-6 | Benzene, 1,2,4-trimethyl- | | 94 | 1.26 |
| 1074-55-1 | Benzene, 1-methyl-4-propyl- | | 94 | 1.02 |
| 824-22-6 | 1H-Indene, 2,3-dihydro-4-methyl- | | 94 | 0.98 |
| 527-84-4 | o-Cymene | | 97 | 0.92 |
| 1074-43-7 | Benzene, 1-methyl-3-propyl- | | 94 | 0.87 |
| 105-05-5 | Benzene, 1,4-diethyl- | | 97 | 0.82 |
| 97664-19-3 | 1-methyl-2-(1-methylallyl)benzene | | 94 | 0.73 |
| 829-26-5 | Naphthalene, 2,3,6-trimethyl- | | 98 | 0.70 |
| 6682-71-9 | 1H-Indene, 2,3-dihydro-4,7-dimethyl- | | 96 | 0.54 |
| 103-65-1 | Benzene, propyl- | | 87 | 0.50 |
| 2245-38-7 | Naphthalene, 1,6,7-trimethyl- | | 98 | 0.41 |
| 581-42-0 | Naphthalene, 2,6-dimethyl- | | 97 | 0.40 |
| 934-80-5 | Benzene, 4-ethyl-1,2-dimethyl- | | 93 | 0.36 |
| 767-58-8 | Indan, 1-methyl- | | 90 | 0.34 |
| 873-49-4 | Benzene, cyclopropyl- | | 87 | 0.31 |
| 1680-51-9 | 6-Methyl-(1,2,3,4-tetrahydronaphthalene) | | 98 | 0.28 |
| 1758-88-6 | Benzene, 2,4-diethyl-1-methyl- | | 95 | 0.27 |
| 939-27-5 | Naphthalene, 2-ethyl- | | 96 | 0.24 |
| 98-82-8 | Benzene, (1-methylethyl)- | | 91 | 0.23 |
| 2049-95-8 | Benzene, (1,1-dimethylpropyl)- | | 83 | 0.23 |
| 91-20-3 | Naphthalene | | 91 | 0.21 |
| 1595-16-0 | Benzene, 1-methyl-4-(1-methylpropyl)- | | 91 | 0.21 |
| 6874-97-6 | 1H-Indene, 4,7-dimethyl- | | 97 | 0.17 |
| 119-64-2 | Naphthalene, 1,2,3,4-tetrahydro- | | 95 | 0.16 |
| 13065-07-1 | 2,7-dimethyltetralin | | 94 | 0.16 |
| 1090370-34-1 | 3,4-Dimethylcumene | | 95 | 0.14 |
| 2050-24-0 | Benzene, 1,3-diethyl-5-methyl- | | 95 | 0.14 |
| 56147-63-8 | 2-Ethyl-2,3-dihydro-1H-indene | | 68 | 0.12 |
| 527-53-7 | Benzene, 1,2,3,5-tetramethyl- | | 95 | 0.12 |
| 3877-19-8 | 2-Methyl-(1,2,3,4-tetrahydronaphthalene) | | 93 | 0.11 |
| 1746-23-2 | 1-(1,1-Dimethylethyl)-4-ethenylbenzene | | 76 | 0.11 |
| Trace Aromatic Hydrocarbons ||||||
| 1595-05-7 | Benzene, 1-methyl-4-butyl- | | 60 | 0.097 |
| 877-44-1 | Benzene, 1,2,4-triethyl- | | 93 | 0.094 |
| 14276-95-0 | 1H-Indene, 2,3-dihydro-1,1,6-trimethyl- | | 93 | 0.091 |
| 56253-64-6 | Benzene, (2-methyl-1-butenyl)- | | 98 | 0.090 |
| 17057-82-8 | 1H-Indene, 2,3-dihydro-1,2-dimethyl- | | 96 | 0.089 |
| 54340-85-1 | Benzene, 1-(2-butenyl)-2,3-dimethyl- | | 86 | 0.089 |
| 941-81-1 | 4,6,8-Trimethylazulene | | 94 | 0.085 |
| 5161-04-6 | Benzene, 1-methyl-4-(2-methylpropyl)- | | 83 | 0.084 |

FIG. 52 CONT

| CAS # | Compound Name | Br# | Q | Area% |
|---|---|---|---|---|
| 102-25-0 | Benzene, 1,3,5-triethyl- | | 60 | 0.082 |
| 14879-13-1 | 1,3,5-trimethyl-2-prop-1-en-2-yl-benzene | | 78 | 0.082 |
| 104-51-8 | Benzene, n-butyl- | | 91 | 0.074 |
| 1127-76-0 | 1-ethylnaphthalene | | 96 | 0.071 |
| 4810-04-2 | Benzene, 1,3,5-trimethyl-2-propyl- | | 87 | 0.068 |
| 42775-75-7 | Naphthalene, 5-ethyl-1,2,3,4-tetrahydro- | | 93 | 0.066 |
| 54774-89-9 | 2-methyl-1-propyl-naphthalene | | 94 | 0.066 |
| 575-41-7 | Naphthalene, 1,3-dimethyl- | | 98 | 0.065 |
| 135-01-3 | Benzene, 1,2-diethyl- | | 93 | 0.062 |
| 13556-58-6 | Naphthalene, 1-ethyl-1,2,3,4-tetrahydro- | | 93 | 0.061 |
| 6682-06-0 | 1H-Indene, 2,3-dihydro-4,5,7-trimethyl- | | 94 | 0.059 |
| 21564-91-0 | 1,5-Dimethyltetralin | | 93 | 0.059 |
| 54340-88-4 | 1H-Indene, 2,3-dihydro-1,5,7-trimethyl- | | 94 | 0.057 |
| 490-65-3 | Naphthalene, 1-methyl-7-(1-methylethyl)- | | 94 | 0.056 |
| 55669-88-0 | 1,4-dimethyl-2-(2-methylpropyl)benzene | | 87 | 0.052 |
| 4706-90-5 | Benzene, 1,3-dimethyl-5-(1-methylethyl)- | | 90 | 0.050 |
| 54340-87-3 | 1H-Indene, 2,3-dihydro-1,4,7-trimethyl- | | 94 | 0.047 |
| 2765-18-6 | 1-propylnaphthalene | | 91 | 0.045 |
| 4481-30-5 | Benzene, (1,2-dimethylpropyl)- | | 87 | 0.045 |
| 2717-39-7 | 1,4,5,8-Tetramethylnaphthalene | | 94 | 0.043 |
| 938-93-2 | Benzene, (2-methylpropyl)- | | 87 | 0.042 |
| 4132-72-3 | Benzene, 1,4-dimethyl-2-(1-methylethyl)- | | 87 | 0.038 |
| 529-05-5 | Chamazulene | | 95 | 0.037 |
| 2613-76-5 | 1H-Indene, 2,3-dihydro-1,1,3-trimethyl- | | 94 | 0.037 |
| 769-57-3 | Benzene, (1,2-dimethyl-1-propenyl)- | | 94 | 0.037 |
| 1000383-71-7 | 4-ethyl-1,6-dimethyl-naphthalene | | 94 | 0.035 |
| 4175-54-6 | 1,4-dimethyltetralin | | 60 | 0.034 |
| 1076-61-5 | 6,7-dimethyltetralin | | 91 | 0.034 |
| 575-43-9 | Naphthalene, 1,6-dimethyl- | | 97 | 0.033 |
| 2177-47-1 | 2-Methylindene | | 92 | 0.031 |
| 933-98-2 | Benzene, 1-ethyl-2,3-dimethyl- | | 95 | 0.028 |
| 828-18-6 | Benzene, 1-pentenyl- | | 64 | 0.028 |
| 17851-27-3 | Benzene, 1-ethyl-2,4,5-trimethyl- | | 70 | 0.026 |
| 1000383-71-2 | 2-Isopropyl-3-methylnaphthalene | | 81 | 0.025 |
| 5557-93-7 | 1-(1-methylethenyl)-2-propan-2-ylbenzene | | 81 | 0.025 |
| 22531-20-4 | Naphthalene, 6-ethyl-1,2,3,4-tetrahydro- | | 83 | 0.023 |
| 32367-54-7 | Naphthalene, 2-ethyl-1,2,3,4-tetrahydro- | | 72 | 0.021 |
| 54340-86-2 | 4-[(E)-but-2-enyl]-1,2-dimethyl-benzene | | 90 | 0.020 |
| 573-98-8 | Naphthalene, 1,2-dimethyl- | | 94 | 0.019 |
| 1483-60-9 | Benzene, 1,3-dimethyl-4-(1-methylpropyl)- | | 90 | 0.018 |
| 95-13-6 | Indene | | 90 | 0.015 |
| 2036-89-6 | Benzene, 2-ethenyl-1,4-dimethyl- | | 93 | 0.015 |
| 1000383-71-8 | 1,6-Dimethyl-3-ethylnaphthalene | | 87 | 0.014 |
| 94410-75-2 | Benzene, 1,2-diethyl-3,4-dimethyl- | | 64 | 0.014 |
| 21693-53-0 | 1,5,7-trimethyltetralin | | 70 | 0.014 |
| 4218-48-8 | Benzene, 1-ethyl-4-(1-methylethyl)- | | 86 | 0.012 |
| 30316-36-0 | 1,6,8-trimethyltetralin | | 89 | 0.012 |
| 605-39-0 | 2,2'-Dimethylbiphenyl | | 60 | 0.011 |
| 300-57-2 | Benzene, 2-propenyl- | | 76 | 0.010 |
| 33930-85-7 | (4,5,5-trimethylcyclopenta-1,3-dien-1-yl)benzene | | 91 | 0.010 |
| 611-43-8 | 1,1'-Biphenyl, 2,3'-dimethyl- | | 94 | 0.009 |
| 1000383-71-3 | 2-Isopropyl-7-methylnaphthalene | | 83 | 0.009 |

FIG. 52 CONT

| CAS # | Compound Name | Br# | Q | Area% |
|---|---|---|---|---|
| 61142-76-5 | 1-Isopropenyl-2,3,4,5-tetramethylbenzene | | 78 | 0.008 |
| 3031-15-0 | Naphthalene, 1,2,3,4-tetramethyl- | | 94 | 0.008 |
| 1000152-22-4 | Cyclopentene, 1,2-dimethyl-4-methylene-3-phenyl- | | 81 | 0.008 |
| 2049-94-7 | Benzene, (3-methylbutyl)- | | 87 | 0.008 |
| 1000294-91-1 | 2-(2,2-dimethylcyclopropyl)ethynylbenzene | | 72 | 0.007 |
| 2131-42-2 | Naphthalene, 1,4,6-trimethyl- | | 81 | 0.007 |
| 768-00-3 | Benzene, (1-methyl-1-propenyl)-, (E)- | | 90 | 0.005 |
| | Trace Oxygenated Aromatics | | | |
| 36052-28-5 | (8-methyltetralin-1-yl)methanol | | 90 | 0.061 |
| 53568-05-1 | 8-hydroxytetralin-2-one | | 60 | 0.043 |
| 35322-84-0 | 3,4,7-trimethyl-2,3-dihydroinden-1-one | | 90 | 0.016 |
| 6148-37-4 | Furan, 4-methyl-2-propyl- | | 72 | 0.013 |
| 41002-74-8 | 1-Acenaphthylenol, 1,2-dihydro-1-methyl- | | 70 | 0.005 |
| | Major n-Alkenes | | | |
| 590-18-1 | 2-Butene, (Z)- | | 90 | 0.22 |
| 624-64-6 | 2-Butene, (E)- | | 81 | 0.17 |
| 109-67-1 | 1-Pentene | | 91 | 0.12 |
| | Trace n-Alkenes | | | |
| 106-98-9 | 1-Butene | | 90 | 0.090 |
| 646-04-8 | 2-Pentene, (E)- | | 91 | 0.080 |
| 592-43-8 | 2-Hexene | | 91 | 0.042 |
| 7642-09-3 | 3-Hexene, (Z)- | | 94 | 0.027 |
| 7688-21-3 | 2-Hexene, (Z)- | | 91 | 0.021 |
| 6443-92-1 | (Z)-2-Heptene | | 87 | 0.011 |
| 592-41-6 | 1-Hexene | | 90 | 0.010 |
| | Major Branched Alkenes | | | |
| 563-79-1 | 2-Butene, 2,3-dimethyl- | 2 | 91 | 0.16 |
| 616-12-6 | 2-Pentene, 3-methyl-, (E)- | 1 | 94 | 0.14 |
| 513-35-9 | 2-Butene, 2-methyl- | 1 | 91 | 0.39 |
| 563-46-2 | 2-Methyl-1-butene | 1 | 91 | 0.29 |
| 115-11-7 | 1-Propene, 2-methyl- | 1 | 91 | 0.30 |
| | Trace Branched Alkenes | | | |
| 756-02-5 | 1,4-Pentadiene, 2,3,3-trimethyl- | 3 | 78 | 0.017 |
| 1515-79-3 | 3,5-Dimethyl-1,3-hexadiene | 2 | 86 | 0.015 |
| 3404-78-2 | 2-Hexene, 2,5-dimethyl- | 2 | 64 | 0.015 |
| 7145-20-2 | 2-Hexene, 2,3-dimethyl- | 2 | 72 | 0.014 |
| 10574-37-5 | 2-Pentene, 2,3-dimethyl- | 2 | 91 | 0.021 |
| 4914-92-5 | 2-Pentene, 3,4-dimethyl-, (E)- | 2 | 81 | 0.018 |
| 2213-32-3 | 1-Pentene, 2,4-dimethyl- | 2 | 83 | 0.008 |
| 2080-89-9 | 1,4-Hexadiene, 3-ethyl- | 1 | 64 | 0.019 |
| 816-79-5 | 2-Pentene, 3-ethyl- | 1 | 72 | 0.010 |
| 2738-19-4 | 2-Hexene, 2-methyl- | 1 | 91 | 0.048 |
| 3404-61-3 | 3-Methyl-3-hexene | 1 | 91 | 0.012 |
| 3404-55-5 | 4-Methyl-2-hexene, c&t | 1 | 91 | 0.037 |
| 15840-60-5 | 3-Hexene, 2-methyl-, (Z)- | 1 | 91 | 0.009 |
| 763-29-1 | 1-Pentene, 2-methyl- | 1 | 90 | 0.040 |
| 625-27-4 | 2-Pentene, 2-methyl- | 1 | 87 | 0.008 |
| 674-76-0 | 2-Pentene, 4-methyl-, (E)- | 1 | 91 | 0.029 |
| 760-20-3 | 1-Pentene, 3-methyl- | 1 | 93 | 0.010 |
| | Major Cyclic Alkenes | | | |
| 473-91-6 | Cyclopentene, 1,2,3-trimethyl- | | 91 | 0.19 |
| 19037-73-3 | Cyclopentene, 4,4-dimethyl- | | 80 | 0.12 |

FIG. 52 CONT

| CAS # | Compound Name | Br # | Q | Area % |
|---|---|---|---|---|
| | Trace Cyclic Alkenes | | | |
| 89656-98-4 | Cyclohexane, (2-methyl-1-propenyl)- | | 72 | 0.016 |
| 1453-24-3 | Cyclohexene, 1-ethyl- | | 72 | 0.013 |
| 97797-57-4 | 1-Ethyl-5-methylcyclopentene | | 87 | 0.017 |
| 2808-80-2 | Cyclohexane, 1-methyl-4-methylene- | | 86 | 0.024 |
| 2808-79-9 | Cyclohexene, 1,4-dimethyl- | | 90 | 0.018 |
| 19780-56-4 | Methyl ethyl cyclopentene | | 81 | 0.020 |
| 591-47-9 | Cyclohexene, 4-methyl- | | 90 | 0.013 |
| 591-49-1 | Cyclohexene, 1-methyl- | | 87 | 0.051 |
| 2146-38-5 | 1-Ethylcyclopentene | | 87 | 0.024 |
| 1528-21-8 | Ethylidenecyclobutane | | 74 | 0.009 |
| 693-89-0 | Cyclopentene, 1-methyl- | | 87 | 0.077 |
| 7459-71-4 | 3,5-Dimethylcyclopentene | | 83 | 0.004 |
| 4372-94-5 | Cyclopropane, 1,1-dimethyl-2-methylene- | | 83 | 0.008 |
| 1120-62-3 | Cyclopentene, 3-methyl- | | 87 | 0.017 |
| 142-29-0 | Cyclopentene | | 91 | 0.011 |
| | Major n-Alkanes | | | |
| 106-97-8 | Butane | | 90 | 1.68 |
| 109-66-0 | Pentane | | 91 | 0.98 |
| 74-98-6 | Propane | | 91 | 0.51 |
| 110-54-3 | n-Hexane | | 91 | 0.32 |
| 142-82-5 | Heptane | | 93 | 0.13 |
| | Major Branched Alkanes | | | |
| 589-43-5 | Hexane, 2,4-dimethyl- | 2 | 64 | 0.12 |
| 589-34-4 | Hexane, 3-methyl- | 1 | 81 | 0.30 |
| 591-76-4 | Hexane, 2-methyl- | 1 | 91 | 0.32 |
| 96-14-0 | Pentane, 3-methyl- | 1 | 91 | 0.67 |
| 107-83-5 | Pentane, 2-methyl- | 1 | 64 | 1.08 |
| 78-78-4 | Butane, 2-methyl- | 1 | 91 | 2.90 |
| 75-28-5 | Isobutane | 1 | 86 | 1.88 |
| | Trace Branched Alkanes | | | |
| 592-13-2 | Hexane, 2,5-dimethyl- | 2 | 72 | 0.008 |
| 565-59-3 | Pentane, 2,3-dimethyl- | 2 | 94 | 0.039 |
| 590-35-2 | Pentane, 2,2-dimethyl- | 2 | 64 | 0.003 |
| 79-29-8 | Butane, 2,3-dimethyl- | 2 | 86 | 0.089 |
| 75-83-2 | Butane, 2,2-dimethyl- | 2 | 78 | 0.012 |
| 2216-34-4 | Octane, 4-methyl- | 1 | 87 | 0.026 |
| 589-53-7 | Heptane, 4-methyl- | 1 | 91 | 0.037 |
| 592-27-8 | Heptane, 2-methyl- | 1 | 95 | 0.089 |
| | Major Cyclic Alkanes | | | |
| 96-37-7 | Cyclopentane, methyl- | | 91 | 0.35 |
| 872-56-0 | Isopropylcyclobutane | | 90 | 0.12 |
| 2813-66-3 | Cyclopentane, 1-ethyl-3-methyl-, cis- | | 93 | 0.11 |
| 2453-00-1 | Cyclopentane, 1,3-dimethyl- | | 87 | 0.11 |
| | Trace Cyclic Alkanes | | | |
| 3726-47-4 | Cyclopentane, 1-ethyl-3-methyl- | | 80 | 0.008 |
| 16747-50-5 | Cyclopentane, 1-ethyl-1-methyl- | | 90 | 0.010 |
| 930-89-2 | Cyclopentane, 1-ethyl-2-methyl-, cis- | | 95 | 0.039 |
| 2207-03-6 | Cyclohexane, 1,3-dimethyl-, trans- | | 87 | 0.019 |
| 4850-28-6 | 1,2,4-Trimethylcyclopentane, cis, trans | | 76 | 0.029 |
| 2815-58-9 | Cyclopentane, 1,2,4-trimethyl- | | 87 | 0.084 |
| 1640-89-7 | Cyclopentane, ethyl- | | 94 | 0.077 |

FIG. 52 CONT

| CAS # | Compound Name | Br# | Q | Area % |
|---|---|---|---|---|
| 108-87-2 | Cyclohexane, methyl- | | 94 | 0.078 |
| 1192-18-3 | Cyclopentane, 1,2-dimethyl-, cis- | | 91 | 0.036 |
| 1638-26-2 | Cyclopentane, 1,1-dimethyl- | | 90 | 0.075 |
| 110-82-7 | Cyclohexane | | 81 | 0.022 |
| 75-19-4 | Cyclopropane | | 90 | 0.037 |
| Major Oxygenates | | | | |
| 67-64-1 | Acetone | | 86 | 0.18 |
| 73992-48-0 | 7-Methoxymethyl-3,7-dimethylcyclohepta-1,3,5-triene | | 72 | 0.14 |
| 4160-82-1 | 4,4-dimethyltetrahydropyran-2,6-quinone | | 64 | 0.11 |
| Trace Oxygenates | | | | |
| 4423-94-3 | Cyclohexanone, 2-ethyl- | | 72 | 0.011 |
| 78-93-3 | 2-Butanone | | 72 | 0.020 |
| 42836-66-8 | 2,2-Dimethylcyclobutanecarboxylic acid | | 64 | 0.006 |
| 60-29-7 | Ethyl ether | | 90 | 0.006 |

FIG. 52 CONT

PROCESSING BIOMASS

CROSS-REFERENCE TO RELATED APPLICATIONS

This application is a continuation of International Patent Application No. PCT/US2018/057878, filed Oct. 26, 2018, titled "Processing Biomass" which claims priority to U.S. Provisional Application No. 62/578,132, filed Oct. 27, 2017, titled "Processing Biomass", U.S. Provisional Application No. 62/641,216, filed Mar. 9, 2018, titled "Processing Biomass", U.S. Provisional Application No. 62/646,204, filed Mar. 21, 2018, titled "Processing Biomass", U.S. Provisional Application No. 62/656,318, filed Apr. 11, 2018, titled "Processing Biomass", U.S. Provisional Application No. 62/660,611, filed Apr. 20, 2018, titled "Processing Biomass", and U.S. Provisional Application No. 62/670,411, filed May 11, 2018, titled "Processing Biomass", the entire contents of each application are incorporated by reference herein in their entirety.

TECHNICAL FIELD

This invention relates to processing biomass into useful products, such as biofuel.

BACKGROUND

Biomass, particularly biomass waste, is abundantly available. It would be useful to derive materials and fuel, such as ethanol, from biomass.

There is presently interest in producing biofuels from a wide variety of feedstocks, in order to provide suitable replacements for fossil fuels. The production of biofuels is desirable because the biosphere is presently overburdened by carbon emissions produced from fossil fuels. The burning of fuels presently contributes to an annual release of 4 billion metric tons of carbon dioxide into the atmosphere and the injection of 2 billion metric tons of carbon dioxide into the world's oceans. By using biomass (an efficient $CO_2$ sequestrator) as the source of fuel, the energy and transportation industries can reduce the release of additional carbon emissions by the mining and refining of fossil fuels.

SUMMARY

In one aspect, a method for producing fuel includes processing a cellulosic and/or lignocellulosic biomass to obtain a feedstock containing one or more saccharide units or saccharide derivative units, and converting the feedstock containing one or more saccharide units or saccharide derivative units, either directly (e.g., by deoxygenation) or through one or more processes (e.g., catalytically, chemically, or biologically) into a fuel (e.g., biofuel).

In one or more embodiments, the saccharide unit includes mono- or disaccharides.

In one or more embodiments, the saccharide unit is processed into an intermediate alcohol using chemical processes and/or catalytic processes.

In one or more embodiments, the intermediate (e.g., an alcohol, ester, acid, hydrocarbon) is processed into a fuel (e.g., biofuel) using one or more catalytic processes.

One of the advantages of the methods described herein is the efficient conversion of biomass to fuel with minimal loss of energy-producing molecular mass. For example, high-value intermediates or building blocks are produced using readily available high-throughput systems such as flow reactors and trickle-bed reactors and cost-effective recyclable catalysts.

In other aspects, the generation of fuel from the processes described herein may further result in lower carbon footprint. Unlike conventional fuels that are mined or drilled, biomass sequesters carbon dioxide from the atmosphere. Green plants and algae use photosynthesis to convert carbon dioxide ($CO_2$) into sugar, cellulose and other carbon-containing carbohydrates that they use for food and growth. Trees, in particular, are able to lock up large amounts of carbon in their wood, and continue to add carbon as they grow. When such biomass is converted into fuel, the process uses sequestered carbon (which may have released some of its carbon back into the atmosphere by normal decay processes anyway, instead of introducing additional carbon from oil, coal and natural gas resources.

In one aspect, the processes described herein provide an improved method of generating transportation fuel, for example, aviation fuel, from biomass. Thus, environment-friendly, low-carbon footprint aviation fuel can be generated by the invention by the catalytic conversion of processed biomass and/or biomass-derived products. Blending ethanol with gasoline is an established to lower carbon footprint of gasoline, but same option is not available for aviation fuel. Thus, aviation fuel will see the benefits of this process because there currently is no alternative available.

In one aspect, provided herein is an improved method of generating fuel comprising catalytic processing of biomass-derived building blocks to produce a hydrocarbon mixture containing a higher amount of higher molecular weight hydrocarbons such as C5-C18 than lower molecular weight hydrocarbons such as C1-C4. In one embodiment, the amount of C1-C4 is less than about 5% by weight.

In one aspect, provided herein is an improved method of generating fuel comprising catalytic processing of biomass-derived building blocks to produce a hydrocarbon mixture containing a higher amount of saturated hydrocarbons such as alkanes and cycloalkanes than unsaturated hydrocarbons such as alkenes and arenes. In one embodiment, the amount of unsaturated hydrocarbons is less than about 30% by weight.

In one aspect, provided herein is an improved method of generating fuel comprising catalytic processing of biomass-derived building blocks to produce a hydrocarbon mixture containing a higher amount of non-aromatic compounds than aromatic compounds. In one embodiment, the amount of aromatic compounds is less than 25% by weight.

In one aspect, provided herein is an improved method of generating fuel comprising catalytic processing of biomass-derived building blocks to produce a hydrocarbon mixture containing a higher amount of even-numbered hydrocarbons than odd-numbered hydrocarbons.

In one aspect, provided herein is an improved method of generating fuel comprising catalytic processing of biomass-derived building blocks to produce a hydrocarbon mixture characterized by one or more of the following characteristics: a higher amount of higher molecular weight hydrocarbons such as C5-C18 than lower molecular weight hydrocarbons such as C1-C4, a higher amount of saturated hydrocarbons such as alkanes and cycloalkanes than unsaturated hydrocarbons such as alkenes and arenes, a higher amount of non-aromatic compounds than aromatic compounds, and a higher amount of even-numbered hydrocarbons than odd-numbered hydrocarbons.

In one aspect, provided herein is a method of generating ethanol from different types of biomass, such that the ethanol generated from one type of biomass may have unique composition and properties compared to that generated from another type of biomass. In one embodiment, described herein is a process of generating ethanol from lignocellulosic biomass that has a unique composition and property compared to ethanol generated from non-lignocellulosic biomass. In one embodiment, described herein is a process of generating ethanol from recalcitrance-reduced biomass, wherein the composition of the ethanol generated from recalcitrance-reduced biomass is different from that of non-recalcitrance-reduced biomass. Also, provided herein is ethanol of unique composition prepared by the processes described herein. In one embodiment, the ethanol composition contains ethanol and about 0.02% acetone, about 0.11 to about 2.5% methanol, about 0.18% n-propanol, about 0.12% of 2-methyl propanol, about 0.01% n-butanol, about 0.53% 2-methyl butanol and about 8.5% isopropyl alcohol. In one aspect, provided herein is a method of converting the ethanol of unique composition described above to other compositions such as hydrocarbons, which are also characterized by unique composition and properties. Thus, in one aspect a product derived from ethanol obtained from one type of biomass may have a different composition and property than a product derived from ethanol obtained from a different type of biomass. For example, a product derived from lignocellulosic ethanol may have a different composition and property than one derived from non-lignocellulosic ethanol. In one embodiment, raw ethanol is used for producing value-added products like hydrocarbons. Raw ethanol is a form of undistilled or partially distilled ethanol. For example, the ethanol generated by the fermentation of biomass-derived materials such as glucose derived from sugars, starch or cellulosic materials may be filtered from the fermentation broth and either subjected to partial distillation or no distillation to produce raw ethanol. The raw ethanol thus produced can be used as the building block for producing value-added products such as hydrocarbons. In some embodiments, the raw ethanol contains about 1% to about 2% water, about 2% to about 3% water, about 3% to about 4% water, about 4% to about 5% water, about 5% to about 6% water, about 6% to about 7% water, about 7% to about 8% water, about 8% to about 9% water, about 9% to about 10% water, about 10% to about 20% water, about 20% to about 30% water, about 30% to about 40% water, about 40% to about 50% water, about 50% to about 60% water, about 60% to about 70% water, about 70% to about 80% water, about 80% to about 90% water by weight, or in a range bounded by any numerical value stated herein above.

In one aspect, provided herein are methods of reducing catalytic deactivation, by either developing deactivation-resistant catalysts or providing methods of regenerating catalysts from deactivated catalysts.

In one aspect, provided herein are methods of catalytically converting biomass-derived ethanol to hydrocarbon fuel in one step, without requiring additional steps such as reforming, blending or hydrogenation.

In one aspect, provided herein are catalytic compositions for efficient conversion of biomass-derived ethanol to hydrocarbon fuel in one step, without requiring additional steps such as reforming, blending or hydrogenation. Also provided are methods of preparing such catalytic compositions. For example, disclosed herein are mono-metallic catalytic compositions such as Ru/HZSM-5 catalysts containing about 0.1-20% of Ru, Pd/HZSM-5 catalysts containing about 0.1-20% of Pd, Pt/HZSM-5 catalysts containing about 0.1-20% of Pt, Pt/$H_3PO_4$—$Al_2O_3$ catalysts containing about 0.1-20% of Pt, and 0.5% Pt/5% $H_3BO_3$—$Al_2O_3$ containing 0.1-20% of Pt. Also, disclosed are bi-metallic catalytic compositions such as Pt—Sn/$Al_2O_3$ catalysts containing about 0.1-20% Pt (w/w) and about 0.1-20% Sn (w/w), Pt—Bi/$Al_2O_3$ catalysts containing about 0.1-20% Pt (w/w) and about 0.1-20% Bi (w/w), and Pt—Ba/$Al_2O_3$ catalysts containing about 0.1-20% Pt (w/w) and about 0.1-20% Ba (w/w). Additionally, disclosed herein are tri-metallic catalyst compositions such as Pt—Sn—Re/$Al_2O_3$ catalysts containing about 0.1-20% Pt (w/w), about 0.1-20% Sn and about 0.1-20% Re (w/w), Pt—Sn—Bi/$Al_2O_3$ catalysts containing about 0.1-20% Pt (w/w), about 0.1-20% Sn and about 0.1-20% Bi (w/w), and Pt—Sn—Ba/$Al_2O_3$ catalysts containing about 0.1-20% Pt (w/w), about 0.1-20% Sn and about 0.1-20% Ba (w/w).

In one aspect, provided herein are methods of catalytically converting biomass-derived ethanol to hydrocarbon fuel in one step, wherein the hydrocarbon mixture contains a higher amount of liquid hydrocarbon than gaseous hydrocarbon at standard temperature and pressure. For example, in one embodiment, the hydrocarbon mixture produced by the processes described herein contains greater than about 10% (w/w), greater than about 20% (w/w), greater than about 30% (w/w), greater than about 40% (w/w), greater than about 50% (w/w), greater than about 60% (w/w), greater than about 70% (w/w), greater than about 80% (w/w), or greater than about 90% (w/w) of liquid hydrocarbon at standard temperature and pressure.

In one aspect, provided herein are methods of catalytically converting biomass-derived ethanol to hydrocarbon fuel in one step, wherein the largest amount of nonhydrocarbon by-product is water.

The inventors of the present invention developed catalytic compositions that provide high yields of higher molecular hydrocarbons. By mixing metals which were known to provide high yield of lower molecular weight hydrocarbons with other low-activity metals, the inventors of the present invention have developed catalytic compositions, which unexpectedly provided high yields of higher molecular hydrocarbons.

The disclosed methods provide several advantages. For example, they allow for the direct conversion of alcohols, such as ethanol, to fuel such as BTEX, gasoline, kerosene, and jet fuel in a single step without reforming, blending or hydrogenation. In one embodiment, they provide a safer process by using inert gases such as nitrogen as the carrier gas. Efficient conversion to hydrocarbon fuel products were achieved by the processes described herein because they produced a higher amount liquid hydrocarbon than gaseous hydrocarbon at standard temperature and pressure. Furthermore, the processes disclosed herein are environment-friendly because the largest hydrocarbon by-product is water.

In one aspect, provided herein is an unblended cellulosic-biomass derived gasoline, wherein the unblended gasoline has a research octane number of greater than about 87, as determined by ASTM D2699. The unblended cellulosic-biomass derived gasoline is the liquid produced by the process described herein without further mixing or blending. And, in some embodiments, the unblended cellulosic-biomass derived gasoline comprises a liquid produced by the processes described herein, that has been further distilled in the gasoline distillation range of 900 F to 4100 F. In one embodiment, the unblended cellulosic-biomass derived gasoline is generated by a process, which involves catalytic conversion.

In another aspect, provided herein is a method of producing fuel comprising: receiving harvested cellulosic-biomass;

treating the cellulosic-biomass in a facility with an electron beam sufficient to reduce its recalcitrance; saccharifying the recalcitrance-reduced biomass to produce sugars and unsaccharified biomass; fermenting the sugars to produce fuel; combusting the fuel in a vehicle; generating heat and power from a portion of the unsaccharified biomass in the facility and using the remaining unprocessed unsaccharified biomass as animal feed; wherein the method has a Global Warming Potential (GWP) in $gCO_2$ eq/MJ at least about 25% less in comparison to fuel generation from starch-derived ethanol, sugar-derived ethanol or regular gasoline mixture.

In one aspect, provided herein is a method for preparing unblended cellulosic gasoline comprising: treating a lignocellulosic biomass with a beam of electrons and saccharifying the irradiated biomass to produce sugars; fermenting the sugars with a microorganism to produce one or more alcohols; and catalytically converting the one or more alcohols in a reactor into a hydrocarbon mixture having a fraction boiling at a range of about 35° C. to about 200° C., thereby producing an unblended cellulosic gasoline, wherein the unblended cellulosic gasoline has an octane number of greater than 60 as determined by ASTM D2699.

In one aspect, provided herein is a hydrocarbon fuel, such as a gasoline, a diesel fuel or a jet fuel, having greater than 50 percent biogenic carbon, as measured using ASTM D6866-18. In some embodiments, the hydrocarbon fuel, such as a blended or an unblended fuel, is greater than 81 percent biogenic carbon, such as greater than 82, 83, 84, 85, 86, 87 or higher, such as greater than 90, 91, 92, 95, 97, 98 or higher, such as greater than 99 percent. The hydrocarbon fuel can be made, for example, by passing an alcohol through a zeolite. In one aspect, the hydrocarbon fuel can directly be used by different types of engines, such as a 2-cycle, 4-cycle, spark plug ignition, glow plug ignition, rotary engine, high compression ignition engines, as well as car engines, prop plane engines, jet engines, lawn mower engines, leaf blower engines, or any other engines that can be configured to run on the unblended cellulosic gasoline described herein.

In one aspect, provided herein is an E80/HOG fuel composition made of about 80% cellulosic ethanol and about 20% of cellulose-derived high-octane gasoline (HOG) in volume. The E80/HOG has a biogenic carbon content of about 100%. According to certain embodiments, less than about 0.01% of motor cleaning agent (such as a deposit control additive) by volume is added to the E80/HOG fuel composition before used in a commercial vehicle. In some embodiments, the percentage is of the motor cleaning agent is much lower than 0.01% such as about 0.002% by volume.

In one aspect, provided herein is a method for preparing the cellulosic ethanol used in the E80/HOG fuel. The method of preparation includes first treating ground corn cobs with electron beam radiation and saccharifying the irradiated ground corn cob to produce sugars. Then the sugars are fermented with active dry yeast capable of generating ethanol.

Also provided is a method of producing cellulosic biomass-derived jet fuel by the catalytic conversion of cellulosic ethanol produced by the methods described herein over catalysts such as the 0.5% Pt-0.25% Re/$\gamma$-$Al_2O_3$ catalyst. In one embodiment, the jet fuel contained about 25% of aromatic hydrocarbons, about 2.5% of alkenes, about 41% of alkanes, and about 8.5% of oxygenated compounds (wt./wt.).

In another aspect, provided herein is a method of generating hydrocarbons from blends of ethanol with longer chain alcohols, branched chain alcohols, esters, aldehydes and ketones. It has been found that higher yields can be obtained if, in addition to ethanol, higher alcohols, branched alcohols, esters and ketones are blended into the ethanol, for example, using greater that about 5% (w/w), 10% (w/w), 15% (w/w), 20% (w/w), 30% (w/w), 40% (w/w) or 50% (w/w) of the longer chain alcohols, branched chain alcohols, esters, aldehydes and ketones.

BRIEF DESCRIPTION OF THE DRAWINGS

The invention is described with reference to the drawings, which is presented for the purpose of illustration and in not intended to be limiting of the invention, and in which:

FIG. 17A shows the element-profile of a fresh, unused Pt-based catalyst. FIG. 17B is shows the element-profile of the same catalyst after it has been used for catalytic conversion.

FIGS. 18A and 18A-2 provide a graphical description of the product distribution of aromatics, alkenes, alkanes and oxygenates of various carbon content in the hydrocarbon mixture generated by the catalytic processing of biomass-derived ethanol produced by the processes described in this application. The biomass-derived ethanol was converted to hydrocarbons in the presence of HZSM-5 catalyst, at a temperature of 350° C., pressure of 500 psig and volumetric linear flow rate (LFR) of 0.125 mL/min. The graph shows the percentage amounts (vertical axis) of aromatics, alkenes, alkanes and of oxygenates containing C2-C18 hydrocarbons (horizontal axis) formed by the catalytic conversion of ethanol. For example, the HZSM-5 catalyzed reaction produced hydrocarbons of average carbon number 8.76, containing about 94.02% aromatics, 0.44% alkenes, 3.38% alkanes and 0.03% oxygenates as determined by total ion chromatography peak area. FIGS. 18B and 18B-2 provide a graphical description of the product distribution of aromatics, alkenes, alkanes and oxygenates of various carbon content in the hydrocarbon mixture generated by the catalytic processing of biomass-derived ethanol produced by the processes described in this application. The biomass-derived ethanol was converted to hydrocarbons in the presence of 0.5% Ru/HZSM-5 catalyst, at a temperature of 350° C., pressure of 500 psig and volumetric linear flow rate (LFR) of 0.125 mL/min. The resulting hydrocarbons had an average carbon number of 8.57 and contained about 91.13% of aromatics, 0.47% of alkenes, 5.87% of alkanes and 0.03% of oxygenates as determined by total ion chromatography peak area.

FIGS. 18C and 18C-2 provides a graphical description of the product distribution when the same reaction was run at a volumetric linear flow rate (LFR) of 0.1875 mL/min. The resulting hydrocarbons had an average carbon number of 7.78 and contained about 69.08% of aromatics, 4.73% of alkenes, 22.94% of alkanes and 0.97% of oxygenates as determined by total ion chromatography peak area.

FIGS. 19A and 19A-2 provide a graphical description of the product distribution of aromatics, alkenes, alkanes and oxygenates of various carbon content in the hydrocarbon mixture generated by the catalytic processing of biomass-derived ethanol produced by the processes described in this application. The biomass-derived ethanol was converted to hydrocarbons in the presence of 0.5% Pt-0.5% Sn/Al$_2$O$_3$, at a temperature of 350° C., pressure of 500 psig and volumetric linear flow rate (LFR) of 0.125 mL/min. The graph shows the percentage amounts (vertical axis) of aromatics, alkenes, alkanes and of oxygenates containing C2-C18 hydrocarbons (horizontal axis) formed by the catalytic conversion of ethanol. For example, the 0.5% Pt-0.5% Sn/Al$_2$O$_3$ catalyzed reaction produced hydrocarbons of average carbon number 9.2, containing about 44.16% aromatics, 0.51% alkenes, 32.32% alkanes and 0.3% oxygenates as determined by total ion chromatography peak area. FIGS. 19B and 19B-2 provide a graphical description of the product distribution when the same reaction was run at a volumetric linear flow rate (LFR) of 0.1875 mL/min. The resulting hydrocarbons had an average carbon number of 7.11 and contained about 25.59% of aromatics, 10.97% of alkenes, 53.03% of alkanes and 0.86% of oxygenates, as determined by total ion chromatography peak area.

FIGS. 20 and 20A provides a graphical description of the product distribution of aromatics, alkenes, alkanes and oxygenates of various carbon content in the hydrocarbon mixture generated by the catalytic processing of biomass-derived ethanol produced by the processes described in this application. The biomass-derived ethanol was converted to hydrocarbons in the presence of 0.5% Pt-0.5% Bi/Al$_2$O$_3$, at a temperature of 350° C., pressure of 500 psig and volumetric linear flow rate (LFR) of 0.125 mL/min. The graph shows the percentage amounts (vertical axis) of aromatics, alkenes, alkanes and of oxygenates containing C2-C18 hydrocarbons (horizontal axis) formed by the catalytic conversion of ethanol. For example, the 0.5% Pt-0.5% Bi/Al$_2$O$_3$ catalyzed reaction produced hydrocarbons of average carbon number 7.14, containing about 17.08% aromatics, 11.09% alkenes, 53.62% alkanes and 6.66% oxygenates, as determined by total ion chromatography peak area.

FIGS. 21A and 21A-2 provide a graphical description of the product distribution of aromatics, alkenes, alkanes and oxygenates of various carbon content in the hydrocarbon mixture generated by the catalytic processing of biomass-derived ethanol produced by the processes described in this application. The biomass-derived ethanol was converted to hydrocarbons in the presence of 0.5% Pt-0.75% Ba/Al$_2$O$_3$, at a temperature of 350° C., pressure of 500 psig and volumetric linear flow rate (LFR) of 0.125 mL/min. The graph shows the percentage amounts (vertical axis) of aromatics, alkenes, alkanes and of oxygenates containing C2-C18 hydrocarbons (horizontal axis) formed by the catalytic conversion of ethanol. For example, the 0.5% Pt-0.75% Ba/Al$_2$O$_3$ catalyzed reaction produced hydrocarbons of average carbon number 8.22, containing about 12.01% aromatics, 4.97% alkenes, 61.88% alkanes and 15.70% oxygenates, as determined by total ion chromatography peak area. FIGS. 21B and 21B-2 provide a graphical description of the product distribution when the same reaction was run with 0.5% Pt-1.0% Ba/Al$_2$O$_3$ catalyst. The resulting hydrocarbons had an average carbon number of 7.72 and contained about 7.87% of aromatics, 4.05% of alkenes, 76.53% of alkanes and 9.19% of oxygenates, as determined by total ion chromatography peak area.

FIGS. 22A and 22A-2 provide a graphical description of the product distribution of aromatics, alkenes, alkanes and oxygenates of various carbon content in the hydrocarbon mixture generated by the catalytic processing of biomass-derived ethanol produced by the processes described in this application. The biomass-derived ethanol was converted to hydrocarbons in the presence of 0.5% Pt-10% H$_3$PO$_4$—Al$_2$O$_3$, at a temperature of 350° C., pressure of 300 psig and volumetric linear flow rate (LFR) of 0.125 mL/min. The graph shows the percentage amounts (vertical axis) of aromatics, alkenes, alkanes and of oxygenates containing C2-C18 hydrocarbons (horizontal axis) formed by the catalytic conversion of ethanol. For example, the 0.5% Pt-10% H$_3$PO$_4$—Al$_2$O$_3$ catalyzed reaction produced hydrocarbons of average carbon number 8.4, containing about 31.09% aromatics, 3.84% alkenes, 48.64% alkanes and 0.41% oxygenates, as determined by total ion chromatography peak area. FIGS. 22B and 22B-2 provides a graphical description of the product distribution when the same reaction was run at a pressure of 500 psig. The resulting hydrocarbons had an average carbon number of 9.66 and contained about 39.53% of aromatics, 1.6% of alkenes, 45.10% of alkanes and 0.30% of oxygenates, as determined by total ion chromatography peak area. FIGS. 22C and 22C-2 provide a graphical description of the product distribution when the same reaction was run at a pressure of 700 psig. The resulting hydrocarbons had an average carbon number of 8.80 and contained about 30.43% of aromatics, 1.78% of alkenes, 47.27% of alkanes and 1.04% of oxygenates, as determined by total ion chromatography peak area.

FIGS. 23A and 23A-2 provide a graphical description of the product distribution of aromatics, alkenes, alkanes and oxygenates of various carbon content in the hydrocarbon mixture generated by the catalytic processing of biomass-derived ethanol produced by the processes described in this application. The biomass-derived ethanol was converted to hydrocarbons in the presence of 0.5% Pt/5.0% H$_3$BO$_3$—Al$_2$O$_3$, at a temperature of 325° C., pressure of 500 psig and volumetric linear flow rate (LFR) of 0.125 mL/min. The graph shows the percentage amounts (vertical axis) of aromatics, alkenes, alkanes and of oxygenates containing C2-C18 hydrocarbons (horizontal axis) formed by the catalytic conversion of ethanol. For example, the 0.5% Pt/5.0% H$_3$BO$_3$—Al$_2$O$_3$ catalyzed reaction produced hydrocarbons of average carbon number 7.2, containing about 4.67% aromatics, 0.95% alkenes, 91.91% alkanes and 0.05% oxygenates, as determined by total ion chromatography peak area. FIGS. 23B, 23B-2, 23C, 23C-2, 23D, and 23D-2 provide a graphical description of the product distribution when the same reaction was run at a temperature of 350° C., and at a pressure of 300 psig, 500 psig, and 700 psig, respectively. When the reaction was run at a temperature of 350° C., and at a pressure of 300 psig, the resulting hydrocarbons had an average carbon number of 7.7, and contained about 19.24% of aromatics, 1.32% of alkenes, 73.01% of alkanes and 0.31% of oxygenates, as determined by total ion chromatography peak area. When the reaction was run at a temperature of 350° C., and at a pressure of 500 psig, the resulting hydrocarbons had an average carbon number of 8.77, and contained about 19.35% of aromatics, 0.24% of alkenes, 64.81% of alkanes and 4.93% of oxygenates, as determined by total ion chromatography peak area. When the reaction was run at a temperature of 350° C., and at a pressure of 700 psig, the resulting hydrocarbons had an average carbon number of 8.17, and contained about 10.42% of aromatics, 1.37% of alkenes, 81.65% of alkanes and 0.88% of oxygenates, as determined by total ion chromatography peak area.

FIGS. 26 and 26A provides a graphical description of the product distribution of aromatics, alkenes, alkanes and oxygenates of various carbon content in the hydrocarbon mixture generated by the catalytic processing of biomass-derived ethanol when it is catalytically converted to hydrocarbons in the presence of 0.5% Pt-0.5% Sn-0.5% Re/Al$_2$O$_3$, at a temperature of 350° C., pressure of 500 psig and volumetric linear flow rate (LFR) of 0.125 mL/min. The graph shows the percentage amounts (vertical axis) of aromatics, alkenes, alkanes and of oxygenates containing C2-C18 hydrocarbons (horizontal axis) formed by the catalytic conversion of ethanol. The reaction produced hydrocarbons of average carbon number 8.19, containing about 31.47% aromatics, 14.34% alkenes, 31.87% alkanes and 1.53% oxygenates, as determined by total ion chromatography peak area.

FIG. 35 provides the results of analyzing samples of blends of high-octane gasoline of samples C1-C6, described above. The API Gravity @ 60° F. is measured according to ASTM D4052, the Dry Vapor Pressure Equivalent (DVPE) EPA is measured according to ASTM D5191-13, the gross heat of combustion is measured according to ASTM D4809, the research octane number (RON) is measured according to ASTM D2699, the motor octane number (MON) is measured according to ASTM D2700, and the antiknock index or octane rating ((RON+MON)/2) is measured according to D4814-X1.4.

FIG. 36 provides the results of analyzing samples of blends of high-octane gasoline. Sample B1 is Trufuel®; sample B2 is a mixture of 5% (v/v) of high-octane gasoline (HOG) generated by the catalytic processing of biomass-derived ethanol described herein, and 95% (v/v) of Trufuel®; sample B3 is a mixture of 10% (v/v) of high-octane gasoline (HOG) generated by the catalytic processing of biomass-derived ethanol described herein, and 90% (v/v) of Trufuel®; sample B4 is a mixture of 20% (v/v) of high-octane gasoline (HOG) generated by the catalytic processing of biomass-derived ethanol described herein, and 80% (v/v) of Trufuel®; sample B5 is a mixture of 20% (v/v) of high-octane gasoline (HOG) generated by the catalytic processing of biomass-derived ethanol described herein, 75% (v/v) of Trufuel®, and 5% anhydrous ethanol derived from cellulosic-biomass. The Dry Vapor Pressure Equivalent (DVPE) EPA is measured according to ASTM D5191, the gross heat of combustion is measured according to ASTM D4809, the research octane number (RON) is measured according to ASTM D2699, the motor octane number (MON) is measured according to ASTM D2700, and the antiknock index or octane rating ((RON+MON)/2) is measured according to D4814-X1.4.

FIG. 37 provides the results of analyzing samples of blends of low-octane gasoline. Sample 1 is Trufuel®, a commercially available premixed high-octane ethanol-free fuel; sample 2 is a mixture of 5% (v/v) of low-octane gasoline (LOG) generated by the catalytic processing of biomass-derived ethanol described herein, and 95% (v/v) of Trufuel®; sample 3 is a mixture of 10% (v/v) of low-octane gasoline (LOG) generated by the catalytic processing of biomass-derived ethanol described herein, and 90% (v/v) of Trufuel®; sample 4 is a mixture of 20% (v/v) of low-octane gasoline (LOG) generated by the catalytic processing of biomass-derived ethanol described herein, and 80% (v/v) of Trufuel®; sample 5 is a mixture of 20% (v/v) of low-octane gasoline (HOG) generated by the catalytic processing of biomass-derived ethanol described herein, 75% (v/v) of Trufuel®, and 5% anhydrous ethanol derived from cellulosic-biomass. The research octane number (RON) is measured according to ASTM D2699, the motor octane number (MON) is measured according to ASTM D2700, and the antiknock index or octane rating ((RON+MON)/2) is measured according to D4814-X1.4.

FIG. 38 provides a Life Cycle Assessment (LCA) evaluating the Global Warming Potential (GWP) of fuel blends containing ethanol generated from cellulosic-biomass by the processes described herein with US corn grain ethanol, Brazilian sugarcane ethanol and US conventional gasoline. Fuel blends of 100% ethanol (E100) (98.5% ethanol with 2.5% gasoline for denaturing purposes as required by the law), 10% ethanol (E10), 85% ethanol (E85), and conventional gasoline were compared.

FIG. 41 shows the volume percentages and the weight percentages of the fractions within one or more samples described in FIG. 40. FIG. 41 shows that sample D3 is a HOG with about 13.06% (v/v) of Fraction 1b, and about 86.93% (v/v) of Fraction 2b. It also has about 11.89 wt. % of Fraction 1, and about 88.10 wt. % of Fraction 2. Sample D5 is a HOG with about 14.30% (v/v) of Fraction 1, about 93.29% (v/v) of Fraction 2, and about 2.40% (v/v) of Fraction 3. It also has about 11.97 wt. % of Fraction 1, about 85.22 wt. % of Fraction 2, and about 2.70 wt. % of Fraction 3. Lastly, Sample D6 is a LOG with about 12.56% (v/v) of Fraction 1, about 74.89% (v/v) of Fraction 2, and about 4.68% (v/v) of Fraction 3. In addition, it has about 18.61 wt. % of Fraction 1, about 75.71 wt. % of Fraction 2, and about 5.67 wt. % of Fraction 3.

FIG. 48 provides the results of analyzing samples of blends of high-octane gasoline of samples D1-D6, described above. The API Gravity @ 60° F. is measured according to ASTM D4052, the Dry Vapor Pressure Equivalent (DVPE) EPA is measured according to ASTM D5191-13, the gross heat of combustion is measured according to ASTM D4809, the research octane number (RON) is measured according to ASTM D2699, the motor octane number (MON) is measured according to ASTM D2700, the sulfur content is measured according to ASTM D7039, the benzene content is measured according to ASTM D3606, the odor is measured according to ASTM D1296, the water content is measured according to ASTM E1064, the corrosion to copper strips is measured according to ASTM D130, and the corrosion to silver strips is measured according to ASTM D4814-A1, and the antiknock index or octane rating ((RON+MON)/2) is measured according to D4814-X1.4.

FIG. 49 describes the compositions (volume %) of samples E1 to E8. Sample E1 is 100% high-octane gasoline (HOG) generated by the catalytic processing of biomass-derived ethanol described herein; sample E2 is 100% low-octane gasoline (LOG) generated by the catalytic processing of biomass-derived ethanol described herein; sample E3 is 100% cellulosic ethanol generated by the process described herein; sample E4 is a mixture of 95% HOG with 5% of cellulosic ethanol, derived by the process described herein; sample E5 is a mixture of 95% LOG with 5% of cellulosic ethanol, derived by the process described herein; sample E6 is a commercially available gasoline—Trufuel®; sample E7 is a mixture of 50% HOG with 50% Trufuel®; sample E8 is a mixture of 50% cellulosic ethanol, derived by the process described herein, with 50% Trufuel®.

FIG. 50 describes the % biogenic carbon content for samples E1 to E8 as determined by ASTM D6866-18. Samples E1-E5 all have about 100% biogenic carbon content (as a fraction of total carbon). Specifically, sample E1 has about 103.17 pMC; sample E2 has about 101.98 pMC; sample E3 has about 102.72 pMC; sample E4 has about 102.45 pMC; sample E5 has about 102.40 pMC. Sample E6, 100% Trufuel®, has about 0% biogenic carbon content (as a fraction of total carbon), and about 100% of fossil carbon content. Specifically, sample E6 has less than 0.44 pMC. Sample E7 has about 62% biogenic carbon content (as a fraction of total carbon), and about 38% of fossil carbon. Specifically, sample E7 has about 62.59 pMC. Lastly, sample E8 has about 44% biogenic carbon content (as a fraction of total carbon), and about 56% of fossil carbon. Specifically, sample E8 has about 44.40 pMC.

DETAILED DESCRIPTION

Figure 1:
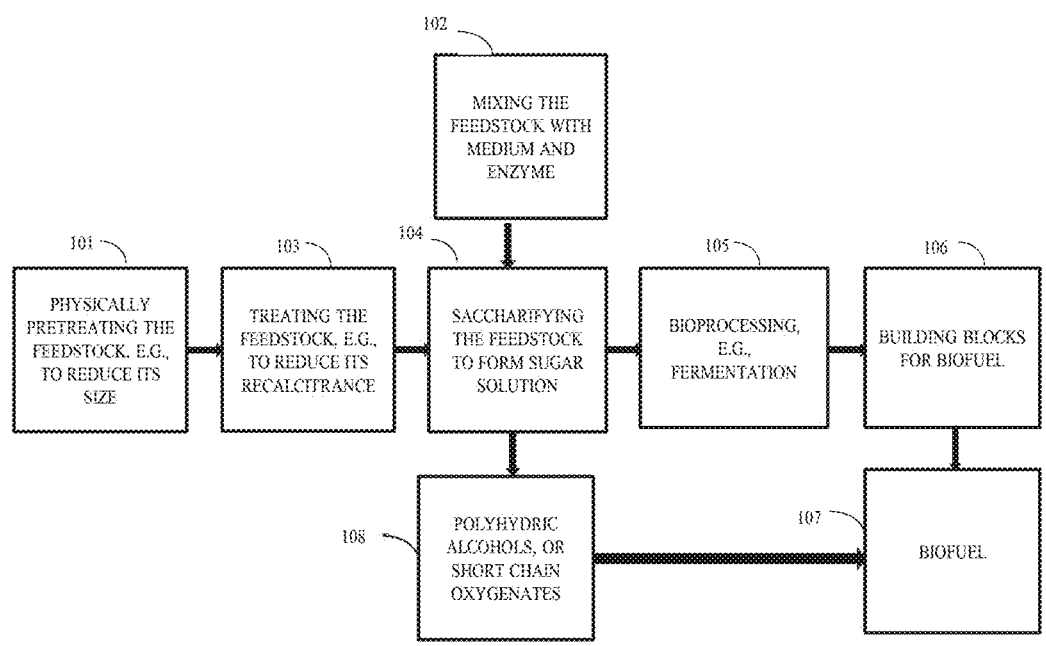
FIG. 1 is a schematic block diagram illustrating the conversion of biomass into products and co-products, including biofuel, according to one or more embodiments.

Carbon-containing materials, such as biomass (e.g., plant biomass, animal biomass, and municipal waste biomass) or coal can be processed to a lower level of recalcitrance (if necessary) and converted into intermediates and products such as those listed by way of examples herein. These intermediate compounds can be further processed into useful products, including fuels. Other products and co-products that can be produced include, for example, human food, animal feed, pharmaceuticals, chemicals, plastics and nutraceuticals.

In one aspect, biomass (e.g., plant biomass, such as those that are or that include one or more low molecular weight sugars, animal biomass, and municipal waste biomass) can be processed to produce useful products such as fuels, e.g., fuels for internal combustion engines, jet engines or feedstocks for fuel cells and for heating oil. Systems and processes are described herein that can use various biomass materials, such as cellulosic materials, lignocellulosic materials, starchy materials or materials that are or that include low molecular weight sugars, as feedstock materials. Such materials are often readily available, but can be difficult to process, e.g., by fermentation, or can give sub-optimal yields at a slow rate. Feedstock materials are first physically prepared for processing, often by size reduction of raw feedstock materials. Physically prepared feedstock can be pretreated or processed using one or more of radiation, sonication, oxidation, pyrolysis, and steam explosion. The feedstock materials can be further processed into sugars, e.g., monosaccharides, disaccharides or other low molecular weight sugars, that can be converted by a microorganism into intermediates that are useful building blocks to fuels. The various pretreatment systems and methods can be used in combinations of two, three, or even four of these technologies.

In some cases, feedstocks that include one or more saccharide units or saccharide derivative units can be treated by any one or more of the processes described herein A saccharide unit as used herein is meant a sugar including monosaccharide, disaccharide, and oligosaccharide sugars. Examples of monosaccharides include glucose (dextrose), fructose, galactose, and ribose. Examples of disaccharides include sucrose and cellobiose. A saccharide derivative unit as used herein is a compound obtained by chemical modification or bioprocessing of a sugar unit, and can include fermentation using microorganisms.

Aviation Fuel

In some embodiments, the final product generated by the invention is aviation gasoline or "avgas." The avgas produced by this invention can be used in various suitable aircrafts, including in aircrafts containing spark-ignited internal-combustion engines. The avgas can consist of chemical blends of hydrocarbons, and additives such as antioxidants and metal deactivators, and fuel dyes. In addition to hydrocarbons such as n-heptanes and isooctanes, avgas can also contain unsaturated hydrocarbons such as olefins, naphthalenes, xylene, mesitylene, and other aromatics, one or more of which are derived from biomass.

The amount of aromatics can vary in the avgas. In some embodiments, Avgas can have 90% or less aromatics, 80% or less aromatics by volume, 70% or less aromatics by volume, 60% or less aromatics by volume, 50% or less aromatics by volume, 40% or less aromatics by volume, 30% or less aromatics by volume, 20% or less aromatics by volume, or 10% or less aromatics by volume. The preferred range for aromatic content in avgas may be 25% or less, by volume. In some embodiments, avgas is limited to mono-aromatics by distillation requirements. In some embodiments, toluene is the only aromatic compound in avgas.

In some embodiments, the avgas contains about 100% pure isooctane, about 95% pure isooctane, about 90% pure isooctane, about 85% pure isooctane, about 80% pure isooctane, about 75% pure isooctane, about 70% pure isooctane, about 65% pure isooctane, about 60% pure isooctane, about 55% pure isooctane, about 50% pure isooctane, about 40% pure isooctane, about 35%, about 30% pure isooctane, about 25% pure isooctane, about 20% pure isooctane, about 15% pure isooctane, about 10% pure isooctane, about 5% pure isooctane. Higher isooctane content (and lower corresponding n-heptane content) is often correlated with a higher octane rating, and hence, preferred.

In some embodiments, the avgas contains about 95% pure n-heptane, about 90% pure n-heptane, about 85% pure n-heptane, about 80% pure n-heptane, about 75% pure n-heptane, about 70% pure n-heptane, about 65% pure n-heptane, about 60% pure n-heptane, about 55% pure n-heptane, about 50% pure n-heptane, about 40% pure n-heptane, about 35%, about 30% pure n-heptane, about 25% pure n-heptane, about 20% pure n-heptane, about 15% pure n-heptane, about 10% pure n-heptane, and about 5% pure n-heptane.

In some embodiments, the avgas can include tetra-ethyl lead, which can potentially improve the anti-knock capabilities of avgas. For example, the avgas produced by this invention can be characterized by varying amounts of lead content, including unleaded avgas, low lead avgas and avgas with high lead content.

The avgas produced by this invention can be of various grades, including different Motor Octane Numbers (MON). In one embodiment, the avgas may have a MON of 100/130, that is 100-octane fuel (or lean setting, usually used for cruising) and a rich setting of 130 (which may be used for take-off and other full-power conditions). Avgas of various grades such as 80/87, 91/96, 91/115, 115/145, 108/135, 82UL, 85UL, 91/96UL, and 100LL may also be produced by this invention, wherein UL refers to unleaded avgas and LL refers to low-lead avgas.

In some embodiments, the avgas can have a minimum smoke point of about 30 mm, about 28 mm, about 26 mm, about 25 mm, about 24 mm, about 22 mm, about 20 mm, about 19 mm, about 18 mm, about 16 mm, and about 15 mm.

The avgas produced by this invention can have a range of density, viscosity, freezing point, volatility and flash point. See Aviation Fuel: Technology Review (2007), available at https://www.cgabusinessdesk.com/document/aviation tech review.pdf.

Biojet Fuel

One of the products that can be produced by this invention is jet fuel. The jet fuel produced by the processes described herein can be used in any aircraft or automotive that is powered by a piston engine, compression ignition engine, or a gas-turbine engine (such as a jet engine, a turboprop engine, aeroderivative gas turbine, turboshaft engine and scale jet engine).

The jet fuel produced by this invention can be a mixture of a large number of different hydrocarbons, such as linear or branched, mono-, and di-substituted $C_7$-$C_{16}$ alkanes, one or more of which is derived from biomass. It may also contain olefins, substituted or unsubstituted cycloalkanes (such as cyclopentanes, cyclohexanes), aromatics (such as benzene, toluene, naphthalenes), mono-substituted aromatics (such as methyl benzene), di-substituted aromatics (such as xylenes), and multi-substituted aromatics (such as trimethylbenzenes), one or more of which is derived from biomass. See https://www.atsdr.cdc.gov/ToxProfiles/tp76-c3.pdf. The jet fuel may further contain nonhydrocarbon compounds such as sulfur compounds, anti-knock additives (such as tetra-ethyl lead), antioxidants, metal deactivators, fuel system icing inhibitors, corrosion inhibitors, and static dissipator additives. Some embodiments may also include combustible oxygen containing components such as esters, and ethers.

In some embodiments, the jet fuel can have about 100-95% saturated hydrocarbons, about 94-90% saturated hydrocarbons, about 89-85% saturated hydrocarbons, about 84-80% saturated hydrocarbons, about 79-75% saturated hydrocarbons, about 74-70% saturated hydrocarbons, about 69-65% saturated hydrocarbons, about 64-60% saturated hydrocarbons, about 59-55% saturated hydrocarbons, about 54-50% saturated hydrocarbons, about 49-45% saturated hydrocarbons, about 44-40% saturated hydrocarbons, about 39-35% saturated hydrocarbons, about 34-30% saturated hydrocarbons, about 29-25% saturated hydrocarbons, about 24-20% saturated hydrocarbons, about 19-15% saturated hydrocarbons, about 14-10% saturated hydrocarbons, about 9-5% saturated hydrocarbons, and about 4-0% saturated hydrocarbons.

In some embodiments, the jet fuel can have about 100-95% aromatic hydrocarbons, about 94-90% aromatic hydrocarbons, about 89-85% aromatic hydrocarbons, about 84-80% aromatic hydrocarbons, about 79-75% aromatic hydrocarbons, about 74-70% aromatic hydrocarbons, about 69-65% aromatic hydrocarbons, about 64-60% aromatic hydrocarbons, about 59-55% aromatic hydrocarbons, about 54-50% aromatic hydrocarbons, about 49-45% aromatic hydrocarbons, about 44-40% aromatic hydrocarbons, about 39-35% aromatic hydrocarbons, about 34-30% aromatic hydrocarbons, about 29-25% aromatic hydrocarbons, about 24-20% aromatic hydrocarbons, about 19-15% aromatic hydrocarbons, about 14-10% aromatic hydrocarbons, about 9-5% aromatic hydrocarbons, and about 4-0% aromatic hydrocarbons.

In some embodiments, the jet fuel can have about 100-95% olefin hydrocarbons, about 94-90% olefin hydrocarbons, about 89-85% olefin hydrocarbons, about 84-80% olefin hydrocarbons, about 79-75% olefin hydrocarbons, about 74-70% olefin hydrocarbons, about 69-65% olefin hydrocarbons, about 64-60% olefin hydrocarbons, about 59-55% olefin hydrocarbons, about 54-50% olefin hydrocarbons, about 49-45% olefin hydrocarbons, about 44-40% olefin hydrocarbons, about 39-35% olefin hydrocarbons, about 34-30% olefin hydrocarbons, about 29-25% olefin hydrocarbons, about 24-20% olefin hydrocarbons, about 19-15% olefin hydrocarbons, about 14-10% olefin hydrocarbons, about 9-5% olefin hydrocarbons, and about 4-0% olefin hydrocarbons.

In one embodiment, the jet fuel may contain 70-85% saturated hydrocarbon, less than 25% aromatic hydrocarbon and less than 5% olefin hydrocarbon. In some embodiments, the jet fuel can have octane rating in the range of 15-25.

The jet fuel produced by this invention can be used in both civilian and military aircrafts. For example, civilian aircrafts may use jet fuels of the type Jet A, Jet A-1 and Jet-B. Jet A-1 is a kerosene grade fuel suitable for most turbine engines and has a flash point of 38° C. and a freezing point of −47° C. Jet A-1 can have 18-25% aromatics and up to 5% olefins by volume. Jet A is a high-purity kerosene-based fuel that has the same flash point and aromatics composition as Jet A-1, but has a higher freezing point, −40° C. Jet B is a distillate covering the naphtha and kerosene fractions, and has a low flash point (between −23 and −1° C.). Jet A-1, Jet A, and Jet B are required to have a minimum smoke point of 25 mm, or 18 mm if they are composed of less than or equal to 3% naphthalene by volume.

The jet fuel developed by this invention can also be military grade jet fuel such as JP-1, JP-2, JP-3, JP-4, JP-5, JP-6, JP-7, JP-8, JP-9, JP-10 and JPTS. For example, JP-8 is the military equivalent of Jet A-1 with the addition of a military fuel additive (such as static dissipater, corrosion inhibitor, lubricity improver, fuel system icing inhibitor, antioxidant and metal deactivators). JP-8 has a freezing point of −47° C. and a flash point of 38° C. JP-8 is required to have a minimum smoke point of 25 mm, or 19 mm if it is composed of 3% or less naphthalene by volume. JP-8 is also required to have a hydrogen content of at least 13.4% by mass. JP-8 can have 0.1-25% aromatics by liquid volume. JP-4 has a freezing point of −46° C. and a flash point between −23 and −1° C. JP-4 can have 10% aromatics by volume. JP-5 is a kerosene-based fuel that has a freezing point of −46° C. and a flash point of 60° C. JP-5 can have 19% aromatics by volume. JP-7 is a mixture composed primarily of hydrocarbons, and has a freezing point of −30° C. and a flash point of 60° C. JP-7 can have 3% aromatics by volume. JPTS or Jet Propellant Thermally Stable fuel has a freezing point of −53° C. and a flash point of 43° C.

Diesel

In some embodiments, the fuel produced by the processes described in this application is diesel. The diesel fuel can be made of a mixture of hydrocarbons, such as $C_8$-$C_{22}$ hydrocarbons, aromatic hydrocarbons and some olefin hydrocarbons, one or more of which is derived from biomass. Additionally, additives such as Alkyl nitrates (e.g., 2-ethylhexyl nitrate) and di-tert-butyl peroxide may be used to raise the cetane number. The cetane number is an indicator of the combustion speed of diesel.

In some embodiments, the diesel fuel can have about 100-95% saturated hydrocarbons, about 94-90% saturated hydrocarbons, about 89-85% saturated hydrocarbons, about 84-80% saturated hydrocarbons, about 79-75% saturated hydrocarbons, about 74-70% saturated hydrocarbons, about 69-65% saturated hydrocarbons, about 64-60% saturated hydrocarbons, about 59-55% saturated hydrocarbons, about 54-50% saturated hydrocarbons, about 49-45% saturated hydrocarbons, about 44-40% saturated hydrocarbons, about 39-35% saturated hydrocarbons, about 34-30% saturated hydrocarbons, about 29-25% saturated hydrocarbons, about 24-20% saturated hydrocarbons, about 19-15% saturated hydrocarbons, about 14-10% saturated hydrocarbons, about 9-5% saturated hydrocarbons, about 4-0% saturated hydrocarbons.

In some embodiments, the diesel fuel can have about 100-95% aromatic hydrocarbons, about 94-90% aromatic hydrocarbons, about 89-85% aromatic hydrocarbons, about 84-80% aromatic hydrocarbons, about 79-75% aromatic hydrocarbons, about 74-70% aromatic hydrocarbons, about 69-65% aromatic hydrocarbons, about 64-60% aromatic hydrocarbons, about 59-55% aromatic hydrocarbons, about 54-50% aromatic hydrocarbons, about 49-45% aromatic hydrocarbons, about 44-40% aromatic hydrocarbons, about 39-35% aromatic hydrocarbons, about 34-30% aromatic hydrocarbons, about 29-25% aromatic hydrocarbons, about 24-20% aromatic hydrocarbons, about 19-15% aromatic hydrocarbons, about 14-10% aromatic hydrocarbons, about 9-5% aromatic hydrocarbons, and about 4-0% aromatic hydrocarbons.

In some embodiments, the diesel can have about 50-45% olefin hydrocarbons, about 44-40% olefin hydrocarbons, about 39-35% olefin hydrocarbons, about 34-30% olefin hydrocarbons, about 29-25% olefin hydrocarbons, about 24-20% olefin hydrocarbons, about 19-15% olefin hydrocarbons, about 14-10% olefin hydrocarbons, about 9-5% olefin hydrocarbons, and about 4-0% olefin hydrocarbons.

In one embodiment, diesel may contain about 75% saturated hydrocarbon, and about 25% aromatic hydrocarbon. In a preferred embodiment, the diesel can have 10% or less aromatic compounds.

The boiling points of the diesel fuel generated by this invention can be in the range of 150 to 380° C.

In some embodiments, the diesel can be a biodiesel, which contains long-chain alkyl esters. For example, biodiesel can be generated by reacting naturally-occurring fatty acids with alcohols generated by fermentation of biomass to produce fatty acid esters. For example, fatty-acid methyl ester (FAME) can be produced by transesterification of fatty acids with methanol. The biodiesel produced by the invention can be used in various biodiesel blends with conventional hydrocarbon-based diesels and is often characterized by their B-factor. For example, 100% biodiesel is referred to as B100, 20% biodiesel, 80% petrodiesel blend is labeled B20, 5% biodiesel, 95% petrodiesel blend is labeled B5, and 2% biodiesel, 98% petrodiesel is labeled as B2.

The diesel produced by this invention can be of any standard diesel fuel grades—Nos. 1-D, 2-D, 4-D—numbered by increasing density and viscosity. For example, 1-D and 2-D grade diesel fuel are used to power diesel automobiles and railroad cars. 4-D is often used to power marine vessels.

In some embodiments, the diesel produced by this invention may have a cetane number (CN) of about 100-95, about 94-90, about 89-80, about 84-80, about 79-75, about 74-70, about 69-65, about 64-60, about 59-55, about 54-50, about 49-45, about 44-40, about 39-35, about 34-30, about 29-25, about 24-20, about 19-15, about 14-10, and about 9-5. The diesel fuel produced by this invention can also be optimized for its density, lubricity, cold-flow properties and sulfur content.

Kerosene

Kerosene can also be produced by the processes described in this invention. The kerosene produced by this invention can consist of straight and branched-chain alkanes containing about 6-16 carbon atoms per molecule, and aromatic compounds and olefins, one or more of which are derived from biomass.

In some embodiments, the kerosene can have about 100-95% saturated hydrocarbons, about 94-90% saturated hydrocarbons, about 89-85% saturated hydrocarbons, about 84-80% saturated hydrocarbons, about 79-75% saturated hydrocarbons, about 74-70% saturated hydrocarbons, about 69-65% saturated hydrocarbons, about 64-60% saturated hydrocarbons, about 59-55% saturated hydrocarbons, about 54-50% saturated hydrocarbons, about 49-45% saturated hydrocarbons, about 44-40% saturated hydrocarbons, about 39-35% saturated hydrocarbons, about 34-30% saturated hydrocarbons, about 29-25% saturated hydrocarbons, about 24-20% saturated hydrocarbons, about 19-15% saturated hydrocarbons, about 14-10% saturated hydrocarbons, about 9-5% saturated hydrocarbons, and about 4-0% saturated hydrocarbons.

In some embodiments, the kerosene can have about 100-95% aromatic hydrocarbons, about 94-90% aromatic hydrocarbons, about 89-85% aromatic hydrocarbons, about 84-80% aromatic hydrocarbons, about 79-75% aromatic hydrocarbons, about 74-70% aromatic hydrocarbons, about 69-65% aromatic hydrocarbons, about 64-60% aromatic hydrocarbons, about 59-55% aromatic hydrocarbons, about 54-50% aromatic hydrocarbons, about 49-45% aromatic hydrocarbons, about 44-40% aromatic hydrocarbons, about 39-35% aromatic hydrocarbons, about 34-30% aromatic hydrocarbons, about 29-25% aromatic hydrocarbons, about 24-20% aromatic hydrocarbons, about 19-15% aromatic hydrocarbons, about 14-10% aromatic hydrocarbons, about 9-5% aromatic hydrocarbons, and about 4-0% aromatic hydrocarbons.

In some embodiments, the kerosene can have about 100-95% olefin hydrocarbons, about 94-90% olefin hydrocarbons, about 89-85% olefin hydrocarbons, about 84-80% olefin hydrocarbons, about 79-75% olefin hydrocarbons, about 74-70% olefin hydrocarbons, about 69-65% olefin hydrocarbons, about 64-60% olefin hydrocarbons, about 59-55% olefin hydrocarbons, about 54-50% olefin hydrocarbons, about 49-45% olefin hydrocarbons, about 44-40% olefin hydrocarbons, about 39-35% olefin hydrocarbons, about 34-30% olefin hydrocarbons, about 29-25% olefin hydrocarbons, about 24-20% olefin hydrocarbons, about 19-15% olefin hydrocarbons, about 14-10% olefin hydrocarbons, about 9-5% olefin hydrocarbons, and about 4-0% olefin hydrocarbons.

In one embodiment, the kerosene may contain about 70% saturated hydrocarbon, less than 25% aromatic hydrocarbon and less than 5% olefin hydrocarbon.

The kerosene produced by the methods described herein can be of 1-K grade, which is a cleaner kerosene that burns with fewer deposits or toxins, or 2-K grade, which can be used for indoor kerosene heaters and stoves. The kerosene can have a boiling point of 150° C. to 300° C., a density of 0.78-0.81 g/cm$^3$, and a flash point between 37 and 65° C., a smoke point between 17-25 mm, an octane rating of 15-25 Anti-knock Index (AKI).

Gasoline

The processes described by the application can also be used to produce gasoline. The gasoline can consist of branched and straight-chain hydrocarbons with 4 to 12 carbon atoms per molecule (such as propane, isobutene, n-butane, n-pentane, n-hexane, methyl-alkanes, dimethyl-alkanes), substituted and un-substituted aromatic compounds (such as xylene, toluene, naphthalene) and olefins (such as butane, pentene), one or more of which are derived from biomass. See http://bcn.boulder.co.us/basin/waterworks/gasolinecomp.pdf. Additives may include oxygenates such as alcohol and ethers, antioxidants (such as butylated hydroxytoluene), antiknock agents (such as tetraethyllead, isooctane, toluene), lead scavengers, nitromethane, picrate, detergents and dyes. Alcohol oxygenates used as additives may include methanol, ethanol, isopropanol, and n-butanol.

The present invention may produce gasolines of different types such as straight-run gasoline (which typically contains some naphthalene and olefins), reformate (which is typically produced in a catalytic reformer and has a high octane rating with high aromatic content and low amount of olefins), catalytic cracked gasoline (also called catalytic cracked naphtha, which is produced from a catalytic cracker, with a moderate octane rating, high olefin (alkene) content, and moderate aromatics level), heavy-, mid-, and high-hydrocrackate (produced from a hydrocracker, with medium to low octane rating and moderate aromatic levels), alkylate (produced in an alkylation unit, using as feedstocks isobutane and alkenes, and contains no aromatics and alkenes and has high MON), isomerate (obtained by isomerizing low octane straight run gasoline to iso-paraffins like isooctane, and has medium RON (research octane number) and MON, but no aromatics and olefins), butane, and blends thereof.

In some embodiments, the gasoline can have about 100-95% saturated hydrocarbons, about 94-90% saturated hydrocarbons, about 89-85% saturated hydrocarbons, about 84-80% saturated hydrocarbons, about 79-75% saturated hydrocarbons, about 74-70% saturated hydrocarbons, about 69-65% saturated hydrocarbons, about 64-60% saturated hydrocarbons, about 59-55% saturated hydrocarbons, about 54-50% saturated hydrocarbons, about 49-45% saturated hydrocarbons, about 44-40% saturated hydrocarbons, about 39-35% saturated hydrocarbons, about 34-30% saturated hydrocarbons, about 29-25% saturated hydrocarbons, about 24-20% saturated hydrocarbons, about 19-15% saturated hydrocarbons, about 14-10% saturated hydrocarbons, about 9-5% saturated hydrocarbons, and about 4-0% saturated hydrocarbons.

In some embodiments, the gasoline can have about 100-95% aromatic hydrocarbons, about 94-90% aromatic hydrocarbons, about 89-85% aromatic hydrocarbons, about 84-80% aromatic hydrocarbons, about 79-75% aromatic hydrocarbons, about 74-70% aromatic hydrocarbons, about 69-65% aromatic hydrocarbons, about 64-60% aromatic hydrocarbons, about 59-55% aromatic hydrocarbons, about 54-50% aromatic hydrocarbons, about 49-45% aromatic hydrocarbons, about 44-40% aromatic hydrocarbons, about 39-35% aromatic hydrocarbons, about 34-30% aromatic hydrocarbons, about 29-25% aromatic hydrocarbons, about 24-20% aromatic hydrocarbons, about 19-15% aromatic hydrocarbons, about 14-10% aromatic hydrocarbons, about 9-5% aromatic hydrocarbons, and about 4-0% aromatic hydrocarbons.

In some embodiments, the gasoline can have about 100-95% olefin hydrocarbons, about 94-90% olefin hydrocarbons, about 89-85% olefin hydrocarbons, about 84-80% olefin hydrocarbons, about 79-75% olefin hydrocarbons, about 74-70% olefin hydrocarbons, about 69-65% olefin hydrocarbons, about 64-60% olefin hydrocarbons, about 59-55% olefin hydrocarbons, about 54-50% olefin hydrocarbons, about 49-45% olefin hydrocarbons, about 44-40% olefin hydrocarbons, about 39-35% olefin hydrocarbons, about 34-30% olefin hydrocarbons, about 29-25% olefin hydrocarbons, about 24-20% olefin hydrocarbons, about 19-15% olefin hydrocarbons, about 14-10% olefin hydrocarbons, about 9-5% olefin hydrocarbons, and about 4-0% olefin hydrocarbons.

In some embodiments, the gasoline contains about 100% pure isooctane, about 95% pure isooctane, about 90% pure isooctane, about 85% pure isooctane, about 80% pure isooctane, about 75% pure isooctane, about 70% pure isooctane, about 65% pure isooctane, about 60% pure isooctane, about 55% pure isooctane, about 50% pure isooctane, about 40% pure isooctane, about 35%, about 30% pure isooctane, about 25% pure isooctane, about 20% pure isooctane, about 15% pure isooctane, about 10% pure isooctane, and about 5% pure isooctane.

In some embodiments, the gasoline contains about 95% pure n-heptane, about 90% pure n-heptane, about 85% pure n-heptane, about 80% pure n-heptane, about 75% pure n-heptane, about 70% pure n-heptane, about 65% pure n-heptane, about 60% pure n-heptane, about 55% pure n-heptane, about 50% pure n-heptane, about 40% pure n-heptane, about 35%, about 30% pure n-heptane, about 25% pure n-heptane, about 20% pure n-heptane, about 15% pure n-heptane, about 10% pure n-heptane, and about 5% pure n-heptane.

In one embodiment, the gasoline is made of about 15% $C_4$-$C_8$ straight-chain alkanes, about 25-40% $C_4$-$C_{10}$ branched alkanes, about 10% cycloalkanes, less than 25% aromatics (benzene less than 1.0%), and about 10% olefins. In some embodiments, gasoline can have a smoke point between 12 and 16 mm, and density of 0.71-0.77 kg/L.

The gasoline produced by the invention described herein can have a wide range of AKI. AKI is the average of research octane number (RON), and motor octane number (MON). For example, the gasoline can have an AKI of about 85, about 86, about 87, about 88, about 89, about 90, about 91, about 92, about 93, about 94, about 95, about 96, about 97, about 98, about 99, about 100, about 101, about 102, about 103, about 104 and about 105.

LPG

One of the fuels produced by the processes described herein is liquefied petroleum gas or liquid petroleum gas (LPG or LP gas). LPG can consist of propane, butane, or other flammable mixtures of hydrocarbons, one or more of which is derived from biomass. In addition, LPG may contain olefins such as propylene, and butylene in small concentrations, one or more of which is derived from biomass. Other additives can include odorants such as ethanediol, tetrahydrothiophene (thiophane) or amyl mercaptan. The LPG can be used as fuel in various systems, including heating appliances, cooking equipment, and vehicles. It can also be used as an aerosol propellant and a refrigerant. When specifically used as a vehicle fuel it is often referred to as autogas.

Heating Oil

Heating oil can also be produced by the processes described herein. Heating oil can consist of hydrocarbons in the C14-C22 range, one or more of which is derived from biomass. Heating oil produced herein can be used to fuel furnaces or boilers in buildings. The heating oil produced by the invention can have several advantages, such as being clean, non-explosive, highly efficient and producing negligible amounts of smoke and soot emissions. Heating oils of different grades can be produced, including those graded 1 through 6. This could also include diesel, such as grade 2 diesel.

RP-1 (Rocket Fuel)

RP-1 also called Rocket Propellant-1 or Refined Petroleum-1, is used as a rocket fuel and can be produced by the methods described herein. RP-1 can be produced by selecting desirable hydrocarbons derived from biomass that increase resistance to thermal breakdown. For example, highly branched and cyclic alkanes are favored over linear alkanes. Alkenes and aromatic compounds are held at very low levels. In one embodiment, RP-1 can have a freezing point of −73° C., density of 0.81-1.02 g/ml and a flash point of 43° C.

BTX

BTX can also be produced by this invention. BTX can contain mixtures of benzene, toluene, and the three xylene isomers, one or more of which is derived from biomass. In some embodiments, ethylbenzene is included, and the mixture is then referred to as BTEX. BTX can be produced by the recovery of aromatic compounds from the processes described herein.

Processing to Prepare Fuels

FIG. 1 shows processes for manufacturing a biofuel, such as any described above. Biofuels can be prepared from sugars and fermentation products from a feedstock (e.g., cellulosic or lignocellulosic materials). In an initial step (101), the method includes, optionally, mechanically treating a cellulosic and/or lignocellulosic feedstock. Before and/or after this treatment, the feedstock can be treated with another physical treatment (103), for example irradiation, sonication, steam explosion, oxidation, pyrolysis or combinations of these, to reduce or further reduce its recalcitrance. A sugar solution e.g., including glucose, xylose and combinations of these, is formed by saccharifying the feedstock (104). The saccharification can be, for example, accomplished efficiently by the addition of one or more enzymes, e.g., cellulases and xylanases (102) and/or one or more acids in any order. The sugar (or saccharide units) can be further processed in step 108 into one or more components of a biofuel. For example, a saccharide can be transformed by catalytic hydrogenation into polyhydric alcohols, or into short chain oxygenates by hydrogenolysis to provide one or more components used in a biofuel.

Alternatively, the sugar solution can be bioprocessed (105), for example by utilizing an organism to ferment the sugars to a primary product, e.g., an alcohol, a carboxylic acid, a ketone, hydrogen and combinations of these to produce an intermediate building block. Optionally, the fermentation can include more than one organism and comprises more than one fermentation step, for example producing one or more products simultaneously or sequentially. Optionally, the fermentation can be selective to one sugar. Optionally, the bioprocessing can include isolation (106) of the intermediate building block, for example by a column extraction, solvent extraction and/or by distillation.

The intermediate building block of the bioprocessing step can be catalytically processed (107) to provide one or more of the components used in a biofuel. For example, an alcohol can be converted to alkenes by dehydration, and then oligomerized into higher olefins. The higher olefins can be subsequently oligomerized and/or hydrogenated to make higher molecular weight alkanes. In another example, a carboxylic acid can be hydrogenated to an alcohol, esterified and/or esterified and then hydrogenated to provide a hydrocarbon component of a biofuel. Catalytic or chemical processing can occur in a batch reactor, or, in a continuous reactor. Optionally, the processing can include isolation of the product for example by a column extraction, solvent extraction and/or by distillation.

In other aspects, the process can be designed to only partially convert the starting alcohol into a fuel. For example, the intermediate building block can be ethanol and the catalyst conversion system can be designed to convert only a portion of the ethanol, for example, by controlling flow rate of alcohol, e.g., ethanol, or reaction temperature over the catalyst bed. In another aspect the process can be designed to convert processed biomass and biomass-derived products into fuel through a catalyst-facilitated process. The resulting product can be a mixture of a hydrocarbon fuel and alcohol, so that no additional blending in needed. In certain embodiments, the final ethanol content can be 10-15% as is required by many regulatory agencies. Ethanol fuel mixtures have "E" numbers which describe the percentage of ethanol fuel in the mixture by volume, for example, E85 is 85% anhydrous ethanol and 15% gasoline. For example, E10, a fuel mixture of 10% anhydrous ethanol and 90% gasoline sometimes called gasohol, can be used in the internal combustion engines of most automobiles. Blends from E20 to E25 have been used in Brazil since the late 1970s. E85 is commonly used in the U.S. and Europe for flexible-fuel vehicles.

Types of Biomass

Generally, any biomass material that is or includes carbohydrates composed entirely of one or more saccharide units or that include one or more saccharide units can be processed by any of the methods described herein. The biomass can be recalcitrant biomass or recalcitrant-reduced biomass. For example, the biomass material can be cellulosic or lignocellulosic materials, or starchy materials, such as kernels of corn, grains of rice or other foods, or materials that are or that include one or more low molecular weight sugars, such as sucrose or cellobiose.

For example, such materials can include paper, paper products, wood, wood-related materials, particle board, grasses, rice hulls, bagasse, cotton, jute, hemp, flax, bamboo, sisal, abaca, straw, corn cobs, rice hulls, coconut hair, algae, seaweed, cotton, synthetic celluloses, or mixtures of any of these. Suitable materials include those listed in the Summary section, above.

Fiber sources include cellulosic fiber sources, including paper and paper products (e.g., polycoated paper and Kraft paper), and lignocellulosic fiber sources, including wood, and wood-related materials, e.g., particle board. Other suitable fiber sources include natural fiber sources, e.g., grasses, rice hulls, bagasse, cotton, jute, hemp, flax, bamboo, sisal, abaca, straw, corn cobs, rice hulls, coconut hair; fiber sources high in α-cellulose content, e.g., cotton; and synthetic fiber sources, e.g., extruded yarn (oriented yarn or un-oriented yarn). Natural or synthetic fiber sources can be obtained from virgin scrap textile materials, e.g., remnants or they can be post-consumer waste, e.g., rags. When paper products are used as fiber sources, they can be virgin materials, e.g., scrap virgin materials, or they can be post-consumer waste. Aside from virgin materials, post-consumer, industrial (e.g., offal), and processing waste (e.g., effluent from paper processing) can also be used as fiber sources. Also, the fiber source can be obtained or derived from human (e.g., sewage), animal or plant wastes. Additional fiber sources have been described in U.S. Pat. Nos. 6,448,307, 6,258,876, 6,207,729, 5,973,035 and 5,952,105.

Examples of biomass include renewable, organic matter, such as plant biomass (defined below), microbial biomass (defined below), animal biomass (e.g., any animal by-product, animal waste, etc.) and municipal waste biomass including any and all combinations of these biomass materials.

Plant biomass and lignocellulosic biomass include organic matter (woody or non-woody) derived from plants, especially matter available on a sustainable basis. Examples include biomass from agricultural or food crops (e.g., sugarcane, sugar beets or corn kernels) or an extract therefrom (e.g., sugar from sugarcane and corn starch from corn), agricultural crop wastes and residues such as corn stover, wheat straw, rice straw, sugar cane bagasse, and the like. Plant biomass further includes, but is not limited to, trees, woody energy crops, wood wastes and residues such as softwood forest thinnings, barky wastes, sawdust, paper and pulp industry waste streams, wood fiber, and the like. Additionally, grass crops, such as switchgrass and the like have potential to be produced on a large-scale as another plant biomass source. For urban areas, the plant biomass feedstock includes yard waste (e.g., grass clippings, leaves, tree clippings, and brush) and vegetable processing waste.

Lignocellulosic feedstock can be plant biomass such as, but not limited to, non-woody plant biomass, cultivated crops, such as, but not limited to, grasses, for example, but not limited to, C4 grasses, such as switchgrass, cord grass, rye grass, miscanthus, reed canary grass, or a combination thereof, or sugar processing residues such as bagasse, or beet pulp, agricultural residues, for example, soybean stover, corn stover, rice straw, rice hulls, barley straw, corn cobs, wheat straw, canola straw, rice straw, oat straw, oat hulls, corn fiber, recycled wood pulp fiber, sawdust, hardwood, for example aspen wood and sawdust, softwood, or a combination thereof. Further, the lignocellulosic feedstock may include cellulosic waste material such as, but not limited to, newsprint, cardboard, sawdust, and the like. Lignocellulosic feedstock may include one species of fiber or alternatively, lignocellulosic feedstock may include a mixture of fibers that originate from different lignocellulosic feedstocks. Furthermore, the lignocellulosic feedstock may comprise fresh lignocellulosic feedstock, partially dried lignocellulosic feedstock, fully dried lignocellulosic feedstock or a combination thereof.

Microbial biomass includes biomass derived from naturally occurring or genetically modified unicellular organisms and/or multicellular organisms, e.g., organisms from the ocean, lakes, bodies of water, e.g., salt water or fresh water, or on land, and that contains a source of carbohydrate (e.g., cellulose). Microbial biomass can include, but is not limited to, for example protists (e.g., animal (e.g., protozoa such as flagellates, amoeboid, ciliates, and sporozoa) and plant (e.g., algae such alveolates, chlorarachniophytes, cryptomonads, euglenids, glaucophytes, haptophytes, red algae, stramenopiles, and viridaeplantae)), seaweed, plankton (e.g., macroplankton, meroplankton, microplankton, nanoplankton, picoplankton, and femptoplankton), phytoplankton, bacteria (e.g., gram positive bacteria, gram negative bacteria, and extremophiles), yeast and/or mixtures of these. In some instances, microbial biomass can be obtained from natural sources, e.g., the ocean, lakes, bodies of water, e.g., salt water or fresh water, or on land. Alternatively, or in addition, microbial biomass can be obtained from culture systems, e.g., large scale dry and wet culture systems.

Animal biomass includes any organic waste material such as animal-derived waste material or excrement or human waste material or excrement (e.g., manure and sewage).

Starchy materials include starch itself, e.g., corn starch, wheat starch, potato starch or rice starch, a derivative of starch, or a material that includes starch, such as an edible food product or a crop. For example, the starchy material can be arracacha, buckwheat, banana, barley, cassava, kudzu, oca, sago, sorghum, regular household potatoes, sweet potato, taro, yams, or one or more beans, such as favas, lentils or peas. Blends of any two or more starchy materials are also starchy materials. In particular embodiments, the starchy material is derived from corn. Various corn starches and derivatives are described in "Corn Starch," Corn Refiners Association (11th Edition, 2006), the contents of which are incorporated herein by reference.

Biomass materials that include low molecular weight sugars can, e.g., include at least about 0.5 percent by weight of the low molecular sugar, e.g., at least about 2, 3, 4, 5, 6, 7, 8, 9, 10, 12.5, 25, 35, 50, 60, 70, 80, 90 or even at least about 95 percent by weight of the low molecular weight sugar. In some instances, the biomass is composed substantially of the low molecular weight sugar, e.g., greater than 95 percent by weight, such as 96, 97, 98, 99 or substantially 100 percent by weight of the low molecular weight sugar.

Biomass materials that include low molecular weight sugars can be agricultural products or food products, such as sugarcane and sugar beets or an extract therefrom, e.g., juice from sugarcane, or juice from sugar beets. Biomass materials that include low molecular weight sugars can be substantially pure extracts, such as raw or crystallized table sugar (sucrose). Low molecular weight sugars include sugar derivatives. For example, the low molecular weight sugars can be oligomeric (e.g., equal to or greater than a 4-mer, 5-mer, 6-mer, 7-mer, 8-mer, 9-mer or 10-mer), trimeric, dimeric, or monomeric. When the carbohydrates are formed of more than a single repeat unit, each repeat unit can be the same or different. Specific examples of low molecular weight sugars include cellobiose, lactose, sucrose, glucose and xylose, along with derivatives thereof. In some instances, sugar derivatives are more rapidly dissolved in solution or utilized by microbes to provide a useful material, such as ethanol or butanol.

In some embodiments, feedstocks are obtained from plants that have been modified with respect to a wild type variety, e.g., by genetic modification or other types of modification, can be processed to produce useful intermediates and products such as those described herein. Such modifications may be for example, by any of the methods described in any patent or patent application referenced herein. As another example, plants may be modified through the iterative steps of selection and breeding to obtain desired traits in a plant. Furthermore, the plants can have had genetic material removed, modified, silenced and/or added with respect to the wild type variety. For example, genetically modified plants can be produced by recombinant DNA methods, where genetic modifications include introducing or modifying specific genes from parental varieties, or, for example, by using transgenic breeding wherein a specific gene or genes are introduced to a plant from a different species of plant and/or bacteria. Another way to create genetic variation is through mutation breeding wherein new alleles are artificially created from endogeneous genes or by exogenous genes.

The advantages of plant modification include, for example, an enhancement of resistance to insects, fungal diseases, and other pests and disease-causing agents; an increased tolerance to herbicides; increased drought resistance; an extended temperature range; enhanced tolerance to poor soil; enhanced stability or shelf-life; a greater yield; larger fruit size; stronger stalks; enhanced shatter resistance; reduced time to crop maturity; more uniform germination times; higher or modified starch production; enhanced nutrient production, such as enhanced steroid, sterol, hormone, fatty acid, glycerol, polyhydroxyalkanoate, amino acid, vitamin and/or protein production; modified lignin content; enhanced cellulose, hemicellulose and/or lignin degradation; inclusion of a phenotype marker to allow qualitative detection (e.g., seed coat color); and modified phytate content. Any feedstock materials derived from these modified plants can also benefit from these many advantages. For example, a feedstock material such as a lignocellulosic material can have better shelf life, be easier to process, have a better land-to-energy conversion ratio, and/or have a better nutritional value to any microbes that are used in processing of the lignocellulosic material. In addition, any feedstock material derived from such plants can be less expensive and/or more plentiful. In some cases, modified plants can be grown in a greater variety of climates and/or soil types, for example in marginal or depleted soils.

In some embodiments, feedstock materials can be obtained from modified plants having an increased resistance to disease. For example, potatoes which have reduced symptoms from the infestation of fungal pathogen *Phytophthora infestans* are discussed in U.S. Pat. No. 7,122,719. A possible advantage of such resistance is that the yield, quality and shelf life of the feedstock materials may be improved.

In some embodiments, feedstock materials can be obtained from modified plants with increased resistance to parasites, for example, by encoding genes for the production of δ-endotoxins as exemplified in U.S. Pat. No. 6,023,013. A possible advantage of such resistance is that the yield, quality and shelf life of the feedstock materials may be improved.

Feedstock materials can also be obtained from modified plants having an increased resistance to herbicides. For example, the alfalfa plant J-101, as described in U.S. Pat. No. 7,566,817, has an increased resistance to glyphosate herbicides. As a further example, modified plants described in U.S. Pat. No. 6,107,549 have an increased resistance to pyridine family herbicides. Furthermore, modified plants described in U.S. Pat. No. 7,498,429 have increased resistance to imidazolinones. A possible advantage of such resistance is that the yield and quality of the feedstock materials may be improved.

In some embodiments, feedstock materials can be obtained from modified plants having an increased stress resistance (for example, water deficit, cold, heat, salt, pest, disease, or nutrient stress). For example, such plants have been described in U.S. Pat. No. 7,674,952. A possible advantage of such resistance is that the yield and quality of the feedstock materials may be improved. Moreover, such plants may be grown in adverse conditions, e.g., marginal or depleted soil or in a harsh climate.

In some embodiments, feedstock materials can be obtained from modified plants with improved characteristics such as larger fruits. Such plants have been described in U.S. Pat. No. 7,335,812. A possible advantage of such resistance is that the yield and quality of the feedstock materials may be improved.

In some embodiments, feedstock materials can be obtained from modified plants with improved characteristics such reduced pod shatter. Such plants have been described in U.S. Pat. No. 7,659,448. A possible advantage of such resistance is that the yield and quality of the feedstock materials may be improved.

In some embodiments, feedstock materials can be obtained from modified plants having enhanced o modified starch content. Such plants have been described in U.S. Pat. No. 6,538,178. A possible advantage of such modification is that the quality of the feedstock is improved.

In some embodiments, feedstock materials can be obtained from modified plants with a modified oil, fatty acid or glycol production. Such plants have been described in U.S. Pat. No. 7,405,344. Fatty acids and oils are excellent substrates for microbial energy-yielding metabolism and may provide an advantage to downstream processing of the feedstock for, for example, fuel production. Fatty acids and oil variation may also be advantageous in changing the viscosity and solubility of various components during downstream processing of the feedstock. The spent feedstock may have a better nutrient mix for use as animal feed or have higher calorie content useful as a direct fuel for burning.

In some embodiments, feedstock materials can be obtained from modified plants with a modified steroid, sterol and hormone content. Such plants have been described in U.S. Pat. No. 6,822,142. A possible advantage is that this may provide a better nutrient mix for microorganisms used in processing of the feedstock. After processing, the spent feedstock may have a better nutrient mix for use as animal feed.

In some embodiments, feedstock materials can be obtained from modified plants with polyhydroxyalkanoate producing ability. Such plants have been described in U.S. Pat. No. 6,175,061. Polyhydroxyalkanoates are a useful energy and carbon reserve for various microorganisms and may be beneficial to the microorganisms used in downstream feedstock processing. Also, since polyhydroxyalkanoate is biodegradable, it may impart advantages by possibly reducing recalcitrance in plant material after an aging period of the stored feedstock. Further downstream, the spent feedstock may have a better nutrient mix for use as animal feed or have higher calorie content useful as a direct fuel for burning.

In some embodiments, feedstock materials can be obtained from modified plants with enhanced amino acid production. Such plants have been described in U.S. Pat. No. 7,615,621. A possible advantage is that this may provide a better nutrient mix for microorganisms used in processing of the feedstock. After processing, the spent feedstock may have a better nutrient mix for use as animal feed.

In some embodiments, feedstock materials can be obtained from modified plants with elevated synthesis of vitamins. Such plants have been described in U.S. Pat. No. 6,841,717. A possible advantage is that this may provide a better nutrient mix for microorganisms used in processing of the feedstock. After processing, the spent feedstock may have a better nutrient mix for use as animal feed.

In some embodiments, feedstock materials can be obtained from modified plants that degrade lignin and cellulose in the plant after harvest. Such plants have been described in U.S. Pat. No. 7,049,485. Feedstock materials can also be obtained from modified plants with modified lignin content. Such plants have been described in U.S. Pat. No. 7,799,906. A possible advantage of such plants is reduced recalcitrance relative to the wild types of the same plants.

In some embodiments, feedstock materials can be obtained from modified plants with a modified phenotype for easy qualitative detection. Such plants have been described in U.S. Pat. No. 7,402,731. A possible advantage is ease of managing crops and seeds for different product streams such as biofuels, building materials and animal feed.

In some embodiments, feedstock materials can be obtained from modified plants with a reduced amount of phytate. Such plants have been described in U.S. Pat. No. 7,714,187. A possible advantage is that this may provide a better nutrient mix for microorganisms used in processing of the feedstock. After processing, the spent feedstock may have a better nutrient mix for use as animal feed.

In some embodiments, the feedstock can be a combination of any of the above-described types of feedstock materials, and any other material. In some embodiments, the above-described biomass can be combined with each other or other biomass non-biological ingredients to provide feedstock material for the processes described herein.

Physical Treatment of Biomass

If the feedstock is to be treated with a physical treatment, the manufacturing facility will be retrofitted to include a physical treatment system. Alternatively, the manufacturing facility may not include this system, and the materials may be physically treated, if necessary, at a remote location. Physical treatment processes can include one or more of any of those described herein, such as mechanical treatment, chemical treatment, irradiation, sonication, oxidation, pyrolysis or steam explosion. Treatment methods can be used in combinations of two, three, four, or even all of these technologies (in any order). When more than one treatment methods are used, the methods can be applied at the same time or at different times. Other processes that change a molecular structure of a biomass feedstock may also be used, alone or in combination with the processes disclosed herein. One or more of the treatment processes described below may be included in the recalcitrance reducing system discussed above. Alternatively, or in addition, other processes for reducing recalcitrance may be included.

Mechanical Treatments

In some cases, methods can include mechanically treating the biomass feedstock. Mechanical treatments include, for example, cutting, milling, pressing, grinding, shearing and chopping. Milling may include, for example, ball milling, hammer milling, rotor/stator dry or wet milling, or other types of milling. Other mechanical treatments include, e.g., stone grinding, cracking, mechanical ripping or tearing, pin grinding or air attrition milling. Mechanical treatment can be advantageous for "opening up," "stressing," breaking and shattering the cellulosic or lignocellulosic materials, making the cellulose of the materials more susceptible to chain scission and/or reduction of crystallinity. The open materials can also be more susceptible to oxidation when irradiated.

In some cases, the mechanical treatment may include an initial preparation of the feedstock as received, e.g., size reduction of materials, such as by cutting, grinding, shearing, pulverizing or chopping. For example, in some cases, loose feedstock (e.g., recycled paper, starchy materials, or switchgrass) is prepared by shearing or shredding.

Alternatively, or in addition, the feedstock material can be physically treated by one or more of the other physical treatment methods, e.g., chemical treatment, radiation, sonication, oxidation, pyrolysis or steam explosion, and then mechanically treated. This sequence can be advantageous since materials treated by one or more of the other treatments, e.g., irradiation or pyrolysis, tend to be more brittle and, therefore, it may be easier to further change the molecular structure of the material by mechanical treatment.

In some embodiments, the feedstock material is in the form of a fibrous material, and mechanical treatment includes shearing to expose fibers of the fibrous material. Shearing can be performed, for example, using a rotary knife cutter. Other methods of mechanically treating the feedstock include, for example, milling or grinding. Milling may be performed using, for example, a hammer mill, ball mill, colloid mill, conical or cone mill, disk mill, edge mill, Wiley mill or grist mill. Grinding may be performed using, for example, a stone grinder, pin grinder, coffee grinder, or burr grinder. Grinding may be provided, for example, by a reciprocating pin or other element, as is the case in a pin mill. Other mechanical treatment methods include mechanical ripping or tearing, other methods that apply pressure to the fibers, and air attrition milling. Suitable mechanical treatments further include any other technique that changes the molecular structure of the feedstock.

If desired, the mechanically treated material can be passed through a screen, e.g., having an average opening size of 1.59 mm or less (1/16 inch, 0.0625 inch). In some embodiments, shearing, or other mechanical treatment, and screening are performed concurrently. For example, a rotary knife cutter can be used to concurrently to shear and screen the feedstock. The feedstock is sheared between stationary blades and rotating blades to provide a sheared material that passes through a screen, and is captured in a bin. The bin can have a pressure below nominal atmospheric pressure, e.g., at least 10 percent below nominal atmospheric pressure, e.g., at least 25 percent below nominal atmospheric pressure, at least 50 percent below nominal atmospheric pressure, or at least 75 percent below nominal atmospheric pressure. In some embodiments, a vacuum source is utilized to maintain the bin below nominal atmospheric pressure.

The cellulosic or lignocellulosic material can be mechanically treated in a dry state (e.g., having little or no free water on its surface), a hydrated state (e.g., having up to ten percent by weight absorbed water), or in a wet state, e.g., having between about 10 percent and about 75 percent by weight water. The fiber source can even be mechanically treated while partially or fully submerged under a liquid, such as water, ethanol or isopropanol. The cellulosic or lignocellulosic material can also be mechanically treated under a gas (such as a stream or atmosphere of gas other than air), e.g., oxygen or nitrogen, or steam.

If desired, lignin can be removed from any feedstock materials that includes lignin. Also, to aid in the breakdown of the materials that include cellulose, the material can be treated prior to or during mechanical treatment or irradiation with heat, a chemical (e.g., mineral acid, base or a strong oxidizer such as sodium hypochlorite) and/or an enzyme. For example, grinding can be performed in the presence of an acid.

Mechanical treatment systems can be configured to produce streams with specific characteristics such as, for example, specific maximum sizes, specific length-to-width, or specific surface areas ratios. Mechanical treatment can increase the rate of reactions or reduce the processing time required by opening up the materials and making them more accessible to processes and/or reagents, such as reagents in a solution. The bulk density of feedstocks can also be controlled using mechanical treatment. For example, in some embodiments, after mechanical treatment the material has a bulk density of less than 0.25 g/cm$^3$, e.g., 0.20 g/cm$^3$, 0.15 g/cm$^3$, 0.10 g/cm$^3$, 0.05 g/cm$^3$ or less, e.g., 0.025 g/cm$^3$. Bulk density is determined using ASTM D1895B. Briefly, the method involves filling a measuring cylinder of known volume with a sample and obtaining a weight of the sample. The bulk density is calculated by dividing the weight of the sample in grams by the known volume of the cylinder in cubic centimeters.

If the feedstock is a fibrous material, the fibers of the mechanically treated material can have a relatively large average length-to-diameter ratio (e.g., greater than 20-to-1), even if they have been sheared more than once. In addition, the fibers of the fibrous materials described herein may have a relatively narrow length and/or length-to-diameter ratio distribution. As used herein, average fiber widths (e.g., diameters) are those determined optically by randomly selecting approximately 5,000 fibers. Average fiber lengths are corrected length-weighted lengths. BET (Brunauer, Emmet and Teller) surface areas are multi-point surface areas, and porosities are those determined by mercury porosimetry.

If the feedstock is a fibrous material, the average length-to-diameter ratio of fibers of the mechanically treated material can be, e.g., greater than 8/1, e.g., greater than 10/1, greater than 15/1, greater than 20/1, greater than 25/1, or greater than 50/1. An average fiber length of the mechanically treated material can be, e.g., between about 0.5 mm and 2.5 mm, e.g., between about 0.75 mm and 1.0 mm, and an average width (e.g., diameter) of the fibrous material can be, e.g., between about 5 µm and 50 µm, e.g., between about 10 µm and 30 µm.

In some embodiments, if the feedstock is a fibrous material, a standard deviation of the fiber length of the mechanically treated material is less than 60 percent of an average fiber length of the mechanically treated material, e.g., less than 50 percent of the average length, less than 40 percent of the average length, less than 25 percent of the average length, less than 10 percent of the average length, less than 5 percent of the average length, or even less than 1 percent of the average length.

In some embodiments, a BET surface area of the mechanically treated material is greater than 0.1 m$^2$/g, e.g., greater than 0.25 m$^2$/g, greater than 0.5 m$^2$/g, greater than 1.0 m$^2$/g, greater than 1.5 m$^2$/g, greater than 1.75 m$^2$/g, greater than 5.0 m$^2$/g, greater than 10 m$^2$/g, greater than 25 m$^2$/g, greater than 35 m$^2$/g, greater than 50 m$^2$/g, greater than 60 m$^2$/g, greater than 75 m$^2$/g, greater than 100 m$^2$/g, greater than 150 m$^2$/g, greater than 200 m$^2$/g, or even greater than 250 m$^2$/g.

A porosity of the mechanically treated material can be, e.g., greater than 20 percent, greater than 25 percent, greater than 35 percent, greater than 50 percent, greater than 60 percent, greater than 70 percent, greater than 80 percent, greater than 85 percent, greater than 90 percent, greater than 92 percent, greater than 94 percent, greater than 95 percent, greater than 97.5 percent, greater than 99 percent, or even greater than 99.5 percent.

In some situations, it can be desirable to prepare a low bulk density material, densify the material (e.g., to make it easier and less costly to transport to another site), and then revert the material to a lower bulk density state. Densified materials can be processed by any of the methods described herein, or any material processed by any of the methods described herein can be subsequently densified, e.g., as disclosed in WO 2008/073186.

Radiation Treatment

One or more radiation processing sequences can be used to process the feedstock, and to provide a structurally modified material which functions as input to further processing steps and/or sequences. Irradiation can, for example, reduce the molecular weight and/or crystallinity of feedstock. In some embodiments, energy deposited in a material that releases an electron from its atomic orbital is used to irradiate the materials. The radiation may be provided by 1) heavy charged particles, such as alpha particles or protons, 2) electrons, produced, for example, in beta decay or electron beam accelerators, or 3) electromagnetic radiation, for example, gamma rays, x rays, or ultraviolet rays. In one approach, radiation produced by radioactive substances can be used to irradiate the feedstock. In some embodiments, any combination in any order or concurrently of (1) through (3) may be utilized. In another approach, electromagnetic radiation (e.g., produced using electron beam emitters) can be used to irradiate the feedstock. The doses applied depend on the desired effect and the particular feedstock. For example, high doses of radiation can break chemical bonds within feedstock components. In some instances when chain scission is desirable and/or polymer chain functionalization is desirable, particles heavier than electrons, such as protons, helium nuclei, argon ions, silicon ions, neon ions, carbon ions, phosphorus ions, oxygen ions or nitrogen ions can be utilized. When ring-opening chain scission is desired, positively charged particles can be utilized for their Lewis acid properties for enhanced ring-opening chain scission. For example, when maximum oxidation is desired, oxygen ions can be utilized, and when maximum nitration is desired, nitrogen ions can be utilized.

In one method, a first material that is or includes cellulose having a first number average molecular weight ($M_{N1}$) is irradiated, e.g., by treatment with ionizing radiation (e.g., in the form of gamma radiation, X-ray radiation, 100 nm to 280 nm ultraviolet (UV) light, a beam of electrons or other charged particles) to provide a second material that includes cellulose having a second number average molecular weight ($M_{N2}$) lower than the first number average molecular weight. The second material (or the first and second material) can be combined with a microorganism (with or without enzyme treatment) that can utilize the second and/or first material or its constituent sugars or lignin to produce a useful intermediate that is or includes hydrogen, an alcohol (e.g., ethanol or butanol, such as n-, sec- or t-butanol), an organic acid, a hydrocarbon or mixtures of any of these.

Since the second material has cellulose having a reduced molecular weight relative to the first material, and in some instances, a reduced crystallinity as well, the second material is generally more dispersible, swellable and/or soluble in a solution containing a microorganism and/or an enzyme. These properties make the second material more susceptible to chemical, enzymatic and/or biological attack relative to the first material, which can greatly improve the production rate and/or production level of a desired product, e.g., ethanol. Radiation can also sterilize the materials or any media needed to bioprocess the material. In some embodiments, the second number average molecular weight ($M_{N2}$) is lower than the first number average molecular weight (MN1) by more than about 10 percent, e.g., 15, 20, 25, 30, 35, 40, 50 percent, 60 percent, or even more than about 75 percent.

In some instances, the second material has cellulose that has as crystallinity ($C_2$) that is lower than the crystallinity ($C_1$) of the cellulose of the first material. For example, ($C_2$) can be lower than ($C_1$) by more than about 10 percent, e.g., 15, 20, 25, 30, 35, 40, or even more than about 50 percent.

In some embodiments, the starting crystallinity index (prior to irradiation) is from about 40 to about 87.5 percent, e.g., from about 50 to about 75 percent or from about 60 to about 70 percent, and the crystallinity index after irradiation is from about 10 to about 50 percent, e.g., from about 15 to about 45 percent or from about 20 to about 40 percent. However, in some embodiments, e.g., after extensive irradiation, it is possible to have a crystallinity index of lower than 5 percent. In some embodiments, the material after irradiation is substantially amorphous.

In some embodiments, the starting number average molecular weight (prior to irradiation) is from about 200,000 to about 3,200,000, e.g., from about 250,000 to about 1,000,000 or from about 250,000 to about 700,000, and the number average molecular weight after irradiation is from about 50,000 to about 200,000, e.g., from about 60,000 to about 150,000 or from about 70,000 to about 125,000. However, in some embodiments, e.g., after extensive irradiation, it is possible to have a number average molecular weight of less than about 10,000 or even less than about 5,000.

In some embodiments, the second material can have a level of oxidation ($O_2$) that is higher than the level of oxidation ($O_1$) of the first material. A higher level of oxidation of the material can aid in its dispersability, swellability and/or solubility, further enhancing the material's susceptibility to chemical, enzymatic or biological attack. In some embodiments, to increase the level of the oxidation of the second material relative to the first material, the irradiation is performed under an oxidizing environment, e.g., under a blanket of air or oxygen, producing a second material that is more oxidized than the first material. For example, the second material can have more hydroxyl groups, aldehyde groups, ketone groups, ester groups or carboxylic acid groups, which can increase its hydrophilicity.

Ionizing Radiation

The cellulosic or lignocellulosic material can be treated to ionizing radiation in a dry state (e.g., having little or no free water on its surface), a hydrated state (e.g., having up to ten percent by weight absorbed water), or in a wet state, e.g., having between about 10 percent and about 75 percent by weight water. Each form of radiation ionizes the carbon-containing material via particular interactions, as determined by the energy of the radiation. Heavy charged particles primarily ionize matter via Coulomb scattering; furthermore, these interactions produce energetic electrons that may further ionize matter. Alpha particles are identical to the nucleus of a helium atom and are produced by the alpha decay of various radioactive nuclei, such as isotopes of bismuth, polonium, astatine, radon, francium, radium, several actinides, such as actinium, thorium, uranium, neptunium, curium, californium, americium, and plutonium.

When particles are utilized, they can be neutral (uncharged), positively charged or negatively charged. When charged, the charged particles can bear a single positive or negative charge, or multiple charges, e.g., one, two, three or even four or more charges. In instances in which chain scission is desired, positively charged particles may be desirable, in part due to their acidic nature. When particles are utilized, the particles can have the mass of a resting electron, or greater, e.g., 500, 1000, 1500, 2000, 10, 000 or even 100,000 times the mass of a resting electron. For example, the particles can have a mass of from about 1 atomic unit to about 150 atomic units, e.g., from about 1 atomic unit to about 50 atomic units, or from about 1 to about 25, e.g., 1, 2, 3, 4, 5, 10, 12 or 15 amu.

Accelerators used to accelerate the particles can be electrostatic DC, electrodynamic DC, RF linear, magnetic induction linear or continuous wave. For example, cyclotron type accelerators are available from IBA, Belgium, such as the RHODATRON® system (an electron accelerator based upon the principle of re-circulating a beam through successive diameters of a single coaxial cavity resonating in metric waves), while DC type accelerators are available from RDI, now IBA Industrial, such as the DYNAMITRON® (an electron beam particle accelerator developed by IBA Industrial). Ions and ion accelerators are discussed in Introductory Nuclear Physics, Kenneth S. Krane, John Wiley & Sons, Inc. (1988), Krsto Prelec, FIZIKA B 6 (1997) 4, 177-206, Chu, William T., "Overview of Light-Ion Beam Therapy" Columbus-Ohio, ICRU-IAEA Meeting, 18-20 Mar. 2006, Iwata, Y. et al., "Alternating-Phase-Focused IH-DTL for Heavy-Ion Medical Accelerators" Proceedings of EPAC 2006, Edinburgh, Scotland and Leaner, C. M. et al., "Status of the Superconducting ECR Ion Source Venus" Proceedings of EPAC 2000, Vienna, Austria.

Gamma radiation has the advantage of a significant penetration depth into a variety of materials. Sources of gamma rays include radioactive nuclei, such as isotopes of cobalt, calcium, technicium, chromium, gallium, indium, iodine, iron, krypton, samarium, selenium, sodium, thalium, and xenon.

Sources of x rays include electron beam collision with metal targets, such as tungsten or molybdenum or alloys, or compact light sources, such as those produced commercially by Lyncean.

Sources for ultraviolet radiation include deuterium or cadmium lamps.

Sources for infrared radiation include sapphire, zinc, or selenide window ceramic lamps.

Sources for microwaves include klystrons, Slevin type RF sources, or atom beam sources that employ hydrogen, oxygen, or nitrogen gases.

In some embodiments, a beam of electrons is used as the radiation source. A beam of electrons has the advantages of high dose rates (e.g., 1, 5, or even 10 Mrad per second), high throughput, less containment, and less confinement equipment. Electrons can also be more efficient at causing chain scission. In addition, electrons having energies of 4-10 MeV can have a penetration depth of 5 to 30 mm or more, such as 40 mm.

Electron beams can be generated, e.g., by electrostatic generators, cascade generators, transformer generators, low energy accelerators with a scanning system, low energy accelerators with a linear cathode, linear accelerators, and pulsed accelerators. Electrons as an ionizing radiation source can be useful, e.g., for relatively thin piles of materials, e.g., less than 0.5 inch, e.g., less than 0.4 inch, 0.3 inch, 0.2 inch, or less than 0.1 inch. In some embodiments, the energy of each electron of the electron beam is from about 0.3 MeV to about 2.0 MeV (million electron volts), e.g., from about 0.5 MeV to about 1.5 MeV, or from about 0.7 MeV to about 1.25 MeV.

Electron beam irradiation devices may be procured commercially from Ion Beam Applications, Louvain-la-Neuve, Belgium or the Titan Corporation, San Diego, Calif. Typical electron energies can be 1 MeV, 2 MeV, 4.5 MeV, 7.5 MeV, or 10 MeV. Typical electron beam irradiation device power can be 1 kW, 5 kW, 10 kW, 20 kW, 50 kW, 100 kW, 250 kW, or 500 kW. The level of depolymerization of the feedstock depends on the electron energy used and the dose applied, while exposure time depends on the power and dose. Typical doses may take values of 1 kGy, 5 kGy, 10 kGy, 20 kGy, 50 kGy, 100 kGy, or 200 kGy.

Ion Particle Beams

Particles heavier than electrons can be utilized to irradiate materials, such as carbohydrates or materials that include carbohydrates, e.g., cellulosic materials, lignocellulosic materials, starchy materials, or mixtures of any of these and others described herein. For example, protons, helium nuclei, argon ions, silicon ions, neon ions carbon ions, phosphorus ions, oxygen ions or nitrogen ions can be utilized. In some embodiments, particles heavier than electrons can induce higher amounts of chain scission (relative to lighter particles). In some instances, positively charged particles can induce higher amounts of chain scission than negatively charged particles due to their acidity.

Heavier particle beams can be generated, e.g., using linear accelerators or cyclotrons. In some embodiments, the energy of each particle of the beam is from about 1.0 MeV/atomic unit to about 6,000 MeV/atomic unit, e.g., from about 3 MeV/atomic unit to about 4,800 MeV/atomic unit, or from about 10 MeV/atomic unit to about 1,000 MeV/atomic unit.

In certain embodiments, ion beams used to irradiate carbon-containing materials, e.g., biomass materials, can include more than one type of ion. For example, ion beams can include mixtures of two or more (e.g., three, four or more) different types of ions. Exemplary mixtures can include carbon ions and protons, carbon ions and oxygen ions, nitrogen ions and protons, and iron ions and protons. More generally, mixtures of any of the ions discussed above (or any other ions) can be used to form irradiating ion beams. In particular, mixtures of relatively light and relatively heavier ions can be used in a single ion beam.

In some embodiments, ion beams for irradiating materials include positively charged ions. The positively charged ions can include, for example, positively charged hydrogen ions (e.g., protons), noble gas ions (e.g., helium, neon, argon), carbon ions, nitrogen ions, oxygen ions, silicon atoms, phosphorus ions, and metal ions such as sodium ions, calcium ions, and/or iron ions. Without wishing to be bound by any theory, it is believed that such positively-charged ions behave chemically as Lewis acid moieties when exposed to materials, initiating and sustaining cationic ring-opening chain scission reactions in an oxidative environment.

In certain embodiments, ion beams for irradiating materials include negatively-charged ions. Negatively charged ions can include, for example, negatively charged hydrogen ions (e.g., hydride ions), and negatively charged ions of various relatively electronegative nuclei (e.g., oxygen ions, nitrogen ions, carbon ions, silicon ions, and phosphorus ions). Without wishing to be bound by any theory, it is believed that such negatively-charged ions behave chemically as Lewis base moieties when exposed to materials, causing anionic ring-opening chain scission reactions in a reducing environment.

In some embodiments, beams for irradiating materials can include neutral atoms. For example, any one or more of hydrogen atoms, helium atoms, carbon atoms, nitrogen atoms, oxygen atoms, neon atoms, silicon atoms, phosphorus atoms, argon atoms, and iron atoms can be included in beams that are used for irradiation of biomass materials. In general, mixtures of any two or more of the above types of atoms (e.g., three or more, four or more, or even more) can be present in the beams.

In certain embodiments, ion beams used to irradiate materials include singly charged ions such as one or more of $H^+$, $H^-$, $He^+$, $Ne^+$, $Ar^+$, $C^+$, $C^-$, $O^+$, $O^-$, $N^+$, $N^-$, $Si^+$, $Si^-$, $P^+$, $P^-$, $Na^+$, $Ca^+$, and Fe. In some embodiments, ion beams can include multiply-charged Ions such as $^+$, $C^{2+}$, $C^{3+}$, $C^{4+}$, $N^{3+}$, $N^{5+}$, $N^{5-}$, $N3^-$, $O^{+2}$, $O^{2-}$, $O_2^{2-}$, $Si^{2+}$, $Si^{4+}$, $Si^{2-}$, and $Si^{4-}$. In general, the ion beams can also include more complex polynuclear ions that bear multiple positive or negative charges. In certain embodiments, by virtue of the structure of the polynuclear ion, the positive or negative charges can be effectively distributed over substantially the entire structure of the ions. In some embodiments, the positive or negative charges can be somewhat localized over portions of the structure of the ions.

Electromagnetic Radiation

In embodiments in which the irradiating is performed with electromagnetic radiation, the electromagnetic radiation can have, e.g., energy per photon (in electron volts) of greater than $10^2$ eV, e.g., greater than $10^3$, $10^4$, $10^5$, $10^6$, or even greater than $10^7$ eV. In some embodiments, the electromagnetic radiation has energy per photon of between $10^4$ and $10^7$, e.g., between $10^5$ and $10^6$ eV. The electromagnetic radiation can have a frequency of, e.g., greater than $10^{16}$ Hz, greater than $10^{17}$ Hz, $10^{18}$, $10^{19}$, $10^{20}$, or even greater than $10^{21}$ Hz. In some embodiments, the electromagnetic radiation has a frequency of between $10^{18}$ and $10^{22}$ Hz, e.g., between $10^{19}$ to $10^{21}$ Hz.

In some embodiments, the irradiating (with any radiation source or a combination of sources) is performed until the material receives a dose of at least 0.25 Mrad, e.g., at least 1.0 Mrad, at least 2.5 Mrad, at least 5.0 Mrad, or at least 10.0 Mrad. In some embodiments, the irradiating is performed until the material receives a dose of between 1.0 Mrad and 6.0 Mrad, e.g., between 1.5 Mrad and 4.0 Mrad. In some embodiments, the irradiating is performed at a dose rate of between 5.0 and 1500.0 kilorads/hour, e.g., between 10.0 and 750.0 kilorads/hour or between 50.0 and 350.0 kilorads/hours.

In some embodiments, two or more radiation sources are used, such as two or more ionizing radiations. For example, samples can be treated, in any order, with a beam of electrons, followed by gamma radiation and UV light having wavelengths from about 100 nm to about 280 nm. In some embodiments, samples are treated with three ionizing radiation sources, such as a beam of electrons, gamma radiation, and energetic UV light.

One or more sonication processing sequences can be used to process materials from a wide variety of different sources to extract useful substances from the materials, and to provide partially degraded organic material (when organic materials are employed) which functions as input to further processing steps and/or sequences. Sonication can reduce the molecular weight and/or crystallinity of the materials, such as one or more of any of the materials described herein, e.g., one or more carbohydrate sources, such as cellulosic or lignocellulosic materials, or starchy materials.

In one method, a first material that includes cellulose having a first number average molecular weight (MN1) is dispersed in a medium, such as water, and sonicated and/or otherwise cavitated, to provide a second material that includes cellulose having a second number average molecular weight (MN2) lower than the first number average molecular weight. The second material (or the first and second material in certain embodiments) can be combined with a microorganism (with or without enzyme treatment) that can utilize the second and/or first material to produce a useful intermediate that is or includes hydrogen, an alcohol, an organic acid, a hydrocarbon or mixtures of any of these.

Since the second material has cellulose having a reduced molecular weight relative to the first material, and in some instances, a reduced crystallinity as well, the second material is generally more dispersible, swellable, and/or soluble in a solution containing the microorganism, e.g., at a concentration of greater than $10^6$ microorganisms/mL. These properties make the second material more susceptible to chemical, enzymatic, and/or microbial attack relative to the first material, which can greatly improve the production rate and/or production level of a desired product, e.g., ethanol or other alcohol. Sonication can also sterilize the materials, but should not be used while the microorganisms are supposed to be alive.

In some embodiments, the second number average molecular weight ($M_{N2}$) is lower than the first number average molecular weight ($M_{N1}$) by more than about 10 percent, e.g., 15, 20, 25, 30, 35, 40, 50 percent, 60 percent, or even more than about 75 percent. In some instances, the second material has cellulose that has as crystallinity ($C_2$) that is lower than the crystallinity ($C_1$) of the cellulose of the first material. For example, ($C_2$) can be lower than ($C_1$) by more than about 10 percent, e.g., 15, 20, 25, 30, 35, 40, or even more than about 50 percent.

In some embodiments, the starting crystallinity index (prior to sonication) is from about 40 to about 87.5 percent, e.g., from about 50 to about 75 percent or from about 60 to about 70 percent, and the crystallinity index after sonication is from about 10 to about 50 percent, e.g., from about 15 to about 45 percent or from about 20 to about 40 percent. However, in certain embodiments, e.g., after extensive sonication, it is possible to have a crystallinity index of lower than 5 percent. In some embodiments, the material after sonication is substantially amorphous.

In some embodiments, the starting number average molecular weight (prior to sonication) is from about 200,000 to about 3,200,000, e.g., from about 250,000 to about 1,000,000 or from about 250,000 to about 700,000, and the number average molecular weight after sonication is from about 50,000 to about 200,000, e.g., from about 60,000 to about 150,000 or from about 70,000 to about 125,000. However, in some embodiments, e.g., after extensive sonication, it is possible to have a number average molecular weight of less than about 10,000 or even less than about 5,000.

In some embodiments, the second material can have a level of oxidation ($O_2$) that is higher than the level of oxidation (01) of the first material. A higher level of oxidation of the material can aid in its dispersability, swellability and/or solubility, further enhancing the material's susceptibility to chemical, enzymatic or microbial attack. In some embodiments, to increase the level of the oxidation of the second material relative to the first material, the sonication is performed in an oxidizing medium, producing a second material that is more oxidized than the first material. For example, the second material can have more hydroxyl groups, aldehyde groups, ketone groups, ester groups or carboxylic acid groups, which can increase its hydrophilicity.

In some embodiments, the sonication medium is an aqueous medium. If desired, the medium can include an oxidant, such as a peroxide (e.g., hydrogen peroxide), a dispersing agent and/or a buffer. Examples of dispersing agents include ionic dispersing agents, e.g., sodium lauryl sulfate, and non-ionic dispersing agents, e.g., poly (ethylene glycol). In other embodiments, the sonication medium is non-aqueous. For example, the sonication can be performed in a hydrocarbon, e.g., toluene or heptane, an ether, e.g., diethyl ether or tetrahydrofuran, or even in a liquefied gas such as argon, xenon, or nitrogen.

Pyrolysis

One or more pyrolysis processing sequences can be used to process carbon containing materials from a wide variety of different sources to extract useful substances from the materials, and to provide partially degraded materials which function as input to further processing steps and/or sequences.

In one example, a first material that includes cellulose having a first number average molecular weight ($M_{N1}$) is pyrolyzed, e.g., by heating the first material in a tube furnace (in the presence or absence of oxygen), to provide a second material that includes cellulose having a second number average molecular weight ($M_{N2}$) lower than the first number average molecular weight. The second material (or the first and second material in certain embodiments) is/are combined with a microorganism (with or without acid or enzymatic hydrolysis) that can utilize the second and/or first material to produce a useful intermediate that is or includes hydrogen, an alcohol (e.g., ethanol or butanol, such as n-, sec or t-butanol), an organic acid, a hydrocarbon or mixtures of any of these.

Since the second material has cellulose having a reduced molecular weight relative to the first material, and in some instances, a reduced crystallinity as well, the second material is generally more dispersible, swellable and/or soluble in a solution containing the microorganism, e.g., at a concentration of greater than $10^6$ microorganisms/mL. These properties make the second material more susceptible to chemical, enzymatic and/or microbial attack relative to the first material, which can greatly improve the production rate and/or production level of a desired product, e.g., ethanol or other alcohol. Pyrolysis can also sterilize the first and second materials. In some embodiments, the second number average molecular weight ($M_{N2}$) is lower than the first number average molecular weight ($M_{N1}$) by more than about 10 percent, e.g., 15, 20, 25, 30, 35, 40, 50 percent, 60 percent, or even more than about 75 percent.

In some instances, the second material has cellulose that has as crystallinity ($C_2$) that is lower than the crystallinity ($C_1$) of the cellulose of the first material. For example, ($C_2$) can be lower than ($C_1$) by more than about 10 percent, e.g., 15, 20, 25, 30, 35, 40, or even more than about 50 percent.

In some embodiments, the starting crystallinity (prior to pyrolysis) is from about 40 to about 87.5 percent, e.g., from about 50 to about 75 percent or from about 60 to about 70 percent, and the crystallinity index after pyrolysis is from about 10 to about 50 percent, e.g., from about 15 to about 45 percent or from about 20 to about 40 percent. However, in certain embodiments, e.g., after extensive pyrolysis, it is possible to have a crystallinity index of lower than 5 percent. In some embodiments, the material after pyrolysis is substantially amorphous.

In some embodiments, the starting number average molecular weight (prior to pyrolysis) is from about 200,000 to about 3,200,000, e.g., from about 250,000 to about 1,000,000 or from about 250,000 to about 700,000, and the number average molecular weight after pyrolysis is from about 50,000 to about 200,000, e.g., from about 60,000 to about 150,000 or from about 70,000 to about 125,000. However, in some embodiments, e.g., after extensive pyrolysis, it is possible to have a number average molecular weight of less than about 10,000 or even less than about 5,000.

In some embodiments, the second material can have a level of oxidation ($O_2$) that is higher than the level of oxidation ($O1$) of the first material. A higher level of oxidation of the material can aid in its dispersability, swellability and/or solubility, further enhancing the materials susceptibility to chemical, enzymatic or microbial attack. In some embodiments, to increase the level of the oxidation of the second material relative to the first material, the pyrolysis is performed in an oxidizing environment, producing a second material that is more oxidized than the first material. For example, the second material can have more hydroxyl groups, aldehyde groups, ketone groups, ester groups or carboxylic acid groups, which can increase its hydrophilicity.

In some embodiments, the pyrolysis of the materials is continuous. In other embodiments, the material is pyrolyzed for a pre-determined time, and then allowed to cool for a second pre-determined time before pyrolyzing again.

Oxidation

One or more oxidative processing sequences can be used to process carbon containing materials from a wide variety of different sources to extract useful substances from the materials, and to provide partially degraded and/or altered material which functions as input to further processing steps and/or sequences.

In one method, a first material that includes cellulose having a first number average molecular weight ($M_{N1}$) and having a first oxygen content ($O_2$) is oxidized, e.g., by heating the first material in a stream of air or oxygen-enriched air, to provide a second material that includes cellulose having a second number average molecular weight ($M_{N2}$) and having a second oxygen content (02) higher than the first oxygen content ($O_2$). Such materials can also be combined with a solid and/or a liquid. The liquid and/or solid can include a microorganism, e.g., a bacterium, and/or an enzyme. For example, the bacterium and/or enzyme can work on the cellulosic or lignocellulosic material to produce a fuel, such as ethanol, or a coproduct, such as a protein. Fuels and coproducts are described in FIBROUS MATERIALS AND COMPOSITES," U.S. Ser. No. 11/453,951, filed Jun. 15, 2006. The entire contents of each of the foregoing applications are incorporated herein by reference.

In some embodiments, the second number average molecular weight is not more 97 percent lower than the first number average molecular weight, e.g., not more than 95 percent, 90, 85, 80, 75, 70, 65, 60, 55, 50, 45, 40, 30, 20, 12.5, 10.0, 7.5, 5.0, 4.0, 3.0, 2.5, 2.0 or not more than 1.0 percent lower than the first number average molecular weight. The amount of reduction of molecular weight will depend upon the application. For example, in some preferred embodiments that provide composites, the second number average molecular weight is substantially the same as the first number average molecular weight. In other applications, such as making ethanol or another fuel or coproduct, a higher amount of molecular weight reduction is generally preferred.

In some embodiments in which the materials are used to make fuel or coproduct, the starting number average molecular weight (prior to oxidation) is from about 200,000 to about 3,200,000, e.g., from about 250,000 to about 1,000,000 or from about 250,000 to about 700,000, and the number average molecular weight after oxidation is from about 50,000 to about 200,000, e.g., from about 60,000 to about 150,000 or from about 70,000 to about 125,000.

However, in some embodiments, e.g., after extensive oxidation, it is possible to have a number average molecular weight of less than about 10,000 or even less than about 5,000.

In some embodiments, the second oxygen content is at least about five percent higher than the first oxygen content, e.g., 7.5 percent higher, 10.0 percent higher, 12.5 percent higher, 15.0 percent higher or 17.5 percent higher. In some preferred embodiments, the second oxygen content is at least about 20.0 percent higher than the first oxygen content of the first material. Oxygen content is measured by elemental analysis by pyrolyzing a sample in a furnace operating at 1300° C. or higher. A suitable elemental analyzer is the LECO CHNS-932 analyzer with a VTF-900 high temperature pyrolysis furnace. Generally, oxidation of a material occurs in an oxidizing environment. For example, the oxidation can be affected or aided by pyrolysis in an oxidizing environment, such as in air or argon enriched in air. To aid in the oxidation, various chemical agents, such as oxidants, acids or bases can be added to the material prior to or during oxidation. For example, a peroxide (e.g., benzoyl peroxide) can be added prior to oxidation. Some oxidative methods of reducing recalcitrance in a carbon-containing material, such as coal or cellulosic or lignocellulosic materials, employ Fenton or Fenten-type chemistry. Such methods are disclosed, for example, in U.S. Provisional Application No. 61/139,473, filed Dec. 19, 2008, the complete disclosure of which is incorporated herein by reference.

Exemplary oxidants include peroxides, such as hydrogen peroxide and benzoyl peroxide, persulfates, such as ammonium persulfate, activated forms of oxygen, such as ozone, permanganates, such as potassium permanganate, perchlorates, such as sodium perchlorate, and hypochlorites, such as sodium hypochlorite (household bleach). In some situations, pH is maintained at or below about 5.5 during contact, such as between 1 and 5, between 2 and 5, between 2.5 and 5 or between about 3 and 5. Conditions can also include a contact period of between 2 and 12 hours, e.g., between 4 and 10 hours or between 5 and 8 hours. In some instances, conditions include not exceeding 300° C., e.g., not exceeding 250, 200, 150, 100 or 50 oc. In special desirable instances, the temperature remains substantially ambient, e.g., at or about 20-25° C.

In some desirable embodiments, the one or more oxidants are applied to a first cellulosic or lignocellulosic material and the one or more compounds as a gas, such as by generating ozone in-situ by irradiating the first cellulosic or lignocellulosic material and the one or more compounds through air with a beam of particles, such as electrons. In particular desirable embodiments, a first cellulosic or lignocellulosic material is firstly dispersed in water or an aqueous medium that includes the one or more compounds dispersed and/or dissolved therein, water is removed after a soak time (e.g., loose and free water is removed by filtration), and then the one or more oxidants are applied to the combination as a gas, such as by generating ozone in-situ by irradiating the first cellulosic or lignocellulosic and the one or more compounds through air with a beam of particles, such as electrons (e.g., each being accelerated by a potential difference of between 3 MeV and 10 MeV). Soaking can open up interior portions to oxidation.

In some embodiments, the mixture includes one or more compounds and one or more oxidants, and a mole ratio of the one or more compounds to the one or more oxidants is from about 1:1000 to about 1:25, such as from about 1:500 to about 1:25 or from about 1:100 to about 1:25.

In some desirable embodiments, the mixture further includes one or more hydroquinones, such as 2,5-dimethoxyhydroquinone (DMHQ) and/or one or more benzoquinones, such as 2,5-dimethoxy-1,4-benzoquinone (DMBQ), which can aid in electron transfer reactions.

In some desirable embodiments, the one or more oxidants are electrochemically-generated in-situ. For example, hydrogen peroxide and/or ozone can be electrochemically produced within a contact or reaction vessel.

Other Processes to Solubilize, Reduce Recalcitrance or to Functionalize

Any of the processes of this paragraph can be used alone without any of the processes described herein, or in combination with any of the processes described herein (in any order): steam explosion, acid treatment (including concentrated and dilute acid treatment with mineral acids, such as sulfuric acid, hydrochloric acid and organic acids, such as trifluoroacetic acid), base treatment (e.g., treatment with lime or sodium hydroxide), UV treatment, screw extrusion treatment (see, e.g., U.S. Patent Application Ser. No. 61/073, 530, filed Nov. 18, 2008, solvent treatment (e.g., treatment with ionic liquids) and freeze grinding or freeze milling (see, e.g., U.S. Patent Application Ser. No. 61/081,709). Further detail on processing of biomass can be found in U.S. Pat. No. 9,342,294, issued May 31, 2016, the contents of which are incorporated in its entirety by reference.

Combinations of Irradiating, Sonicating, and Oxidizing Devices

In some embodiments, it may be advantageous to combine two or more separate irradiation, sonication, pyrolization, and/or oxidation devices into a single hybrid machine. For such a hybrid machine, multiple processes may be performed in close juxtaposition or even simultaneously, with the benefit of increasing pretreatment throughput and potential cost savings.

For example, consider the electron beam irradiation and sonication processes. Each separate process is effective in lowering the mean molecular weight of cellulosic material by an order of magnitude or more, and by several orders of magnitude when performed serially.

Both irradiation and sonication processes can be applied using a hybrid electron beam/sonication device. For example, a hybrid electron beam/sonication device can include a shallow pool (depth ~3-5 cm) of a slurry of cellulosic material dispersed in an aqueous, oxidant medium, such as hydrogen peroxide or carbamide peroxide. Hybrid device has an energy source, which powers both electron beam emitter and sonication horns. Electron beam emitter generates electron beams which pass through an electron beam aiming device to impact the slurry containing cellulosic material. On either side of the electron beam emitter are sonication horns, which deliver ultrasonic wave energy to the slurry. The sonication horns end in a detachable end-piece that is in contact with the slurry. Further detail on processing of biomass can be found in U.S. Pat. No. 9,342,294, issued May 31, 2016, the contents of which are incorporated in its entirety by reference.

A further benefit of such a simultaneous electron beam and ultrasound process is that the two processes have complementary results. With electron beam irradiation alone, an insufficient dose may result in cross-linking of some of the polymers in the cellulosic material, which lowers the efficiency of the overall depolymerization process. Lower doses of electron beam irradiation and/or ultrasound radiation may also be used to achieve a similar degree of depolymerization as that achieved using electron beam irradiation and sonication separately.

An electron beam device can also be combined with one or more of high-frequency, rotor-stator devices, which can be used as an alternative to ultrasonic energy devices, and performs a similar function.

Further combinations of devices are also possible. For example, an ionizing radiation device that produces gamma radiation emitted from, e.g., $^{60}$Co pellets, can be combined with an electron beam source and/or an ultrasonic wave source. Shielding requirements may be more stringent in this case.

The radiation devices for pretreating biomass discussed above can also be combined with one or more devices that perform one or more pyrolysis processing sequences. Such a combination may again have the advantage of higher throughput. Nevertheless, caution must be observed, as there may be conflicting requirements between some radiation processes and pyrolysis. For example, ultrasonic radiation devices may require the feedstock be immersed in a liquid oxidizing medium. On the other hand, as discussed previously, it may be advantageous for a sample of feedstock undergoing pyrolysis to be of a particular moisture content. In this case, the new systems automatically measure and monitor for a particular moisture content and regulate the same. Further, some or all of the above devices, especially the pyrolysis device, can be combined with an oxidation device as discussed previously.

Saccharification

In order to convert the feedstock to fermentable sugars, the cellulose in the feedstock is hydrolyzed by a saccharifying agent, e.g., an enzyme, a process referred to as saccharification. The materials that include the cellulose are treated with the enzyme, 10 e.g., by combining the material and the enzyme in a solvent, e.g., in an aqueous solution. Enzymes and biomass-destroying organisms that break down biomass, such as the cellulose and/or the lignin portions of the biomass, contain or manufacture various cellulolytic enzymes (cellulases), ligninases or various small molecule biomass destroying metabolites. These enzymes may be a complex of enzymes that act 15 synergistically to degrade crystalline cellulose or the lignin portions of biomass.

Examples of cellulolytic enzymes include: endoglucanases, cellobiohydrolases, and cello biases (~-glucosidases). A cellulosic substrate is initially hydrolyzed by endoglucanases at random locations producing oligomeric intermediates. These intermediates are then substrates for exo-splitting glucanases such as cellobiohydrolase to produce cellobiose from the ends of the cellulose polymer. Cellobiose is a water-soluble 1,4-linked dimer of glucose. Finally, cellobiase cleaves cellobiose to yield glucose.

The saccharification process can be partially or completely performed in a tank 30 (e.g., a tank having a volume of at least 4000, 40,000, 400,000, or 1,000,000 L) in a manufacturing plant, and/or can be partially or completely performed in transit, e.g., in a rail car, tanker truck, or in a supertanker or the hold of a ship. The time required for complete saccharification will depend on the process conditions and the feedstock and enzyme used. If saccharification is performed in a manufacturing plant under controlled conditions, the cellulose may be substantially entirely converted to glucose in about 12-96 hours. If saccharification is performed partially or completely in transit, saccharification may take longer.

It is generally preferred that the tank contents be mixed during saccharification, e.g., using jet mixing as described in U.S. Provisional Application No. 61/218,832, the full disclosure of which is incorporated by reference herein. The addition of surfactants can enhance the rate of saccharification. Examples of surfactants include non-ionic surfactants, such as a Tween® 20 or Tween® 80 polyethylene glycol surfactants, ionic surfactants, or amphoteric surfactants.

A cellulase is capable of degrading biomass and may be of fungal or bacterial origin. Suitable cellulolytic enzymes include cellulases from the genera *Bacillus, Pseudomonas, Humicola, Fusarium, Thielavia, Acremonium, Chrysosporium* and *Trichoderma*, and include species of *Humicola, Coprinus, Thielavia, Fusarium, Myceliophthora, Acremonium, Cephalosporium, Scytalidium, Penicillium* or *Aspergillus* (see, e.g., EP 458162), especially those produced by a strain selected from the species *Humicola insolens* (reclassified as *Scytalidium thermophilum*, see, e.g., U.S. Pat. No. 4,435,307), *Coprinus cinereus, Fusarium oxysporum, Myceliophthora thermophila, Meripilus giganteus, Thielavia terrestris, Acremonium* sp., *Acremonium persicinum, Acremonium, Acremonium brachypenium, Acremonium dichromosporum, Acremonium obclavatum, Acremonium pinkertoniae, Acremonium roseogriseum, Acremonium incoloratum*, and *Acremonium furatum*; preferably from the species *Humicola insolens* DSM 1800, *Fusarium oxysporum* DSM 2672, *Myceliophthora thermophila* CBS 117.65, *Cephalosporium* sp. RYM-202, *Acremonium* sp. CBS 478.94, *Acremonium* sp. CBS 265.95, *Acremonium persicinum* CBS 169.65, *Acremonium* AHU 9519, *Cephalosporium* sp. CBS 535.71, *Acremonium brachypenium* CBS 866.73, *Acremonium dichromosporum* CBS 683.73, *Acremonium obclavatum* CBS 311.74, *Acremonium pinkertoniae* CBS 157.70, *Acremonium roseogriseum* CBS 134.56, *Acremonium incoloratum* CBS 146.62, and *Acremonium furatum* CBS 299.70H. Cellulolytic enzymes may also be obtained from *Chrysosporium*, preferably a strain of *Chrysosporium lucknowense*. Additionally, *Trichoderma* (particularly *Trichoderma viride, Trichoderma reesei*, and *Trichoderma koningii*), alkalophilic *Bacillus* (see, for example, U.S. Pat. No. 3,844,890 and EP 458162), and *Streptomyces* (see, e.g., EP 458162) may be used. The bacterium, *Saccharophagus degradans*, produces a mixture of enzymes capable of degrading a range of cellulosic materials and may also be used in this process.

Enzymes which break down biomass, such as cellulose, to lower molecular weight carbohydrate-containing materials, such as glucose, during saccharification are referred to as cellulolytic enzymes or cellulase. These enzymes may be a complex of enzymes that act synergistically to degrade crystalline cellulose. Examples of cellulolytic enzymes include: endoglucanases, cellobiohydrolases, and cellobiases (β-glucosidases). A cellulosic substrate is initially hydrolyzed by endoglucanases at random locations producing oligomeric intermediates. These intermediates are then substrates for exo-splitting glucanases such as cellobiohydrolase to produce cellobiose from the ends of the cellulose polymer. Cellobiose is a water-soluble β-1,4-linked dimer of glucose. Finally, cellobiase cleaves cellobiose to yield glucose.

Anaerobic cellulolytic bacteria have also been isolated from soil, e.g., a novel cellulolytic species of *Clostiridium, Clostridium phytofermentans* sp. nov. (see Leschine et. al, *International Journal of Systematic and Evolutionary Microbiology* (2002), 52, 1155-1160).

Cellulolytic enzymes using recombinant technology can also be used (see, e.g., WO 2007/071818 and WO 2006/110891).

The cellulolytic enzymes used can be produced by fermentation of the above-noted microbial strains on a nutrient medium containing suitable carbon and nitrogen sources and inorganic salts, using procedures known in the art (see, e.g., Bennett, J. W. and LaSure, L. (eds.), *More Gene Manipulations in Fungi*, Academic Press, CA 1991). Suitable media are available from commercial suppliers or may be prepared according to published compositions (e.g., in catalogues of the American Type Culture Collection). Temperature ranges and other conditions suitable for growth and cellulase production are known in the art (see, e.g., Bailey, J. E., and Ollis, D. F., *Biochemical Engineering Fundamentals*, McGraw-Hill Book Company, N Y, 1986).

Treatment of cellulose with cellulase is usually carried out at temperatures between 30° C. and 65° C. Cellulases are active over a range of pH of about 3 to 7. A saccharification step may last up to 120 hours. The cellulase enzyme dosage achieves a sufficiently high level of cellulose conversion. For example, an appropriate cellulase dosage is typically between 5.0 and 50 Filter Paper Units (FPU or IU) per gram of cellulose. The FPU is a standard measurement and is defined and measured according to Ghose (1987, Pure and Appl. Chem. 59:257-268).

In certain embodiments, the concentration of the resulting glucose solution can be relatively high, e.g., greater than 40%, or greater than 50, 60, 70, 80, 90 or even greater than 95% by weight. This reduces the volume to be shipped, if saccharification and fermentation are performed at different locations, and also inhibits microbial growth in the solution. However, lower concentrations may be used, in which case it may be desirable to add an antimicrobial additive, e.g., a broad spectrum antibiotic, in a low concentration, e.g., 50 to 150 ppm. Other suitable antibiotics include amphotericin B, ampicillin, chloramphenicol, ciprofloxacin, gentamicin, hygromycin B, kanamycin, neomycin, penicillin, puromycin, streptomycin. Antibiotics will inhibit growth of microorganisms during transport and storage, and can be used at appropriate concentrations, e.g., between 15 and 1000 ppm by weight, e.g., between 25 and 500 ppm, or between 50 and 150 ppm. If desired, an antibiotic can be included even if the sugar concentration is relatively high.

A relatively high concentration solution can be obtained by limiting the amount of water added to the feedstock with the enzyme. The concentration can be controlled, e.g., by controlling how much saccharification takes place. For example, concentration can be increased by adding more feedstock to the solution. In order to keep the sugar that is being produced in solution, a surfactant can be added, e.g., one of those discussed above. Solubility can also be increased by increasing the temperature of the solution. For example, the solution can be maintained at a temperature of 40-50° C., 60-80° C., or even higher.

In some embodiments, the feedstock is processed to convert it to a convenient and concentrated solid material, e.g., in a powdered, granulate or particulate form. The concentrated material can be in a purified, or a raw or crude form. The concentrated form can have, for example, a total sugar concentration of between about 90 percent by weight and about 100 percent by weight, e.g., 92, 94, 96 or 98 percent by weight sugar. Such a form can be particularly cost effective to ship, e.g., to a bioprocessing facility, such as a biofuel manufacturing plant. Such a form can also be advantageous to store and handle, easier to manufacture and becomes both an intermediate and a product, providing an option to the biorefinery as to which products to manufacture.

In some instances, the powdered, granulate or particulate material can also include one or more of the materials, e.g., additives or chemicals, described herein, such as the food-based nutrient or nutrient package, a nitrogen source, e.g., urea, a surfactant, an enzyme, or any microorganism described herein. In some instances, all materials needed for a bioprocess are combined in the powdered, granulate or particulate material. Such a form can be a particularly convenient form for transporting to a remote bioprocessing facility, such as a remote biofuels manufacturing facility. Such a form can also be advantageous to store and handle.

In some instances, the powdered, granulate or particulate material (with or without added materials, such as additives and chemicals) can be treated by any of the physical treatments described in U.S. Ser. No. 12/429,045, incorporated by reference above. For example, irradiating the powdered, granulate or particulate material can increase its solubility and can sterilize the material so that a bioprocessing facility can integrate the material into their process directly as may be required for a contemplated intermediate or product.

In certain instances, the powdered, granulate or particulate material (with or without added materials, such as additives and chemicals) can be carried in a structure or a carrier for ease of transport, storage or handling. For example, the structure or carrier can include or incorporate a bag or liner, such as a degradable bag or liner. Such a form can be particularly useful for adding directly to a bioprocess system.

Optionally, the sugar solution can be processed prior to any fermentation step. For example, a saccharified solution as prepared by the methods described herein can be purified and/or processed by filtration (e.g., including rotary vacuum drum filtration), chromatography (e.g., simulated moving bed chromatography), electrodialysis including bipolar electrodialysis, crystallization and combinations of these. Optionally, processing can include fermenting one sugar in a mixture of two sugars and removal of the fermentation product, leaving a sugar solution of substantially the second sugar which can be more easily utilized, for example isolated and/or fermented (e.g. to a carboxylic acid). Some exemplary methods for purification and/or processing that can be utilized are discussed in U.S. Provisional Application Ser. Nos. 61/774,775, 61/774,780 and 61/774,761, the disclosures of which are incorporated herein by reference. In some cases, a biomass source can provide a higher amount of essentially only one sugar, for example some paper products, cotton and other biomass that is almost entirely a glucose source with little if any xylose. Other biomass sources may provide mostly xylose and/or lignin.

Fermentation

Generally, various microorganisms can produce a number of useful products, such as a fuel, by operating on, e.g., fermenting the pretreated biomass materials. For example, Natural Force™ Chemistry methods can be used to prepare biomass materials for use in fermentation. Alcohols, organic acids, hydrocarbons, hydrogen, proteins or mixtures of any of these materials, for example, can be produced by fermentation or other processes.

The microorganism can be a natural microorganism or an engineered microorganism. For example, the microorganism can be a bacterium, e.g., a cellulolytic bacterium, a fungus, e.g., a yeast, a plant or a protist, e.g., an algae, a protozoa or a fungus-like protist, e.g., a slime mold. When the organisms are compatible, mixtures of organisms can be utilized.

To aid in the breakdown of the materials that include the cellulose, one or more enzymes, e.g., a cellulolytic enzyme can be utilized. In some embodiments, the materials that include the cellulose are first treated with the enzyme, e.g., by combining the material and the enzyme in an aqueous solution. This material can then be combined with the microorganism. In other embodiments, the materials that include the cellulose, the one or more enzymes and the microorganism are combined at the concurrently, e.g., by combining in an aqueous solution.

Also, to aid in the breakdown of the materials that include the cellulose, the materials can be treated post irradiation with heat, a chemical (e.g., mineral acid, base or a strong oxidizer such as sodium hypochlorite), and/or an enzyme.

During the fermentation, sugars released from cellulolytic hydrolysis or the saccharification step, are fermented to, e.g., ethanol, by a fermenting microorganism such as yeast. Suitable fermenting microorganisms have the ability to convert carbohydrates, such as glucose, xylose, arabinose, mannose, galactose, oligosaccharides or polysaccharides into fermentation products. Fermenting microorganisms include strains of the genus *Saccharomyces* spp. e.g., *Saccharomyces cerevisiae* (baker's yeast), *Saccharomyces distaticus*, *Saccharomyces uvarum*; the genus *Kluyveromyces*, e.g., species *Kluyveromyces marxianus*, *Kluyveromyces fragilis*; the genus *Candida*, e.g., *Candida pseudotropicalis*, and *Candida brassicae*, *Pichia stipitis* (a relative of *Candida shehatae*, the genus *Clavispora*, e.g., species *Clavispora lusitaniae* and *Clavispora opuntiae* the genus *Pachysolen*, e.g., species *Pachysolen tannophilus*, the genus *Bretannomyces*, e.g., species *Bretannomyces clausenii* (Philippidis, G. P., 1996, Cellulose bioconversion technology, in Handbook on Bioethanol: Production and Utilization, Wyman, C. E., ed., Taylor & Francis, Washington, D.C., 179-212). Commercially available yeast includes, for example, Red Star®/Lesaffre Ethanol Red (available from Red Star/Lesaffre, USA) FALI® (available from Fleischmann's Yeast, a division of Burns Philip Food Inc., USA), SUPERSTART® (available from Alltech, now Lallemand), GERT STRAND® (available from Gert Strand AB, Sweden) and FERMOL® (available from DSM Specialties).

Bacteria that can ferment biomass to ethanol and other products include, e.g., *Zymomonas mobilis* and *Clostridium thermocellum* (Philippidis, 1996, supra). Leschine et al. (*International Journal of Systematic and Evolutionary Microbiology* 2002, 52, 1155-1160) isolated an anaerobic, mesophilic, cellulolytic bacterium from forest soil, *Clostridium phytofermentans* sp. nov., which converts cellulose to ethanol.

Fermentation of biomass to ethanol and other products may be carried out using certain types of thermophilic or genetically engineered microorganisms, such *Thermoanaerobacter* species, including *T. mathranii*, and yeast species such as *Pichia* species. An example of a strain of *T. mathranii* is A3M4 described in Sonne-Hansen et al. (*Applied Microbiology and Biotechnology* 1993, 38, 537-541) or Ahring et al. (*Arch. Microbiol.* 1997, 168, 114-119). Other microorganisms can produce ethanol from sugars by fermentation in addition to other products. Examples include heterolactic acid fermentation in which *Leuconostoc* bacteria produce lactate, ethanol and $CO_2$, mixed acid fermentation where *Escherichia* produce ethanol mixed with lactate, acetate, succinate, formate, $CO_2$ and Hz, and 2,3-butanediol fermentation by Enterobacteri producing ethanol, butanediol, lactate, formate, $CO_2$ and $H_2$.

Yeast and *Zymomonas* bacteria can be used for fermentation or conversion. The optimum pH for yeast is from about pH 4 to 5, while the optimum pH for *Zymomonas* is from about pH 5 to 6. Typical fermentation times are about 24 to 96 hours with temperatures in the range of 26° C. to 40° C.; however thermophilic microorganisms prefer higher temperatures.

During fermentation, the pH of the fermentation media can be an important parameter to control. Buffers, for example, phosphate, sulfate and acetate buffers can help maintain a target pH. Addition of acids and bases (e. g., ammonium hydroxide, sodium and potassium hydroxides, acetic acid, sulfuric acid, phosphoric acid, nitric acids) can also be added before, after and during the fermentation to maintain and or change or control the pH. During fermentation, the pH is optimally between about 2 and 8 (e.g., between about 3 and 8, between about 4 and 8, between about 4 and 7). Maintaining the pH above a critical value, for example above about 3 (e.g., above about 3.5, above about 4) by the addition of a base can often improve the fermentation. This control can be particularly important while using acidogenic bacteria since the acid products can lower the pH during the fermentation to values that are toxic to the organisms.

The temperature can also be a controlling and important parameter during fermentation. Optimally the temperature is maintained between about 20 and 50° C. (e.g., between about 20 and 40° C., between about 30 and 40° C.). In some instances, lower or higher temperatures from an optimal temperature can be utilized to induce a desired fermentation phase, e.g., acidogenisis, solventogenisis, log growth, sporulation.

The fermenting microorganism strains can be chosen, which can predominantly ferment certain types of sugar (such as C5 or C6 sugars) to ethanol effectively can also be used. For example, C5 Fuel™, Xyloferm® (both available from Lallemand), and CelluX™ 4 (available from Leaf-Lesaffre Advanced Fermentations) can be used to ferment xylose.

For anaerobic organisms it is preferable to conduct the fermentation in the absence of oxygen e.g., under a blanket of an inert gas such as $N_2$, Ar, He, $CO_2$ or mixtures thereof Additionally, the mixture may have a constant purge of an inert gas flowing through the tank or bioreactor during part of or all of the fermentation.

The fermenting or saccharifying organism can be immobilized on a support. For example, an application of this process is described in U.S. Pat. No. 5,563,069. The organism can be supported on a cellulosic or lignocellulosic material as describe in U.S. patent Ser. No. 12/782,543 the entire disclosure of which is herein incorporated by reference.

Mobile fermenters can be utilized, as described in U.S. Provisional Patent Application Ser. 60/832,735, now Published International Application No. WO 2008/011598.

It can be beneficial to supply additives during fermentation, for example acids, bases, buffers, amino acids, vitamins, blackstrap molasses, reinforced Clostridia media (RCM), metal ions, yeast extract, distillate bottoms, meat extracts, vegetable extracts, peptones, carbon sources and proteins. For example, the addition of metal ions of Fe, Mn, Mg, Na, Cu, Zn and combinations of these can be beneficial. Other additives, for example, p-aminobenzoic acids, choline, inositol, thiamin, and albumin can be beneficial.

A preferred additive that can be utilized is the distillate bottom from a fermented saccharified lignocellulosic or cellulosic material (e.g., biomass). For example, the yeast fermentation of a saccharified material as described herein producing ethanol can be distilled to produce a distillation bottom. The distillate bottom containing yeast cells and spent biomass (e.g., lignin, non-fermented sugars, proteins) can be used as an additive to a second fermentation. The distillate bottom can be optionally purified prior to use, for example, by methods described herein (e.g., rotary vacuum drum filters, simulated moving bed chromatography and improvements to simulated moving bed chromatography, filtration, precipitation). The concentration of solids (e.g., dissolved and/or suspended solids) can be at least about 5 wt. % (e.g., at least about 10 wt. %, at least about 20 wt. %, at least about 20 wt. %, at least about 30 wt. %, at least about 40 wt. %, at least about 50 wt. %, at least about 60 wt. %, between about 10 and 90 wt. %, between about 20 and 60 wt. %). The distillate bottom be used directly in the distillation or it can be diluted with a solvent (e.g., water) and used as at least 5 wt. % distillate bottom to solvent (e.g., at least 10 wt. %, at least 20 wt. %, at least 30 wt. %, at least 40 wt. %, between about 10 and 80 wt. %, between about 10 and 60 wt. %, between about 10 and 50 wt. %, between about 20 and 50 wt. %, between about 20 and 40 wt. %). The distillation bottom additive can be used in combination with other additive as herein described and additional sugars (e.g., glucose and/or xylose).

Fermentation can be used to provide a variety of products. Generally, various microorganisms can produce a number of useful products by operating on, converting, bioconverting, or fermenting the materials. For example, alcohols, organic acids, hydrocarbons, hydrogen, proteins, carbohydrates, fats/oils/lipids, amino acids, vitamins, or mixtures of any of these materials can be produced by fermentation or other processes.

In one or more embodiments, the fermentation can produce an alcohol. Ethanol fermentation, also called alcoholic fermentation, is a biological process which converts sugars such as glucose, fructose, and sucrose into cellular energy, producing ethanol and carbon dioxide as a side-effect. Because yeasts perform this conversion in the absence of oxygen, alcoholic fermentation is considered an anaerobic process. Yeast fermentation of various carbohydrate products is also used to produce the ethanol that can be used in one or more embodiments to produce gasoline or other fuels or fuel additives. Ethanol fermentation also produces unharvested byproducts such as heat, carbon dioxide, food for livestock, and water.

In one embodiment, the ethanol generated from lignocellulosic biomass by the processes described herein can include other components such as acetone, methanol, n-propanol, 2-methyl propanol, n-butanol, 2-methyl butanol and isopropyl alcohol. In some embodiments, the ethanol may contain about 0.0001% to about 0.001% acetone, about 0.001% to about 0.01% acetone, about 0.01% to about 0.1% acetone, about 0.1% to about 1% acetone, or in a range bounded by any numerical value stated herein above. In some embodiments, the ethanol may contain about 0.01% to about 0.1% methanol, about 0.1% to about 1% methanol, about 1% to about 2% methanol, about 2% to about 3% methanol, about 3% to about 4% methanol, about 4% to about 5% methanol, about 5% to about 10% methanol, or in a range bounded by any numerical value stated herein above. In some embodiments, the ethanol may contain about 0.01% to about 0.05% n-propanol, 0.05% to about 0.1% n-propanol, about 0.1% to about 0.15% n-propanol, about 0.15% to about 0.2% n-propanol, about 0.2% to about 0.3% n-propanol, about 0.3% to about 0.4% n-propanol, about 0.4% to about 0.5% n-propanol, about 0.5% to about 1% n-propanol, about 1% to about 2% n-propanol, or in a range bounded by any numerical value stated herein above. In some embodiments, the ethanol may contain about 0.01% to about 0.05% 2-methyl propanol, 0.05% to about 0.1% 2-methyl propanol, about 0.1% to about 0.15% 2-methyl propanol, about 0.15% to about 0.2% 2-methyl propanol, about 0.2% to about 0.3% 2-methyl propanol, about 0.3% to about 0.4% 2-methyl propanol, about 0.4% to about 0.5% 2-methyl propanol, about 0.5% to about 1% 2-methyl propanol, about 1% to about 2% 2-methyl propanol, or in a range bounded by any numerical value stated herein above. In some embodiments, the ethanol may contain about 0.001% to about 0.005% n-butanol, 0.005% to about 0.01% n-butanol, about 0.01% to about 0.015% n-butanol, about 0.015% to about 0.02% n-butanol, about 0.02% to about 0.03% n-butanol, about 0.03% to about 0.04% n-butanol, about 0.04% to about 0.05% n-butanol, about 0.05% to about 0.1% n-butanol, about 0.1% to about 0.2% n-butanol, or in a range bounded by any numerical value stated herein above. In some embodiments, the ethanol may contain about 0.1% to about 0.15% 2-methyl butanol, about 0.15% to about 0.2% 2-methyl butanol, about 0.2% to about 0.3% 2-methyl butanol, about 0.3% to about 0.4% 2-methyl butanol, about 0.4% to about 0.5% 2-methyl butanol, about 0.5% to about 0.6% 2-methyl butanol, about 0.6% to about 0.7% 2-methyl butanol, about 0.7% to about 0.8% 2-methyl butanol, about 0.8% to about 0.9% 2-methyl butanol, about 0.9% to about 1% 2-methyl butanol, about 1% to about 2% 2-methyl butanol, about 2% to about 3% 2-methyl butanol, about 3% to about 4% 2-methyl butanol, about 4% to about 5% 2-methyl butanol, or in a range bounded by any numerical value stated herein above. In some embodiments, the ethanol may contain about 0.01% to about 0.1% isopropyl alcohol, about 0.1% to about 1% isopropyl alcohol, about 1% to about 2% isopropyl alcohol, about 2% to about 3% isopropyl alcohol, about 3% to about 4% isopropyl alcohol, about 4% to about 5% isopropyl alcohol, about 5% to about 10% isopropyl alcohol, about 10% to about 15% isopropyl alcohol, about 15% to about 20% isopropyl alcohol, about 20% to about 25% isopropyl alcohol, or in a range bounded by any numerical value stated herein above. In some embodiments, the ethanol may contain about 0.02% acetone, about 0.11 to about 2.5% methanol, about 0.18% n-propanol, about 0.12% of 2-methyl propanol, about 0.01% n-butanol, about 0.53% 2-methyl butanol and about 8.5% isopropyl alcohol.

In some embodiments, the composition of ethanol described above is measured by using a Flame Ionization Detector (FID) gas chromatography method. Other detectors may also be used to analyze the composition of ethanol derived by the processes described herein. For example, thermal conductivity detector, catalytic combustion detector, discharge ionization detector, dry electrolytic conductivity detector, electron capture detector, flame photometric detector, atomic emission detector, infrared detector, mass spectrometer, photoionization detector, pulse discharge ionization detector, NMR spectrometer and ultraviolet detector may also be used to analyze the ethanol generated by the processes described herein. In some embodiments, these detectors may be used with liquid chromatography.

Figure 10:
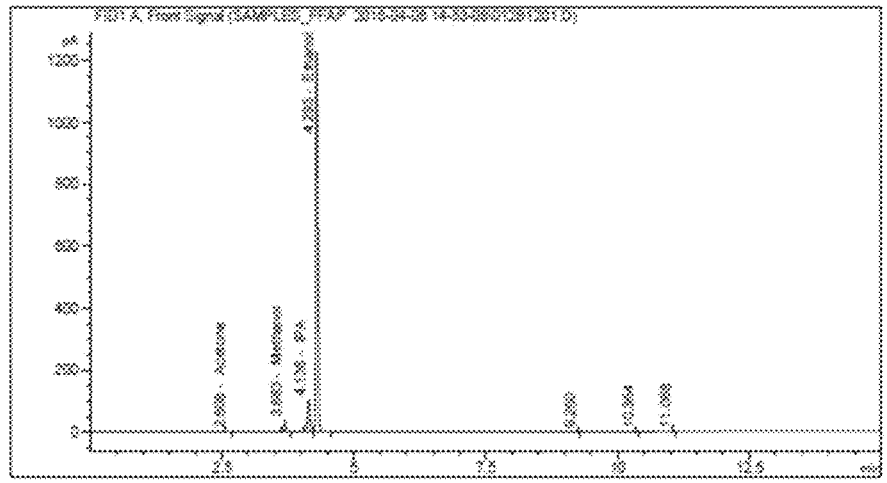
FIG. 10 is a chromatogram obtained by analyzing ethanol produced from lignocellulosic biomass generated by the processes described in this application using Flame Ionization Detector (FID) gas chromatography.
Figure 12A:
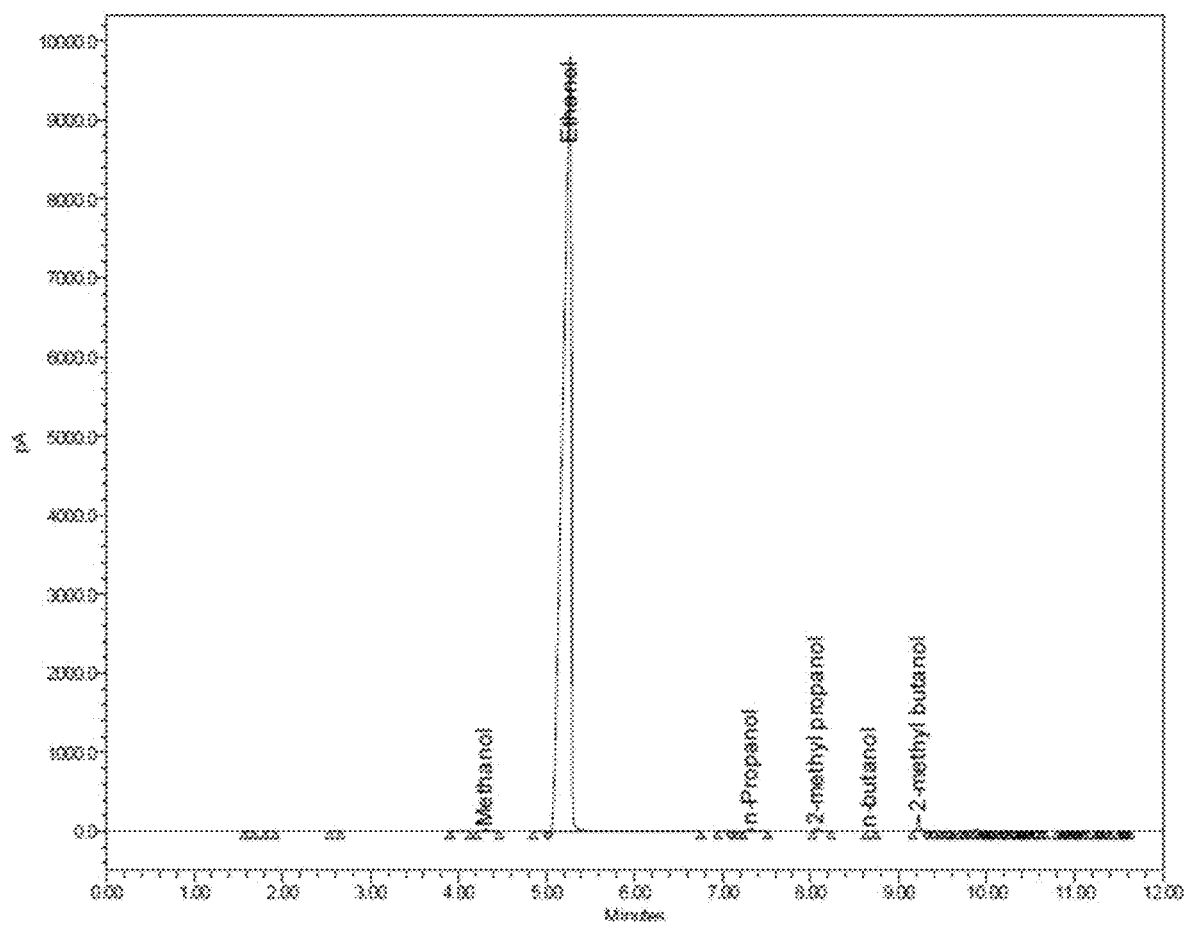
FIG. 12A is a Flame Ionization Detector (FID) gas chromatogram obtained by analyzing ethanol produced from lignocellulosic biomass generated by the processes described in this application.
Figure 13A:
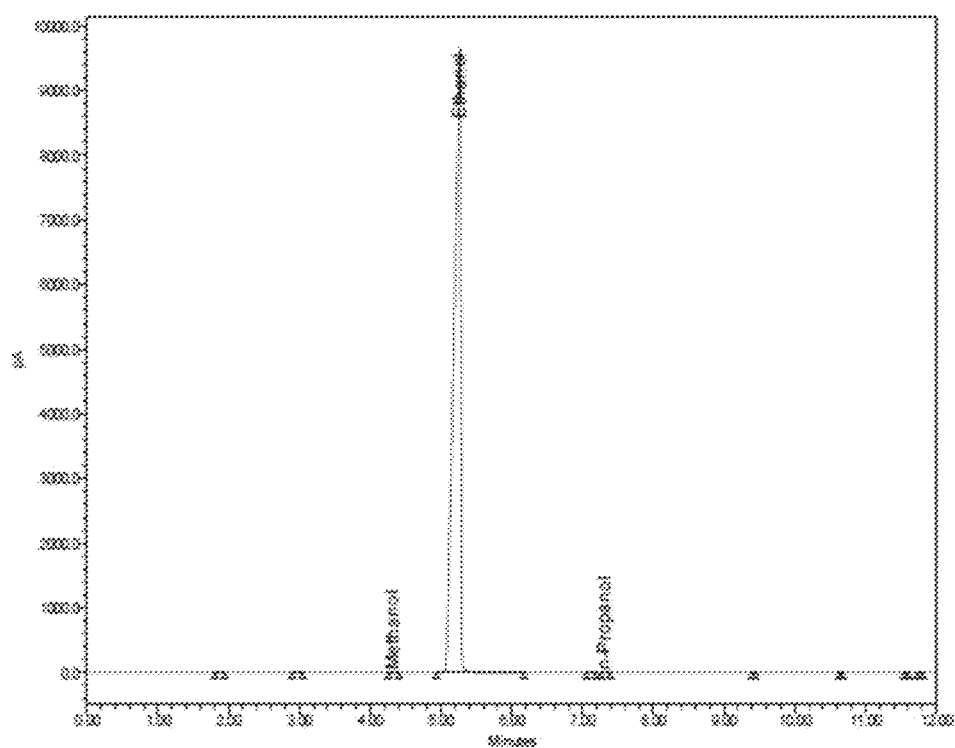
FIG. 13A is a Flame Ionization Detector (FID) gas chromatogram obtained by analyzing ethanol produced from cane.
Figure 13B:
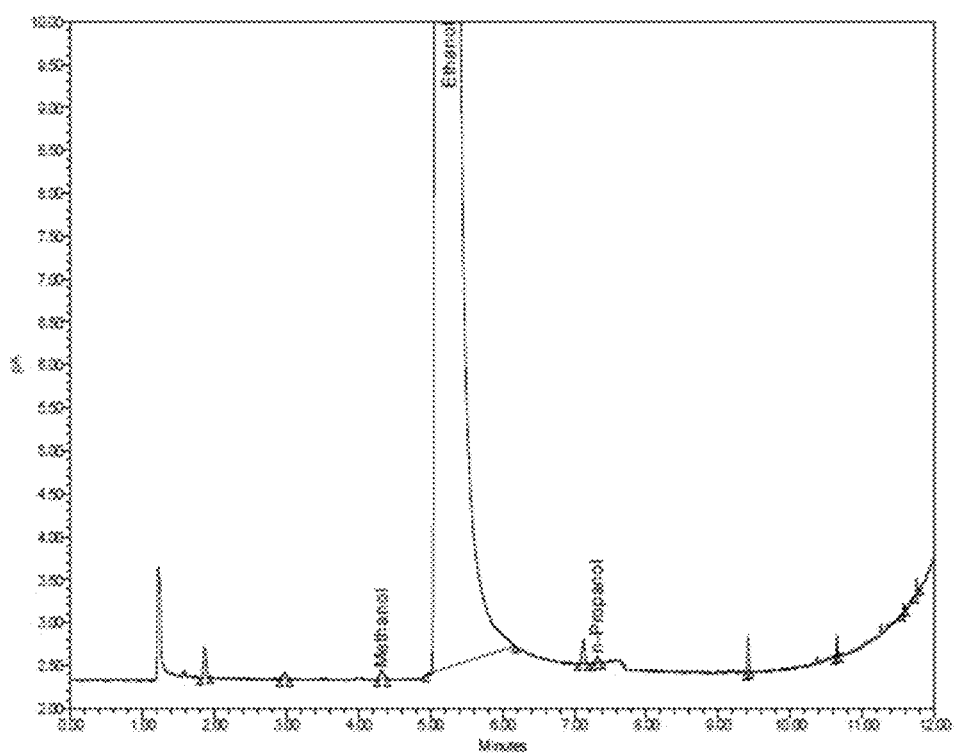
FIG. 13B shows a magnified version of the same chromatogram.
Figure 14A:
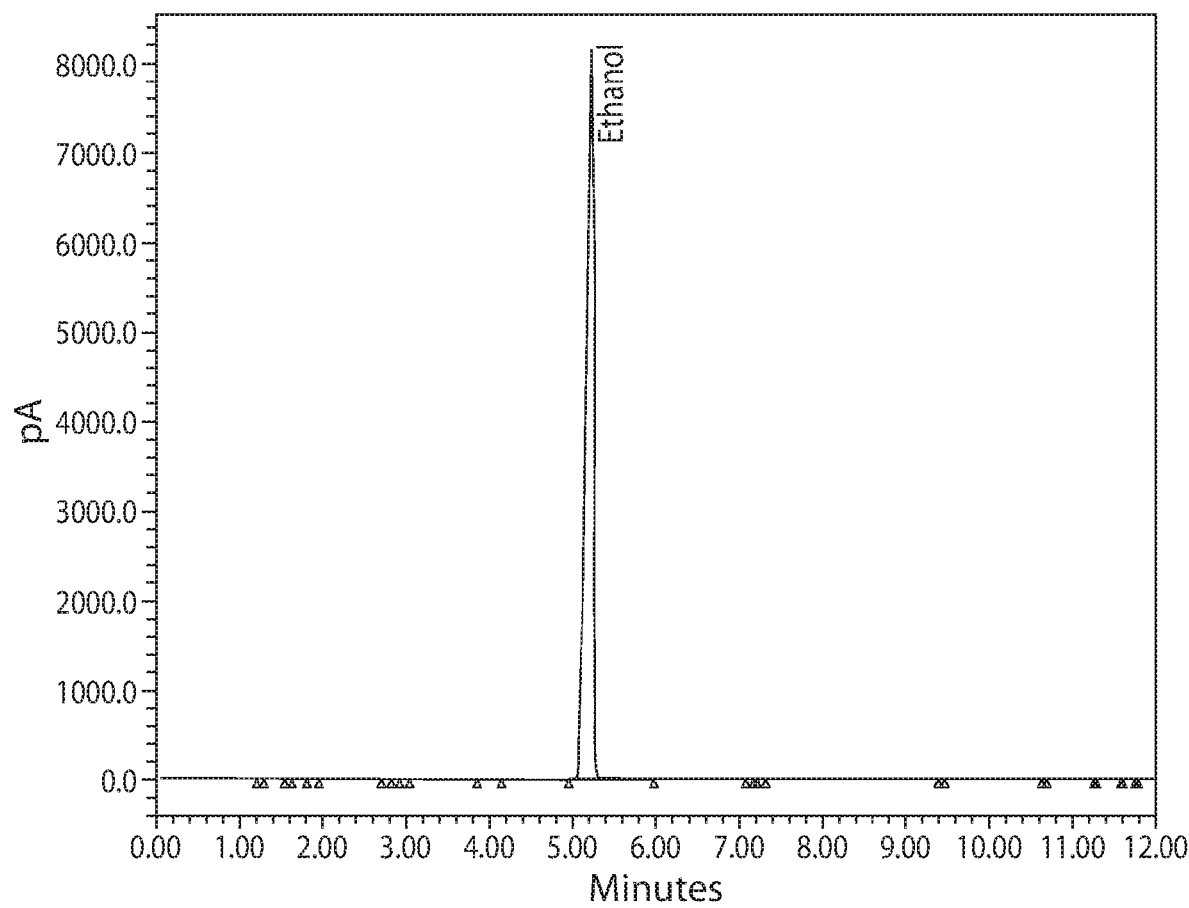
FIG. 14A is a Flame Ionization Detector (FID) gas chromatogram obtained by analyzing ethanol produced from corn.
Figure 14B:
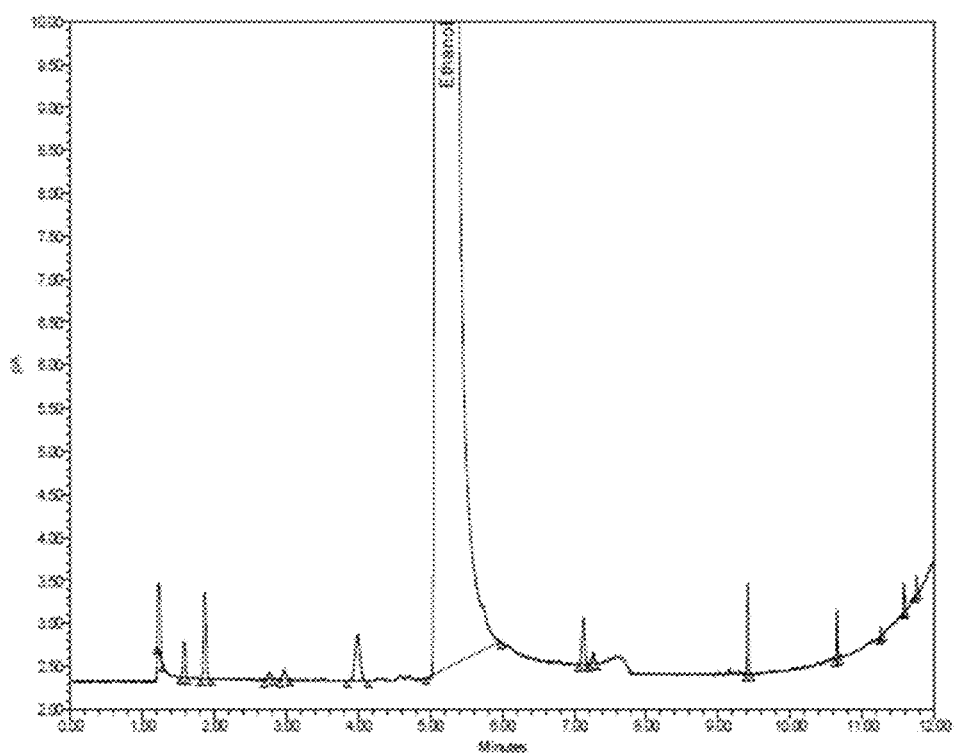
FIG. 14B shows a magnified version of the same chromatogram.
Figure 15A:
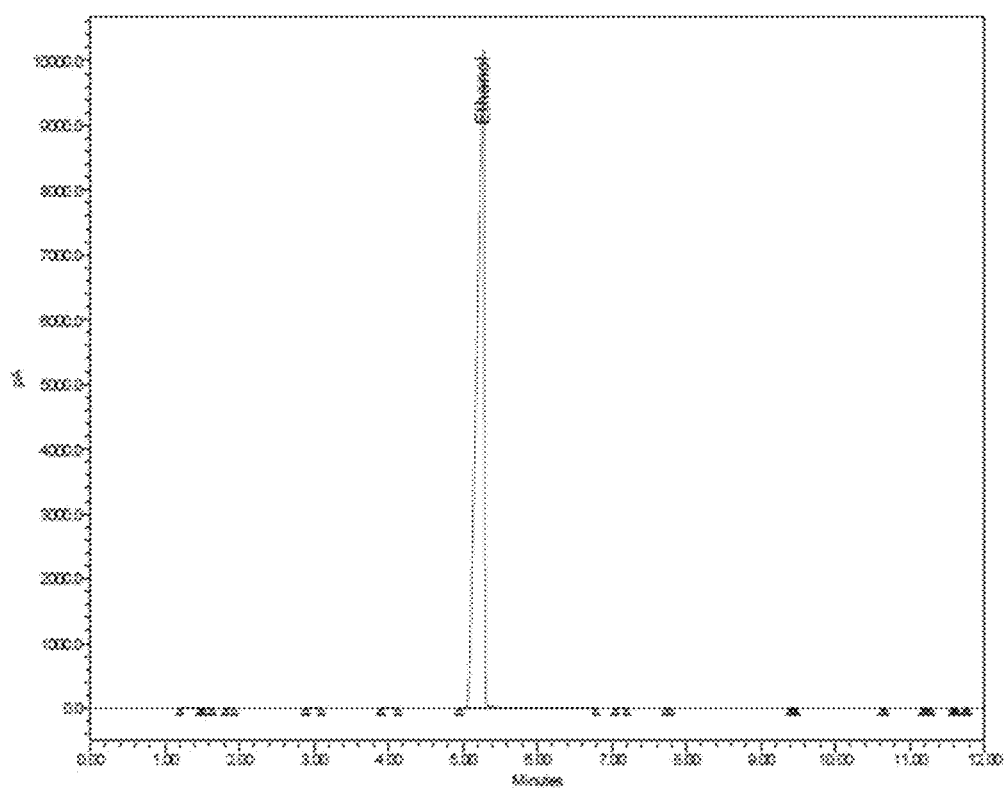
FIG. 15A is a Flame Ionization Detector (FID) gas chromatogram obtained by analyzing ethanol produce from grape.
Figure 15B:
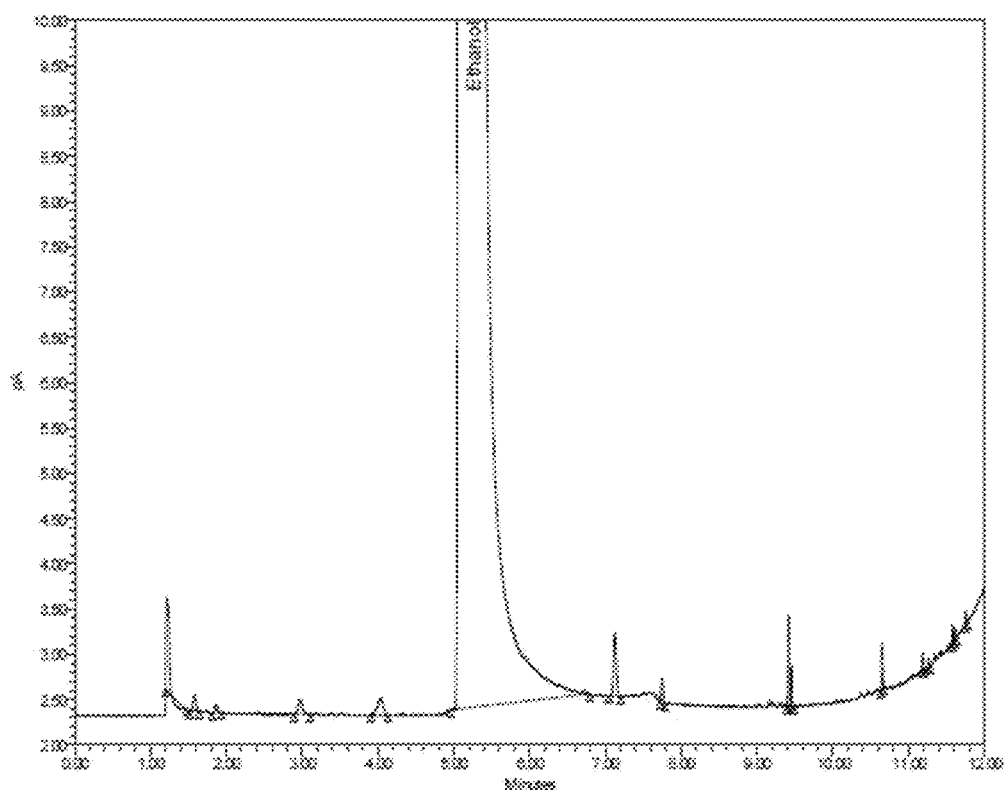
FIG. 15B shows a magnified version of the same chromatogram.
Figure 16A:
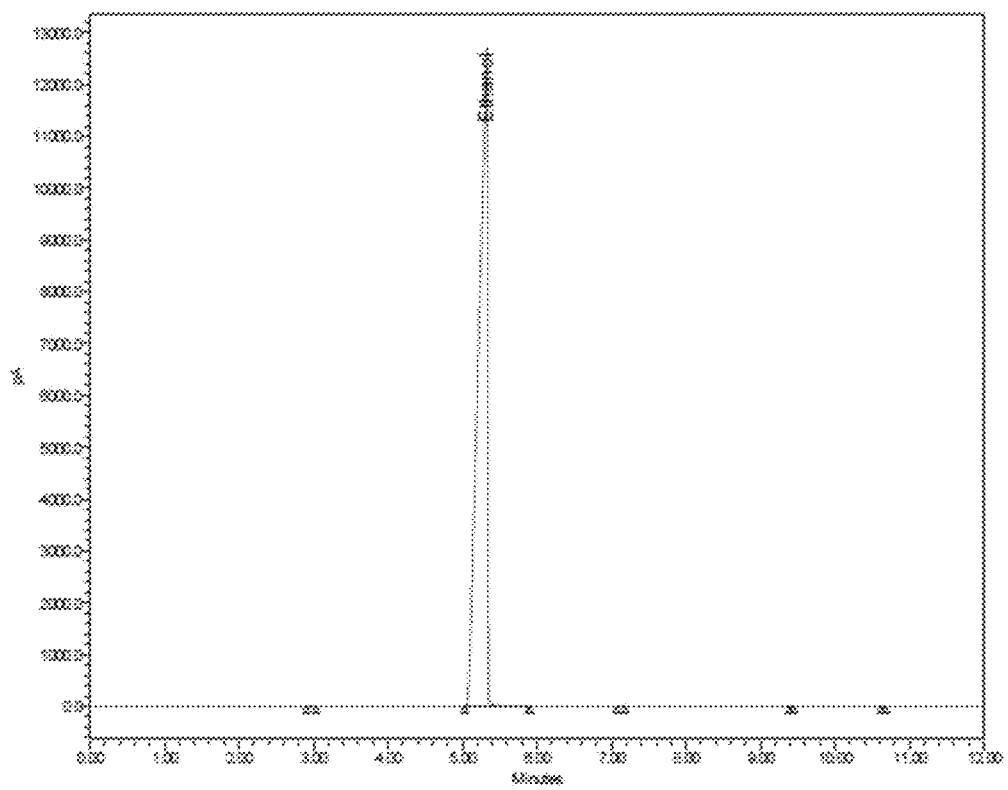
FIG. 16A is a Flame Ionization Detector (FID) gas chromatogram obtained by analyzing ethanol produced from wheat.
Figure 16B:
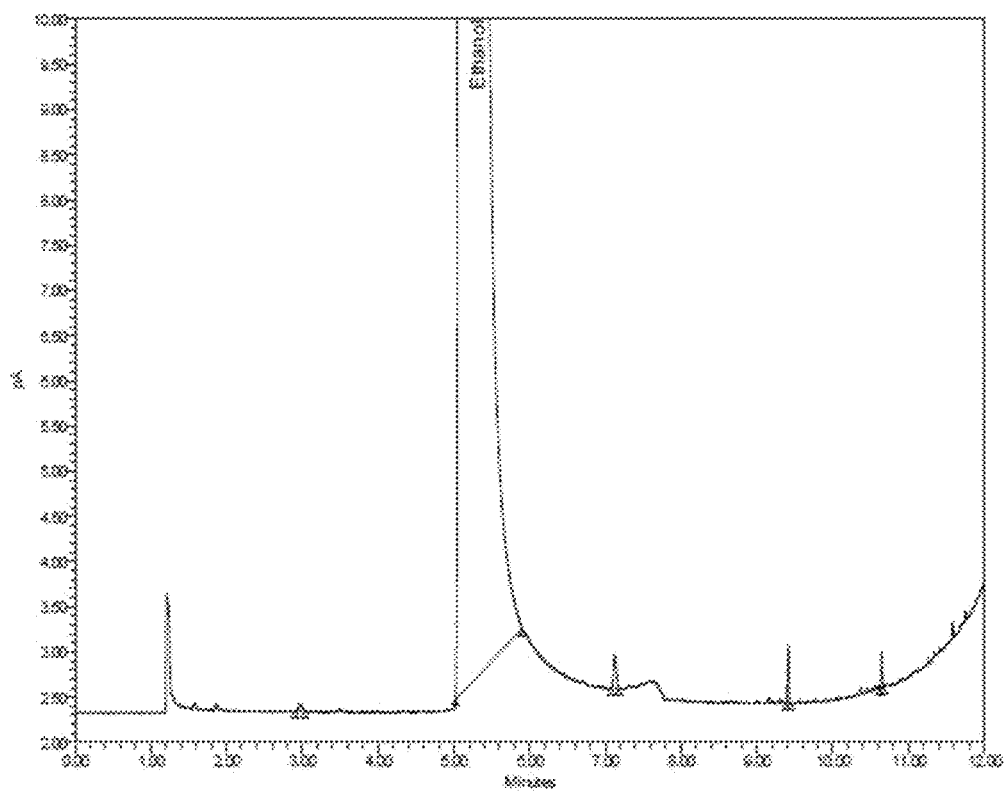
FIG. 16B shows a magnified version of the same chromatogram.

FIG. 10 provides a chromatogram analyzing ethanol produced from cellulosic or lignocellulosic biomass generated by the processes described herein. It shows that, in some embodiments, the ethanol produced from cellulosic or lignocellulosic biomass contains other constituents such acetone, methanol and isopropyl alcohol (IPA). FIGS. 12A, B provide a chromatogram obtained by analyzing ethanol produced from lignocellulosic biomass generated by the processes described in this application by using Flame Ionization Detector (FID) gas chromatography. It shows that, in some embodiments, the ethanol from cellulosic and lignocellulosic biomass studied herein contains other constituents such acetone, methanol, n-propanol, 2-methylpropanol, n-butanol, 2-methyl butanol and isopropyl alcohol (IPA). FIGS. 13 A, B provide a Flame Ionization Detector (FID) gas chromatogram obtained by analyzing ethanol produced from cane. FIGS. 13 A, B show the composition of ethanol produced from cane. They show that, in some embodiments, the ethanol from cane does not contain the constituents observed in ethanol obtained from the cellulosic and lignocellulosic biomass studied herein. FIGS. 14 A, B provide a Flame Ionization Detector (FID) gas chromatogram obtained by analyzing ethanol produced from corn. FIGS. 14 A, B show the composition of ethanol produced from corn. They show that in some embodiments, the ethanol from corn does not contain the constituents observed in ethanol obtained from the cellulosic and lignocellulosic biomass studied herein. FIGS. 15 A, B provide a Flame Ionization Detector (FID) gas chromatogram obtained by analyzing ethanol produced from grape. FIGS. 15 A, B show the composition of ethanol produced from grape. They show that in some embodiments, the ethanol from grape does not contain the constituents observed in ethanol obtained from the cellulosic and lignocellulosic biomass studied herein. FIGS. 16 A, B provide a Flame Ionization Detector (FID) gas chromatogram obtained by analyzing ethanol produced from wheat. FIGS. 16 A, B show the composition of ethanol produced from wheat. They show that, in some embodiments, the ethanol from wheat does not contain the constituents observed in ethanol obtained from the cellulosic and lignocellulosic biomass studied herein.

The ethanol samples in FIGS. 10 and 12A, B to 16 A, B were analyzed using a FID gas chromatography method with a head space probe and an Agilent DB-FFAP column. Specifically, the carrier gas used in the column was Helium, and that in the Front Detector FID included hydrogen and air. The oven was maintained at a temperature of 55° C., the loop at 90° C., and the transfer line at 105° C. The pressure in the column was 13.036 psi, and the flow-rate ranged from 3.52 ml/min to 51.521 ml/min.

The above studies show that ethanol produced by the processes described herein can have unique composition and/or properties, which distinguishes ethanol obtained from one type of biomass from that derived from another type of biomass. The examples provided herein are however, not limiting. One can obtain ethanol of unique composition and/or properties from the processes described herein from all types of biomass material. Generally, any biomass material including carbohydrates composed entirely of one or more saccharide units can be processed to produce ethanol of unique composition by the methods described herein. The biomass can be recalcitrant biomass or recalcitrant-reduced biomass. The biomass material can be cellulosic or lignocellulosic materials, or starchy materials, such as kernels of corn, grains of rice or other foods, or materials that are or that include one or more low molecular weight sugars, such as sucrose or cellobiose. Biomass can also include paper, paper products, wood, wood-related materials, particle board, grasses, rice hulls, bagasse, cotton, jute, hemp, flax, bamboo, sisal, abaca, straw, corn cobs, rice hulls, coconut hair, algae, seaweed, cotton, synthetic celluloses, or mixtures of any of these. Fiber sources can also be used, for example, cellulosic fiber sources, including paper and paper products (e.g., polycoated paper and Kraft paper), and lignocellulosic fiber sources, including wood, and wood-related materials, e.g., particle board. Other suitable fiber sources include natural fiber sources, e.g., grasses, rice hulls, bagasse, cotton, jute, hemp, flax, bamboo, sisal, abaca, straw, corn cobs, rice hulls, coconut hair; fiber sources high in α-cellulose content, e.g., cotton; and synthetic fiber sources, e.g., extruded yarn (oriented yarn or un-oriented yarn). Lignocellulosic feedstock can be plant biomass such as, but not limited to, non-woody plant biomass, cultivated crops, such as, but not limited to, grasses, for example, but not limited to, C4 grasses, such as switchgrass, cord grass, rye grass, miscanthus, reed canary grass, or a combination thereof, or sugar processing residues such as bagasse, or beet pulp, agricultural residues, for example, soybean stover, corn stover, rice straw, rice hulls, barley straw, corn cobs, wheat straw, canola straw, rice straw, oat straw, oat hulls, corn fiber, recycled wood pulp fiber, sawdust, hardwood, for example aspen wood and sawdust, softwood, or a combination thereof. It can also include microbial biomass such as those derived from naturally occurring or genetically modified unicellular organisms and/or multicellular organisms, e.g., organisms from the ocean, lakes, bodies of water, e.g., salt water or fresh water, or on land, and that contains a source of carbohydrate (e.g., cellulose). Microbial biomass can include, but is not limited to, for example protists (e.g., animal (e.g., protozoa such as flagellates, amoeboid, ciliates, and sporozoa) and plant (e.g., algae such alveolates, chlorarachniophytes, cryptomonads, euglenids, glaucophytes, haptophytes, red algae, stramenopiles, and viridaeplantae)), seaweed, plankton (e.g., macroplankton, mesoplankton, microplankton, nanoplankton, picoplankton, and femptoplankton), phytoplankton, bacteria (e.g., gram positive bacteria, gram negative bacteria, and extremophiles), yeast and/or mixtures of these. In some instances, microbial biomass can be obtained from natural sources, e.g., the ocean, lakes, bodies of water, e.g., salt water or fresh water, or on land. Alternatively, or in addition, microbial biomass can be obtained from culture systems, e.g., large scale dry and wet culture systems. In some embodiments, the animal biomass can be used to generate ethanol of unique composition and/or properties. Animal biomass includes any organic waste material such as animal-derived waste material or excrement or human waste material or excrement (e.g., manure and sewage). In some embodiments, feedstocks are obtained from plants that have been modified with respect to a wild type variety, e.g., by genetic modification or other types of modification, can be processed to produce useful intermediates and products such as those described herein. Such modifications may be for example, by any of the methods described in any patent or patent application referenced herein. As another example, plants may be modified through the iterative steps of selection and breeding to obtain desired traits in a plant. Furthermore, the plants can have had genetic material removed, modified, silenced and/ or added with respect to the wild type variety. For example, genetically modified plants can be produced by recombinant DNA methods, where genetic modifications include introducing or modifying specific genes from parental varieties, or, for example, by using transgenic breeding wherein a specific gene or genes are introduced to a plant from a different species of plant and/or bacteria. Another way to create genetic variation is through mutation breeding wherein new alleles are artificially created from endogeneous genes or by exogenous genes.

In some embodiments, the ethanol of unique compositions and/or properties derived from various types of biomass can be mixed with each other in various combinations. For example, in some embodiments, the ethanol compositions described in FIGS. 10 and 12A, B to 16 A, B can be mixed with each other in various combinations. In some embodiments, the ethanol of unique composition and/or properties derived from various types of biomass can be mixed with each other and with ethanol obtained from other sources. In some embodiments, the ethanol of unique composition and/or properties derived from various types of biomass can be mixed with each other and/or with hydrocarbons, aromatics or other sources of energy. Since the ethanol feedstock has unique composition and/or properties, the resulting mixture can also have unique composition and/or properties. In some embodiments, the mixture contains lignocellulosic ethanol containing about 0.02% acetone, about 0.11 to about 2.5% methanol, about 0.18% n-propanol, about 0.12% of 2-methyl propanol, about 0.01% n-butanol, about 0.53% 2-methyl butanol and about 8.5% isopropyl alcohol.

In some embodiments, the ethanol or ethanol combination described above can be used as fuel, fuel blends or additives or as building blocks for other value-added products. Since the ethanol feedstock has unique composition and/or properties, the resulting fuel, fuel blends, additives or intermediates can also have unique composition and/or properties. For example, when used as fuel, the fuel may have an octane number of about 1 to about 10, about 10 to about 20, about 20 to about 30, about 30 to about 40, about 40 to about 50, about 50 to about 60, about 60 to about 70, about 70 to about 80, about 90 to about 100, about 100 to about 110, about 110 to about 120, about 120 to about 130, about 130 to about 140, about 140 to about 150, about 150 to about 160, about 160 to about 170, about 170 to about 180, about 180 to about 190, about 190 to about 200, or in a range bounded by any numerical value stated herein above. The resulting fuel may also have other unique properties such as density, viscosity, freezing point, volatility and flash point.

Figure 12B:
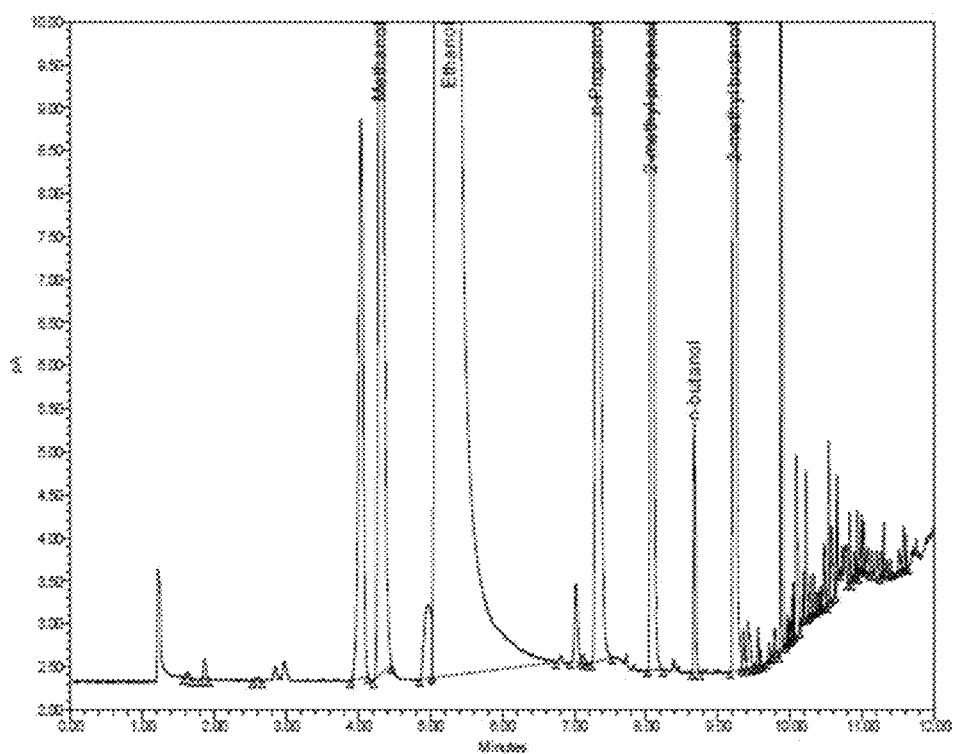
FIG. 12B shows a magnified version of the same chromatogram.

In some embodiments, the ethanol of unique composition and/or properties derived from various types of biomass can be used as feedstocks for making hydrocarbon mixtures of unique composition by using the processes described herein. Details of such processes, including catalytic processes have been described elsewhere in this application. For example, the ethanol compositions described in FIGS. 10 and 12A, B to 16 A, B can be used as feedstocks for making hydrocarbon mixtures of unique composition by using the processes described herein. In some embodiments, the hydrocarbons derived from one type of biomass may have a different composition than that derived from another type of biomass. For example, the hydrocarbon composition derived from lignocellulosic ethanol (eg., ethanol shown in FIGS. 10 and 12 A, B) may have a different composition from those obtained from cane-derived ethanol (eg., ethanol shown in FIGS. 13 A, B). In some embodiments, the hydrocarbon composition derived from lignocellulosic ethanol may have a different composition than that derived from other biomass sources, such as cane, corn, wheat, and grape. The hydrocarbon composition derived from one type of ethanol can be different from that derived from another type of ethanol (such as ethanol derived from another type or source of biomass, or a non-biomass material). For example, the hydrocarbon composition may have unique ratio of unsaturated hydrocarbons to saturated hydrocarbons, aromatic to non-aromatic hydrocarbons, odd-numbered to even-numbered hydrocarbons, and low molecular weight to high molecular weight hydrocarbons.

In some embodiments, the hydrocarbons obtained from the ethanol of unique composition may exhibit unique properties. For example, the resulting hydrocarbons may have an octane number of about 1 to about 10, about 10 to about 20, about 20 to about 30, about 30 to about 40, about 40 to about 50, about 50 to about 60, about 60 to about 70, about 70 to about 80, about 90 to about 100, about 100 to about 110, about 110 to about 120, about 120 to about 130, about 130 to about 140, about 140 to about 150, about 150 to about 160, about 160 to about 170, about 170 to about 180, about 180 to about 190, about 190 to about 200, or in a range bounded by any numerical value stated herein above. The resulting hydrocarbon mixture may also have other unique properties such as density, viscosity, freezing point, volatility and flash point.

The hydrocarbon mixtures of unique composition generated by the processes described herein can be used as fuel or fuel blends, for example, as components of aviation fuel, jet fuel, gasoline, diesel, kerosene, LPG, heating oil, rocket fuel, and various other types of transportation and heating fuel. Examples of energy products that can be generated from the hydrocarbon compositions described above include gaseous fuels (eg., biogas, syngas, hydrogen, methane, etc.), solid fuels (eg., coke, pellets, lignin etc.), and liquid fuels (eg., ethanol, diesel, jet fuel etc.). They may be also converted to other value-added products, such as coke, carbon, additives, waxes, greases, lubricants, and asphalts. The hydrocarbon mixtures of unique compositions and/or properties can be mixed with other hydrocarbons, whether produced by the processes described herein or produced by other methods.

Similarly, a number of other products such as fatty esters, aromatics, higher alcohols and oxygenated polyols can be obtained from the ethanol of unique composition and/or properties described above. These products can also exhibit unique compositions and/or properties depending on the type of ethanol used as feedstock in their preparation. For example, the products derived from lignocellulosic ethanol (eg., ethanol shown in FIGS. 10 and 12 A, B) may have a different composition and property than those obtained from cane-derived ethanol (eg., ethanol shown in FIGS. 13 A, B). In some embodiments, the products derived from lignocellulosic ethanol may have a composition that is different than that derived from other biomass sources, such as cane, corn, wheat, and grape. The products derived from one type of ethanol can have a different composition and property than that derived from another type of ethanol (such as ethanol derived from another type or source of biomass, or a non-biomass material).

The products produced from the unique ethanol compositions described above can further act as building blocks for a large number of biochemical products that can be used in the textile industry (eg., in making carpets, fibers, fabrics etc.), food industry (eg., in food packaging, preservatives etc.), transportation industry (eg., in making tires, molded plastics etc.), housing industry (eg., in making paints, resins, cements, garbage bags, glue etc.), furnitures, sports industry (eg., in making athletic gears, balls, roller blades, camera films etc.), communications industry (eg., in making dyes, fiber coatings), cosmetic industry (eg., perfumes, deodarants, shampoos, toothpaste etc.) and health industry (eg., in making medical devices and pharmaceuticals).

In one or more embodiments, the fermentation can produce a carboxylic acid, for example, as described in U.S. application Ser. No. 13/177,827 filed on Jul. 7, 2011 and U.S. application Ser. No. 13/668,358 filed on Nov. 5, 2012, the entire disclosure of which are incorporated herein by reference. The carboxylic acid can be, for example any carboxylic acid with between 1 to 20 carbons and 1 to 5 carboxylic acid ($—CO_2H$) groups (e.g., 1 to 10 carbons and 1 to 4 carboxylic acid groups, 1 to 5 carbons and 1 to 3 carboxylic acid groups). For example some carboxylic acids that can be utilized in the methods described herein are acetic acid, propionic acid, tartaric acid, malonic acid, succinic acid, glutaric acid, adipic acid, benzoic acid, phthalic acid, maleic acid, gluconic acid, traumatic acid, muconic acid, butyric acid (e.g., n-butyric acid, isobutyric acid), valeric acid, caproic acid, lauric acid, palmitic acid, stearic acid and arachidic acid. Some suitable microorganisms to produce butyrate can include C. saccharobutylacetonicum, C. saccharoperbutylacetonicum, C. saccharobutylicum, C. Puniceum, C. beijernckii, C. acetobutylicum, C. acetobutylicum, C. roseum, C. aurantibutyricum, C. felsineum and C. tyrobutyricum.

Figure 2:
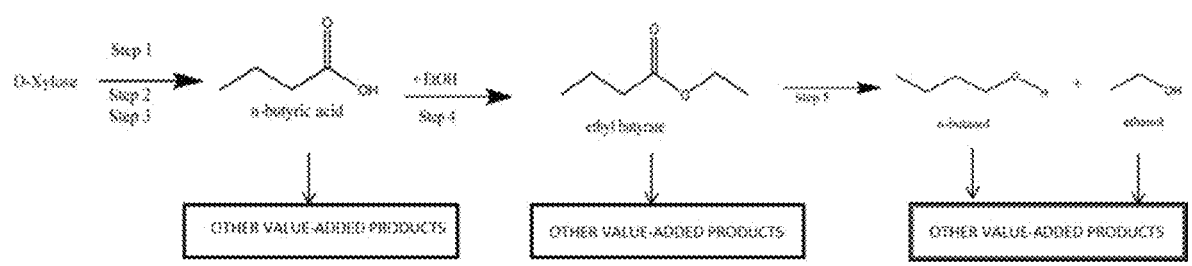
FIG. 2 is a reaction scheme for converting a sugar to butanol, ethanol, butyric acid, ethylbutyrate, which can be further converted to fuel or other value-added products through one or more processes.

FIG. 2 shows an example of a reaction scheme for converting a sugar to an alcohol, specifically butanol. In a first step, for example, xylose is fermented to n-butyric acid. It should be understood that the iso-butyric acid may also undergo a similar reaction scheme. In a second step the butyric acid is contacted with the quaternary amine functionalized resin Amberlite™ 400. Butyrate becomes associated with the quaternary amine groups and is extracted from solution in this second step. In a third step the resin and bound butyrate is contacted with a strong acid, e.g., aqueous sulfuric acid, with the effect of protonating the butyrate and forming free butyric acid. The butyric acid can then be extracted by ethanol or other alcohol providing butyric acid in an alcoholic solution. In a fourth step the butyric acid and ethanol (optionally additional ethanol can be added) is contacted with an optionally catalyst and heated (e.g., to refluxing temperatures around 80 to 90° C. at atmospheric pressure) so that an esterification reaction occurs producing ethyl butyrate. Alternatively, butyric acid and ethanol can be converted to other value-added products, including fuel by various processes such as oligomerization. In a fifth step, the ethyl butyrate is hydrogenated to butanol and ethanol utilizing hydrogen and a catalyst (e.g., Re/Al$_2$O$_3$). The hydrogenation step can be carried out in any reactor suited for hydrogenations. The ethylbutyrate can alternatively be converted to other value-added products, including fuel by various processes such as deoxygenation, dehydration, and/ or oligomerization. In some embodiments, n-butanol acts can be converted to other value-added products such as fuel by various processes such as deoxygenation, dehydration, and/or oligomerization.

In other embodiments, sugars with reduced recalcitrance can also be converted to terpenes. Terpenes can be generated from the bioconversion of fermentable sugars derived from lignocellulosic biomass using organisms such as E. coli or S. cerevisiae. There are at least two known metabolic pathway for the generation of terpenes and their precursors, isopentenyl pyrophosphate (IPP): the mevalonic acid (MVA) pathway and the deoxyxylulose-phosphate (DXP) pathway.

Isolating the Intermediate Building Block from Fermentation Bath:

Distillation

After fermentation, the resulting fluids can be purified using any useful method. For example, some useful methods are distillation, adsorption, liquid-liquid extraction, perstraction, reverse osmosis, pervaporation and gas stripping (see, e.g., J. Ind. Microbiol. Biotechnol. (2009) 36:1127-1138).

After fermentation, the resulting fluids can be distilled using, for example, a "beer column" to separate ethanol and other alcohols from the majority of water and residual solids. The vapor exiting the beer column can be, e.g., 35% by weight ethanol and can be fed to a rectification column. A mixture of nearly azeotropic (92.5%) ethanol and water from the rectification column can be purified to pure (99.5%) ethanol using vapor-phase molecular sieves. The beer column bottoms can be sent to the first effect of a three-effect evaporator. The rectification column reflux condenser can provide heat for this first effect. After the first effect, solids can be separated using a centrifuge and dried in a rotary dryer. A portion (25%) of the centrifuge effluent can be recycled to fermentation and the rest sent to the second and third evaporator effects. Most of the evaporator condensate can be returned to the process as fairly clean condensate with a small portion split off to waste water treatment to prevent build-up of low-boiling compounds.

In other embodiments, carboxylic acid, e.g., butyric acid, and other fermentation products can be removed/purified by adding base to the fermentation solution, adding acid to the fermented solution, extraction, filtration, centrifugation, distillation, cross flow filtration, membrane filtration, pertraction, electrodialysis, adsorption and/or bonding to a resin or other solid, and combinations of these methods. Optionally, after purification, if the product is wet, the product can be dried, for example by contacting the product with molecular sieves or other drying agents (e.g., sodium sulfate, magnesium sulfate). An extraction method for organic acids including formation of an alkyl amine adduct in an aqueous solution that can be subsequently extracted from the aqueous phase is described in U.S. application Ser. No. 12/935,075 filed Mar. 27, 2009, the entire disclosure of which is incorporated herein by reference. In one preferred embodiment, organic acids (e.g., butyric acid) can be extracted by adsorption/adduct formation/bonding to on a solid support, for example a resin, solid and/or polymer support.

In some embodiments the fermented product can be extracted directly from the fermentation solution or from a solution that has been distilled. The extracting solvent can be, for example, an alcohol, an ether, an oil (e.g., castor oil, coconut oil, palm oil). For example, for the extraction of carboxylic acid (e.g., butyric acid), some particularly useful alcohols are fatty alcohols, for example, having between 6 and 20 carbons and 1 to 5 alcoholic functional groups (e.g., n-hexanol, n-octanol, n-decanol, n-dodecanol, lauryl alcohol, myristyl alcohol, cetyl alcohol, stearyl alcohol, oleyl alcohol, linoleyl alcohol, isomers of these and combinations of these). The acid can be protonated by treating the solution containing the acid with a mineral acid to adjust the pH to about pH 3 (e.g., between about pH 2 and 4) prior to extraction.

The acid can be esterified as discussed herein to the ester. The alcohols listed herein can be also utilized to esterify the fermentation derived acid. The esterification can be done in the extraction solution. For example, an alcohol can be added to the extracting solvent. If the extracting solvent is an alcohol, then the alcohol can be directly utilized for esterification with or without concentration or dilution of the alcohol. For example, butyric acid derived from the fermentation of a biomass can be protonated by the addition of sulfuric acid to the fermented solution. The butyric acid can be subsequently distilled away from the acidified solution. The distillate can then be extracted in an alcohol (e.g., n-octanol). An acid catalyst can be added to the extracted acid and alcohol and the solution heated to produce an ester. Alternatively, fermented solution can be acidified and then directly extracted with an alcohol (e.g., octanol). The mixture can then be esterified.

In some embodiments the resins utilized to adsorb organic acids (e.g., butyric acid) can be polymers with ion exchange properties, for example having quaternary amine functional groups that can ion exchange with the acidic proton of the acid. For example, Amberlite™ IRA 410, Amberlite™ IRA-67, Amberlite™ 96, Amberlite™ XAD-1180M, Amberlite™ XAD-2, Amberlite™ 400 and Amberlite™ IRN150. A solution containing the organic acid can be contacted with the ion exchange resin by passing the solution through a packed column (e.g., glass, metal, plastic) of the resin.

Optionally, the solution containing the organic acid can be combined with the resin in a vessel (e.g., in a batch mode) and agitated (e.g., shaken, stirred) for several minutes to several hours (e.g., 1 min to 24 hours, 1 min to 12 hours, 1 min to 8 hours, 1 min to 4 hours, 1 min to 1 hour, 1 hour to 4 hours, 1 hour to 12 hours). In batch mode the organic acid depleted solution can be decanted or filtered from the resin after a sufficient time to adsorb/bond at least some of the organic acid. The amount of butyric acid in the batch separation or column separation methods can be monitored by any useful method, for example, head space analysis, titrations and HPLC.

A resin for adsorbing an organic acid can be contacted with the fermenting solution while the fermentation is still processing or after the fermentation is complete. For example, the active fermentation media can be pumped through a column of the resin or the resin can be added to the fermentation broth.

The organic acid can, for example, be removed from the resin by contacting the resin and bound organic acid with an acid solution. For example, the acid solution can include a mineral acid (e.g., hydrochloric, sulfuric, phosphoric, nitric) or the acid can be an organic acid (acetic acid, trifluoroacetic acid). It is generally preferable to use an acid with a low pKa, e.g., about lower than the pKa of butyric acid e.g., a pKa of less than about 4, less than about 3, less than about 2. The pH of the solution after acidification is optimally between about 1 and 6 (e.g., between about 2 and 5, between about 2 and 4). It can be advantageous to utilize a solvent with or without water to aid in extracting the organic acid or organic acid salt from the resin. For example, the solvent can be an alcohol (e.g., methanol, ethanol, propanol, butanol or the fatty acid alcohols previously described), an ether (e.g., diethyl ether, tetrahydrofuran, methyl tert-butyl ether, di-isopropyl ether), acetonitrile, acetone, butyl acetate, dimethylformamide, ethyl acetate and combinations of these. These can be combined in any percentage with water and each other. A preferred method of removing adsorbed organic acid from a resin packed column is elution with acidified alcohol (e.g. ethanol and/or methanol with and added acid) or an acidified alcohol/water solution (e.g., ethanol/water, methanol/water with and added acid). Resins can be recycled after removal of the acid, for example by flushing with excess of the acidified solution followed by flushing with water, optionally deionized water.

The acidified eluent/extracting solution from the resin processing containing the carboxylic acid can be neutralized by addition of a base. This can produce the salt of the carboxylic acid. The salts of the carboxylic acid can be evaporated to dryness and then oven dried (e.g. at 80 to 100° C.). The salts can be subsequently utilized in esterification reactions, with optionally re-acidification prior to the reaction.

In an alternative to acidification to remove the organic acid from the resin, the acidic proton of the organic acid can be removed by ion exchange with a cation to form the salt of an organic acid. Some useful exchanging ions include, for example, quaternary ammonium ions, alkali metal ions and alkali earth metal ions, transition metal ion and combinations of these. The salt of the carboxylic acid thus produced can be further processed as previously discussed.

Conversion of Building Blocks from Processed Biomass to Fuel

Biomass feedstocks can be converted into intermediate building blocks through gasification, into alcohols through biochemical or thermochemical processes, into sugars through biochemical processes, and into bio-oil through pyrolysis processes. Syngas, alcohols, sugars, and bio-oils can be further upgraded to biofuel or components of biofuel blendstock via a variety of synthesis, fermentative, or catalytic processes.

Catalytic Processes Used in the Conversion of Building Blocks to Fuel

A large variety of building blocks, such as alcohols formed from fermentation process can be used in making components of fuel blendstock. Exemplary alcohols include methanol, ethanol, n-propanol, iso-propanol, n-butanol, iso-butanol, sec-butanol, as well as longer chained alcohols, R C5-C20. Longer chained alcohols may be particularly attractive, since the larger R group (relative to OH) can provide a better mass loss on conversion to hydrocarbon. Other biofuel products such as fatty esters, aromatics and oxygenated polyols can also be obtained by the stepwise methods described herein.

In some embodiments, building blocks produced by the invention can be converted to alkanes and/or other components of a biofuel using one or more steps in which multiple chemical conversions can occur simultaneously. Catalysts can be used to, for example, promote a number of reactions simultaneously. In one or more embodiments, catalysts are provided that can e.g. simultaneously reduce hydrogen content (e.g., dehydrogenation) and reduce oxygen content (e.g., dehydration). In one embodiment, a tin-doped $Pt/Al_2O_3$ catalyst generated by solvent-impregnation process is used to convert biomass-derived building blocks to fuel constituents. In other embodiments, the building blocks can be subjected to a process that simultaneously reduce hydrogen content, and reduce oxygen content, and increases molecular weight. The ability to effect multiple changes on the building blocks in a single reactor can make available a more complex biocomposition. The ability to effect multiple changes on the building blocks in a single reactor can also provide complex mixtures that more closely parallel fuels currently being used in the transportation industry. Additional advantages also a simplification of the complexity and cost of the conversion process. By way of example, an alcohol building block can be treated with a catalyst that is capable of promoting a number of reactions so that the input building blocks do not need to pass through multiple catalyst beds.

Conversion Processes for Alcohols to Fuel

Figure 3A:
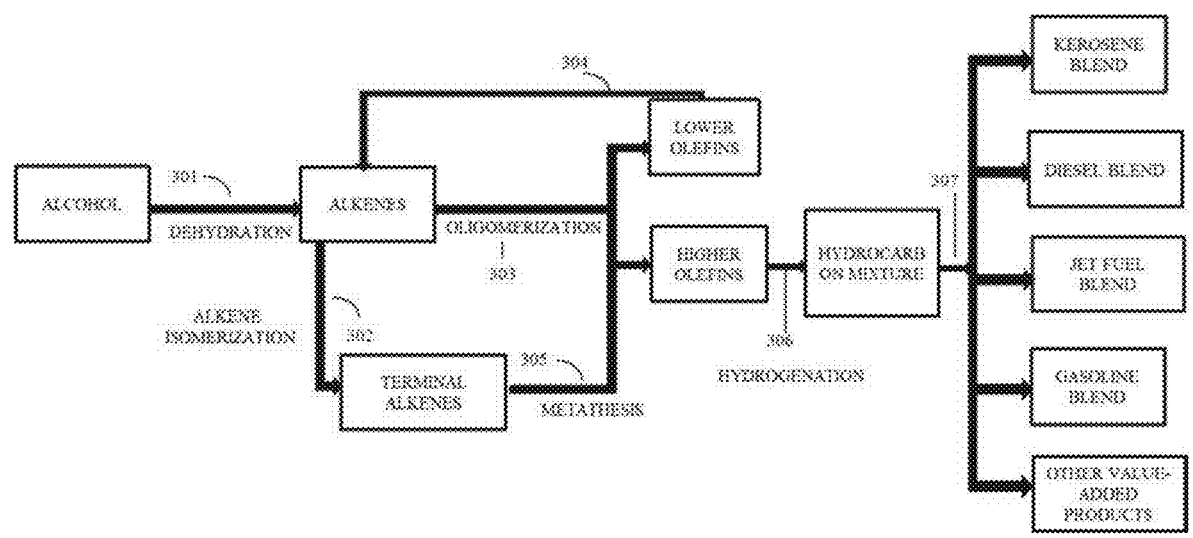
FIG. 3A is a schematic block diagram illustrating the conversion of alcohol derived from processed biomass to fuel blends and other value-added products through dehydration and hydrogenation.
Figure 3B:
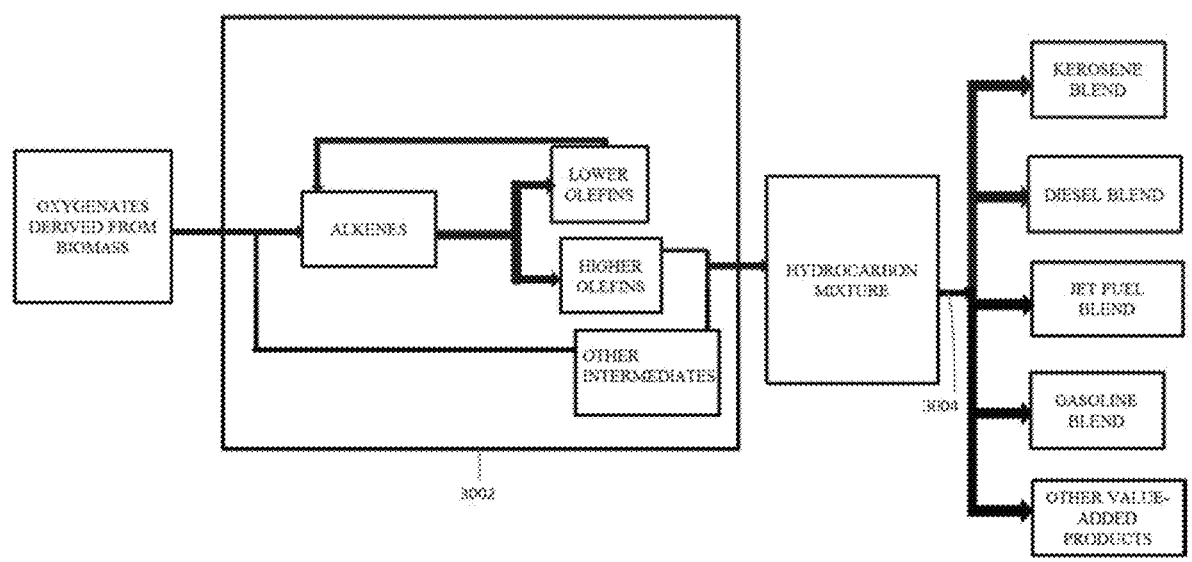
FIG. 3B is a schematic block diagram illustrating the conversion of oxygenates derived from biomass to fuel blends and other value-added products through a reforming process in the presence of reforming catalyst.

In some embodiments, alcohols produced from biomass can be converted to alkanes and/or other components of a fuel through one or more steps. For example, alcohols can be converted alkenes by dehydration, and the dehydrated alkene can be oligomerized into higher olefins. The higher olefins may be subsequently hydrogenated to produce alkanes. For example, FIG. 3A is a schematic block diagram illustrating the conversion of alcohol derived from processed biomass to fuel blends and other value-added products through dehydration and hydrogenation. In step 301, alcohols are dehydrated (preferably catalytically) to alkenes. The alkenes obtained from the dehydration of alcohols can then be oligomerized in step 303. Alternatively, the alkenes may be isomerized to convert internal alkenes to terminal alkenes in step 302, followed by alkene metathesis in step 305. The aim of both the oligomerization and the metathesis step is to produce higher olefins. Any lower olefins that remain in the mixture are separated from the higher olefins and fed back into the loop for further oligomerization and/or metathesis. In step 306, the higher olefins are hydrogenated (preferably catalytically) to produce a mixture of hydrocarbons, which are then separated by distillation and/or other separation methods in step 307 to form components of various fuel blends or other value-added products. FIG. 3B is a schematic block diagram illustrating the conversion of oxygenates derived from biomass to fuel blends and other value-added products through a reforming process in the presence of reforming catalyst. In step 3002, oxygenates derived from biomass is subjected to catalytic reforming. Depending upon the catalysts and reaction conditions, hydrocarbons are formed through alkene intermediates or through non-alkene intermediates. In some embodiments, a non-reducing atmosphere may facilitate the production of alkenes. In other embodiments, such as under reducing atmosphere, aromatics and hydrocarbons (cyclic and acyclic) can be predominantly produced. In step 3004, the hydrocarbon mixture is separated into components suitable for use in various fuel blendstocks and other value-added products.

In some embodiments, the dehydration of alcohols to alkenes is accomplished catalytically. Dehydration catalysts may include, for example, alumina, transition metal oxides (such as nickel oxide, bismuth oxide, titanium oxide, rhodium chloride), silicoaluminophosphates (SAPO), zeolite catalysts, and acidic catalysts (such as sulfuric acid, polyphosphoric acid heteropolyacid catalysts). For example, zeolites of different types such as ZSM-5 zeolites, X-type zeolites, Y-type zeolites, including those of various ionic compositions and substitutions and pore sizes can be used to catalytically dehydrate alcohols. In some embodiments, dehydration of alcohols to alkenes can be done by using biocatalysts such as enzymes. The dehydration step may use homogeneous and/or heterogeneous catalysts. Exemplary dehydration catalysts include alumina/transition metal oxides, slicoaluminum phosphates (SAPO), H-ZSM-5 zeolite e.g., (0.5% La-2% P H-ZSM-5 catalyst), heteropolyacid catalyst. Ethanol and n-butanol are preferred alcohols. In one embodiment, N-butanol can be dehydrated to 1-butene using, for example, at 380° C. and 2.1 bar. Ethanol can be dehydrated using, for example, 0.1-5% Pt/transition metal dopants, such as W or Mo or $TiO_2$.

In some embodiments, the olefins obtained from the dehydration of alcohols are further subjected to oligomerization. Oligomerization can be used, for example, to convert ethylene and other smaller olefins into linear α-olefins. Oligomers can grow by chain growth through olefinic bond, which usually provides products with an even number of carbons. Depending on the catalyst and reaction conditions, oligomerization reactions can form dimers, trimers, and tetramers.

The oligomerization may be further achieved catalytically. Various catalysts such as Ziegler Natta-type catalyst, chromium diphosphine catalysts, transition metal catalysts (such as nickel oxide, titanium oxide, bismuth oxide, rhodium chloride), zeolites, acidic catalysts (such as sulfuric acid, polyphosphoric acid heteropolyacid catalysts), and Amberlyst-35 catalyst may be used to catalyze the oligomerization of olefins. The catalysts may be homogeneous and/or heterogeneous.

In some embodiments, the higher olefins obtained by oligomerization are further subjected to dimerization. The dimerization may be further achieved catalytically. Various catalysts such Nafion catalyst, Ziegler Natta-type catalysts, transition metal catalysts (such as nickel oxide, bismuth oxide, Rhodium chloride), zeolites, alumina, silicoaluminophosphates (SAPO), and acidic catalysts (such as sulfuric acid, polyphosphoric acid heteropolyacid catalysts) may be used for dimerization. The catalysts may be homogeneous and/or heterogeneous.

Examples of industrially important linear alpha-olefins include 1-butene, 1-hexene, 1-octene, 1-decene, 1-dodecene, 1-tetradecene, 1-hexadecene, 1-octadecene and higher blends of $C_{20}$-$C_{24}$, $C_{24}$-$C_{30}$, and $C_{20}$-$C_{30}$ ranges. For example, in some embodiments, oligomerization of 1-butene with group 4 transition-metal catalysts in the presence of methylaluminoxane (Cp2ZrC22/MAO) can lead to higher weight C8-C32; 2-butene does not react and can be recycled. In another embodiment, oligomerization of ethylene using Ziegler-Natta catalyst at 90-110° C. and 89 bar pressure can give 96-97% yield of C4-C20 carbons In other embodiments, the molecular weight of olefins can be increased by alkene metathesis through the formation of metal-carbenes ($M=CH_2$) or metal-alkylidene complexes. This reaction facilitates the reaction of alkenes or alkynes, typically containing terminal double or triple bonds to form different or higher olefins. Different types of metathesis reactions can be used to form higher olefins, including cross-metathesis, ring closing metathesis, acyclic diene metathesis polymerization, ring opening metathesis polymerization, enyne metathesis, and ring-opening cross-metathesis. It can be used to generate both homodimers and heterodimers, polymeric compounds, cyclic and linear olefins.

In some embodiments, alkene metathesis is preceded by an isomerization process that can convert internal alkenes to terminal alkenes. The isomerization can be accomplished in a liquid medium in the presence of catalysts, such as alkaline alumina catalysts. Alternatively, internal alkenes can be reacted with excess ethylene in the presence of catalysts such as rhenium (IV) oxide supported on alumina in a process called ethanolysis, which causes the internal double bond to break up to form a mixture of α-olefins with odd and even carbon chain-length of the desired molecular weight.

The alkene metathesis process can be carried out in the presence of catalysts such as Schrock catalysts (such as $CpTa(=CH-t-Bu)Cl_2$, and other Mo(IV)-based, and W(IV)-based catalysts), Grubbs catalysts (Ru-based catalysts containing phosphine ligands), Hoveyda-Grubbs catalyst (Ru-based catalysts containing isopropoxystyrene ligands), Osmium-based catalyst, tungsten-halide-based catalysts, lithium aluminum tetraheptyl and titanium tetrachloride, tungsten(VI) oxytetrachloride and tetrabutyltin, cis-bis(triphenylphosphine)dichloroplatinum(II), and several other transition metal catalysts.

The resulting products from oligomerization and/or alkene metathesis can have a broad carbon number distribution and the pressure, temperature, catalytic conditions can be varied to achieve the desired carbon distribution. For example, the oligomerized products may have about 5% $C_4$, about 10% $C_4$, about 20% $C_4$, about 30% $C_4$, about 40% $C_4$, about 50% $C_4$, about 60% $C_4$, about 70% $C_4$, about 80% $C_4$, about 90% $C_4$. The oligomerized products may have about 5% $C_{6-10}$, about 10% $C_{6-10}$, about 20% $C_{6-10}$, about 30% $C_{6-10}$, about 40% $C_{6-10}$, about 50% $C_{6-10}$, about 60% $C_{6-10}$, about 70% $C_{6-10}$, about 80% $C_{6-10}$, about 90% $C_{6-10}$. The oligomerized products may have about 5% $C_{12-14}$, about 10% $C_{12-14}$, about 20% $C_{12-14}$, about 30% $C_{12-14}$, about 40% $C_{12-14}$, about 50% $C_{12-14}$, about 60% $C_{12-14}$, about 70% $C_{12-14}$, about 80% $C_{12-14}$, and about 90% $C_{12-14}$. The oligomerized products may have about 5% $C_{16-18}$, about 10% $C_{16-18}$, about 20% $C_{16-18}$, about 30% $C_{16-18}$, about 40% $C_{16-18}$, about 50% $C_{16-18}$, about 60% $C_{16-18}$, about 70% $C_{16-18}$, about 80% $C_{16-18}$, and about 90% $C_{16-18}$. The oligomerized products may have about 5% $C_{20}$, about 10% $C_{20}$, about 20% $C_{20}$, about 30% $C_{20}$, about 40% $C_{20}$, about 50% $C_{20}$, about 60% $C_{20}$, about 70% $C_{20}$, about 80% $C_{20}$, and about 90% $C_{20}$. The oligomerized products may have about 5% $C_{20}$, about 10% $C_{20+}$, about 20% $C_{20+}$, about 30%

$C_{20+}$, about 40% $C_{20+}$, about 50% $C_{20+}$, about 60% $C_{20+}$, about 70% $C_{20+}$, about 80% $C_{20+}$, and about 90% $C_{20+}$.

The olefins produced from the process described in this invention can be separated by distillation. Lighter olefins (such as $C_4$-$C_8$) may be further subjected to dimerization, oligomerization and/or alkene metathesis. The higher olefins are distilled into fractions suitable for making various types of fuels such as gasoline, diesel, aviation fuel, jet fuel, kerosene or other value-added products. The higher olefins can be hydrotreated to decrease the carbon-to-hydrogen balance either before or after the separation of the olefins to fuel-appropriate fractions. Hydrotreating can be used to either hydrogenate unsaturated bonds, or to remove oxygen. For example, the higher olefins can be hydrogenated to corresponding hydrocarbons. Alternatively, the olefins can be dehydrogenation to produce aldehydes and/or ketones, which can then be deoxygenated to produce hydrocarbons.

Hydrogenation of higher olefins to the desired hydrocarbons may be accomplished by treating the olefins with hydrogen in the presence of catalysts. Catalysts are utilized during the hydrogenolysis. The catalysts may be homogeneous and/or heterogeneous. Catalysts can include the metals Pd, Pt, Os, Ru, Rb, Re, Ir, Rh, Ni, Co, Mo, W, Cu, Zn, Cr, oxides of these and combinations of these. Examples of hydrogenation catalysts include, but are not limited to, palladium or platinum on activated carbon or Calcium Carbonate, $PtO_2$, Raney/Ni, RhCl $(PPh_3)_3$, Ru catalysts, Lindlar's catalyst, and various transition metal catalysts. In some cases, promoter or moderator species are added/combined including Cr, Mn, Pb, Zn, Cd, Ag, Ba, Ca, Mg, Sn, Ni, Co, U, As and Ge oxides and combinations of these. One or more catalyst and one or more promoter can be combined in any concentration and ratio. The promoters increase the performance of the catalyst, for example, by increasing the conversion and selectivity.

Figure 4:
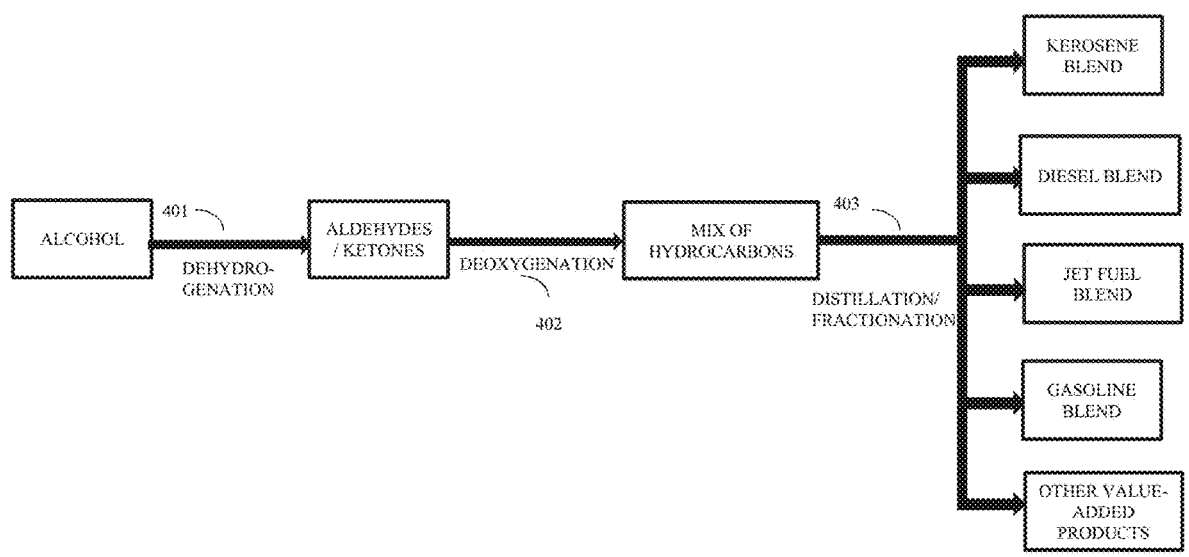
FIG. 4 is a schematic block diagram illustrating the conversion of alcohol derived from processed biomass to fuel blends and other value-added products through dehydrogenation and deoxygenation.

In some embodiments, the alcohols may be subjected to dehydrogenation to produce aldehydes and/or ketones. These ketones and aldehydes can then be deoxygenated to produce hydrocarbons. In some embodiments, dehydrogenation of alcohols can be achieved catalytically. For example, catalysts such as Pd/C—$K_3PO_4$, copper-chromium oxide catalyst, $RuCl_2(PPh_3)_3$, $(\eta^5\text{-Cp})RuCl(PPh_3)_2$, $[(\eta^5\text{-Cp})IrCl_2]_2$, Rh-catalysts such as Noyori catalyst, Grützmacher catalyst, Ru-catalysts such as Shvo catalyst, Stradiotto catalyst, Milstein catalyst, 0.1-5% Pt/transition metal dopants, such as W or Mo on active carbon or alumina, and several other transition metal catalysts may be used to dehydrogenate alcohols to aldehydes or ketones. Next, the aldehydes and ketones generated in the previous step can be deoxygenated by using catalysts. Removal of oxygen may be accomplished by decarboxylation ($CO_2$) and/or dehydration ($H_2O$) and can be done in the presence/absence of hydrogen. Several deoxygenation catalysts, homogeneous or non-homegeneous, may be used for this step. For example, transition metal catalysts such as CoMo-based catalysts, sulfide CoMo/Alumina, NiMo/Alumina, Pd-based catalysts (such as palladium-supported activated carbon), Pt-based catalysts, mixed metal oxides (such as $MgO+MgAl_2O_4$), and precious metal catalysts can be used. FIG. 4 provides a schematic block diagram illustrating an example of the process that can be used to convert alcohol derived from processed biomass to fuel blends and other value-added products. The first step, 401, involves the dehydrogenation of alcohols (preferably catalytically) to aldehydes and/or ketones. The aldehydes and/or ketones are then subjected to deoxygenation (preferably catalytically) in step 402 to produce a mixture of hydrocarbons. The mixture of hydrocarbons are then separated in step 403 by using various methods such as distillation to components suitable for use in various fuel blends and other value-added products.

Suitable dopants that can also be used to improve the dispersion of the metal catalysts and reduce the formation of coke include alkali metals (such as Li, Na, and K), transition metals (such as Ti, Zr, Hf, Nb, Cr, Mo, W, Mn, Re, Fe, Ru, Os, Co, Rh, Ir, Ni, Pd, Pt, Cu, Ag, Au), mixtures of transition metals (such as Ti/Hf, Ti/Zr, Zr/Cr), organometallic complexes (such as Cp2 V, $(butadiene)_3$ Mo, Bis-(arene) complexes of zero-valent Ti, Zr or Hf), promoter metals (such as germanium, indium, gallium, thallium), rare earth elements (such as La), halogens (such as fluorine, chlorine, bromine and iodine), hydrogen, hydrogen sulfide, tin, and sulfur.

Ethanol

In one embodiment, ethanol obtained from biomass is dehydrated to ethylene over 0.5% La-2% H-ZSM-5 catalyst. Higher yields and selectivity can be achieved by optimizing the temperature and time of dehydration. Commercial processes for making olefins may use both homogeneous and heterogeneous catalysts. The dehydrated ethylene can then be turned into linear olefins via a catalytic oligomerization process. Catalysts such as a Ziegler Natta-type catalyst, chromium diphosphine catalyst and zeolites may be used for the oligomerization process. For example, a temperature of 90-110° C. and a pressure of 89 bar over a Ziegler Natta-type catalyst may produce 96-97% yield of linear α-olefins with a carbon range of $C_4$-$C_{20}$. The oligomerization process may yield olefins of broad carbon number distribution, such a 5% $C_4$, 50% $C_6$-$C_{10}$, 30% $C_{12}$ and $C_{14}$, 12% $C_{16}$ and $C_{18}$, 3% $C_{20}$ and $C_{20+}$, at 200° C. and 250 bar. The resulting olefins are distilled to gasoline-, diesel-, jet fuel-, aviation fuel, kerosene-range fuels and light olefins. Light olefins (C4-C8) separated by distillation are recycled back to the oligomerization step. Higher olefins, such as jet fuel-range products are subjected to hydrogenation, at temperatures of 370° C. and weight hourly space velocity (WHSV) of 3 $h^{-1}$, by feeding hydrogen over 5% by weight of Pd or Pt-based catalyst on activated carbon. Alternatively, the higher olefins can be subjected to stepwise catalytic dehydrogenation and deoxygenation to produce higher alkanes. The higher alkanes can be separated and use as components of different fuels and value-added products.

N-Butanol

In one embodiment, n-butanol derived from biomass can be dehydrated to 1-butene at 380° C. and 2.1 bar over the γ-alumina catalyst. In one embodiment, the dehydration produces 1-butene with high yield and selectivity. A by-product such as 2-butene can also be produced as a result of isomerization from 1-butene. The 2-butene, containing cis- and trans-2-butenes, may be considered as unreacted olefins and separated by temperature controlled distillation. The 1-butene thus produced may be subjected to the oligomerization process to produce olefins ranging from $C_8$ to $C_{32}$. In some embodiments, the conversion to higher olefin is accomplished with a high yield by varying factors such temperature, time, flow-rate and catalysts. In some embodiments, the product distributions of the mixed olefins may be about 26% $C_8$, about 25% $C_{12}$, about 18% $C_{16}$, about 12% $C_{20}$, about 8% $C_{24}$, about 5% $C_{28}$ and about 4% $C_{32}$. In one embodiment, the reaction can be operated at ambient temperature with stirring for 16 h over the Group 4 transition-metal catalysts in the presence of methylaluminoxane (eg., $Cp_2ZrCl_2$/MAO). The $C_8$ olefin, 2-ethyl-1-hexene, can be distillated and sent to the dimerization reactor. The dimerization of the $C_8$ olefin can be operated at 116° C. for 2 h over Nafion catalyst. As a result of the dimerization, the $C_8$ olefin may be converted with high yield to $C_{16}H_{32}$. The products from the oligomerization and dimerization steps, ranging from $C_{12}$ to $C_{32}$, can be further subjected to hydrogenation over 0.08 wt % $PtO_2$ catalyst. The resulting $C_{12}$-$C_{16}$ paraffins can be blended with jet fuel components, and the $C_{20}$-$C_{32}$ alkanes are separated and sold as lubricants.

In some embodiments, n-butanol derived from biomass can be dehydrogenated over a catalyst such as Pd/C—$K_3PO_4$ catalyst, producing $C_5$-$C_{11}$ ketones. These ketones can be catalytically deoxygenated to produce normal paraffins, and the components of jet, gasoline, and diesel fuels. Examples of dehydrogenation and deoxygenation catalysts have been previously described.

Isobutanol

In one embodiment, iso-butanol produced from a process such as *Escherichia coli* fermentation is dehydrated to a mixture of isobutene, n-butene (1-butene), and 2-butene (cis-2-butene and trans-2-butene). Catalysts such as ZSM-5 zeolites, Y-type zeolites, and Amberlyst acidic resins can be used to catalyze a dehydration reaction, and different catalysts affect the selectivity of isobutene and the overall linear butenes. In one embodiment, a high selectivity and yield of isobutene may be obtained by using ZSM-5 catalyst at 2 h$^{-1}$ WHSV. In addition, isobutanol can be converted into isobutylene in high yield and selectivity through a dehydration process operated at 310° C. over γ-Alumina catalyst. In another embodiment, the isobutene can be converted to oligomers, trimers, and tetramers at 100° C. using an Amberlyst-35 catalyst at a WHSV of 2 h$^{-1}$. In some embodiments, the isobutene oligomerization produces about 20%, about 70%, and about 10% for $C_8$, $C_{12}$ and $C_{16}$ olefins, respectively. To increase the yield of higher olefins, the $C_8$ olefins can be distilled and sent to one additional dimerization process, operating at for example, 116° C. over a Nafion catalyst. Alternatively, $C_8$ olefins can be either converted into $C_{16}H_{32}$ through dimerization or reacted with butenes to produce $C_{12}$ olefins, leading to the increase of $C_{12}$ and $C_{16}$ for the jet-range chemicals. These olefins can then be hydrogenated or subjected to dehydrogenation followed by deoxygenation to produce the corresponding alkanes.

Conversion of Polyalcohols (Reduced Sugars) to fuel

In some embodiments, the sugars obtained from the processing of lignocellulosic material such as glucose ($C_6$) or xylose ($C_5$), can be hydrogenated to produce the corresponding reduced sugars, sorbitol ($C_6H_{14}O_6$) or xylitol ($C_5H_{12}O_5$). In some embodiments, the sugar used is raw sugar, which has not been purified, and is unrefined, or partially refined. For example, raw sugar can be extracted from plants such as sugarcane or beet. In addition to sucrose, raw sugar may also contain about 1% molasses by volume, about 2% molasses by volume, about 3% molasses by volume, about 4% molasses by volume, about 5% molasses by volume, about 6% molasses by volume, about 7% molasses by volume, about 8% molasses by volume, about 9% molasses by volume, about 10% molasses by volume, about 20% molasses by volume, about 30% molasses by volume, about 40% molasses by volume, and about 50% molasses by volume. This hydrogenation step can be performed by heterogeneous catalysis or homogeneous catalysis, and sometimes can also combined with the hydrolysis step of the cellulose. Polyols such as sorbitol and xylitol can then be converted to hexanes and pentanes respectively by catalytic dehydration, followed by hydrogenation. There are several ways that sugars and reduced sugars can be converted to fuel, including catalytic decarboxylation, dehydration and hydrodeoxygenation.

In one embodiment, following the pretreatment and fractionation processes, lignocellulosic biomass is converted and separated to cellulose, hemi-cellulose, and lignin. Lignin, in this process, is sent to the combustor to provide process heat. Using enzymatic or acid hydrolysis, the fractionated cellulose and hemicellulose can then be turned into sugars with five and six carbons. The carbohydrates are converted into polyhydric alcohols via hydrogenation or short-chain oxygenates via hydrogenolysis. Longer polyols may be further converted to shorter polyols (eg., glycerol, ethylene glycol) by catalytic conversion such as by using nickel-based catalyst in a basic environment.

Aqueous Based Dehydration to Alkenes Followed by Hydrogenation (APD/H)

In some embodiments, polyols derived from biomass may be used to produce the corresponding alkanes by an aqueous phase dehydration/hydrogenation process (APD/H). In some embodiments, the process may involve treatment with hydrogen, while in some embodiments, hydrogen may not be needed. The process may be catalyzed by a number of catalysts, including bifunctional catalysts combining a metal phase (eg., platinum) on an acid support (eg., silica-alumina). The support acidity assists in the dehydration reactions that eliminate oxygen in the form of $H_2O$. A number of acidic support can be used for the catalysts, including activated carbon, $SiO_2$—$Al_2O_3$, $TiO_2$, $ZrO_2$, Zeolites (HZSM-5, H-mordenite and HY), phosphated zirconia, niobium oxide, phosphated titanium oxide, phosphated niobium oxide, tungstated zirconia, molybdenum doped zirconia, NaY, ZnO and MgO. Catalysts such as Raney Copper catalyst, Ru/C catalyst, Pt/C, Pt/$Al_2O_3$, Pt/NaY, Ru/C catalyst+acid resin (Amberlyst) may also be used.

The resulting alkenes are then saturated to alkanes by hydrogenation. Methods of hydrogenation, including the various types of catalysts have been described earlier. Alternatively, the alkenes can be oligomerized to heavier alkenes, cracked, cyclized and dehydrogenated to aromatics To obtain alkanes from long-chain polyols, the dehydration/hydrogenation steps must be repeated several times without undesired C—C bond cleavage. One advantage of the aqueous dehydration/hydrogenation process is that separation of the products is supposed to be simplified as the alkanes theoretically form a hydrophobic phase that separates from an aqueous environment. Alkanes can then be integrated into the classic refinery circuit and fractionated into components suitable for use in fuel blends and as other value-added products.

Aqueous Phase Reforming

In some embodiments, polyols derived from biomass can be used to produce hydrogen by a process called aqueous phase reforming (APR). APR consists of two steps: the first step involves reforming of the polyol into hydrogen and CO, and the second step involves transforming the CO to $CO_2$ and hydrogen by the Water Gas Shift (WGS) reaction. These two reactions can be catalyzed by catalysts such as supported metal catalyst (eg., Pt/alumina). Hydrogen produced from APR can be used to support a hydrotreating process before the APR step and a hydro-refining processes after the APR step. In some embodiments the APR process is combined with the APD/H process described above.

Aldol Condensation on Multi-Functional Solid-Base Catalysts

In one embodiment, polyols derived from biomass can be converted to alkanes by direct catalytic condensation over multifunctional solid-base catalysts. An aldol mechanism can occur on metallic sites under basic conditions. For example, a polyol like sorbitol can first be dehydrogenated, probably on a metal site, to form a ketone group in position 2 or 3; that ketone is then involved in the retro-aldol reaction mechanism that leads to the formation of an aldol and an aldehyde. These products are then deoxygenated and hydrogenated on the metal surface. The products from this route can then be used, for example, in the jet fuel blends.

Sugar to Hydrocarbons Via Polyhydroxybutyrate

Hydrocarbons can also be produced from sugars via a polyhydroxybutyrate intermediate. In one embodiment, a sugar like glucose is converted to polyhydroxybutyrate (PHB) by bacterial fermentation. PHB-producing strains, such as *Alcaligene eutrophis, Ralstonia eutropha, Azotobacter vinelandii, Alcaligenes latus, Hydrogenophaga pseudoflava,* and *Pseudomonas pseudoflava* can be used for this process. Genetically modified microorganisms may also be used for this process. The PHB, thus produced, is then depolymerized to crotonic acid, which is then decarboxylated to produce propene. Examples of depolymerization catalysts include dibutyltin dimethoxide, p-toluenesulfonic acid $CaCl_2$, $MgCl_2$. MgO, and Mg $(OH)_2$. In some embodiments, the depolymerization and decarboxylation step can be combined in one step, for example, by heating at 400° C., with or without a catalyst.

The propene is then oligomerized to generate hydrocarbons. Various catalysts such as Ziegler Natta-type catalyst, chromium diphosphine catalysts, transition metal catalysts (such as nickel oxide, titanium oxide, bismuth oxide, rhodium chloride), zeolites, acidic catalysts (such as sulfuric acid, polyphosphoric acid heteropolyacid catalysts), and Amberlyst-35 catalyst may be used to catalyze the oligomerization of olefins. The catalysts may be homogeneous and/or heterogeneous. In some embodiments, the higher olefins obtained by oligomerization are further subjected to dimerization. The dimerization may be further achieved catalytically. Various catalysts such Nafion catalyst, Ziegler Natta-type catalysts, transition metal catalysts (such as nicker oxide, bismuth oxide, Rhodium chloride), zeolites, alumina, silicoaluminophosphates (SAPO), and acidic catalysts (such as sulfuric acid, polyphosphoric acid heteropolyacid catalysts) may be used for dimerization. The catalysts may be homogeneous and/or heterogeneous. Pressure, heat, reaction time and other parameters can be varied to affect the distribution of products such as cyclic ketones and phenols.

Sugar to Hydrocarbons Via Furfural-Derived Intermediates

Sugars like pentose, xylose and glucose can also be used as building blocks for the production of fuel and additives by converting them to furfural-derivatives. These sugars can be dehydrated to furfural, and other derivatives such as methylfurfural and hydroxymethylfurfural. Catalysts such as protonated micro-porous zeolites, $MgF_2$, $H_2SO_4$, $CrCl_3$, $ZnCl_2$, $FeCl_2$, $CuCl_2$, $CrCl_2$, $C_6H_5$—B—$Cl_2$ and $TiO_2$. Acid-catalyzed condensation of these products with aldehydes and ketones can then result in products with higher carbon numbers. Alternatively, these products can undergo cross-coupling reactions with alcohols to give high molecular weight adducts via a transfer hydrogenation-aldol condensation pathway. Examples of alcohols include 1-propanol, 1-butanol, 3-methyl-1-butanol, 1-pentanol, 1-hexanol, 1phenylethanol, 1-octanol, 2-propanol. The alcohols used in such cross-coupling reactions can be obtained by fermentative or non-fermentative routes from sugar, as well as various by various other methods described herein. Examples of catalysts that could be used for such cross-coupling include $Fe(BF_4).6H_2O$, $Cu(OAc)_2$, $Ni(dppe)Cl_2$, in the presence of bases like $K_2CO_3$ and $Mg_6Al_2(OH)_{16}CO_3.4H2O$.

These high carbon products can then be converted to C12 and C15 hydrocarbons by hydrodeoxygenation. Examples of suitable catalysts include heterogenous bifunctional platinum on niobium phosphate ($Pt/NbOPO_4$), and $Pt$—$SiO_2/Al_2O_3$. For example, hydrodeoxygenation can be undertaken at 300° C., 100 bar $H_2$ over $Pt$—$SiO_2/Al_2O_3$ catalyst, or at 250° C., 100 psi Hz, in the presence of $Pt/NbOPO_4$ catalyst. The $H_2$ used in these reactions can be produced on site by the various processes described herein.

As discussed in this application, the hydrocarbon molecules produced by any of the processes described herein are often in mixtures, and are separated in a fractionation process to components specifically tailored towards various fuels such jet, gasoline, and diesel fuels. Depending upon the carbon content of the hydrocarbons generated by the already described process they can be used in different types of fuels. For example, C8-C16 hydrocarbons are suitable for jet fuels, C9-C22 hydrocarbons may be suitable for diesel, and C4-C12 hydrocarbons may be used for making gasoline.

In addition, the processes described herein can be used to generate additives. In some embodiments, additives are blended with oil products to modify their properties including modification of octane number, cetane number, cold properties, lubricity, viscosity, contaminants, and as antioxidants, stabilizers and biocides.

A number of other compounds produced by the above-described process can further act as building blocks for a large number of biochemical products that can be used in the textile industry (eg., in making carpets, fibers, fabrics etc.), food industry (eg., in food packaging, preservatives etc.), transportation industry (eg., in making tires, molded plastics etc.), housing industry (eg., in making paints, resins, cements, garbage bags, glue etc.), furnitures, sports industry (eg., in making athletic gears, balls, roller blades, camera films etc.), communications industry (eg., in making dyes, fiber coatings), cosmetic industry (eg., perfumes, deodarants, shampoos, toothpaste etc.) and health industry (eg., in making medical devices and pharmaceuticals). For example, furfural can be used for the production of furfuryl alcohol, 2-methyltetrahydrofuran (MTHF) and other 5-membered oxygen-containing heterocyclic compounds such as methylfuran, acetylfuran and furoic acid.

Sugar-to-Fuel Pipeline

Lignocellulosic sugars produced by pretreatment and enzymatic hydrolysis of biomass feedstocks typically need a certain level of purification and concentration of biomass before catalytically upgrading sugar to hydrocarbons, which converts sugar or its intermediates to a range of hydrocarbon molecules and hydrogen in an APR and/or APD/H process.

The hydrosylate slurry of lignocellulosic sugars produced by reducing fermentation and irradiation is purified through a number of steps for further downstream processing requirements of the catalytic upgrading processes. Insoluble solids, resulting from unreacted or recondensed biomass components are removed by centrifugation or filtration because they can build up in a fixed bed reactor system and cause high pressure drop. Proteins and inorganic compounds in hydrolysates are also problematic for catalytic processing, as they impact materials of construction, accumulate in heat exchangers and contribute to catalyst poisoning. Removal of these contaminants is achieved utilizing technologies, such as ion exchange methods. Alternative biomass pre-processing methods may also help to reduce the amount of contaminants introduced into the process and lower purification costs. The hydrolysate is further dewatered to increase the concentration of sugars in the highly dilute hydrolysate stream (typical range of sugar concentration is 10-15 wt %). The excess water which is unreactive, results in higher heating requirements and larger process equipment. A vacuum evaporator is utilized to increase sugar concentrations while minimizing sugar degradation.

The purified hydrolysate slurry is sent to the catalytic conversion process. The first step in the conversion is the aqueous phase reforming (APR or APD/H) process, which takes the wide range of solubilized carbohydrate stream and utilizes heterogeneous catalysis to reduce the oxygen content of the feedstock. The reactions in this step include reforming to generate hydrogen, dehydrogenation of alcohols/hydrogenation of carbonyls, deoxygenation reactions, hydrogenolysis, and cyclization. This process is operated at 175°-300° C., 145-1,300 psi. The reactor effluent is sent to the acid condensation reactor, where conversion over a tailored catalyst such as ZSM-5 can result in for example, a gasoline-range blendstock. To obtain high selectivity for certain types of fuels, a catalyst that helps generate hydrocarbons with low oxygen content and with the appropriate amount of branching, cyclic, and aromatic content can be used. The catalyst should be able to deal with a wide range of sugars and contaminants, including sulfur, nitrogen and ash. In addition, the ideal catalyst should be able to handle lignin and its decomposed products with high carbon efficiency and long catalyst lifetime. This process can also be used to produce hydrocarbon "drop-in" fuels.

Figure 5:
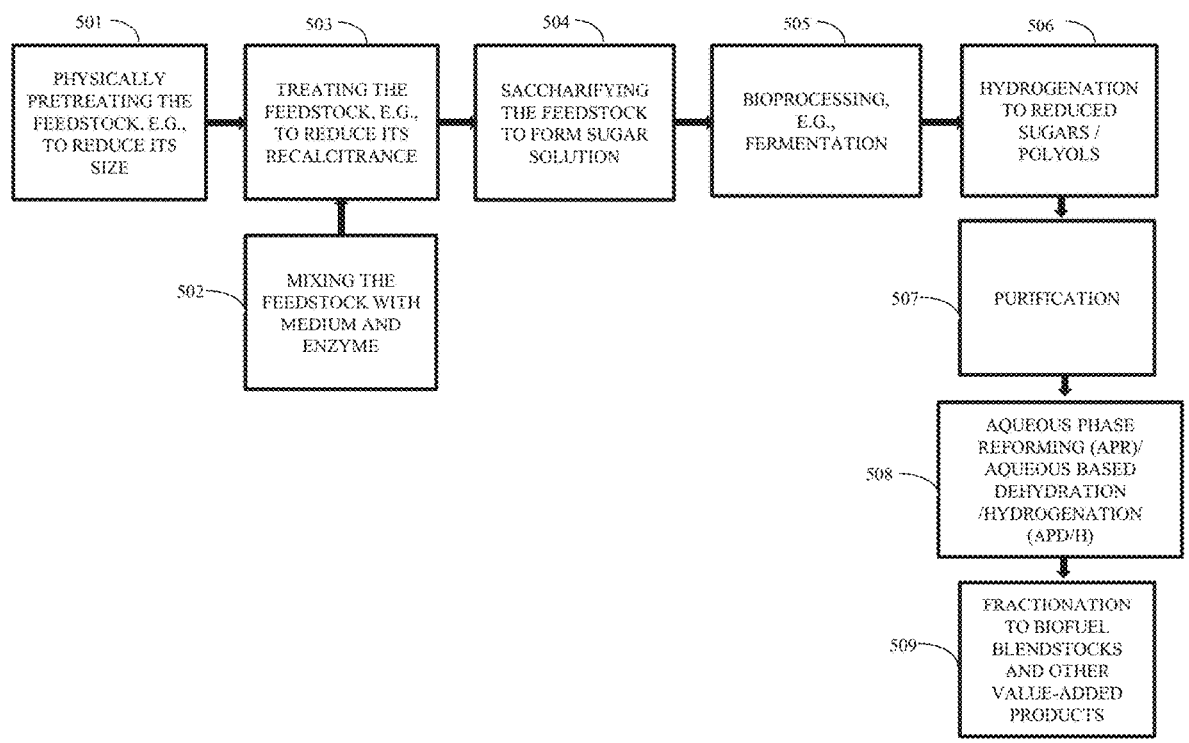
FIG. 5 is a schematic block diagram illustrating the conversion of biomass to biofuel through the aqueous phase reforming/dehydration and dehydrogenation of polyols.

The product of the catalytic conversion process is sent to fractionation where it is separated to various hydrocarbon blendstocks. Plant wastewater streams are treated by anaerobic and aerobic digestion. The methane-rich biogas from anaerobic digestion can be sent to the combustor, where sludge from the digesters is also burned. The treated water is suitable for recycling and is returned to the process. The solids from hydrolysate purification and wastewater treatment and the biogas from anaerobic digestion can be combusted to produce high pressure steam for electricity production and process heat. The boiler produces excess steam that can be converted to electricity for use in the plant and for sale. FIG. 5 is a schematic block diagram illustrating the conversion of biomass to biofuel through the aqueous phase reforming/dehydration and dehydrogenation of polyols. In an initial step (501), the method includes, optionally, mechanically treating a cellulosic and/or lignocellulosic feedstock. Before and/or after this treatment, the feedstock can be treated with another physical treatment (503), for example irradiation, sonication, steam explosion, oxidation, pyrolysis or combinations of these, to reduce or further reduce its recalcitrance. A sugar solution e.g., including glucose, xylose and combinations of these, is formed by saccharifying the feedstock (504). The saccharification can be, for example, accomplished efficiently by the addition of one or more enzymes, e.g., cellulases and xylanases (502) and/or one or more acids in any order.

Figure 6:
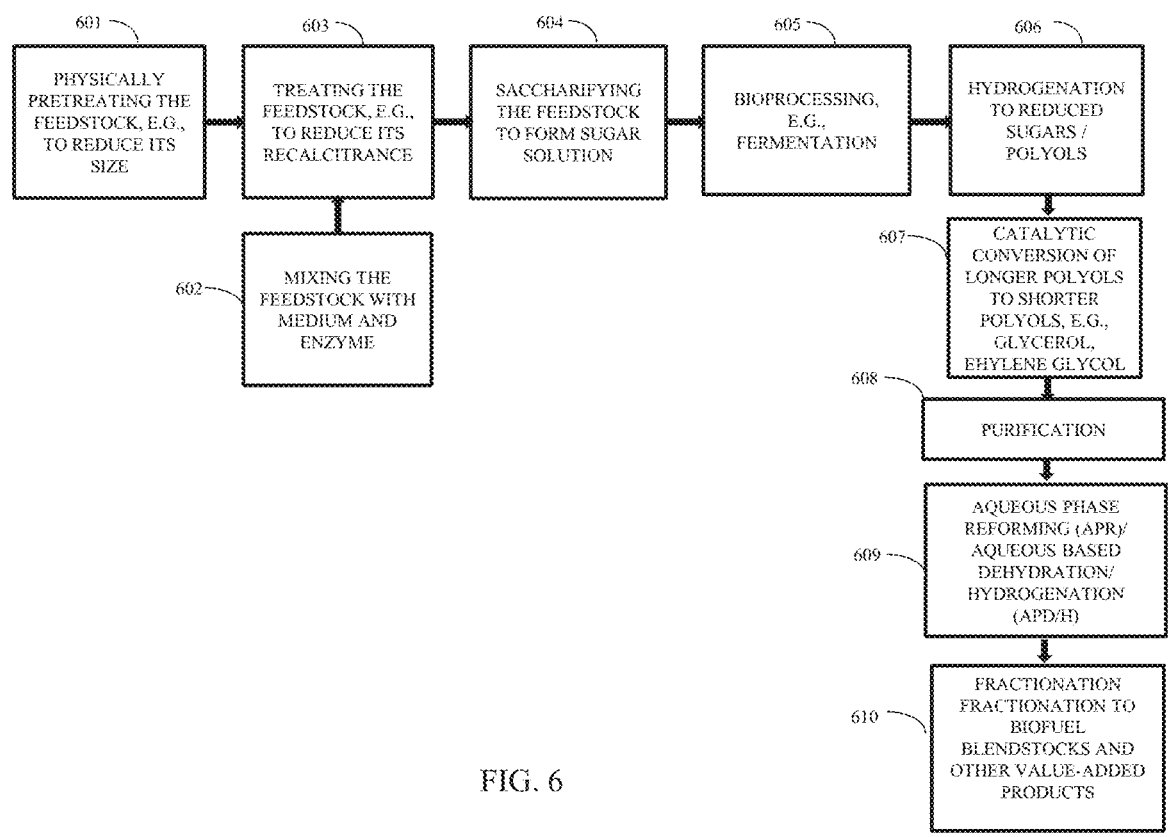
FIG. 6 is a schematic block diagram illustrating the conversion of biomass to biofuel through the aqueous phase reforming/dehydration and dehydrogenation of polyols, further including the catalytic conversion of longer polyols to shorter polyols.

Alternatively, the sugar solution can be bioprocessed (505), for example by utilizing an organism to ferment the sugars to a smaller saccharides, such as monosaccharides (eg., glucose and xylose). These smaller sugars are then hydrogenated (preferably catalytically) in step 506 to reduced sugars or polyols such as sorbitol and xylitol. The resulting hydrosylate slurry is purified through a number of processes such as centrifugation or filtration in step 507. The purified hydrolysate slurry is subjected to catalytic conversion process in step 508. This step involves aqueous phase reforming (APR or APD/H) process, which takes the wide range of solubilized carbohydrate stream and utilizes heterogeneous catalysis to reduce the oxygen content of the feedstock. The product of the catalytic conversion process is sent to fractionation in step 509, where it is separated to various biofuel blendstocks. FIG. 6 is a schematic block diagram illustrating the conversion of biomass to biofuel through the aqueous phase reforming/dehydration and dehydrogenation of polyols, further including the catalytic conversion of longer polyols to shorter polyols. In an initial step (601) the method includes, optionally, mechanically treating a cellulosic and/or lignocellulosic feedstock. Before and/or after this treatment, the feedstock can be treated with another physical treatment (603), for example irradiation, sonication, steam explosion, oxidation, pyrolysis or combinations of these, to reduce or further reduce its recalcitrance. A sugar solution e.g., including glucose, xylose and combinations of these, is formed by saccharifying the feedstock (604). The saccharification can be, for example, accomplished efficiently by the addition of one or more enzymes, e.g., cellulases and xylanases (602) and/or one or more acids in any order. Alternatively, the sugar solution can be bioprocessed (605), for example by utilizing an organism to ferment the sugars to a smaller saccharides, such as monosaccharides (eg., glucose and xylose). These smaller sugars are then hydrogenated (preferably catalytically) in step 606 to reduced sugars or polyols such as sorbitol and xylitol. The reduced sugars can be further catalytically converted to shorter polyols such as glycerol and ethylene glycol in step 607. The resulting hydrosylate slurry is purified through a number of processes such as centrifugation or filtration in step 608. The purified hydrolysate slurry is subjected to catalytic conversion process in step 609. This step involves aqueous phase reforming (APR or APD/H) process, which takes the wide range of solubilized carbohydrate stream and utilizes heterogeneous catalysis to reduce the oxygen content of the feedstock. The product of the catalytic conversion process is sent to fractionation in step 610, where it is separated to various biofuel blendstocks and other value-added products.

Isomerization and Fractionation of Hydrocarbons

The hydrocarbon molecules produced by any of the processes described herein are often in mixtures, and are separated in a fractionation process to components specifically tailored towards various fuels such jet, gasoline, and diesel fuels. Depending upon the carbon content of the hydrocarbons generated by the already described process they can be used in different types of fuels. For example, C8-C16 hydrocarbons are suitable for jet fuels, C9-C22 hydrocarbons may be suitable for diesel, and C4-C12 hydrocarbons may be used for making gasoline.

Figure 9A:
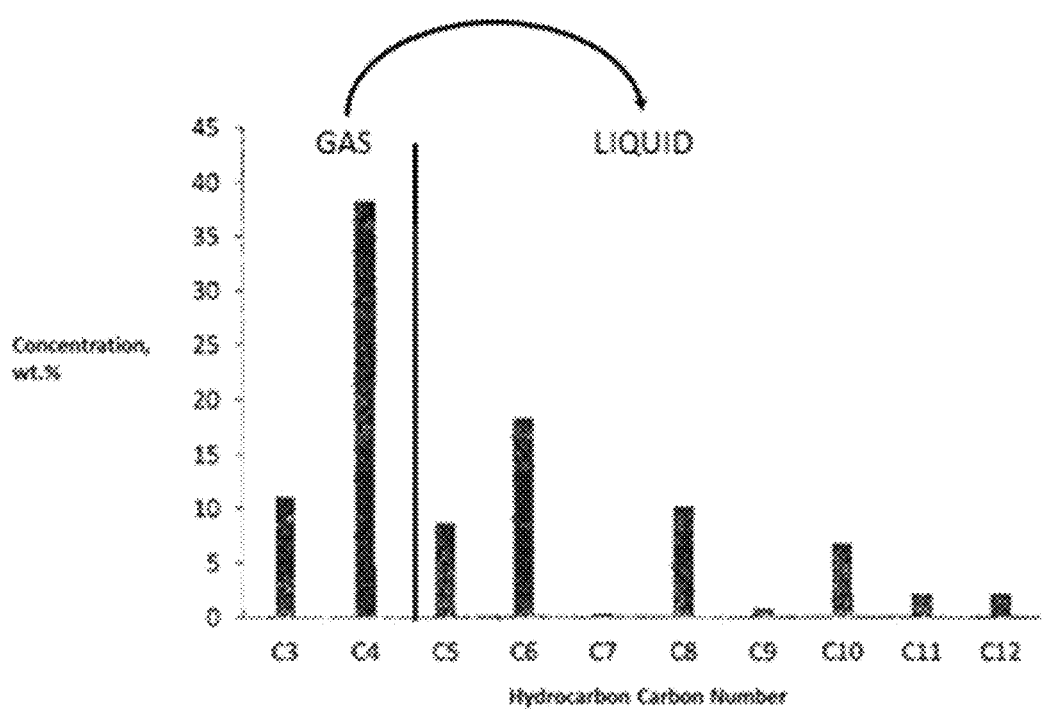
FIG. 9A provides a graphical description of the distribution of hydrocarbons of various carbon content in the hydrocarbon mixture that may be generated, and/or further processed during the catalytic conversion of biomass-derived building blocks.

FIG. 9A provides a graphical description of the distribution of hydrocarbons of various carbon content in the hydrocarbon mixture that may be generated, and/or further processed during the catalytic conversion of biomass-derived building blocks. In some embodiments, the lower gaseous hydrocarbons such as C3 and C4 may be further converted to higher liquid hydrocarbons such as C8-C20 hydrocarbons. In some embodiments, the hydrocarbons can be converted to corresponding cyclic or aromatic compounds, suitable for use in certain types of fuel such as BTX. In some embodiments, heavier hydrocarbons are converted to lighter hydrocarbons by using, for example, Fluidized Catalytic Crackers (FCCs), Cokers, Hydrocrackers, or Catalytic Reformers.

Figure 9B:
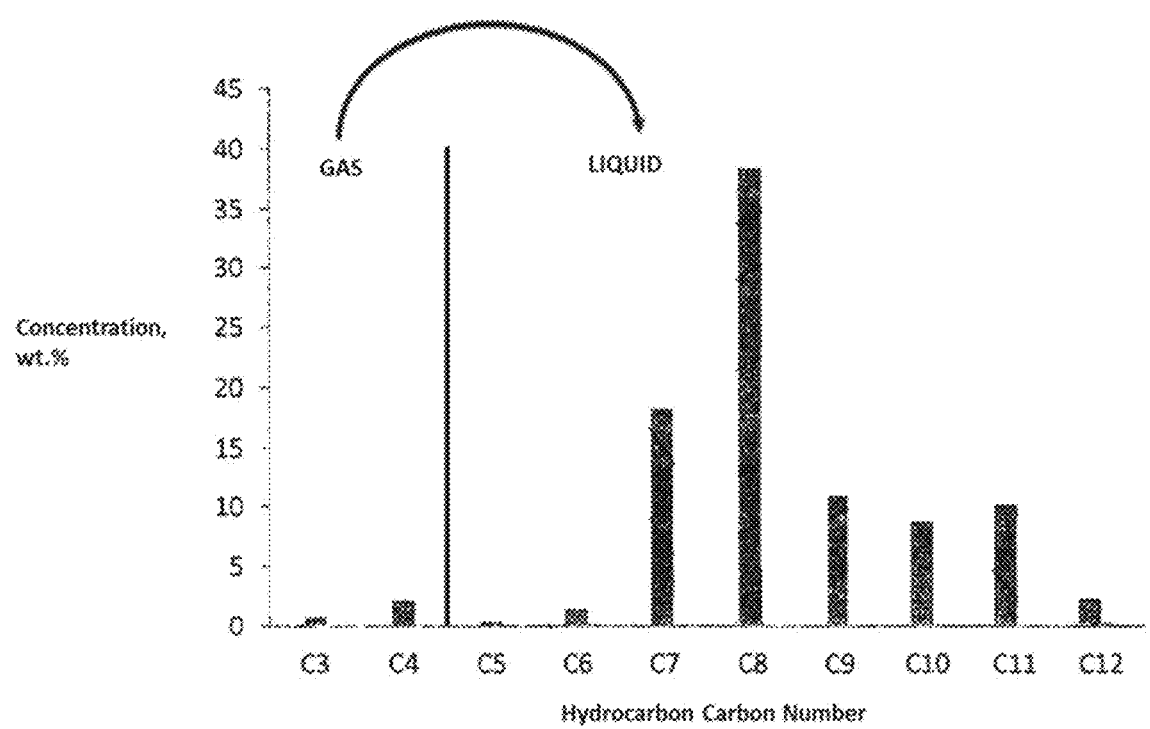
FIG. 9B provides a graphical description of the distribution of hydrocarbons of various carbon content in the hydrocarbon mixture that has been subjected to catalytic processing to convert lower molecular hydrocarbons (typically gases) to higher molecular weight hydrocarbons (typically liquid). The figure depicts an example, where the hydrocarbon mixture contains a higher proportion of higher molecular weight hydrocarbons as a result of the catalytic processing of the hydrocarbon mixture.

FIG. 9B provides a graphical description of the distribution of hydrocarbons of various carbon content in the hydrocarbon mixture that has been subjected to catalytic processing to convert lower molecular hydrocarbons (typically gases) to higher molecular weight hydrocarbons (typically liquid). For example, the figure shows that after catalytic conversion, lower hydrocarbons such as C3 and C4 may be further converted to higher hydrocarbons such as C5-C12. In some embodiments, the conversion of lower hydrocarbons to higher hydrocarbons is accomplished by using C—H activation catalysts. In some embodiments, the higher hydrocarbons resulting from the conversion of lower hydrocarbons constitute at least about 50% by weight, about 55% by weight, about 60% by weight, about 65% by weight, about 70% by weight, about 75% by weight, about 80% by weight, about 85% by weight, about 90% by weight, about 95% by weight, and about 99% by weight of the hydrocarbon mixture after catalytic conversion. In one embodiment, the amount of C1-C4 is less than 5% by weight of the mixture of hydrocarbons after the catalytic conversion of lower hydrocarbons to higher hydrocarbons.

To meet the jet fuel specification, the produced bio-fuel can have a high flash point, and good cold flow properties. Therefore, some alkanes such as n-pentane and n-hexane can be hydrocracked and hydroisomerized to produce the desired alkanes. The cracking and isomerization reactions are either concurrent or sequential. The isomerization process takes the straight-chain hydrocarbons and turns them into the branched structures to reduce the freeze point to meet the jet fuel standard. The conversion takes place in the presence of acidic catalysts, generally chlorinated alumina, that require strong drying of the feeds upstream of the process. Bifunctional catalysts containing metallic sites for hydrogenation/dehydrogenation and acid sites for skeletal isomerization via carbenium ions are used in isomerization. In a typical isomerization reaction, normal paraffins are dehydrogenated on the metal sites of the catalyst and reacting on the acid sites to produce protonated olefins with formation of the alkylcarbenium ion. The alkylcarbenium ion is rearranged to monobranched, dibranched, and tribranched alkylcarbenium ions on the acid site. The branched alkylcarbenium ions are deprotonated and hydrogenated to produce the corresponding paraffins. Isomerization can be accompanied by a hydrocracking reaction, which results in more or less yield from the isomerized species. The hydrocracking reactions are exothermic and result in the production of lighter liquids and gas products. They are relatively slow reactions; thus, most of the hydrocracking takes place in the last section of the reactor. The hydrocracking reactions primarily involve cracking and saturation of paraffins. Overcracking will result in low yields of jet-fuel-range alkanes and high yields of light species ranging from C1 to C4 and naphtha ranging from C5 to C8. Both of these are out of jet fuel range and also have lower economic value than diesel or jet fuel.

In some embodiments, the conversion of lower hydrocarbons to higher hydrocarbons is accomplished by using C—H activation catalysts. Carbon-hydrogen bond activation is a type of reaction in which a carbon-hydrogen bond is cleaved and replaced with a carbon-X bond (where X is usually carbon, oxygen, or nitrogen). For example, C—H bond activating catalysts may be used to convert a low molecular weight hydrocarbon like butane to a high molecular weight hydrocarbon like octane. Examples of C—H bond activating catalysts include transition metal catalysts such as Rhodium-based catalysts (eg., Cp*(Me$_3$P)RhH$_2$, Cp*(CO)$_2$Rh where Cp* is pentamethylcyclopentadienyl), Iridium-based catalysts (eg., Cp*(Me$_3$P)IrH$_2$, Cp*(CO)$_2$Ir), Platinum-based catalysts (eg., PtCl$_6^{2-}$, [(N—N)Pt(CH$_3$)(solv)]$^+$, where N—N is a bidentate nitrogen-centered ligand and 'solv' is a weakly coordinating solvent), Tungsten-based catalysts (eg., Cp*W(CO)$_3$(Bcat'), Cp$_2$WH$_2$, Cp*W(NO)(η3-allyl) (CH$_2$CMe$_3$) where cat' is 3, 5-dimethylcatecholate, and Cp is cyclopentadienyl), Rhenium-based catalysts (eg., Cp*Re), Ruthenium-based catalysts (eg., [Cp*RuCl$_2$]$_2$), Titanium-based catalysts (eg., Ti(NMe$_2$)$_4$), Iron-based catalysts (eg., Ferric catalysts using ligands such as N, N'-Dimethylethylenediamine (DMEDA), acetylacetonate (acac)), and Osmium-based catalysts (eg., OsO$_4$, OsCl$_3$ alone or in the presence of nitrogenated ligands such as 2,5-dichloropyridine or 2,2'-bipyridine).

In some embodiments, catalytic conversion of lower hydrocarbons to higher hydrocarbons may result in the conversion of at least about 50% by weight, about 55% by weight, about 60% by weight, about 65% by weight, about 70% by weight, about 75% by weight, about 80% by weight, about 85% by weight, about 90% by weight, about 95% by weight, about 99% by weight, and about 99.9% by weight of lower hydrocarbons to higher hydrocarbons.

In some embodiments, the hydrocarbon mixture produced by the processes described herein can have a ratio of saturated hydrocarbons (such as alkanes and cycloalkanes) to unsaturated hydrocarbons (such as alkenes and arenes) of greater than 1, greater than 2, greater than 3, greater than 4, greater than 5, greater than 6, greater than 7, greater than 8, greater than 9, greater than 10, greater than 11, greater than 12, greater than 13, greater than 14, greater than 15, greater than 16, greater than 17, greater than 18, greater than 19, greater than 20, greater than 25, greater than 30, greater than 35, greater than 40, greater than 45, greater than 50, greater than 55, greater than 60, greater than 65, greater than 70, greater than 75, greater than 80, greater than 85, greater than 90, greater than 95, and greater than 100. In one embodiment, the ratio of saturated to unsaturated hydrocarbons is greater than 3.

In some embodiments, the amount of unsaturated hydrocarbons in the hydrocarbon mixture produced by the processes described herein is less than about 50% by weight, less than about 45% by weight, less than about 40% by weight, less than about 35% by weight, less than about 30% by weight, less than about 25% by weight, less than about 20% by weight, less than about 15% by weight, less than about 10% by weight, less than about 5% by weight, and less than about 1% by weight.

In some embodiments, the hydrocarbon mixture produced by the processes described herein can have a ratio of aromatic compounds to non-aromatic compounds of less than 1, less than 0.9, less than 0.8, less than 0.7, less than 0.6, less than 0.5, less than 0.4, less than 0.3, less than 0.2, less than 0.1, less than 0.09, less than 0.08, less than 0.07, less than 0.06, less than 0.05, less than 0.04, less than 0.03, less than 0.02, less than 0.01, and less than 0.001. In one embodiment, the ratio of aromatics to non-aromatic compounds is less than 0.4.

In some embodiments, the amount of aromatic compounds in the hydrocarbon mixture produced by the processes described herein is less than about 50% by weight, less than about 45% by weight, less than about 40% by weight, less than about 35% by weight, less than about 30% by weight, less than about 25% by weight, less than about 20% by weight, less than about 15% by weight, less than about 10% by weight, less than about 5% by weight, and less than about 1% by weight.

In some embodiments, the hydrocarbon mixture produced by the processes described herein can have less than about 50% by weight of C1-C4, less than about 45% by weight of C1-C4, less than about 40% by weight of C1-C4, less than about 35% by weight of C1-C4, less than about 30% by weight of C1-C4, less than about 25% by weight of C1-C4, less than about 20% by weight of C1-C4, less than about 15% by weight of C1-C4, less than about 10% by weight of C1-C4, less than about 5% by weight of C1-C4, and less than about 1% by weight of C1-C4.

In some embodiments, the hydrocarbon mixture produced by the processes described herein can have greater than about 50% by weight of C5-C18, greater than about 55% by weight of C5-C18, greater than about 60% by weight of C5-C18, greater than about 65% by weight of C5-C18, greater than about 70% by weight of C5-C18, greater than about 75% by weight of C5-C18, greater than about 80% by weight of C5-C18, greater than about 85% by weight of C5-C18, greater than about 90% by weight of C5-C18, greater than about 95% by weight of C5-C18, and greater than about 99% by weight of C5-C18.

It has been observed that the hydrocarbon mixture produced by some of the processes described herein contain a higher amount of even-numbered hydrocarbons than odd-numbered hydrocarbons. Without being bound by hypothesis, it is possible that the even-numbered hydrocarbons are produced by the oligomerization of ethylene molecules, and odd-numbered hydrocarbons are produced via metal-carbon double bond (M=CH$_2$) species. It is also hypothesized that cracking may enhance the production of odd-numbered hydrocarbons. Thus, in some embodiments, the production of even-numbered hydrocarbons is facilitated by lowering the heat applied to the catalytic reactors converting biomass-derived building blocks to hydrocarbons. For example, the catalytic conversion described above may be done at about a temperature of about 50° C. to about 100° C., about 100° C. to about 150° C., about 150° C. to about 200° C., about 200° C. to about 250° C., about 250° C. to about 300° C., about 300° C. to about 350° C., about 350° C. to about 400° C., or in a range bounded by any numerical value stated herein above.

In some embodiments, the ratio of even-numbered hydrocarbons to odd-numbered hydrocarbons in the hydrocarbon mixture produced by the processes described herein can be greater than 1, greater than 2, greater than 3, greater than 4, greater than 5, greater than 6, greater than 7, greater than 8, greater than 9, greater than 10, greater than 11, greater than 12, greater than 13, greater than 14, greater than 15, greater than 16, greater than 17, greater than 18, greater than 19, greater than 20, greater than 25, greater than 30, greater than 35, greater than 40, greater than 45, greater than 50, greater than 55, greater than 60, greater than 65, greater than 70, greater than 75, greater than 80, greater than 85, greater than 90, greater than 95, and greater than 100.

In some embodiments, the amount of odd-numbered hydrocarbons in the hydrocarbon mixture produced by the processes described herein is less than about 50% by weight, less than about 45% by weight, less than about 40% by weight, less than about 35% by weight, less than about 30% by weight, less than about 25% by weight, less than about 20% by weight, less than about 15% by weight, less than about 10% by weight, less than about 5% by weight, and less than about 1% by weight.

The hydro-isomerization and hydrocracking processes are followed by a fractionation process to separate the mixtures to paraffinic kerosene, paraffinic diesel, naphtha, and light gases. The lighter alkanes such as C1-C4 hydrocarbons, are sent to the combustor to provide additional process heat. The heavier species of the products can be distilled and blended into jet fuel. One of the byproducts of the isomerization process is glycerol, which has many pharmaceutical, technical, and personal care product applications. Closed loop processes that recover and recycle the unreacted species are significant to improve the process economics.

Biorefinery

In one aspect, the methods and products described herein are part of a biorefinery concept. The biorefinery embraces a wide range of technologies able to convert biomass into certain building blocks (alcohols, hydrocarbons, carbohydrates, proteins, triglycerides etc.), which can be converted to value added products, biofuels and chemicals. Analogous to the petroleum refinery, a biorefinery is a facility (or network of facilities) that integrates biomass conversion processes and equipment to produce transportation biofuels, power, and chemicals from biomass. It involves the sustainable processing of biomass into a spectrum of marketable products and energy.

The products of biorefinery systems can be grouped in two broad categories: material products and energy products. Energy products are those products which are used because of their energy content, providing electricity, heat or transportation service. On the other hand, material products are not used for an energy generation purpose but for their chemical or physical properties.

Figure 11:
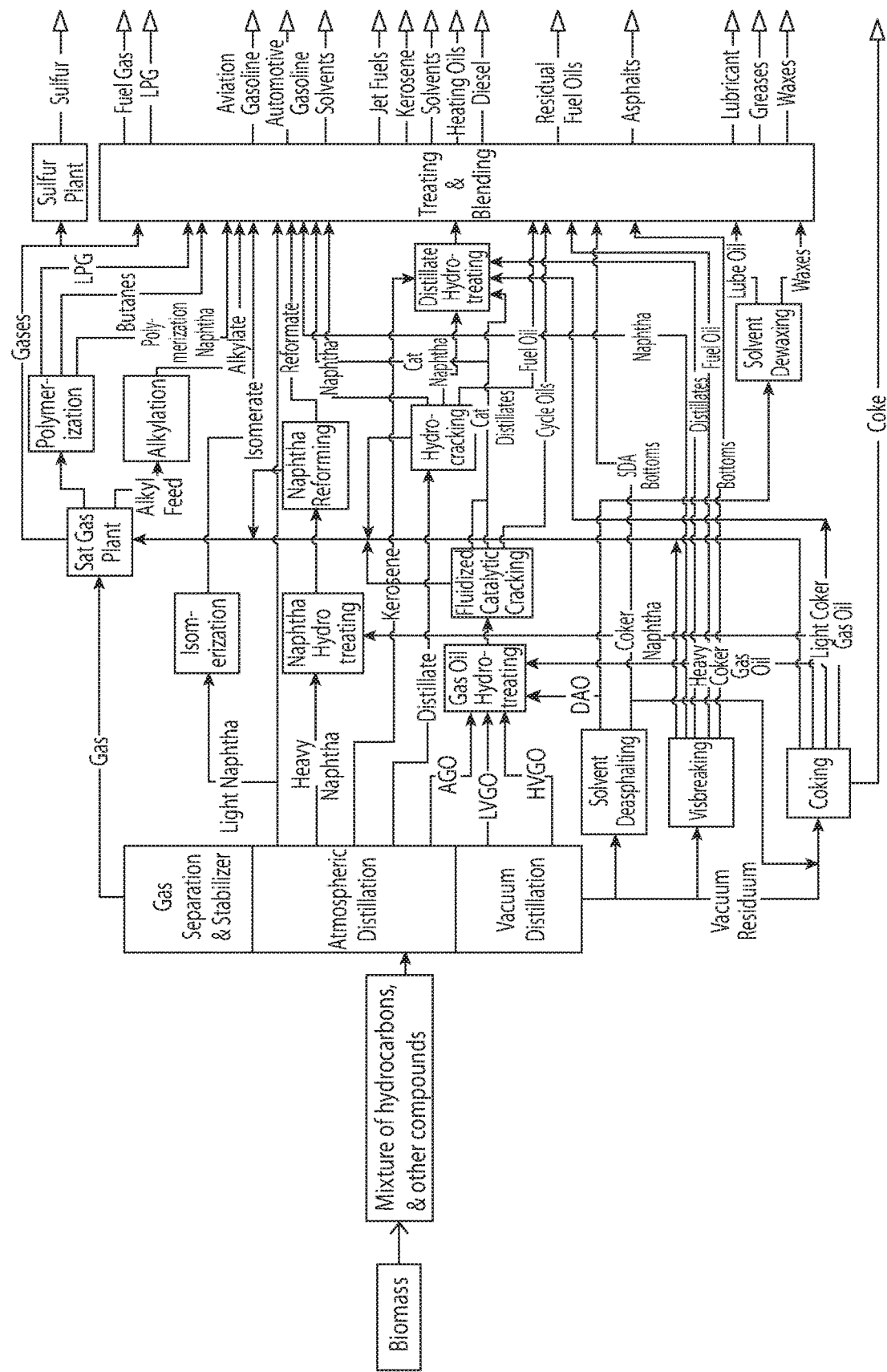
FIG. 11 provides a schematic block diagram illustrating the conversion of biomass to various fuel, fuel-components, and other value-added products.

FIG. 11 provides a schematic block diagram illustrating the conversion of biomass to various fuel, fuel-components, and other value-added products. For example, mixtures of hydrocarbons and other compounds derived from biomass through various processes described herein, can be further subjected to separation, and modification to produce various types of end-products. They can be separated, for example, by various types of distillation and gas separation methods to gaseous components, light naphtha, heavy naphtha, light vacuum gas oil (LVGO), heavy vacuum gas oil (HVGO), atmospheric gas oil (AGO), kerosene, coke and other components. These components may be then subjected to various processes such as isomerization, hydro-treating, distillation, coking, catalytic cracking, reforming, hydrocracking, solvent deasphalting, visbreaking, solvent dewaxing, polymerization, alkylation etc. to convert them to other value-added products or intermediates or components of value-added products, such as coke, waxes, greases, lubricants, asphalts, residual fuel oils, diesel, heating oils, solvents, kerosene, jet fuels, solvents, automotive gasoline, aviation gasoline, LPG fuel gas, and sulfur.

Examples of energy products include gaseous fuels (eg., biogas, syngas, hydrogen, methane, etc.), solid fuels (eg., coke, pellets, lignin etc.), and liquid fuels (eg., ethanol, diesel, jet fuel etc.).

Gases generated during the processes described herein can be used as energy source within the biorefinery system as well as outside it. For example, the gaseous fuel can be diverted to a combustion engine connected to an electric generator to produce electricity. It can also be used as a fuel source for a spark-ignited natural gas engine. As another example, the gas can be used as a fuel source for a direct-injection natural gas engine. As another example, the gas can be used as a fuel source for a combustion turbine.

In some embodiments biogases arising from the anaerobic fermentation of biomass and the gasification of solid biomass (including biomass in wastes) can be used as fuel to support other processes in the pipeline or as a chemical feedstock. The biogases from anaerobic fermentation are composed principally of methane and carbon dioxide and comprise landfill gas, sewage sludge gas and other biogases from anaerobic fermentation. Biogases can also be produced from thermal processes (by gasification or pyrolysis) of biomass and are mixtures containing hydrogen and carbon monoxide (usually known as syngas) along with other components. These gases may be further processed to modify their composition and can be further processed to produce substitute natural gas. The gases are divided into two groups according to their production: biogases from anaerobic fermentation and biogases from the thermal processes.

Multiple gasification technologies exist to convert reduced-size biomass to syngas. In one embodiment, a high-temperature (slagging) gasification process is used, wherein the biomass is pressurized and converted into raw synthesis gas during gasification at temperatures around 1300° C. in the presence of high purity oxygen and steam. A combustor is included to provide heat to dry the biomass. A direct-quench syngas cooling system next to the gasifier removes ash and tars. A water-gas-shift system after quench is applied to adjust the $H_2$:CO ratio to 2.1:1. In another embodiment, the endothermic gasification process is indirectly heated by the circulation of hot olivine and the material in the gasifier is fluidized by the steam. Gasification occurs at atmospheric conditions and at 880° C. The syngas is further conditioned such that the residual tars, methane and light hydrocarbons are reformed to syngas in a fluid catalytic cracker. Water gas shift also occurs in the reformer. Compared to the high temperature gasification, this design has the benefits of energy self-sufficient, improved capital cost associated with the smaller process scale, and neutral electrical energy. Syngas can be used directly as a stationary biofuel or can be a chemical intermediate (platform) for the production of fuels (FT-fuels, dimethyl ether, ethanol, isobutene, etc.) or chemicals (alcohols, organic acids, ammonia, methanol, etc.).

Gasification and reforming pathways starting from biomass can also provide hydrogen. There are a number of processes for the production of hydrogen from carbon-containing feedstocks, such as catalytic steam reforming (SR), autothermal reforming (AR) and partial oxidation (PO), as well as other configurations, which contain various aspects of any of the aforementioned processes. In addition, methane can be cracked into hydrogen and carbon; for higher hydrocarbons, cracking reactions also come into play, and heteroatoms, which are almost invariably present in the feedstocks, react as well under the conditions of the hydrogen-generating reactions. Hydrogen can also be generated during the fermentation process.

In some embodiments, refinery gas is generated by the processes described herein. Refinery gas typically includes a mixture of non-condensable gases mainly consisting of hydrogen, methane, ethane and olefins obtained during distillation of hydrocarbon products (e.g. cracking). It is used mainly as a fuel within the refinery.

In some embodiments, solid fuel can be generated from the processes described herein. For example, coke generated during the processes described herein can be used as fuel for other processes described herein or can be commercialized. Coke can also be obtained by cracking and carbonizing the hydrocarbon products generated by the processes described herein. The two most important categories are "green coke" and "calcined coke." Green coke (raw coke) is the primary solid carbonisation product from high boiling hydrocarbon fractions obtained at temperatures below 630° C. It contains 4-15 percent by weight of matter that can be released as volatiles during subsequent heat treatment at temperatures up to approximately 1330° C. Calcined coke is obtained by heat treatment of green coke to about 1330° C. It will normally have a hydrogen content of less than 0.1 percent by weight. Coking processes that can be employed for making coke can include contact coking, fluid coking, flexicoking and delayed coking. For example, in some embodiments, a Delayed Coker is used to convert the heavy material, resid, at the bottom of a vacuum bed tower into more valuable products. The delayed coker uses high temperature to break the hydrocarbon chains into smaller hydrocarbons, which can then be reformed into high-value hydrocarbons. Delayed coking also produces coke as a by-product.

In some embodiments, carbon is isolated from biomass by the processes described herein. The carbon thus produced can be used in other value-added products, or as a building blocks for other value-added products. For example, carbon in the form of charcoal and coke can be used in metal smelting, in industries such as the iron and steel industries. Carbon in the form of graphite can be used in pencils, to make brushes in electric motors and in furnace linings. Activated charcoal can be used for purification and filtration, example in respirators and kitchen extractor hoods. Carbon fiber generated from carbon can be used strong, yet lightweight, material in many products such as tennis rackets, skis, fishing rods, rockets and airplanes. Carbon can also be used to prepare carbon nanotubes, fullerenes and atom-thin sheets of graphene, which can be used for example, in hardware developments in the electronics industry and in nanotechnology.

In some embodiments, lignin liberated in any process described herein can be captured and utilized. In some instances, it can be utilized as an energy source, e.g., burned to provide heat. In some instances, it can also be converted to lignosulfonates, which can be utilized as binders, dispersants, emulsifiers or as sequestrants. Lignin-containing residues from primary and pretreatment processes have value as a high/medium energy fuel and can be used to generate power and steam for use in plant processes. In some cases, gasification of the lignin residues can convert it to a higher value product with lower cost. As a heating source, lignin generally has a higher energy content than holocellulose (cellulose and hemicellulose) since it contains more carbon than holocellulose. For example, dry lignin can have an energy content of between about 11,000 and 12,500 BTU per pound, compared to 7,000 an 8,000 BTU per pound of holocellulose. Lignin can be densified and converted into briquettes and pellets for burning. For example, the lignin can be converted into pellets by any method described herein. For a slower burning pellet or briquette, the lignin can be crosslinked, such as by applying a radiation dose of between about 0.5 Mrad and 5 Mrad. Crosslinking can provide a slower burning form factor. The form factor, such as a pellet or briquette, can be converted to a "synthetic coal" or charcoal by pyrolyzing in the absence of air, e.g., at between 400 and 950° C. Prior to pyrolyzing, it can be desirable to crosslink the lignin to maintain structural integrity. Lignocellulosic biomass in its original form usually have a low bulk density of 30 kg/m$^3$ and a moisture content ranging from 10% to 70%. Pelleting increases the specific density (gravity) of biomass to more than 1000 kg/m$^3$. Pelleted biomass is low and uniform in moisture content. It can be handled and stored cheaply and safely using well developed handling systems for grains.

In some embodiments, the sludge, and post-distillate solids can be burned to heat water flowing through a heat exchanger. In some embodiments, the water flowing through the heat exchanger is evaporated and superheated to steam. The steam can be used, for example, in a pretreatment reactor. Additionally, or alternatively, the steam expands to power a multi-stage steam turbine connected to an electric generator. Steam exiting the steam turbine is condensed with cooling water and returned to the heat exchanger for reheating to steam.

A number of other compounds produced by processing a cellulosic and/or lignocellulosic biomass can act as building blocks for a large number of biochemical products that can be used in the textile industry (eg., in making carpets, fibers, fabrics etc.), food industry (eg., in food packaging, preservatives etc.), transportation industry (eg., in making tires, molded plastics etc.), housing industry (eg., in making paints, resins, cements, garbage bags, glue etc.), furnitures, sports industry (eg., in making athletic gears, balls, roller blades, camera films etc.), communications industry (eg., in making dyes, fiber coatings), cosmetic industry (eg., perfumes, deodarants, shampoos, toothpaste etc.) and health industry (eg., in making medical devices and pharmaceuticals).

For example, ethylene can be an important building block in the biochemical, biopolymers and plastic industry, given that six major polymer classes can be derived from ethylene (PE, PET, PEG, PVA, PVC, PS). Propanol can be converted to propylene, which is also an important intermediate for producing polypropylene, acrylamide and propylene glycol. Propanol can also be used as a building block for isoprene, acrylonitrile, acrylamide, acrolein, propylene oxide, and glycidol. Lactic acid is a precursor of polylactic acid (PLA), lactate esters, and peroxyacetic acid.

Another precursor, glycerol, can be a source of a wealth of downstream products, such as acetol, 3-hydroxypropionaldehyde (3-HPA), 3-HP(acid) epicholohydrin, docosahexanoic acid, 3-hydroxypropanal, mesoxalic acid, glycolic acid, hydroxypyruvic acid, propylene glycol, ethylene glycol, glycerol carbonate, glycidol, acrolein, acrylic acid, malonic acid, propiolactone, polyglycidol and methyl acrylate.

Succinic acid can be used to generate a large range of products including poly(butylenesuccinate) (PBS), THF and poly (THF), acrylonitrile, succinonitrile, putrescine, poly (butyleneterephthalate) (PBT), and a range of acid and amine compounds.

Buta-1,3-diene can be used in producing furan, adipic acid, hexane 1,6-diol, hexane 1-6-diamine, styrene, and poly(butylenesuccinate) (PBS).

Isobutanol can be used as a starting point for the important intermediate of isobutylene, for para-xylene, and polyisobutylene (PIB). It can also be used to make a number of other value-added products such as polymers of methacrylic acid (eg., PMMA), isoprene (eg., polyisoprene), and urethanes (PU).

C5 sugars can be used in the production of furfural, and then furfuryl alcohol to produce levulinic acid, or furan for THF. Levulinic acid can act as a starting "feedstock" for several downstream products (such as pentane 1,4-diol, butene (which can be converted into diesel, jet or petrol alkanes) via δ-Valerolactone. Xylose and arabinose, for example, can be used to produce xylitol and arabinotol respectively, which can be reacted under hydrogenolysis conditions to produce ethylene glycol.

C6 sugars such as glucose and fructose can be dehydrated to produce 5-hydroxymethylfurfural (5-HMF), which can produce value-added products such as para-xylene and 2, 5-furandicarboxylic acid (FDCA)(which can then produce polymers such as polyethylenefuranoate (PEF) and polybutylenefuranoate (PBF)). Glucose can also be converted to adipic acid (an important monomer for nylons), and sorbitol (which can be used to produce isosorbide and polycarbonates).

Sugars with reduced recalcitrance can also be converted to hydrocarbon fuel through the formation of terpenes. Terpenes can be generated from the bioconversion of fermentable sugars derived from lignocellulosic biomass using organisms such as E. coli or S. cerevisiae. There are at least two known metabolic pathway for the generation of terpenes and their precursors, isopentenyl pyrophosphate (IPP): the mevalonic acid (MVA) pathway and the deoxyxylulose-phosphate (DXP) pathway. The terpenes, assembled by condensing IPP and its isomer dimethylallyl pyrophosphate, represent the candidates of biologically-derived fuel. Large terpenes can be cracked to liquid fuel and the branched olefins can be hydrogenated to isoparaffins.

In some embodiments, the reduced recalcitrance sugar is processed through the MVA pathway and converted into artemisinic acid, isopentenyl pyrophosphate, and jet/gasoline precursors. The artemisinic acid is then turned into an anti-malarial drug, and isopentenyl pyrophosphate is further transformed into farnesenyl pyrophosphate and C15 isoprenoids, which are the precursors of diesel and chemicals. The fermentation waste could be optionally processed with anaerobic digestion to reduce the effluent. After purification, through downstream hydro-processing, the jet/gasoline precursors can be turned into biojet fuel.

In some embodiments, a two-stage process can be used to convert sugar derived from biomass into 2,5-dimethylfuran (DMF). The fructose, obtained directly from biomass or by isomerizing of glucose, is dehydrated to form 5-hydroxymethylfurfural (HMF) by removing five oxygen atoms over an acid catalyst. HMF is then turned into DMF through hydrogenolysis over a CuRu catalyst. DMF has a number of attractions as a biofuel. It has higher energy density by 40% and a higher boiling point by 20 K than ethanol. Since it is water insoluble it does not absorb moisture from the atmosphere.

Methods of obtaining organic acids have already been described. The organic acids produced by the processes described herein can include monocarboxylic acids or a polycarboxylic acids. Examples of organic acids include formic acid, acetic acid, propionic acid, butyric acid, valeric acid, caproic, palmitic acid, stearic acid, oxalic acid, malonic acid, succinic acid, glutaric acid, oleic acid, linoleic acid, glycolic acid, lactic acid, γ-hydroxybutyric acid or mixtures of these acids. These organic acids can also serve as building blocks of other compounds.

In some embodiments, the organic acids that can be produced are further converted to other compounds such as aspartic acid, glutamic acid and the amino substituted malonic, adipic, pimelic, suberic, azelaic and sebacic acids or their corresponding acidic or basic salts, e.g., their $Na^+$, $K^+$, $Ca^{2+}$, or ammonium salts and mixtures of salts and acids. In one implementation of the method, the amino-alpha, omega-dicarboxylic acids are converted chemically or biochemically, for example, by converting aspartic acid or glutamic acid to the respective polyamides. Other methods of chemically converting that can be utilized include polymerization, isomerization, esterification, amidation, cyclization, oxidation, reduction, disproportionation and combinations of these.

In some embodiments, converting comprises polymerizing an acid, such as aspartic or glutamic acid to a polymer (e.g., polymerizing in a melt such as without an added solvent). For example, polymerizing methods can be selected from direct condensation of the aspartic or glutamic acid, azeotropic dehydrative condensation of the aspartic or glutamic acid, and cyclizing the aspartic or glutamic acid followed by ring opening polymerization. The polymerization can be in a melt (e.g., without a solvent and above the melting point of the polymer) or can be in a solution (e.g., with an added solvent). A polyamide can be a product of the polymerization process. Optionally, polymerizations can be done utilizing catalysts and/or promoters. For example, protonic acids, $H_3PO_4$, $H_2SO_4$, methane sulfonic acid, p-toluene sulfonic acid, NAFION® NR 50 H+ form from DuPont, Wilmington Del., acids supported on polymers, Mg, Al, Ti, Zn, Sn, metal oxides, $TiO_2$, ZnO, $GeO_2$, $ZrO_2$, SnO, $SnO_2$, $Sb_2O_3$, metal halides, $ZnCl_2$, $SnCl_2$, $SnCl_4$, $Mn(AcO)_2$, $Co(AcO)_2$, $Ni(AcO)_2$, $Al(i-PrO)_3$, $Ti(BuO)_4$, $TiO(acac)_2$, $(Bu)_2SnO$, tin octoate, solvates and hydrates of any of these and mixtures of these can be used.

Optionally, when the polymerization method is direct condensation, the polymerization can include utilizing coupling agents and/or chain extenders to increase the molecular weight of the polymer. For example, the coupling agents and/or chain extenders can include triphosgene, carbonyl diimidazole, dicyclohexylcarbodiimide, diisocyanate, acid chlorides, acid anhydrides, epoxides, thiirane, oxazoline, orthoester, and mixtures of these. Alternatively, the polymer can have a co-monomer which is a polycarboxylic acid polyamide or polyamines or a combination of these.

In some embodiments, when polymers are made, the method can further include branching and/or cross linking the polymer. For example, the polymers can be treated with a cross linking agent including 5,5'-bis(oxepane-2-one)(bis-ε-caprolactone)), spiro-bis-dimethylene carbonate, peroxides, dicumyl peroxide, benzoyl peroxide, unsaturated alcohols, hydroxyethyl methacrylate, 2-butene-1,4-diol, unsaturated anhydrides, maleic anhydride, saturated epoxides, glycidyl methacrylate, irradiation and combinations of these. Optionally, a molecule (e.g., a polymer) can be grafted to the polymer. For example, grafting can be done treating the polymer with irradiation, peroxide, crossing agents, oxidants, heating or any method that can generate a cationic, anionic or radicle on the polymer.

Lignin can also be used in ceramics, for binding carbon black, for binding fertilizers and herbicides, as a dust suppressant, in the making of plywood and particle board, for binding animal feeds, as a binder for fiberglass, as a binder in linoleum paste and as a soil stabilizer. As a dispersant, the lignin or lignosulfonates can be used, e.g., concrete mixes, clay and ceramics, dyes and pigments, leather tanning and in gypsum board. As an emulsifier, the lignin or lignosulfonates can be used, e.g., in asphalt, pigments and dyes, pesticides and wax emulsions. As a sequestrant, the lignin or lignosulfonates can be used, e.g., in micro-nutrient systems, cleaning compounds and water treatment systems, e.g., for boiler and cooling systems.

In addition the processes described herein can be used to generate additives. In some embodiments, additives are blended with oil products to modify their properties including modification of octane number, cetane number, cold properties, lubricity, viscosity, contaminants, and as antioxidants, stabilizers and biocides. Examples of additives include oxygenates, such as alcohols (methanol, ethanol), ethers (such as MTBE (methyl tertiary butyl ether), ETBE (ethyl tertiary butyl ether), TAME (tertiary amyl methyl ether), esters (e.g. rapeseed or dimethylester, etc.), and other chemical compounds (such as TML, and TEL and detergents). For example, Bioether (also referred to as fuel ethers or oxygenated fuels) a fuel additive, which acts as octane rating enhancers, can be one of the products generated by the processes described herein. Bioethers can be obtained for example, by processing a cellulosic and/or lignocellulosic biomass from sources such as wheat. In some embodiments, iso-olefins (such as iso-butylene) and ethanol derived from biomass can be reacted to produce bioethers. Bioethers enhance engine performance, while significantly reducing engine wear and toxic exhaust emissions. By replacing petroethers in fuel blends, they can contribute to improved air-quality by reducing pollutants and ozone emissions. Examples of bioethers that can be produced by the processes described herein include dimethyl ether (DME), diethyl ether (DEE), methyl tertiary-butyl ether (MTBE), ethyl ter-butyl ether (ETBE), ter-amyl methyl ether (TAME), and ter-amyl ethyl ether (TAEE).

Various types of additives can be produced from the building blocks generated by the processes described herein. Examples include detergent additives (used to clean and neutralize oil impurities), corrosion or rust inhibiting additives (which retard the oxidation of metal inside an engine), antioxidant additives (which retard the degradation of the stock oil by oxidation), metal deactivators (which create a film on metal surfaces to prevent the metal from causing the oil to be oxidized), viscosity modifiers (which modifies an oil's viscosity higher at elevated temperatures, improving its viscosity index (VI)), friction modifiers or friction reducers (eg., molybdenum disulfide, which are used for increasing fuel economy by reducing friction between moving parts), extreme pressure agents (which bond to metal surfaces, keeping them from touching even at high pressure), anti-wear additives or wear inhibiting additives (which cause a film to surround metal parts, helping to keep them separated), dispersants (which keep contaminants (e.g. soot) suspended in the oil to prevent them from coagulating), anti-foam agents (which inhibit the production of air bubbles and foam in the oil which can cause a loss of lubrication), anti-misting agents (which prevent the atomization of the oil), and wax crystal modifiers (which are dewaxing aids that improve the ability of oil filters to separate wax from oil).

In some embodiments, the heavy fraction that sinks to the bottom of vacuum towers in the process of separating the hydrocarbons can be used to produce asphalt or bitumen. This heavy material is also called Vacuum Tower Bottoms (VTB) or "resid." If allowed to cool to room temperature, it would become a solid. This can be used as a blend in asphalt. Asphalt consists of saturated hydrocarbons (which correlate with softening point of the material), naphthalene aromatics (consisting of partially hydrogenated polycyclic aromatic compounds), polar aromatics (eg., high molecular weight phenols and carboxylic acids) and asphaltenes, consisting of high molecular weight phenols and heterocyclic compounds.

In some embodiments, the processes described herein can result in the formation of lubricants. Lubricant base stocks are obtained from vacuum distillates which result from further distillation of the residue from atmospheric distillation of the hydrocarbon oil. The lubricant base stocks are then further processed to produce lubricants with the desired properties. In some embodiments, paraffin waxes are extracted when dewaxing lubricant oils. The waxes have a crystalline structure which varies in fineness according to the grade and are colourless, odourless and translucent, with a melting point above 45° C. In some embodiments, greases, which are semi-solid lubricants are obtained from the processes described herein.

In some embodiments, food products or components of food products are generated by the processes described herein. For example, intermediate fermentation products include high concentrations of sugar and carbohydrates. These intermediate fermentation products can be used in preparation of food for human or animal consumption. In some embodiments, irradiation pretreatment of the cellulosic material will render the intermediate fermentation products sterile (e.g., fit for human consumption). In some embodiments, the intermediate fermentation products will require post-processing prior to use as food. For example, a dryer can be used to remove moisture from the intermediate.

Distillers grains and solubles can be converted into a valuable byproduct of the distillation-dehydration process. After the distillation-dehydration process, distillers grains and solubles can be dried to improve the ability to store and handle the material. The resulting dried distillers grains and solubles (DDGS) is low in starch, high in fat, high in protein, high in fiber, and high in phosphorous. Thus, for example, DDGS can be valuable as a source of animal feed (e.g., as a feed source for dairy cattle). DDGS can be subsequently combined with nutritional additives to meet specific dietary requirements of specific categories of animals (e.g., balancing digestible lysine and phosphorus for swine diets).

In some embodiments, the processes described above can be used to produce materials, which can have therapeutic value or can act as building blocks or components of pharmaceuticals or neutriceuticals. For example, the pretreatment processes discussed above can be applied to plants with medicinal properties. In some embodiments, sonication can stimulate bioactivity and/or bioavailabilty of the medicinal components of plants with medicinal properties. Additionally or alternatively, irradiation stimulates bioactivity and/or bioavailabilty of the medicinal components of plants with medicinal properties. For example, sonication and irradiation can be combined in the pretreatment of willow bark to stimulate the production of salicin. In some embodiments, intermediate fermentation products (e.g., products that include high concentrations of sugar and carbohydrates) can be supplemented to create a nutriceutical. For example, intermediate fermentation products can be supplemented with calcium create a nutriceutical that provides energy and helps improve or maintain bone strength.

In some embodiments, the processes described herein can generate products, such as fertilizers, soil amendments, and soil regenerating products, or building blocks for their generation. For example, the solids left over after the treatments at the biomass, can be used as a fertilizer after drying. In some embodiments, stripping, which is process where ammonia from the air is scrubbed with sulphuric acid and recovered as a 40% TS (total solids, dry matter) ammonium sulfate solution is used. Ammonium sulfate, thus produced can be utilized in a fertilizer and/or for soil enrichment production. In some embodiments, boiler and/or fly ash of the facility may be used for drying the solid residue of the biorefinery so that the residue may be used as a fertilizer. Adding of boiler and/or fly ash in the fertilizer not only dries the fertilizer by binding the water therein, but also improves the properties of the fertilizer so that the resulting fertilizer may be used not only as a fertilizer but also to replace the use of potassium as the soil improving agent.

Catalytic Pyrolysis to Generate Aromatic Compounds

In one embodiment, catalytic fast pyrolysis (CFP) of processed biomass is used to produce aromatic compounds such as benzene, toluene and xylene, which could be used to generate TX. BTX is a mixture of aromatic compounds, including benzene, toluene, thiophene, ethylbenzene, p-xylene, m-xylene, o-xylene, and styrene, and typically containing a low amount of non-aromatic compounds, such as cylcopentane, and indene.

BTX can be used as fuel, fuel blend or additives. The components of BTX can also act as building blocks of other value-added products. For example, benzene can be converted to polystyrene through ethylbenzene and styrene. Benzene may also be converted to cumene, which can be modified to phenolic compounds, which can serve as building blocks for phenolic resins, and polycarbonates. Benzene can also form Nylon through cyclohexane and caprolactams. Similarly, toluene can be used as a starting material for making polyurethane and several gasoline components, p-xylene could be used as a starting material for making polyester fibers and resins, and o-xylene could be used to make phthalic anhydride.

There are various ways of generating BTX and components thereof from biomass. For example, the processed biomass can be fed into a fluidized-bed reactor where it is thermally decomposed to form pyrolysis vapors. These pyrolysis vapors then enter catalysts (such as zeolites) present in the fluidized bed reactor, where they get converted into the desired aromatic compounds and olefins along with CO, $CO_2$, $H_2O$, and coke. In some embodiments, it may be preferred to convert the pyrolysis vapors to aromatics outside the pyrolysis reactor. The spent catalyst and coke can then be sent to a regenerator where they can be burned to provide heat.

In some embodiments, naptha generated from biomass can be treated in catalytic reformers under high temperature catalytic dehydrogenation conditions to convert it into aromatics. These reformers can produce large quantities of the primary aromatic chemicals. Benzene, toluene, and a mixed xylene stream can be subsequently recovered by extractive distillation using a solvent. Recovery of various types of xylene from a mixed xylene stream could be accomplished by a further processing step of crystallization and filtration or adsorption followed by desorption on beds of molecular sieves.

Pyrolysis of processed biomass can produce a mixture of compounds such as anhydro sugars and olefins. The anhydro sugars can undergo acid-catalyzed dehydration to furan-derivatives. The furan can undergo either decarbonylation to form allene ($C_3H_4$) and CO, or Diels-Alder condensation to form benzofuran ($C_8H_6O$) and water. The allene can undergo either oligomerization to form a series of olefins, or alkylation with other aromatics to form heavier aromatics and ethylene. The olefins can react with furan to form aromatics and water. The benzofuran may also undergo decarbonylation to form benzene, CO, and coke. The olefins produced during CFP can be recycled into the reactor to form more aromatics. See Yu-Ting Cheng, et al., *Production of Renewable Aromatic Compounds by Catalytic Fast Pyrolysis of Lignocellulosic Biomass with Bifunctional Ga/ZSM-5 Catalysts, Angew.* Chem. Int. Ed., 2012, 51, 1387-1390.

The yield and composition of the aromatic products can be optimized by modifying the catalysts, the temperature, pressure, ratio of biomass to catalysts and other factors. Various catalysts can be used, such as ZSM-5/Zn/La, ZSM-5/Ga, Al-MSU-S Foam, HZSM, MCM-41, β-zeolite, sulfated zirconia ($SO_4^{2-}$ $ZrO_2$), 20% $SO_4^{2-}$ $ZrO_2$ dispersed on a mesoporous MCM-41 silica and support.

Figure 7:
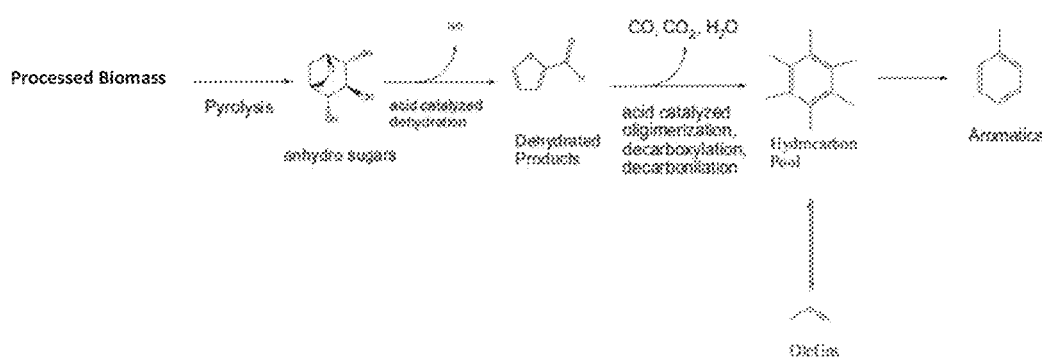
FIG. 7 is a reaction scheme of converting processed biomass to aromatic compounds.

CFP has several advantages, including the fact that all the desired chemistry can occur in one single reactor, it does not require process hydrogen, typically needs low pressure and inexpensive silica-alumina catalysts. FIG. 7 is a reaction scheme of converting processed biomass to aromatic compounds. Pyrolysis of processed biomass can produce a mixture of compounds such as anhydro sugars and olefins. The anhydro sugars can undergo acid-catalyzed dehydration to furan-derivatives. The furan can undergo catalyzed oligomerization, decarboxylation, and/or decarbonylation to form aromatic compounds. The olefins produced during CFP can be recycled into the reactor to form more aromatics.

Catalytic Systems and Processes

One or more of the catalytic conversion processes described herein may be accomplished by zeolite or alumina supported catalysts. For example, in some embodiments, ethanol derived from the processing of lignocellulosic feedstock can be converted to a hydrocarbon mixture by one or more zeolite or alumina-based catalysts.

In some embodiments, alumina (e.g., high purity γ-alumina, 150-200 m$^2$/g) can be used as the support for catalyst preparation. Various metals can be used for the catalyst preparation, such as Pt, Pd, Sn, Re, Rh, Bi, Ba, Ti, Ni, and combinations thereof. The catalyst prepared could be mono-metallic catalyst, bi-metallic catalyst, or tri-metallic catalyst. In some embodiments, the catalyst can be prepared by an incipient wetness impregnation method using the desired salt solution. After impregnation of the support with the appropriate metal salt, the catalyst samples can be dried at room temperature, followed by oven drying. Finally, the catalysts can be calcined under air, for example, at 500° C.

In some embodiments, acidified alumina catalysts can be used as the support for metal catalyst preparation. For example, alumina can be pre-treated with acids such as $H_3BO_3$, $H_3PO_4$, HCl, $H_2SO_4$, citric acid, oxalic acid, or acetic acid. The amount of acid present in the pre-treated catalyst can vary, and can be about 0.1% to about 1%, about 1% to about 5%, about 5% to about 10%, about 10% to about 20%, about 20% to about 30%, about 30% to about 40%, about 40% to about 50%, about 50% to about 60%, about 60% to about 70%, about 70% to about 80%, about 80% to about 90% by weight, or in any numerical range stated hereinabove. After the treatment with acid, the acid-treated $Al_2O_3$ support can be dried at room temperature, followed by oven drying, and calcined under air, for example, at 500° C. In the second step, incipient wetness impregnation method can be used for the preparation of metal-modified catalyst. Various metals can be used for the catalyst preparation, such as Pt, Pd, Sn, Re, Rh, Bi, Ba, Ti, Ni, and combinations thereof. The catalyst prepared could be a mono-metallic catalyst, bi-metallic catalyst, or tri-metallic catalyst. After impregnation with the appropriate salt, the catalyst samples can be dried at room temperature, followed by oven drying. Finally, the catalysts can be calcined under air, for example, at 500° C.

In some embodiments, zeolites can be used as support for catalyst preparation. For example, HZSM-5 catalysts can be prepared by incipient wetness impregnation method. Various metals can be used for the catalyst preparation, such as Pt, Pd, Sn, Re, Rh, Ru, Bi, Ba, Ti, Ni, and combinations thereof. The catalyst prepared could be a mono-metallic catalyst, bi-metallic catalyst, or tri-metallic catalyst. In some embodiments, the catalyst can be prepared by an incipient wetness impregnation method using the desired salt solution. After impregnation, the zeolite-metal catalyst samples can be dried at room temperature, followed by oven drying. Finally, the catalysts can be calcined under air, for example, at 500° C.

Mono-metallic catalysts include one metal such as Pt, Pd, Sn, Re, Rh, Ru, Bi, Ba, Ti, Ni in a support, such as an alumina-based support, zeolite-based support, or acidified alumina based support. The mono-metallic catalysts used in these processes may contain about 0.1% to about 1% (w/w), about 1% to about 5% (w/w), about 5% to about 10% (w/w), about 10% to about 20% (w/w), about 20% to about 30% (w/w), about 30% to about 40% (w/w), about 40% to about 50% (w/w), about 50% to about 60% (w/w), about 60% to about 70% (w/w), about 70% to about 80% (w/w), about 80% to about 90% (w/w), or greater than 90% (w/w) of the metal, or in a range bounded by any numerical value stated herein above. In some preferred embodiments, the catalysts may contain about 0.05% to about 0.075&, about 0.075% to about 0.1%, about 0.1% to about 1%, about 1% to about 2%, and about 2% to about 5% of the metal, or in a range bounded by any numerical value stated herein above. Examples of such mono-metallic catalysts include 0.5% Ru/ZSM-5, 1% Ru/ZSM-5, 1.5% Ru/ZSM-5, 0.5% Pd/ZSM-5, 1% Pd/ZSM-5, 1.5% Pd/ZSM-5, 0.5% Pt/ZSM-5, 1% Pt/ZSM-5, 1.5% Pt/ZSM-5, 0.5% Pt/10% $H_3PO_4$—$Al_2O_3$, 0.5% Pt/5% $H_3PO_4$—$Al_2O_3$, 1% Pt/10% $H_3PO_4$-$Al_2O_3$, 0.5% Pt/5% $H_3PO_4$—$Al_2O_3$, 1% Pd/10% $H_3PO_4$—$Al_2O_3$, 0.5% Pd/5% $H_3PO_4$—$Al_2O_3$, 1% Pd/10% $H_3PO_4$—$Al_2O_3$, 0.5% Pd/5% $H_3PO_4$—$Al_2O_3$, 0.5% Pt/5.0% $H_3BO_3$—$Al_2O_3$, 0.5% Pd/5.0% $H_3BO_3$—$Al_2O_3$, 0.5% Ru/5.0% $H_3BO_3$—$Al_2O_3$, 1% Pt/5.0% $H_3BO_3$—$Al_2O_3$, 1% Pd/5.0% $H_3BO_3$—$Al_2O_3$, and 1% Ru/5.0% $H_3BO_3$—$Al_2O_3$.

Bi-metallic catalysts include a combination of two metals selected from metals such Pt, Pd, Sn, Re, Rh, Ru, Bi, Ba, Ti, Ni in supports such an alumina-based support, zeolite-based support, or acidified alumina based support. The bi-metallic catalysts used in these processes may contain two metals wherein each metal may be present in about 0.1% to about 1% (w/w), about 1% to about 5% (w/w), about 5% to about 10% (w/w), about 10% to about 20% (w/w), about 20% to about 30% (w/w), about 30% to about 40% (w/w), about 40% to about 50% (w/w), about 50% to about 60% (w/w), about 60% to about 70% (w/w), about 70% to about 80% (w/w), about 80% to about 90% (w/w), or greater than 90% (w/w), in any possible combination with the other metal, and in a range bounded by any numerical value stated herein above. or in a range bounded by any numerical value stated herein above. Examples of such bi-metallic catalysts include 0.5% Pt-0.5% Sn/$Al_2O_3$, 0.5% Pd-0.5% Sn/$Al_2O_3$, 0.5% Pt-0.75% Sn/$Al_2O_3$, 0.5% Pd-0.75% Sn/$Al_2O_3$, 0.5% Pt-1% Sn/$Al_2O_3$, 0.5% Pd-1% Sn/$Al_2O_3$, 0.5% Pt-0.5% Bi/$Al_2O_3$, 0.5% Pd-0.5% Bi/$Al_2O_3$, 0.5% Pt-0.75% Bi/$Al_2O_3$, 0.5% Pd-0.75% Bi/$Al_2O_3$, 0.5% Pt-1% Bi/$Al_2O_3$, 0.5% Pd-1% Bi/$Al_2O_3$, 0.5% Pt-0.5% Ba/$Al_2O_3$, 0.5% Pd-0.5% Ba/$Al_2O_3$, 0.5% Pt-0.75% Ba/$Al_2O_3$, 0.5% Pd-0.75% Ba/$Al_2O_3$, 0.5% Pt-1% Ba/$Al_2O_3$, and 0.5% Pd-1% Ba/$Al_2O_3$.

Tri-metallic catalysts include a combination of three metals selected from metals such Pt, Pd, Sn, Re, Rh, Ru, Bi, Ba, Ti, Ni in supports such as an alumina-based support, zeolite-based support, or acidified alumina based support. The tri-metallic catalysts used in these processes may contain three metals wherein each metal may be present in about 0.1% to about 1% (w/w), about 1% to about 5% (w/w), about 5% to about 10% (w/w), about 10% to about 20% (w/w), about 20% to about 30% (w/w), about 30% to about 40% (w/w), about 40% to about 50% (w/w), about 50% to about 60% (w/w), about 60% to about 70% (w/w), about 70% to about 80% (w/w), about 80% to about 90% (w/w), or greater than 90% (w/w), in any possible combination with the other two metals, and in a range bounded by any numerical value stated herein above. or in a range bounded by any numerical value stated herein above. Examples of such tri-metallic catalysts include 0.5% Pt-0.5% Sn-0.5% Bi/$Al_2O_3$, 0.5% Pt-0.5% Sn-0.75% Bi/$Al_2O_3$, 0.75% Pt-0.5% Sn-0.75% Bi/$Al_2O_3$, 0.5% Pd-0.5% Sn-0.5% Bi/$Al_2O_3$, 0.5% Pt-0.5% Sn-0.5% Ba/$Al_2O_3$, 0.5% Pt-0.5% Sn-0.75% Ba/$Al_2O_3$, 0.75% Pt-0.5% Sn-0.75% Ba/$Al_2O_3$, 0.5% Pd-0.5% Sn-0.5% Ba/$Al_2O_3$.

The general reaction conditions under which the feedstock containing ethanol can be converted to hydrocarbons in a catalytic reactor includes temperature in the range of 300-400° C., pressure in the range of 20-50 atm, gas flow (e.g., $N_2$) at the rate of 1.5-6 h$^{-1}$ and Liquid Hourly Space Velocity (LHSV) of 2-4 h$^{-1}$. The specific catalyst compositions for each reaction, and the reaction conditions are recited in the descriptions of the FIGS. 18A-23C, with corresponding product distribution shown in the respective figures. As discussed in this application, these reaction conditions can be appropriately adjusted to achieve a desired reaction product composition.

In some embodiments, the hydrocarbon mixture produced from the above-described processes contains hydrocarbons of average carbon number of about 6, 7, 8, 9, 10, 11, 12, 13, 14, 15, 16, 17, 18, 19, 20, 21, or 22. In some embodiments, the hydrocarbon mixture produced from the above-described processes contains hydrocarbons of average carbon number of about 6, 7, 8, 9, or 10.

In some embodiments, the hydrocarbon mixture produced from the above-described processes contains about 0.1% to about 1% (w/w), about 1% to about 5% (w/w), about 5% to about 10% (w/w), about 10% to about 20% (w/w), about 20% to about 30% (w/w), about 30% to about 40% (w/w), about 40% to about 50% (w/w), about 50% to about 60% (w/w), about 60% to about 70% (w/w), about 70% to about 80% (w/w), about 80% to about 90% (w/w), or greater than 90% (w/w) aromatics, or in a range bounded by any numerical value stated herein above.

In some embodiments, the hydrocarbon mixture produced from the above-described processes contains about 0.1% to about 1% (w/w), about 1% to about 5% (w/w), about 5% to about 10% (w/w), about 10% to about 20% (w/w), about 20% to about 30% (w/w), about 30% to about 40% (w/w), about 40% to about 50% (w/w), about 50% to about 60% (w/w), about 60% to about 70% (w/w), about 70% to about 80% (w/w), about 80% to about 90% (w/w), or greater than 90% (w/w) alkenes, or in a range bounded by any numerical value stated herein above.

In some embodiments, the hydrocarbon mixture produced from the above-described processes contains about 0.1% to about 1% (w/w), about 1% to about 5% (w/w), about 5% to about 10% (w/w), about 10% to about 20% (w/w), about 20% to about 30% (w/w), about 30% to about 40% (w/w), about 40% to about 50% (w/w), about 50% to about 60% (w/w), about 60% to about 70% (w/w), about 70% to about 80% (w/w), about 80% to about 90% (w/w), or greater than 90% (w/w) alkanes, or in a range bounded by any numerical value stated herein above.

In some embodiments, the hydrocarbon mixture produced from the above-described processes contains less than about 0.01% (w/w), less than about 0.1% (w/w), less than about 1% (w/w), less than about 5% (w/w), less than about 10% (w/w), less than about 20% (w/w), or less than about 30% (w/w) of oxygenates. As used herein, the term "oxygenates" is defined to include oxygen containing organic compounds such as alcohols, ethers, carbonyl compounds (aldehydes, ketones, carboxylic acids, carbonates, and the like). Representative oxygenates include, but are not necessarily limited to, lower straight chain or branched aliphatic alcohols, their unsaturated counterparts. Examples include but are not necessarily limited to: methanol; ethanol; n-propanol; iso-propanol; C4-C10 alcohols; methyl ethyl ether; dimethyl ether; diethyl ether; di-isopropyl ether; methyl mercaptan; methyl formate, methyl acetate, formaldehyde; di-methyl carbonate; trimethyl orthoformate, and dimethyl ketone.

In some embodiments, the hydrocarbon mixture produced from the above-described processes contains greater than about 10% (w/w), greater than about 20% (w/w), greater than about 30% (w/w), greater than about 40% (w/w), greater than about 50% (w/w), greater than about 60% (w/w), greater than about 70% (w/w), greater than about 80% (w/w), or greater than about 90% (w/w) of liquid hydrocarbon at standard temperature and pressure.

In some embodiments, the hydrocarbon mixture produced from the above-described processes contains less than about 0.01% (w/w), less than about 0.1% (w/w), less than about 1% (w/w), less than about 5% (w/w), less than about 10% (w/w), less than about 20% (w/w), or less than about 30% (w/w) of gaseous hydrocarbon at standard temperature and pressure.

In some embodiments, commercially available reforming catalysts can be used in the practice of the invention that are available from manufacturers such as Tanaka Kikinzoju Group, Holder Topsoe, UOP, Axens, Johnson Matthey, Criterion, Süd-Chemie, Albermarle, Grace Davison, BASF, ExxonMobil Chemical, and JSC Angarsk.

In one embodiment, the reforming catalysts used in the methods described herein can include $Ru/Al_2O_3$ produced by Tanaka such as TRC10-2A and TRC10-1A. The reforming catalysts may also be chosen from Johnson Matthey's KATALCO$_{JM}$™ catalysts such as the KATALCO$_{JM}$™ 23-series, 57-series, 25-series and 46-series catalysts. Examples of reforming catalysts that may be obtained from UOP include CCR Platforming Catalysts (eg., R-134, R-234, R-254, R-262, R-264, R-274, R-284), Semi-Regenerative Platforming Catalysts (eg., R-56, R-86, R-98, R-500), Cyclic Reforming Catalysts (eg., R-85, R-88), Naphtha Hydrotreating Catalysts (S-120, S-125), In some embodiments, catalysts produced by JSC Angarsk may also be used in the processes described herein. Such catalysts may include reforming catalysts (eg., RB-35YuKA, RB-33U, RB-44U, PR-81, PR-71, APM-99, AP-56, and AP-64), isomerization catalysts (eg., SI-1, SI-2, IP-82, IP-62M, and KI-16M), hydrogenation catalysts (eg., APU, APKB, APKGS, APKGU, GIPH-108, PALLADIUM CHARCOAL, PU-A, PKA-25 PALLADIUM SIBUNITE, PALLADIUM ON ACTIVE ALLUMINIUM OXIDE IN SULFURATED FORM, NVS-A, AP-15, AP-10), hydrotreating catalysts (eg., GO-38A, GO-15, AGKD-400, and A-GPV), oxidation catalysts (eg., KO-10), hydrocracking catalysts (eg., SGK-1, SGK-5, GI-03M, GKM-21M, and KDM-10), methanation catalysts (eg., ANKM), conversion catalysts (eg., GIAP-8, AKN-M, STK-05, and GIAP-3-6N), adsorbents catalysts (eg., MOA-98, A-09-MOA, PS-17, PS-17 M, AGS-60, PS-2003, AR-25, and APS), and protective bed catalysts (eg., FOR-1, FOR-2).

In one embodiment, the reforming catalyst may be mixed with a gas-to-liquid catalyst to convert gaseous mixtures to liquid hydrocarbon. In one embodiment of a gas-to-liquid conversion process, synthesis gas, a mixture of hydrogen and carbon monoxide, generated during the processing of the biomass is purified to remove impurities and converted into liquid hydrocarbons using a gas to liquid catalyst. In another embodiment, a gas to liquid catalyst can be used to convert low molecular weight hydrocarbons such as propane or butane that can form in the catalytic conversion process into higher molecular weight hydrocarbons. Examples of gas-to-liquid catalysts that can be used include cobalt-based synthesis catalysts developed by Criterion, and Fischer-Tropsch catalysts and modifications thereof. The gas to liquid catalyst can be in the same bed as the reforming catalyst or the light gases can be collected and directed to another reactor for further treatment of the gases.

Figure 8A:
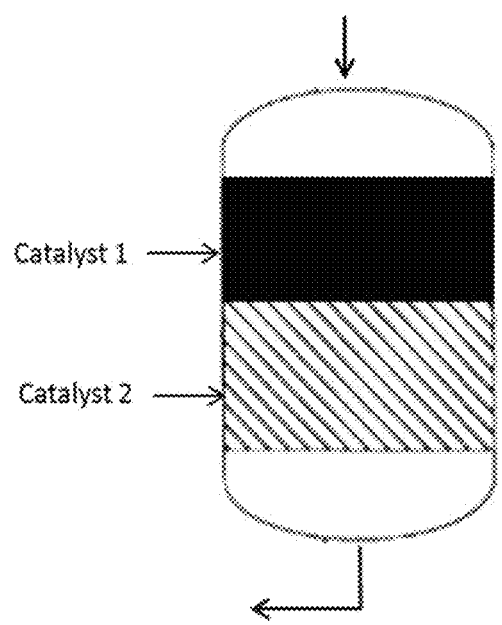
FIG. 8A provides a schematic diagram of the longitudinal section of a reactor (e.g., a trickle-bed reactor), in which a catalytic conversion of biomass-derived building blocks takes place. This diagram depicts an example where two catalysts, Catalyst 1 and Catalyst 2, are in separate layers.
Figure 8B:
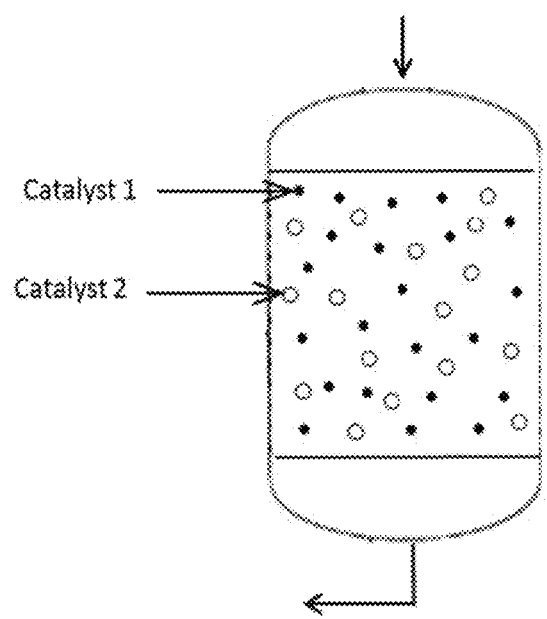
FIG. 8B provides a schematic diagram of the longitudinal section of another reactor (e.g., a trickle-bed reactor), in which catalytic conversion of biomass-derived building blocks takes place. This diagram depicts an example where two catalysts, Catalyst 1 and Catalyst 2 are blended together.
Figure 8C:
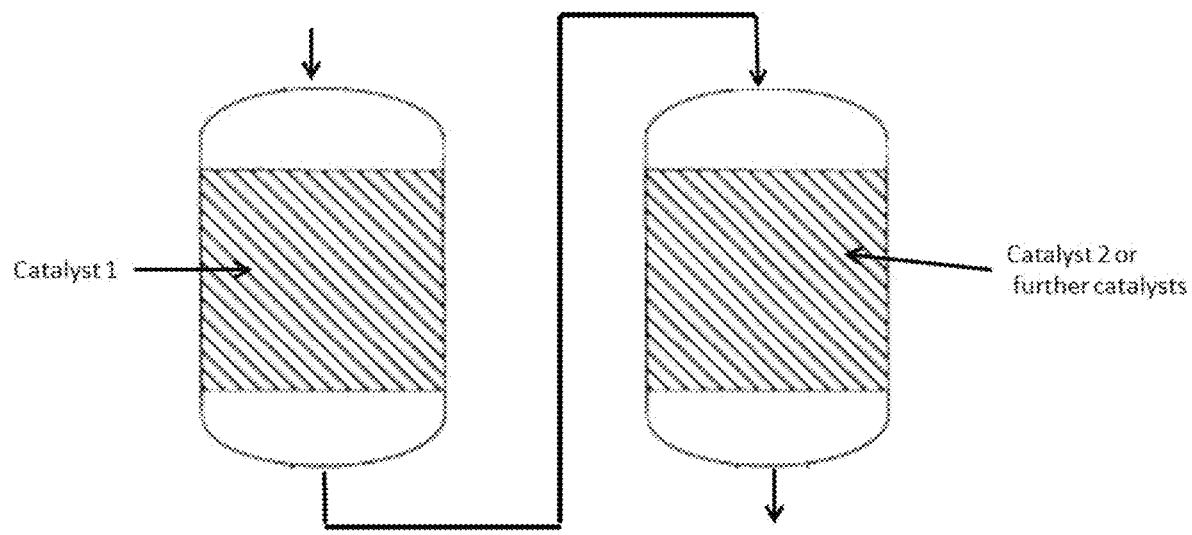
FIG. 8C provides a schematic diagram of the longitudinal sections of two reactors (eg., trickle-bed reactors), in which catalytic conversion of biomass-derived building blocks takes place such that products and/or unreacted constituents from the first reactor are directed into the second reactor for further catalytic conversion. The first reactor has a catalyst bed made of Catalyst 1 and the second reactor has a catalyst bed made of Catalyst 2.

In one embodiment, the reforming catalyst can be combined with one or more catalysts such as gas-to-liquid catalysts. For example, a combination of reforming catalyst and gas-to-liquid catalyst may be used in a catalytic reactor to convert processed biomass or biomass-derived products into constituents of fuel such as gasoline, diesel, kerosene, jet fuel and aviation fuel. FIG. 8A, for example, provides a schematic diagram of the longitudinal section of a reactor (eg., a trickle-bed reactor), in which a catalytic conversion of biomass-derived building blocks takes place in the presence of two catalysts. This diagram depicts an example where two catalysts, Catalyst 1 and Catalyst 2, are in separate layers. The flow of gas and liquid constituents is shown by the arrows entering and leaving the catalytic reactor. Another embodiment is depicted by FIG. 8B, which also provides a schematic diagram of the longitudinal section of another reactor (eg., a trickle-bed reactor), in which catalytic conversion of biomass-derived building blocks takes place in the presence of two catalysts. This diagram depicts an example where two catalysts, Catalyst 1 and Catalyst 2 are blended together. The flow of gas and liquid constituents is shown by the arrows entering and leaving the catalytic reactor. FIG. 8C provides a schematic diagram of another embodiment, in which two reactors are connected in a pipeline such that products and/or unreacted constituents from the first reactor are directed into the second reactor for further catalytic conversion. The catalyst bed in the first reactor is denoted by Catalyst 1 and that in the second reactor is denoted by Catalyst 2. Various combinations of Catalyst 1 and Catalyst 2 may be used. For example, in one embodiment, Catalyst 1 can be a dehydration catalyst and Catalyst 2 can be an oligomerization catalyst. In another embodiment, Catalyst 1 can be a dehydration catalyst and Catalyst 2 can be a hydrogenation catalyst. In one embodiment, Catalyst 1 can be a dehydration catalyst and Catalyst 2 can be a C—H bond activating catalysts. In some embodiments, Catalyst 1 and Catalyst 2 may be same, while in some embodiments, they may be different. In some embodiments, Catalyst 2 is a hydrogenation catalyst selected from the group consisting of Raney/Ni, Rh catalysts, Re catalyts, Pt catalysts, Ru catalysts, Lindlar's catalyst, and various transition metal catalysts. If the catalysts are same, then the two reactors may be operating under different conditions such as temperature, pressure, flow-rates, and running time.

In some embodiments, two or more catalytic reactors may be arranged in a manner such that products and/or unreacted constituents from one or more of the catalytic reactors may be directed to other reactors in the system. Various combinations of catalysts may be used in these reactors, including a dehydration catalyst, an oligomerization catalyst, a hydrogenation, a C—H bond activating catalysts, a reforming catalyst, and mixtures thereof. In some embodiments, the two or more reactors may be operating under different conditions such as temperature, pressure, flow-rates, and running time.

Similar mixed catalyst arrangements can be used with other catalyst combinations.

In other embodiments, catalysts or subsequent processing steps can be included to reduce the molecular weight of at least one component of the catalyst process. In this stage, a liquid is formed which looks and feels like wax at room temperature. The high molecular weight components and be separated and in a subsequent process, a cracking and isomerization step can occur, which "tailors" the molecule chains into products with desired properties. This yields high-quality liquids such as diesel, kerosene and lubricant oil.

The catalytic processes described herein may also be performed in the presence of solid supports. A catalyst support is a material, usually a solid with a high surface area, to which a catalyst is affixed. While it is generally considered to be inert and mainly considered to be useful in providing high surface area, in many cases the supports can facilitate the catalysis by providing appropriate conditions. For example, solid supports may provide acidic sites for dehydration and basic sites for retro-aldol reaction. The choice of a particular support depends on the nature of application and reaction conditions. The preparation steps and the quality of the raw materials strongly affect the support properties. Examples of supports include alumina, silica, magnesia, zirconia, zeolites, and polymeric resins (such as polystyrene-divinyl benzene, Nafion, poly(vinylpyridinium dichromate)).

Acidity and basicity of a catalyst support may play a role in the catalytic performance. A variety of methods can be used to characterize the acidity of solid supports. For example, in some embodiments, an indicator may be used to measure the acidity of the solid catalysts. An indicator is usually a neutral organic base, which upon absorption on the solid is changed to its conjugated acid form. The neutral base form of the indicator has a different color than the conjugated acid form. Examples of neutral base indicators include neutral red, methyl red, phenylazonaphthylamine, p-dimethylaminobenzene, 2-amino-5-azotoluene, benzeneazodephenylamine, 4-dimethylaminoazo-1-naphthalene, crystal violet, p-nitrobenzeneazo-(p'-nitro) diphenylamine, dicinnamalacetone, benzalacetophenone, and anthraquinone. Acid strength can also be measured by gaseous base absorption methods. In this method, the amount of gaseous base that a solid acid can absorb chemically from the gaseous phase is used as a measure of the number of acidic sites on its surface. Examples of bases that can be used include ammonia, pyridine, n-butylamine, and isopropylamine. In another method, called the $\alpha$ test, the catalytic activity of the solid catalyst is used to measure the acidity. The test uses n-hexane as the probe molecule, and the $\alpha$ value of a catalyst is defined as the ratio of the first-order rate constant for n-hexane cracking over the sample to that obtained over an arbitrary standard, measured at 538° C. Other methods such as microcalorimetric methods, conductometric titration, UV-Visible spectroscopy, aromatics absorption, NMR, luminescence, electron spin resonance, and other spectrophotometric methods may also be used to determine the acidity and basicity of the solid support. Catalytic characteristics can be evaluated using other methods, such as BET, temperature programmed desorption of ammonia (NH3-TPD) and carbon dioxide ($CO_2$-TPD), FTIR spectroscopy and XRD.

In one embodiment, an automated chemisorption analysis instrument is used to characterize the catalyst. For example, AMI-300, an automated chemisorption analysis instrument offered by Altamira Instruments may be used to characterize the catalyst. AMI-300 is capable of performing the major dynamic techniques required for fully characterizing a catalyst, using dynamic procedures such as temperature programmed desorption (TPD), temperature programmed reduction/oxidation (TPR/O), temperature programmed reaction (TPRx), pulse chemisorption, catalyst treatment, dynamic BET surface area and pulse calibration. The AMI-300 is a fully automated catalyst characterization instrument which uses proprietary software to switch gas streams, control gas flow rates, blend gases, control temperatures, control ramp rates, and to collect all the data needed to quantify the adsorption and desorption of gas molecules on the surface of a catalyst. The AMI-300 comes standard with a highly linear thermal conductivity detector (TCD). In addition to the TCD, AMI instruments may be equipped with a wide range of auxiliary detection devices such as Mass Spectrometer, Flame Ionization Detector, Flame Photometric Detector, Gas Chromatograph and FTIR.

A number of methods may be used to prepare supported catalysts. In the impregnation method, a suspension of the solid support is treated with a solution of a precatalyst, and the resulting material is then activated under conditions that will convert the precatalyst (often a metal salt) to a more active state. In such cases, the catalyst support is usually in the form of pellets. For example, a solid support such as alumina or silica may be treated with a solution of metal nitrates or metal halides. The catalyst can then be dried and calcined to drive off the volatile components within the solution, depositing the metal salt on the solid support. The maximum loading is limited by the solubility of the precursor in the solution. In some embodiments, the calcination step involves the conversion of the dispersed metal salt solution into an oxide by heating at a high temperature in the presence of air or oxygen. Finally, the metal oxide may be reduced to the metallic state by reducing conditions such as by passing a stream of hydrogen to give the final metal/support catalyst. Other gases such as hydrogen sulfide, ammonia, and carbon monoxide may also be used to reduce the metal oxide. The calcination and the reduction steps are often referred to as the activation steps in this process. In some embodiments, the above steps are repeated till the desired results are achieved.

Although direct reduction of many precursors can lead to well-dispersed catalysts, direct reduction is often highly exothermic and can lead to mixed metal-support phases. Moreover, it can produce a pyrophoric catalyst that needs to be passivated, often making it impractical for use on an industrial scale. Therefore, a calcination procedure is usually performed to form the pure metal oxide particles before further treatment such as reduction. Both the heating rate and air flow during calcination have been shown to be highly important in influencing the property of the final catalyst.

A number of impregnation methods can be used in the processes described herein, such as wet impregnation (WI), whereby an excess amount of solution is used, and pore volume impregnation (PVI), in which an amount to just fill the pore volume of the support is used. The latter method is also known as incipient wetness impregnation (IWI) or dry impregnation (DI), because the impregnated material keeps a dry character at a macroscopic scale.

In one embodiment, the catalytic system is prepared using amorphous silica-alumina (ASA) supports in combination with USY and β-zeolites. These supports are ASA, SIRAL 40 (from Condea GmbH Germany), USY zeolite (from Toso Chemical Company, Japan) and β-zeolite (from Sud-Chemie). Alumina-based Cataloid AP-1 (from Catalyst and Chemical Industry, Japan) is used as a binder to prepare extrudates. Cataloid AP-I comprises 71 wt. % alumina, 11 wt. % acetic acid and 18 wt. % water and it has an average particle size of 54 µm. The supports selected are first weighed and then mixed with a weighed amount of AP-1 and formed into 1/32 in. extrudates. This procedure is started with the weighing of the supports, Cataloid AP-I and water in predetermined quantities and then mixing them together. The mixture is agitated strongly to change it to hard paste. The paste is put into the syringe barrel and pressed to form extrudates which are collected on a filter paper tray. The extrudates are dried in an oven maintained at 120° C. for 2 h and then broken into small 3-4 mm pieces, sieved and calcined in a quartz tube calcination setup provided with air flow. The extrudates are housed between the glass wool in the quartz tube and fixed in the heating furnace and connected to an airflow of 250 ml/min. The temperature is raised to 120° C. and maintained for 30 min. Then the temperature is increased to 550° C. and maintained at this temperature for 2 h. Then the heating is stopped, the furnace is opened and the extrudates are allowed to cool to ambient temperature while the air is flowing to provide rapid cooling. The extrudates are then removed from the quartz tube and sieved to remove any powder present. Then the extrudates are weighed to record the weight of extrudates formed.

The extrudates are impregnated with metals pairs Ni—W or Ni—Mo using co-impregnation technique, the metal loading of NiO 4 wt. % and $WO_3$ 15 wt. %, or $MoO_3$ 15 wt. %. Two types of solutions are prepared: one containing Ni and W while the other has Ni and Mo. The solutions are prepared using deionized water. The metal salts used are nickel nitrate hexahydrate [$Ni(NO_3)_2 \cdot 6H_2O$], ammonium metatungstate pentahydrate [$(NH_4)_6W_{12}O_{39} \cdot 5H_2O$] and ammonium molybdate tetrahydrate [$(NH_4)_6Mo_7O_{24} \cdot 4H_2O$]. In case of NiMo solution, the ammonium molybdate tetrahydrate is added first in water and dissolved completely. Then the predetermined quantity of nickel nitrate is added; the mixture is stirred quickly, and the solution is used within 1-2 min before the solution gets turbid due to complex formation. The metals are impregnated on a batch of 10 g of extrudates in a wide-mouthed crucible. The solutions are added dropwise till all the extrudates are completely wet. The extrudates are then allowed to adsorb the metals for 2 h. Then the extrudates are placed in an oven maintained at 120° C. under a reduced pressure of 410 mmHg pressure for 2 h. The purpose of drying under vacuum is to segregate and bring the Mo ions onto the surface of the catalysts and convert them into $MoO_3$ and thus to provide high hydrogenation activity on the surface of the catalyst. At the end of the drying process, the extrudates are placed in a temperature-programmed furnace for calcination. The calcination is conducted under the following heating program: The temperature is raised to 120° C. and maintained for 2 h, then the temperature is raised to 550° C. at a heating rate of 2° C./min and maintained for 2 h at this temperature. Then the furnace is allowed to cool overnight. The samples are kept in airtight glass bottles for characterization and catalytic evaluation. The weights of the finished catalysts obtained after calcination are in the range 12.6-13.0 g per batch.

Alternatively, supported catalysts can be prepared from homogeneous solution by co-precipitation. In co-precipitation, salts of the active metal and support are dissolved and mixed such that nucleation and growth of a combined solid precursor of the active metal and support is obtained in a single step. Very high metal loadings of 70 wt. % and higher can be achieved while maintaining small particle sizes, and as such, it is a convenient way to produce catalysts with a high metal weight to volume ratio. For example, an acidic solution of aluminum salts and precatalyst can be treated with base to precipitate the mixed hydroxide, which is subsequently calcined. Co-precipitation can be utilized to produce catalysts such as nickel alumina for steam reforming, iron copper potassium for Fischer-Tropsch synthesis, and $Cu/ZnO/Al_2O_3$ catalysts for methanol synthesis.

In some embodiments, the catalysts have a surface area of about 1 $m^2/g$, about 10 $m^2/g$, about 20 $m^2/g$, about 30 $m^2/g$, about 40 $m^2/g$, about 50 $m^2/g$, about 60 $m^2/g$, about 70 $m^2/g$, about 80 $m^2/g$, about 100 $m^2/g$, about 110 $m^2/g$, about 120 $m^2/g$, about 130 $m^2/g$, about 140 $m^2/g$, about 150 $m^2/g$, about 160 $m^2/g$, about 170 $m^2/g$, about 180 $m^2/g$, about 190 $m^2/g$, about 200 $m^2/g$, about 210 $m^2/g$, about 220 $m^2/g$, about 230 $m^2/g$, about 240 $m^2/g$, about 250 $m^2/g$, about 260 $m^2/g$, about 270 $m^2/g$, about 280 $m^2/g$, about 290 $m^2/g$, about 300 $m^2/g$, about 310 $m^2/g$, about 320 $m^2/g$, about 330 $m^2/g$, about 340 $m^2/g$, about 350 $m^2/g$, about 360 $m^2/g$, about 370 $m^2/g$, about 380 $m^2/g$, about 390 $m^2/g$, about 400 m²/g, about 410 m²/g, about 410 m²/g, about 410 m²/g, about 420 m²/g, about 430 m²/g, about 440 m²/g, about 450 m²/g, about 460 m²/g, about 470 m²/g, about 480 m²/g, about 500 m²/g, about 550 m²/g, about 600 m²/g, about 650 m²/g, about 700 m²/g, about 750 m²/g, about 800 m²/g, about 850 m²/g, about 900 m²/g, about 950 m²/g, and about 1000 m²/g.

In some embodiments, the catalyst may have a pore volume of about 0.01 cm³/g, about 0.02 cm³/g, about 0.03 cm³/g, about 0.04 cm³/g, about 0.05 cm³/g, about 0.06 cm³/g, about 0.07 cm³/g, about 0.08 cm³/g, about 0.09 cm³/g, about 0.1 cm³/g, about 0.2 cm³/g, about 0.3 cm³/g, about 0.4 cm³/g, about 0.5 cm³/g, about 0.6 cm³/g, about 0.7 cm³/g, about 0.8 cm³/g, about 0.9 cm³/g, about 1.0 cm³/g, about 1.1 cm³/g, about 1.2 cm³/g, about 1.3 cm³/g, about 1.4 cm³/g, about 1.5 cm³/g, about 1.6 cm³/g, about 1.7 cm³/g, about 1.8 cm³/g, about 1.9 cm³/g, about 2.0 cm³/g, about 2.1 cm³/g, about 2.2 cm³/g, about 2.3 cm³/g, about 2.4 cm³/g, about 2.5 cm³/g, about 2.6 cm³/g, about 2.7 cm³/g, about 2.8 cm³/g, about 2.9 cm³/g, about 3.0 cm³/g, about 3.1 cm³/g, about 3.2 cm³/g, about 3.3 cm³/g, about 3.4 cm³/g, about 3.5 cm³/g, about 3.6 cm³/g, about 3.7 cm³/g, about 3.8 cm³/g, about 3.9 cm³/g, about 4.0 cm³/g, about 4.1 cm³/g, about 4.2 cm³/g, about 4.3 cm³/g, about 4.4 cm³/g, about 4.5 cm³/g, about 4.6 cm³/g, about 4.7 cm³/g, about 4.8 cm³/g, about 4.9 cm³/g, about 5.0 cm³/g, about 5.1 cm³/g, about 5.2 cm³/g, about 5.3 cm³/g, about 5.4 cm³/g, about 5.5 cm³/g, about 5.6 cm³/g, about 5.7 cm³/g, about 5.8 cm³/g, about 5.9 cm³/g, about 6.0 cm³/g, about 7.0 cm³/g, about 8.0 cm³/g, about 9.0 cm³/g, and about 10.0 cm³/g.

In some embodiments, the average pore size of the catalyst can be about 0.1 Å, about 0.2 Å, about 0.3 Å, about 0.4 Å, about 0.5 Å, about 0.6 Å, about 0.7 Å, about 0.8 Å, about 0.9 Å, about 1.0 Å, about 2.0 Å, about 3.0 Å, about 4.0 Å, about 5.0 Å, about 6.0 Å, about 7.0 Å, about 8.0 Å, about 9.0 Å, about 10.0 Å, about 20.0 Å, about 25.0 Å, about 30.0 Å, about 35.0 Å, about 40.0 Å, about 45.0 Å, about 50.0 Å, about 55.0 Å, about 60.0 Å, about 65.0 Å, about 70.0 Å, about 75.0 Å, about 80.0 Å, about 85.0 Å, about 90.0 Å, about 95.0 Å, and about 100.0 Å.

In some embodiments, the pressure drop across the catalytic column may be about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, and about 50%.

In some embodiments, the amount of active metal catalyst loading in the catalyst bed can be about 1 wt. %, about 2 wt. %, about 3 wt. %, about 4 wt. %, about 5 wt. %, about 6 wt. %, about 7 wt. %, about 8 wt. %, about 9 wt. %, about 10 wt. %, about 15 wt. %, about 20 wt. %, about 25 wt. %, about 30 wt. %, about 35 wt. %, about 40 wt. %, about 45 wt. %, about 50 wt. %, about 55 wt. %, about 60 wt. %, about 65 wt. %, about 70 wt. %, about 80 wt. %, about 90 wt. %, about 95 wt. %, and about 100 wt. %.

In some embodiments, the gas flow rate in the reactor is about 1 ml/min, about 2 ml/min, about 3 ml/min, about 4 ml/min, about 5 ml/min, about 6 ml/min, about 7 ml/min, about 8 ml/min, about 9 ml/min, about 10 ml/min, about 20 ml/min, about 30 ml/min, about 40 ml/min, about 50 ml/min, about 60 ml/min, about 70 ml/min, about 80 ml/min, about 90 ml/min, about 100 ml/min, about 150 ml/min, about 200 ml/min, about 250 ml/min, about 300 ml/min, about 350 ml/min, about 400 ml/min, about 450 ml/min, about 500 ml/min, about 550 ml/min, about 600 ml/min, about 650 ml/min, about 700 ml/min, about 750 ml/min, about 800 ml/min, about 850 ml/min, about 900 ml/min, about 950 ml/min, and about 1000 ml/min.

In some embodiments, the liquid flow rate in the reactor is about 1 ml/min, about 2 ml/min, about 3 ml/min, about 4 ml/min, about 5 ml/min, about 6 ml/min, about 7 ml/min, about 8 ml/min, about 9 ml/min, about 10 ml/min, about 20 ml/min, about 30 ml/min, about 40 ml/min, about 50 ml/min, about 60 ml/min, about 70 ml/min, about 80 ml/min, about 90 ml/min, about 100 ml/min, about 150 ml/min, about 200 ml/min, about 250 ml/min, about 300 ml/min, about 350 ml/min, about 400 ml/min, about 450 ml/min, about 500 ml/min, about 550 ml/min, about 600 ml/min, about 650 ml/min, about 700 ml/min, about 750 ml/min, about 800 ml/min, about 850 ml/min, about 900 ml/min, about 950 ml/min, and about 1000 ml/min.

In some embodiments, product selectivity, product distribution and poisoning of the catalysts is impacted by the operating pressure of the gases that contact the catalyst.

In some embodiments, the pressure within a reactor can vary from a low-pressure zone to a high pressure zone, and vice-versa. In some embodiments, a reactor may contain a combination of various pressure zones. In some embodiments, there is a difference in pressure between two or more reactors within the system. In some embodiments, the pressure can change by 2-fold, 3-fold, 5-fold, 10-fold, 20-fold, 30-fold, 40-fold, 50-fold, 100-fold, or any range described hereinabove. The operating pressure, for example, may vary from 10 psi to 50 psi. The operating pressure can be anywhere in the range of about 0.1 psi, 1 psi, 5 psi, 10 psi, 20 psi, 30 psi, 40 psi, 50 psi, 60 psi, 70 psi, 80 psi, 90 psi, 100 psi, 200 psi, 300 psi, 400 psi, 500 psi, 1000 psi, or bound by any numerical value stated herein above.

In some embodiments, product selectivity, product distribution and poisoning of the catalysts is impacted by the operating temperature of the reactor. In some embodiments, the temperature within a reactor can vary from a low temperature zone to a high temperature zone, and vice-versa. In some embodiments, a reactor may contain a combination of various temperature zones. In some embodiments, there is a difference in temperature between two or more reactors within the system. In some embodiments, there is a difference in pressure between two or more reactors within the system. In some embodiments, the temperature can change by 2-fold, 3-fold, 5-fold, 10-fold, 20-fold, 30-fold, 40-fold, 50-fold, 100-fold, or any range described hereinabove. The operating temperature, for example, may vary from 10° C. to 50° C. The operating temperature can be anywhere in the range of about 50° C., 60° C., 70° C., 80° C., 90° C., 100° C., 200° C., 300° C., 400° C., 500° C., 1000° C., or bound by any numerical value stated herein above.

In some embodiments, product selectivity, product distribution and poisoning of the catalysts is impacted by the flow-rate of fluids within a reactor. In some embodiments, the flow-rate within a reactor can vary from a low flow-rate zone to a high flow-rate zone, and vice-versa. In some embodiments, a reactor may contain a combination of various flow-rate zones. In some embodiments, there is a difference in flow-rates between two or more reactors within the system. In some embodiments, there is a difference in flow-rate between two or more reactors within the system. In some embodiments, the flow-rate can change by 2-fold, 3-fold, 5-fold, 10-fold, 20-fold, 30-fold, 40-fold, 50-fold, 100-fold, or any range described hereinabove. The flow-rates for example, may vary from 5 ml/min to 50 ml/min. The flow-rates can be about 1 ml/min, about 2 ml/min, about 3 ml/min, about 4 ml/min, about 5 ml/min, about 6 ml/min, about 7 ml/min, about 8 ml/min, about 9 ml/min, about 10 ml/min, about 20 ml/min, about 30 ml/min, about 40 ml/min, about 50 ml/min, about 60 ml/min, about 70 ml/min, about 80 ml/min, about 90 ml/min, about 100 ml/min, about 150 ml/min, about 200 ml/min, about 250 ml/min, about 300 ml/min, about 350 ml/min, about 400 ml/min, about 450 ml/min, about 500 ml/min, about 550 ml/min, about 600 ml/min, about 650 ml/min, about 700 ml/min, about 750 ml/min, about 800 ml/min, about 850 ml/min, about 900 ml/min, about 950 ml/min, and about 1000 ml/min, or bound by any numerical value stated herein above.

In some embodiments, product selectivity, product distribution and poisoning of the catalysts is impacted by the viscosity of the reaction mixture within a reactor. In some embodiments, the viscosity within a reactor can vary from a low viscosity zone to a high viscosity zone, and vice-versa. In some embodiments, a reactor may contain a combination of various viscosity zones. In some embodiments, there is a difference in viscosities between two or more reactors within the system. In some embodiments, there is a difference in viscosity between two or more reactors within the system. In some embodiments, the viscosity can change by 2-fold, 3-fold, 5-fold, 10-fold, 20-fold, 30-fold, 40-fold, 50-fold, 100-fold, or any range described hereinabove. The viscosty for example, may vary from 5 cP to 50 cP. In some embodiments, the viscosity of the reaction mixture in the reactor may range from about 1 centipoise (cP) to about 5 Cp, about 5 cP to about 10 cP, about 10 cP to about 15 cP, about 15 cP to about 20 cP, about 20 cP to about 25 cP, about 25 cP to about 30 cP, about 30 cP to about 35 cP, about 40 cP to about 45 cP, about 45 cP to about 50 cP, about 50 cP to about 55 cP, about 55 cP to about 60 cP, about 60 cP to about 65 cP, about 65 cP to about 70 cP, about 70 cP to about 75 cP, about 75 cP to about 80 cP, about 80 cP to about 85 cP, about 85 cP to about 90 cP, about 90 cP to about 95 cP, about 95 cP to about 100 cP, about 100 cP to about 200 cP, about 200 cP to about 300 cP, about 300 cP to about 400 cP, about 400 cP to about 500 cP, about 500 cP to about 600 cP, about 600 cP to about 700 cP, about 700 cP to about 800 cP, about 800 cP to about 900 cP, about 900 cP to about 1000 cP, or in a range bounded by any numerical value stated herein above.

In some embodiments, all or one of the above described parameters, including temperature, pressure, viscosity and flow-rate are optimized to increase yield and minimize catalytic poisoning. In some embodiments, all or one of the above described parameters, including temperature, pressure and flow-rate are optimized to decrease the production of certain compounds, such as alkenes.

The carrier gas used in the reactor can be for example, hydrogen, nitrogen, argon, carbon monoxide, carbon dioxide, helium or mixtures thereof. In some embodiments, the carrier gas used in the reactor can be a mixture of hydrogen and another gas such as nitrogen containing about 1% hydrogen, about 2% hydrogen, about 3% hydrogen, about 4% hydrogen, about 5% hydrogen, about 6% hydrogen, about 7% hydrogen, about 8% hydrogen, about 9% hydrogen, about 10% hydrogen, about 15% hydrogen, about 20% hydrogen, about 25% hydrogen, about 30% hydrogen, about 35% hydrogen, about 40% hydrogen, about 45% hydrogen, about 50% hydrogen, about 55% hydrogen, about 60% hydrogen, about 65% hydrogen, about 70% hydrogen, about 75% hydrogen, about 80% hydrogen, about 85% hydrogen, about 90% hydrogen, and about 95% hydrogen. In one embodiment, the carrier gas used in the reactors is a mixture of hydrogen and nitrogen containing about 5% hydrogen.

In some embodiments, the reaction is carried out using liquid diluents or carriers such as an alcohol (such as methanol, ethanol, propanol etc.), dimethylsulfoxide, water, or a mixture thereof. In some embodiments, the liquid diluents or carrier can contain a mixture of water and an alcohol containing about 1% of water by volume, 2% of water by volume, 3% of water by volume, 4% of water by volume, 5% of water by volume, 6% of water by volume, 7% of water by volume, 8% of water by volume, 9% of water by volume, 10% of water by volume, 15% of water by volume, 20% of water by volume, 25% of water by volume, 30% of water by volume, 35% of water by volume, 40% of water by volume, 45% of water by volume, 50% of water by volume, 55% of water by volume, 60% of water by volume, 65% of water by volume, 70% of water by volume, 75% of water by volume, 80% of water by volume, 85% of water by volume, 90% of water by volume, and about 95% of water by volume.

In some embodiments, the reactor may be subjected to a temperature gradient of about 25° C. to about 50° C., about 50° C. to about 75° C., about 75° C. to about 100° C., about 125° C. to about 150° C., about 150° C. to about 175° C., about 175° C. to about 200° C., about 200° C. to about 250° C., about 250° C. to about 300° C., about 300° C. to about 325° C., about 325° C. to about 350° C., about 350° C. to about 375° C., about 375° C. to about 400° C., about 400° C. to about 425° C., about 425° C. to about 450° C., about 450° C. to about 475° C., about 475° C. to about 500° C., about 500° C. to about 1000° C., or in a range bounded by any numerical value stated herein above.

In some embodiments, the reactor may be subjected to a pressure gradient of about 10 bar to about 25 bar, about 25 bar to about 50 bar, about 50 bar to about 75 bar, about 75 bar to about 100 bar, about 125 bar to about 150 bar, about 150 bar to about 175 bar, about 175 bar to about 200 bar, about 200 bar to about 250 bar, about 250 bar to about 300 bar, about 300 bar to about 325 bar, about 325 bar to about 350 bar, about 350 bar to about 375 bar, about 375 bar to about 400 bar, about 400 bar to about 425 bar, about 425 bar to about 450 bar, about 450 bar to about 475 bar, about 475 bar to about 500 bar about 500 bar to about 1000 bar, or in a range bounded by any numerical value stated herein above.

In some embodiments, the viscosity of the reaction mixture in the reactor may range from about 1 centipoise (cP) to about 5 Cp, about 5 cP to about 10 cP, about 10 cP to about 15 cP, about 15 cP to about 20 cP, about 20 cP to about 25 cP, about 25 cP to about 30 cP, about 30 cP to about 35 cP, about 40 cP to about 45 cP, about 45 cP to about 50 cP, about 50 cP to about 55 cP, about 55 cP to about 60 cP, about 60 cP to about 65 cP, about 65 cP to about 70 cP, about 70 cP to about 75 cP, about 75 cP to about 80 cP, about 80 cP to about 85 cP, about 85 cP to about 90 cP, about 90 cP to about 95 cP, about 95 cP to about 100 cP, about 100 cP to about 200 cP, about 200 cP to about 300 cP, about 300 cP to about 400 cP, about 400 cP to about 500 cP, about 500 cP to about 600 cP, about 600 cP to about 700 cP, about 700 cP to about 800 cP, about 800 cP to about 900 cP, about 900 cP to about 1000 cP, or in a range bounded by any numerical value stated herein above.

Many reforming catalysts suffer from catalyst deactivation over time. The biggest cause of deactivation is the accumulation of carbon, e.g., coke, on the catalyst surface. One way, coke formation can be reduced or eliminated is by doping the catalysts with a suitable organic or inorganic material. Suitable dopants that can improve the dispersion of the metal catalyst and reduce the formation of coke include alkali metals (such as Li, Na, and K), transition metals (such as Ti, Zr, Hf, Nb, Cr, Mo, W, Mn, Re, Fe, Ru, Os, Co, Rh, Ir, Ni, Pd, Pt, Cu, Ag, Au), mixtures of transition metals (such as Ti/Hf, Ti/Zr, Zr/Cr), organometallic complexes (such as Cp2 V, (butadiene)$_3$ Mo, Bis-(arene) complexes of zero-valent Ti, Zr or Hf), promoter metals (such as germanium, indium, gallium, thallium), rare earth elements (such as La), halogens (such as fluorine, chlorine, bromine and iodine), hydrogen, hydrogen sulfide, tin, and sulfur.

In one embodiment, the catalyst contains about 0.001%, about 0.01%, about 0.1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20% by weight of at least one doping agent.

The catalyst can also be regenerated if the coke level on the catalyst is too high. The regeneration of coked catalysts can be accomplished by flowing a gas stream containing a few percent of oxygen over the catalyst at elevated temperatures, for example, 0.5% O2 in N2 and H2 at 500° C. The temperature of the reaction it controlled to avoid exothermic combustion of the deposited coke so as to prevent sintering of the catalyst. Regeneration can take place in a variety of reactors, including adiabatic fixed beds and polytropic reactors (reactors with multiple inlets).

The catalysts described herein can be used as bulk catalysts (e.g., not on a support). Bulk catalysts can be formed into shapes to increase surface area and allow flow of reactants over its surface. For example, in the form of: wool, a mesh, a grid, a wire, a perforated solid with channels, a sponge, beads and/or a powder. The catalysts and promoters can be mixed when utilized in bulk, for example powers of one or more catalyst and powders of one or more promoters can be combined/mixed. The metals or metal with promoter species can be advantageously adsorbed and or bonded onto a support. The support can be, for example, alumina, silica, aluminosilicates, clays, zeolites (e.g., USY and beta zeolite) or other inorganic materials. The supported catalysts typically have between about 0.1 wt. % and 10 wt. % of each metal (e.g., between 0.1 and 1 wt.), although higher amounts can be used. One or more metal and one or more promoter can be combined with one or more support in all combinations. These supported catalysts may be formed into any convenient form.

The catalysts can be homogeneous catalysts, for example, tris(triphenylphosphine)rhodium(I) chloride, and similar catalysts wherein the metal is complexed with stabilizing ligand(s) (e.g., amines, phosphines, alcohols, ethers, ketones, carboxylates, acetylacetonates, optionally bis, tri or tetrakis chelating ligands, combinations of these). The catalyst can be a polymer supported analog of a homogeneous catalyst, for example, wherein the ligands are attached to a polymer, e.g., functionalized polystyrenes wherein the functional groups are the ligands previously mentioned. Some catalysts, conditions, equipment and systems that can be utilized herein for the hydrogenolysis and esterification reaction are described in: "Catalysis of Organic Reactions" edited John R. Sowa, Jr., CRC Press (2005); "Catalytic Naphtha Reforming Second Edition, Revised and Expanded" edited George J. Antos and Abdullah M. Aitani, Marcel Dekker (2005) chapters 6, 8 and 9; and "Steam reforming catalysts Natural gas, associated gas and LPG" Johnson Matthey, pages 1-15. For example, bi and tri metallic supported catalysts of SnRu and SnRePt can be utilized for the hydrogenolysis of ethyl butyrate.

Supported catalysts can be prepared by any useful means, for example, by using the incipient wetness method, a decomposition precipitation method, a solution self-assembly method, and/or by vapor phase deposition/decomposition. For example, utilizing the incipient wetness method, a desired metal precursor can be dissolved or suspended in a volume of solvent similar to the pore volume of the support and it is combined with the support. The catalyst can be activated. Activation can include removal of the solvent under vacuum, calcination, for example in the presence of oxygen, nitrogen, hydrogen or other gasses, in any order and repeatedly. The catalysts can be added before the promoter, with the promoter, after the promoter or in combinations of addition steps. The supported catalysts can be formed into beads or extruded into rods and other shapes. Often these are combined with binders (e.g., inert ceramic material, porous binders).

Catalysts can be utilized in a batch mode. For example, the ester is combined, often with a solvent, in a vessel (e.g., a Parr™ reactor). The vessel can be sparged with hydrogen and/or pressurized with hydrogen. The vessels can be equipped with heaters, (e.g., heating jackets) and agitators (e.g., propellers, impellers). The catalysts can also be utilized in a fluidized bed reactor. These require a high gas flow rate, e.g., of an inert gas (e.g., nitrogen, He, Ar) in addition to hydrogen and the ester. The catalyst is fluidized by the rapid flow of gases through the reactor. One or more catalysts can be utilized sequentially or in combination (e.g., mixed together). A loop reactor may be used as it is a design option of a batch reactor, except the liquid in the vessel is recirculated outside of the reactor. If utilized sequentially, the catalysts can be utilized under different reaction conditions, e.g., temperatures, pressures (e.g., hydrogen pressures) and/or agitation (e.g., stirring rates). These combinations can, for example, optimize throughputs and combined conversion/selectivity.

Optionally, the catalysts are utilized in a fixed bed flow reactors (e.g., a flow reactor, packed bed reactor, trickle bed reactor). For example, a trickle-bed reactor (TBR) is a chemical reactor that uses the downward movement of a liquid and the downward (co-current) or upward (counter-current) movement of gas over a packed bed of (catalyst) particles. It is considered to be the simplest reactor type for performing catalytic reactions where a gas and liquid (normally both reagents) are present in the reactor and accordingly it is extensively used in processing plants. Typical examples are liquid-phase hydrogenation, hydrodesulfurization, and hydrodenitrogenation in refineries (three phase hydrotreater). These reactors are configured as a column packed with the catalysts (e.g., bulk or supported catalyst) through which the reactants (e.g., esters and hydrogen) are flowed. The columns can be heated, for example, by a heating jacket charged with a heating fluid (e.g., water, high pressure water, oil), steam, electric heaters (e.g., resistive heating), or any other heating means. The columns can also be designed to withstand high pressures e.g., at least about 50 psi, at least about 100 psi, at least about 150 psi, at least about 200 psi, at least about 300 psi, at least about 500 psi. The columns can also be equipped with safety equipment e.g., pressure release valves, and high temperature process shut off (e.g., flow shut off, venting). Optionally, two or more fixed bed reactors can be utilized in series for one flow stream of reactants (e.g., up to 20, up to 10, 2 to 5, 3 to 10, 1 to 3). In some optional configurations some of the reactors are by-passed, for example, to keep them as a backup.

Having available backups is particularly useful to avoid down time when one or more of the flow reactors are not operating within acceptable parameters e.g., if catalysts in the reactor are deactivated. Another advantage of utilizing reactors in series is that the reactors can be charged with different catalysts, for example having different selectivity and conversion rates, for optimal throughputs and combined conversion/selectivity. The columns can also be run under different conditions, e.g., flow rates, pressures and temperatures. For example, two or more columns can be utilized wherein the difference in temperatures can be about 0 to 10° C. (e.g., about 10 to 200° C., about 50 to 200° C., about 50 to 150° C., about 50 to 100° C.). In addition to or alternatively the difference in pressure (e.g., hydrogen pressure) when using at least more than one column, can be between about 0 to 5 atm. (e.g. between about 5 and 50 atm., between about 10 and 50 atm., between about 30 and 50 atm.).

The catalysts as described can be recycled/regenerated. For example, often the catalysts are oxidized by heating to high temperature in an oxidizing environment (e.g., in the presence of oxygen) e.g., between about 200 and 800° C. (e.g., 400 to 600° C.). After purging with an inert gas (e.g., nitrogen, argon, helium) the catalysts are reduced at a high temp e.g., between about 200 and 800° C. The reducing agent, for example, can be hydrogen gas made to flow over the catalyst.

Catalyst deactivation, the loss over time of catalytic activity and/or selectivity, is a problem of great and continuing concern in the practice of industrial catalytic processes. In one aspect, provided herein are methods of reducing catalytic deactivation, by either developing deactivation-resistant catalysts or providing methods of regenerating catalysts from deactivated catalysts.

Catalysts can be deactivated by various mechanisms, such as poisoning (strong chemisorption of species on catalytic sites which block sites for catalytic reaction), fouling (physical deposition of species from fluid phase onto the catalytic surface and in catalyst pores), thermal degradation and sintering (thermally induced loss of catalytic surface area, support area, and active phase-support reactions), vapor formation (reaction of gas with catalyst phase to produce volatile compound), vapor-solid, liquid-solid and solid-solid reactions, attrition and crushing (loss of catalytic material due to abrasion; loss of internal surface area due to mechanical-induced crushing of the catalyst particle).

Catalyst deactivators can include a number of materials, such as carbonized material (eg., coke), hydrogen, carbon monoxide, sulfur oxides, phosphorus oxides, inorganic ions such as halide, cyanide, sulfide, sulfite, and phosphite, and organic molecules such as nitriles, amine, thiols, nitro-compounds, oximes, nitrogen-containing heterocycles, benzene, acetylene, other unsaturated hydrocarbons, and certain metals and metal ions (such as As, Pb, Hg, Bi, Sn, Cd, Cu, Fe). For example, FIG. 17A shows that even in a fresh Pt-containing catalyst (eg., TVG-105), some amount of carbon deposition is observed. The figure depicts the element-profile of the catalyst. In this instance, 14% by weight of carbon was observed on the fresh, unused catalyst. Without being bound by hypothesis, it is possible that the carbon deposition took place during the process of securing the catalyst into the processing system. Alternatively, the carbon may have been deposited during catalyst production. FIG. 17B, provides an example of the element-profile of the same catalyst (TVG-105) after it has been used for catalytic conversion. As indicated by the figure, the amount of the carbon deposited on the used catalyst almost doubled to about 27.5% by weight. On the other hand, the amount of Pt was below the detection threshold of the analysis, indicating that the carbon deposition was covering the platinum surface, and was likely one of the causes of the loss of catalytic activity, that was observed with this catalyst.

In some embodiments, the catalytic deactivation can be reduced by generating deactivation-resistant catalysts. In some embodiments, catalytic deactivation can be reduced by controlling catalyst properties, process conditions (i.e., temperatures, pressures), feedstock impurities, methods of contacting, and process design. In some embodiments, the impact of catalytic deactivation may be reduced by regenerating the catalysts or separating the deactivating material from the catalysts.

In some embodiments, deactivation-resistant catalytic compositions are generated by designing catalytic compositions of certain pore sizes. For example, an optimal pore size can be designed to prevent access of large deactivating molecules to the catalytic ions, but allowing easy access to the reactant molecules. For example, the catalytic composition may have a pore-size of about the same size as that of the reactant molecule, about 2 times, about 3 times, about 4 times, about 5 times, about 6 times, about 7 times, about 8 times, about 9 times, about 10 times, about 11 times, about 12 times, about 13 times, about 14 times, about 15 times, about 16 times, about 17 times, about 18 times, about 19 times, about 20 times, about 30 times, about 40 times, about 50 times, about 60 times, about 70 times, about 80 times, about 90 times, about 100 times the size of the reactant molecule, and any size between any of the above pore sizes. In some embodiments, the catalytic composition may have a pore-size less than the size of the deactivating molecules, about 0.9 times the size of the deactivating molecule, about 0.8 times the size of the deactivating molecule, about 0.7 times the size of the deactivating molecule, about 0.6 times the size of the deactivating molecule, about 0.5 times the size of the deactivating molecule, about 0.4 times the size of the deactivating molecule, about 0.3 times the size of the deactivating molecule, about 0.2 times the size of the deactivating molecule, about 0.1 times the size of the deactivating molecule, about 0.01 times the size of the deactivating molecule, about 0.001 times the size of the deactivating molecule, and any size between any of the above pore sizes. In some embodiments, the catalytic composition may have a pore size of about 10 to about 20 Å, about 20 to about 30 Å, about 30 to about 40 Å, about 40 to about 50 Å, about 50 to about 60 Å, about 60 to about 70 Å, about 70 to about 80 Å, about 80 to about 90 Å, about 90 to about 100 Å, about 100 to about 150 Å, about 150 to about 200 Å, about 200 to about 250 Å, about 250 to about 300 Å, about 300 to about 350 Å, about 350 to about 400 Å, about 400 to about 450 Å, about 450 to about 500 Å, about 500 to 1000 Å, or in a range bounded by any numerical value stated herein above.

In some embodiments, deactivation-resistant catalytic compositions are generated by designing catalytic compositions of certain surface area. For example, the catalysts can have a surface area of about 1 m$^2$/g, about 10 m$^2$/g, about 20 m$^2$/g, about 30 m$^2$/g, about 40 m$^2$/g, about 50 m$^2$/g, about 60 m$^2$/g, about 70 m$^2$/g, about 80 m$^2$/g, about 100 m$^2$/g, about 110 m$^2$/g, about 120 m$^2$/g, about 130 m$^2$/g, about 140 m$^2$/g, about 150 m$^2$/g, about 160 m$^2$/g, about 170 m$^2$/g, about 180 m$^2$/g, about 190 m$^2$/g, about 200 m$^2$/g, about 210 m$^2$/g, about 220 m$^2$/g, about 230 m$^2$/g, about 240 m$^2$/g, about 250 m$^2$/g, about 260 m$^2$/g, about 270 m$^2$/g, about 280 m$^2$/g, about 290 m$^2$/g, about 300 m$^2$/g, about 310 m$^2$/g, about 320 m$^2$/g, about 330 m$^2$/g, about 340 m$^2$/g, about 350 m$^2$/g, about 360 m$^2$/g, about 370 m$^2$/g, about 380 m$^2$/g, about 390 m²/g, about 400 m²/g, about 410 m²/g, about 410 m²/g, about 410 m²/g, about 420 m²/g, about 430 m²/g, about 440 m²/g, about 450 m²/g, about 460 m²/g, about 470 m²/g, about 480 m²/g, about 500 m²/g, about 550 m²/g, about 600 m²/g, about 650 m²/g, about 700 m²/g, about 750 m²/g, about 800 m²/g, about 850 m²/g, about 900 m²/g, about 950 m²/g, and about 1000 m²/g.

In some embodiments, deactivation-resistant catalytic compositions are generated by designing catalytic compositions of certain pore volume. For example, the catalyst can have a pore volume of about 0.01 cm³/g, about 0.02 cm³/g, about 0.03 cm³/g, about 0.04 cm³/g, about 0.05 cm³/g, about 0.06 cm³/g, about 0.07 cm³/g, about 0.08 cm³/g, about 0.09 cm³/g, about 0.1 cm³/g, about 0.2 cm³/g, about 0.3 cm³/g, about 0.4 cm³/g, about 0.5 cm³/g, about 0.6 cm³/g, about 0.7 cm³/g, about 0.8 cm³/g, about 0.9 cm³/g, about 1.0 cm³/g, about 1.1 cm³/g, about 1.2 cm³/g, about 1.3 cm³/g, about 1.4 cm³/g, about 1.5 cm³/g, about 1.6 cm³/g, about 1.7 cm³/g, about 1.8 cm³/g, about 1.9 cm³/g, about 2.0 cm³/g, about 2.1 cm³/g, about 2.2 cm³/g, about 2.3 cm³/g, about 2.4 cm³/g, about 2.5 cm³/g, about 2.6 cm³/g, about 2.7 cm³/g, about 2.8 cm³/g, about 2.9 cm³/g, about 3.0 cm³/g, about 3.1 cm³/g, about 3.2 cm³/g, about 3.3 cm³/g, about 3.4 cm³/g, about 3.5 cm³/g, about 3.6 cm³/g, about 3.7 cm³/g, about 3.8 cm³/g, about 3.9 cm³/g, about 4.0 cm³/g, about 4.1 cm³/g, about 4.2 cm³/g, about 4.3 cm³/g, about 4.4 cm³/g, about 4.5 cm³/g, about 4.6 cm³/g, about 4.7 cm³/g, about 4.8 cm³/g, about 4.9 cm³/g, about 5.0 cm³/g, about 5.1 cm³/g, about 5.2 cm³/g, about 5.3 cm³/g, about 5.4 cm³/g, about 5.5 cm³/g, about 5.6 cm³/g, about 5.7 cm³/g, about 5.8 cm³/g, about 5.9 cm³/g, about 6.0 cm³/g, about 7.0 cm³/g, about 8.0 cm³/g, about 9.0 cm³/g, and about 10.0 cm³/g.

In some embodiments, the formation of catalytic deactivation can be reduced by choosing appropriate reaction conditions. For example, catalytic deactivation may be reduced by introducing gasifying agents (e.g., $H_2$, $H_2O$, $O_2$) or gas diluents, and by minimizing the void space available for homogeneous reaction. Similarly, the formation and growth of carbon or coke species on metal surfaces can be minimized by choosing reaction conditions that minimize the formation of atomic carbon or coke precursors and by introducing gasifying agents. Selective membranes or supercritical conditions can also be used to lower the gas-phase and surface concentrations of coke precursors. In some embodiments, moving-bed reactors may be preferred over fixed-bed reactors to prevent the deposition of deactivators on the catalysts.

In some embodiments, deactivation-resistant catalytic compositions are generated by modifying the catalytic composition. For example, catalytic compositions can be designed, which prevent catalyst deactivators from sticking to the surface or pores of a catalyst, by treatment with colloidal dispersions, or lubricants. In some embodiments, introduction of modifiers that change ensemble sizes (e.g., Cu or S in Ni or Ru) or that lower the solubility of deactivators such as carbon (e.g., Pt in Ni) can be used in reducing deactivation. In some embodiments, deactivation can be reduced by modifying the acidity and basicity of the catalytic composition. In some embodiments, some coating (eg., alumina or zeolite coating) can be applied to the catalytic material, or the catalyst can be prepared such that the active phase is in a sublayer, thereby providing a diffusion barrier that prevents or slows the access of deactivators to the catalyst surface. In some embodiments, catalysts may include "traps" for deactivating molecules (eg., oxides of thulium, cerium, and zinc), which can act as sacrificial stoichiometric reactants to protect the active catalyst by preferentially adsorbing the deactivators. For example, the formation of catalytic deactivators such as coke or carbon can be reduced by choosing reaction conditions that minimize the formation of free radicals, or by using free-radical traps. In some embodiments, the catalysts are produced in morphologically advantageous form, such that deactivators can be readily removed from them. Examples of advantageous morphological changes include modification of the shape, texture, density, viscosity, strength and crystallinity of the catalytic compositions.

Several catalytic and non-catalytic materials, can be advantageously used to improve deactivation-resistance of catalysts including silica, alumina, magnesium, zirconia, boria, titania chromia and combinations thereof, combinations of inorganic oxide typified by silica-alumina, silica-zirconia, silica-boria, silica-magnesia, silica-titania or ternary combinations such as silica-alumina-zirconia, silica-alumina-magnesia, particularly with silica as silica-alumina and silica-magnesia-alumina. In some embodiments, zeolite catalytic material, including X and Y aluminosilicate zeolites, ZSM-4, ZSM-5, ZSM-11, ZSM-12, ZSM-35, ZSM-38 and other similar materials, such as erionite, mordenite and faujasite, may also be useful in improving resistance to catalyst deactivation.

In some embodiments, the catalytic compositions are designed such that catalyst deactivators can be removed from them upon certain type of treatment. Both chemical and mechanical treatments may be used. For example, the deactivated catalysts can be subjected to shaking, spinning, abrasion, elution with gas or liquid, sonication, heating, drying, pressure-treatment, irradiation and treatment with magnetic forces.

In one embodiment, carbonaceous deposits can be removed by gasification with $O_2$, $H_2O$, $CO_2$, and Hz. The temperature required to gasify these deposits at a reasonable rate can be varied with the type of gas, the structure and reactivity of the carbon or coke, and the activity of the catalyst.

In some embodiments, the removal of deactivators may be accomplished by using a combination of treatment methods. For example, the catalysts may be subjected to a sequence of treatment steps, such as a first step involving treatment with a compressed gas, a second step involving washing the catalyst in a suitable solution, a third step involving rinsing, and a fourth step involving drying. In another example, a catalyst regeneration procedure can include the following steps: (1) vigorous shaking; (2) pressurized wet and dry treatments to remove channel blockages and outer dust layers; (3) washing of catalyst units in tanks containing agitated water augmented with surfactants, dispersants, ion-exchange materials, emulsifiers, acid, base, and/or acoustic radiation; (4) rinsing repeatedly in deionized water and repeating ultrasonic treatments between or in concert with chemical treatments, with a final rinse to finish removal of any catalyst or fouling residue; (5) reimpregnation of the clean support with the catalyst; and (5) drying (calcining) at low heating rates to convert the salts of the active catalytic materials to active metal oxides.

The deactivating material that is separated from the catalyst during the process of catalyst-regeneration, can be collected and used as commercially value-added products, or as building blocks or constituents of commercially value-added products. For example, carbon in the form of charcoal and coke can be used in metal smelting, in industries such as the iron and steel industries. Carbon in the form of graphite can be used in pencils, to make brushes in electric motors and in furnace linings. Activated charcoal can be used for purification and filtration, example in respirators and kitchen extractor hoods. Carbon fiber generated from carbon can be used strong, yet lightweight, material in many products such as tennis rackets, skis, fishing rods, rockets and airplanes. Carbon can also be used to prepare carbon nanotubes, fullerenes and atom-thin sheets of graphene, which can be used for example, in hardware developments in the electronics industry and in nanotechnology.

Syngas-to-Fuel

In one embodiment, gasification can be employed to generate fuel gases along with various other gaseous, liquid, and solid products. To perform gasification, the pre-treated feedstock is introduced into a pyrolysis chamber and heated to a high temperature, typically 700° C. or more. The temperature used depends upon a number of factors, including the nature of the feedstock and the desired products.

Quantities of oxygen (e.g., as pure oxygen gas and/or as air) and steam (e.g., superheated steam) are also added to the pyrolysis chamber to facilitate gasification. These compounds react with carbon-containing feedstock material in a multiple-step reaction to generate a gas mixture called synthesis gas (or "syngas"). Essentially, during gasification, a limited amount of oxygen is introduced into the pyrolysis chamber to allow some feedstock material to combust to form carbon monoxide and generate process heat. The process heat can then be used to promote a second reaction that converts additional feedstock material to hydrogen and carbon monoxide.

In a first step of the overall reaction, heating the feedstock material produces a char that can include a wide variety of different hydrocarbon-based species. Certain volatile materials can be produced (e.g., certain gaseous hydrocarbon materials), resulting in a reduction of the overall weight of the feedstock material. Then, in a second step of the reaction, some of the volatile material that is produced in the first step reacts with oxygen in a combustion reaction to produce both carbon monoxide and carbon dioxide. The combustion reaction releases heat, which promotes the third step of the reaction. In the third step, carbon dioxide and steam (e.g., water) react with the char generated in the first step to form carbon monoxide and hydrogen gas. Carbon monoxide can also react with steam, in a water gas shift reaction, to form carbon dioxide and further hydrogen gas.

Multiple gasification technologies exist to convert reduced-size biomass to syngas. In one embodiment, a high-temperature (slagging) gasification process is used, wherein the biomass is pressurized and converted into raw synthesis gas during gasification at temperatures around 1300° C. in the presence of high purity oxygen and steam. A combustor is included to provide heat to dry the biomass. A direct-quench syngas cooling system next to the gasifier removes ash and tars. A water-gas-shift system after quench is applied to adjust the $H_2$:CO ratio to 2.1:1.

In another embodiment, the endothermic gasification process is indirectly-heated by the circulation of hot olivine and the material in the gasifier is fluidized by the steam. Gasification occurs at atmospheric conditions and at 880° C. The syngas is further conditioned such that the residual tars, methane and light hydrocarbons are reformed to syngas in a fluid catalytic cracker. Water gas shift also occurs in the reformer. Compared to the high temperature gasification, this design has the benefits of energy self-sufficient, improved capital cost associated with the smaller process scale, and neutral electrical energy.

Other than syngas, a number of products, including pyrolysis oils and gaseous hydrocarbon-based substances, can also be obtained during and/or following gasification; these can be separated and stored or transported as desired.

In one embodiment, liquid hydrocarbon fuels and liquid alcohols can be produced catalytically from the syngas through a Fischer-Tropsch (F-T) process. After syngas is produced, it is polished with zinc oxide and an activated carbon sorbent and compressed to 25 bar, the F-T operating pressure. $H_2$ used in the hydro-processing stage can be purified through a pressure swing adsorption. The syngas is then processed by F-T synthesis to produce liquid fuel. Various catalysts, such as those based on transition metals iron, cobalt, nickel and ruthenium can be used. Product selectivity and product distribution depend strongly on the operating temperature and the partial pressure of the gases that contact the catalyst.

There are two well-known F-T operating modes; high temperature and low temperature. The high-temperature process runs at 300-350° C. with iron-based catalysts. Gasoline and linear low-molecular-mass olefins are produced in this process. The low-temperature process operates at 200-240° C. with either iron or cobalt catalysts. Linear waxes produced in the low-temperature process have higher molecular mass than those produced in the high-temperature process. In the F-T process, the products range from methane to long-chain hydrocarbons. Besides alkanes and alkenes, oxygenated compounds such as alcohols, aldehydes, and carboxylic acids are also formed. Aromatics and ketones are also produced in the high temperature process. The F-T process is a highly exothermic process; therefore, the heat of reaction has to be removed quickly to avoid overheating and deactivating the catalyst and also to prevent production of undesired methane.

Conventional refinery processes, such as hydrocracking, isomerization, hydrogenation, and fractionation, can be applied to upgrade the F-T synthesis product to high-quality, low-aromatic, and almost zero-sulfur-content fuels. Hydrocracking/isomerization is used to convert the wax into lighter products with shorter chain length and lower boiling points. Products from the hydrocracking isomerization reactor are heated and distilled to produce jet fuel, diesel fuel, and lubricants. Hydrogenation is applied to produce naphtha from the F-T liquid. The F-T tail gas, which contains $H_2$, water, methane, CO, $CO_2$, nitrogen, argon, and heavier hydrocarbons, is recycled back to the syngas generation system. $H_2$ in the tail gas can be purified through a pressure swing absorber and can be further used in the hydrocracking/isomerization process.

F-T fuels are typically free of sulfur and contain very few aromatics compared to gasoline and diesel, which leads to lower emissions when used in jet engines. The use of the F-T technology to convert biomass to synthetic fuels may provide a promising carbon-neutral alternative to conventional diesel, kerosene, and gasoline.

Instead of catalytically upgrading syngas to fuel, it is also possible to ferment syngas to liquid biofuels. For example, lignocellulosic biomass is converted into syngas via gasification, and the cooled syngas is then fermented to ethanol or butanol by acetagenic bacteria. The acetogenic bacteria *Clostridium* is used to consume CO and $H_2$ to produce ethanol and 2,3-butanediol. Other products such as acetate, acetone, isopropanol, and butanol can be produced by other biosynthetic pathways with different microbe strains. The mixed alcohol, ethanol, or 2,3-butanediol can be upgraded into jet fuel via previously described methods that include dehydration, oligomerization, distillation, and hydrogenation processes.

Syngas fermentation has several potential advantages over catalytic upgradation. It is able to produce more products than the traditional biochemical or thermochemical pathways and it has an overall energy efficiency of 57%. The process requires lower temperature and pressure, as well as less expensive enzymes. Gas fermentation can convert not only energy crops and typical agricultural wastes, but also municipal and industrial organic waste.

Bio-Oil to Fuel

In some embodiments, processed biomass can be converted to stable, concentrated bio-oil (biocrude) by the processes described herein. The bio-oil can be compatible with existing refinery technology as well as can be converted into advanced fuels. For example, in a hydrothermal upgrading process, biomass can be treated with water at high temperature and pressure (300-350° C. & 120-180 bar) to produce bio-oil. This can be separated by flashing or extraction to heavy crude (suitable for co-combustion in coal power stations) and light crude, which can be catalytically upgraded to fuels.

In one embodiment, bio-oil can be converted to fuel components using the following steps. Catalytic hydrogenation can be used to convert liquid-phase unsaturated fatty acids or glycerides into saturated ones with the addition of hydrogen; the glycerol portion of the triglyceride molecule is turned into propane by adding $H_2$. The next step involves cleaving the propane to form three moles of free fatty acids (FFAs).

In another embodiment, glycerides can be converted to FFAs by a process called thermal hydrolysis. Oils and fats that contain mostly triglycerides are converted into three moles of FFAs and one mole of glycerol by processing the feedstocks with three moles of water. High temperature (250-260° C.) is required for water to dissolve in the oil phase. High pressure is also necessary to maintain the reactants in liquid phase.

In another embodiment, catalytic hydro-thermolysis (CH) also named hydrothermal liquefaction is used. The hydrothermal process contains a series of reactions, including cracking, hydrolysis, decarboxylation, isomerization, and cyclization, that turn triglycerides into a mixture of straight chain, branched, and cyclic hydrocarbons. The CH reaction is conducted at temperatures from 450° C. to 475 C.° and pressures of 210 bar with water and a catalyst (or without a catalyst). The resulting products-including carboxylic acids, oxygenated species, and unsaturated molecules—are sent through decarboxylation and hydrotreating processes for saturation and oxygen removal. The treated products, ranging from 6 to 28 carbon numbers, contain n-alkanes, iso-alkanes, cyclo-alkanes, and aromatics, which require a fractionation step for separation to naphtha, jet fuel, and diesel fuel.

Alternatively, pyrolysis oil can be upgraded to hydrocarbon fuels, including jet fuel, through integrated pyrolysis and hydro-conversion. This integrated biorefinery system can combine commercial RTP (Rapid Thermal Processing) pyrolysis technology with catalytic hydroconversion. The resulting hydrocarbon components can be separated by batch vacuum distillation.

EXAMPLES

Example 1

General Method for Alumina-Based Catalyst Preparation

Stream chemical alumina (high purity γ-alumina, 150-200 m$^2$/g) was used as the support for metals (e.g., Pt, Pd, Sn, Ba, Bi) in catalyst preparation. The catalyst was prepared by an incipient wetness impregnation method. The volume of the de-ionized water used to dissolve the metal precursors was equal to the pore volume of the alumina support (0.7 cm$^3$/g). After impregnation, the catalyst samples were dried at room temperature for 3 h, and subsequently for 12 h at 110° C. in vacuum dried oven. Finally, these catalysts were calcined under air at 500° C. for 3 h.

Example 2

Preparation of Metal/ZSM-5 Catalysts

Metal (e.g., Ru, Pt and Pd)/HZSM-5 catalysts were prepared by incipient wetness impregnation method. Zeolite HZSM-5 was procured from ACS materials. The metal precursor salts used for the catalyst preparation were Ruthenium Chloride ($RuCl_6$), Hexachloroplatinic acid ($H_2PtCl_6$), Palladium (II) Chloride ($PdCl_6 \cdot XH_2O$). Predetermined amounts of metal salts dissolved in De-ionized (DI) water were added dropwise to the zeolite. After the completion of the addition of the metal salts, the metal impregnated zeolite was kept at room temperature for 3 h. Subsequently, the catalyst was dried at 110° C. for 10 h in a vacuum dried oven and calcined under air at 500° C. for 3 h.

Example 2A: 0.5% Pt/HZSM-5 Catalyst

The catalyst was prepared by incipient wetness impregnation method. About 3.3 grams of $H_2PtCl_6xH_2O$ solution (8%, Sigma Aldrich) was dissolved in 15 mL of de-ionized water. This solution was added drop-wise to the 25 grams of HZSM-5 support with proper mixing. Finally, the catalyst was dried at 110° C. for 10 h under vacuum oven and then calcined under air at 500° C. for 3 h.

Example 2B: 0.5% Pd/HZSM-5 Catalyst

The catalyst was prepared by incipient wetness impregnation method. About 0.2095 grams of $PdCl_3$ was dissolved in 15 mL of de-ionized water. This solution was added drop-wise to the 25 grams of HZSM-5 support with proper mixing. Finally, the catalyst was dried at 110° C. for 10 h under vacuum oven and then calcined under air at 500° C. for 3 h.

Example 2C: 0.5% Ru/HZSM-5 Catalyst

The catalyst was prepared by incipient wetness impregnation method. About 0.62128 grams of $RuCl_3 xH_2O$ (40-43% Ru content) was dissolved in 15 mL of de-ionized water. This solution was added drop-wise to the 25 grams of HZSM-5 support with proper mixing. Finally, the catalyst was dried at 110° C. for 10 h under vacuum oven and then calcined under air at 500° C. for 3 h.

Example 3

Preparation of Alumina Supported Catalysts

Example 3A: 0.5% Pt-0.5% Sn/$Al_2O_3$

Bimetallic Pt—Sn catalyst was prepared by a sequential incipient wetness impregnation method. The metal precursor salts used for generating this catalyst were Hexachloroplatinic acid ($H_2PtCl_6$), and Tin (II) Chloride ($SnCl_6 \cdot XH_2O$). In the first step, 0.5% Sn/$Al_2O_3$ catalyst was prepared. $SnCl_6$ (0.2436 grams) was dissolved in 17.5 ml of DI water and two drops of conc. HCl was added to dissolve the metal salt. This metal salt solution was then added dropwise to 25 grams of $Al_2O_3$ with proper mixing. After the completion of the addition, the Sn-alumina catalyst was dried at 110° C. for 10 h under vacuum oven. The catalyst was then calcined under air at 500° C. for 3 h. In the second step, the 0.5% $Sn/Al_2O_3$ catalyst was impregnated with Pt. 3.3 grams of $H_2PtCl_6.xH_2O$ (8% Sigma Aldrich) was dissolved in 14.2 ml of 0.2M HCl and added dropwise to the 0.5% $Sn/Al_2O_3$ catalyst. Subsequently, the catalyst was dried at 110° C. for 10 h in a vacuum oven and calcined under air at 500° C. for 3 h. This method is also used in preparation of Pt—Sn/$Al_2O_3$ catalysts containing different amounts of Pt and Sn, such as 0.1 to 20% Pt (w/w) and 0.1% to 20% Sn (w/w), and different combinations thereof.

Example 3B: 0.5% Pt-0.5%/$Al_2O_3$

Bimetallic Pt—Bi catalyst was prepared by a sequential incipient wetness impregnation method similar to the one used in preparing the Pt—Sn/$Al_2O_3$ catalyst above. Initially 0.2975 grams of $Bi(NO_3)_3.2H_2O$ was dissolved in 17.5 mL of de-ionized water. To this solution, 0.5 mL of concentrated $HNO_3$ was added to completely dissolve of the metal precursor. This solution was added drop-wise to the 25 grams of $Al_2O_3$ support with proper mixing. After that, the 0.5% $Bi/Al_2O_3$ catalyst was dried at room temperature for 3 h then dried at 110° C. for 10 h under vacuum oven, and subsequently, calcined under air at 500° C. for 3 h. Then, 3.3 grams of $H_2PtCl_6xH_2O$ solution (8%, Sigma Aldrich) was dissolved in 14.2 mL, to which 0.2M HCl was added. This solution was added drop-wise to the 25 grams of 0.5% $Bi/Al_2O_3$ catalyst with proper mixing. Finally, the catalyst was dried at 110° C. for 10 h under vacuum oven and then calcined under air at 500° C. for 3 h. This method is also used in preparation of Pt—Bi/$Al_2O_3$ catalysts containing different amounts of Pt and Bi, such as 0.1 to 20% Pt (w/w) and 0.1% to 20% Bi (w/w), and different combinations thereof.

Example 3C: 0.5% Pt-0.5% Ba/$Al_2O_3$

Bimetallic Pt—Ba catalyst was prepared by a sequential incipient wetness impregnation method similar to the one used in preparing the Pt—Sn/$Al_2O_3$ catalyst above. Initially, 0.1846 grams of $Ba(NO_3)_2$(99.5%) was dissolved in 17.5 mL of de-ionized water, and this solution was added drop-wise to the 25 grams of $Al_2O_3$ support with proper mixing. After that, the 0.5% $Ba/Al_2O_3$ catalyst was dried at room temperature for 3 h then dried at 110° C. for 10 h under vacuum oven, and subsequently calcined under air at 500° C. for 3 h. Then, 3.3 grams of $H_2PtCl_6xH_2O$ solution (8%, Sigma Aldrich) was dissolved in 14.2 mL, to which 0.2M HCl was added. This solution was added drop-wise to the 25 grams of 0.5% $Ba/Al_2O_3$ catalyst with proper mixing. Finally, the catalyst was dried at 110° C. for 10 h under vacuum oven and then calcined under air at 500° C. for 3 h. This method is also used in preparation of Pt—Ba/$Al_2O_3$ catalysts containing different amounts of Pt and Ba, such as 0.1 to 20% Pt (w/w) and 0.1% to 20% Ba (w/w), and different combinations thereof.

Example 3D: 0.5% Pt-0.5% Sn-0.5% Re/$Al_2O_3$

Trimetallic Pt—Sn—Re catalyst was prepared by sequential incipient wetness impregnation method. Initially, 0.2975 g ammonium perrhenate ($NH_4ReO_4$) was dissolved in 17.5 mL of de-ionized water, and this solution was added drop-wise to the 25 grams of $Al_2O_3$ support with proper mixing. After that, the catalyst at room temperature for 3 h then dried at 110° C. for 10 h under vacuum oven to produce the 0.5% Re/$Al_2O_3$ catalyst. Then, 0.2436 grams of $SnCl_2.2H_2O$ was dissolved in 17.5 mL of de-ionized water, and two drops of concentrated HCl was added to this solution to completely dissolve the metal precursor. This solution was then added drop-wise to the 25 grams of 0.5% Re/$Al_2O_3$ catalyst with proper mixing. After that, the catalyst was dried at room temperature for 3 h then dried at 110° C. for 10 h under vacuum oven. Subsequently, the catalyst calcined under air at 500° C. for 3 h. In the next step, 3.3 grams of $H_2PtCl_6xH_2O$ solution (8%, Sigma Aldrich) was dissolved in 14.2 mL of 0.2M HCl. This solution was then added drop-wise to the 25 grams of 0.5% Re/0.5% Sn/$Al_2O_3$ catalyst with proper mixing. Finally, the catalyst was dried at 110° C. for 10 h under vacuum oven and then calcined under air at 500° C. for 3 h. This method is also used in preparation of Pt—Sn—Re/$Al_2O_3$ catalysts containing different amounts of Pt, Sn, and Re, such as 0.1 to 20% Pt (w/w), 0.1% to 20% Sn (w/w), 0.1% to 20% Re (w/w), and different combinations thereof.

Example 3E: 0.5% Pt-0.5% Sn-0.5% Bi/$Al_2O_3$

Trimetallic Pt—Sn—Bi catalyst was prepared by sequential incipient wetness impregnation method. Initially 0.2975 grams of $Bi(NO_3)_3.2H_2O$ was dissolved in 17.5 mL of de-ionized water, and 0.5 mL of concentrated $HNO_3$ was added to the above solution to completely dissolve the metal precursor. This solution was then added drop-wise to the 25 grams of $Al_2O_3$ support with proper mixing. After that, the catalyst was dried at 110° C. for 10 h under vacuum oven and then calcined under air at 500° C. for 3 h. Then, 0.2436 grams of $SnCl_2.2H_2O$ was dissolved in 17.5 mL of de-ionized water. Two drops of concentrated HCl was added to the above solution to completely dissolve the metal precursor, and the solution was then added drop-wise to the 25 grams of 0.5% $Bi/Al_2O_3$ catalyst with proper mixing. After that, the catalyst was dried at 110° C. for 10 h under vacuum oven and then calcined under air at 500° C. for 3 h. In the next step, 3.3 grams of $H_2PtCl_6xH_2O$ solution (8%, Sigma Aldrich) was dissolved in 14.2 mL of 0.2M HCl. This solution was added drop-wise to the 25 grams of 0.5% Sn/0.5% $Bi/Al_2O_3$ catalyst with proper mixing. The catalyst was then dried at 110° C. for 10 h under vacuum oven and calcined under air at 500° C. for 3 h. This method is also used in preparation of Pt—Sn—Bi/$Al_2O_3$ catalysts containing different amounts of Pt, Sn, and Bi, such as 0.1 to 20% Pt (w/w), 0.1% to 20% Sn (w/w), 0.1% to 20% Bi (w/w), and different combinations thereof.

Example 3F: 0.5% Pt-0.5% Sn-0.5% Ba/$Al_2O_3$

Trimetallic Pt—Sn—Ba catalyst was prepared by sequential incipient wetness impregnation method. Initially, 0.1846 grams of $Ba(NO_3)_2$(99.5%) was dissolved in 17.5 mL of de-ionized water, and this solution was added drop-wise to the 25 grams of $Al_2O_3$ support with proper mixing. After that, the catalyst was dried at 110° C. for 10 h under vacuum oven and then calcined under air at 500° C. for 3 h to produce 0.5% $Ba/Al_2O_3$ catalyst. Then 0.2436 grams of $SnCl_2.2H_2O$ was dissolved in 17.5 mL of de-ionized water. Two drops of concentrated HCl was added to this solution to completely dissolve the metal precursor. This solution was added drop-wise to the 25 grams of 0.5% $Ba/Al_2O_3$ catalyst with proper mixing. After that, the catalyst was dried at 110° C. for 10 h under vacuum oven and then calcined under air at 500° C. for 3 h. In the next step, 3.3 grams of $H_2PtCl_6xH_2O$ solution (8%, Sigma Aldrich) was dissolved in 14.2 mL of 0.2M HCl was added. This solution was added drop-wise to the 25 grams of 0.5% Sn/0.5% Ba/$Al_2O_3$ catalyst with proper mixing. Finally, the catalyst was dried at 110° C. for 10 h under vacuum oven and then calcined under air at 500° C. for 3 h. This method is also used in preparation of Pt—Sn—Ba/$Al_2O_3$ catalysts containing different amounts of Pt, Sn, and Ba, such as 0.1 to 20% Pt (w/w), 0.1% to 20% Sn (w/w), 0.1% to 20% Ba (w/w), and different combinations thereof.

Example 4: Preparation of Acid-Treated Alumina Catalysts

Example 4A: 0.5% Pt/$H_3PO_4$—$Al_2O_3$Catalyst

In the first step, $Al_2O_3$ support was pretreated with X % $H_3PO_4$ (e.g., X=2.5%, 5% and 10%) solution prepared from 85% Phosphoric acid ($H_3PO_4$) solution. The required amount of 85% $H_3PO_4$ was dissolved in appropriate amount of water and added dropwise to 25 grams of $Al_2O_3$ support with proper mixing. After the addition was completed, the $H_3PO_4$ treated $Al_2O_3$ support was kept at room temperature for 3 h. Then, the $H_3PO_4$—$Al_2O_3$ catalyst was dried at 110° C. for 10 h in a vacuum oven and calcined under air at 500° C. for 3 h. In the second step, incipient wetness impregnation method used for the preparation of Pt-modified catalyst. In the next step, 3.3 grams of $H_2PtCl_6xH_2O$ solution (8%, Sigma Aldrich) was dissolved in 14.2 mL of 0.2M HCl, and this solution was added drop-wise to the 25 grams of X % $H_3PO_4$—$Al_2O_3$ catalyst with proper mixing. After the addition was completed, the catalyst was dried at 110° C. for 10 h in vacuum oven and calcined under air at 500° C. for 3 h. This method was used to prepare 0.5% Pt/2.5% $H_3PO_4$—$Al_2O_3$, 0.5% Pt/5% $H_3PO_4$—$Al_2O_3$ and 0.5% Pt/10% $H_3PO_4$—$Al_2O_3$ catalysts. This method is also used in preparation of Pt/$H_3PO_4$—$Al_2O_3$ catalysts containing different amounts of Pt, and $H_3PO_4$ such as 0.1 to 20% Pt (w/w), 0.1% to 20% $H_3PO_4$ (w/w), and different combinations thereof.

Example 4B: 0.5% Pt/$H_3BO_3$—$Al_2O_3$Catalyst

In the first step, $Al_2O_3$ support was pretreated 5% $H_3BO_3$ using Boric acid ($H_3BO_3$) solution. The 2.6368 grams of $H_3BO_3$ was dissolved in 34 mL of water and then added drop-wise to the 25 grams of $Al_2O_3$ support with proper mixing. After the addition was completed, the $H_3BO_3$ treated $Al_2O_3$ support was kept at room temperature for 3 h. Then, the $H_3BO_3$—$Al_2O_3$ catalyst was dried at 110° C. for 10 h in a vacuum oven and calcined under air at 500° C. for 3 h. In the second step, incipient wetness impregnation method used for the preparation of Pt-modified catalyst. 3.3 grams of $H_2PtCl_6xH_2O$ solution (8%, Sigma Aldrich) was dissolved in 14.2 mL of 0.2M HCl and this solution was added drop-wise to the 25 grams of 5% $H_3BO_3$—$Al_2O_3$ catalyst with proper mixing After the addition was completed, the catalyst was dried at 110° C. for 10 h in vacuum oven and calcined under air at 500° C. for 3 h. This method was used to prepare 0.5% Pt/5% $H_3BO_3$—$Al_2O_3$ catalyst. This method is also used in preparation of Pt/$H_3BO_3$—$Al_2O_3$ catalysts containing different amounts of Pt, and $H_3BO_3$ such as 0.1 to 20% Pt (w/w), 0.1% to 20% $H_3BO_3$ (w/w), and different combinations thereof.

Example 5

General Reaction Conditions for Catalytic Conversion of Ethanol to Hydrocarbons

The general reaction conditions under which the feedstock containing ethanol can be converted to hydrocarbons in a catalytic reactor involves a temperature in the range of 300-400° C., pressure in the range of 20-50 atm, gas flow (e.g., $N_2$) at the rate of 1.5-6 and Liquid Hourly Space Velocity (LHSV) of 2-4 $h^{-1}$. The specific catalyst compositions, and reaction conditions are recited in the descriptions of the FIGS. 18A-23C, with corresponding product distribution shown in the respective figures. A detailed compound composition breakdown is provided for each product. Because of a slight compound characterization variation, the complete hydrocarbon report for some products displays minor differences in composition percentages.

Example 5A: Catalytic Conversion with HZSM-5

Figure 18A:
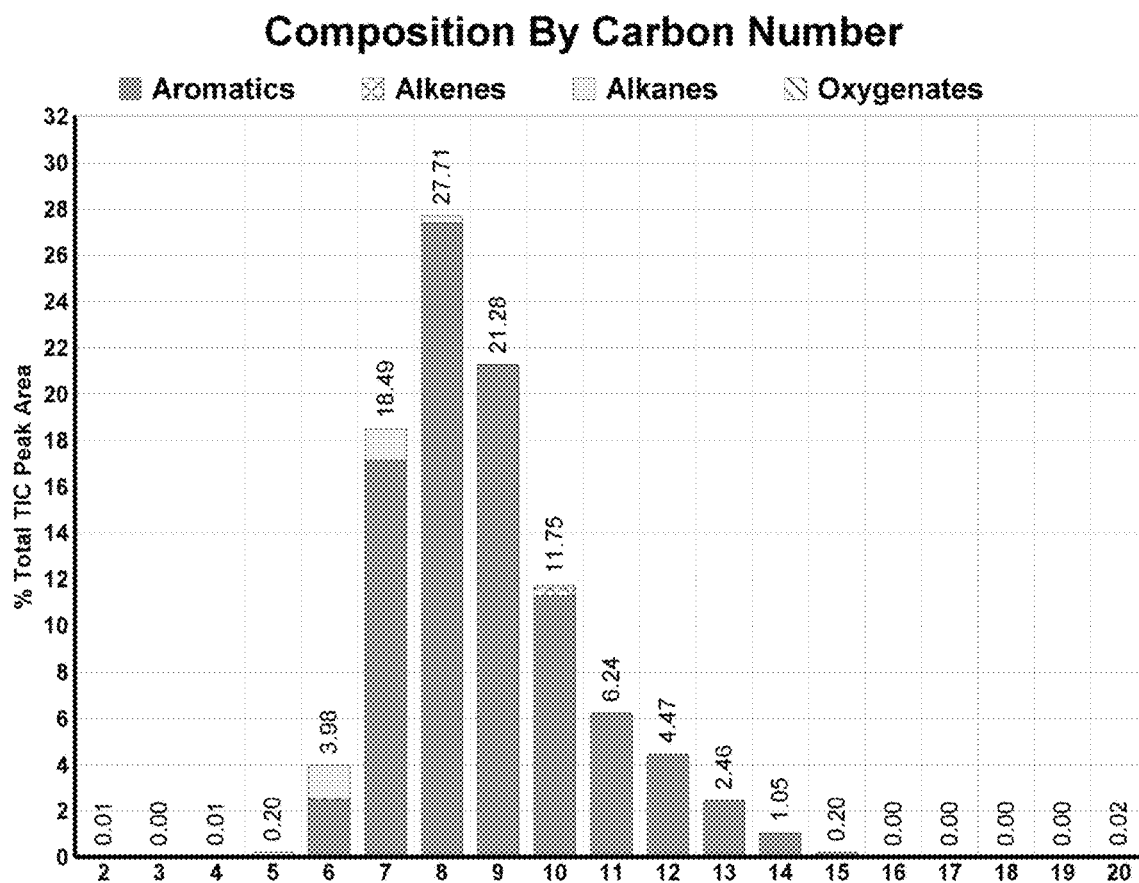
Figures 2, 18A:
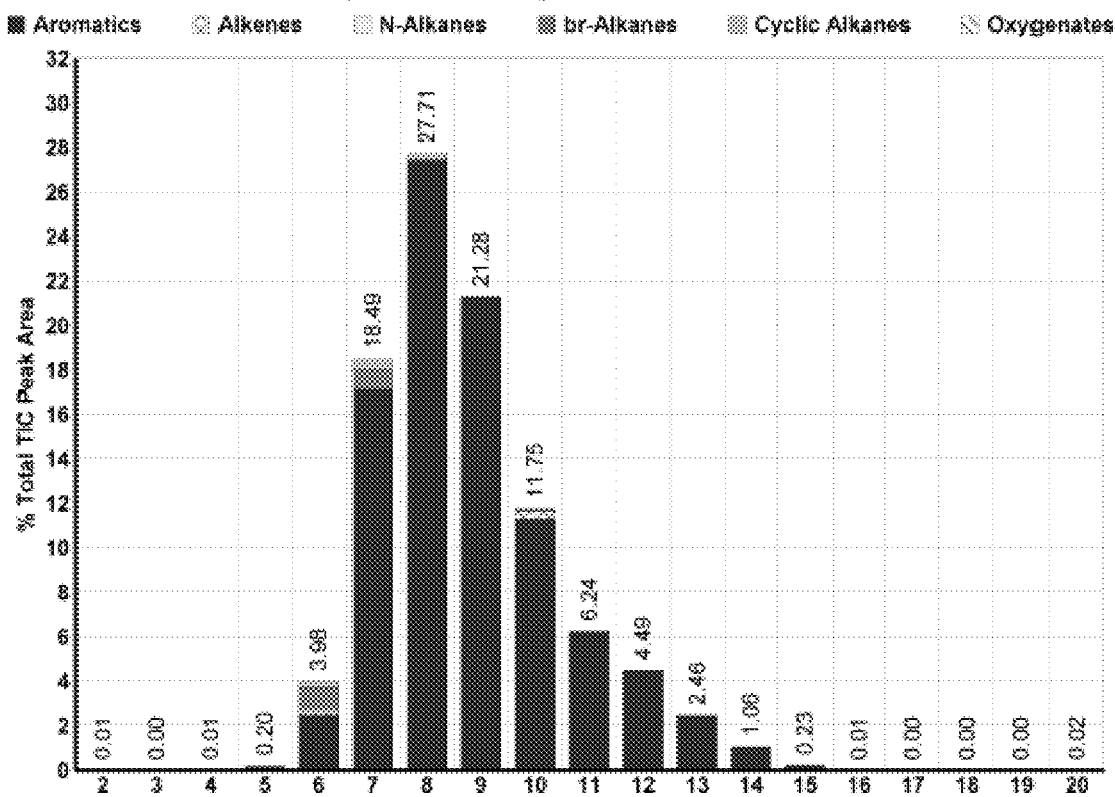
Figure 18B:
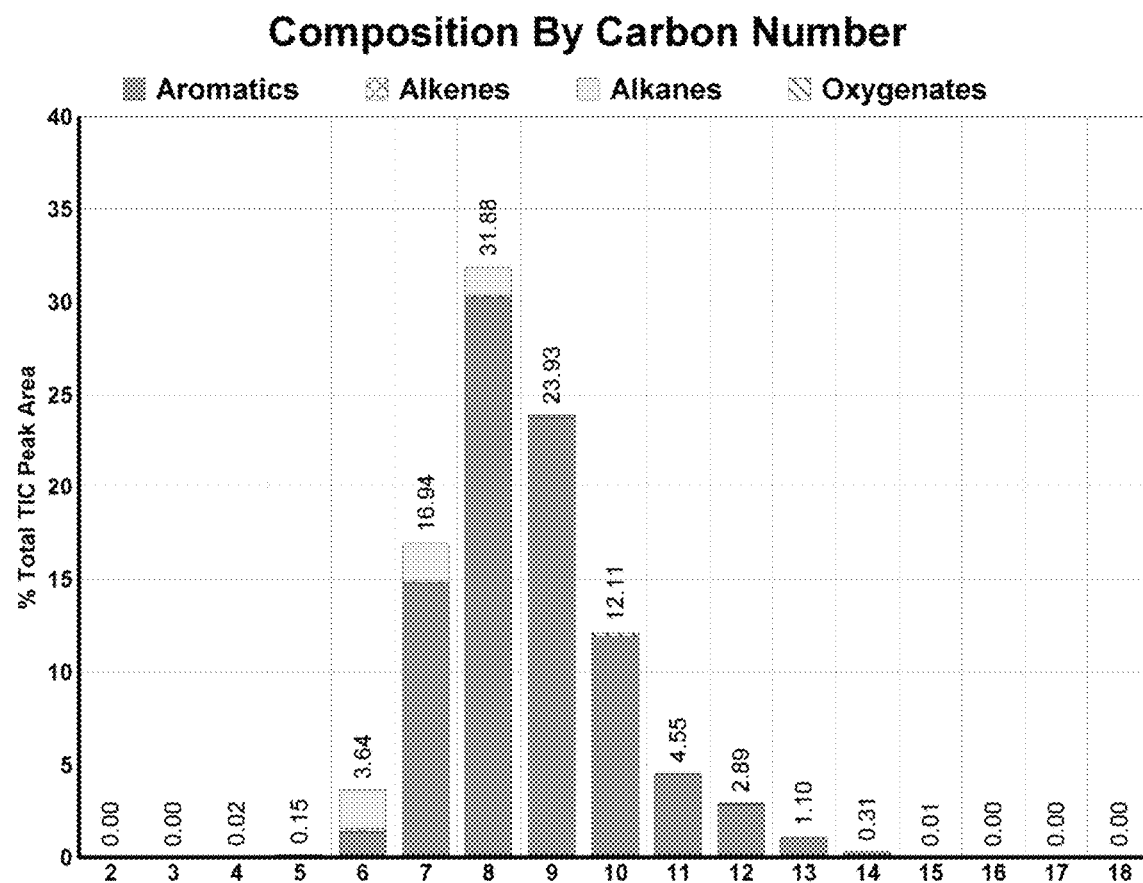
Figure 18C:
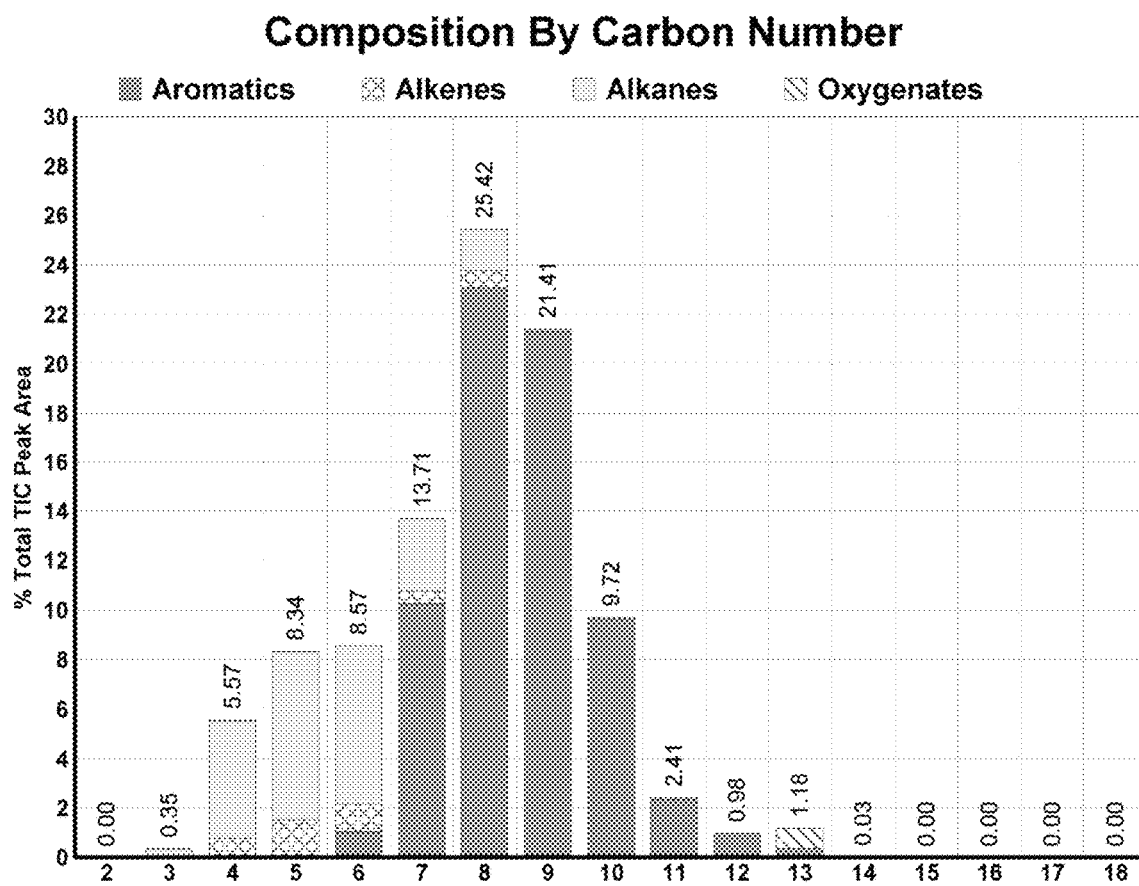
Figures 2, 18C:
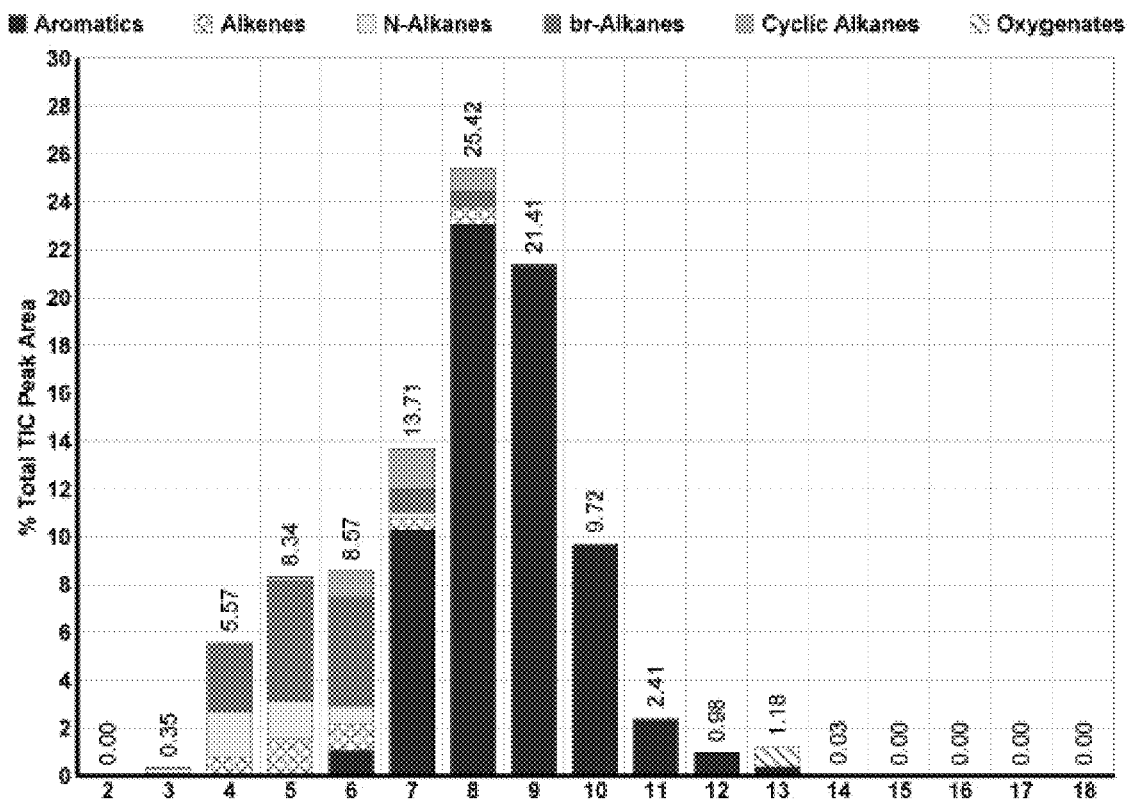

The biomass-derived ethanol was converted to hydrocarbons in the presence of 2.3 g of HZSM-5 catalyst, at a temperature of 350° C., pressure of 500 psig and volumetric linear flow rate (LFR) of 0.125 mL/min. The process was carried out in a 3.7 $cm^3$ reactor. FIG. 18A provides a graphical description of the product distribution of aromatics, alkenes, alkanes and oxygenates of various carbon content in the hydrocarbon mixture generated by this process. The graph shows the percentage amounts (vertical axis) of aromatics, alkenes, alkanes and of oxygenates containing C2-C18 hydrocarbons (horizontal axis) formed by the catalytic conversion of ethanol. For example, the HZSM-5 catalyzed reaction produced hydrocarbons of average carbon number 8.76, containing about 94.02% aromatics, 0.44% alkenes, 3.38% alkanes and 0.03% oxygenates, as determined by total ion chromatography peak area. FIG. 18A-2 provides a complete hydrocarbon report of the product described in FIG. 18A including a detailed breakdown of all the compound types. FIG. 18B provides a graphical description of the product distribution of aromatics, alkenes, alkanes and oxygenates of various carbon content in the hydrocarbon mixture generated by the catalytic processing of biomass-derived ethanol when the biomass-derived ethanol is converted to hydrocarbons in the presence of 0.5% Ru/HZSM-5 catalyst, at a temperature of 350° C., pressure of 500 psig and volumetric linear flow rate (LFR) of 0.125 mL/min. The resulting hydrocarbons had an average carbon number of 8.57 and contained about 91.13% of aromatics, 0.47% of alkenes, 5.87% of alkanes and 0.03% of oxygenates, as determined by total ion chromatography peak area. FIG. 18B-2 provides a complete hydrocarbon report of the product described in FIG. 18B including a detailed breakdown of all the compound types. FIGS. 18C and 18C-2 provide a graphical description of the product distribution when the same reaction is run at a volumetric linear flow rate (LFR) of 0.1875 mL/min. The resulting hydrocarbons had an average carbon number of 7.78 and contained about 69.08% of aromatics, 4.73% of alkenes, 22.94% of alkanes and 0.97% of oxygenates, as determined by total ion chromatography peak area. FIG. 18C-2 provides a complete hydrocarbon report of the product described in FIG. 18C including a detailed breakdown of all the compound types.

Example 5B: Catalytic Conversion with 0.5% Pt-0.5% Sn/$Al_2O_3$

Figure 19A:
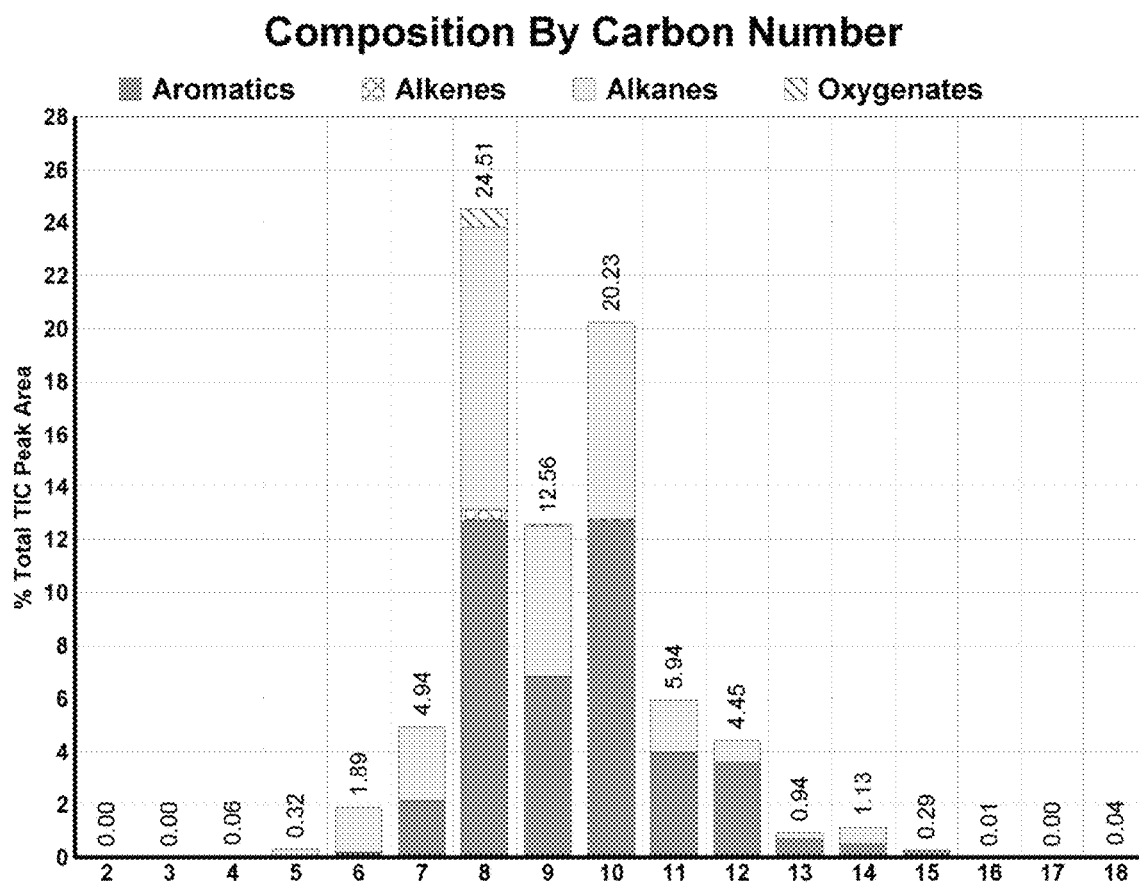
Figures 2, 19A:
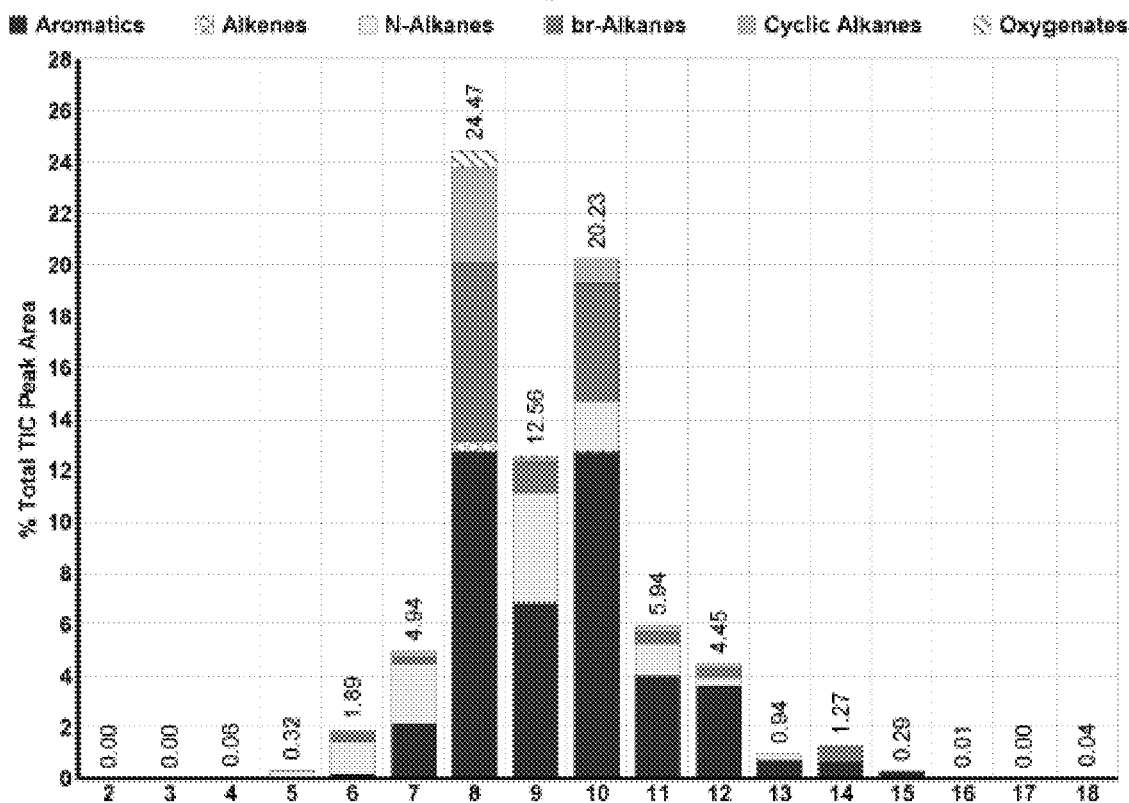
Figure 19B:
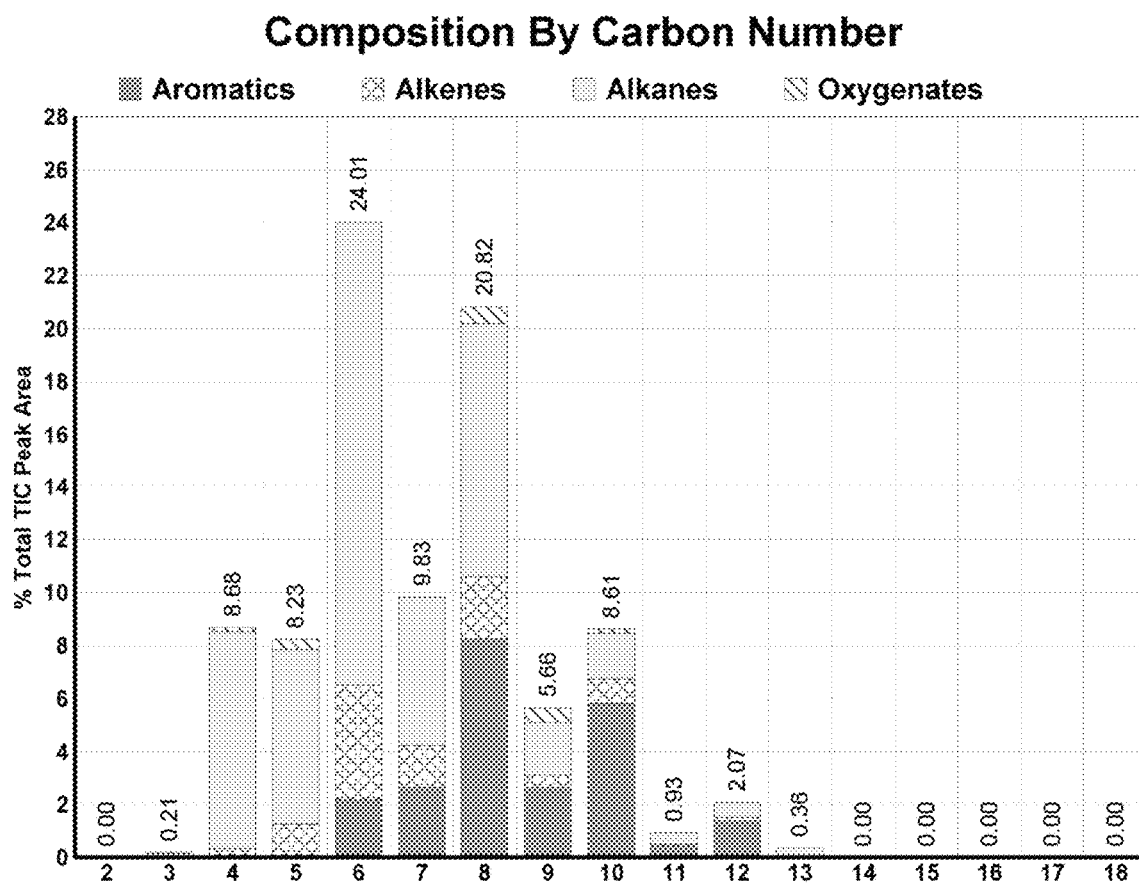
Figures 2, 19B:
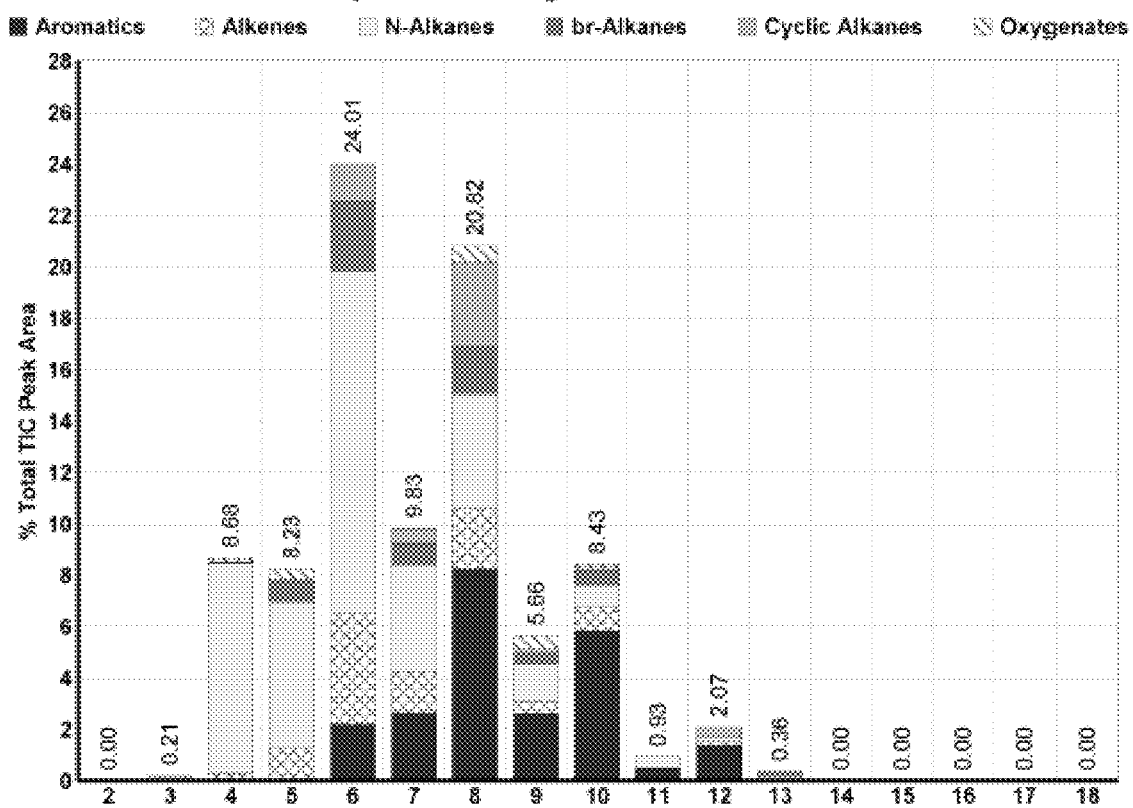

Biomass-derived ethanol was converted to hydrocarbons in the presence of 2.3 g of 0.5% Pt-0.5% Sn/$Al_2O_3$, at a temperature of 350° C., pressure of 500 psig and volumetric linear flow rate (LFR) of 0.125 mL/min. The process was carried out in a 3.7 cm³ reactor. FIG. 19A provides a graphical description of the product distribution of aromatics, alkenes, alkanes and oxygenates of various carbon content in the hydrocarbon mixture generated by this process. The graph shows the percentage amounts (vertical axis) of aromatics, alkenes, alkanes and of oxygenates containing C2-C18 hydrocarbons (horizontal axis) formed by the catalytic conversion of ethanol. For example, the 0.5% Pt-0.5% Sn/$Al_2O_3$ catalyzed reaction produced hydrocarbons of average carbon number 9.2, containing about 44.16% aromatics, 0.51% alkenes, 32.32% alkanes and 0.3% oxygenates, as determined by total ion chromatography peak area. FIG. 19A-2 provides a complete hydrocarbon report of the product described in FIG. 19A including a detailed breakdown of all the compound types. FIG. 19B provides a graphical description of the product distribution when the same reaction was run at a volumetric linear flow rate (LFR) of 0.1875 mL/min. The resulting hydrocarbons had an average carbon number of 7.11 and contained about 25.59% of aromatics, 10.97% of alkenes, 53.03% of alkanes and 0.86% of oxygenates, as determined by total ion chromatography peak area. FIG. 19B-2 provides a complete hydrocarbon report of the product described in FIG. 19B including a detailed breakdown of all the compound types.

Example 5C: Catalytic Conversion with 0.5% Pt-0.5% Bi/$Al_2O_3$

Figure 20:
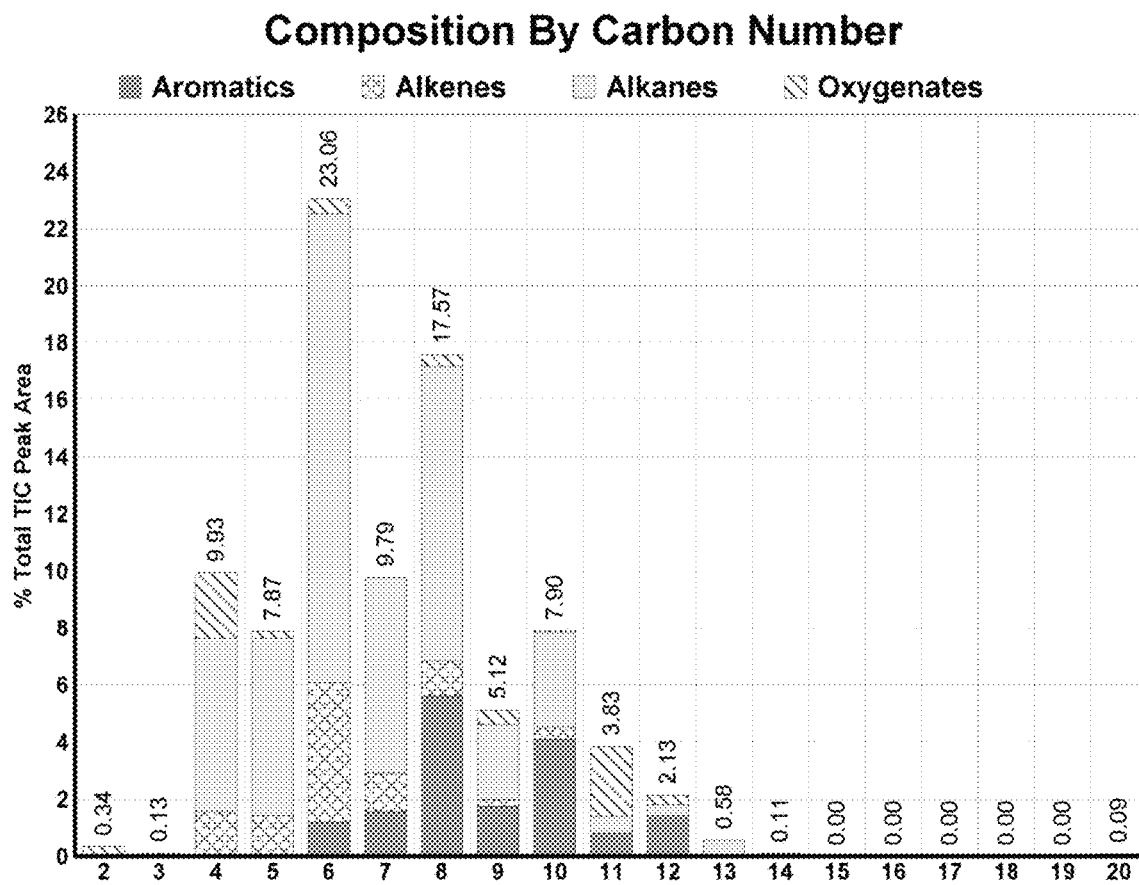

Biomass-derived ethanol was converted to hydrocarbons in the presence of 2.3 g of 0.5% Pt-0.5% Bi/$Al_2O_3$, at a temperature of 350° C., pressure of 500 psig and volumetric linear flow rate (LFR) of 0.125 mL/min. The process was carried out in a 3.7 cm³ reactor. FIG. 20 provides a graphical description of the product distribution of aromatics, alkenes, alkanes and oxygenates of various carbon content in the hydrocarbon mixture generated by this process. The graph shows the percentage amounts (vertical axis) of aromatics, alkenes, alkanes and of oxygenates containing C2-C18 hydrocarbons (horizontal axis) formed by the catalytic conversion of ethanol. For example, the 0.5% Pt-0.5% Bi/$Al_2O_3$ catalyzed reaction produced hydrocarbons of average carbon number 7.14, containing about 17.08% aromatics, 11.09% alkenes, 53.62% alkanes and 6.66% oxygenates, as determined by total ion chromatography peak area. FIG. 20A provides a complete hydrocarbon report of the product described in FIG. 20 including a detailed breakdown of all the compound types.

Figure 21A:
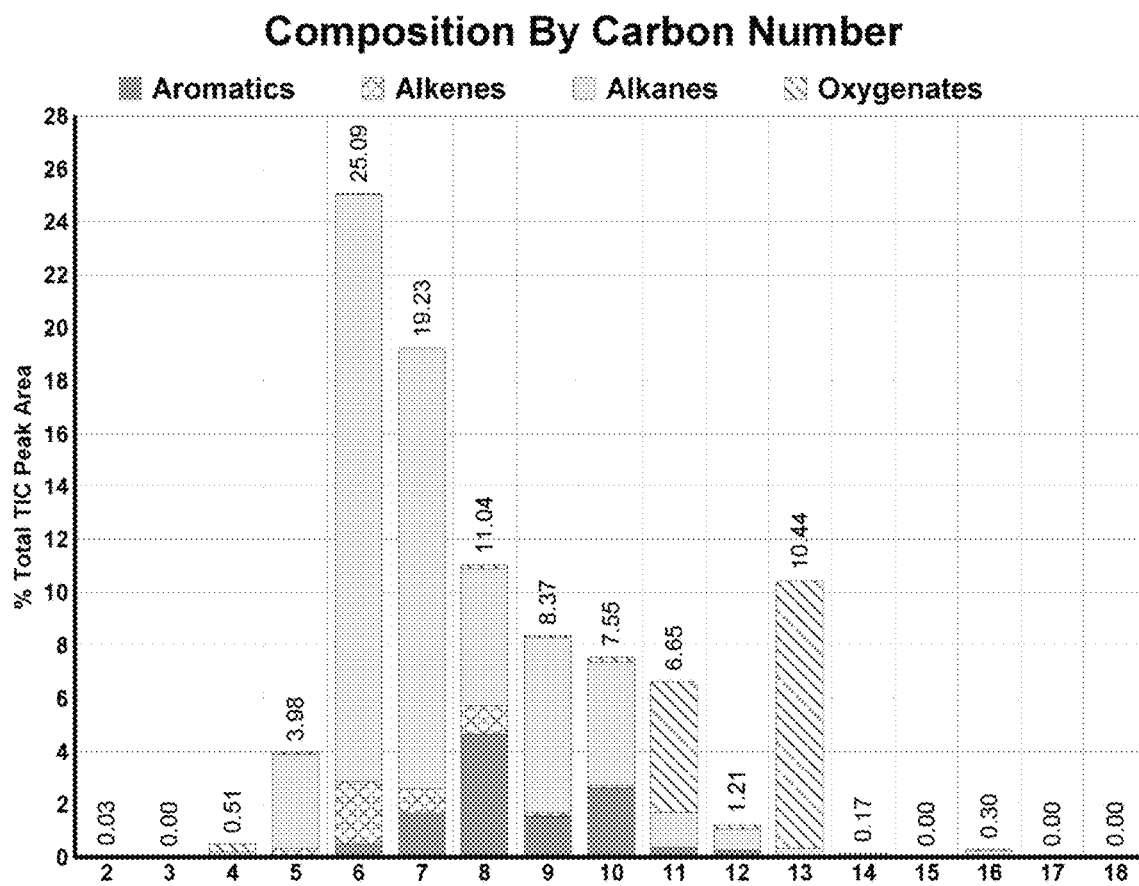
Figure 21B:
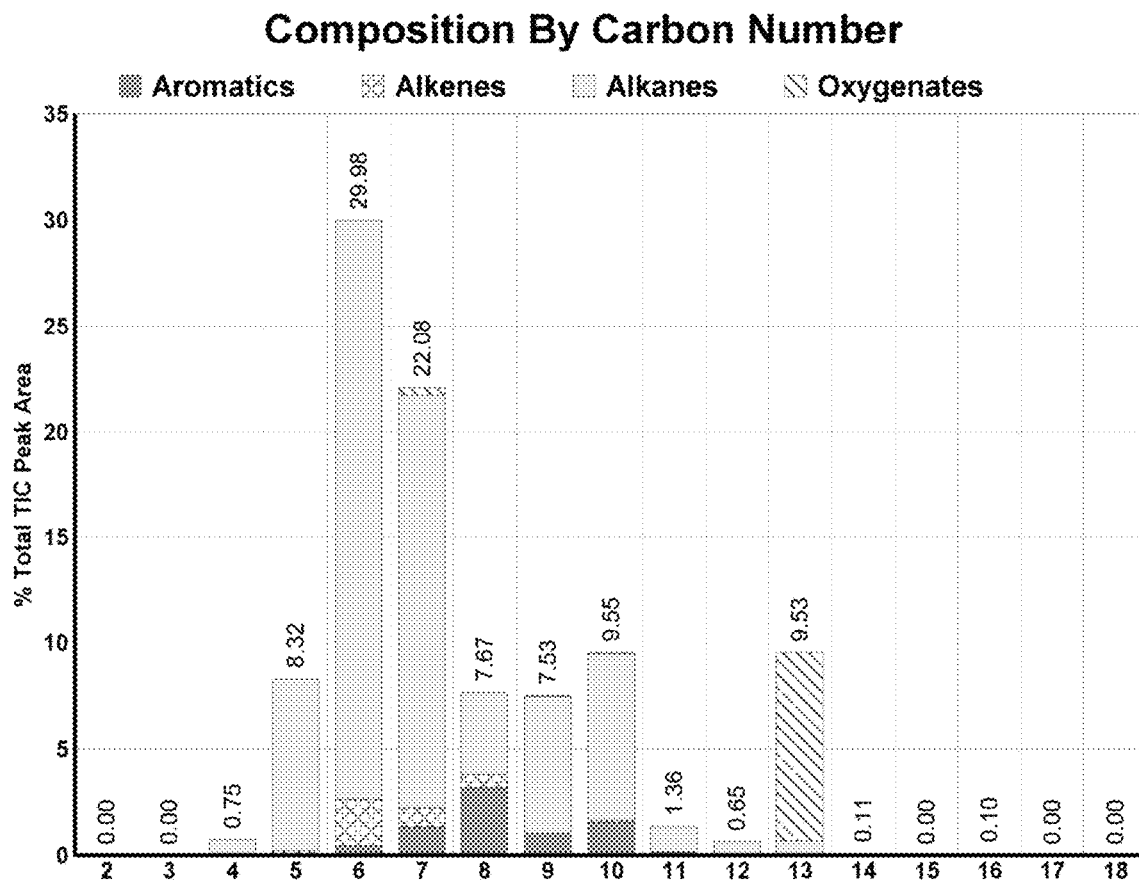
Figures 2, 21B:
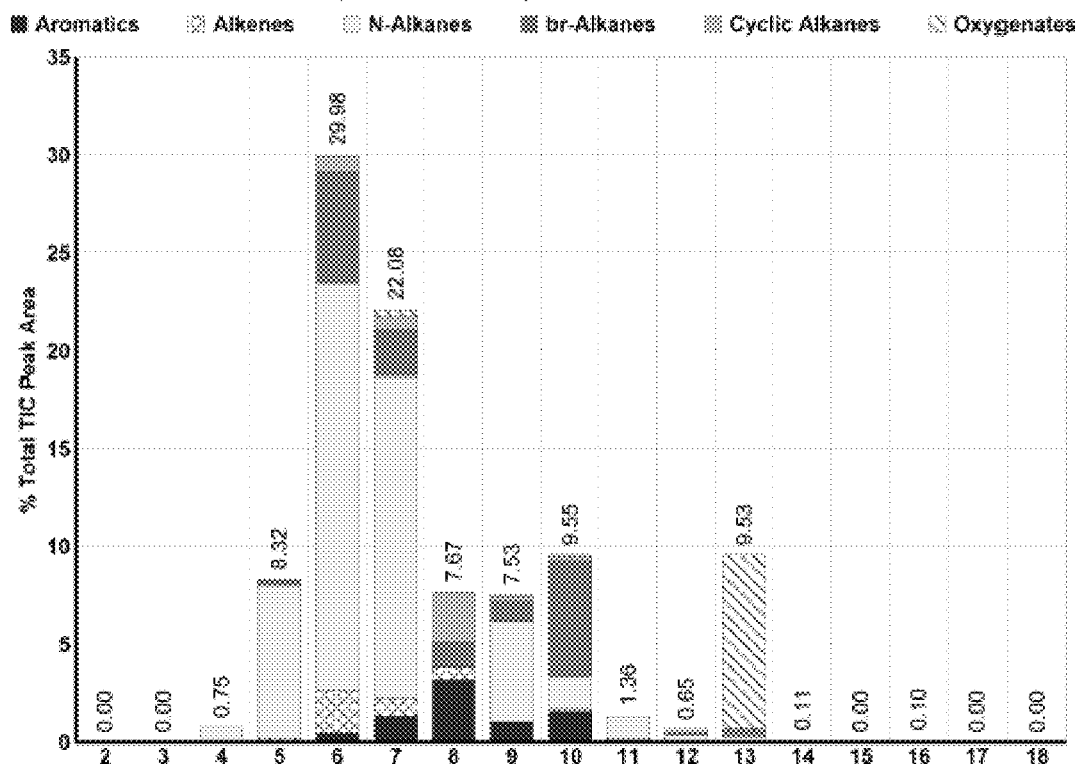

Example 5D: Catalytic Conversion with 0.5% Pt-0.75% Ba/$Al_2O_3$, and 0.5% Pt-1.0% Ba/$Al_2O_3$ Biomass-derived ethanol was converted to hydrocarbons in the presence of 2.3 g of 0.5% Pt-0.75% Ba/$Al_2O_3$, at a temperature of 350° C., pressure of 500 psig and volumetric linear flow rate (LFR) of 0.125 mL/min. The process was carried out in a 3.7 cm³ reactor. FIG. 21A provides a graphical description of the product distribution of aromatics, alkenes, alkanes and oxygenates of various carbon content in the hydrocarbon mixture generated by this process. The graph shows the percentage amounts (vertical axis) of aromatics, alkenes, alkanes and of oxygenates containing C2-C18 hydrocarbons (horizontal axis) formed by the catalytic conversion of ethanol. For example, the 0.5% Pt-0.75% Ba/$Al_2O_3$ catalyzed reaction produced hydrocarbons of average carbon number 8.22, containing about 12.01% aromatics, 4.97% alkenes, 61.88% alkanes and 15.70% oxygenates, as determined by total ion chromatography peak area. FIG. 21A-2 provides a complete hydrocarbon report of the product described in FIG. 21A including a detailed breakdown of all the compound types. FIG. 21B provides a graphical description of the product distribution when the same reaction was run with 0.5% Pt-1.0% Ba/$Al_2O_3$ catalyst. The resulting hydrocarbons had an average carbon number of 7.72 and contained about 7.87% of aromatics, 4.05% of alkenes, 76.53% of alkanes and 9.19% of oxygenates, as determined by total ion chromatography peak area. FIG. 21B-2 provides a complete hydrocarbon report of the product described in FIG. 21B including a detailed breakdown of all the compound types.

Example 5E: Catalytic Conversion with 0.5% Pt-10% $H_3PO_4$—$Al_2O_3$

Figure 22A:
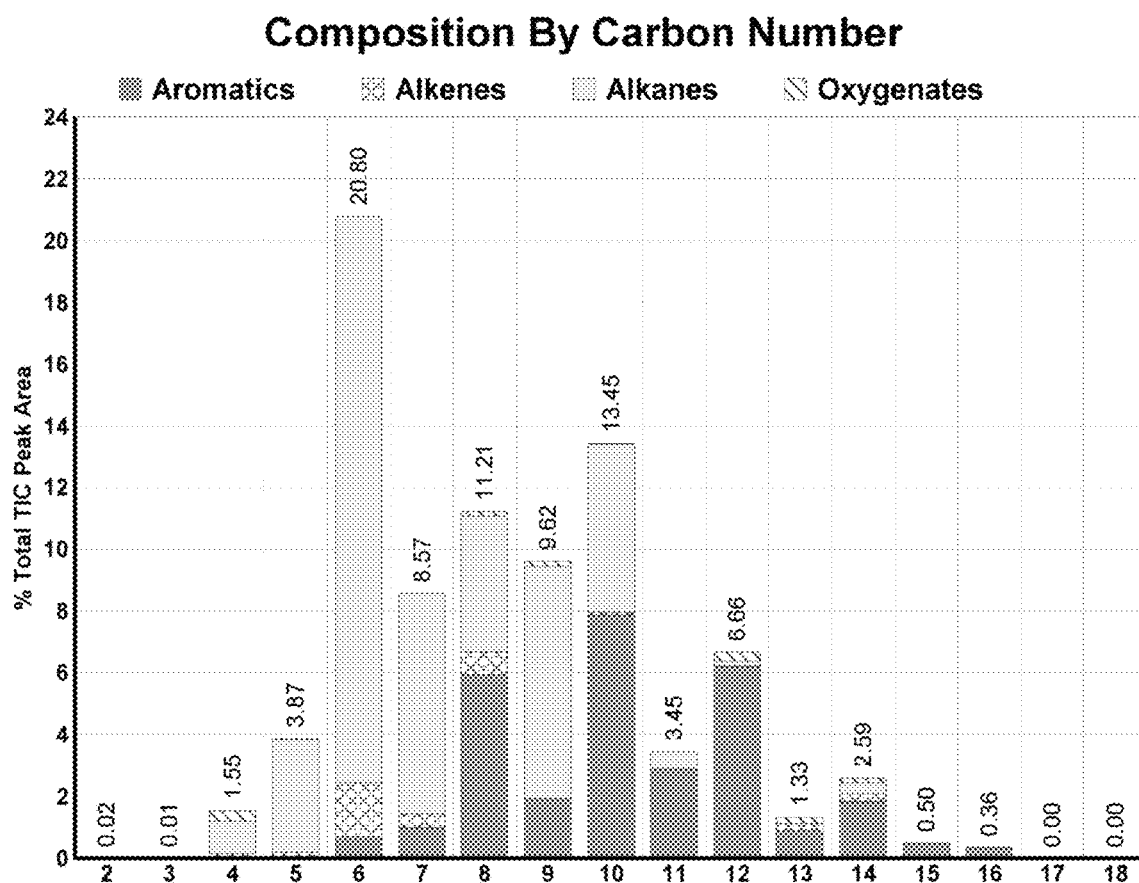
Figures 2, 22A:
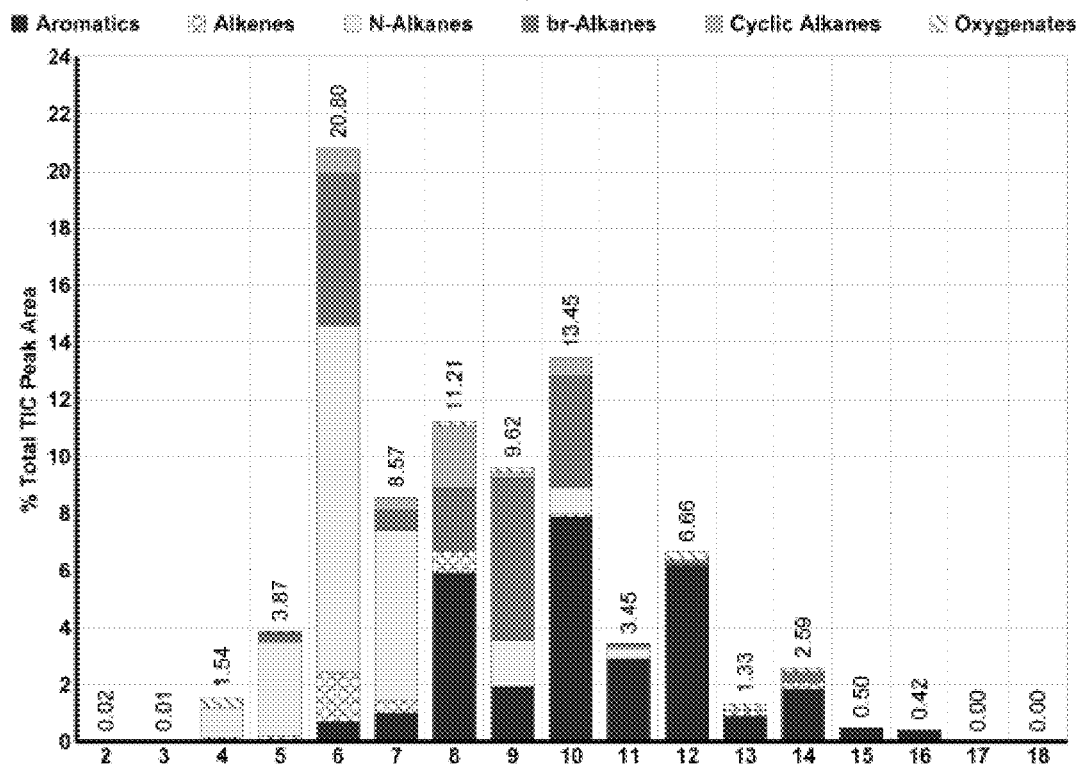
Figure 22B:
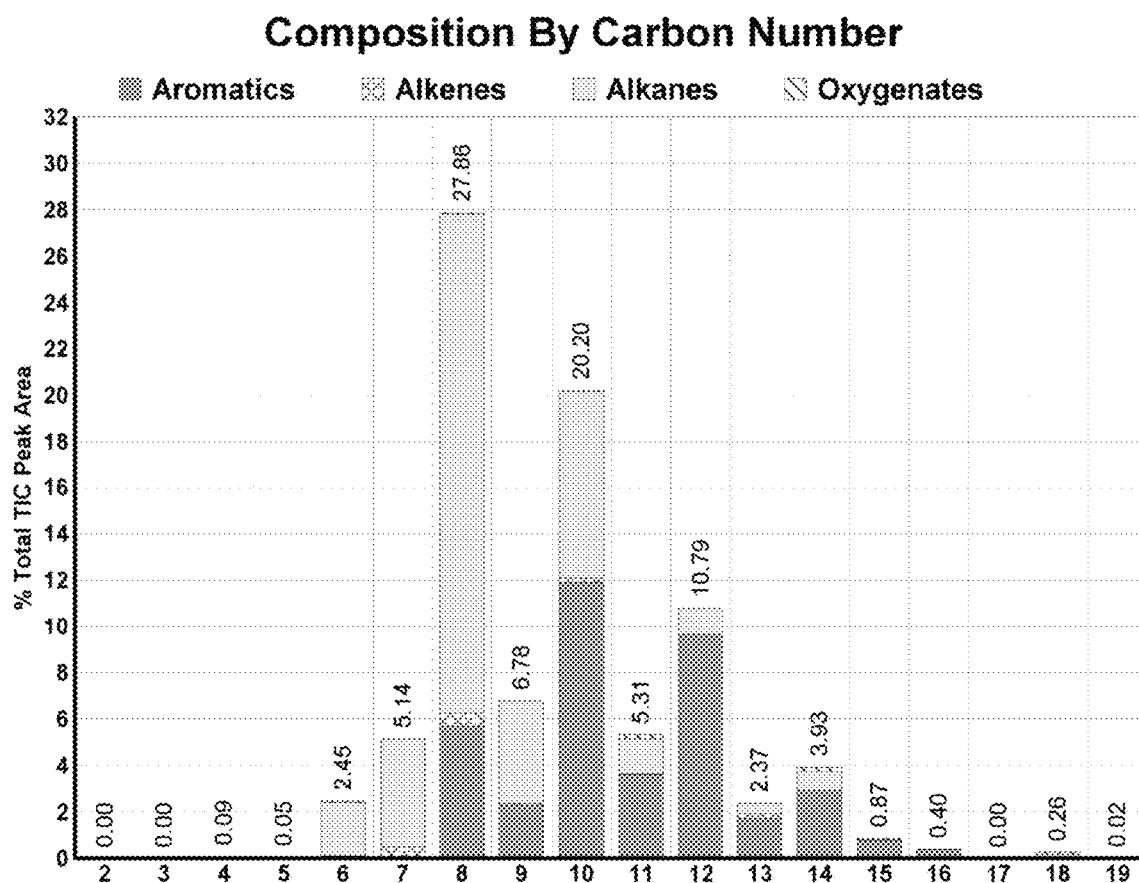
Figures 2, 22B:
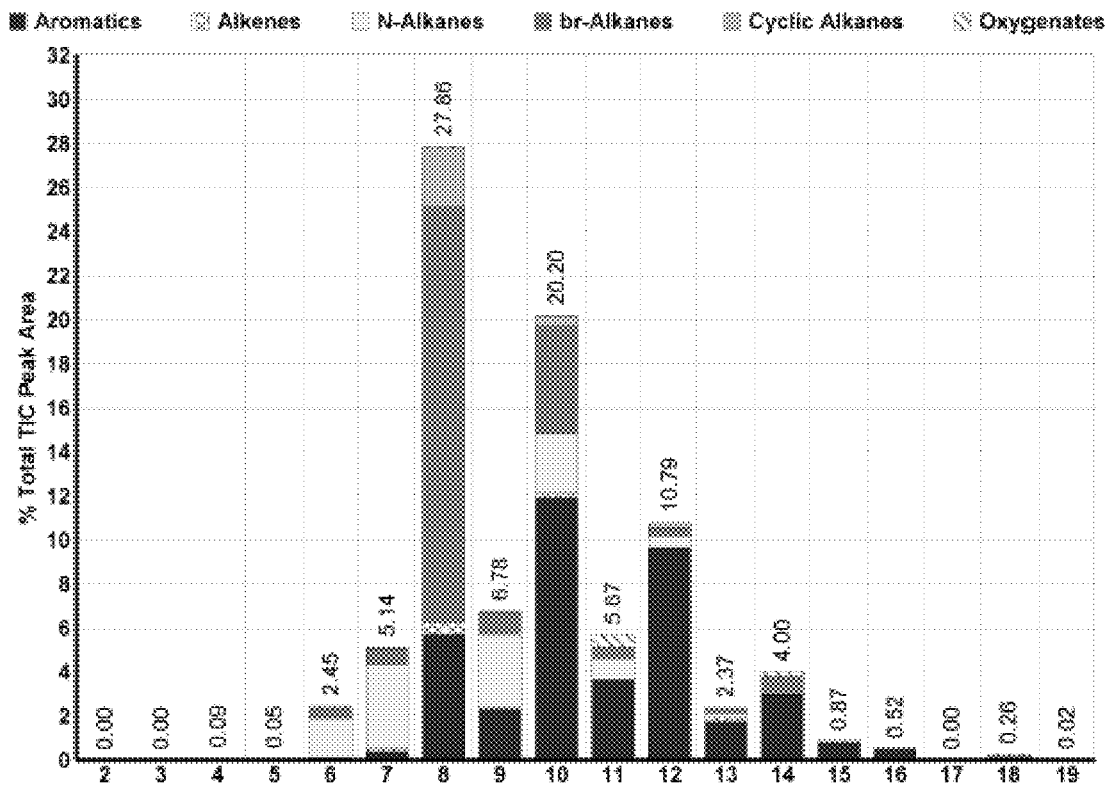
Figure 22C:
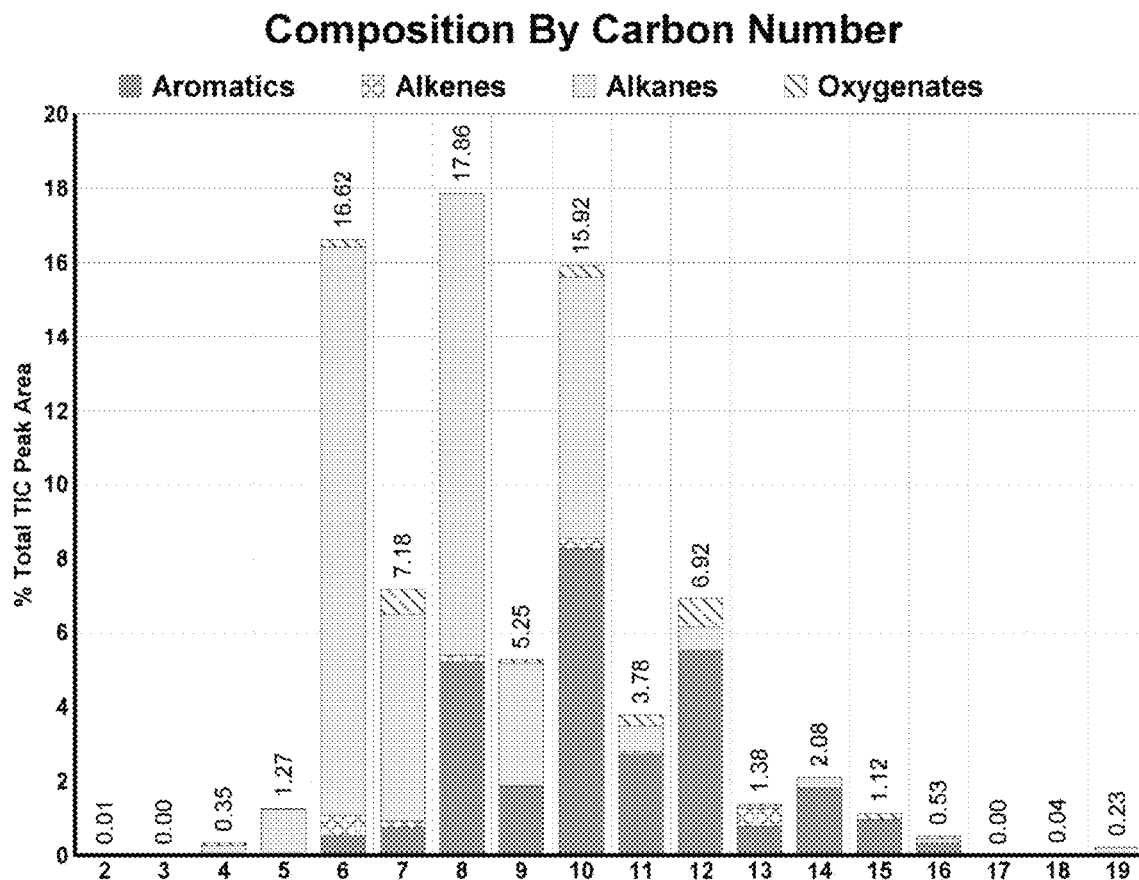
Figures 2, 22C:
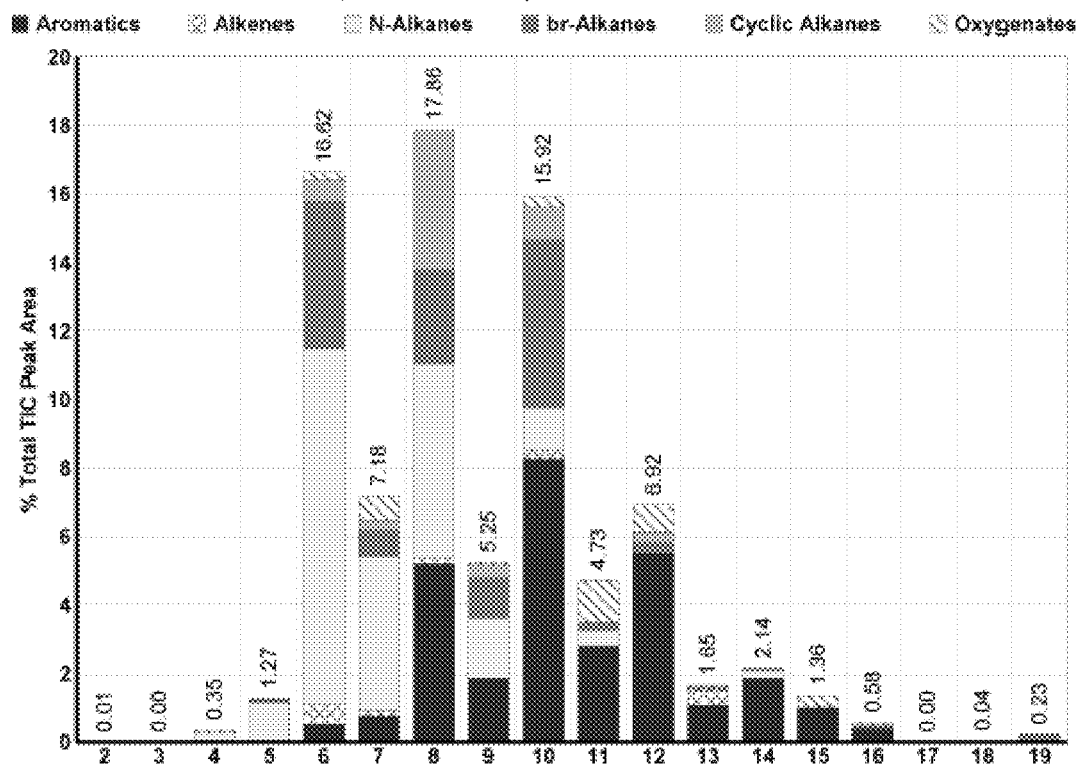

Biomass-derived ethanol is converted to hydrocarbons in the presence of 2.3 g of 0.5% Pt-10% $H_3PO_4$—$Al_2O_3$, at a temperature of 350° C., pressure of 300 psig and volumetric linear flow rate (LFR) of 0.125 mL/min. The process was carried out in a 3.7 cm³ reactor. FIG. 22A provides a graphical description of the product distribution of aromatics, alkenes, alkanes and oxygenates of various carbon content in the hydrocarbon mixture generated by this process. The graph shows the percentage amounts (vertical axis) of aromatics, alkenes, alkanes and of oxygenates containing C2-C18 hydrocarbons (horizontal axis) formed by the catalytic conversion of ethanol. For example, the 0.5% Pt-10% $H_3PO_4$—$Al_2O_3$ catalyzed reaction produced hydrocarbons of average carbon number 8.4, containing about 31.09% aromatics, 3.84% alkenes, 48.64% alkanes and 0.41% oxygenates, as determined by total ion chromatography peak area. FIG. 22A-2 provides a complete hydrocarbon report of the product described in FIG. 22A including a detailed breakdown of all the compound types. FIGS. 22B and 22B-2 provides a graphical description of the product distribution when the same reaction was run at a pressure of 500 psig. The resulting hydrocarbons had an average carbon number of 9.66 and contained about 39.53% of aromatics, 1.6% of alkenes, 45.10% of alkanes and 0.30% of oxygenates, as determined by total ion chromatography peak area. FIG. 22B-2 provides a complete hydrocarbon report of the product described in FIG. 22B including a detailed breakdown of all the compound types. FIG. 22C provides a graphical description of the product distribution when the same reaction was run at a pressure of 700 psig. The resulting hydrocarbons had an average carbon number of 8.80 and contained about 30.43% of aromatics, 1.78% of alkenes, 47.27% of alkanes and 1.04% of oxygenates, as determined by total ion chromatography peak area. FIG. 22C-2 provides a complete hydrocarbon report of the product described in FIG. 22C including a detailed breakdown of all the compound types.

Example 5F: Catalytic Conversion with 0.5% Pt/5.0% $H_3BO_3$—$Al_2O_3$

Figure 23A:
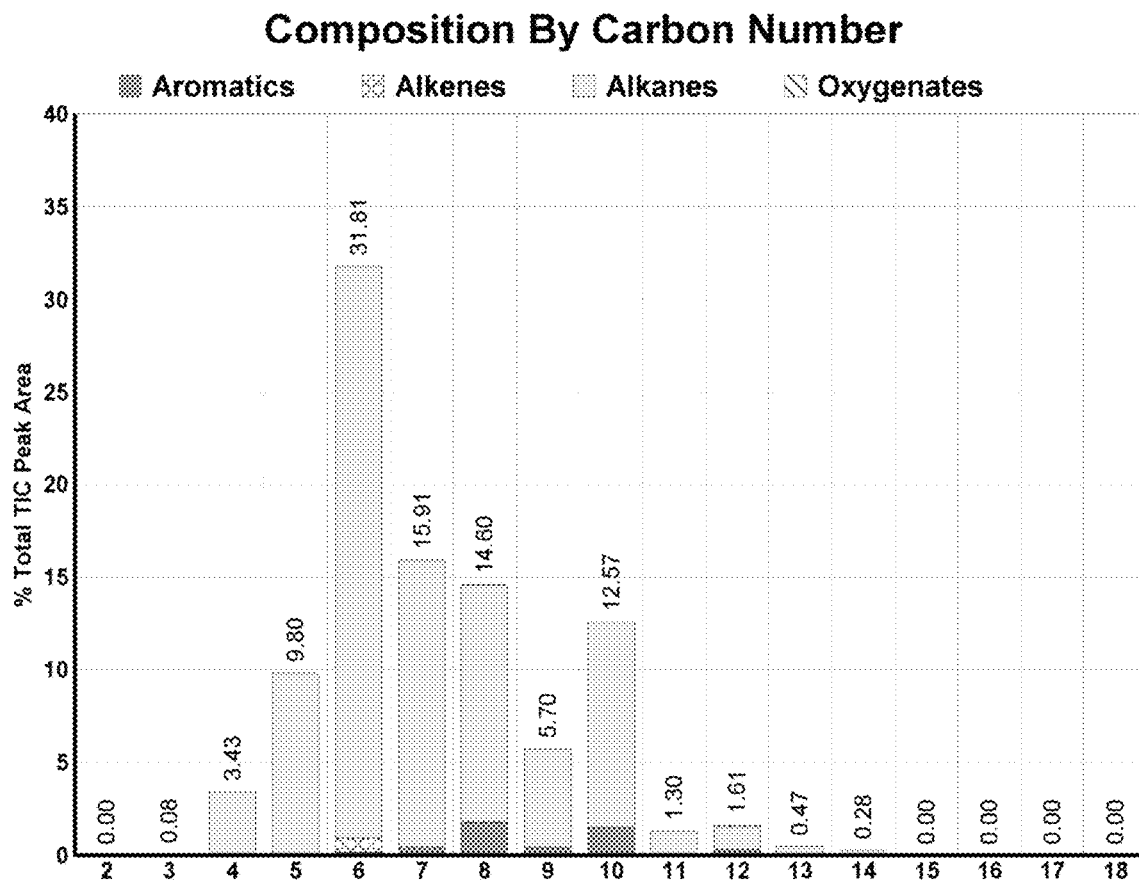
Figures 2, 23A:
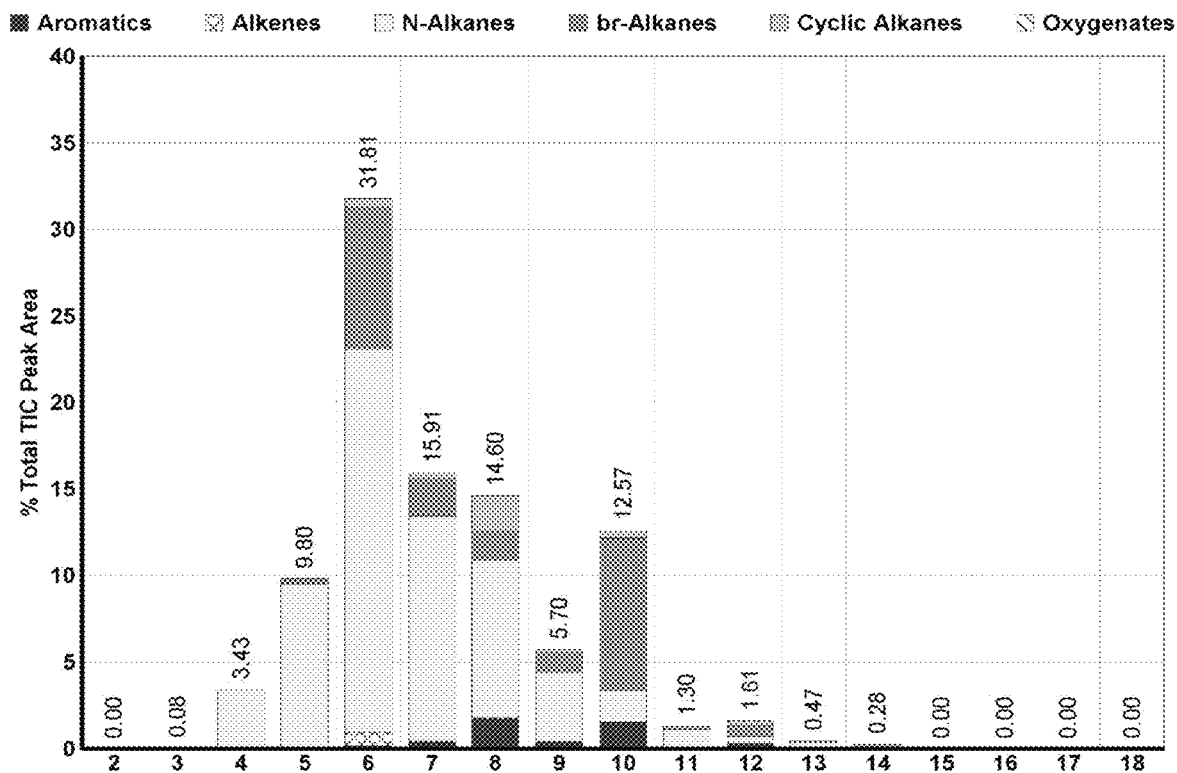
Figure 23B:
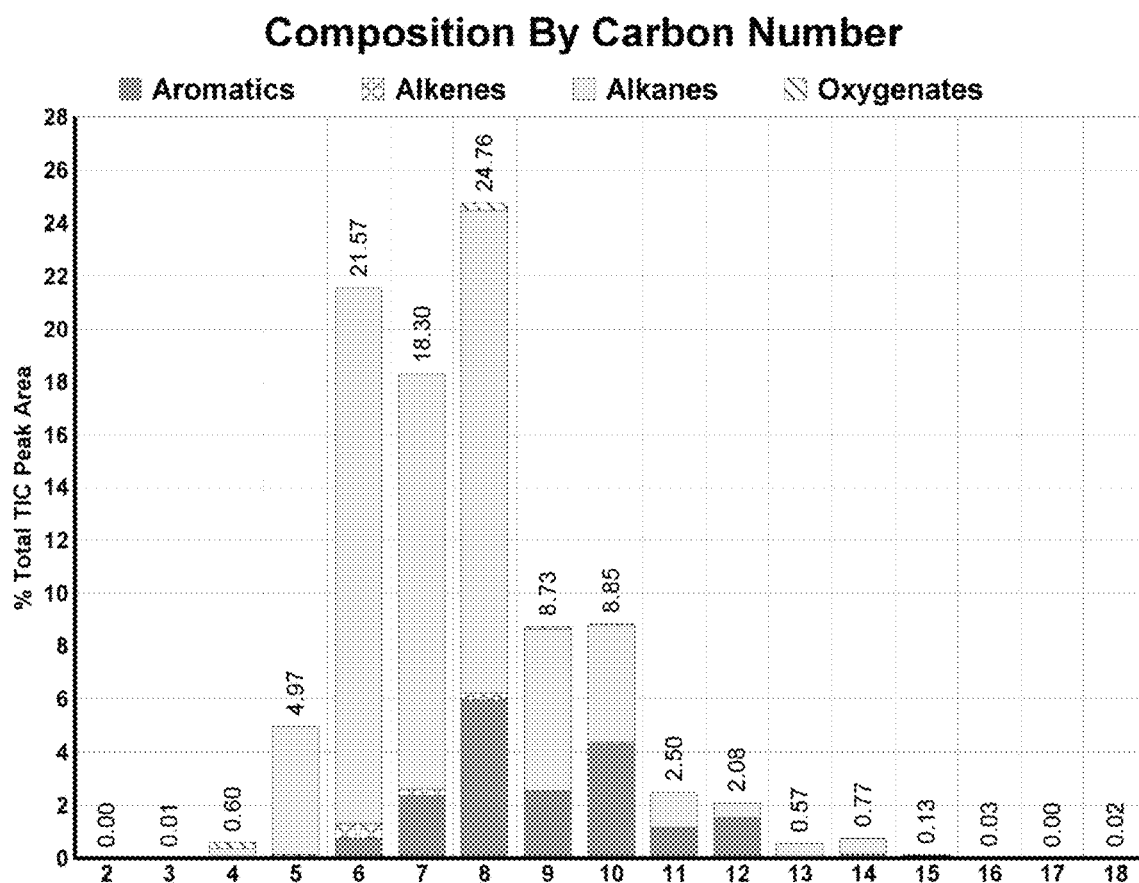
Figures 2, 23B:
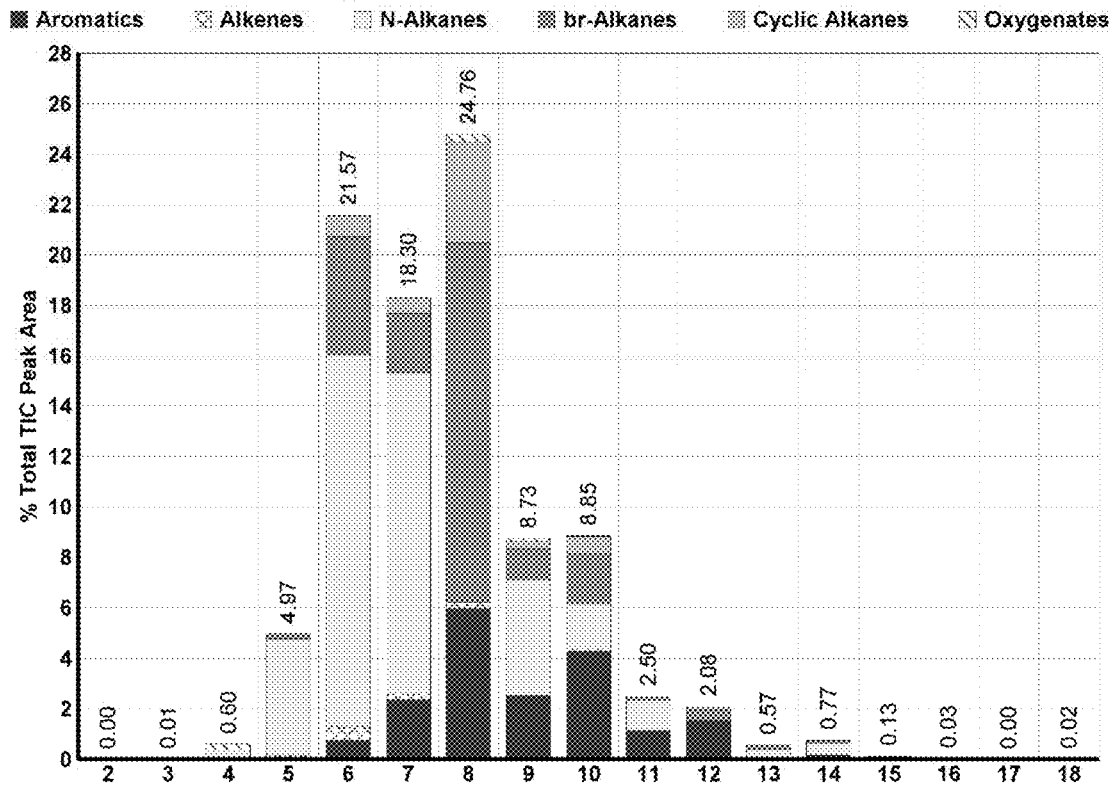
Figure 23C:
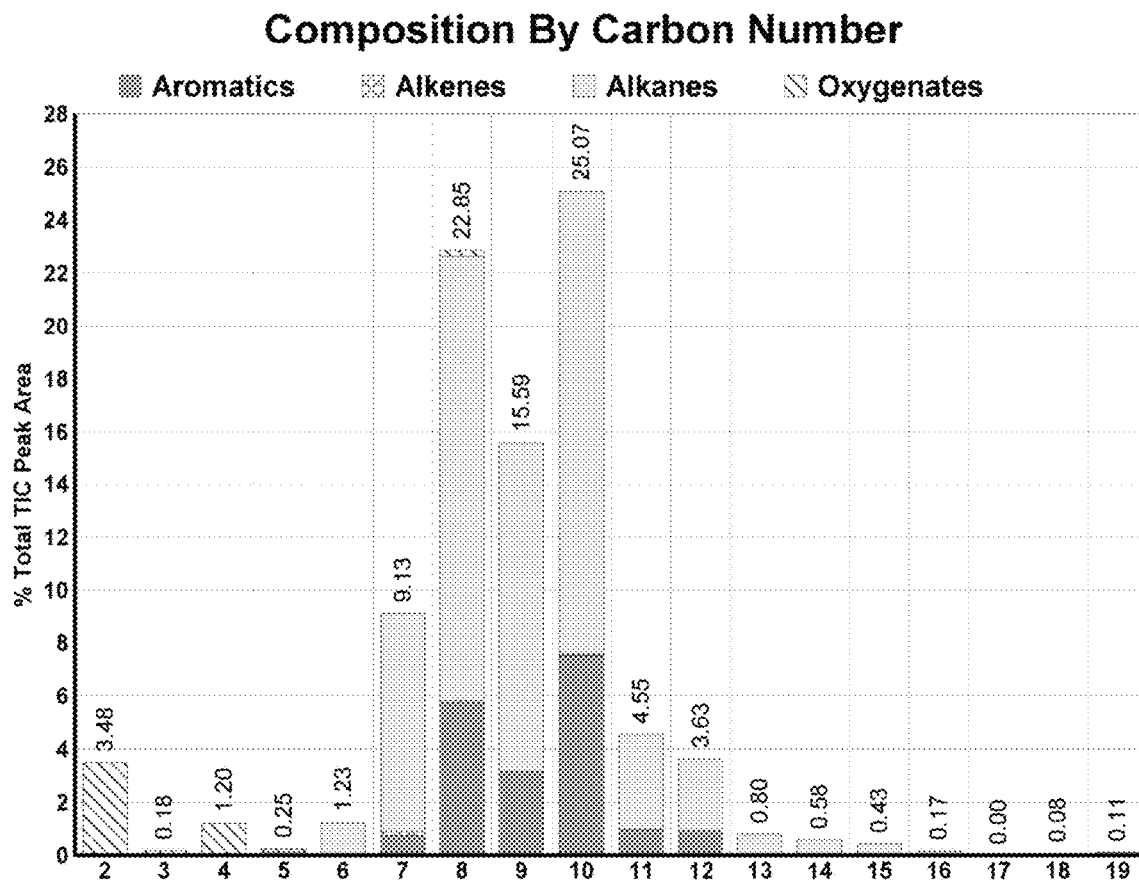
Figure 23D:
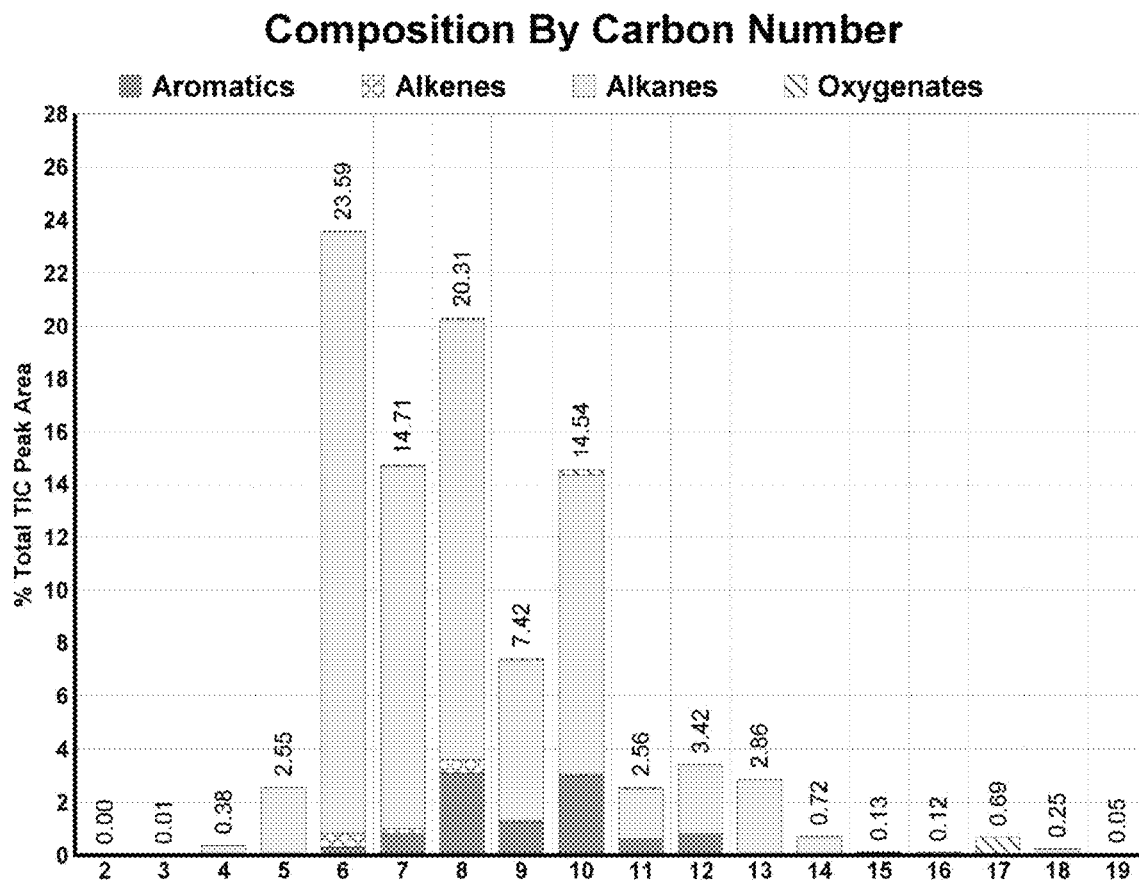
Figures 2, 23D:
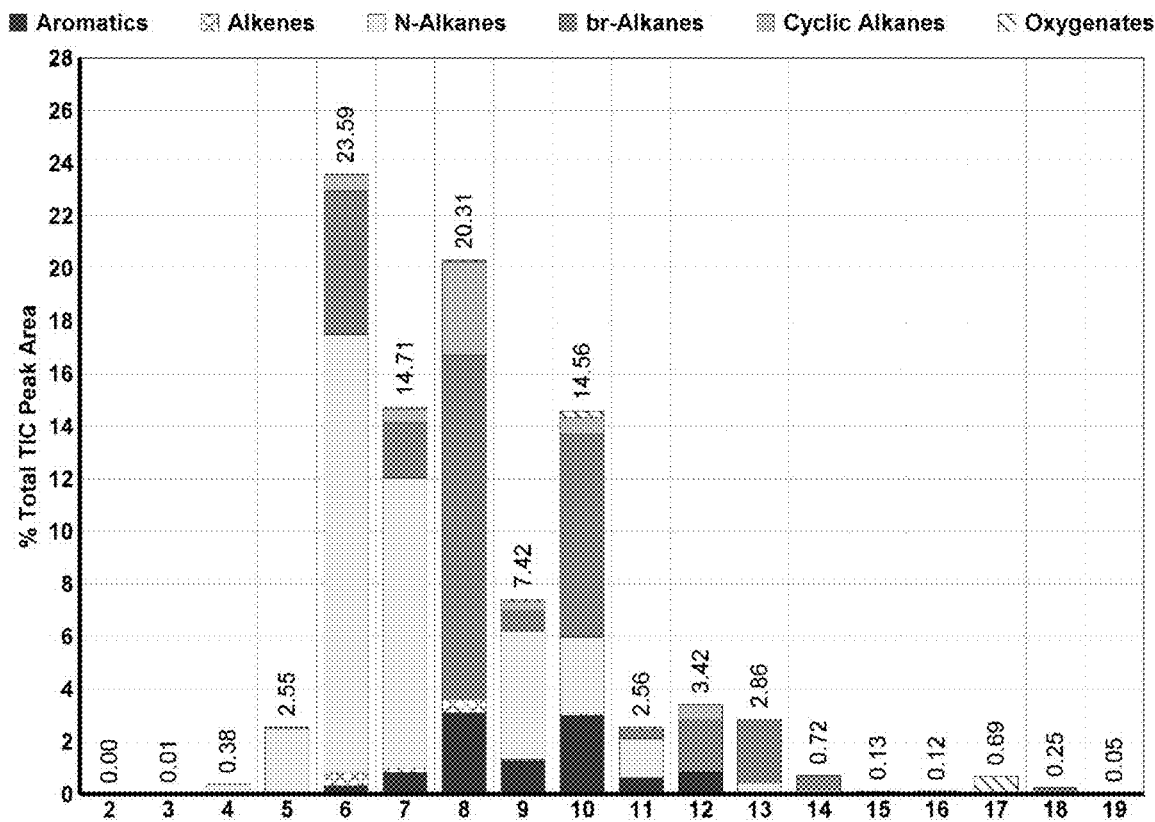
Figure 24:
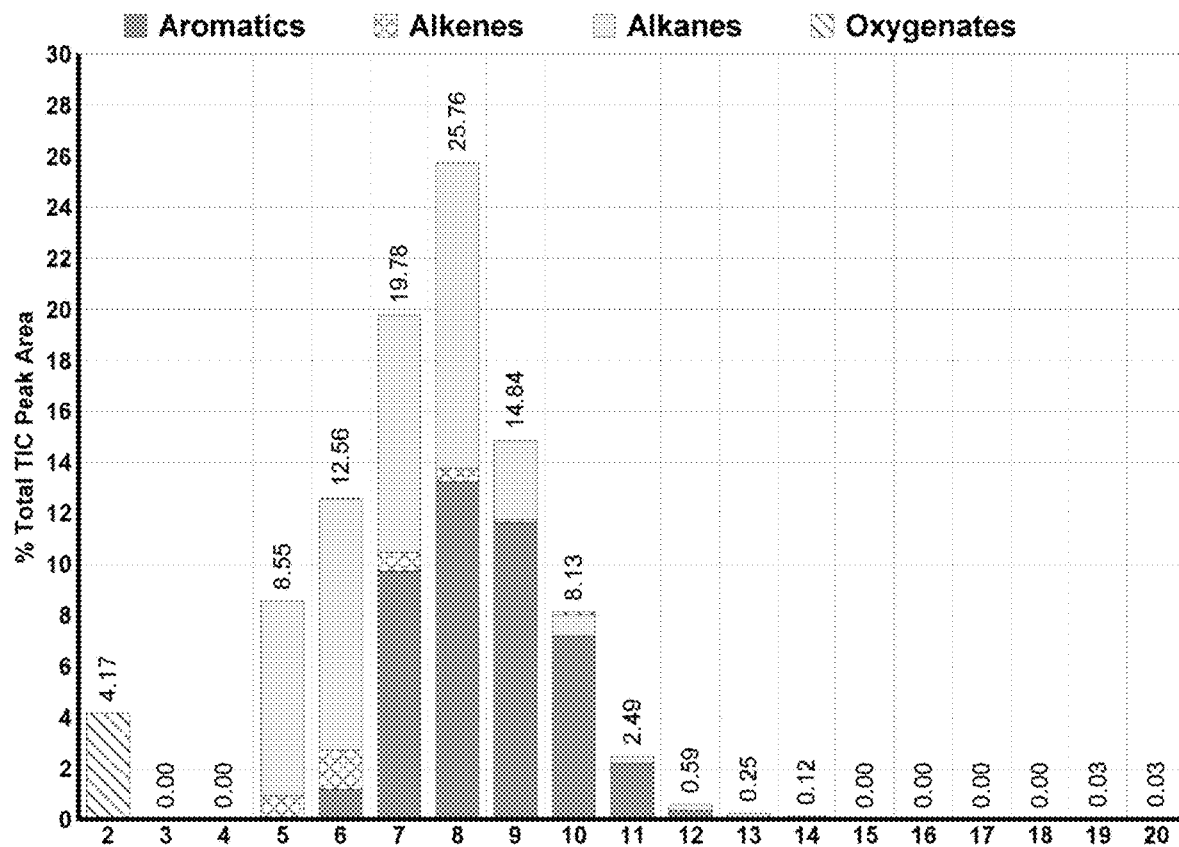
FIG. 24 provides a graphical description of the product distribution of aromatics, alkenes, alkanes and oxygenates of various carbon content in a standard gasoline sample. A standard gasoline sample was found to contain hydrocarbons with an average carbon number of 7.47, and about 45.54% aromatics, 4.00% alkenes, 43.53% of alkanes and 4.20% of oxygenates, as determined by total ion chromatography peak area.

Biomass-derived ethanol is converted to hydrocarbons in the presence of 2.3 g of 0.5% Pt/5.0% $H_3BO_3$—$Al_2O_3$, at a temperature of 325° C., pressure of 500 psig and volumetric linear flow rate (LFR) of 0.125 mL/min. The process was carried out in a 3.7 cm³ reactor. FIG. 23A provides a graphical description of the product distribution of aromatics, alkenes, alkanes and oxygenates of various carbon content in the hydrocarbon mixture generated by this process. The graph shows the percentage amounts (vertical axis) of aromatics, alkenes, alkanes and of oxygenates containing C2-C18 hydrocarbons (horizontal axis) formed by the catalytic conversion of ethanol. For example, the 0.5% Pt/5.0% $H_3BO_3$—$Al_2O_3$ catalyzed reaction produced hydrocarbons of average carbon number 7.2, containing about 4.67% aromatics, 0.95% alkenes, 91.91% alkanes and 0.05% oxygenates, as determined by total ion chromatography peak area. FIG. 23A-2 provides a complete hydrocarbon report of the product described in FIG. 23A including a detailed breakdown of all the compound types. FIGS. 23B, 23B-2, 23C, 23C-2, 23D, and 23D-2 provide a graphical description of the product distribution when the same reaction was run at a temperature of 350° C., and at a pressure of 300 psig, 500 psig, and 700 psig, respectively. When the reaction was run at a temperature of 350° C., and at a pressure of 300 psig, the resulting hydrocarbons had an average carbon number of 7.7, and contained about 19.24% of aromatics, 1.32% of alkenes, 73.01% of alkanes and 0.31% of oxygenates, as determined by total ion chromatography peak area. When the reaction was run at a temperature of 350° C., and at a pressure of 500 psig, the resulting hydrocarbons had an average carbon number of 8.77, and contained about 19.35% of aromatics, 0.24% of alkenes, 64.81% of alkanes and 4.93% of oxygenates, as determined by total ion chromatography peak area. When the reaction was run at a temperature of 350° C., and at a pressure of 700 psig, the resulting hydrocarbons had an average carbon number of 8.17, and contained about 10.42% of aromatics, 1.37% of alkenes, 81.65% of alkanes and 0.88% of oxygenates, as determined by total ion chromatography peak area. FIGS. 23B-2, 23C-2, and 23D-2 provide a complete hydrocarbon report of the respective product described in FIGS. 23B, 23C, and 23D including a detailed breakdown of all the compound types.

Example 5G: Catalytic Conversion with 0.5% Pt-0.5% Sn-0.5% Bi/$Al_2O_3$

Figure 25:
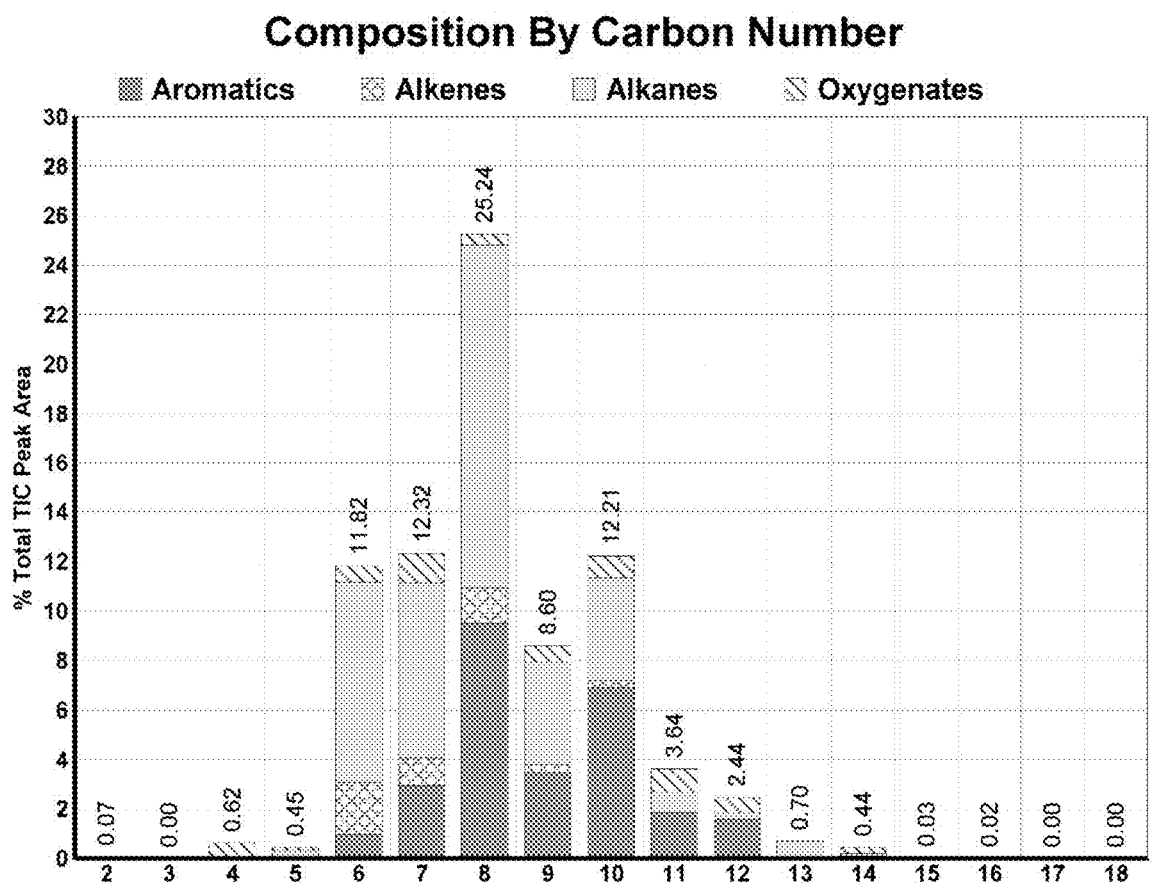
FIGS. 25 and 25A provides a graphical description of the product distribution of aromatics, alkenes, alkanes and oxygenates of various carbon content in the hydrocarbon mixture generated by the catalytic processing of biomass-derived ethanol when it is catalytically converted to hydrocarbons in the presence of 0.5% Pt-0.5% Sn-0.5% Bi/Al$_2$O$_3$, at a temperature of 350° C., pressure of 500 psig and volumetric linear flow rate (LFR) of 0.125 mL/min. The graph shows the percentage amounts (vertical axis) of aromatics, alkenes, alkanes and of oxygenates containing C2-C18 hydrocarbons (horizontal axis) formed by the catalytic conversion of ethanol. The reaction produced hydrocarbons of average carbon number 8.25, containing about 30.51% aromatics, 5.29% alkenes, 39.35% alkanes and 3.43% oxygenates, as determined by total ion chromatography peak area.
Figure 25A:
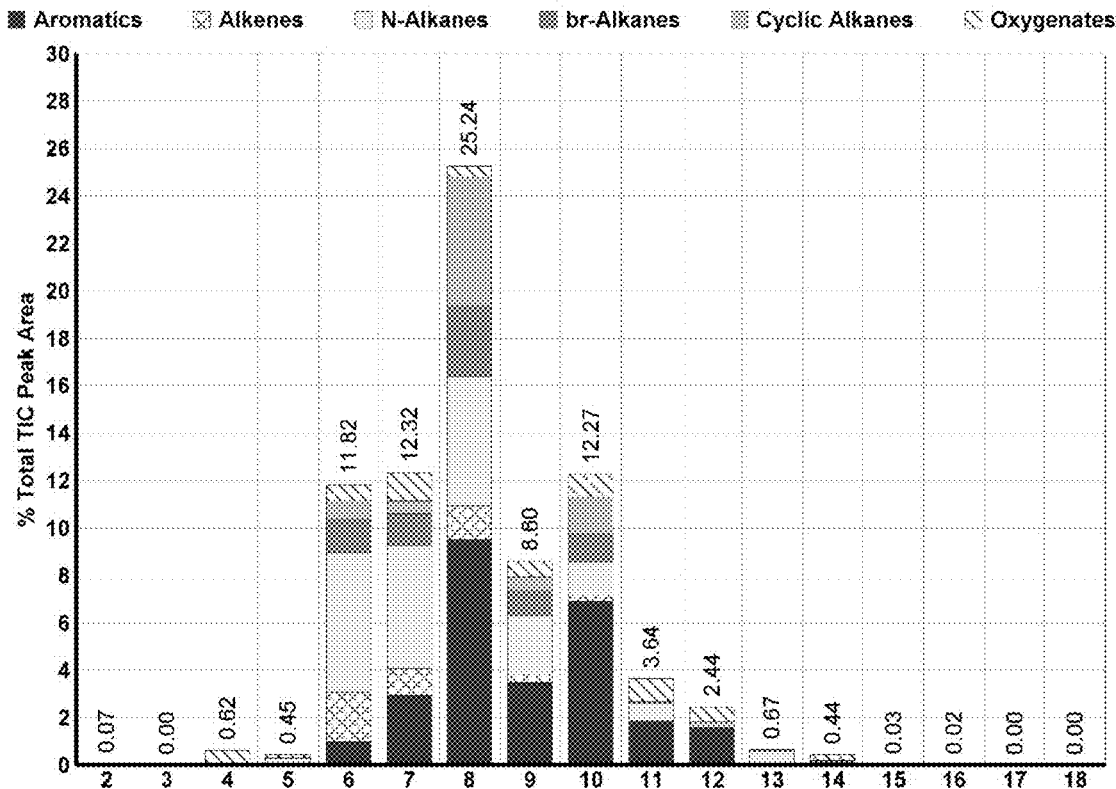

Biomass-derived ethanol was catalytically converted to hydrocarbons in the presence of 2.3 g of 0.5% Pt-0.5% Sn-0.5% Bi/$Al_2O_3$, at a temperature of 350° C., pressure of 500 psig and volumetric linear flow rate (LFR) of 0.125 mL/min. The process was carried out in a 3.7 $cm^3$ reactor. FIG. 25 provides a graphical description of the product distribution of aromatics, alkenes, alkanes and oxygenates of various carbon content in the hydrocarbon mixture generated by this process. The graph shows the percentage amounts (vertical axis) of aromatics, alkenes, alkanes and of oxygenates containing C2-C18 hydrocarbons (horizontal axis) formed by the catalytic conversion of ethanol. The reaction produced hydrocarbons of average carbon number 8.25, containing about 30.51% aromatics, 5.29% alkenes, 39.35% alkanes and 3.43% oxygenates, as determined by total ion chromatography peak area. FIG. 25A provides a complete hydrocarbon report of the product described in FIG. 25 including a detailed breakdown of all the compound types.

Example 5H: Catalytic Conversion with 0.5% Pt-0.5% Sn-0.5% Bi/$Al_2O_3$

Figure 26:
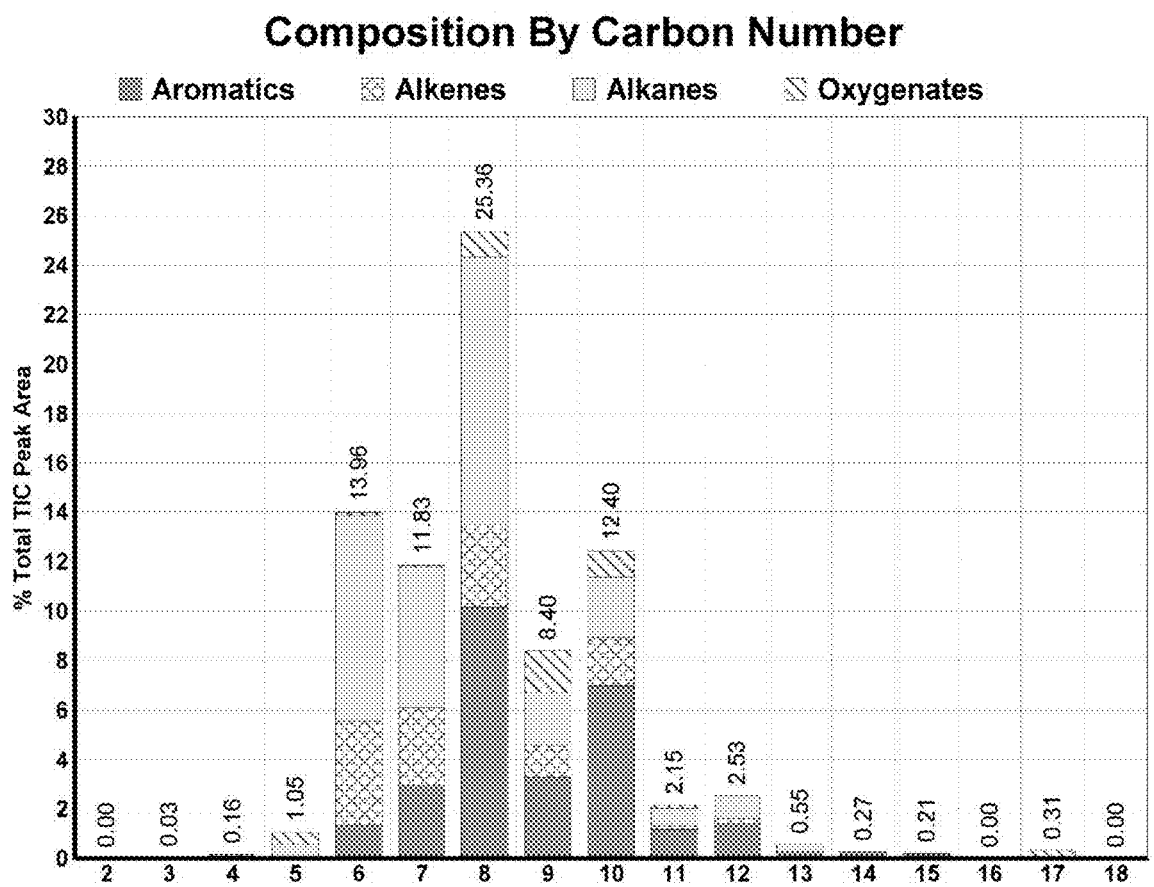

Biomass-derived ethanol was catalytically converted to hydrocarbons in the presence of 2.3 g of 0.5% Pt-0.5% Sn-0.5% Re/$Al_2O_3$, at a temperature of 350° C., pressure of 500 psig and volumetric linear flow rate (LFR) of 0.125 mL/min. The process was carried out in a 3.7 $cm^3$ reactor. FIG. 26 provides a graphical description of the product distribution of aromatics, alkenes, alkanes and oxygenates of various carbon content in the hydrocarbon mixture generated by this reaction. The graph shows the percentage amounts (vertical axis) of aromatics, alkenes, alkanes and of oxygenates containing C2-C18 hydrocarbons (horizontal axis) formed by the catalytic conversion of ethanol. The reaction produced hydrocarbons of average carbon number 8.19, containing about 31.47% aromatics, 14.34% alkenes, 31.87% alkanes and 1.53% oxygenates, as determined by total ion chromatography peak area. FIG. 26A provides a complete hydrocarbon report of the product described in FIG. 26 including a detailed breakdown of all the compound types.

Superior Quality Unblended Cellulosic-Biomass Derived Gasoline—without Fractional Distillation Provided herein is an unblended cellulosic-biomass derived gasoline of high research octane number, and a method for producing the same. The unblended cellulosic-biomass derived gasoline is a liquid produced by the process described herein without further mixing or blending. And, in some embodiments, the unblended cellulosic-biomass derived gasoline comprises a liquid produced by the processes described herein that has been further distilled in the gasoline distillation with range from 900 F to 4100 F. In one embodiment, the unblended cellulosic-biomass derived gasoline is produced by catalytic processing of the cellulosic-biomass or a product derived therefrom. In one embodiment, the research octane number of the unblended cellulosic-biomass derived gasoline is greater than about 87, as determined by ASTM D2699. For example, the unblended gasoline can have a research octane number (RON) of greater than about 87, about 90, about 91, about 92, about 93, about 94, about 95, about 96, about 97, about 98, or about 99. This application refers to a number of ASTM methods or standards, including ASTM D2699 (approved Oct. 1, 2017), ASTM D2700 (approved Dec. 1, 2017), ASTM D5191 (approved Oct. 1, 2015), ASTM D4809 (approved May 1, 2013), ASTM D4814-X1.4 (approved Jan. 1, 2018), and ASTM D4052 (approved Dec. 1, 2016), all of which are incorporated here by reference. The catalyst used in this process can be any of the catalysts disclosed herein, including an alumina-based catalyst and/or a zeolite-based catalyst. In some embodiments, the catalyst is a mono-metallic catalyst, bi-metallic catalyst, or tri-metallic catalyst. In some embodiments, the catalysts contain metals selected from the group consisting of Pt, Pd, Sn, Re, Rh, Bi, Ba, Ti, Ni, and any combinations thereof.

In some embodiments, the unblended cellulosic-biomass derived gasoline has a relatively high motor octane number (MON) of greater than about 80 as determined by ASTM D2700 (approved Dec. 1, 2017). For example, the MON can be greater than about 80, about 81, about 82, about 83, about 84, about 85, about 86, about 87, about 88, about 89, about 90, or about 92.

In some embodiments, the unblended cellulosic-biomass derived gasoline has a dry vapor pressure equivalent, EPA that is greater than about 4 psi, as determined by ASTM D5191 (approved Oct. 1, 2015). For example, the dry vapor pressure equivalent, EPA can be greater than about 4 psi, about 5 psi, about 6 psi, about 7 psi, about 8 psi, about 9 psi, or about 10 psi.

In some embodiments, the unblended cellulosic-biomass derived gasoline has a relatively high energy content such as a gross heat of combustion, as determined by ASTM D4809 (approved May 1, 2013). For example, the heat of combustion can be greater about 120,0000 Btu/gal, about 121,000

Btu/gal, about 122,000 Btu/gal, about 123,000 Btu/gal, about 124,000 Btu/gal, about 125,000 Btu/gal, about 126,000 Btu/gal, or about 128,000 Btu/gal.

In some embodiments, the unblended cellulosic-biomass derived gasoline has a superior antiknock index or octane rating ((RON+MON)/2), as determined by ASTM D4814-X1.4 (approved Jan. 1, 2018). For example, the antiknock index can be greater than about 85, about 86, about 87, about 88, about 89, about 90, about 91, about 92, about 93, about 94, or about 95.

In some embodiments, the unblended cellulosic-biomass derived gasoline may have an API Gravity at 60° F. of greater than about 40° API, as determined by ASTM D4052 (approved Dec. 1, 2016), e.g., greater than about 41° API, about 42° API, about 43° API, about 44° API, about 45° API, about 46° API, about 47° API, about 48° API, about 49° API, about 50° API, about 51° API, about 52° API, about 53° API, about 54° API, about 55° API, about 56° API, about 57° API, about 58° API, about 59° API, or about 60° API.

The unblended cellulosic-biomass derived gasoline described herein can have any combination of RON, MON, dry vapor pressure equivalent, gross heat of combustion, antiknock index, and API Gravity at 60° F. discussed above. For example, in one embodiment, the unblended cellulosic-biomass derived gasoline has an RON of greater than 88, a MON of greater than 86, an antiknock index greater than 87, a dry vapor pressure equivalent, EPA of 6 psi, an API gravity at 60° F. of between about 40 and 65, and a gross heat of combustion of between about 120,000 Btu/gal and 130,000 Btu/gal.

In one embodiment, the unblended cellulosic-biomass derived gasoline is produced by catalytically processing a cellulosic-biomass derived ethanol using the methods and the catalysts described herein. The cellulosic-biomass may be further pretreated with electron beam radiation. In some embodiments, the irradiating (with any radiation source or a combination of sources) is performed until the cellulosic-biomass receives a dose of at least 0.25 Mrad, e.g., at least 1.0 Mrad, at least 2.5 Mrad, at least 5.0 Mrad, or at least 10.0 Mrad. In some embodiments, the irradiating is performed until the material receives a dose of between 1.0 Mrad and 6.0 Mrad, e.g., between 1.5 Mrad and 4.0 Mrad. In some embodiments, the irradiating is performed at a dose rate of between 5.0 and 1500.0 kilorads/hour, e.g., between 10.0 and 750.0 kilorads/hour or between 50.0 and 350.0 kilorads/hours.

The unblended cellulosic-biomass derived gasoline produced by this invention can be a mixture of different hydrocarbons, such as linear or branched, mono-, and di-substituted $C_7$-$C_{16}$ alkanes, one or more of which is derived from cellulosic-biomass. It may also contain olefins, substituted or unsubstituted cycloalkanes (such as cyclopentanes, cyclohexanes), aromatics (such as benzene, toluene, naphthalenes), mono-substituted aromatics (such as methyl benzene), di-substituted aromatics (such as xylenes), and multi-substituted aromatics (such as trimethylbenzenes), one or more of which is derived from the cellulosic-biomass.

In some instances, the unblended cellulosic-biomass derived gasoline contains less than about 5 percent by weight benzene, such as less than 4.5, 4.0, 3.5, 3.0, 2.5, 2.0, 1.5, or even less than 1.0 percent by weight, e.g., less than 0.9, 0.8, 0.7, 0.6, 0.5, 0.4, 0.3, or even less than 0.25 percent by weight, e.g., less than 0.2, 0.15, 0.1 or even less than 0.05 percent by weight. In particular, the methods and catalysts can, for example, if desired, give the low benzene content directly, without active removal or separation, such as by distillation of the benzene from other components. Low concentrations of benzene can be useful in jurisdictions, such as the United States, that strictly limit its concentration in gasoline. In the United States, the USEPA sets a limit of benzene to be less than 1.3 percent by weight in gasoline.

In some embodiments, the unblended cellulosic-biomass derived gasoline described herein, such as a high-octane gasoline (HOG) contains a high aromatics content. For example, the unblended cellulosic-biomass derived gasoline may contain greater than about 25% (w/w), about 30% (w/w), about 35% (w/w), about 40% (w/w), about 45% (w/w), about 50% (w/w), about 55% (w/w), about 60% (w/w), about 65% (w/w), about 70% (w/w), about 75% (w/w), about 80% (w/w), about 285% (w/w), about 90% (w/w) of aromatic hydrocarbons. In some instances, the aromatics can include toluene and xylenes, for example, as o, m- or para-xylene. In some instances, the predominant aromatics produced are toluene and xylenes, making up more than about 60 percent by weight of the aromatics produced, for example, greater than 65, 66, 67, 68, 69, 70, or 72 percent by weight or even greater, such as greater than about 75 percent by weight toluene and xylenes. In these instances, these materials can be distilled to produce pure toluene and xylenes, which can, respectively, be used to produce compounds such as toluene diisocyanate and isomers of terephthalic acid.

In some embodiments, the unblended cellulosic-biomass derived gasoline described herein, such as a HOG can have relatively low amount of alkanes. For example, the gasoline may contain less than about 50% (w/w), about 40% (w/w), about 30% (w/w), about 20% (w/w), about 10% (w/w), about 5% (w/w), about 2% (w/w), or about 1% (w/w) of alkanes. In some embodiments, the unblended cellulosic-biomass derived gasoline described herein, such as a HOG have a ratio of alkanes:aromatics of between about 1:10 and 1:100, such as between 1:10 and 1:50, or between 1:15 and 1:40 or between about 1:15 and 1:25.

Note that, in some instances, adjusting the methods and/or the catalysts used in the catalytical process described herein may directly change the chemical properties of the resulting unblended cellulosic-biomass derived gasoline, and therefore, enabling the process to obtain an ideal concentration of hydrocarbons without the need for further dilution, distillation, or blending.

In some embodiments, the unblended cellulosic-biomass derived gasoline of such mixtures can be used directly as transportation fuels, as blending components in transportation fuels, such as commercial gasoline.

In one embodiment, the methods and catalysts can, for example, if needed, produce desired fuels, e.g., motor fuels, directly without upgrading or downgrading the fuel, such as by blending. For example, in some instances, the unblended gasoline produced from reactors can be used in fuel tanks of transportation vehicles without any additional treatment. The gasolines can be, for example, a regular octane grade, a mid-octane grade or a high-octane grade gasoline. In other instances, the gasolines produced from reactors can be used directly in fuel tanks of transportation vehicles only after filtering the fuel to remove particulates, and/or after distillation to remove low boiling fractions and/or high boiling fractions. In still other embodiments, the unblended gasolines obtained from the reactors described herein, can form a blend stock as obtained or after some purification. For example, in some instances, the unblended gasolines obtained from the reactors described herein can be a high-octane blending component, such as having a research octane number of greater than about 87, about 90, about 91, about 92, about 93, about 94, about 95, about 96, about 97, about 98, or about 99.

In some embodiments, the unblended cellulosic-biomass derived gasoline described herein has a boiling point range of about 35° C. to 200° C. In some embodiments, less than about 10%, about 9%, about 8%, about 7%, about 6%, about 5%, about 4%, about 3%, about 2%, or about 1% of the fraction of the unblended cellulosic-biomass derived gasoline boils at a temperature above 160° C.

In some embodiments, the unblended cellulosic-biomass derived gasoline described herein has an oxygenate level of less than about 0.5% (wt/.wt.), about 0.4% (wt/.wt.), about 0.25% (wt/.wt.), or about 0.1% (wt./wt.). As used herein, the term "oxygenates" is defined to include oxygen containing organic compounds such as alcohols, ethers, carbonyl compounds (aldehydes, ketones, carboxylic acids, carbonates, and the like). Representative oxygenates include, but are not necessarily limited to, lower straight chain or branched aliphatic alcohols, their unsaturated counterparts. Examples include but are not necessarily limited to: methanol; ethanol; n-propanol; isopropanol; C4-C10 alcohols; methyl ethyl ether; dimethyl ether; diethyl ether; di-isopropyl ether; methyl mercaptan; methyl formate, methyl acetate, formaldehyde; di-methyl carbonate; trimethyl orthoformate, and dimethyl ketone. Oxygenates such as acetaldehyde and acetone can be corrosive and can damage gaskets in engine components. They can also make the fuel hygroscopic, allowing it to absorb water, thereby impacting the quality of gasoline. So, in some embodiments having low oxygenate content in gasoline may be desirable.

In some embodiments, the unblended cellulosic-biomass derived gasoline described herein has a naphthalene content of less than about 0.5% (wt./wt.), about 0.4% (wt./wt.), about 0.25% (wt./wt.), or about 0.1% (wt./wt.). Naphthalenes are toxic air pollutants, add unfavorable smell to gasoline and are recognized as possible human carcinogens. So, in some embodiments having low naphthalene content in gasoline may be desirable.

In some embodiments, the unblended cellulosic-biomass derived gasoline described herein has an aromatic content of greater than about 75% (wt./wt.), about 76% (wt./wt.), about 77% (wt./wt.), about 78% (wt./wt.), about 79% (wt./wt.), about 80% (wt./wt.), about 85% (wt./wt.).

EXAMPLES

Figure 27:
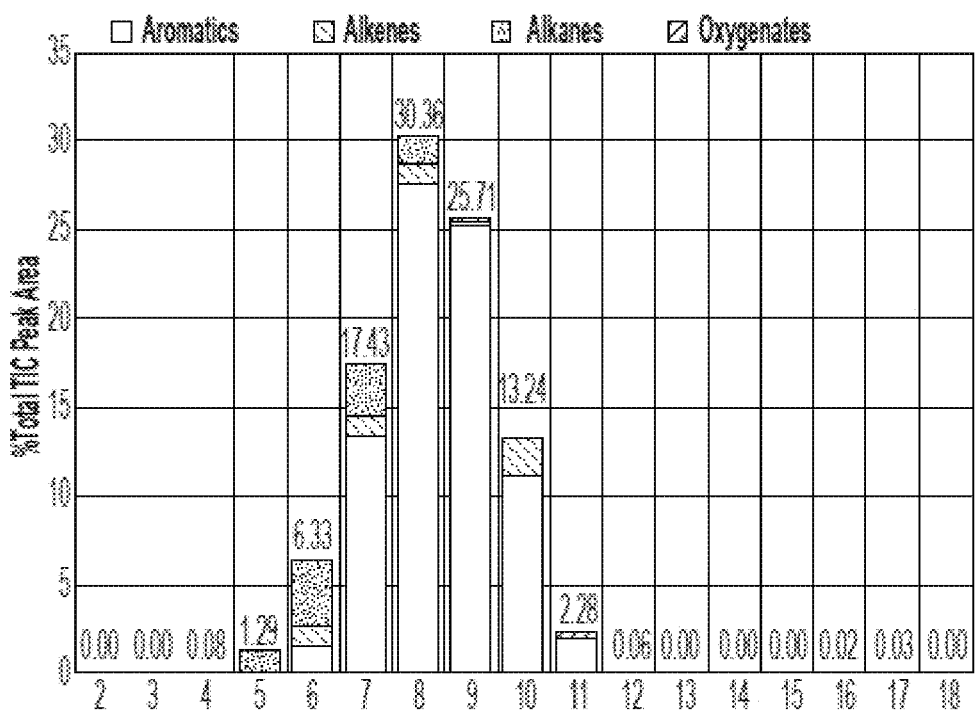
FIG. 27 provides a graphical description of the product distribution of aromatics, alkenes, alkanes and oxygenates of various carbon content in the high-octane hydrocarbon distillate or high-octane gasoline (HOG) generated by the catalytic processing of biomass-derived ethanol described herein.
Figure 27:
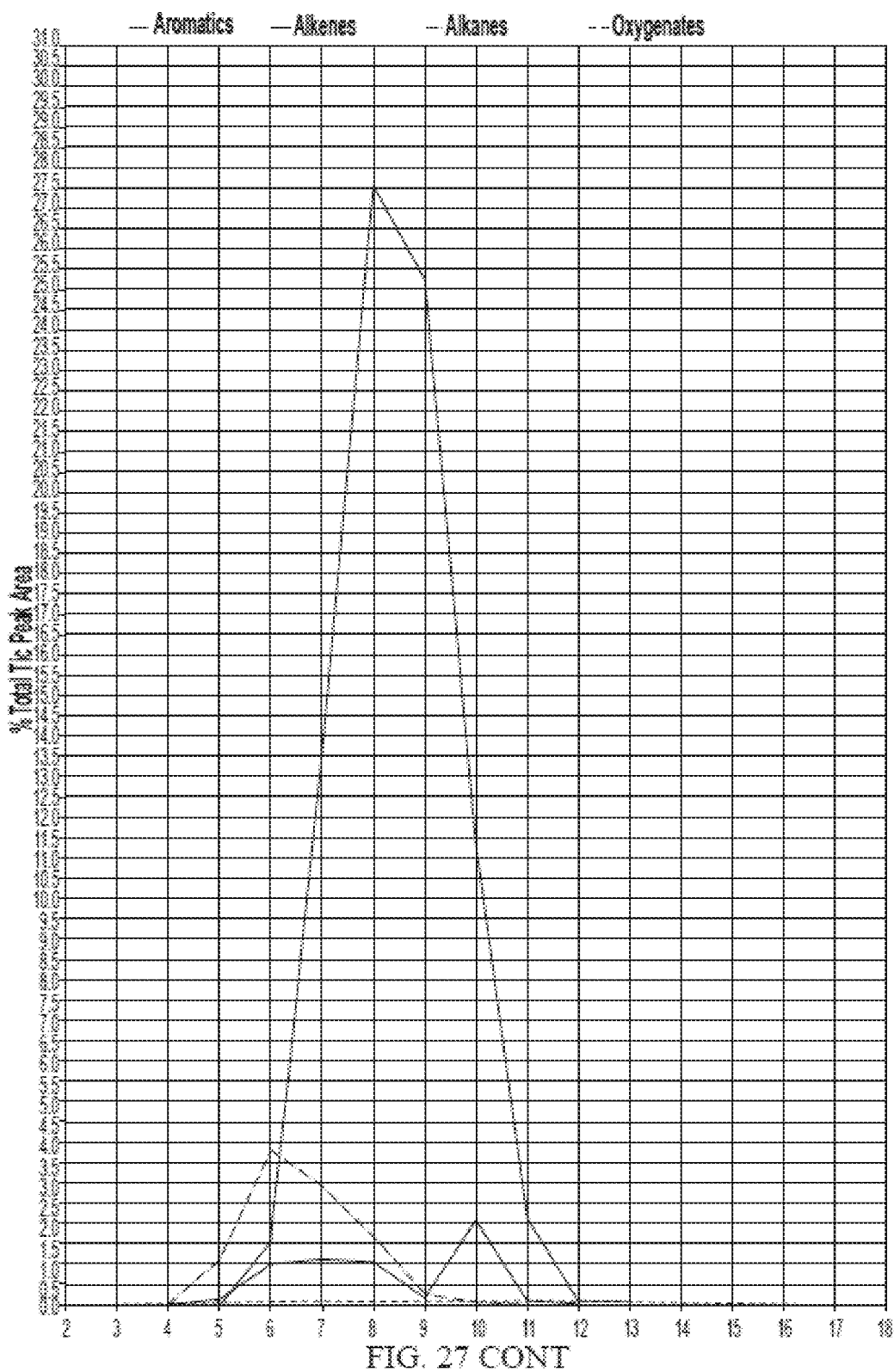

A graphical depiction of the product distribution of aromatics, alkenes, alkanes and oxygenates of various carbon content in a high-octane hydrocarbon distillate or high-octane gasoline (HOG) generated by the catalytic processing of biomass-derived ethanol described herein is shown in FIG. 27. The product distribution shows a significantly high amount of aromatic components. Based on the total known components, the HOG contained about 81.17% of aromatic hydrocarbons, about 5.57% of alkenes, about 9.77% of alkanes, and about 0.28% of oxygenated compounds (wt./wt.). FIG. 27 also provides a detailed breakdown of all the detectable compounds in the composition.

Figure 28:
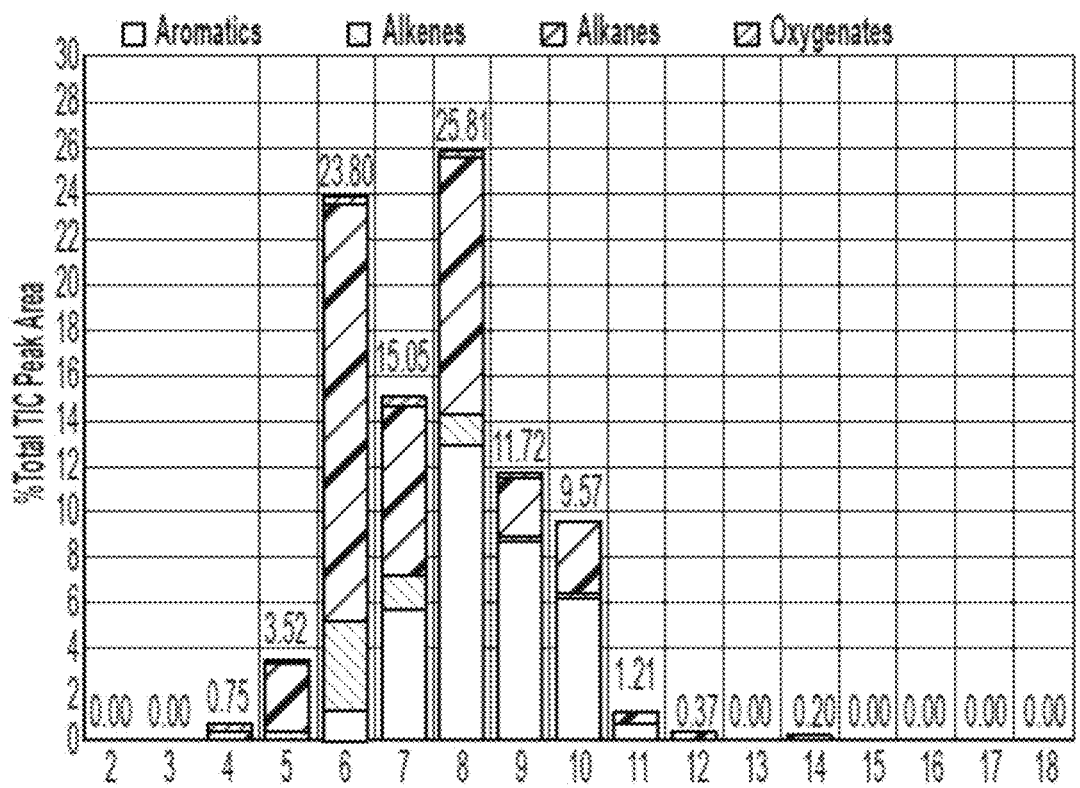
FIG. 28 provides a graphical description of the product distribution of aromatics, alkenes, alkanes and oxygenates of various carbon content in the low-octane hydrocarbon distillate or low-octane gasoline (LOG) generated by the catalytic processing of biomass-derived ethanol described herein.
Figure 28:
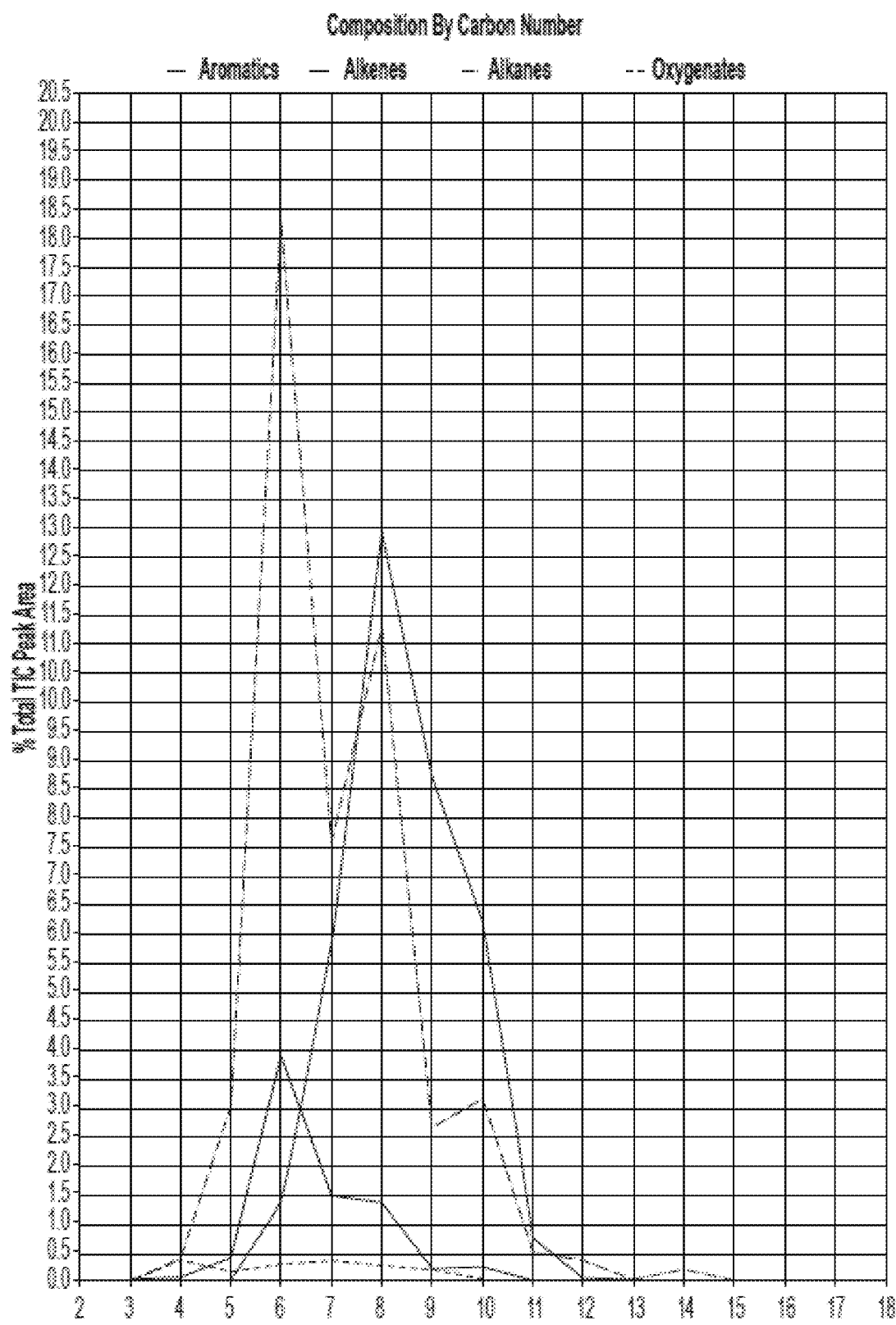

A graphical description of the product distribution of aromatics, alkenes, alkanes and oxygenates of various carbon content in a low-octane hydrocarbon distillate or low-octane gasoline (LOG) generated by the catalytic processing of biomass-derived ethanol described herein is shown in FIG. 28. Based on the total known components, the LOG contained about 35.75% of aromatic hydrocarbons, about 7.53% of alkenes, about 47.20% of alkanes, and about 1.44% of oxygenated compounds (wt./wt.). FIG. 28 also provides a detailed breakdown of all the detectable compounds in the composition.

Figure 29:
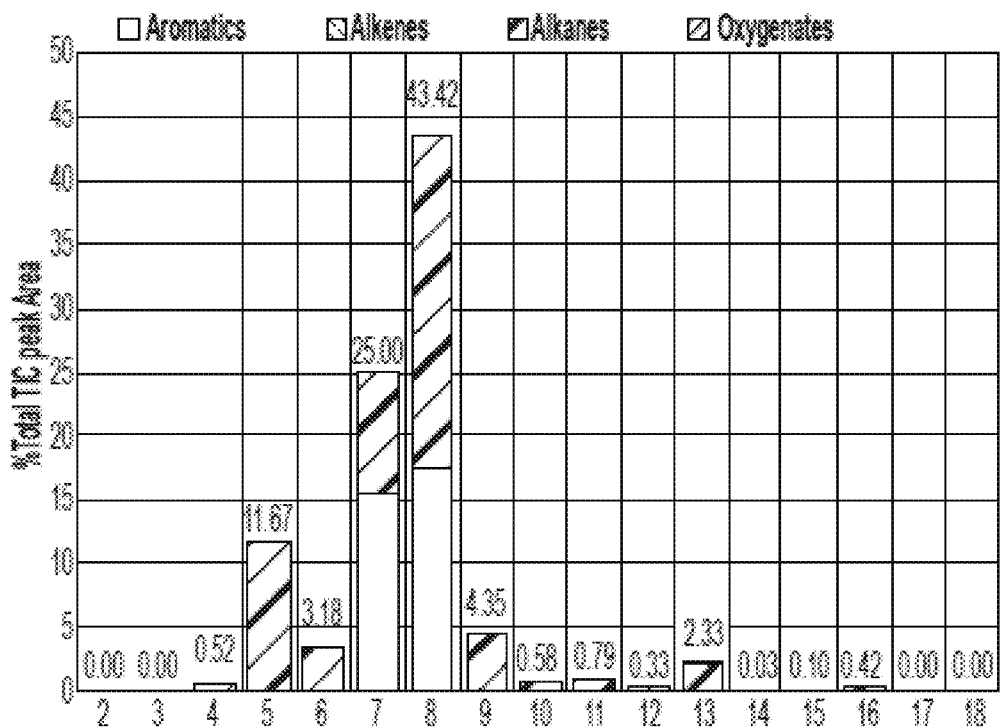
FIG. 29 provides a graphical description of the product distribution of aromatics, alkenes, alkanes and oxygenates of various carbon content in sample C1, which contains Trufuel®, a commercially available premixed high-octane ethanol-free fuel.
Figure 29:
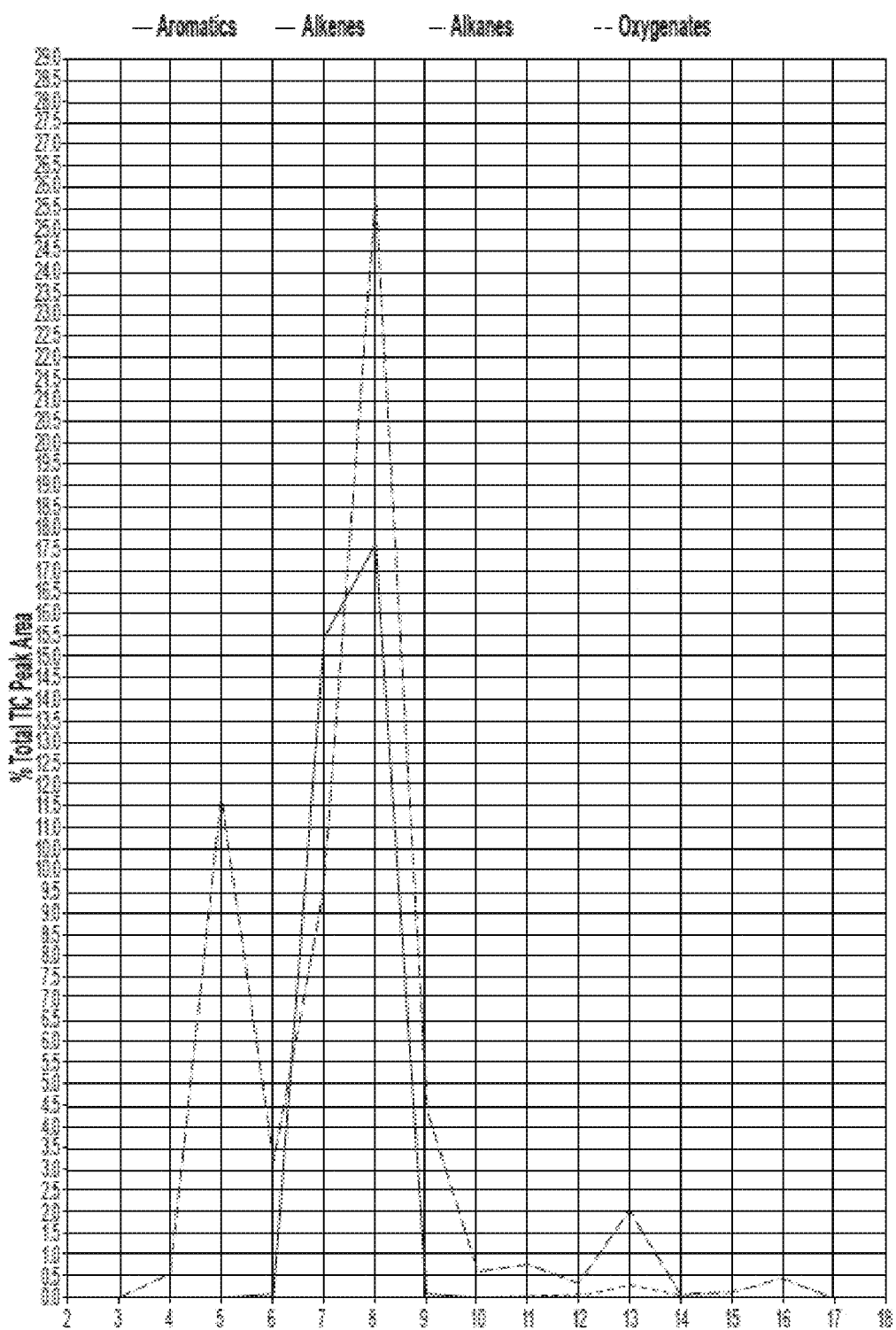

A graphical description of the product distribution of aromatics, alkenes, alkanes and oxygenates of various carbon content in sample C1, which contains Trufuel®, a commercially available premixed high-octane ethanol-free fuel, is shown in FIG. 29. Based on the total known components, Trufuel® contained about 33.13% of aromatic hydrocarbons, about 0.01% of alkenes, about 59.25% of alkanes, and about 0.33% of oxygenated compounds (wt./wt.). FIG. 29 also provides a detailed breakdown of all the detectable compounds in sample C1.

Figure 30:
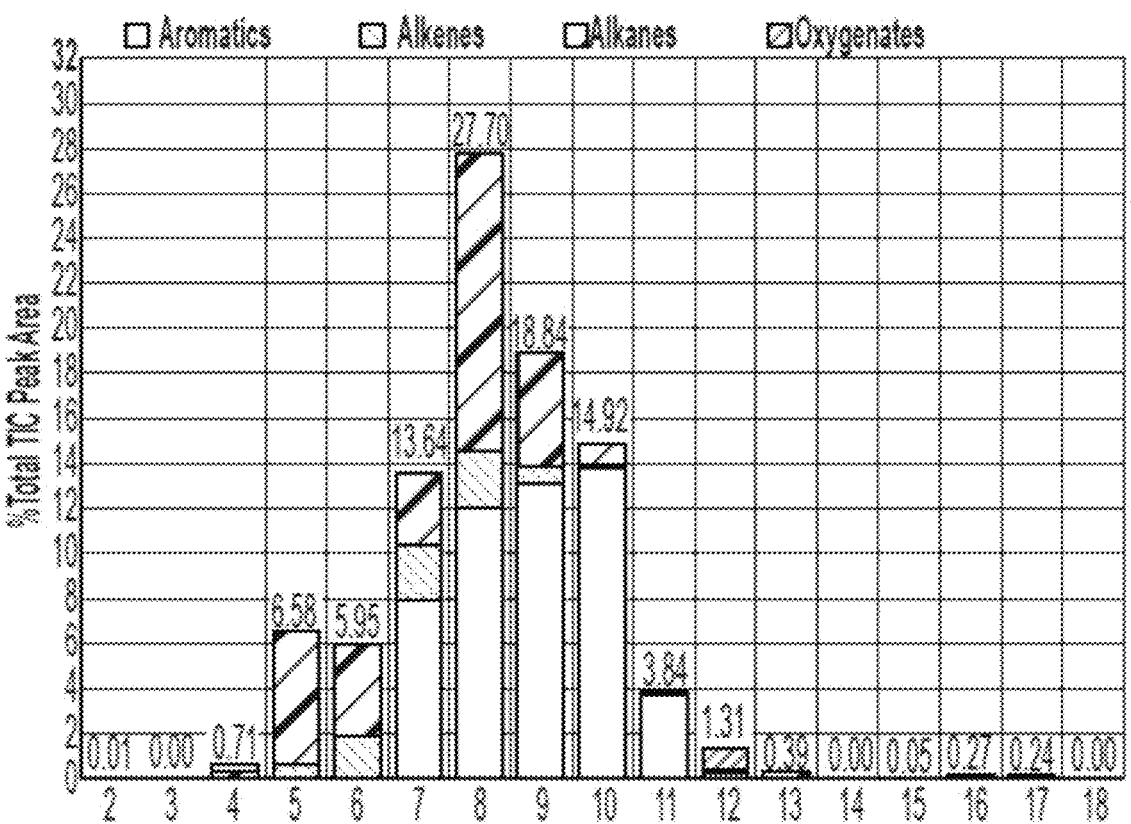
FIG. 30 provides a graphical description of the product distribution of aromatics, alkenes, alkanes and oxygenates of various carbon content in sample C2, which is a mixture of about 50% (v/v) of high-octane gasoline (HOG) generated by the catalytic processing of biomass-derived ethanol described herein, and about 50% (v/v) of Trufuel®.
Figure 30:
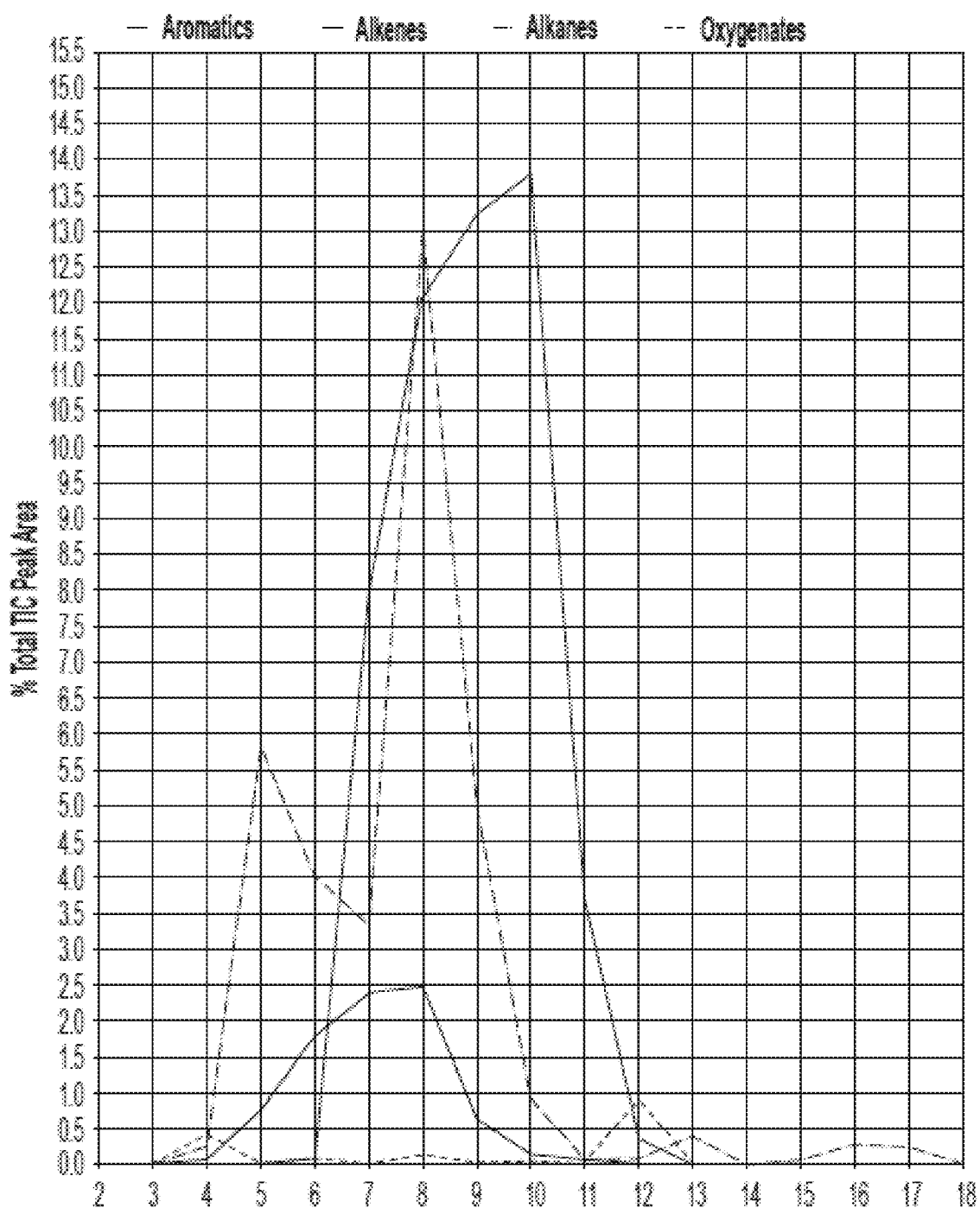

A graphical description of the product distribution of aromatics, alkenes, alkanes and oxygenates of various carbon content in sample C2, which is a mixture of about 50% (v/v) of a high-octane gasoline (HOG) generated by the catalytic processing of biomass-derived ethanol described herein, and about 50% (v/v) of Trufuel® is shown in FIG. 30. Based on the total known components, it contained about 51.32% of aromatic hydrocarbons, about 8.25% of alkenes, about 33.36% of alkanes, and about 1.45% of oxygenated compounds (wt./wt.). FIG. 30 also provides a detailed breakdown of all the detectable compounds in sample C2.

Figure 31:
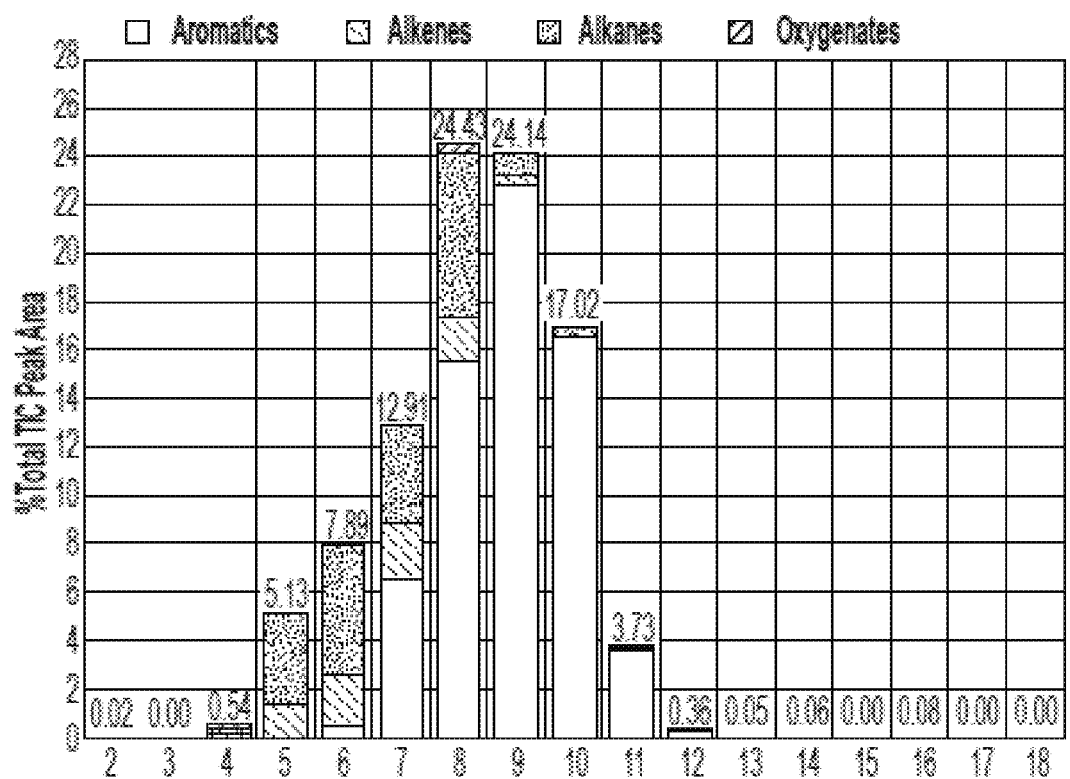
FIG. 31 provides a graphical description of the product distribution of aromatics, alkenes, alkanes and oxygenates of various carbon content in sample C3, which is a mixture of about 85% (v/v) of high-octane gasoline (HOG) generated by the catalytic processing of biomass-derived ethanol described herein, and about 15% (v/v) of Trufuel®.
Figure 31:
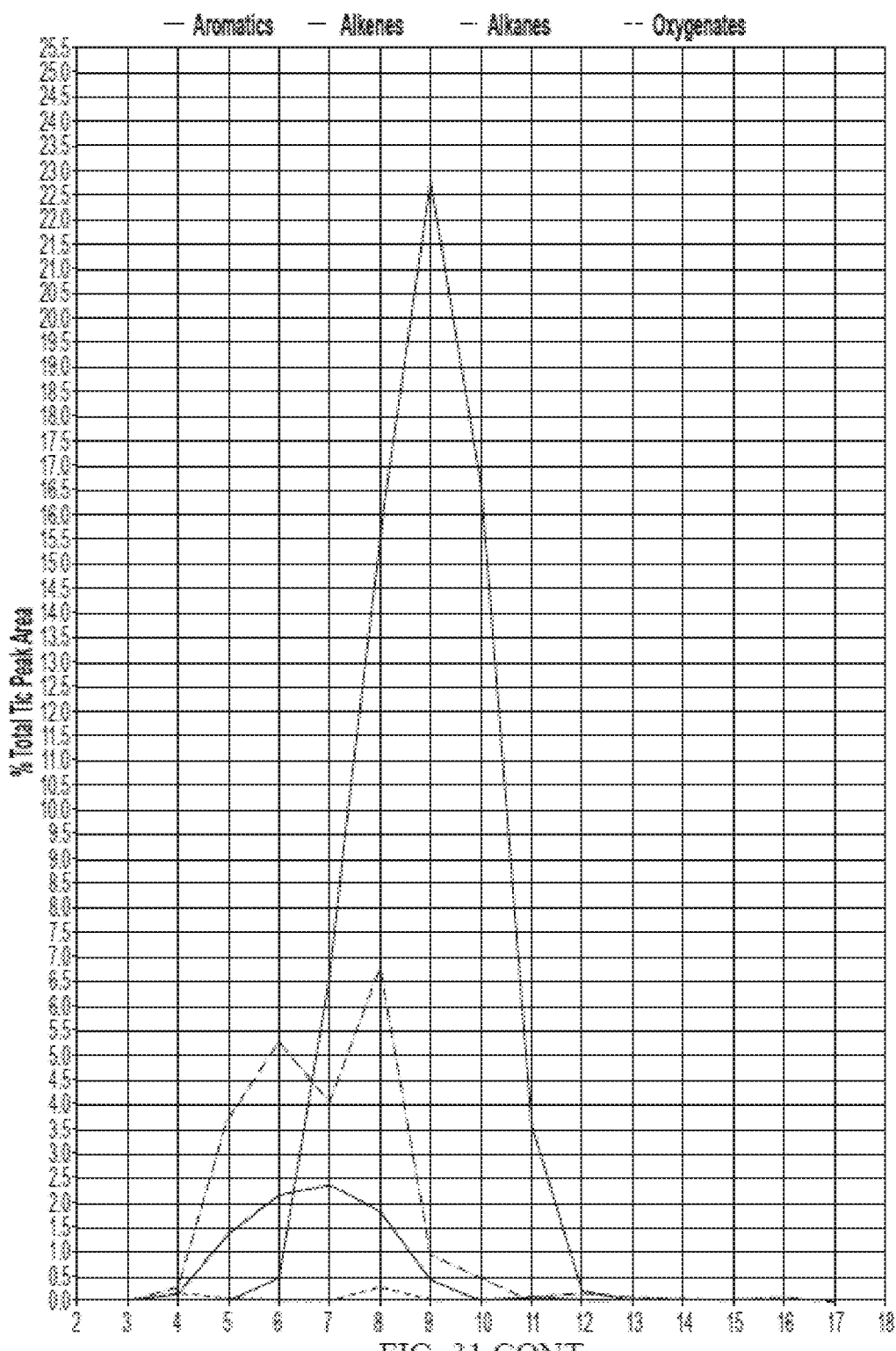

A graphical description of the product distribution of aromatics, alkenes, alkanes and oxygenates of various carbon content in sample C3, which is a mixture of about 85% (v/v) of high-octane gasoline (HOG) generated by the catalytic processing of biomass-derived ethanol described herein, and about 15% (v/v) of Trufuel® is shown in FIG. 31. Based on the total known components, it contained about 65.93% of aromatic hydrocarbons, about 8.31% of alkenes, about 21.70% of alkanes, and about 0.30% of oxygenated compounds (wt./wt.). FIG. 31 also provides a detailed breakdown of all the detectable compounds in sample C3.

Figure 32:
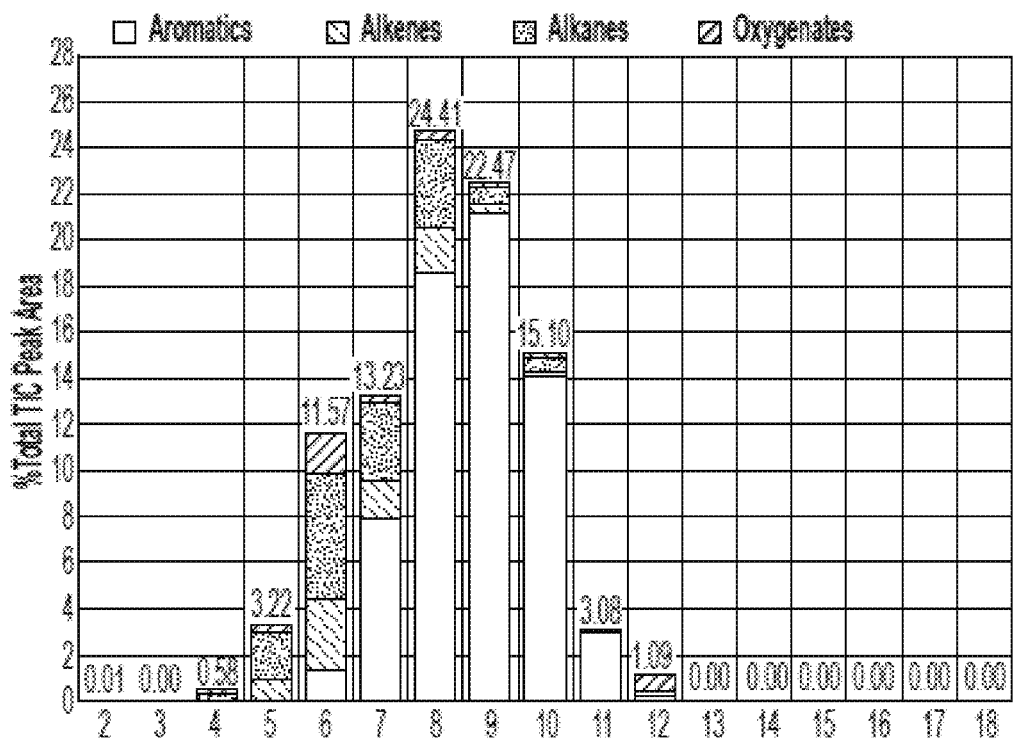
FIG. 32 provides a graphical description of the product distribution of aromatics, alkenes, alkanes and oxygenates of various carbon content in sample C4, which is a mixture of about 70% (v/v) of high-octane gasoline (HOG) generated by the catalytic processing of biomass-derived ethanol described herein, and about 30% (v/v) of low-octane gasoline (LOG), generated by the catalytic processing of biomass-derived ethanol described herein.
Figure 32:
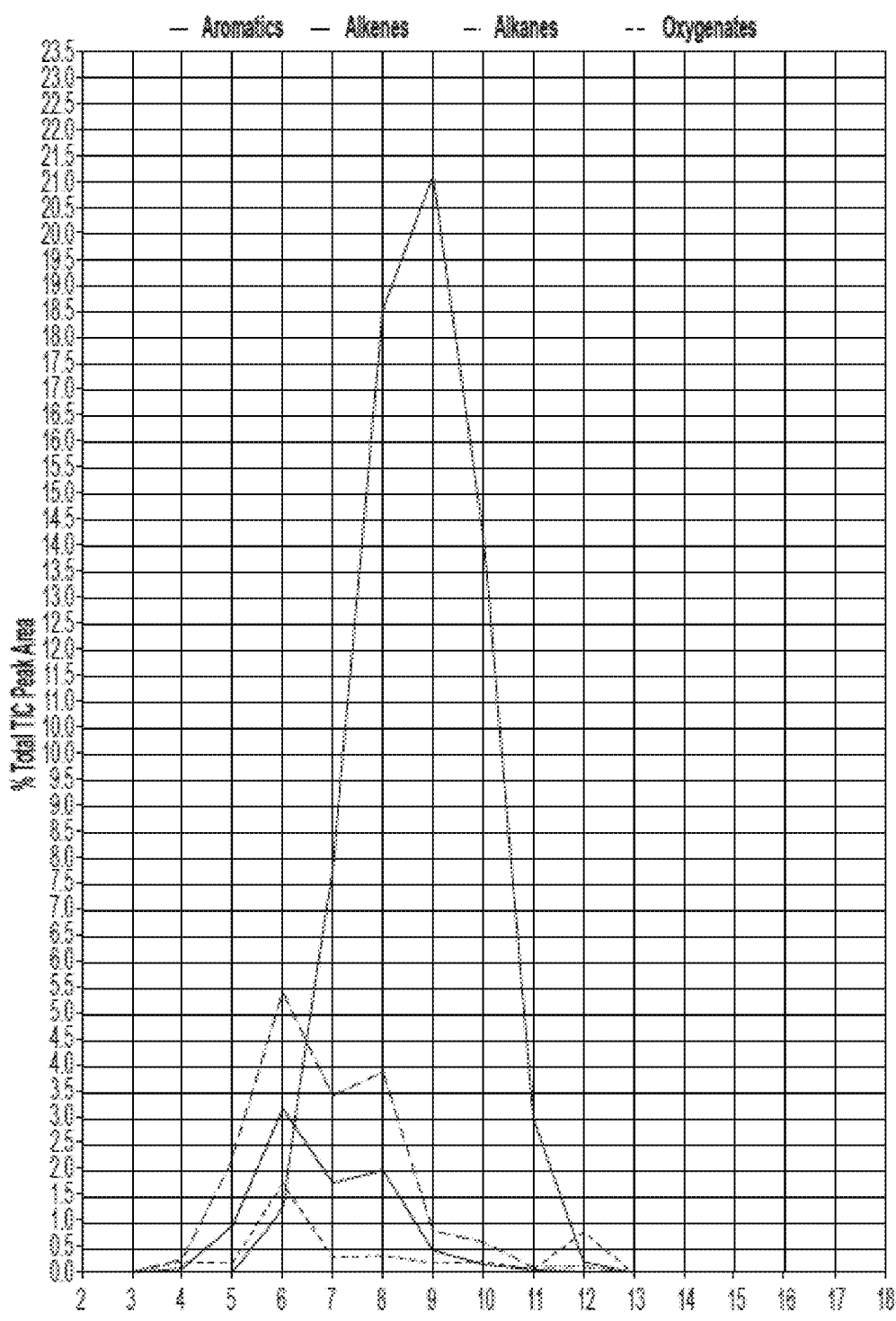

A graphical description of the product distribution of aromatics, alkenes, alkanes and oxygenates of various carbon content in sample C4, which is a mixture of about 70% (v/v) of high-octane gasoline (HOG) generated by the catalytic processing of biomass-derived ethanol described herein, and about 30% (v/v) of low-octane gasoline (LOG), generated by the catalytic processing of biomass-derived ethanol described herein is shown in FIG. 32. Based on the total known components, it contained about 66.37% of aromatic hydrocarbons, about 8.43% of alkenes, about 16.70% of alkanes, and about 3.57% of oxygenated compounds (wt./wt.). FIG. 32 also provides a detailed breakdown of all the detectable compounds in sample C4.

Figure 33:
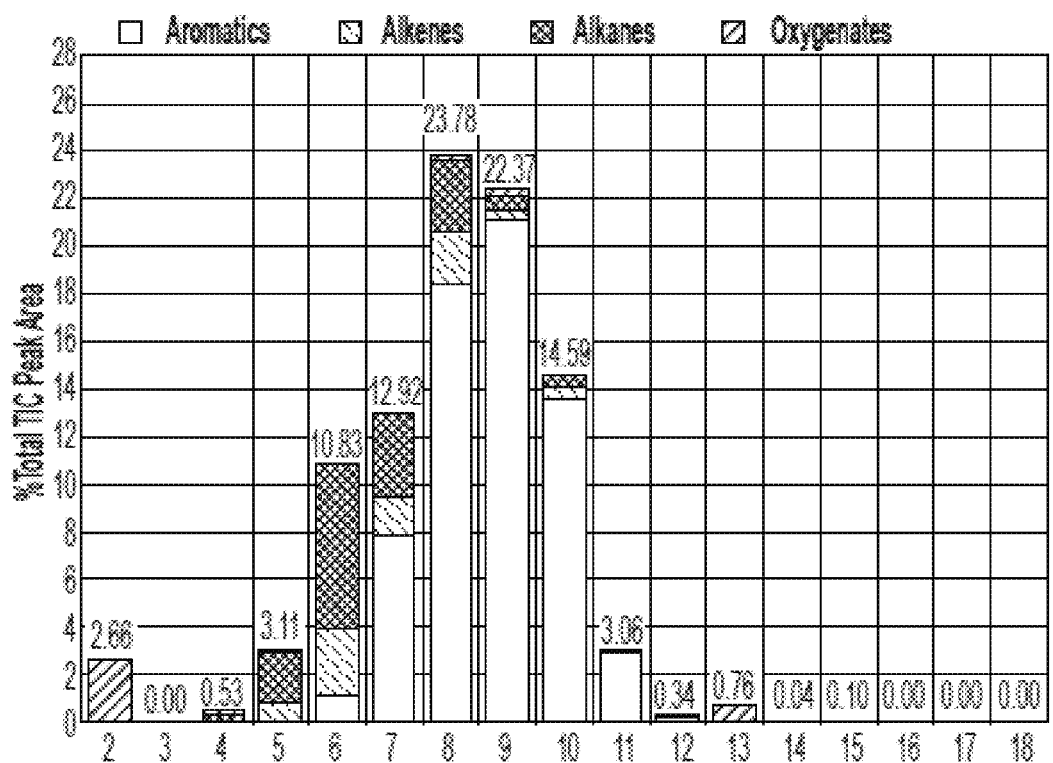
FIG. 33 provides a graphical description of the product distribution of aromatics, alkenes, alkanes and oxygenates of various carbon content in sample C5, which is a mixture of about 65% (v/v) of high-octane gasoline (HOG) generated by the catalytic processing of biomass-derived ethanol described herein, about 25% (v/v) of low-octane gasoline (LOG), generated by the catalytic processing of biomass-derived ethanol described herein, and about 10% of anhydrous ethanol derived from cellulosic-biomass.
Figure 33:
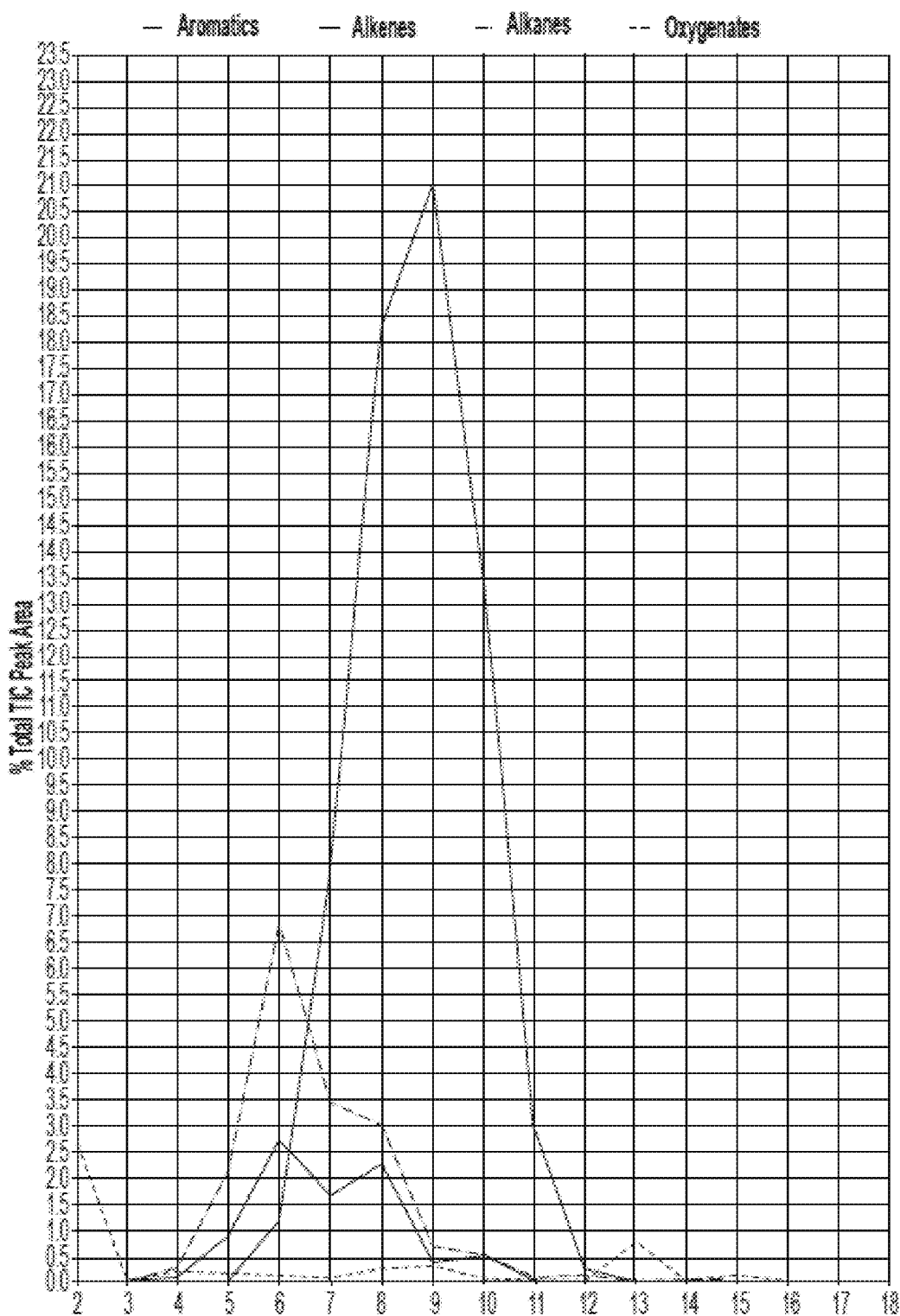

A graphical description of the product distribution of aromatics, alkenes, alkanes and oxygenates of various carbon content in sample C5, which is a mixture of about 65% (v/v) of high-octane gasoline (HOG) generated by the catalytic processing of biomass-derived ethanol described herein, about 25% (v/v) of low-octane gasoline (LOG), generated by the catalytic processing of biomass-derived ethanol described herein, and about 10% of anhydrous ethanol derived from cellulosic-biomass is shown in FIG. 33. Based on the total known components, it contained about 65.27% of aromatic hydrocarbons, about 8.37% of alkenes, about 16.88% of alkanes, and about 4.40% of oxygenated compounds (wt./wt.). FIG. 33 also provides a detailed breakdown of all the detectable compounds in sample C5.

Figure 34:
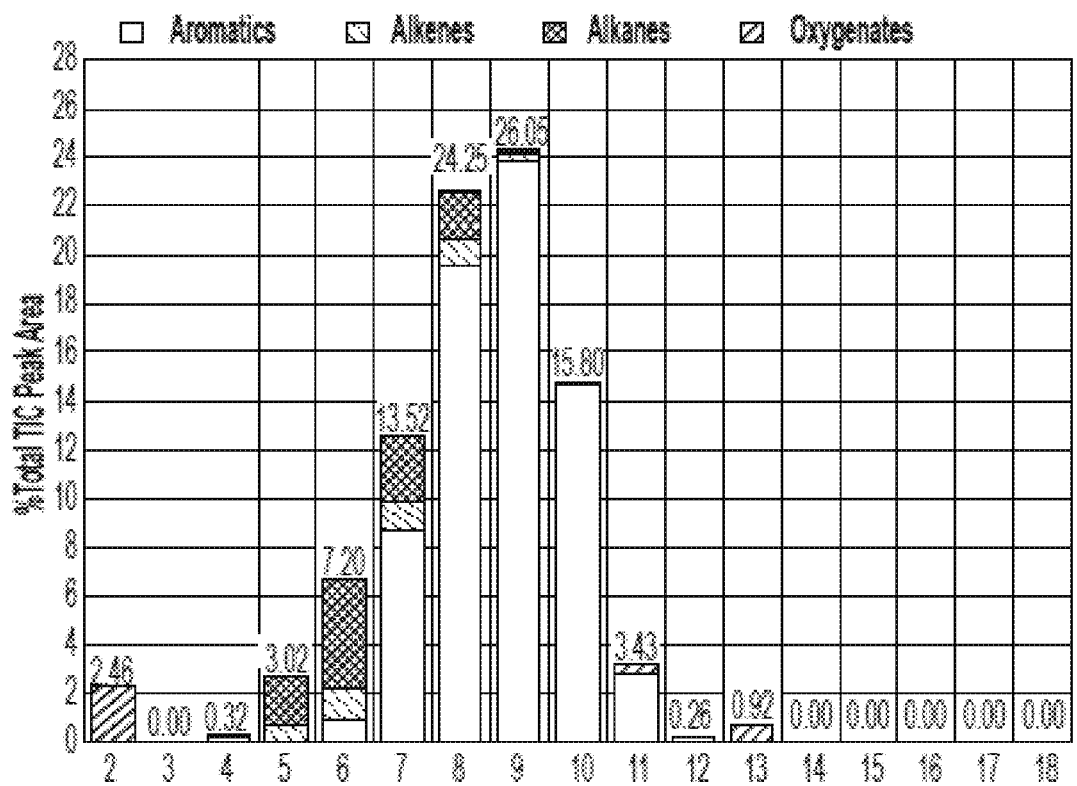
FIG. 34 provides a graphical description of the product distribution of aromatics, alkenes, alkanes and oxygenates of various carbon content in sample C6, which is a mixture of about 90% (v/v) of high-octane gasoline (HOG) generated by the catalytic processing of biomass-derived ethanol described herein, and about 10% of anhydrous ethanol derived from cellulosic-biomass.
Figure 34:
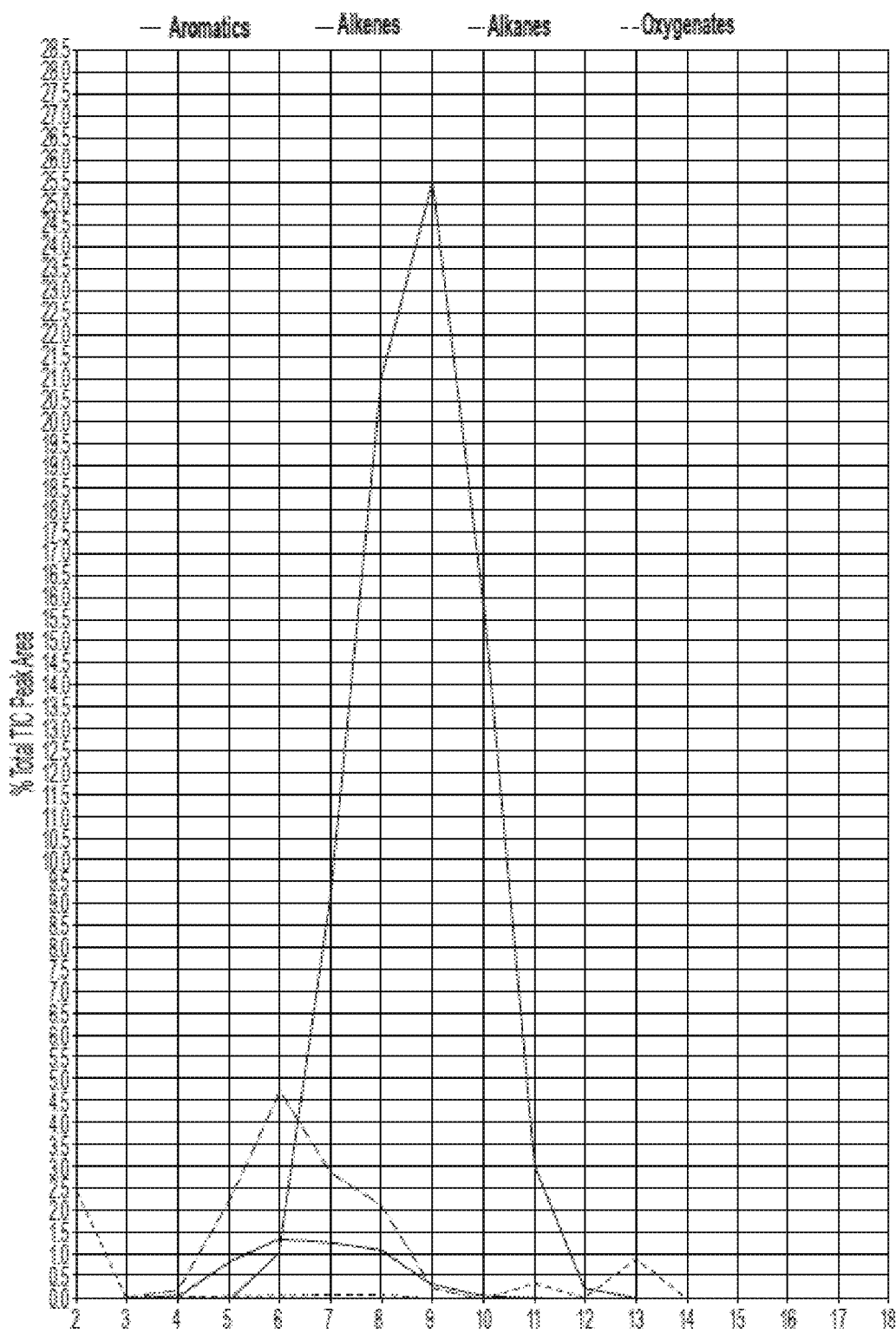

A graphical description of the product distribution of aromatics, alkenes, alkanes and oxygenates of various carbon content in sample C6, which is a mixture of about 90% (v/v) of high-octane gasoline (HOG) generated by the catalytic processing of biomass-derived ethanol described herein, and about 10% of anhydrous ethanol derived from cellulosic-biomass, is shown in FIG. 34. Based on the total known components, it contained about 75.96% of aromatic hydrocarbons, about 4.98% of alkenes, about 12.31% of alkanes, and about 3.91% of oxygenated compounds (wt./wt.). FIG. 34 also provides a detailed breakdown of all the detectable compounds in sample C6.

FIG. 35 provides the results of analyzing samples of blends of high-octane gasoline of samples C1-C6, described above. The API Gravity @ 60° F. is measured according to ASTM D4052, the Dry Vapor Pressure Equivalent (DVPE) EPA is measured according to ASTM D5191-13, the gross heat of combustion is measured according to ASTM D4809, the research octane number (RON) is measured according to ASTM D2699, the motor octane number (MON) is measured according to ASTM D2700, and the antiknock index or octane rating ((RON+MON)/2) is measured according to D4814-X1.4. The data shows that blending the gasolines produced by the processes described herein does not significantly alter the RON, MON, gross heat of combustion and antiknock index of the blend. This demonstrates that the unblended cellulosic-biomass derived gasolines, in particular the HOGs have a high octane rating similar to that of Trufuel®. In fact, sample C6, which contains only 90% of HOG produced by the processes described herein, and 10% anhydrous cellulosic ethanol has a high RON of 101.3, MON of 89.2, antiknock index of 95.2, and gross heat of combustion of 128,832 BTU/gal.

FIG. 36 provides the results of analyzing samples of blends of high-octane gasoline. Sample B1 is Trufuel®; sample B2 is a mixture of 5% (v/v) of high-octane gasoline (HOG) generated by the catalytic processing of biomass-derived ethanol described herein, and 95% (v/v) of Trufuel®; sample B3 is a mixture of 10% (v/v) of high-octane gasoline (HOG) generated by the catalytic processing of biomass-derived ethanol described herein, and 90% (v/v) of Trufuel®; sample B4 is a mixture of 20% (v/v) of high-octane gasoline (HOG) generated by the catalytic processing of biomass-derived ethanol described herein, and 80% (v/v) of Trufuel®; sample B5 is a mixture of 20% (v/v) of high-octane gasoline (HOG) generated by the catalytic processing of biomass-derived ethanol described herein, 75% (v/v) of Trufuel®, and 5% anhydrous ethanol derived from cellulosic-biomass. The Dry Vapor Pressure Equivalent (DVPE) EPA is measured according to ASTM D5191, the gross heat of combustion is measured according to ASTM D4809, the research octane number (RON) is measured according to ASTM D2699, the motor octane number (MON) is measured according to ASTM D2700, and the antiknock index or octane rating ((RON+MON)/2) is measured according to D4814-X1.4. The data shows that blending the HOGs produced by the processes described herein does not significantly alter the RON, MON, gross heat of combustion and antiknock index of the blend. This demonstrates that the unblended cellulosic-biomass derived gasolines, in particular the HOGs, have a high octane rating similar to that of Trufuel®. In fact, sample B5, which contains the greatest amount of HOG among the studied samples (20% (v/v)) has a high RON of 100, MON of 91.2, antiknock index of 95.6, and gross heat of combustion of 124,355 BTU/gal.

FIG. 37 provides the results of analyzing samples of blends of low-octane gasoline. Sample 1 is Trufuel®, a commercially available premixed high-octane ethanol-free fuel; sample 2 is a mixture of 5% (v/v) of low-octane gasoline (LOG) generated by the catalytic processing of biomass-derived ethanol described herein, and 95% (v/v) of Trufuel®; sample 3 is a mixture of 10% (v/v) of low-octane gasoline (LOG) generated by the catalytic processing of biomass-derived ethanol described herein, and 90% (v/v) of Trufuel®; sample 4 is a mixture of 20% (v/v) of low-octane gasoline (LOG) generated by the catalytic processing of biomass-derived ethanol described herein, and 80% (v/v) of Trufuel®; sample 5 is a mixture of 20% (v/v) of low-octane gasoline (LOG) generated by the catalytic processing of biomass-derived ethanol described herein, 75% (v/v) of Trufuel®, and 5% anhydrous ethanol derived from cellulosic-biomass. The research octane number (RON) is measured according to ASTM D2699, the motor octane number (MON) is measured according to ASTM D2700, and the antiknock index or octane rating ((RON+MON)/2) is measured according to D4814-X1.4.

A Method of Producing Fuel with Reduced Global Warming Potential (GWP)

Provided herein is a method of producing fuel comprising: receiving harvested cellulosic-biomass; treating the cellulosic-biomass in a facility with an electron beam sufficient to reduce its recalcitrance; saccharifying the recalcitrance-reduced biomass to produce sugars and unsaccharified biomass; fermenting the sugars to produce fuel; combusting the fuel in a vehicle; generating heat and power from the unsaccharified biomass in the facility, and using the remaining unprocessed unsaccharified biomass as animal feed; wherein the method has a Global Warming Potential (GWP) in $gCO_2$ eq/MJ at least about 25% less in comparison to a fuel generation process from starch-derived ethanol, sugar-derived ethanol or conventional gasoline.

In some embodiments, the method further comprises transporting the cellulosic-biomass to a facility. In some embodiments, the method further comprises transporting the fuel to a blending point and a point of use. In one embodiment, the fuel produced by this method is ethanol. In some embodiments, the starch-derived ethanol is obtained from corn. In some embodiments, the sugar-derived ethanol is obtained from sugar. The cellulosic-biomass used in the method described herein can be corn cobs, soybean stover, corn stover, rice straw, rice hulls, barley straw, corn cobs, wheat straw, canola straw, rice straw, oat straw, oat hulls, corn fiber, recycled wood pulp fiber, sawdust, hardwood, for example aspen wood and sawdust, softwood, or a combination thereof.

In some embodiments, the method for producing fuel described herein reduces the Global Warming Potential (GWP) in $gCO_2$ eq/MJ by at least about 5%, about 10%, about 20%, about 25%, about 30%, about 35%, about 40%, about 45%, about 50%, about 55%, about 60%, about 65%, about 70%, about 75%, or about 80% in comparison to a fuel generation process from corn ethanol, sugarcane ethanol or conventional gasoline.

A Life Cycle Assessment (LCA) was conducted to evaluate the Global Warming Potential (GWP) of the ethanol derived from cellulosic-biomass (for, example corn stover) by the processes described herein as compared to US corn grain ethanol, Brazilian sugarcane ethanol, and US conventional gasoline in fuel blends including E100 (98.5% ethanol with 2.5% gasoline for denaturing purposes as required by the law), E10 (10% ethanol), E85 (85% ethanol), and conventional gasoline. Regulatory frameworks, such as the Renewable Fuels Standard (RFS2) and California Low Carbon Fuel Standard (CA LCFS) focus primarily on GWP and are a significant economy driver of the adoption of cellulosic ethanol. The GWP was assessed using the Intergovernmental Panel on Climate Change's (IPCC) Fifth Assessment Report (AR5) 100-year time-scale excluding biogenic carbon method.

The LCA was conducted from cradle-to-grave, which included the upstream production of corn stover as a feedstock for the processes described herein as well as the production of all other inputs to the process (e.g., natural gas, electricity, and chemicals) as well as the downstream combustion of the fuel in an average US passenger car. This ethanol production results in a biomass solid co-product that can be burned in a Combined Heat and Power (CHP) facility to produce on-site heat and electricity that satisfies most of the facility's needs. The remaining biomass solids can be sold locally as an animal feed which displaces corn and soy in the diets of livestock.

Figures 39, 40:
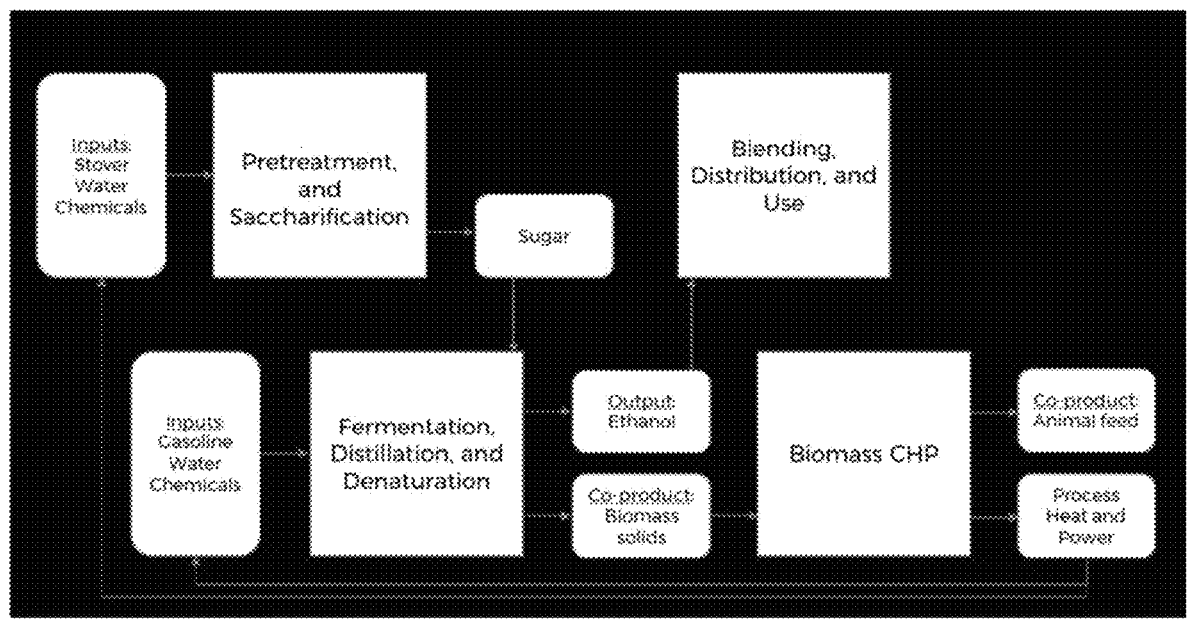
FIG. 39 provides a diagram of the process for generating ethanol from cellulosic-biomass from cradle-to-grave, which formed the basis of the LCA analysis shown in FIG. 38.
FIG. 40 describes the compositions (volume %) of samples D1 to D6. Sample D1 is 100% Trufuel®; sample D2 is a mixture of 90% (v/v) high-octane gasoline (HOG) (Fraction 2b) generated by the catalytic processing of biomass-derived ethanol described herein, and 10% (v/v) of ethanol; sample D3 is 100% (v/v) high-octane gasoline (HOG) (Fractions 1b and 2b) generated by the catalytic processing of biomass-derived ethanol described herein; sample D4 is 100% (v/v) high-octane gasoline (HOG) (Fraction 2b) generated by the catalytic processing of biomass-derived ethanol described herein; sample D5 is 100% (v/v) of high-octane gasoline (HOG) (all fractions) generated by the catalytic processing of biomass-derived ethanol described herein; sample D6 is a mixture of 50% (v/v) low-octane gasoline (LOG) (Fractions 1a and 2a) generated by the catalytic processing of biomass-derived ethanol described herein, and 50% (v/v) of ethanol. Fraction 1 is a portion of the HOG or LOG that has a boiling range below 30° C. ("low boiling range fractions"), Fraction 2 is a portion of the HOG or LOG that has a boiling range between 35 to 200° C. ("mid boiling range fractions"), and Fraction 3 is a portion of the HOG or LOG that has a boiling range above 200° C. ("high boiling range fraction"). Letters "a" and "b" distinguishes the fractions from the HOG from the fractions from the LOG. For example, Fraction 1a represents low boiling range fractions from the LOG, while Fraction 1b represents low boiling range fractions from the HOG.

FIG. 39 provides a diagram of the process for generating ethanol from cellulosic-biomass from cradle-to-grave, which formed the basis of the LCA analysis. The process begins with production of cellulosic feedstock and ends with combustion of fuel. The specific phases of the fuel life cycle include:
Production and harvesting of cellulosic-biomass
Transportation of biomass to the processing facility
Pretreatment and enzyme treatment of biomass to produce saccharified sugars
Fermentation of sugar to produce ethanol
Distillation of ethanol fuel to remove water
Denaturation of ethanol to produce fuel-grade ethanol
On-site combined heat and power production
Transportation and distribution of fuel-grade ethanol to blending and point of use
Combustion of fuel in a passenger vehicle In addition, the above-described process uses a Combined Heat and Power (CHP) facility on-site. The CHP combusts the biomass solid co-product of the ethanol production. This heat and energy generated by combusting the biomass solids provides heat and power to other portions of the process. The remaining biomass solids are sold as an animal feed co-product. The transportation distance for co-product feed is 60 miles (97 km) from the facility based on the density of animal production in the region (USDA, 2017).

The key phases of production, transportation, and distribution of the comparative corn grain ethanol, sugarcane ethanol, and gasoline fuels mirror Xyleco fuel production. Modeling for all systems in this study were conducted in the LCA software GaBi ts, developed by thinkstep (http://www.gabi-software.com/America/index/). The comparative fuel dataset used for ethanol derived from corn is thinkstep USLCI (2013-2017), for ethanol derived from sugarcane is ecoinvent v3.3 (2015), and for regular gasoline mix is thinkstep (2013-2017). The average distance from refineries to filing station in the US is 93 miles (150 km), based on GaBi data documentation for gasoline, therefore, this distance has been applied to all fuels to maintain consistency of system boundaries. Combustion for all fuels is assumed in the same passenger vehicle with the same fuel efficiency in miles per gallon with adjustment made for the difference in energy density between ethanol and gasoline.

The GWP analysis resulting from the above-described calculation method is shown in FIG. 38. It provides the Global Warming Potential (GWP) (in $gCO_2$ eq/MJ) of fuel blends containing ethanol generated from cellulosic-biomass by the processes described herein in comparison with fuel blends containing US corn grain ethanol, Brazilian sugarcane ethanol and US conventional gasoline. Fuel blends of 100% ethanol (E100) (98.5% ethanol with 2.5% gasoline for denaturing purposes as required by the law), 10% ethanol (E10), 85% ethanol (E85), and conventional gasoline were compared.

As shown in FIG. 38, the ethanol produced by the processes described herein have a lower GWP by about 77% (for E100), about 62% (for E85), and about 5% (for E10) in comparison to corn grain ethanol. Similarly, the ethanol produced by the processes described herein lower the GWP by about 40% (for E100), about 25% (for E85), and about 2% (for E10) in comparison to sugarcane ethanol. Additionally, the ethanol produced by the processes described herein lower the GWP by about 83% (for E100), about 71% (for E85), and about 10% (for E10) in comparison to regular gasoline.

Superior Quality Unblended Cellulosic-Biomass Derived Gasoline—with Fractional Distillation Provided herein is an unblended cellulosic-biomass derived gasoline of high research octane number, and a method for producing the same. The unblended cellulosic-biomass derived gasoline is a liquid produced by the process described herein without further mixing or blending with substance not produced by the process described herein. In some instances, the unblended cellulosic-biomass derived gasoline includes a mix of liquid fractions produced by one or more processes described herein such as ethanols that do not get catalytically converted to the unblended cellulosic-biomass derived gasoline. And, in some embodiments, the unblended cellulosic-biomass derived gasoline comprises a liquid produced by the processes described herein that has been further distilled in the gasoline distillation with range from 900 F to 4100 F. In one embodiment, the unblended cellulosic-biomass derived gasoline is produced by catalytic processing of the cellulosic-biomass or a product derived therefrom. In one embodiment, the research octane number of the unblended cellulosic-biomass derived gasoline is greater than about 60, as determined by ASTM D2699. For example, the unblended gasoline can have a research octane number (RON) of greater than about 87, about 90, about 91, about 92, about 93, about 94, about 95, about 96, about 97, about 98, or about 99. This application refers to a number of ASTM methods or standards, including ASTM D2699 (approved Oct. 1, 2017), ASTM D2700 (approved Dec. 1, 2017), ASTM D5191 (approved Oct. 1, 2015), ASTM D4809 (approved May 1, 2013), ASTM D4814-X1.4 (approved Jan. 1, 2018), and ASTM D4052 (approved Dec. 1, 2016), ASTM D7039 (approved Jul. 1, 2015), ASTM D3606 (approved Dec. 1, 2017), ASTM D1296 (approved Jul. 1, 2012), ASTM E1064 (approved Apr. 1, 2016), ASTM D130 (approved Nov. 1, 2012), ASTM D4814-A1 (approved Jan. 1, 2018), all of which are incorporated here by reference. The catalyst used in this process can be any of the catalysts disclosed herein, including an alumina-based catalyst and/or a zeolite-based catalyst. In some embodiments, the catalyst is a mono-metallic catalyst, bi-metallic catalyst, or tri-metallic catalyst. In some embodiments, the catalysts contain metals selected from the group consisting of Pt, Pd, Sn, Re, Rh, Bi, Ba, Ti, Ni, and any combinations thereof.

In some embodiments, the unblended cellulosic-biomass derived gasoline may contain a mixture of different liquid fractions produced by the process described herein. In some embodiments, the fractions are separated based on their boiling range. For instance, in some embodiments, the unblended cellulosic-biomass derived gasoline may have a mix percentage of fractions with boiling ranges below 35° C. ("low boiling range"), with boiling range between 35° C. to about 200° C. ("mid boiling range"), and with boiling range above 200° C. ("high boiling range"). In some embodiments, the low, mid and high boiling ranges may be based on different temperature ranges.

In some embodiments, the unblended cellulosic-biomass derived gasoline has a relatively high motor octane number (MON) of greater than about 80 as determined by ASTM D2700 (approved Dec. 1, 2017). For example, the MON can be greater than about 80, about 81, about 82, about 83, about 84, about 85, about 86, about 87, about 88, about 89, about 90, or about 92.

In some embodiments, the unblended cellulosic-biomass derived gasoline may have an API Gravity at 60° F. of greater than about 40° API, as determined by ASTM D4052 (approved Dec. 1, 2016), e.g., greater than about 41° API, about 42° API, about 43° API, about 44° API, about 45° API, about 46° API, about 47° API, about 48° API, about 49° API, about 50° API, about 51° API, about 52° API, about 53° API, about 54° API, about 55° API, about 56° API, about 57° API, about 58° API, about 59° API, or about 60° API. In some embodiments, the API Gravity at 60° F. is between about 45 and 68° API, such as between about 48 and 65, or 50 and 62° API.

In some embodiments, the unblended cellulosic-biomass derived gasoline may have a sulfur content of less than about 3.2 mg/kg, as determined by ASTM D7039, e.g., less than about 3.0 mg/kg, about 2.5 mg/kg, about 2.0 mg/kg, about 1.5 mg/kg, or about 1.0 mg/kg.

In some embodiments, the unblended cellulosic-biomass derived gasoline may have a benzene level of less than about 1.0 vol. %, as determined by ASTM D3606, e.g., less than about 0.9 vol. %, about 0.8 vol. %, about 0.7 vol. %, about 0.6 vol. %, about 0.5 vol. %, about 0.4 vol. %, about 0.3 vol. %, or about 0.2 vol. %.

In some embodiments, the unblended cellulosic-biomass derived gasoline may have either characteristic or noncharacteristic odor as determined by ASTM D1296, but not foul.

In some embodiments, the unblended cellulosic-biomass derived gasoline may have a water content less than about 750 ppm by weight, as determined by ASTM D1064, e.g., less than about 500 mg/kg, about 400 mg/kg, about 300 mg/kg, about 250 mg/kg, or about 100 mg/kg.

In some embodiments, the unblended cellulosic-biomass derived gasoline has a dry vapor pressure equivalent, EPA that is greater than about 4 psi, as determined by ASTM D5191 (approved Oct. 1, 2015). For example, the dry vapor pressure equivalent, EPA can be greater than about 4 psi, about 5 psi, about 6 psi, about 7 psi, about 8 psi, about 9 psi, about 10 psi, or about 11 psi.

In some embodiments, the unblended cellulosic-biomass derived gasoline has a relatively high energy content such as a gross heat of combustion, as determined by ASTM D4809 (approved May 1, 2013). For example, the heat of combustion can be greater about 120,0000 Btu/gal, about 121,000 Btu/gal, about 122,000 Btu/gal, about 123,000 Btu/gal, about 124,000 Btu/gal, about 125,000 Btu/gal, about 126,000 Btu/gal, or about 128,000 Btu/gal.

In some embodiments, the unblended cellulosic-biomass derived gasoline has copper strip corrosion of 1 or less, as determined by ASTM D130. For example, 1a or 1b.

In some embodiments, the unblended cellulosic-biomass derived gasoline has silver strip corrosion of 1 or less, as determined by ASTM D4818-A1 (approved Jan. 1, 2018). For example, 1 or 0.

In some embodiments, the unblended cellulosic-biomass derived gasoline has a superior antiknock index or octane rating ((RON+MON)/2), as determined by ASTM D4814-X1.4 (approved Jan. 1, 2018). For example, the antiknock index can be greater than about 85, about 86, about 87, about 88, about 89, about 90, about 91, about 92, about 93, about 94, or about 95.

The unblended cellulosic-biomass derived gasoline described herein can have any combination of RON, MON, API Gravity at 60° F., sulfur content, benzene level, odor, water content, dry vapor pressure equivalent, gross heat of combustion, copper corrosion level, silver corrosion level, and antiknock index discussed above. For example, in one embodiment, the unblended cellulosic-biomass derived gasoline has an RON of greater than 97, a MON of greater than 85, an antiknock index greater than 91, an API gravity at 60° F. of between about 40 and 65, a sulfur content less than 3.2 mg/kg, a benzene level less than about 0.7 vol. %, a noncharacteristic odor, a water content less than 250 mg/kg, dry vapor pressure equivalent, EPA of 10.87 psi, a gross heat of combustion of between about 120,000 Btu/gal and 130,000 Btu/gal, a copper strip corrosion of 1a, a silver strip corrosion of 0, and an antiknock index of 91.4.

In one embodiment, the unblended cellulosic-biomass derived gasoline is produced by catalytically processing a cellulosic-biomass derived ethanol using the methods and the catalysts described herein. The cellulosic-biomass may be further pretreated with electron beam radiation. In some embodiments, the irradiating (with any radiation source or a combination of sources) is performed until the cellulosic-biomass receives a dose of at least 0.25 Mrad, e.g., at least 1.0 Mrad, at least 2.5 Mrad, at least 5.0 Mrad, or at least 10.0 Mrad. In some embodiments, the irradiating is performed until the material receives a dose of between 1.0 Mrad and 6.0 Mrad, e.g., between 1.5 Mrad and 4.0 Mrad. In some embodiments, the irradiating is performed at a dose rate of between 5.0 and 1500.0 kilorads/hour, e.g., between 10.0 and 750.0 kilorads/hour or between 50.0 and 350.0 kilorads/hours.

The unblended cellulosic-biomass derived gasoline produced by this invention can be a mixture of different hydrocarbons, such as linear or branched, mono-, and di-substituted $C_7$-$C_{16}$ alkanes, one or more of which is derived from cellulosic-biomass. It may also contain olefins, substituted or unsubstituted cycloalkanes (such as cyclopentanes, cyclohexanes), aromatics (such as benzene, toluene, naphthalenes), mono-substituted aromatics (such as methyl benzene), di-substituted aromatics (such as xylenes), and multi-substituted aromatics (such as trimethylbenzenes), one or more of which is derived from the cellulosic-biomass.

In some instances, the unblended cellulosic-biomass derived gasoline contains less than about 5 percent by weight benzene, such as less than 4.5, 4.0, 3.5, 3.0, 2.5, 2.0, 1.5, or even less than 1.0 percent by weight, e.g., less than 0.9, 0.8, 0.7, 0.6, 0.5, 0.4, 0.3, or even less than 0.25 percent by weight, e.g., less than 0.2, 0.15, 0.1 or even less than 0.05 percent by weight. In particular, the methods and catalysts can, for example, if desired, give the low benzene content directly, without active removal or separation, such as by distillation of the benzene from other components. Low concentrations of benzene can be useful in jurisdictions, such as the United States, that strictly limit its concentration in gasoline. In the United States, the USEPA sets a limit of benzene to be less than 1.3 percent by weight in gasoline.

In some embodiments, the unblended cellulosic-biomass derived gasoline described herein, such as a high-octane gasoline (HOG) contains a high aromatics content. For example, the unblended cellulosic-biomass derived gasoline may contain greater than about 25% (w/w), about 30% (w/w), about 35% (w/w), about 40% (w/w), about 45% (w/w), about 50% (w/w), about 55% (w/w), about 60%

(w/w), about 65% (w/w), about 70% (w/w), about 75% (w/w), about 80% (w/w), about 285% (w/w), about 90% (w/w) of aromatic hydrocarbons. In some instances, the aromatics can include toluene and xylenes, for example, as o, m- or para-xylene. In some instances, the predominant aromatics produced are toluene and xylenes, making up more than about 60 percent by weight of the aromatics produced, for example, greater than 65, 66, 67, 68, 69, 70, or 72 percent by weight or even greater, such as greater than about 75 percent by weight toluene and xylenes. In these instances, these materials can be distilled to produce pure toluene and xylenes, which can, respectively, be used to produce compounds such as toluene diisocyanate and isomers of terephthalic acid.

In some embodiments, the unblended cellulosic-biomass derived gasoline described herein, such as a HOG can have relatively low amount of alkanes. For example, the gasoline may contain less than about 50% (w/w), about 40% (w/w), about 30% (w/w), about 20% (w/w), about 10% (w/w), about 5% (w/w), about 2% (w/w), or about 1% (w/w) of alkanes. In some embodiments, the unblended cellulosic-biomass derived gasoline described herein, such as a HOG have a ratio of alkanes:aromatics of between about 1:10 and 1:100, such as between 1:10 and 1:50, or between 1:15 and 1:40 or between about 1:15 and 1:25.

In some embodiments, the unblended cellulosic-biomass derived gasoline described herein, such as a high-octane gasoline (HOG) contains a low content of dicyclopentadiene. For example, the gasoline may contain less than 0.4 percent by weight of dicyclopentadiene, such as less than 0.3, 0.2 or less, such as less than 0.1 percent by weight.

Note that, in some instances, adjusting the methods and/or the catalysts used in the catalytical process described herein may directly change the chemical properties of the resulting unblended cellulosic-biomass derived gasoline, and therefore, enabling the process to obtain an ideal concentration of hydrocarbons without the need for further dilution, distillation, or blending.

In some embodiments, the unblended cellulosic-biomass derived gasoline of such mixtures can be used directly as transportation fuels, as blending components in transportation fuels, such as commercial gasoline.

In one embodiment, the methods and catalysts can, for example, if needed, produce desired fuels, e.g., motor fuels, directly without upgrading or downgrading the fuel, such as by blending. For example, in some instances, the unblended gasoline produced from reactors can be used in fuel tanks of transportation vehicles without any additional treatment. The gasolines can be, for example, a regular octane grade, a mid-octane grade or a high-octane grade gasoline. In other instances, the gasolines produced from reactors can be used directly in fuel tanks of transportation vehicles only after filtering the fuel to remove particulates, and/or after distillation to remove low boiling fractions and/or high boiling fractions. In still other embodiments, the unblended gasolines obtained from the reactors described herein, can form a blend stock as obtained or after some purification. For example, in some instances, the unblended gasolines obtained from the reactors described herein can be a high-octane blending component, such as having a research octane number of greater than about 87, about 90, about 91, about 92, about 93, about 94, about 95, about 96, about 97, about 98, or about 99.

In some embodiments, the unblended cellulosic-biomass derived gasoline described herein has a boiling point range of about 35° C. to 200° C. In some embodiments, less than about 10%, about 9%, about 8%, about 7%, about 6%, about 5%, about 4%, about 3%, about 2%, or about 1% of the fraction of the unblended cellulosic-biomass derived gasoline boils at a temperature above 160° C. In some embodiments, weight percent of material boiling greater than 220° C. is less than 0.5 percent, such as less than 0.4, 0.3, 0.25 or less, such as less than 0.1 percent by weight.

In some embodiments, the unblended cellulosic-biomass derived gasoline described herein has an oxygenate level of less than about 0.5% (wt/.wt.), about 0.4% (wt/.wt.), about 0.25% (wt/.wt.), or about 0.1% (wt./wt.). As used herein, the term "oxygenates" is defined to include oxygen containing organic compounds such as alcohols, ethers, carbonyl compounds (aldehydes, ketones, carboxylic acids, carbonates, and the like). Representative oxygenates include, but are not necessarily limited to, lower straight chain or branched aliphatic alcohols, their unsaturated counterparts. Examples include but are not necessarily limited to: methanol; ethanol; n-propanol; isopropanol; C4-C10 alcohols; methyl ethyl ether; dimethyl ether; diethyl ether; di-isopropyl ether; methyl mercaptan; methyl formate, methyl acetate, formaldehyde; di-methyl carbonate; trimethyl orthoformate, and dimethyl ketone. Oxygenates such as acetaldehyde and acetone can be corrosive and can damage gaskets in engine components. They can also make the fuel hygroscopic, allowing it to absorb water, thereby impacting the quality of gasoline. So, in some embodiments having low oxygenate content in gasoline may be desirable.

In some embodiments, the unblended cellulosic-biomass derived gasoline described herein has a naphthalene content of less than about 0.5% (wt./wt.), about 0.4% (wt./wt.), about 0.25% (wt./wt.), or about 0.1% (wt./wt.). Naphthalenes are toxic air pollutants, add unfavorable smell to gasoline and are recognized as possible human carcinogens. So, in some embodiments having low naphthalene content in gasoline may be desirable.

In some embodiments, the unblended cellulosic-biomass derived gasoline described herein has an aromatic content of greater than about 75% (wt./wt.), about 76% (wt./wt.), about 77% (wt./wt.), about 78% (wt./wt.), about 79% (wt./wt.), about 80% (wt./wt.), about 85% (wt./wt.).

In some embodiments, the unblended cellulosic-biomass derived gasoline contains carbon between about 82 to 94 percent by weight, such as between 85 and 94, or 89 and 93 percent by weight.

In some embodiments, the unblended cellulosic-biomass derived gasoline contains hydrogen between about 6 and 18 percent by weight, such as between 6 and 10 or 7 and 9 percent by weight.

In some embodiments, the unblended cellulosic-biomass derived gasoline contains oxygen and nitrogen where each are less than 1 percent by weight, such as 0.9, 0.8, 0.7, 0.6, 0.5 or less, such as less than 0.25 or less, such as less than 0.1 or less, such as even less than 0.01 percent by weight.

In some embodiments, the unblended cellulosic-biomass derived gasoline has sulfur content meets or exceeds tier 3 requirements of less than 10 ppmw, such as less than less than 9, 8, 7, 6, 5, 4, or even less than 3, such as less than 1 ppmw.

In some embodiments, the unblended cellulosic-biomass derived gasoline has a total acid content, defined as a sum of all carboxylic and phenolic compounds present, of less than 0.25 percent by weight, such as less than 0.2, 0.15, 0.1 or less, such as less than 0.01 percent by weight.

In some embodiments, the unblended cellulosic-biomass derived gasoline described herein has the vapor pressure less than 14 psi. For example, the vapor pressure can be less than about 13 psi, about 12 psi, about 11 psi, about 10 psi, about 9 psi, about 8 psi, about 7 psi, about 6 psi or less, such as less than 5 psi.

EXAMPLES

Several biomass-derived fuel samples generated by the processes disclosed herein are further described in more detail below.

FIG. 40 describes the compositions (volume %) of samples D1 to D6. Sample D1 is 100% Trufuel®; sample D2 is a mixture of 90% (v/v) high-octane gasoline (HOG) (Fraction 2b) generated by the catalytic processing of biomass-derived ethanol described herein, and 10% (v/v) of ethanol; sample D3 is 100% (v/v) high-octane gasoline (HOG) (Fractions 1b and 2b) generated by the catalytic processing of biomass-derived ethanol described herein; sample D4 is 100% (v/v) high-octane gasoline (HOG) (Fraction 2b) generated by the catalytic processing of biomass-derived ethanol described herein; sample D5 is 100% (v/v) of high-octane gasoline (HOG) (all fractions) generated by the catalytic processing of biomass-derived ethanol described in Example 6; sample D6 is a mixture of 50% (v/v) low-octane gasoline (LOG) (Fractions 1a and 2a) generated by the catalytic processing of biomass-derived ethanol described in Example 7, and 50% (v/v) of ethanol. Fraction 1 is a portion of the HOG or LOG that has a boiling range below 30° C. ("low boiling range fractions"), Fraction 2 is a portion of the HOG or LOG that has a boiling range between 35 to 200° C. ("mid boiling range fractions"), and Fraction 3 is a portion of the HOG or LOG that has a boiling range above 200° C. ("high boiling range fraction"). Letters "a" and "b" distinguishes the fractions from the HOG from the fractions from the LOG. For example, Fraction 1a represents low boiling range fractions from the LOG, while Fraction 1b represents low boiling range fractions from the HOG.

For samples composed of a mix of fractions, FIG. 41 shows the volume percentages and the weight percentages of the fractions within. FIG. 41 shows that sample D3 is a HOG with about 13.06% (v/v) of Fraction 1b, and about 86.93% (v/v) of Fraction 2b. It also has about 11.89 wt. % of Fraction 1, and about 88.10 wt. % of Fraction 2. Sample D5 is a HOG with about 14.30% (v/v) of Fraction 1, about 93.29% (v/v) of Fraction 2, and about 2.40% (v/v) of Fraction 3. It also has about 11.97 wt. % of Fraction 1, about 85.22 wt. % of Fraction 2, and about 2.70 wt. % of Fraction 3. Lastly, Sample D6 is a LOG with about 12.56% (v/v) of Fraction 1, about 74.89% (v/v) of Fraction 2, and about 4.68% (v/v) of Fraction 3. In addition, it has about 18.61 wt. % of Fraction 1, about 75.71 wt. % of Fraction 2, and about 5.67 wt. % of Fraction 3.

Figure 42:
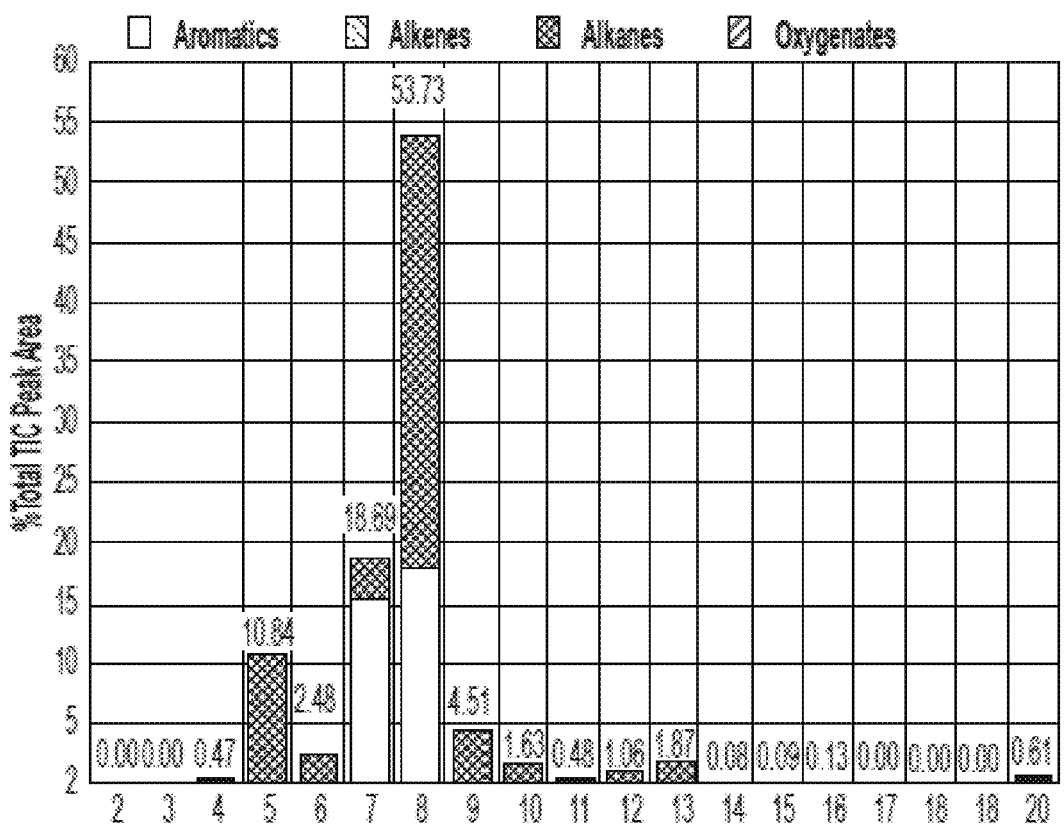
FIG. 42 provides a graphical description of the product distribution of aromatics, alkenes, alkanes and oxygenates of various carbon content in sample D1, which contains Trufuel®, a commercially available premixed high-octane ethanol-free fuel.
Figure 42:
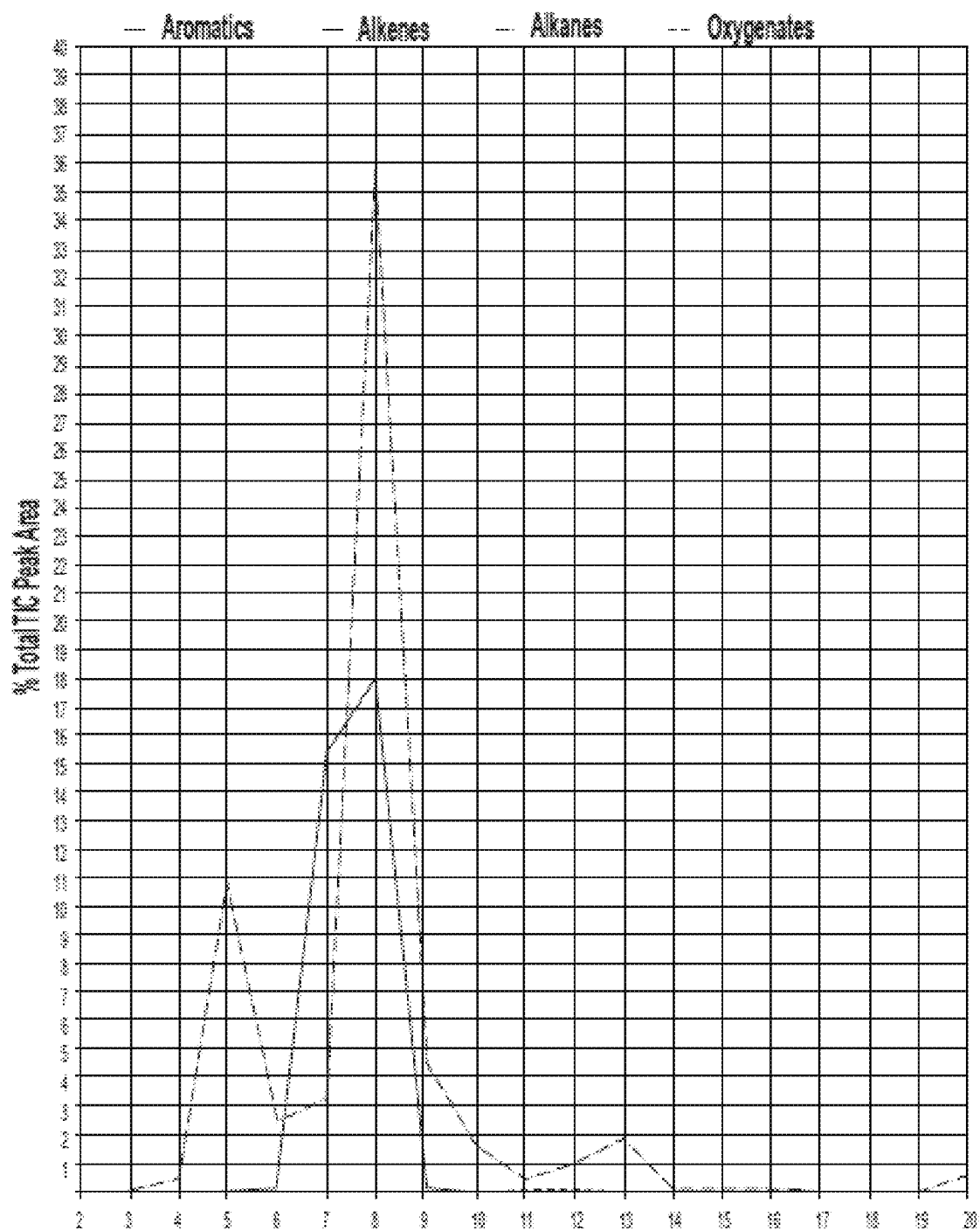

A graphical description of the product distribution of aromatics, alkenes, alkanes and oxygenates of various carbon content in sample D1, which contains Trufuel®, a commercially available premixed high-octane ethanol-free fuel, is shown in FIG. 42. Based on the total known components, it contained about 33.47% of aromatic hydrocarbons, about 0.01% of alkenes, about 63.07% of alkanes, and about 0.13% of oxygenated compounds (wt./wt.). FIG. 42 also provides a detailed breakdown of all the detectable compounds in sample D1.

Figure 43:
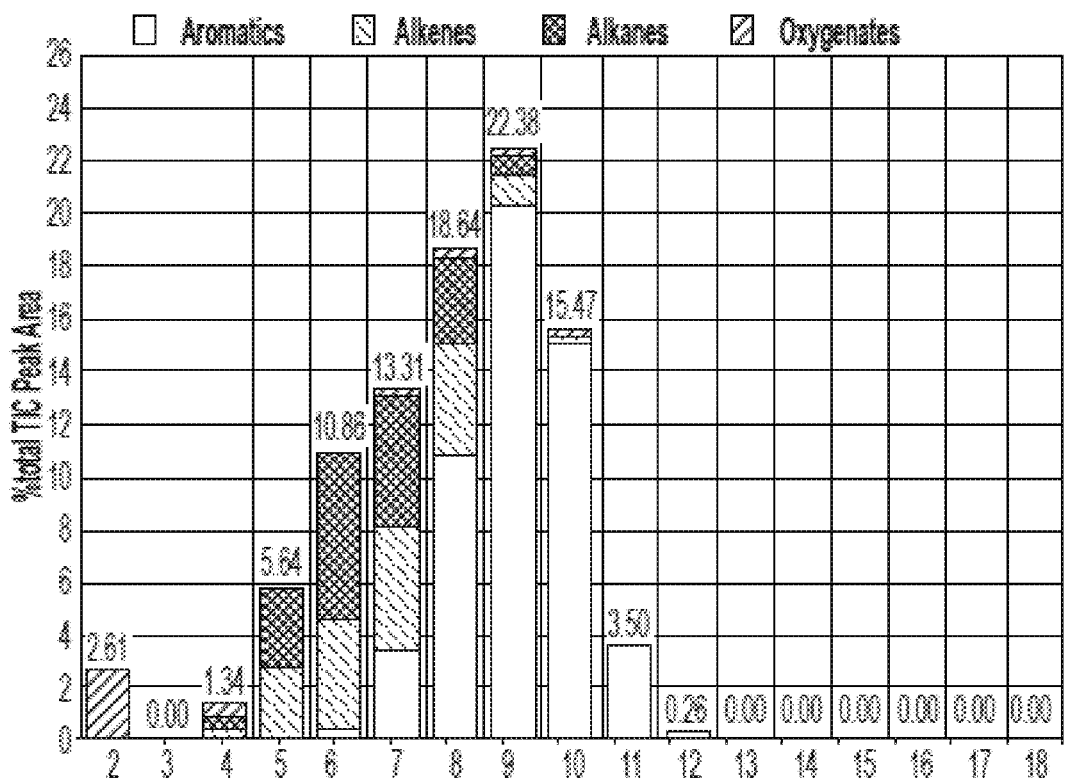
FIG. 43 provides a graphical description of the product distribution of aromatics, alkenes, alkanes and oxygenates of various carbon content in sample D2, which is a mixture of about 90% (v/v) of Fraction 2b distilled from the high-octane gasoline (HOG) generated by the catalytic processing of biomass-derived ethanol described herein, and about 10% (v/v) of biomass-derived ethanol.
Figure 43:
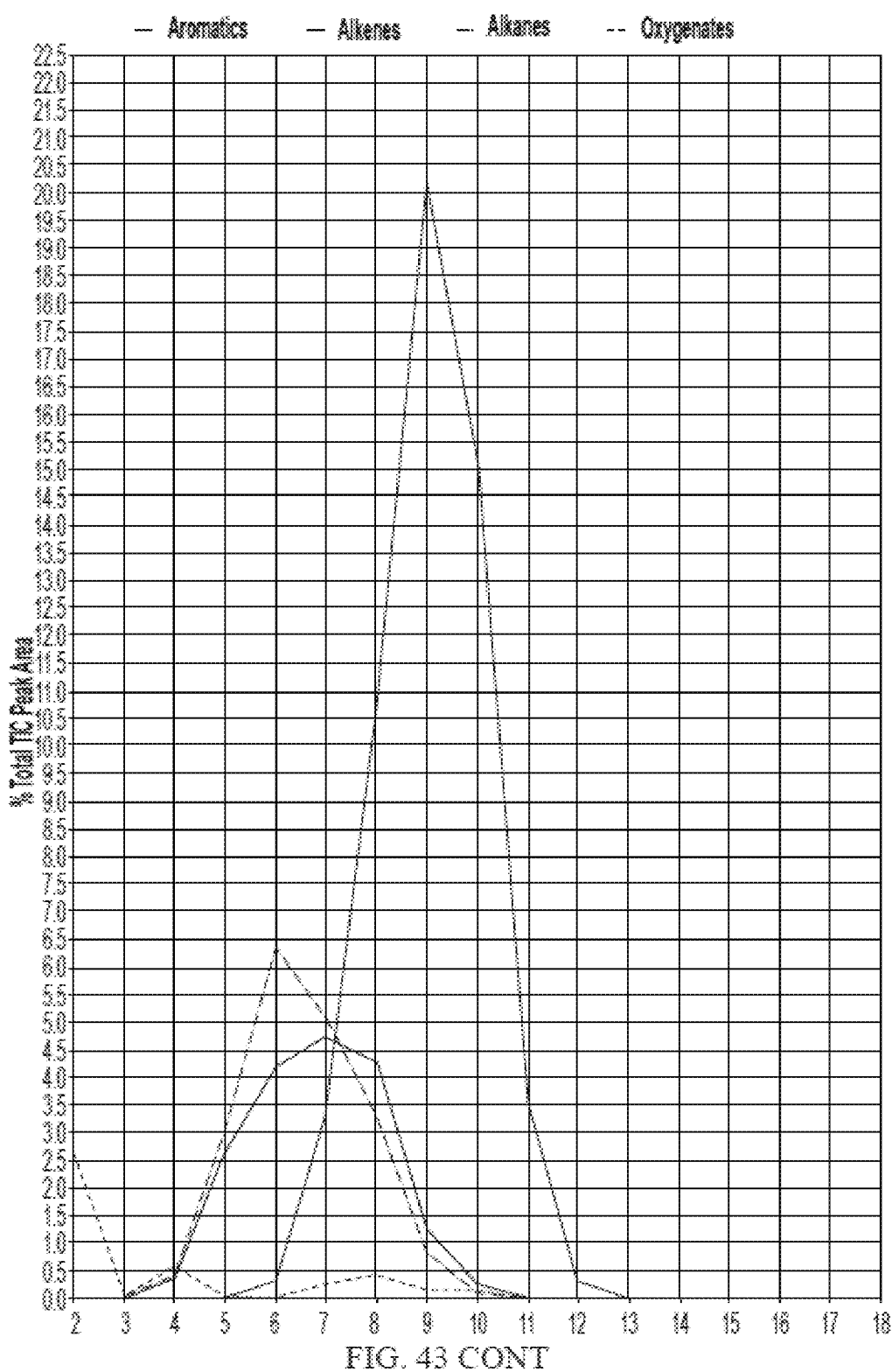

A graphical description of the product distribution of aromatics, alkenes, alkanes and oxygenates of various carbon content in sample D2, which is a mixture of about 90% (v/v) of Fraction 2b distilled from the high-octane gasoline (HOG) generated by the catalytic processing of biomass-derived ethanol described herein, and about 10% (v/v) of biomass-derived ethanol, is shown in FIG. 43. Based on the total known components, it contained about 53.79% of aromatic hydrocarbons, about 17.61% of alkenes, about 18.64% of alkanes, and about 3.64% of oxygenated compounds (wt./wt.). FIG. 43 also provides a detailed breakdown of all the detectable compounds in sample D2.

Figure 44:
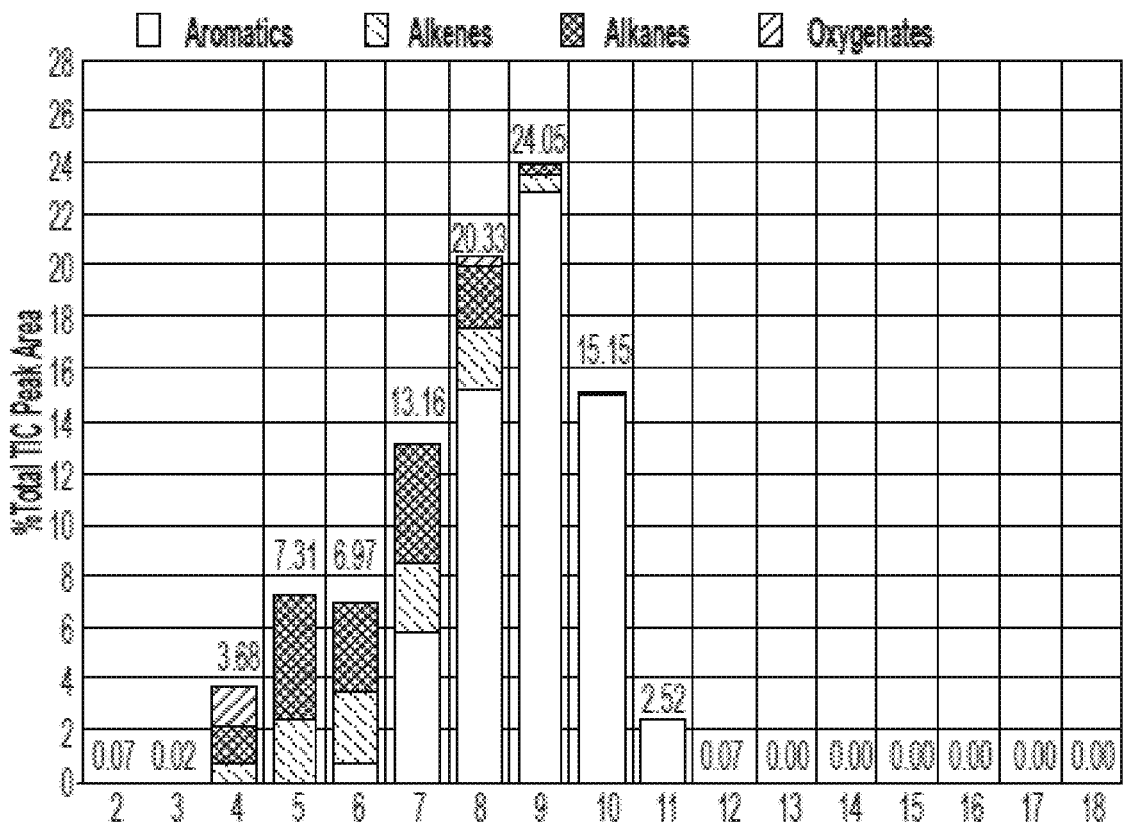
FIG. 44 provides a graphical description of the product distribution of aromatics, alkenes, alkanes and oxygenates of various carbon content in sample D3, which contains 100% (v/v) of Fraction 1b and Fraction 2b of the high-octane gasoline (HOG) generated by the catalytic processing of biomass-derived ethanol described herein.
Figure 44:
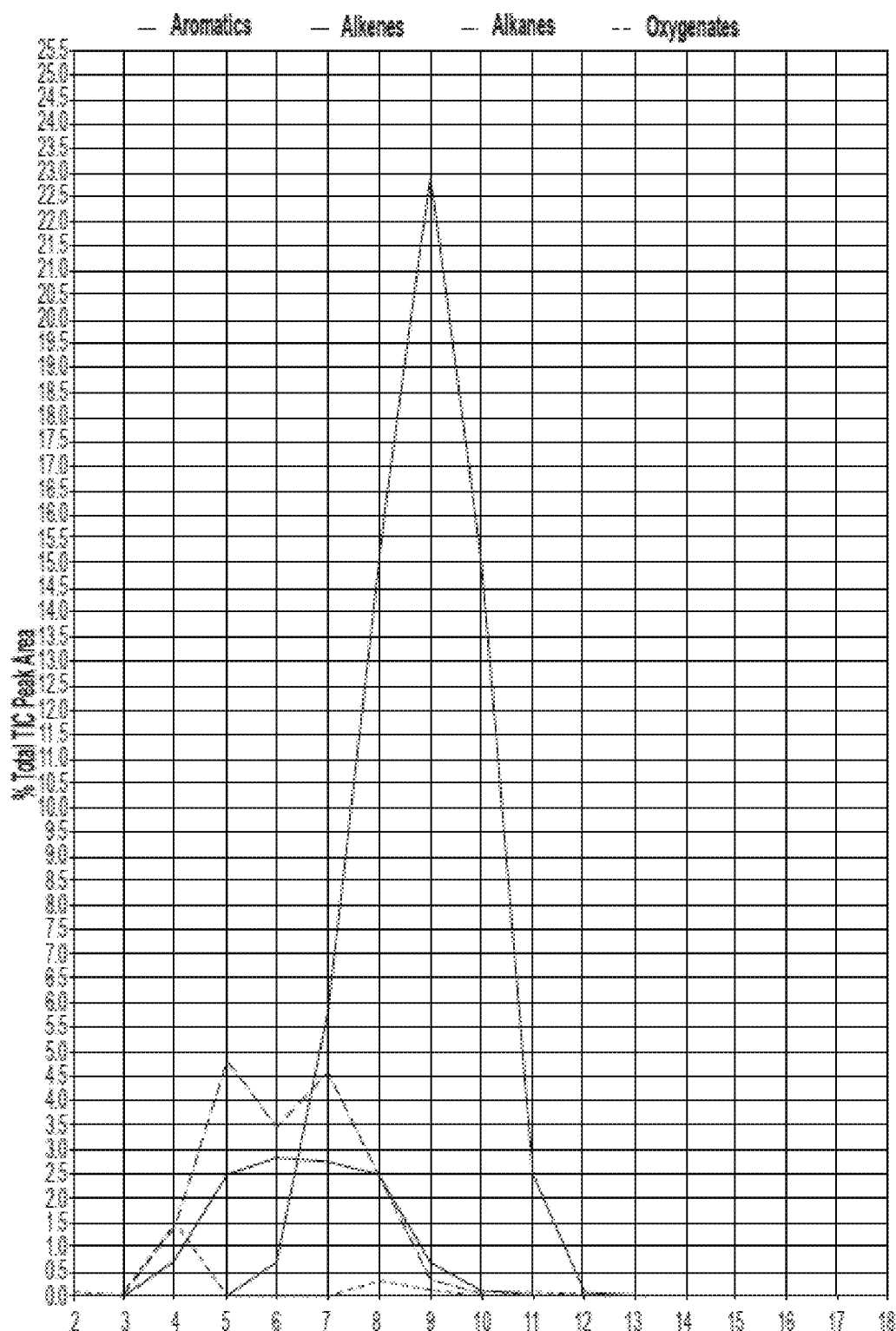

A graphical description of the product distribution of aromatics, alkenes, alkanes and oxygenates of various carbon content in sample D3, which contains 100% (v/v) of Fraction 1b and Fraction 2b of the high-octane gasoline (HOG) generated by the catalytic processing of biomass-derived ethanol described herein, is shown in FIG. 44. Based on the total known components, it contained about 62.51% of aromatic hydrocarbons, about 11.96% of alkenes, about 16.97% of alkanes, and about 1.72% of oxygenated compounds (wt./wt.). FIG. 44 also provides a detailed breakdown of all the detectable compounds in sample D3.

Figure 45:
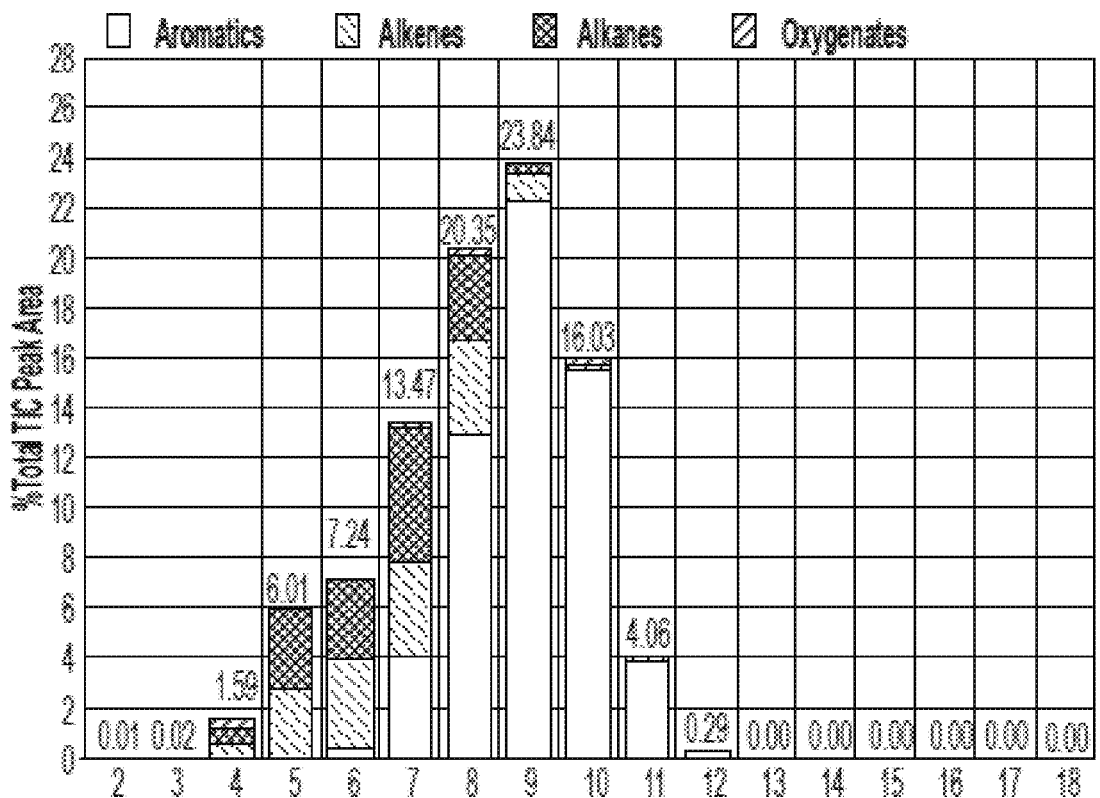
FIG. 45 provides a graphical description of the product distribution of aromatics, alkenes, alkanes and oxygenates of various carbon content in sample D4, which contains 100% (v/v) of Fraction 2b of the high-octane gasoline (HOG) generated by the catalytic processing of biomass-derived ethanol described herein.
Figure 45:
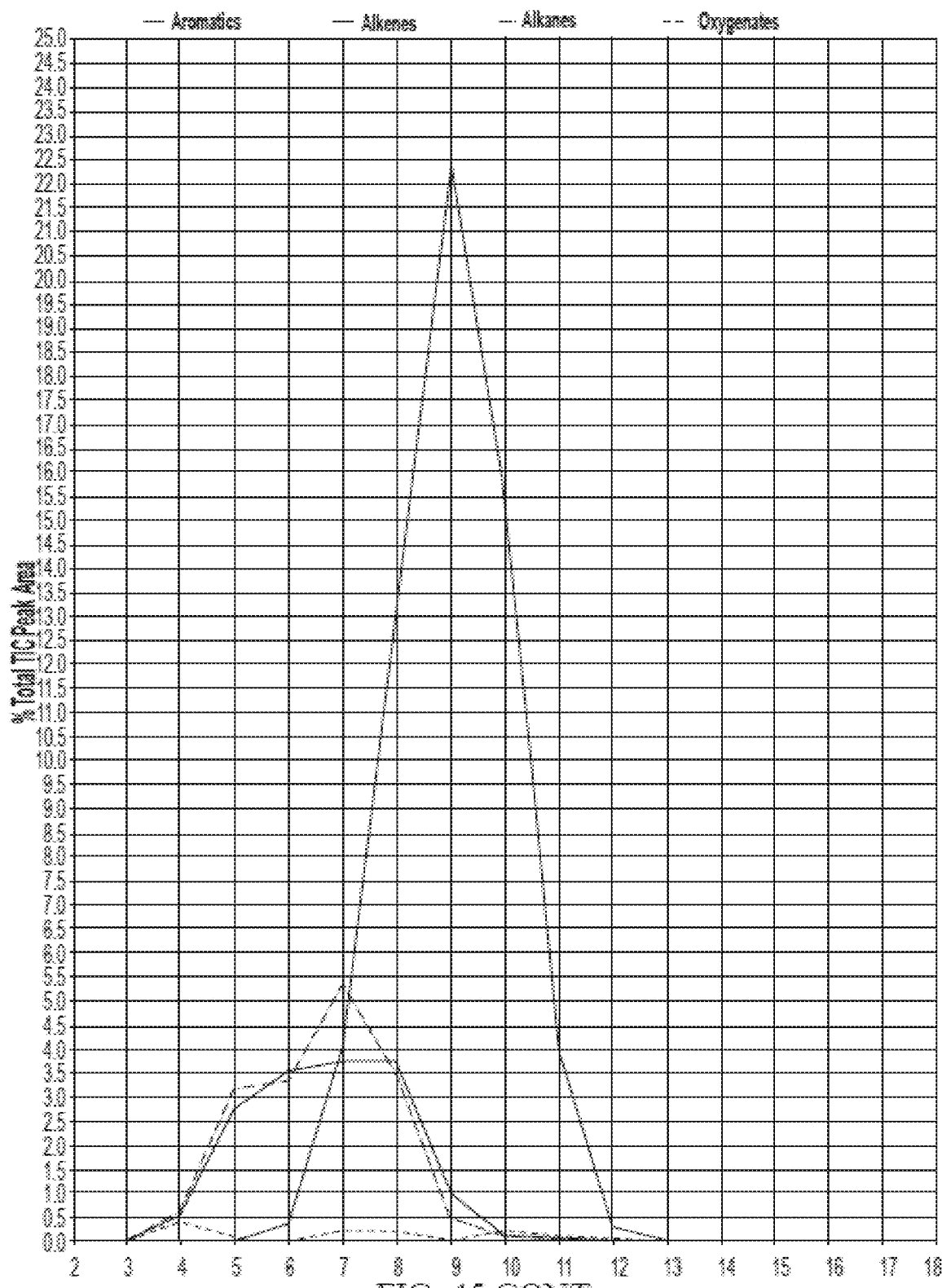

A graphical description of the product distribution of aromatics, alkenes, alkanes and oxygenates of various carbon content in sample D4, which contains 100% (v/v) of Fraction Fraction 2b of the high-octane gasoline (HOG) generated by the catalytic processing of biomass-derived ethanol described herein, is shown in FIG. 45. Based on the total known components, it contained about 60.04% of aromatic hydrocarbons, about 15.48% of alkenes, about 16.39% of alkanes, and about 0.85% of oxygenated compounds (wt./wt.). FIG. 45 also provides a detailed breakdown of all the detectable compounds in sample D4.

Figure 46:
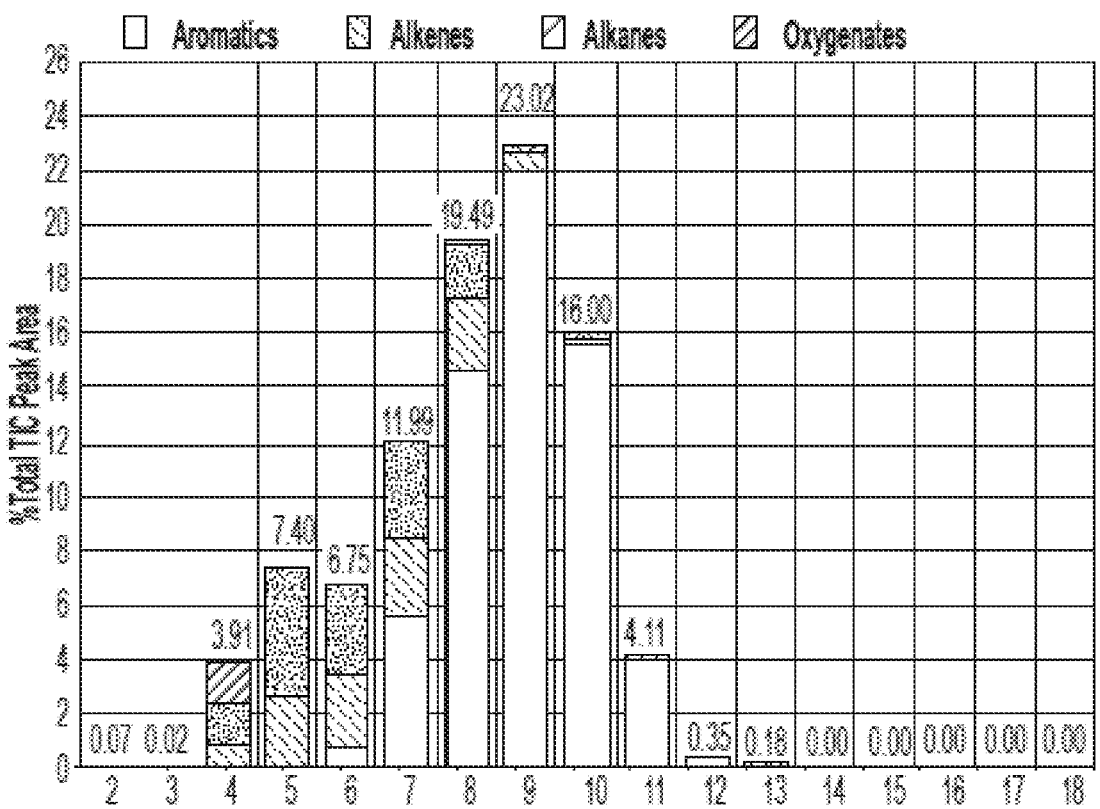
FIG. 46 provides a graphical description of the product distribution of aromatics, alkenes, alkanes and oxygenates of various carbon content in sample D5, which contains 100% (v/v) of the high-octane gasoline (HOG) generated by the catalytic processing of biomass-derived ethanol described herein without further distillation.
Figure 46:
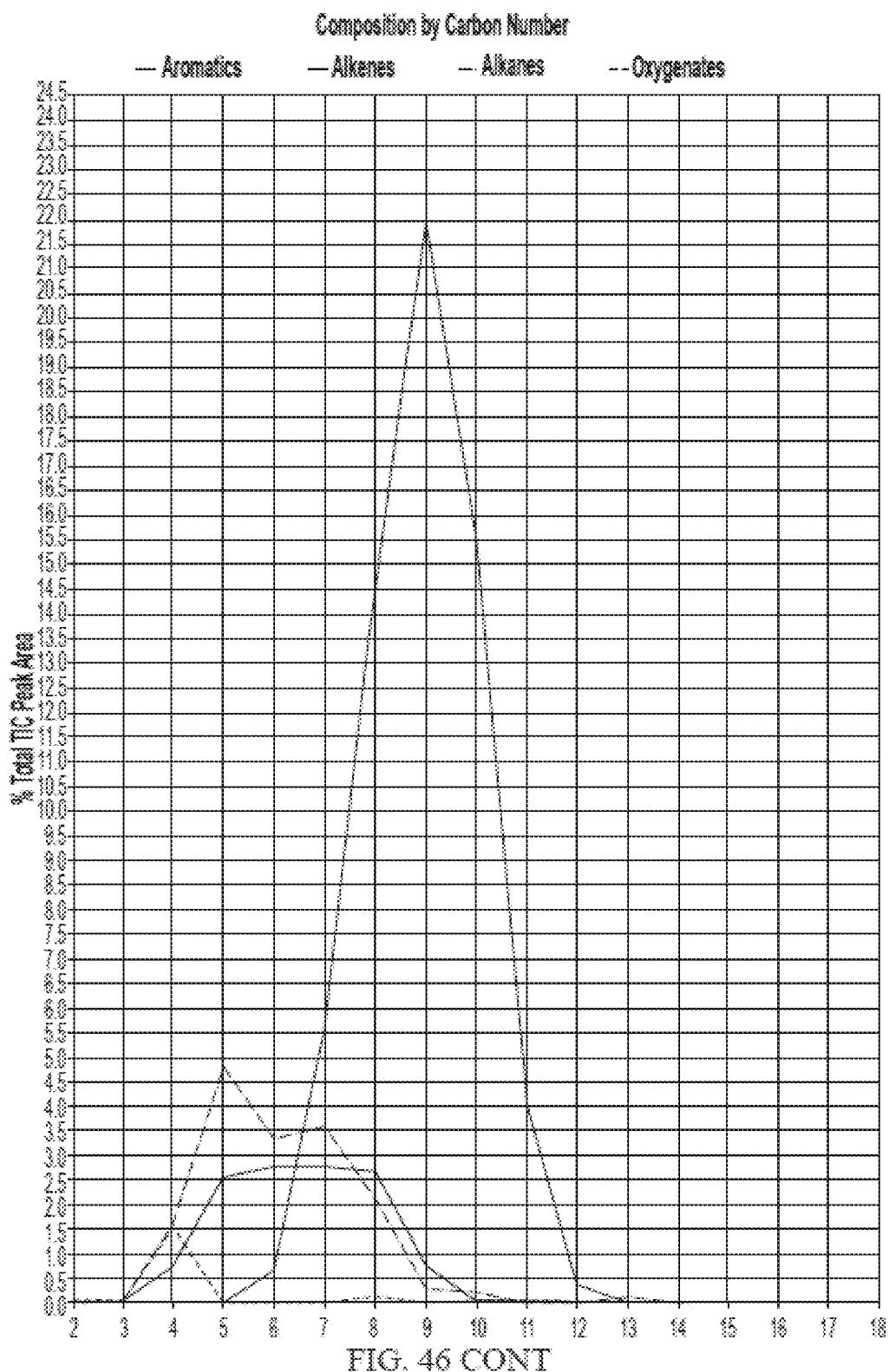

A graphical description of the product distribution of aromatics, alkenes, alkanes and oxygenates of various carbon content in sample D5, which contains 100% (v/v) of the high-octane gasoline (HOG) generated by the catalytic processing of biomass-derived ethanol described herein without further distillation, is shown in FIG. 46. Based on the total known components, sample D5 contained about 62.98% of aromatic hydrocarbons, about 12.41% of alkenes, about 16.02% of alkanes, and about 1.74% of oxygenated compounds (wt./wt.). FIG. 46 also provides a detailed breakdown of all the detectable compounds in sample D5.

Figure 47:
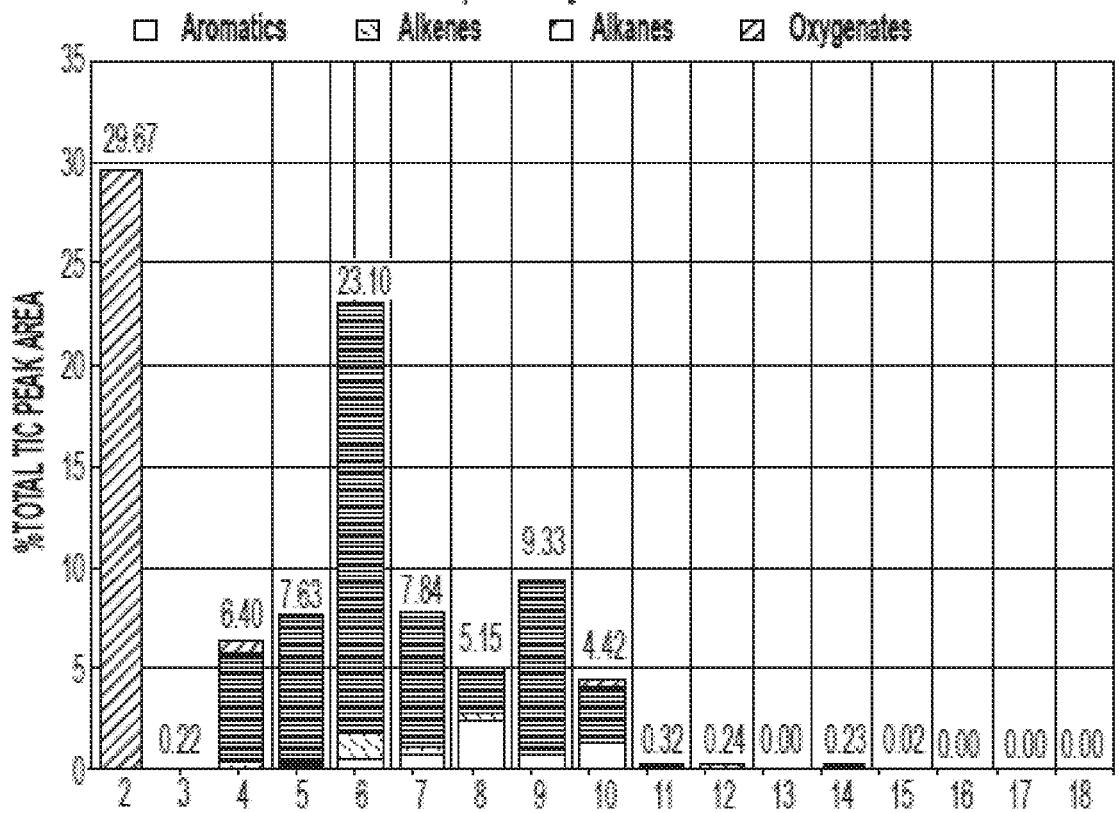
FIG. 47 provides a graphical description of the product distribution of aromatics, alkenes, alkanes and oxygenates of various carbon content in sample D6, which is a mixture of about 50% (v/v) of fractions 1a and 2a distilled from the low-octane gasoline (LOG) generated by the catalytic processing of biomass-derived ethanol described herein, and about 50% (v/v) of biomass-derived ethanol.
Figure 47:
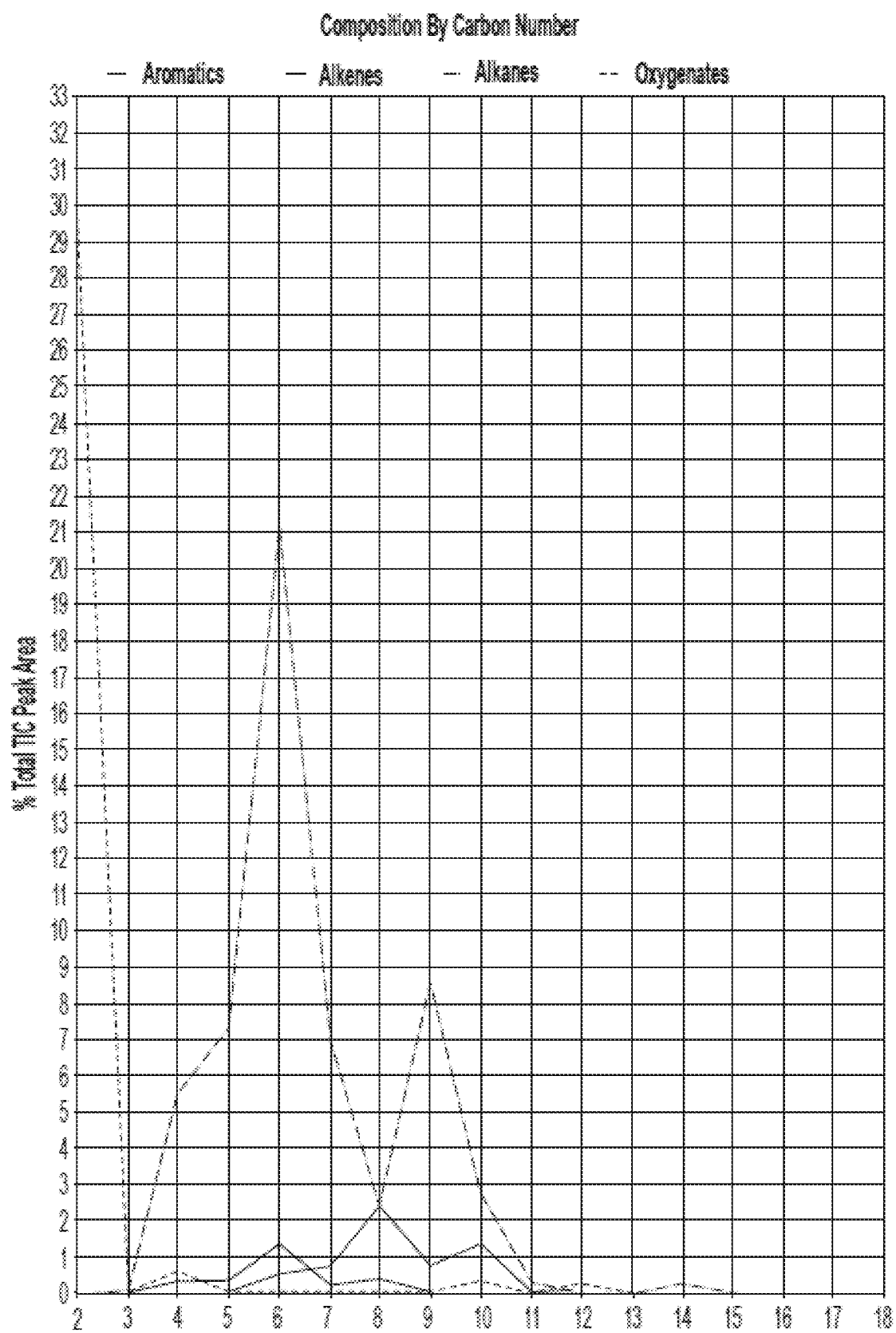

A graphical description of the product distribution of aromatics, alkenes, alkanes and oxygenates of various carbon content in sample D6, which is a mixture of about 50% (v/v) of fractions 1a and 2a distilled from the low-octane gasoline (LOG) generated by the catalytic processing of biomass-derived ethanol described herein, and about 50% (v/v) of biomass-derived ethanol, is shown in FIG. 47. Based on the total known components, it contained about 5.77% of aromatic hydrocarbons, about 2.61% of alkenes, about 55.00% of alkanes, and about 30.99% of oxygenated compounds (wt./wt.). FIG. 47 also provides a detailed breakdown of all the detectable compounds in sample D6.

FIG. 48 provides the results of analyzing samples of blends of high-octane gasoline of samples D1-D6, described above. The API Gravity @ 60° F. is measured according to ASTM D4052, the Dry Vapor Pressure Equivalent (DVPE) EPA is measured according to ASTM D5191-13, the gross heat of combustion is measured according to ASTM D4809, the research octane number (RON) is measured according to ASTM D2699, the motor octane number (MON) is measured according to ASTM D2700, the sulfur content is measured according to ASTM D7039, the benzene content is measured according to ASTM D3606, the odor is measured according to ASTM D1296, the water content is measured according to ASTM E1064, the corrosion to copper strips is measured according to ASTM D130, and the corrosion to silver strips is measured according to ASTM D4814-A1, and the antiknock index or octane rating ((RON+MON)/2) is measured according to D4814-X1.4. The data shows that blending the gasolines produced by the processes described herein does not significantly alter the RON, MON, gross heat of combustion and antiknock index of the blend. This demonstrates that the unblended cellulosic-biomass derived gasolines, in particular the HOGs have a high octane rating similar to that of Trufuel®. In fact, sample D5, which contains only 100% of HOG produced by the processes described herein has a high RON of 97.4, MON of 85.3, antiknock index of 91.4, and gross heat of combustion of 128,194 BTU/gal. Notably, it also contains other desirable attributes similar to that of Trufuel®. For instance, the sulfur level is below 3.2 mg/kg, the odor level is noncharacteristic, the corrosion to copper strips is at 1a, and the corrosion to silver strips is at 0.

Methods for Producing the Unblended Gasoline

Provided herein is an exemplary method for preparing unblended gasoline comprising: treating a lignocellulosic biomass with a beam of electrons and saccharifying the irradiated biomass to produce sugars; fermenting the sugars with a microorganism to produce one or more alcohols; and catalytically converting the one or more alcohols in a reactor into a hydrocarbon mixture having a fraction boiling at a range of about 35° C. to about 200° C., thereby producing an unblended gasoline, wherein the unblended gasoline has an octane number of greater than 60 as determined by ASTM D2699.

An unblended gasoline is a liquid gasoline produced by the processes described herein without further mixing or blending with other components. For example, an unblended gasoline refers to the liquid reaction product obtained from the one or more reactors, in which alcohol is catalytically converted to hydrocarbons by the processes. In some embodiments, the unblended gasoline is the product emerging from a single reactor without further processing. In some embodiments, the unblended gasoline could be produced by distillation of the reaction product from the one or more reactors into a fraction with a specified boiling point range, such as HOG and LOG, while in other embodiments, no distillation of the reaction products may be involved. The unblended gasoline could be further mixed with other components such as ethanol or additional hydrocarbons to produce blended compositions with superior properties. In some embodiments these additional components for blending, such as ethanol and hydrocarbons, are produced from cellulosic biomass by the processes described herein.

In some embodiments, corn cobs are used as the lignocellulosic biomass, but other suitable feedstocks disclosed herein can also be used.

In some embodiments, the method further comprises treating corn cobs a beam of electrons. In some embodiments, the irradiating (with any radiation source or a combination of sources) is performed until the cellulosic-biomass receives a dose of at least 0.25 Mrad, e.g., at least 1.0 Mrad, at least 2.5 Mrad, at least 5.0 Mrad, or at least 10.0 Mrad. In some embodiments, the irradiating is performed until the material receives a dose of between 1.0 Mrad and 6.0 Mrad, e.g., between 1.5 Mrad and 4.0 Mrad. In some embodiments, the irradiating is performed at a dose rate of between 5.0 and 1500.0 kilorads/hour, e.g., between 10.0 and 750.0 kilorads/hour or between 50.0 and 350.0 kilorads/hours.

In some embodiments, the method further comprises saccharifying the treated corn cobs with an enzyme in an aqueous solution to produce sugars. In some embodiments, the enzyme used is produced by *Trichoderma reesei* strain. In some embodiments, the enzymes used is one or more of endoglucanases, cellobiohydrolases, or cellobiase.

In some embodiments, the method further comprises fermenting the sugars with a microorganism to produce one or more alcohols. In some embodiments, the microorganism is at least one of a bacterium, a yeast, a fungus, a plant, a protozoa, or a fungus-like protist. In some embodiments, the method further uses *Saccharomyces cerevisiae, C. acetobutylicum*, or a type of C5 fuel yeast, to ferment the sugars.

In some embodiments, the method further requires the fermenting process to include adding acids or bases to control the pH level, and maintaining fermentation temperature between about 20 and 50° C. In some embodiments, the alcohols produced by the process is one or more of methanol, ethanol, n-propanol, iso-propanol, n-butanol, iso-butanol, sec-butanol, as well as longer chained alcohols, R C5-C20, aldehydes, ketone, acetone, or any combination thereof.

In some embodiments, subsequent to the fermenting process, the method catalytically converts the one or more alcohols in a reactor into a hydrocarbon mixture having a fraction boiling at a range of about 35° C. to about 200° C. In some embodiments, the conversion process uses one or more catalysts selected from alumina, transition metal oxides, silicoaluminophosphates, zeolite catalysts, and acidic catalysts.

In some embodiments, the reactor used in the process is a single stage reactor. A single stage reactor uses only one reactor for the reactions described herein, such as the catalytic conversion of alcohol to hydrocarbons. For example, in a reactor converting alcohol to hydrocarbon, the feedstock containing alcohol is fed into the reactor and the reaction products are collected without sending them into another reactor for further reaction. Thus, the catalytic conversion of alcohol to hydrocarbon is achieved in one reactor only as opposed to multiple reactors involving multiple types of reactions. In operation, although more than one reaction may occur in the single stage reactor, the temperature and pressure generally do not vary across the single stage reactor. In some embodiments, the pressure, temperature and other reaction conditions can be varied across the reactor temporally and spatially. In some embodiments, the temperature, pressure, and other operating conditions are kept constant. In some embodiments, the temperature varies across the reactor as a function of the catalyst occupying the reactor, but the pressure and other operating conditions are held constant. In some embodiments, the pressure varies across the reactor as a function of the catalyst occupying the reactor, but the temperature and other operating conditions are held constant. Furthermore, in some embodiments, the single stage reactor may contain only one catalyst bed. In some embodiments, the single stage reactor may contain more than one catalyst bed. In some embodiments, the single stage reactor may be further connected to a fractionation or distillation tower in which the products of the single stage reactor are distilled into different factions.

In one embodiment, the reactor used has a liquid hourly space velocity (LHSV) of about 3.5 per hour. LHSV equals to the volumetric flow rate of reactants entering the reactor divided by the volume of the reactor. LHSV defines the amount of reactant that a known volume reactor can process per hour. For example, if a reactor has LHSV about 3.5 per hour and the volume of the reactor is about 3 mL, the reactor will theoretically be able to process about 10.5 mL of reactant per hour. In some embodiments, the LHSV of the reactor is between about 0.1 per hour to 50 per hour, between about 1.5 per hour and 10 per hour, between about 2.0 and 6.0, or between about 2.5 and 5 per hour. In some embodiments, the LHSV of the reactor is about 0.1 per hour, about 1 per hour, about 1.5 per hour, about 2 per hour, about 2.5 per hour, about 3 per hour, about 3.5 per hour, about 4 per hour, about 4.5 per hour, about 5 per hour, about 5.5 per hour, about 6 per hour, about 6.5 per hour, about 7 per hour, about 7.5 per hour, about 8 per hour, about 8.5 per hour, about 9 per hour, about 9.5 per hour, or about 10 per hour.

In one embodiment, the catalyst used is zeolite HZSM-5. And the method further comprises: pre-activating Zeolite HZSM-5 at about 450° C., under about 500 psi of an inert gas, and for about two hours; setting the reactor's internal temperature to about 350° C.; pre-heating the alcohol from the fermenting step to about 100° C.; and pumping the heated alcohol from the fermenting step into the reactor. In some embodiments, the inert gas is nitrogen. One of the unique features of the claimed method is that the conversion of alcohol to hydrocarbon takes place without needing to supply a reducing gas such as hydrogen.

In one embodiment, the catalyst used is 0.5% Pt/0.5% $H_3BO_3$—$Al_2O_3$. And the method further comprises: reducing 0.5% Pt/0.5% $H_3BO_3$—$Al_2O_3$ catalyst in-situ at about 450° C., under about 725 psi of hydrogen gas, and for about 10 hours; purging the reactor with an inert gas; setting the reactor's internal temperature to about 350° C. in inert gas flow; pre-heating the alcohol from the fermenting step to about 100° C.; and pumping the heated alcohol from the fermenting step into the reactor. In some embodiments, the inert gas is nitrogen. One of the unique features of the claimed method is that the conversion of alcohol to hydrocarbon takes place without needing to supply a reducing gas such as hydrogen.

Example 6: Process for Producing Unblended HOGs

One of methods for producing an unblended high-octane gasoline (HOG) from cellulosic biomass is described here. Batches of corn cobs were initially treated with a beam of electrons to a dose of between about 5 to 50 Mrad to reduce the recalcitrance of the lignocellulosic material. Subsequently, the electron-beam-treated corn cobs were saccharified with an enzyme produced from a *Trichoderma reesei* strain to make sugars. The sugars, then, were fermented using *Saccharomyces cerevisiae*. *Saccharomyces cerevisiae* is a microorganism capable of fermenting both glucose and xylose to produce ethanol.

To convert the ethanol into a gasoline, a single stage reactor was used. Before feeding the ethanol into the reactor, about 2.3 grams of zeolite HZSM-5 catalyst was pre-activated inside the reactor. The zeolite HZSM-5 was pre-activated at about 450° C., under about 500 psi of pressure, and exposed to nitrogen gas flow at about 50 mL/min for about two hours. Once the zeolite HZSM-5 was activated, the reactor's internal temperature was adjusted to about 350° C., the pressure was set to 500 psi, and the flow rate of nitrogen gas was set to 50 mL/min. This operating condition was maintained throughout the conversion process. The ethanol obtained from the fermenting step was then heated to about 100° C. before feeding into the reactor. The single stage reactor had a volume of about 3.1 mL. The LHSV for the reaction was about 3.5 per hour. Hence, the reactor catalytically converted approximately 10.85 mL of ethanol into the HOG every hour.

The process described above produced the HOG with the attributes and characteristics shown in FIG. 46 without further distillation or dilution.

Example 7: Process for Producing Unblended LOGs

One of the methods for producing an unblended low-octane cellulosic gasoline (LOG) is described here. Batches of corn cobs were initially treated with a beam of electrons to a dose of between about 5 to 50 Mrad to reduce the recalcitrance of the lignocellulosic material. Subsequently, the electron-beam-treated corn cobs were saccharified with an enzyme produced from a *Trichoderma reesei* strain to make sugars. The sugars, then, were fermented using *Saccharomyces cerevisiae*.

To convert the ethanol into a gasoline, a single stage reactor was used. Before feeding the ethanol into the single stage reactor, a 0.5% Pt/0.5% $H_3BO_3$—$Al_2O_3$ catalyst was prepared. The preparation involved pre-treating $Al_2O_3$ support with 5% $H_3BO_3$. The 2.6368 grams of $H_3BO_3$ was dissolved in 34 mL of water and then added drop-wise to the 25 grams of $Al_2O_3$ support with proper mixing. After the addition was completed, the $H_3BO_3$ treated $Al_2O_3$ support was kept at room temperature for 3 hours. Then, the $H_3BO_3$—$Al_2O_3$ catalyst was dried at 110° C. for 10 hours in a vacuum oven and calcined under air at 500° C. for 3 hours. Following the preparation steps, the catalyst was reduced in-situ at about 450° C., under about 725 psi of pressure, and exposed to a hydrogen gas flow at about 100 mL/min for about 10 hours. The reactor was subsequently purged with nitrogen gas. With the 0.5% Pt/0.5% $H_3BO_3$—$Al_2O_3$ catalyst prepared, the reactor's internal temperature was then adjusted to about 350° C., the pressure was set to 500 Psi, and the flow rate of nitrogen gas was set to about 50 mL/min. This operating condition was maintained throughout the conversion process. The ethanol obtained from the fermenting step was heated to about 100° C. before feeding into the reactor. The single stage reactor used here has a volume of about 3.1 mL. The LHSV for the reaction was about 3.5 per hour. Hence, the reactor catalytically converted approximately 10.85 mL of ethanol into a LOG every hour.

Unblended Gasoline with High Percentage of Biogenic Carbon Content

Provided herein is an unblended gasoline of high research octane number derived from cellulosic biomass, and a method for producing the same. The unblended gasoline is a liquid produced by the process described herein without further mixing or blending. And, in some embodiments, the unblended gasoline comprises a liquid produced by the processes described herein that has been further distilled in the gasoline distillation range from 900 F to 4100 F. In one embodiment, the unblended gasoline is produced by catalytic processing of the cellulosic-biomass or a product derived therefrom. In one embodiment, the research octane number of the unblended gasoline is greater than about 87, as determined by ASTM D2699. For example, the unblended gasoline can have a research octane number (RON) of greater than about 60, about 65, about 70, about 75, about 80, about 85, about 87, about 90, about 91, about 92, about 93, about 94, about 95, about 96, about 97, about 98, or about 99. The catalyst used in this process can be any of the catalysts disclosed herein, including an alumina-based catalyst and/or a zeolite-based catalyst. In some embodiments, the catalyst is a mono-metallic catalyst, bi-metallic catalyst, or tri-metallic catalyst. In some embodiments, the catalysts contain metals selected from the group consisting of Pt, Pd, Sn, Re, Rh, Bi, Ba, Ti, Ni, and any combinations thereof.

In some embodiments, the unblended gasoline has a relatively high percentage of biogenic carbon content as determined by ASTM D6866-18 (approved Mar. 1, 2018), which is incorporated here by reference. For example, the percentage of biogenic carbon content ("% biogenic carbon") can be greater than about 50, about 55, about 60, about 65, about 70, about 75, about 80, about 85, about 90, about 91, about 92, about 93, about 94, about 95, about 96, about 97, about 98, or about 99. In some embodiments, the unblended gasoline has about 100 percent of biogenic carbon content. A value of 100% biogenic carbon would indicate that 100 percent of the carbon came from plants or animal by-products (biomass) existing in the natural environment, other than fossil fuels, and a value of 0% would mean that all of the carbon was derived from petrochemicals, coal and other fossil sources. A value between 0-100% would indicate a mixture. The higher the value, the greater the proportion of biomass-sourced components is in the material.

According to ASTM D6866-18, % biogenic carbon content is the amount of biogenic carbon in the material or product as a percent of the total carbon (Total Carbon) in the product. In some instances, the percentage of the biologically-derived carbon can also be reported as "% biobased carbon," which refers to the amount of biogenic carbon in the material or product as a percent of the total organic carbon. In contrast to biobased carbon, biogenic carbon refers to the amount of biomass-derived carbon as a percentage of total carbon (organic and inorganic). In practice, both "% biogenic carbon" and "% biobased carbon" are standard units in regulatory and industrial applications. In addition, both units are obtained by using the same analytical procedure for measuring radiocarbon contents.

EXAMPLES

Several biomass-derived fuel samples generated by the processes disclosed herein are further analyzed under ASTM D6866-18, as described below.

FIG. 49 describes the compositions (volume %) of samples E1 to E8. Sample E1 is 100% high-octane gasoline (HOG) generated by the catalytic processing of biomass-derived ethanol described herein; sample E2 is 100% low-octane gasoline (LOG) generated by the catalytic processing of biomass-derived ethanol described herein; sample E3 is 100% cellulosic ethanol generated by the process described herein; sample E4 is a mixture of 95% HOG with 5% of cellulosic ethanol, derived by the process described herein; sample E5 is a mixture of 95% LOG with 5% of cellulosic ethanol, derived by the process described herein; sample E6 is a commercially available gasoline—Trufuel®; sample E7 is a mixture of 50% HOG with 50% Trufuel®; sample E8 is a mixture of 50% cellulosic ethanol, derived by the process described herein, with 50% Trufuel®. The HOG and LOG in samples E1, E2, E4, E5 and E6 are distilled to contain fractions from three different boiling ranges. Fraction 1 is a portion of the HOG or LOG that has a boiling range below 30° C. ("low boiling range fractions"), fraction 2 is a portion of the HOG or LOG that has a boiling range between 35 to 200° C. ("mid boiling range fractions"), and fraction 3 is a portion of the HOG or LOG that has a boiling range above 200° C. ("high boiling range fraction"), excluding a small portion that has a boiling point significantly higher than 200° C.

Figure 50:
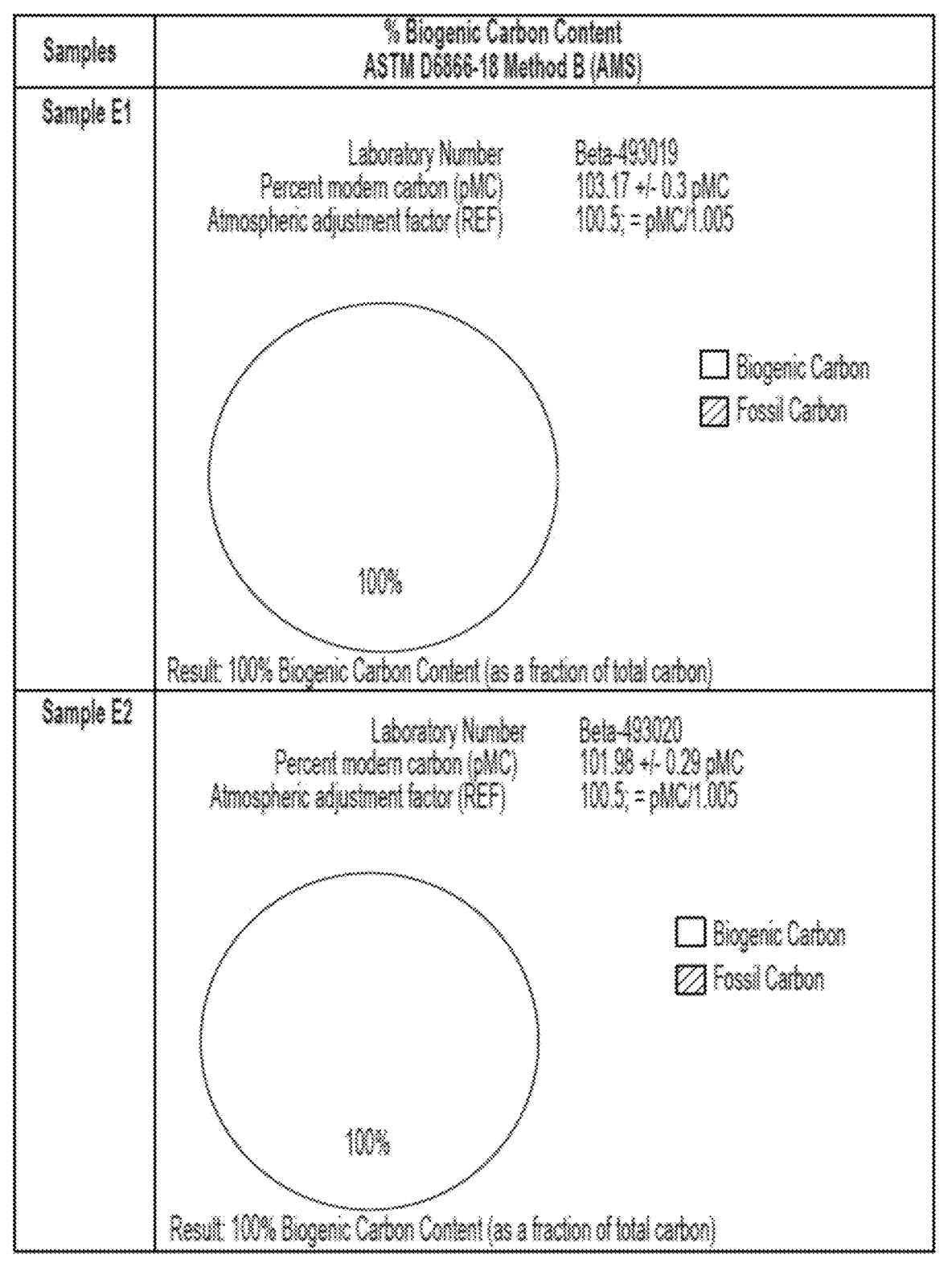
Figure 50:
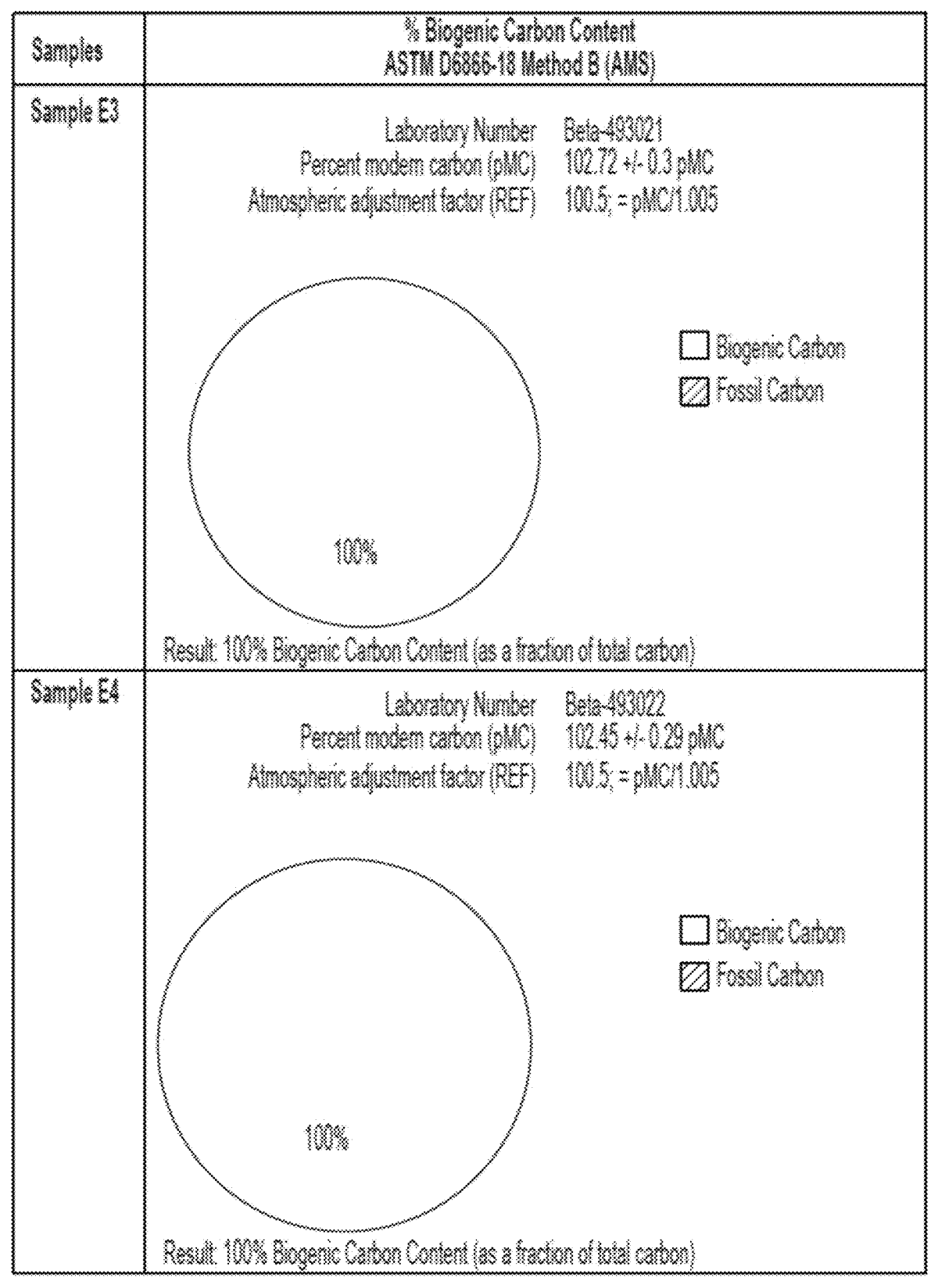
Figure 50:
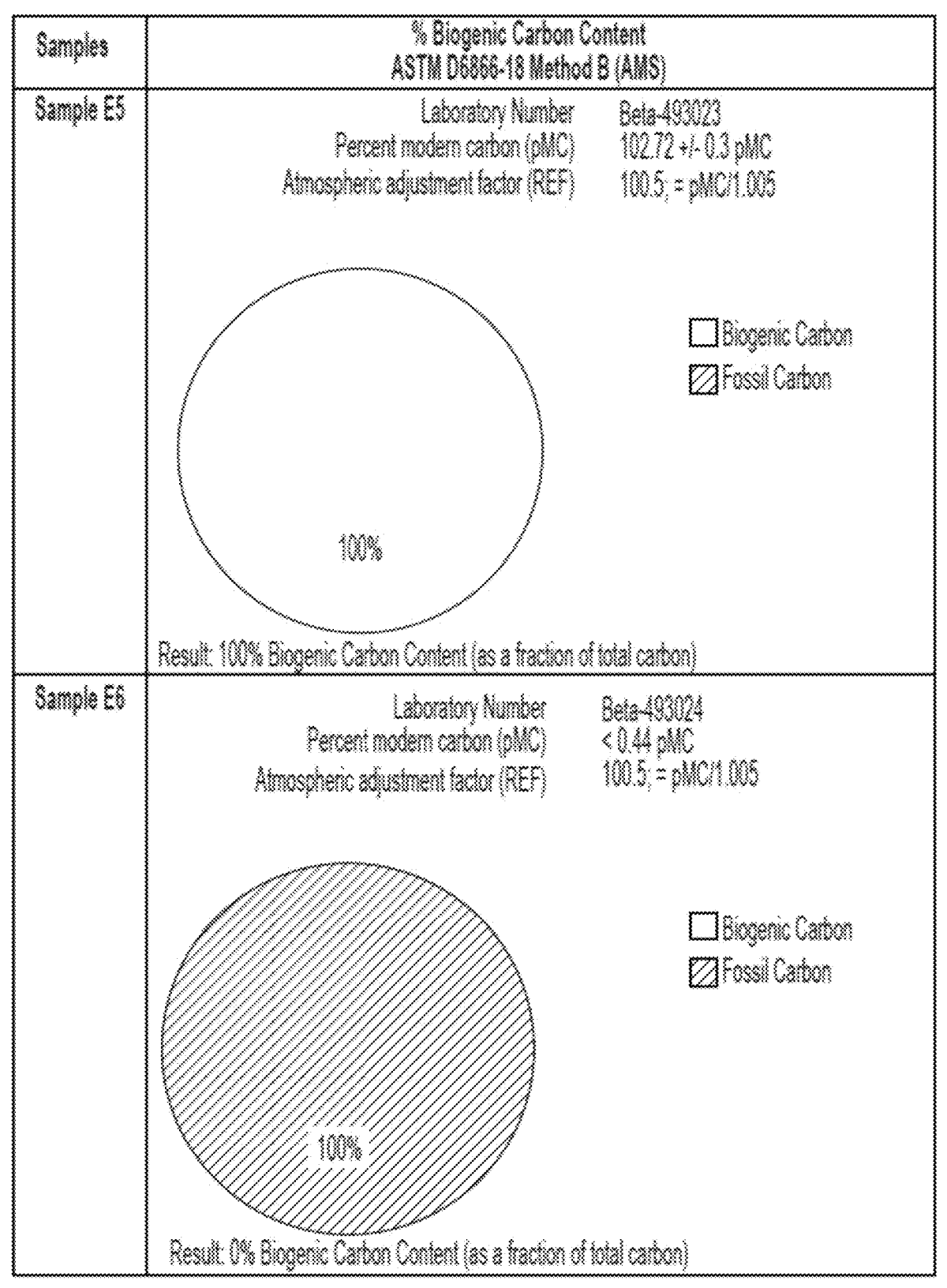
Figure 50:
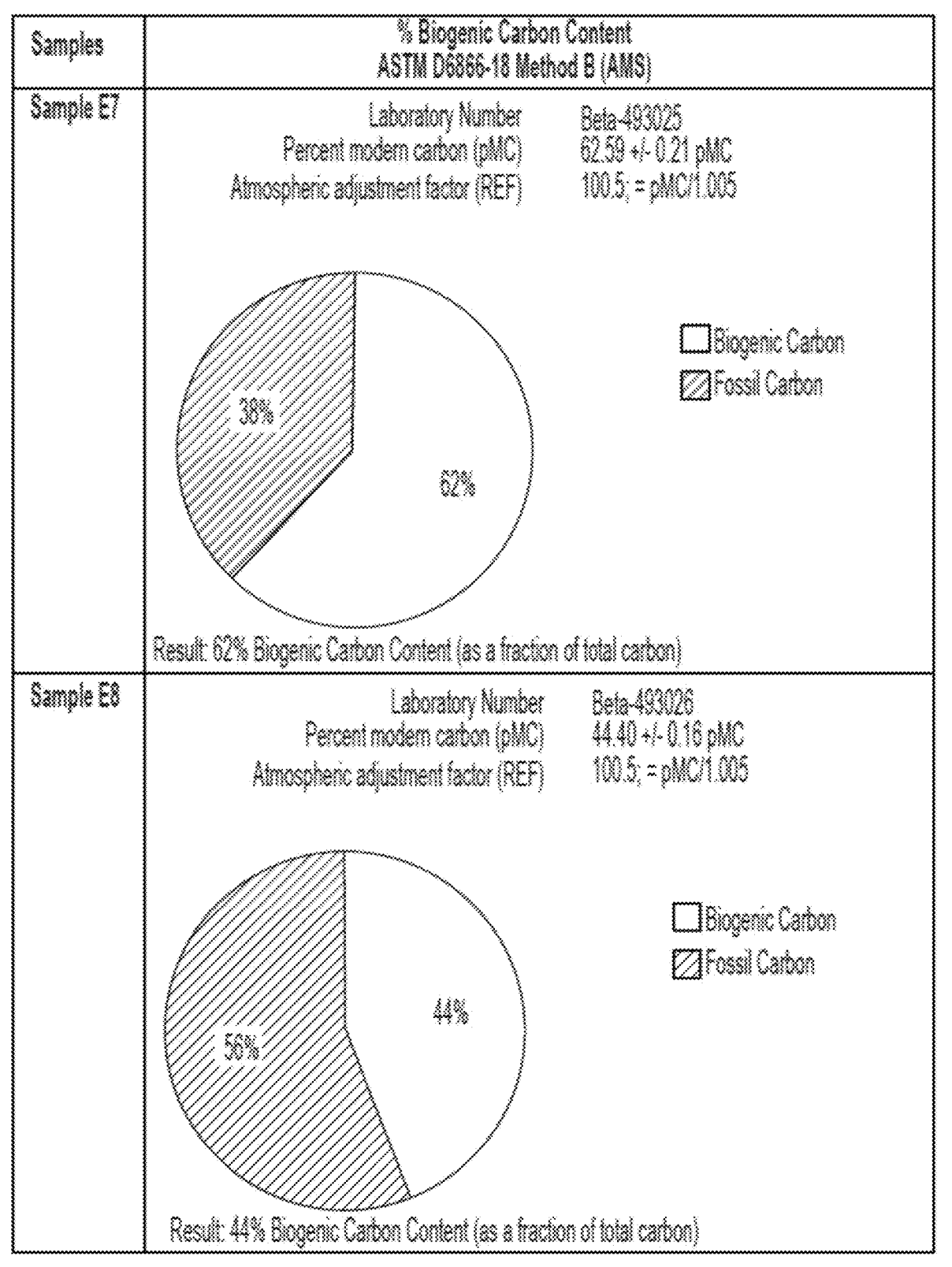

FIG. 50 describes the % biogenic carbon content in samples E1 to E8 as determined by ASTM D6866-18. The test results in FIG. 50 were obtained from a test procedure described in ASTM D6866-18 Method B (AMS). The analytical measurement is cited as percent modern carbon (pMC). This is the percentage of C14 measured in the sample relative to modern reference standard, NIST SRM 4990C, which is incorporated here by reference. Zero pMC represents the entire lack of measurable C14 atoms in a material above background signals thus indicating a fossil (for example, petroleum based) carbon source. One hundred pMC indicates an entirely modern carbon source. A pMC value between 0 and 100 indicates a proportion of carbon derived from fossil vs. modern source. The pMC can be greater than 100% due to the continuing but diminishing effects from injection of C14 into the atmosphere with atmospheric nuclear testing programs discussed in ASTM D6866-18. Because all sample C14 activities are referenced to the pre-bomb NIST traceable standard, all pMC values must be adjusted by atmospheric correction factor ("REF") to obtain the true biobased content of the sample. The correction factor is based on the excess C14 activity in the atmosphere at the time of testing. Hence, in FIG. 50, all % biogenic carbon contents were adjusted by a REF value for C14 in carbon dioxide at the time of the testing.

In FIG. 50, samples E1-E5 all have about 100% biogenic carbon content (as a fraction of total carbon). Specifically, sample E1 has about 103.17 pMC; sample E2 has about 101.98 pMC; sample E3 has about 102.72 pMC; sample E4 has about 102.45 pMC; and, sample E5 has about 102.40 pMC. Sample E6, 100% Trufuel®, has about 0% biogenic carbon content (as a fraction of total carbon), and about 100% of fossil carbon. Specifically, sample E6 has less than about 0.44 pMC. Sample E7 has about 62% biogenic carbon content (as a fraction of total carbon), and about 38% of fossil carbon. Specifically, sample E7 has about 62.59 pMC. Lastly, sample E8 has about 44% biogenic carbon content (as a fraction of total carbon), and about 56% of fossil carbon. Specifically, sample E8 has about 44.40 pMC.

E80/HOG Gasoline

In an embodiment, a fuel containing about 80% cellulosic ethanol (E80) and 20% of cellulose-derived high-octane gasoline (HOG) by volume was produced and tested. The cellulosic ethanol was prepared according to the following method. About 45,000 lbs of ground corn cobs were treated with a dose of 40 Mrad electron beam radiation. The ground corn cobs had a maximum dimension of about 1 mm in size. The treated corn cobs were then added to a 50,000 gallon stainless steel vessel containing 30,000 gallons of water. Subsequently, about 30 metric tons of cellulase enzyme cocktail produced by genetically modified *T. reesei* (such as one originating from the RUT-C30 strain) (1.0% active) solution (approximately 8,250 gallons) was added for saccharification. A jet mixer was used during the saccharification phase to continuously agitate the mixture. During the saccharification reaction, the pH was adjusted and maintained at 5.0 by adding sodium hydroxide and 85 percent phosphoric acid. The saccharification reaction continued for 72 hours at about 50° C. At the 72-hour mark, the total sugar concentration was about 74 g/L. The mixture was then cooled to 33° C. and inoculated with Angel Cellulosic Ethanol Active Dry Yeast capable of generating ethanol from both the xylose and glucose. The yeast fermented the sugar for about 30 hours. The end product had an ethanol concentration of about 31 g/L (approximately 3.1 percent in volume). The solids in the end product were removed by a filter belt and two-stage ultrafiltration (UF) systems. The two-stage UF system contains a first membrane, which is a tubular membrane having a molecular weight cutoff of 200,000 and a second membrane, which is a spiral membrane having a molecular weight cutoff of 10,000. The filter belt was obtained from Westech Engineering, Salt Lake City, Utah and run at 75 gpm. After the filtration, the end product was distilled and dehydrated to produce anhydrous ethanol, approximately 1500 gallons.

The HOG used in this fuel composition is the same gasoline described as sample D5 above. Its attributes are shown in FIGS. 46 and 48. The E80/HOG has a biogenic carbon content of about 100%. The cellulosic ethanol and the cellulose-derived HOG also have their respective biogenic carbon content at about 100% as determined by ASTM D6866-18. See FIGS. 49 and 50 (sample E1 represents the HOG, and sample E3 represents the cellulosic ethanol). The cellulose-derived HOG used in the E80/HOG mixture has a boiling range between 35 to 200° C. And among other attributes, the cellulose-derived HOG also has a research octane number of about 97 as determined by ASTM D2699, a motor octane number of about 85, as determined by ASTM D2700, an antiknock index of about 91, as determined by ASTM D4814-X1.4, API Gravity at 60° F. of about 53° API, as determined by ASTM D4052, a dry vapor pressure of about 10 psi, as determined by ASTM D5191, and a gross heat of combustion of about 128,0000 Btu/gal.

The E80/HOG fuel was tested in a commercial vehicle and no operational or performance differences were observed in comparison to commercially available gasoline. In the test, about 5.25 oz of STP® gas treatment was added to about 20 gallons of the E80/HOG unblended gasoline. By volume, the STP® gas treatment constituted about 0.002% of the fuel mixture. The fuel mixture was then added to the gas tank of a Ford 350 flex fuel truck. A week of testing on both the highway and local roads showed no observable difference in the truck's operation and performance. STP® gas treatment was added to keep fuel injectors and intake valves clean. It provides the benefit of keeping fuel intake system clean, prevent fuel line freeze, and prevent deposit build up. While STP® gas treatment was used as the cleaning agent of choice here, other types of cleaning agents can also be used.

Methods of Producing Cellulosic Biomass-Derived Jet Fuel

Also provided herein is a method of producing jet fuel from cellulosic biomass produced from by the methods described herein. For example, cellulosic ethanol can be converted to jet fuel by catalytic conversion over one or more of the catalysts described herein. Jet fuel produced thereby can be based on either an unleaded kerosene (Jet A-1), or a naphtha-kerosene blend (Jet B). The jet fuels produced hereby can be used to operate compression ignition engines and jet turbines, with or without blending with additional components.

In one embodiment, the cellulosic-biomass derived jet fuel is produced by catalytically processing a cellulosic-biomass derived ethanol. The cellulosic-biomass may be further pretreated with electron beam radiation. In some embodiments, the irradiating (with any radiation source or a combination of sources) is performed until the cellulosic-biomass receives a dose of at least 0.25 Mrad, e.g., at least 1.0 Mrad, at least 2.5 Mrad, at least 5.0 Mrad, or at least 10.0 Mrad. In some embodiments, the irradiating is performed until the material receives a dose of between 1.0 Mrad and 6.0 Mrad, e.g., between 1.5 Mrad and 4.0 Mrad. In some embodiments, the irradiating is performed at a dose rate of between 5.0 and 1500.0 kilorads/hour, e.g., between 10.0 and 750.0 kilorads/hour or between 50.0 and 350.0 kilorads/hours.

The cellulosic-biomass derived jet fuel produced by this invention can be a mixture of different hydrocarbons, such as linear or branched, mono-, and di-substituted $C_7$-$C_{16}$ alkanes, one or more of which is derived from cellulosic-biomass. It may also contain olefins, substituted or unsubstituted cycloalkanes (such as cyclopentanes, cyclohexanes), aromatics (such as benzene, toluene, naphthalenes), mono-substituted aromatics (such as methyl benzene), di-substituted aromatics (such as xylenes), and multi-substituted aromatics (such as trimethylbenzenes), one or more of which is derived from the cellulosic-biomass.

In some instances, the cellulosic-biomass derived jet fuel contains less than about 5 percent by weight alkene, such as less than about 4.5, 4.0, 3.5, 3.0, 2.5, 2.0, 1.5, or even less than 1.0 percent by weight, e.g., less than 0.9, 0.8, 0.7, 0.6, 0.5, 0.4, 0.3, or even less than 0.25 percent by weight, e.g., less than 0.2, 0.15, 0.1 or even less than 0.05 percent by weight. In some embodiments, the jet fuel has about 2.5% (w/w) of alkenes. In particular, the methods and catalysts can, for example, give the low alkene content directly, without active removal or separation, such as by distillation of the alkene from other components.

In some embodiments, the cellulosic-biomass derived jet fuel described herein has an aromatics content of about 15-20% (w/w), about 20-25% (w/w), about 25-30% (w/w), about 30-35% (w/w), about 35-40% (w/w), about 40-45% (w/w), about 45-50% (w/w) of aromatic hydrocarbons. In some embodiment, the jet fuel has about 25% (w/w) of aromatic hydrocarbons.

In some embodiments, the cellulosic-biomass derived jet fuel described herein has 25-30% (w/w), about 30-35% (w/w), about 35-40% (w/w), about 40-45% (w/w), about 45-50% (w/w), about 50-55% (w/w), 55-60% (w/w), 60-65% (w/w), 65-70% (w/w) of alkanes. In some embodiment, the jet fuel has about 41% (w/w) of alkanes.

Note that, in some instances, adjusting the methods and/or the catalysts used in the catalytical process described herein may directly change the chemical properties of the resulting unblended cellulosic-biomass derived jet fuel, and therefore, enabling the process to obtain an ideal concentration of hydrocarbons without the need for further dilution, distillation, or blending.

In some embodiments, the cellulosic-biomass derived jet fuel of such mixtures can be used directly as transportation fuels, as blending components in transportation fuels, such as commercial jet fuel.

In some embodiments, the cellulosic-biomass derived jet fuel described herein has an oxygenate level of less than about 10% (wt./wt.), about 5% (wt/wt.), about 3% (wt/wt.), about 0.5% (wt/.wt.), about 0.4% (wt/.wt.), about 0.25% (wt/.wt.), or about 0.1% (wt./wt.). In some embodiment, the jet fuel has about 8-9% (wt./wt.) of oxygenates. As used herein, the term "oxygenates" is defined to include oxygen containing organic compounds such as alcohols, ethers, carbonyl compounds (aldehydes, ketones, carboxylic acids, carbonates, and the like). Representative oxygenates include, but are not necessarily limited to, lower straight chain or branched aliphatic alcohols, their unsaturated counterparts. Examples include but are not necessarily limited to: methanol; ethanol; n-propanol; isopropanol; C4-C10 alcohols; methyl ethyl ether; dimethyl ether; diethyl ether; di-isopropyl ether; methyl mercaptan; methyl formate, methyl acetate, formaldehyde; di-methyl carbonate; trimethyl orthoformate, and dimethyl ketone. Oxygenates such as acetaldehyde and acetone can be corrosive and can damage gaskets in engine components. They can also make the fuel hygroscopic, allowing it to absorb water, thereby impacting the quality of gasoline. So, in some embodiments having low oxygenate content in gasoline may be desirable.

EXAMPLES

Preparation of 0.5% Pt-0.25% Re/γ-Al$_2$O$_3$ 0.5% Pt-0.25% Re/γ-Al$_2$O$_3$ catalyst was prepared by sequential incipient wetness impregnation method. The metal precursor salts Hexachloroplatinic acid (H$_2$PtCl$_6$), and ammonium perrhenate (NH$_4$ReO$_4$) were used for the preparation of bimetallic Pt—Re catalysts. First, 0.25% Re/γ-Al$_2$O$_3$ catalyst was prepared by dissolving the corresponding amount of NH$_4$ReO$_4$ in appropriate amount of DI water and adding to stoichiometric amounts of γ-Al$_2$O$_3$ dropwise with proper mixing. It was subsequently dried at 110° C. for 10 h under vacuum oven, and calcined under air at 500° C./3 h. Second, 0.25% Re/γ-Al$_2$O$_3$ was impregnated with 0.5% Pt using stoichiometric amount of H$_2$PtCl$_6$ dissolve in required amount of DI water and by dropwise addition of metal salt solution to the 0.25% Re/γ-Al$_2$O$_3$ catalyst. This was then dried at 110° C. for 10 h under vacuum oven and calcined under air at 500° C./3 h.

Reaction Conditions:

Cellulosic ethanol produced by the methods described herein is converted to jet fuel by catalytic conversion over the 2.3 g of 0.5% Pt-0.25% Re/γ-Al$_2$O$_3$ prepared above. The process was carried out in a 3.7 cm$^3$ reactor. Before the reaction, the catalyst was reduced at 450° C., 700 Psi H$_2$-100 cc/min for 10 h. The reaction was run at a temperature of 400° C., pressure of 700-900 Psi N$_2$-50 cc/min and ethanol flow rate of 0.4 mL/min. All condensable hydrocarbons and water were collected. The entire hydrocarbon portion was subsequently used as jet fuel without any purification or further distillation.

Analysis of the Cellulosic Biomass-derived Jet Fuel

Figure 51:
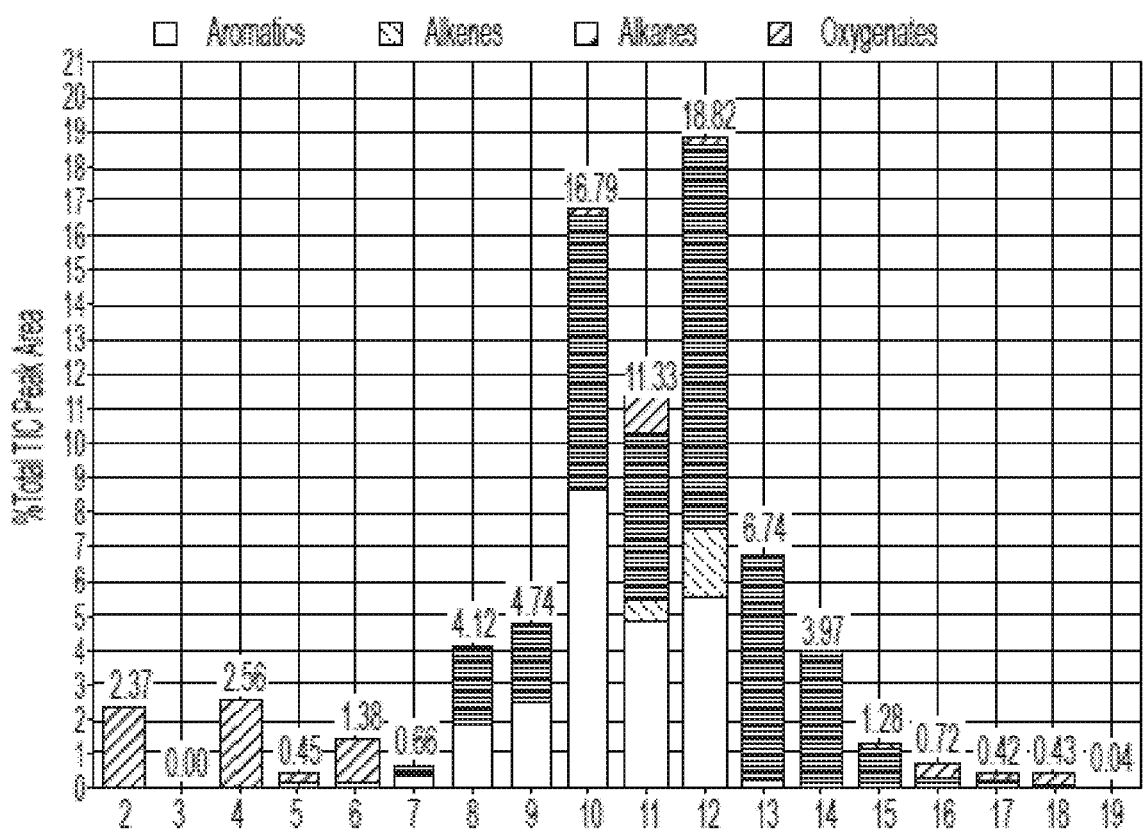
FIG. 51 provides a graphical depiction of the product distribution of aromatics, alkenes, alkanes and oxygenates of various carbon content in the jet fuel generated by the catalytic processing of biomass-derived ethanol described herein. Based on the total known components, the jet fuel contained about 25% of aromatic hydrocarbons, about 2.5% of alkenes, about 41% of alkanes, and about 8.5% of oxygenated compounds (wt./wt.).
Figure 51:
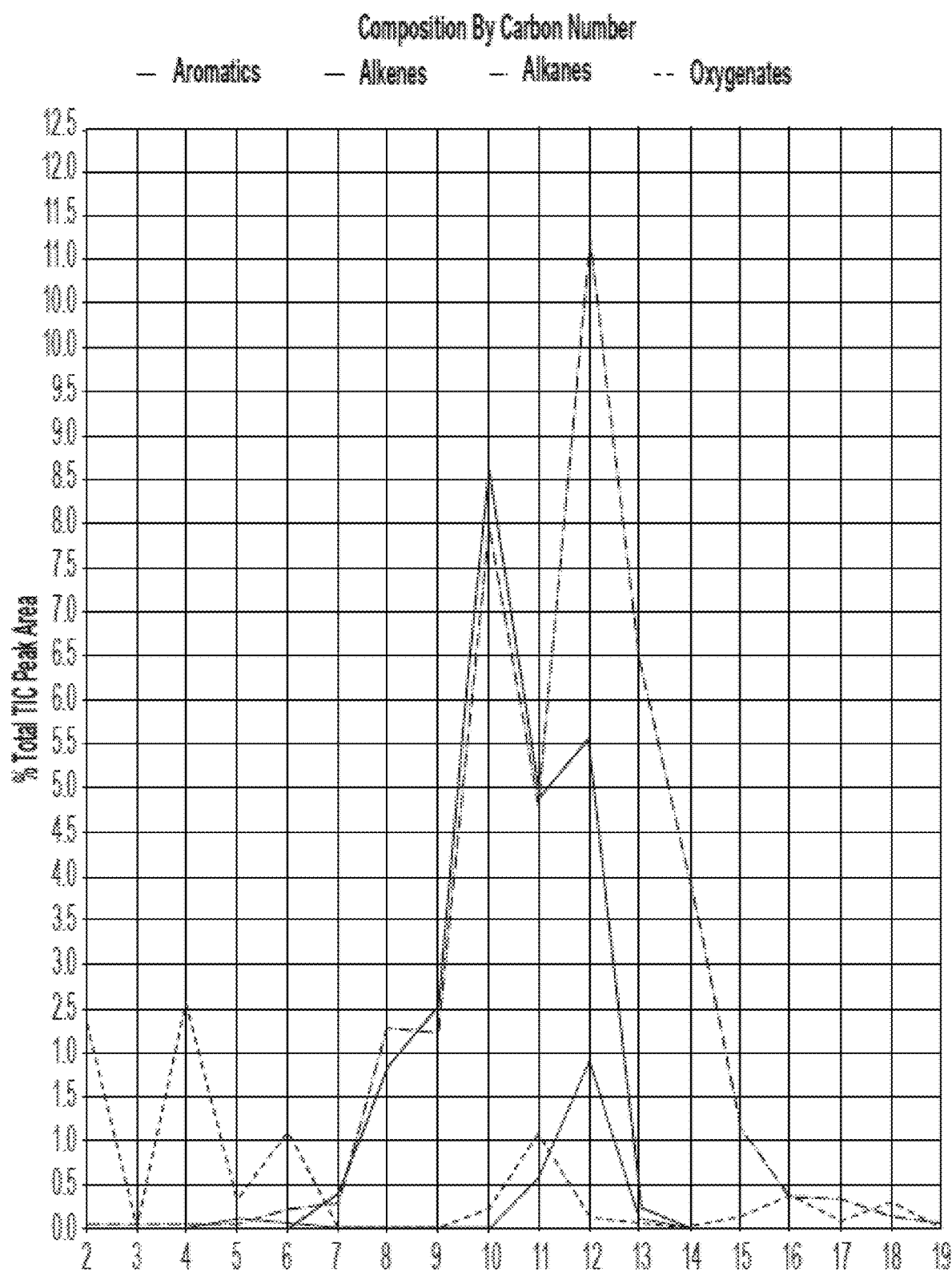

The jet fuel produced by the method described above was further analyzed for its carbon content and distribution. A graphical depiction of the product distribution of aromatics, alkenes, alkanes and oxygenates of various carbon content in the jet fuel generated by the catalytic processing of biomass-derived ethanol described herein is shown in FIG. 51. Based on the total known components, the jet fuel contained about 25% of aromatic hydrocarbons, about 2.5% of alkenes, about 41% of alkanes, and about 8.5% of oxygenated compounds (wt./wt.). FIG. 51 also provides a detailed breakdown of all the detectable compounds in the jet fuel.

The unblended cellulosic biomass derived jet fuel was then tested on a Rhino SE® series turbine from Jet Central. About 49% (w/w) of the jet fuel was blended with about 49% (w/w) of Kerosene 1-K Heater Fuel from Kleanstrip™, and 2% (w/w) Torco 2-stroke GP-7 racing oil (as lubricant), and the turbine was run on this fuel mixture. No operational or performance differences were observed in comparison to 98% (w/w) Kerosene 1-K Heater Fuel from Kleanstrip™, and 2% (w/w) Torco 2-stroke GP-7 racing oil.

Generating Hydrocarbons from Blends of Longer Chain Alcohols

In another aspect, provided herein is a method of generating hydrocarbons from blends of ethanol with longer chain alcohols, branched chain alcohols, esters, aldehydes and ketones. It has been found that higher yields can be obtained if, in addition to ethanol, higher alcohols, branched alcohols, esters and ketones are blended into the ethanol, for example, using greater that about 5% (w/w), 10% (w/w), 15% (w/w), 20% (w/w), 30% (w/w), 40% (w/w) or 50% (w/w) of the higher chain molecules. This can be particularly useful when making heavier weight products such as kerosene, jet fuel or diesel. Starting materials containing longer chains were found to produce more higher molecular weight products.

Figure 52:
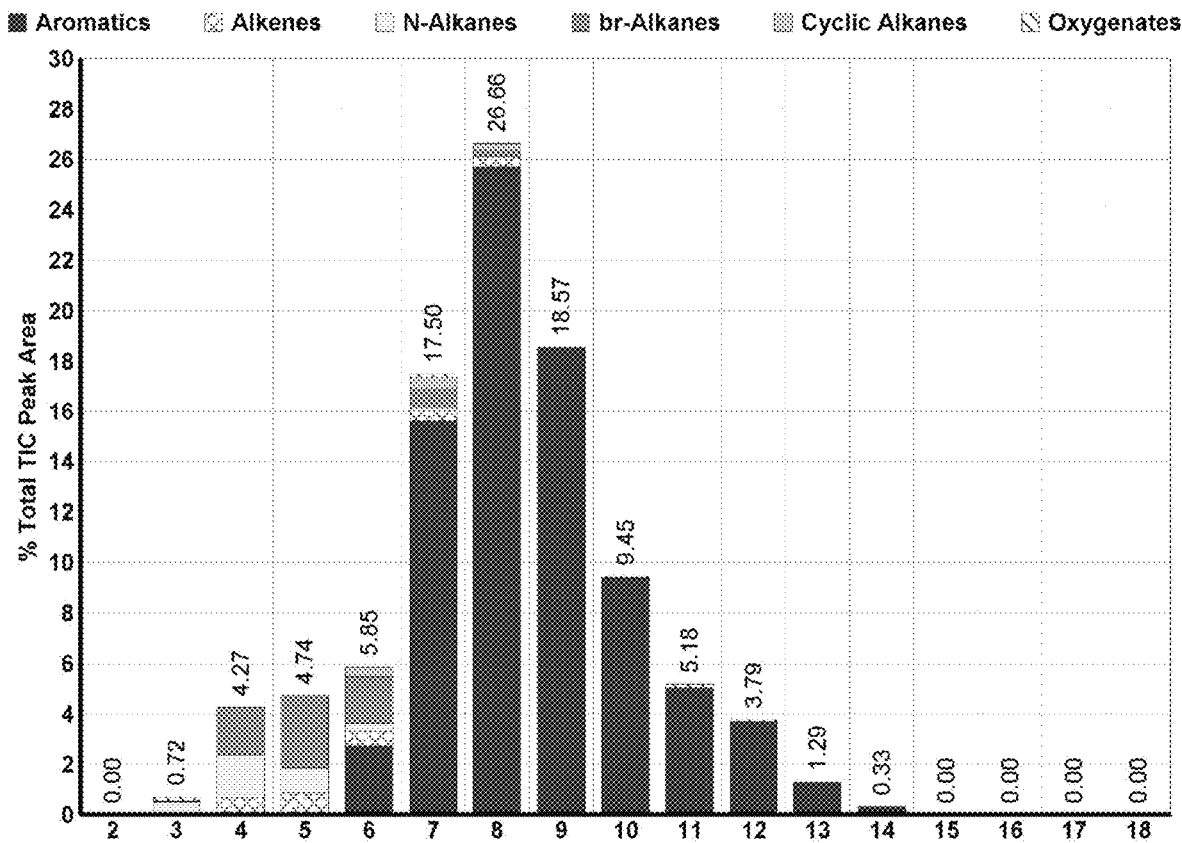
FIG. 52 provides a graphical description of the product distribution of aromatics, alkenes, alkanes and oxygenates of various carbon content in the hydrocarbon mixture generated by the catalytic conversion of a composition of acetone, butanol and ethanol (ABE). The graph shows the percentage amounts (vertical axis) of aromatics, alkenes, alkanes and of oxygenates containing C2-C18 hydrocarbons (horizontal axis) formed by the catalytic conversion of ABE. The resulting hydrocarbon contained about 82.5% of aromatics, 2.9% alkenes, 12.48% alkanes, and 7% of other compounds, included oxygenated species.

For example, a composition of acetone, butanol ethanol (ABE) was prepared by fermenting sugars derived from cellulosic material with anaerobic bacteria (e.g., bacteria of the *clostridium* family listed in paragraphs 250, 267). The ABE composition contained about 62.8% acetone (w/w), 29.1% butanol (w/w), and 8% ethanol (w/w). This composition was catalytically converted to hydrocarbons in the presence of 2.3 g of zeolite catalyst, HZSM-5. The temperature was 350° C., pressure was 500 Psi, N$_2$ was passed at a flow rate of 50 cc/min, and a liquid flow rate of 0.1875 cc/min. The resulting product was analyzed, and FIG. 52 provides a graphical description of the product distribution of aromatics, alkenes, alkanes and oxygenates of various carbon content in the hydrocarbon mixture generated by this process. The graph shows the percentage amounts (vertical axis) of aromatics, alkenes, alkanes and of oxygenates containing C2-C18 hydrocarbons (horizontal axis) formed by the catalytic conversion of ABE. The resulting hydrocarbon contained about 82.5% of aromatics, 2.9% alkenes, 12.48% alkanes, and 7% of other compounds, included oxygenated species. FIG. 52 also provides a detailed breakdown of all the detectable compounds in the ABE composition.

The Examples disclosed in this application are to be considered in all respects as illustrative and not limiting. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications, patents, and PCT publications, are incorporated herein by reference for all purposes.

What is claimed is:

1. An cellulosic-biomass derived gasoline, wherein the gasoline is unblended, wherein the gasoline has a research octane number of greater than about 87, as determined by ASTM D2699, and wherein the gasoline has a motor octane number of greater than about 85, as determined by ASTM D2700.

2. The cellulosic-biomass derived gasoline of claim 1, wherein the gasoline is derived from a catalytic processing of ethanol obtained from a cellulosic-biomass.

3. The cellulosic-biomass derived gasoline of claim 2, wherein the catalyst processing uses one or more catalysts comprising of an alumina-based catalyst and/or a zeolite-based catalyst.

4. The cellulosic-biomass derived gasoline of claim 2, wherein the catalyst processing uses one or more catalysts comprising of a mono-metallic catalyst, a bi-metallic catalyst, or a tri-metallic catalyst.

5. The cellulosic-biomass derived gasoline of claim 4, wherein the one or more catalysts comprise at least one metals selected from the group consisting of Pt, Pd, Sn, Re, Rh, Bi, Ba, Ti, Ni, and any combinations thereof.

6. The cellulosic-biomass derived gasoline of claim 1, wherein the research octane number is greater than about 90.

7. The cellulosic-biomass derived gasoline of claim 1, wherein the research octane number is greater than about 92.

8. The cellulosic-biomass derived gasoline of claim 1, wherein the research octane number is greater than about 96.

9. The cellulosic-biomass derived gasoline of claim 1, wherein the motor octane number is greater than about 90.

10. The cellulosic-biomass derived gasoline of claim 1, wherein the gasoline has a dry vapor pressure equivalent of greater than about 4 psi, as determined by ASTM D5191.

11. The cellulosic-biomass derived gasoline of claim 10, wherein the dry vapor pressure equivalent is greater than about 5 psi.

12. The cellulosic-biomass derived gasoline of claim 1, wherein the gasoline has a gross heat of combustion of greater than about 120,000 Btu/gal.

13. The cellulosic-biomass derived gasoline of claim 12, wherein the gross heat of combustion is greater than about 122,000 Btu/gal.

14. The cellulosic-biomass derived gasoline of claim 12, wherein the gross heat of combustion is greater than about 124,000 Btu/gal.

15. The cellulosic-biomass derived gasoline of claim 12, wherein the gross heat of combustion is greater than about 126,000 Btu/gal.

16. The cellulosic-biomass derived gasoline of claim 1, wherein the gasoline has an antiknock index of greater than about 85, as determined by ASTM D4814-X1.4.

17. The cellulosic-biomass derived gasoline of claim 16, wherein the antiknock index is greater than about 90.

18. The cellulosic-biomass derived gasoline of claim 1, wherein the gasoline has an API Gravity at 60° F. of greater than about 40° API, as determined by ASTM D4052.

19. The cellulosic-biomass derived gasoline of claim 18, wherein the API Gravity at 60° F. is greater than about 50° API.

20. The cellulosic-biomass derived gasoline of claim 18, wherein the API Gravity at 60° F. is greater than about 60° API.

21. The cellulosic-biomass derived gasoline of claim 1, wherein the gasoline has an aromatic content of greater than about 25% (wt./wt.).

22. The cellulosic-biomass derived gasoline of claim 21, wherein the aromatic content is greater than about 30% (wt./wt.).

23. The cellulosic-biomass derived gasoline of claim 21, wherein the aromatic content is greater than about 40% (wt./wt.).

24. The cellulosic-biomass derived gasoline of claim 21, wherein the aromatic content is greater than about 50% (wt./wt.).

25. The cellulosic-biomass derived gasoline of claim 1, having a boiling point range of about 35° C. to 200° C.

26. The cellulosic-biomass derived gasoline of claim 25, wherein the cellulosic-biomass derived gasoline has an oxygenate level of less than about 0.5% (wt./wt.).

27. The cellulosic-biomass derived gasoline of claim 25, wherein the cellulosic-biomass derived gasoline has an oxygenate level of less than about 0.4% (wt./wt.).

28. The cellulosic-biomass derived gasoline of claim 25, wherein the cellulosic-biomass derived gasoline has an oxygenate level of less than about 0.25% (wt./wt.).

29. The cellulosic-biomass derived gasoline of claim 25, wherein the cellulosic-biomass derived gasoline has a naphthalene content of less than about 0.5% (wt./wt.).

30. The cellulosic-biomass derived gasoline of claim 25, wherein the cellulosic-biomass derived gasoline has a naphthalene content of less than about 0.4% (wt./wt.).

31. The cellulosic-biomass derived gasoline of claim 25, wherein the cellulosic-biomass derived gasoline has a naphthalene content of less than about 0.25% (wt./wt.).

32. The cellulosic-biomass derived gasoline of claim 25, wherein the cellulosic-biomass derived gasoline has an aromatic content of greater than about 75% (wt./wt.).

33. The cellulosic-biomass derived gasoline of claim 25, wherein the cellulosic-biomass derived gasoline has an aromatic content of greater than about 76% (wt./wt.).

34. The cellulosic-biomass derived gasoline of claim 25, wherein the cellulosic-biomass derived gasoline has an aromatic content of greater than about 77% (wt./wt.).

35. The cellulosic-biomass derived gasoline of claim 25, wherein the cellulosic-biomass derived gasoline has an aromatic content of greater than about 78% (wt./wt.).

36. The cellulosic-biomass derived gasoline of claim 25, wherein the cellulosic-biomass derived gasoline has an aromatic content of greater than about 79% (wt./wt.).

37. The cellulosic-biomass derived gasoline of claim 25, wherein the cellulosic-biomass derived gasoline has an aromatic content of greater than about 80% (wt./wt.).

38. The cellulosic-biomass derived gasoline of claim 25, wherein the cellulosic-biomass derived gasoline has an aromatic content of greater than about 85% (wt./wt.).

39. The cellulosic-biomass derived gasoline of claim 25, wherein less than about 10% of the fraction of the cellulosic-biomass derived gasoline boils at a temperature above 160° C.

40. The cellulosic-biomass derived gasoline of claim 25, wherein less than about 9% of the fraction of the cellulosic-biomass derived gasoline boils at a temperature above 160° C.

41. The cellulosic-biomass derived gasoline of claim 25, wherein less than about 8% of the fraction of the cellulosic-biomass derived gasoline boils at a temperature above 160° C.

42. The cellulosic-biomass derived gasoline of claim 25, wherein less than about 7% of the fraction of the cellulosic-biomass derived gasoline boils at a temperature above 160° C.

43. The cellulosic-biomass derived gasoline of claim 25, wherein less than about 6% of the fraction of the cellulosic-biomass derived gasoline boils at a temperature above 160° C.

44. The cellulosic-biomass derived gasoline of claim 25, wherein less than about 5% of the fraction of the cellulosic-biomass derived gasoline boils at a temperature above 160° C.

45. The cellulosic-biomass derived gasoline of claim 25, wherein less than about 4% of the fraction of the cellulosic-biomass derived gasoline boils at a temperature above 160° C.

46. A cellulosic-biomass derived gasoline, wherein the gasoline is unblended, wherein the gasoline has a research octane number of greater than about 87, as determined by ASTM D2699, and wherein the gasoline has an antiknock index of greater than about 85, as determined by ASTM D4814-X1.4.

47. The cellulosic-biomass derived gasoline of claim 46, wherein the gasoline has a dry vapor pressure equivalent of greater than about 4 psi, as determined by ASTM D5191.

48. The cellulosic-biomass derived gasoline of claim 46, wherein the gasoline has a gross heat of combustion of greater than about 120,000 Btu/gal.

49. The cellulosic-biomass derived gasoline of claim 46, wherein the gasoline has an API Gravity at 60° F. of greater than about 40° API, as determined by ASTM D4052.

50. The cellulosic-biomass derived gasoline of claim 46, wherein the gasoline has an aromatic content of greater than about 25% (wt./wt.).

51. A cellulosic-biomass derived gasoline, wherein the gasoline is unblended, wherein the gasoline has a research octane number of greater than about 87, as determined by ASTM D2699, wherein the gasoline has a motor octane number of greater than about 85, as determined by ASTM D2700, and wherein the gasoline has a boiling point range of about 35° C. to 200° C.

52. The cellulosic-biomass derived gasoline of claim 51, wherein the gasoline has a dry vapor pressure equivalent of greater than about 4 psi, as determined by ASTM D5191.

53. The cellulosic-biomass derived gasoline of claim 51, wherein the gasoline has a gross heat of combustion of greater than about 120,000 Btu/gal.

54. The cellulosic-biomass derived gasoline of claim 51, wherein the gasoline has an API Gravity at 60° F. of greater than about 40° API, as determined by ASTM D4052.

55. The cellulosic-biomass derived gasoline of claim 51, wherein the gasoline has an aromatic content of greater than about 25% (wt./wt.).

\* \* \* \* \*